US010562912B2

(12) United States Patent
Park et al.

(10) Patent No.: US 10,562,912 B2
(45) Date of Patent: Feb. 18, 2020

(54) HETEROCYCLIC DERIVATIVES AND USE THEREOF

(71) Applicant: C&C Research Laboratories, Gyeonggi-do (KR)

(72) Inventors: Chan Hee Park, Gyeonggi-do (KR); Sang Hwi Lee, Gyeonggi-do (KR); Junhwan Im, Gyeonggi-do (KR); Soon Ok Lee, Gyeonggi-do (KR); Hoe Moon Kim, Gyeonggi-do (KR); Sung Hyun Moon, Seoul (KR); Seunghee Kim, Gyeonggi-do (KR); Jongmin Kim, Gyeonggi-do (KR); Kwang Seok Ko, Gyeonggi-do (KR); Bu Young Choi, Seoul (KR); Byungho Kim, Gyeonggi-do (KR)

(73) Assignee: C&C Research Laboratories, Gyeonggi-do (KR)

( * ) Notice: Subject to any disclaimer, the term of this patent is extended or adjusted under 35 U.S.C. 154(b) by 0 days.

(21) Appl. No.: 14/892,378

(22) PCT Filed: Jun. 3, 2014

(86) PCT No.: PCT/KR2014/004947
§ 371 (c)(1),
(2) Date: Nov. 19, 2015

(87) PCT Pub. No.: WO2014/196793
PCT Pub. Date: Dec. 11, 2014

(65) Prior Publication Data
US 2016/0108056 A1    Apr. 21, 2016

(30) Foreign Application Priority Data

Jun. 5, 2013  (KR) .................. 10-2013-0064972

(51) Int. Cl.
| C07D 495/04 | (2006.01) |
| C07D 409/12 | (2006.01) |
| C07D 471/04 | (2006.01) |
| C07D 277/68 | (2006.01) |
| C07D 209/42 | (2006.01) |
| C07D 333/70 | (2006.01) |

(52) U.S. Cl.
CPC ......... *C07D 495/04* (2013.01); *C07D 209/42* (2013.01); *C07D 277/68* (2013.01); *C07D 333/70* (2013.01); *C07D 409/12* (2013.01); *C07D 471/04* (2013.01)

(58) Field of Classification Search
CPC .................................................. C07D 495/04
See application file for complete search history.

(56) References Cited

U.S. PATENT DOCUMENTS

| 5,780,480 A | 7/1998 | Wai et al. |
| 7,332,497 B2 * | 2/2008 | Hirst .................... C07D 487/04 514/262.1 |
| 2008/0132503 A1 | 6/2008 | Moradei et al. |
| 2009/0054508 A1 | 2/2009 | Kanda et al. |

FOREIGN PATENT DOCUMENTS

| EA | 201070618 | 12/2010 | |
| EP | 0416581 | 3/1991 | |
| EP | 1 847 532 | 10/2007 | |
| EP | 2 151 435 A1 | 2/2010 | |
| JP | 2000-256358 | * 9/2000 | ........... C07D 413/12 |
| JP | 3-169860 | 8/2011 | |
| JP | 2012-107001 | 6/2012 | |
| JP | 2012107001 A | * 6/2012 | ........... C07D 207/34 |
| JP | 2012-529518 | 11/2012 | |
| JP | 2013-503174 | 1/2013 | |
| RU | 2012152354 | 6/2014 | |
| WO | WO 1991/016324 | 10/1991 | |
| WO | WO 97/31910 A1 | 9/1997 | |
| WO | WO 01/96313 A1 | 12/2001 | |
| WO | WO 2001/096313 | 12/2001 | |
| WO | WO 03/006454 A2 | 1/2003 | |
| WO | WO 2003/006454 A2 | 1/2003 | |
| WO | WO 03/022806 A2 | 3/2003 | |
| WO | WO 2003/044018 A1 | 5/2003 | |
| WO | WO 2004/018461 A2 | 3/2004 | |
| WO | WO 2005/085177 A2 | 9/2005 | |
| WO | WO 2006/080450 A1 | 8/2006 | |
| WO | WO 2008/058037 | 5/2008 | |
| WO | WO 2008/124000 A2 | 10/2008 | |
| WO | WO 2009/085256 | 7/2009 | |
| WO | WO 2011/093672 A2 | 8/2011 | |

OTHER PUBLICATIONS

Database CAPLUS in STN, Acc. No. 1970:36890, Nekrasov et al., Izvestiya Akademii Nauk SSSR, Seriya Khimicheskaya (1969), 10, pp. 2181-2188 (abstract).*
Database CAPLUS in STN, Acc. No. 2000:658115, Kubota et al., JP 2000256358 A (dated Sep. 19, 2000) (abstract).*
CAS RN 928747-36-8, STN entry date Mar. 30, 2007, N-(2-benzoyl-4-chlorophenyl)-5-[nnethyl(methylsulfonyl)amino]-benzo[b]thiophene-2-carboxamide, 1 page.*
SciFinder CAS RN 928747-36-8 commerical source result obtained on May 25, 2018: Aurora Screening Library (Aurora Fine Chemicals, LLC).*
SciFinder CAS RN 1223767-12-1 commercial source result obtained on Nov. 2, 2018; ChemDiv Screening Collection (ChemDiv, Inc.).*
CAS SciFinder English language abstract of JP 2012107001 A (dated Jun. 78, 2012).*
International Search Report and Written Opinion for Application No. PCT/KR2014/004947 dated Sep. 30, 2014.

(Continued)

*Primary Examiner* — Brian J Davis
(74) *Attorney, Agent, or Firm* — Alston & Bird LLP

(57) ABSTRACT

A heterocyclic derivative represented by formula (I), or a pharmaceutically acceptable salt or a stereoisomer thereof, which has an inhibitory effect on the activation of STAT3 protein, and is useful for the prevention or treatment of diseases associated with the activation of STAT3 protein.

18 Claims, No Drawings

(56) References Cited

OTHER PUBLICATIONS

Akira, S. *Roles of STAT3 Defined by Tissue-Specific Gene Targeting*, Oncogene, 19 (2000) 2607-2611.
Becker, S. et al., *Three-dimensional structure of the Stat3β homodimer bound to DNA*, Nature, vol. 394 (1998)145-151.
Benekli, M. et al., *Constitutive Activity of Signal Transducer and Activator of Transcription 3 Protein in Acute Myeloid Leukemia Blasts is Associated With Short Disease-Free Survival*, Blood, 99 (2002) 252-257.
Roger, D. L. et al., *Parallel Synthesis and Evaluation of 132 (+)-1.2.9.9a-Tetrahydrocyclopropal[c]benz[e]indol-4-one (CBI) Analogues of CC-1065 and the Duocarmycins Defining the Contribution of the DNA-Binding Domain*, J. Org. Chem, vol. 66 (2001) 6654-6661.
Chen, X. et al.,*Crystal Structure of a Tyrosin Phosphorylated STAT-1 Dimer Bound to DNA*, Cell, vol. 93 (1998) 827-839.
Coleman, D. R. et al., *Investigation of the Binding Determnants of Phosphopeptides Targeted to the Src Homology 2 Domain of the Signal Transducer and Activator of Transcription 3. Development of a High-Affinity Peptide Inhibitor*, J. Med. Chem., 48 (2005) 6661-6670.
Eubanks, L. M. et al., *An in vitro and in vivo disconnect uncovered through high-throughput identification of botulinum neurotoxin A antagonists*, PANS, vol. 104, No. 8 (2007) 2602-2607.
Ho, A.S. et al., *A Receptor for Interleukin 10 is Related to Interferon Receptors*, Proc. Natl. Acad. Sci., vol. 90 (1993) 11267-11271.
Kishimoto, T. et al., *Cytokine Signal Transduction*, Cell, vol. 76 (1994) 253-262.
Levy, D. E. et al., *STATS: Transcriptional Control and Biological Impact*, Nat. Rev. Mol. Cell Biol., vol. 3 (2002) 651-662.
Lin, L. et al., *A Novel Small Molecule, LLL12, Inhibits STAT3 Phosphorylation and Activities and Exhibits Potent Growht-Suppressive Activity in Human Cancel Cells*, Neoplasia, vol. 12, No. 1 (2010) 39-50.
Masuda, M. et al., *Constitutive Activation of Signal Transducers and Activators of Transcription 3 Correlates With Cyclin D1 Overexpression and May Provide a Novel Prognostic Marker in Head and Neck Squamous Cell Carcinoma*, Cancer Res., 62 (2002) 3351-3355.
Matsuno, K. et al., *Identification of a New Series of STAT 3 Inhibitors by Virtual Screening*, ACS Med. Chem. Lett., 1 (2010) 371-375.
Neculai, D. et al., *Structure of the Unphosphorylated STAT5α Dimer*, J. Biol. Chem., vol. 280, No. 49 (2005) 40782-40787.
Novick, D. et al., *The Human Interferon α/β Receptor: Characterization and Molecular Cloning*, Cell, vol. 77 (1994) 391-400.
Pensa, S. et al., *STAT1 and STAT3 in Tumorigerzesis: Two Sides of the Same Coin*? Review, Landes Bioscience (2000) [online] [retrieved Jan. 15, 2016]. Reetrieved from the Internet: <URL:http://www.ncbi.nlm.nih.gov/books/NBK6568/?report=printable>. 23 pages.
Siddiquee, K. et al., *Selective Chemical Proble Inhibitor of Stat3, Identified Through Structure-Based Virtual Screening, Induces Antitumor Activity*, Proc. Natl. Acad. Sci, vol. 104, No. 18 (2007) 7391-7396.
Siddiquee, K. A. Z. et al., *An Oxazole-Based Small-Molecule Stat3 Inhibitor Modulates Stat3 Stability and Processing and Induces Antitumor Cell Effects*, ACS Chem. Biol., vol. 2, No. 12 (2007) 787-798.
Schindler, C. et al., *Transcriptional Responses to Polypeptide Ligands: The JAK-STAT Pathway*, Annu. Rev. Biochem., 64 (1995) 621-651.
Schust, J. et al., *Stattic: A Small-Molecule Ihibitor of STAT3 Activation and Dimerization*, Chemistry & Biology, 13 (2006) 1235-1242.
Song, H. et al., *A Low-Molecular-Weight Compound Discovered Through Virtual Database Screen Inhibits Stat3 Function in Breast Cancer Cells*, Proc. Natl. Acad. Sci, vol. 102, No. 13 (2005) 4700-4705.
Stark, G. R. et al., *How Cells Respond to Interferons*, Annu. Rev. Biochem., 67 (1998) 227-264.
Vinkemeier, U. et al., *Structure of the Amino-Terminal Protein Interaction Domain of STAT-4*, Science, vol. 279 (1998) 1048-152.
Yakata, Y. et al., *Expression of p-STAT3 in Human Gastric Carcinoma: Significant Correlation in Tumour Invasion and Prognosis*, Int. J. Oncology, 30 (2007) 437-442.
Zhang, X. et al., *A Novel Small-Molecule Disrupts Stat3 SH2 Domain-Phosphotyrosine Interactions and Stat3-Dependent Tumor Processes*, Biochem. Pharm., 79 (2010) 1398-1409.
Zhong, Z. et al., *Stat3: A STAT Family Member Activated by Tyrosin Phosphorylation in Response to Epidermal Growth Factor and Interleukin-6*, Science, vol. 264 (1994) 95-98.
Doebelin et al. *Trisubstitution of pyridine through sequential and regioselective palladium cross-coupling reactions affording analogs of known GPR54 antagonists*, RSC Publishing, vol. 3; 10296-10300 (2013).
European Search Report for corresponding European Application No. 14806807.5 dated Sep. 30, 2016, 6 pages.
Examination Report No. 1 for Standard Patent Application from corresponding Australian Patent Application No. 2014275643, dated Nov. 23, 2017, 13 pages.
CAS RN 1317311-56-0; STN entry date Aug. 14, 2011; N-[3-(1,3-dihydro-1,3-dioxo-2H-isoindol-2-yl)phenyl]-7-nitro-1H-indole-2-carboxamide, 3 pages.
CAS RN 1302594-97-3; STN Entry Date May 30, 2011; N-[3-(4-ethyl-1,6-dihydro-6-oxo-2-pyrimidinyl)phenyl]-5-nitro-benzo[b]thiophene-2-carboxamide, 3 pages.
CAS RN 1296796-53-6; STN Entry Date May 18, 2011; 5-nitro-N-[3-(5,6,7,8-tetrahydroimidazo[1,2-a]pyridin-2-yl)phenyl]-1H-indole-2-carboxamide, 3 pages.
CAS RN 1294598-35-8; STN Entry Date May 15, 2011; N-[3-(4-ethyl-1,6-dihydro-6-oxo-2-pyrimidinyl)phenyl]-5-nitro-1H-indole-2-carboxamide, 3 pages.
CAS RN 1316626-03-5; STN Entry Date Aug. 12, 2011; N-(3-benzoylphenyl)-7-nitro-1H-indole-2-carboxamide, 4 pages.
CAS RN 1302378-01-3; STN Entry Date May 29, 2011; N-[3-[(4-ethyl-1-piperazinyl)sulfonyl]phenyl]-5-1H-indole-2-carboxamide, 3 pages.
CAS RN 1295091-90-5; STN Entry Date May 15, 2011; 5-nitro-N-[3-(1-piperidinylsulfonyl)phenyl]-benzo[b]thiophene-2-carboxamide, 3 pages.
CAS RN 1293965-15-7; STN Entry Date May 12, 2011; 5-nitro-N-[3-(1-piperidinylcarbonyl)phenyl]-benzo[b]thiophene-2-carboxamide, 4 pages.
CAS RN 1290249-55-6; STN Entry Date May 5, 2011; N-[3-[(4-methyl-1-piperazinyl)methyl]phenyl]-5-nitro-benzo[b]thiophene-2-carboxamide, 4 pages.
CAS RN 1014427-50-9; STN Entry Date Apr. 14, 2008; N-[3-(4-molpholinylsulfonyl)phenyl]-5-benzo[b]thiophene-2-carboxamide, 3 pages.
CAS RN 1319319-98-6; STN Entry Date Aug. 18, 2011; N-[3-(1,3-dihydro-1,3-dioxo-2H-isoindol-2-yl)phenyl]-5-nitro-1H-indole-3-carboxamide, 3 pages.
CAS RN 1316565-33-9; STN Entry Date Aug. 12, 2011; 5-nitro-N-[3-(6,7,8,9-tetrahydro-5H-1,2,4-triazolo[4,3-a]azepin-3-yl)phenyl]-1H-indole-3-carboxamide, 3 pages.
CAS RN 1318547-27-1; STN Entry Date Aug. 16, 2011; N-(3-benzoylphenyl)-5-nitro-1H-indole-3-carboxamide, 4 pages.
CAS RN 1322404-68-1; STN Entry Date Aug. 24, 2011; 5-nitro-N-[3-(1-piperidinylsulfonyl)phenyl]-1H-indole-3-carboxamide, 3 pages.
Japanese Copyright No. 928747-36-8, dated Mar. 30, 2007.
Office Action for Russian Application No. 2015-153063, dated Mar. 26, 2018, 11 pages.
CAS RN 1223767-12-1; STN Entry Date May 16, 2010; 5-[ethy l(m ethy ls ulfony l)a m ino]-N-(4-p henoxy p heny l)-benz o[b]thiop hene-2-carboxamide Category: X Claims 1-5, 7 and 11.
CAS RN 122380 5-43-3; STN Entry Date May 16, 2010; 5-[(ethylsulfonyl)methylamino]-N-(4-phenoxypheny l)-benzo[b]thiophene-2-carboxamide Category: X Claims 1-5, 7 and 11.
CAS RN 1241181-35-0 ; STN Entry Date Sep. 15, 2010; N-n1-(3-pyridinylmethy l)-1H-pyrazol-3-yl]-6-(trifluoromethoxy )-1H-Indole-2-carboxamide Category: X Claims 1-5, 7 and 11.

(56) References Cited

OTHER PUBLICATIONS

CAS RN 928737-85-3; STN Entry Date Mar. 30, 2007; 5-[(methyl(methylsulfonyl)amino]-N-(4-phenoxyphenyl)-benzo[b]thiophene-2-carboxamide Category: X Claims 1-5, 7 and 11.
CAS RN 928747-36-8, STN entry date Mar. 30, 2007, N-(2-benzoyl-4-chlorophenyl)-5-[nnethyl(nnethylsulfonyl)annino]-benzo[b]thiophene-2-carboxamide, Category: X Claims 1-5, 7 and 11.
Office Action for Australian Application No. 2014275643 dated Apr. 30, 2018, 13 pages.

* cited by examiner

HETEROCYCLIC DERIVATIVES AND USE THEREOF

FIELD OF THE INVENTION

The present invention relates to novel heterocyclic compounds, uses thereof for the prevention or treatment of diseases associated with the activation of STAT proteins, particularly, STAT3 protein and pharmaceutical compositions comprising them.

BACKGROUND OF THE INVENTION

Signal transducer and activator of transcription (STAT) proteins are transcription factors which transduce signals from various extracellular cytokines and growth factors to a nucleus. Seven (7) subtypes of STAT proteins (i.e., STAT1, STAT2, STAT3, STAT4, STAT5a, STAT5b and STAT6) are currently known, and generally they consist of about 750-850 amino acids. In addition, each subtype of STAT proteins contains several conserved domains which play an important role in exhibiting the function of STAT proteins. Specifically, five (5) domains from N-terminus to C-terminus of STAT proteins have been reported including coiled-coiled domain, DNA binding domain, linker domain, SH2 domain and transactivation domain (TAD)). Further, X-ray crystalline structures of STAT1, STAT3, STAT4 and STAT5 have been reported since 1998 (Becker S et al., *Nature*, 1998, 394; Vinkemeier U et al., *Science*, 1998, 279; Chen X et al., *Cell*, 1998, 93; D. Neculai et al., *J. Biol. Chem.*, 2005, 280). In general, receptors to which cytokines and growth factors bind are categorized into Class I and Class II. IL-2, IL-3, IL-5, IL-6, IL-12, G-CSF, GM-CSF, LIF, thrombopoietin, etc., bind to Class I receptors, while INF-α, INF-γ, IL-10, etc., bind to Class II receptors (Schindler C et al., *Annu. Rev. Biochem.*, 1995, 64; Novick D et al., *Cell*, 1994, 77; Ho AS et al., *Proc. Natl. Acad. Sci.*, 1993, 90). Among them, the cytokine receptors involved in the activation of STAT proteins can be classified depending on their structural forms of extracellular domains into a gp-130 family, an IL-2 family, a growth factor family, an interferon family and a receptor tyrosine kinase family. Interleukin-6 family cytokines are representative multifunctional cytokines which mediate various physiological activities. When interleukin-6 cytokine binds to IL-6 receptor, it attracts gp-130 receptor to form an IL-6-gp-130 receptor complex. At the same time, JAK kinases (JAK1, JAK2, JAK3 and Tyk2) in the cytoplasm are recruited to a cytoplasmic region of gp130 to be phosphorylated and activated. Subsequently, latent cytoplasmic STAT proteins are attracted to a receptor, phosphorylated by JAK kinases and activated. Tyrosine-705 near the SH2 domain located in the C-terminus of STAT proteins is phosphorylated, and the activated tyrosine-705 of each STAT protein monomer binds to the SH2 domain of another monomer in a reciprocal manner, thereby forming a homo- or heterodimer. The dimers are translocalized into a nucleus and bind to a specific DNA binding promoter to promote the transcription. Through its transcription process, various proteins (Myc, Cyclin D1/D2, Bcl-xL, Mcl, survivin, VEGF, HIF-1, immune suppressors, etc.) associated with cell proliferation, survival, angiogenesis and immune evasion are produced (Stark et al., *Annu. Rev. Biochem.*, 1997, 67; Levy et al., *Nat. Rev. Mol. Cell Biol.*, 2002, 3).

In particular, STAT3 protein is known to play a crucial role in the acute inflammatory response and the signal transduction pathway of IL-6 and EGF (Akira et al., *Cell*, 1994, 76; Zhong et al., *Science*, 1994, 264). According to the recent clinical report, STAT3 protein is constantly activated in patients with solid cancers occurring in prostate, stomach, breast, lung, pancreas, kidney, uterine, ovary, head and neck, etc., and also in patients with blood cancer such as acute and chronic leukemia, multiple myeloma, etc. Further, it has been reported that the survival rate of a patient group with activated STAT3 is remarkably lower than that of a patient group with inactivated STAT3 (Masuda et al., *Cancer Res.*, 2002, 62; Benekli et al., *Blood*, 2002, 99; Yuichi et al., *Int. J. Oncology*, 2007, 30). Meanwhile, STAT3 was identified to be an essential factor for the growth and maintenance of murine embryonic stem cells in a study employing a STAT3 knockout mouse model. Also, a study with a tissue-specific STAT3-deficient mouse model, reveals that STAT3 plays an important role in cell growth, apoptosis, and cell motility in a tissue-specific manner (Akira et al., *Oncogene* 2000, 19). Moreover, since apoptosis by anti-sensing STAT3 was observed in various cancer cell lines, STAT3 is considered as a promising new anticancer target. STAT3 is also considered as a potential target in the treatment of patients with diabetes, immune-related diseases, hepatitis C, macular degeneration, human papillomavirus infection, non-Hodgkin's lymphoma, tuberculosis, etc. In contrast, although STAT1 has identical intracellular response pathways of cytokines and growth factors to those of STAT3, STAT1 increases inflammation and congenital and acquired immunities to inhibit the proliferation of cancer cells or cause pro-apoptotic responses, unlike STAT3 (Valeria Poli et al., *Review, Landes Bioscience*, 2009).

In order to develop STAT3 inhibitors, the following methods can be considered: i) inhibition of the phosphorylation of STAT3 protein by IL-6/gp-130/JAK kinase, ii) inhibition of the dimerization of activated STAT3 protein, and iii) inhibition of the binding of STAT3 dimer to nuclear DNA. Small molecular STAT3 inhibitors are currently under development. Specifically, OPB-31121 and OPB-51602 are under clinical studies on patients with solid cancers or blood cancers by Otsuka Pharmaceutical Co., Ltd. Further, S3I-201 (Siddiquee et al., *Proc. Natl. Acad. Sci.*, 2007, 104), S3I-M2001 (Siddiquee et al., *Chem. Biol.*, 2007, 2), LLL-12 (Lin et al., *Neoplasia*, 2010, 12), Stattic (Schust et al., *Chem. Biol.* 2006, 13), STA-21 (Song et al., *Proc. Natl. Acad. Sci.*, 2005, 102), SF-1-066 (Zhang et al., *Biochem. Pharm.*, 2010, 79) and STX-0119 (Matsuno et al., *ACS Med. Chem. Lett.*, 2010, 1), etc. have been tested in a cancer cell growth inhibition experiment and in animal model (in vivo Xenograft model). Furthermore, although peptide compounds mimicking the adjacent amino acid sequence of pY-705 (STAT3) which binds to SH2 domain or the amino acid sequence of gp-130 receptor that JAK kinases bind were studied (Coleman et al., *J. Med. Chem.*, 2005, 48), the development of the peptide compounds has not been successful due to the problems such as solubility and membrane permeability.

SUMMARY OF THE INVENTION

Accordingly, it is an object of the present invention to provide novel heterocyclic derivatives for the inhibition of the activation of STAT3 protein.

It is another object of the present invention to provide uses of the heterocyclic derivatives for the prevention or treatment of diseases associated with the activation of STAT3 protein.

In accordance with one aspect of the present invention, there is provided a compound selected from the group consisting of a heterocyclic derivative represented by formula (I), and a pharmaceutically acceptable salt and a stereoisomer thereof:

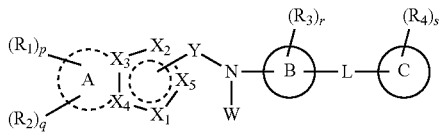
(I)

wherein

A is present or absent, and, if present, A is a saturated or unsaturated $C_{3-10}$ carbocycle or a 5- to 10-membered heterocycle, and if A is absent, $X_3$ and $X_4$ are each independently optionally substituted with $R_1$ or $R_2$;

B is a benzene or a 5- to 12-membered heterocycle;

C is a benzene, a 5- to 12-membered heterocycle, or $C_{3-6}$ carbocycle;

Y is —C(=O)— connected to $X_2$ or $X_5$;

$X_1$ is —O—, —S—, —S(=O)—, —S(=O)$_2$—, or —N($W_1$)—;

$X_2$ is a carbon atom connected to Y, or —N=, —NH—, —C($W_2$)= or —CH($W_2$)— not connected to Y;

$X_3$ and $X_4$ are each independently a carbon or nitrogen atom;

$X_5$ is a carbon atom connected to Y, or —CH= not connected to Y;

wherein the 5-membered ring comprising $X_1$ to $X_5$ is aromatic or non-aromatic;

W is hydrogen, halogen, $C_{1-6}$ alkyl, or 5- or 6-membered heterocyclyl-$C_{1-3}$ alkyl;

$W_1$ is hydrogen, $C_{1-6}$ alkyl, $C_{1-6}$ alkoxycarbonyl, or 5- to 8-membered heterocyclyl-$C_{1-4}$ alkyl;

$W_2$ is hydrogen, halogen, $C_{1-6}$ alkyl, or 5- to 8-membered heterocyclyl-$C_{1-4}$ alkyl;

L is —(CR$_9$R$_{10}$)$_m$—, —(CR$_9$R$_{10}$)$_m$—O—, —NH—, —N($C_{1-6}$ alkyl)-, —S(=O)$_2$—, —C(=O)—, —C(=CH$_2$)—, or $C_{3-7}$ cycloalkylene, wherein m is an integer of 0 to 3, and $R_9$ and $R_{10}$ are each independently hydrogen, hydroxy, halogen, or $C_{1-6}$ alkyl;

$R_1$ is nitro, amino, $C_{1-6}$ alkylsulfonyl, halo$C_{1-6}$ alkoxy, or any one of the following structural formulae i) to iv):

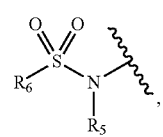
i)

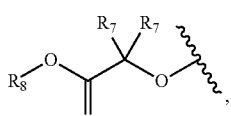
ii)

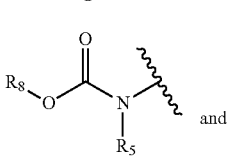
iii)
and

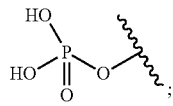
iv)

$R_2$ is hydrogen, halogen, nitro, amino, $C_{1-6}$alkoxy, halo$C_{1-6}$alkoxy, $C_{1-6}$ alkylsulfonyl, or 5- or 6-membered heterocycloalkyl;

$R_3$ is hydrogen, halogen, cyano, $C_{1-6}$ alkyl, halo$C_{1-6}$ alkyl, cyano$C_{1-6}$ alkyl, $C_{1-6}$ alkylcarbonyl, $C_{1-6}$ alkoxy, halo$C_{1-6}$ alkoxy, cyano$C_{1-6}$ alkoxy, $C_{1-6}$ alkylamino, di$C_{1-6}$ alkylamino, $C_{1-6}$ alkylthio, $C_{1-6}$ alkylaminocarbonyl, di$C_{1-6}$ alkylaminocarbonyl, $C_{2-8}$ alkynyl, $C_{6-10}$ aryl, halo$C_{6-10}$ aryl, 5- to 10-membered heterocyclyl, or 5- to 10-membered heterocyclylcarbonyl, wherein the heterocyclyl moiety is optionally substituted with one to three substituents selected from the group consisting of halogen, hydroxy, cyano, amino, $C_{1-6}$ alkyl, halo$C_{1-6}$ alkyl, $C_{1-6}$ alkoxy and $C_{1-6}$ alkoxycarbonyl;

$R_4$ is hydrogen, halogen, hydroxy, cyano, nitro, amino, oxo, aminosulfonyl, sulfonylamido, $C_{1-6}$ alkylamino, $C_{1-6}$ alkyl, halo$C_{1-6}$ alkyl, cyano$C_{1-6}$ alkyl, $C_{1-6}$ alkoxy, halo$C_{1-6}$ alkoxy, cyano$C_{1-6}$ alkoxy, $C_{3-8}$ cycloalkyl-oxy, $C_{2-8}$ alkynyl, $C_{1-6}$ alkylamino-$C_{1-6}$ alkoxy, di$C_{1-6}$ alkylamino-$C_{1-6}$ alkoxy, $C_{1-6}$ alkoxy-carbonyl, carbamoyl, carbamoyl-$C_{1-6}$ alkoxy, $C_{1-6}$ alkylthio, $C_{1-6}$ alkylsulfinyl, $C_{1-6}$ alkylsulfonyl, 5- to 10-membered heterocyclyl, 5- to 10-membered heterocyclyl-$C_{1-6}$ alkyl, 5- to 10-membered heterocyclyl-$C_{1-6}$ alkoxy, or 5- to 10-membered heterocyclyl-oxy, wherein the heterocyclyl moiety is optionally substituted with one or two substituents selected from the group consisting of hydroxy, oxo, $C_{1-6}$ alkyl, $C_{1-6}$ alkylcarbonyl, $C_{1-6}$ alkoxycarbonyl, $C_{1-6}$ alkylsulfonyl, di$C_{1-3}$ alkylsulfonyl, $C_{1-6}$ alkylcarbonyl, $C_{1-6}$ alkylaminocarbonyl, di$C_{1-3}$ alkylaminocarbonyl, $C_{1-6}$ alkylaminosulfonyl, and non-substituted or $C_{1-6}$ alkyl-substituted 5- to 10-membered heterocyclyl;

$R_5$ is hydrogen, $C_{1-6}$ alkyl, carbamoyl$C_{1-6}$ alkyl, $C_{1-6}$ alkylamino$C_{1-6}$ alkyl, di$C_{1-6}$ alkylamino$C_{1-6}$ alkyl, or 5- to 10-membered heterocyclyl$C_{1-6}$ alkyl, or is fused with $R_6$ to form $C_{3-4}$ alkylene;

$R_6$ is $C_{1-6}$ alkyl, halo$C_{1-6}$ alkyl, $C_{1-6}$ alkoxy$C_{1-6}$ alkyl, $C_{1-6}$ alkylcarbonyl$C_{1-6}$ alkyl, $C_{2-7}$ alkenyl, amino, amino$C_{1-6}$ alkyl, $C_{3-7}$ cycloalkyl, 5- to 10-membered heterocyclyl, or 5- to 10-membered heterocyclyl-$C_{1-6}$ alkyl, or is fused with $R_5$ to form $C_{3-4}$ alkylene, wherein the amino moiety is optionally substituted with one or two substituents selected from hydroxy or $C_{1-6}$ alkyl, and the heterocyclyl moiety is optionally substituted with one to four substituents selected from the group consisting of oxo, $C_{1-6}$ alkyl and $C_{1-6}$ alkylcarbonyl;

$R_7$ and $R_8$ are each independently hydrogen or $C_{1-6}$ alkyl;

p and q are each independently 0 or 1;

r is an integer of 0 to 3, and, when r is 2 or higher, $R_3$ moieties are the same or different; and s is an integer of 0 to 3, and, when s is 2 or higher, $R_4$ moieties are the same or different;

all of said heterocycle or heterocyclyl moieties each independently have a saturated or unsaturated single or multiple ring and contain one to three heteroatoms selected from N, O or S; and all of said aryl moieties each independently have an aromatic single or multiple ring.

In accordance with another aspect of the present invention, there is provided a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

In accordance with a further aspect of the present invention, there is provided a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

In accordance with a still further aspect of the present invention, there is provided a method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

The heterocyclic derivative represented by formula (I) above, or a pharmaceutically acceptable salt or a stereoisomer thereof has an excellent inhibitory effect on the activation of STAT3 protein, and thus it can be used for the prevention or treatment of diseases associated with the activation of STAT3 protein.

DETAILED DESCRIPTION OF THE INVENTION

The present invention will be further described in detail herein below.

In the specification of the present invention, the term "halogen" refers to fluorine, chlorine, bromine or iodine, unless specified otherwise.

The term "alkyl" refers to a linear or branched hydrocarbon residue, unless specified otherwise.

The terms "haloalkyl", "haloalkoxy", "halophenyl", etc., respectively refer to alkyl, alkoxy, and phenyl substituted with at least one halogen.

The term "carbocycle" refers to an aromatic or non-aromatic hydrocarbon ring, which may be saturated or unsaturated, and a monocyclic or polycyclic radical.

The term "carbocyclyl" refers to a radical of "carbocycle", and is used as a term inclusive of "cycloalkyl" and "aryl".

The term "cycloalkyl" refers to a saturated hydrocarbon radical, which may be monocyclic or polycyclic.

The term "aryl" refers to an aromatic hydrocarbon ring, which may be monocyclic or polycyclic.

The terms "carbocycle", "carbocyclyl", "cycloalkyl" and "aryl" may refer to, for example, a mono- or polycycle having 3 to 20 carbon atoms, and will be indicated as "$C_{3-20}$ carbocycle", "$C_{3-20}$ carbocyclyl", "$C_{3-20}$ cycloalkyl", and "$C_{3-20}$ aryl", respectively.

The term "heterocycle" refers to an aromatic or non-aromatic ring having at least one heteroatom, which may be saturated or unsaturated, and a monocycle or polycycle.

The term "heterocyclyl". refers to a radical of "heterocycle", which is used as a term inclusive of "heterocycloalkyl" and "heteroaryl".

The term "heterocycloalkyl" refers to a saturated ring radical having at least one heteroatom, which may be monocyclic or polycyclic.

The term "heteroaryl" refers to an aromatic ring radical having at least one heteroatom, which may be monocyclic or polycyclic.

The term "heteroatom" may be selected from N, O and S.

The terms "heterocycle", "heterocyclyl", "heterocycloalkyl" and "heteroaryl" may refer to, for example, a mono- or polycycle having 3 to 20 heteroatoms and/or carbon atoms, and will be indicated as "3- to 20-membered heterocycle", "3- to 20-membered heterocyclyl", "3- to 20-membered heterocycloalkyl", and "3- to 20-membered heteroaryl".

According to an embodiment of the compound of formula (I), the substituents may be defined as follows (definition I):

A is a saturated or unsaturated $C_{3-10}$ carbocycle, or a 5- to 10-membered heterocycle containing one to three heteroatoms selected from N, O or S;

B is benzene or a 5- to 12-membered heterocycle containing one to three N atoms;

C is benzene, or a 5- to 12-membered heterocycle containing one to three heteroatoms selected from N, O or S;

Y is —C(=O)— connected to $X_5$;

$X_1$ is —O—, —S—, —S(=O)—, —S(=O)$_2$—, or —N($W_1$)—;

$X_2$ is —N=, —C($W_2$)= or —CH($W_2$)— not connected to Y;

$X_3$ and $X_4$ are a carbon atom;

$X_5$ is a carbon atom connected to Y;

wherein the 5-membered ring comprising $X_1$ to $X_5$ is aromatic or non-aromatic;

W is hydrogen, halogen, or $C_{1-6}$ alkyl;

$W_1$ is hydrogen, $C_{1-6}$ alkyl, $C_{1-6}$ alkoxycarbonyl, or 5- to 8-membered heterocycloalkyl-$C_{1-4}$ alkyl containing one or two heteroatoms selected from N or O;

$W_2$ is hydrogen, $C_{1-6}$ alkyl, or 5- to 8-membered heterocycloalkyl-$C_{1-4}$ alkyl containing one or two heteroatoms selected from N or O;

L is —(CR$_9$R$_{10}$)$_m$—, —(CR$_9$R$_{10}$)$_m$—O—, —NH—, —N($C_{1-6}$ alkyl)-, —S(=O)$_2$—, —C(=O)—, —C(=CH$_2$)—, or $C_{3-7}$ cycloalkylene, wherein m is an integer of 0 to 3, and R$_9$ and R$_{10}$ are each independently hydrogen, hydroxy, halogen, or $C_{1-6}$ alkyl;

R$_1$ is nitro, amino, $C_{1-6}$ alkylsulfonyl, halo$C_{1-6}$ alkoxy, or any one of the following structural formulae i) to iv):

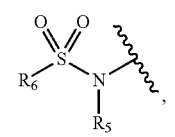

i)

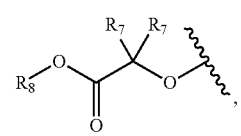

ii)

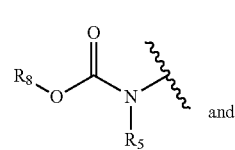

iii)

and

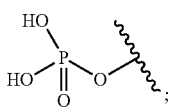

iv)

;

R$_2$ is hydrogen, halogen, $C_{1-6}$ alkoxy, halo$C_{1-6}$ alkoxy, or $C_{1-6}$ alkylsulfonyl;

$R_3$ is hydrogen, halogen, cyano, $C_{1-6}$ alkyl, halo$C_{1-6}$ alkyl, cyano$C_{1-6}$ alkyl, $C_{1-6}$ alkylcarbonyl, $C_{1-6}$ alkoxy, halo$C_{1-6}$ alkoxy, cyano$C_{1-6}$ alkoxy, $C_{1-6}$ alkylamino, di$C_{1-6}$ alkylamino, $C_{1-6}$ alkylthio, $C_{1-6}$ alkylaminocarbonyl, di$C_{1-6}$ alkylaminocarbonyl, $C_{2-8}$ alkynyl, $C_{6-10}$ aryl, 5- to 10-membered heteroaryl containing one or two heteroatoms selected from N or S, 5- to 10-membered heterocycloalkyl containing one or two heteroatoms selected from N or O, or 5- to 10-membered heterocycloalkyl-carbonyl containing one or two heteroatoms selected from N or O;

$R_4$ is hydrogen, halogen, hydroxy, cyano, nitro, amino, oxo, aminosulfonyl, sulfonylamido, $C_{1-6}$ alkylamino, $C_{1-6}$ alkyl, halo$C_{1-6}$ alkyl, cyano$C_{1-6}$ alkyl, $C_{1-6}$ alkoxy, halo$C_{1-6}$ alkoxy, cyano$C_{1-6}$ alkoxy, $C_{3-8}$ cycloalkyl-oxy, $C_{2-8}$alkynyl, $C_{1-6}$ alkylamino-$C_{1-6}$ alkoxy, $C_{1-6}$ alkoxycarbonyl, carbamoyl, carbamoyl-$C_{1-6}$ alkoxy, $C_{1-6}$ alkylthio, $C_{1-6}$ alkylsulfonyl, 5- to 10-membered heterocyclyl-$C_{1-6}$ alkyl containing one or two heteroatoms selected from N or O, 5- to 10-membered heterocyclyl-$C_{1-6}$ alkoxy containing one or two heteroatoms selected from N or O, or 5- to 10-membered heterocyclyl-oxy containing one or two heteroatoms selected from N or O, wherein the heterocyclyl moiety is optionally substituted with one or two substituents selected from the group consisting of hydroxy, $C_{1-6}$ alkoxycarbonyl, $C_{1-6}$ alkylsulfonyl, $C_{1-6}$ alkylcarbonyl, $C_{1-6}$ alkylaminocarbonyl, $C_{1-6}$ alkylaminosulfonyl, and non-substituted or $C_{1-6}$ alkyl-substituted 5- to 10-membered heterocyclyl containing one or two heteroatoms selected from N, O or S;

$R_5$ is hydrogen, $C_{1-6}$ alkyl, carbamoyl$C_{1-6}$ alkyl, $C_{1-6}$ alkylamino-$C_{1-6}$ alkyl, or 5- to 10-membered heterocycloalkyl-$C_{1-6}$ alkyl containing one to three heteroatoms selected from N, O or S;

$R_6$ is $C_{1-6}$ alkyl, halo$C_{1-6}$ alkyl, $C_{1-6}$ alkoxy$C_{1-6}$ alkyl, $C_{1-6}$ alkylcarbonyl$C_{1-6}$ alkyl, $C_{2-7}$ alkenyl, amino, amino$C_{1-6}$ alkyl, $C_{3-7}$ cycloalkyl, 5- to 10-membered heterocyclyl containing one to three heteroatoms selected from N, O or S, or 5- to 10-membered heterocyclyl$C_{1-6}$ alkyl containing one to three heteroatoms selected from N, O or S, wherein the amino moiety is optionally substituted with one or two substituents selected from hydroxy or $C_{1-6}$ alkyl, and the heterocyclyl moiety is optionally substituted with one to four substituents selected from the group consisting of $C_{1-6}$ alkyl and $C_{1-6}$ alkylcarbonyl;

$R_7$ and $R_8$ are each independently hydrogen or $C_{1-6}$ alkyl;

p is 1, and q is 0 or 1;

r is an integer of 0 to 3, and, when r is 2 or higher, $R_3$ moieties are the same or different; and s is an integer of 0 to 3, and, when s is 2 or higher, $R_4$ moieties are the same or different;

all of said heterocycle or heterocyclyl moieties each independently have a saturated or unsaturated single or multiple ring;

all of said heterocycloalkyl moieties each independently have a saturated single or multiple ring; and all of said aryl or heteroaryl moieties each independently have an aromatic single or multiple ring.

In the definition I, some of the substituents may be defined more specifically as follows (definition Ia):

A is a saturated or unsaturated $C_6$ carbocycle, or 6-membered heterocycle containing one to three N atoms, B is benzene, or a 5- to 10-membered heterocycle containing one to three N atoms, C is benzene, or a 5- to 12-membered heteroaryl containing one to three heteroatoms selected from N, O or S, L is $-(CR_9R_{10})_m-$, $-O-$, $-NH-$, $-N(C_{1-6}$ alkyl$)-$, $-S(=O)_2-$, $-C(=O)-$, $-C(=CH_2)-$, or $C_{3-7}$ cycloalkylene, wherein m is an integer of 0 to 3, and $R_9$ and $R_{10}$ are each independently hydrogen, hydroxy, halogen or $C_{1-6}$ alkyl; and $R_1$ is nitro, amino, or any one of the following structural formulae i) to iv):

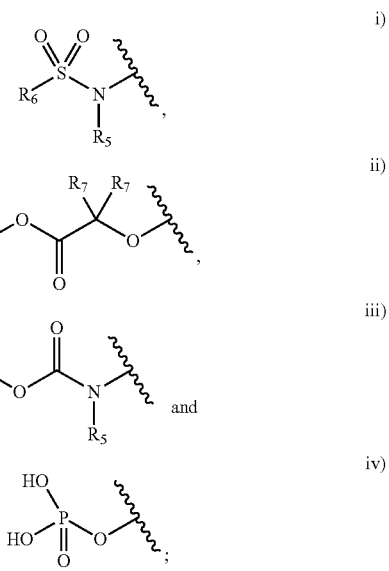

wherein $R_5$ to $R_8$ are the same as defined in definition I above;

all of said heterocycle moieties each independently have a saturated or unsaturated single or multiple ring; and said heteroaryl moiety has an aromatic single or multiple ring.

In the definition I, some of the substituents may be defined more specifically as follows (definition Ib):

A is saturated or unsaturated $C_{3-10}$ carbocycle, or 5- to 10-membered heterocycle containing one to three heteroatoms selected from N, O or S;

B is benzene or a 9- to 12-membered heterocycle containing one to three N atoms;

C is benzene, or a 5- to 10-membered heterocycle containing one to three heteroatoms selected from N, O or S;

$R_3$ is hydrogen, halogen, cyano, $C_{1-6}$ alkyl, halo$C_{1-6}$ alkyl, cyano$C_{1-6}$ alkyl, $C_{1-6}$ alkoxy, halo$C_{1-6}$ alkoxy, cyano$C_{1-6}$ alkoxy, $C_{1-6}$ alkylamino, di$C_{1-6}$ alkylamino, $C_{1-6}$ alkylaminocarbonyl, di$C_{1-6}$ alkylaminocarbonyl, $C_{2-8}$ alkynyl, 5- to 10-membered heterocyclyl containing one to three heteroatoms selected from N, O or S, or 5- to 10-membered heterocycloalkyl-carbonyl containing one or two heteroatoms selected from N or O, wherein the heterocyclyl moiety is optionally substituted with one to three substituents selected from the group consisting of halogen, hydroxy, cyano, amino, $C_{1-6}$ alkyl, halo$C_{1-6}$ alkyl, $C_{1-6}$ alkoxy, and $C_{1-6}$ alkoxycarbonyl; and r is 0 or 1;

all of said heterocycle moieties and heterocyclyl moieties each independently have a saturated or unsaturated single or multiple ring; and said heterocycloalkyl moiety has a saturated single or multiple ring.

In the definition Ib, some of the substituents may be defined more specifically as the following (i) or (ii):

(i) A is a saturated or unsaturated $C_6$ carbocycle, or a 6-membered heterocycle containing one to three N atoms.

(ii) B is

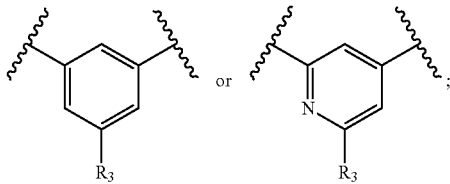

and R₃ is the same as defined in definition Ib.

According to another embodiment of the compound of formula (I), the substituents may be defined as follows (definition II):

A is present or absent, and, if present, A is benzene or 6-membered heterocycle containing one to three N atoms, and if A is absent, $X_3$ and $X_4$ are each independently optionally substituted with $R_1$ or $R_2$;

B is benzene, or a 6- to 10-membered heterocycle containing one to three N atoms;

C is benzene, a 6- to 10-membered heterocycle containing one to three heteroatoms selected from N, O or S, or $C_{5-6}$ carbocycle;

Y is —C(=O)— connected to $X_2$ or $X_5$;

$X_1$ is —O—, —S—, —S(=O)—, —S(=O)$_2$—, or —N(W$_1$)—;

$X_2$ is a carbon atom connected to Y, or —NH—, —C(W$_2$)= or —CH(W$_2$)— not connected to Y;

$X_3$ and $X_4$ are each independently a carbon or nitrogen atom; $X_5$ is a carbon atom connected to Y, or —CH= not connected to Y;

wherein the 5-membered ring comprising of $X_1$ to $X_5$ is aromatic or non-aromatic;

W is hydrogen, $C_{1-3}$ alkyl, or 5- or 6-membered heterocycloalkyl-$C_{1-3}$ alkyl containing one or two heteroatoms selected from N or O;

$W_1$ is hydrogen, $C_{1-3}$ alkyl, t-butoxycarbonyl, or 5- or 6-membered heterocycloalkyl-$C_{1-3}$ alkyl containing one or two heteroatoms selected from N or O;

$W_2$ is hydrogen, halogen, or $C_{1-3}$ alkyl;

L is —(CR$_9$R$_{10}$)$_m$—, —O—, —S(=O)$_2$—, $C_{3-6}$ cycloalkylene, —NH—, —N(C$_{1-3}$ alkyl)-, —C(=CH$_2$)—, or —C(=O)—, wherein m is 0 or 1, and R$_9$ and R$_{10}$ are each independently hydrogen, halogen, hydroxy or $C_{1-3}$ alkyl;

$R_1$ is any one of the following structural formulae i) to iv):

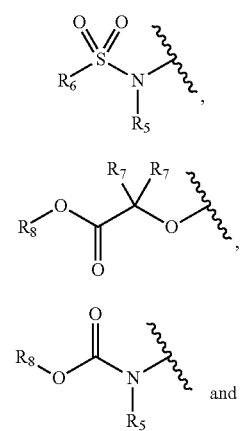

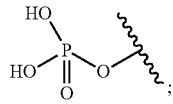

$R_2$ is hydrogen, halogen, nitro, amino, $C_{1-3}$ alkoxy, haloC$_{1-3}$ alkoxy, $C_{1-3}$ alkylsulfonyl, or 5- or 6-membered heterocycloalkyl containing one or two heteroatoms selected from N or O;

$R_3$ is hydrogen, halogen, $C_{1-3}$ alkylcarbonyl, cyano, cyanoC$_{1-3}$ alkyl, $C_{1-3}$ alkyl, haloC$_{1-3}$ alkyl, $C_{2-3}$ alkynyl, haloC$_{1-3}$ alkoxy, cyanoC$_{1-3}$ alkoxy, $C_{1-6}$ alkoxy, $C_{1-3}$ alkylamino, diC$_{1-3}$ alkylamino, $C_{1-3}$ alkylaminocarbonyl, diC$_{1-3}$ alkylaminocarbonyl, phenyl, halophenyl, 5- or 6-membered heterocyclyl, or 5- or 6-membered heterocyclyl-carbonyl, wherein the heterocyclyl moiety contains one to three heteroatoms selected from N, O or S, and is optionally substituted with one to three substituents selected from the group consisting of halogen, hydroxy, cyano, amino, $C_{1-3}$ alkyl, haloC$_{1-3}$ alkyl, $C_{1-3}$ alkoxy, and t-butoxycarbonyl;

$R_4$ is hydrogen, oxo, hydroxy, nitro, cyano, halogen, aminosulfonyl, amino, $C_{1-3}$ alkylamino, diC$_{1-3}$ alkylamino-$C_{1-3}$ alkoxy, $C_{1-3}$ alkylthio, $C_{1-3}$ alkylsulfinyl, $C_{1-3}$ alkylsulfonyl, $C_{1-3}$ alkyl, cyanoC$_{1-3}$ alkyl, $C_{2-4}$ alkynyl, $C_{1-3}$ alkoxy, cyanoC$_{1-3}$ alkoxy, haloC$_{1-3}$ alkoxy, carbamoyl-C$_{1-3}$ alkoxy, $C_{3-6}$ cycloalkyl-oxy, 4- to 10-membered heterocyclyl, 4- to 10-membered heterocyclyl-oxy, or 4- to 10-membered heterocyclyl-$C_{1-3}$ alkyl, wherein the heterocyclyl moiety contains one to three heteroatoms selected from N, O or S, and is optionally substituted with one or two substituents selected from the group consisting of hydroxy, oxo, $C_{1-3}$ alkyl, t-butylcarbonyl, t-butoxycarbonyl, $C_{1-3}$ alkylsulfonyl, diC$_{1-3}$ alkylsulfonyl, diC$_{1-3}$ alkylaminocarbonyl, 4- to 6-membered heterocyclyl and $C_{1-6}$ alkyl-substituted 4- to 6-membered heterocyclyl;

$R_5$ is hydrogen, $C_{1-3}$ alkyl, carbamoylC$_{1-3}$ alkyl, diC$_{1-3}$ alkylamino-C$_{1-3}$ alkyl, or morpholino-C$_{1-3}$ alkyl, or is fused with $R_6$ to form $C_{3-4}$ alkylene;

$R_6$ is $C_{1-3}$ alkyl, haloC$_{1-3}$ alkyl, $C_{1-3}$ alkoxyC$_{1-3}$ alkyl, $C_{2-3}$ alkenyl, amino, aminoC$_{1-3}$ alkyl, $C_{3-6}$ cycloalkyl, 5- or 6-membered heterocyclyl, or 5- or 6-membered heterocyclyl-C$_{1-3}$ alkyl, or is fused with $R_5$ to form $C_{3-4}$ alkylene, wherein the heterocyclyl moiety contains one to three heteroatoms selected from N, O or S, and is optionally substituted with one to four substituents selected from the group consisting of hydrogen, oxo, $C_{1-3}$ alkyl and acetyl, and the amino moiety is unsubstituted or substituted with one or two substituents selected from hydroxy or $C_{1-3}$ alkyl;

$R_7$ is hydrogen or $C_{1-3}$ alkyl;

$R_8$ is hydrogen or $C_{1-6}$ alkyl;

p and q are each independently 0 or 1;

r is 0 or 1; and s is an integer of 0 to 3, and, when s is 2 or higher, $R_4$ moieties are the same or different;

all of said heterocycle and heterocyclyl moieties each independently have a saturated or unsaturated single or double ring.

In the definition II, some of the substituents may be defined more specifically as the following (i), (ii), (iii) or (iv):

(i) B is

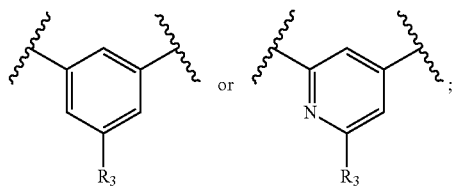

and R$_3$ is the same as defined in definition II.

(ii) m is 1; and R$_9$ and R$_{10}$ are each independently halogen, hydroxy, or C$_{1-3}$ alkyl.

(iii) m is 0; and R$_3$ is hydrogen, phenyl, halophenyl, saturated or unsaturated 5- or 6-membered heterocyclyl or 5- to 6-membered heterocyclyl-carbonyl wherein the heterocyclyl moiety contains one to three heteroatoms selected from N, O or S, and is optionally substituted with one to three substituents selected from the group consisting of halogen, hydroxy, cyano, amino, C$_{1-3}$ alkyl, haloC$_{1-3}$ alkyl, C$_{1-3}$ alkoxy, and t-butoxycarbonyl.

(iv) X$_1$ is —S— or —NH—; X$_2$ is —CH= not connected to Y; X$_3$ and X$_4$ are a carbon atom; and R$_1$ is the structural formula i).

Preferable examples of the compound according to the present invention are listed below, and a pharmaceutically acceptable salt and a stereoisomer thereof are also included in the scope of the present invention:

1) N-(3-(2-(4-fluorophenyl)propan-2-yl)phenyl)-6-(methylsulfonamido)-1H-indole-2-carboxamide;
2) 6-(methylsulfonamido)-N-(3-(2-phenylpropan-2-yl)phenyl)-1H-indole-2-carboxamide;
3) N-(3-(2-(4-fluorophenyl)propan-2-yl)phenyl)-5-methoxy-6-(methylsulfonamido)-1H-indole-2-carboxamide;
4) N-(3-methoxy-5-(2-(3-(trifluoromethoxy)phenyl)propan-2-yl)phenyl)-6-(methylsulfonamido)-1H-indole-2-carboxamide;
5) N-(3-(2-(4-fluorophenyl)propan-2-yl)phenyl)-6-((N-methylsulfamoyl)amino)-1H-indole-2-carboxamide;
6) N-(3-(2-(4-fluorophenyl)propan-2-yl)phenyl)-6-(methylsulfonyl)-1H-indole-2-carboxamide;
7) N-(3-(2-(2-fluorophenyl)propan-2-yl)phenyl)-6-(methylsulfonamido)-1H-indole-2-carboxamide;
8) 6-(methylsulfonamido)-N-(3-(2-(3-(trifluoromethoxy)phenyl)propan-2-yl)phenyl)-1H-indole-2-carboxamide;
9) N-(3-(2-(3-methoxy-5-(trifluoromethoxy)phenyl)propan-2-yl)phenyl)-6-(methylsulfonamido)-1H-indole-2-carboxamide;
10) N-(3-(1-(3-methoxy-5-(trifluoromethoxy)phenyl)ethyl)phenyl)-6-(methylsulfonamido)-1H-indole-2-carboxamide;
11) N-(3-(2-(2,4-difluorophenyl)propan-2-yl)phenyl)-6-(methylsulfonamido)-1H-indole-2-carboxamide;
12) N-(3-(2-(3-methoxyphenyl)propan-2-yl)phenyl)-6-(methylsulfonamido)-1H-indole-2-carboxamide;
13) N-(3-methoxy-5-(2-(3-methoxy-5-(trifluoromethoxy)phenyl)propan-2-yl)phenyl)-6-(methylsulfonamido)-1H-indole-2-carboxamide;
14) N-(3-bromo-5-(2-(4-fluorophenyl)propan-2-yl)phenyl)-6-(methylsulfonamido)-1H-indole-2-carboxamide;
15) N-(3-bromo-5-(2-(2,4-difluorophenyl)propan-2-yl)phenyl)-6-(methylsulfonamido)-1H-indole-2-carboxamide;
16) N-(3-bromo-5-(2-(3-methoxy-5-(trifluoromethoxy)phenyl)propan-2-yl)phenyl)-6-(methylsulfonamido)-1H-indole-2-carboxamide;
17) N-(3-(difluoromethoxy)-5-(2-(4-fluorophenyl)propan-2-yl)phenyl)-6-(methylsulfonamido)-1H-indole-2-carboxamide;
18) N-(3-(2-(3-(2-amino-2-oxoethoxy)phenyl)propan-2-yl)-5-bromophenyl)-6-(methylsulfonamido)-1H-indole-2-carboxamide;
19) N-(3-bromo-5-(2-(4-fluorophenyl)propan-2-yl)phenyl)-5-methoxy-6-(methylsulfonamido)-1H-indole-2-carboxamide;
20) N-(3-bromo-5-(2-(3-(difluoromethoxy)phenyl)propan-2-yl)phenyl)-6-(methylsulfonamido)-1H-indole-2-carboxamide;
21) N-(3-chloro-5-(2-(4-fluorophenyl)propan-2-yl)phenyl)-6-(methylsulfonamido)-1H-indole-2-carboxamide;
22) N-(3-bromo-5-(2-(3-ethoxy-5-(trifluoromethoxy)phenyl)propan-2-yl)phenyl)-6-(methylsulfonamido)-1H-indole-2-carboxamide;
23) N-(3-bromo-5-(2-(2-fluoro-5-(trifluoromethoxy)phenyl)propan-2-yl)phenyl)-6-(methylsulfonamido)-1H-indole-2-carboxamide;
24) N-(3-chloro-5-(2-(3-methoxy-5-(trifluoromethoxy)phenyl)propan-2-yl)phenyl)-6-(methylsulfonamido)-1H-indole-2-carboxamide;
25) N-(3-(2-(4-fluorophenyl)propan-2-yl)phenyl)-5-(trifluoromethoxy)-1H-indole-2-carboxamide;
26) N-(3-(2-(4-fluorophenyl)propan-2-yl)phenyl)-5-(methylsulfonamido)benzo[b]thiophene-2-carboxamide;
27) N-(3-(2-(2,4-difluorophenyl)propan-2-yl)phenyl)-5-(methylsulfonamido)benzo[b]thiophene-2-carboxamide;
28) N-(3-(2-(4-fluorophenyl)propan-2-yl)phenyl)-5-(methylsulfonamido)benzofuran-2-carboxamide;
29) N-(3-(2-(2,4-difluorophenyl)propan-2-yl)phenyl)-5-(methylsulfonamido)benzofuran-2-carboxamide;
30) N-(3-(2-(4-fluorophenyl)propan-2-yl)phenyl)-6-(methylsulfonamido)benzo[b]thiophene-2-carboxamide;
31) N-(3-(2-(2-fluorophenyl)propan-2-yl)phenyl)-5-(methylsulfonamido)benzo[b]thiophene-2-carboxamide;
32) N-(3-bromo-5-(2-(4-fluorophenyl)propan-2-yl)phenyl)-5-(methylsulfonamido)benzo[b]thiophene-2-carboxamide;
33) N-(3-(2-(3-methoxy-5-(trifluoromethoxy)phenyl)propan-2-yl)phenyl)-5-(methylsulfonamido)benzo[b]thiophene-2-carboxamide;
34) N-(3-methoxy-5-(2-(3-methoxy-5-(trifluoromethoxy)phenyl)propan-2-yl)phenyl)-5-(methylsulfonamido)benzo[b]thiophene-2-carboxamide;
35) N-(3-bromo-5-(2-(2,4-difluorophenyl)propan-2-yl)phenyl)-5-(methylsulfonamido)benzo[b]thiophene-2-carboxamide;
36) N-(3-bromo-5-(2-(3-methoxy-5-(trifluoromethoxy)phenyl)propan-2-yl)phenyl)-5-(methylsulfonamido)benzo[b]thiophene-2-carboxamide;
37) 5-(methylsulfonamido)-N-(3-(2-(3-(trifluoromethoxy)phenyl)propan-2-yl)phenyl)benzo[b]thiophene-2-carboxamide;
38) N-(3-(2-(3-methoxyphenyl)propan-2-yl)phenyl)-5-(methylsulfonamido)benzo[b]thiophene-2-carboxamide;
39) N-(3-(difluoromethoxy)-5-(2-(4-fluorophenyl)propan-2-yl)phenyl)-5-(methylsulfonamido)benzo[b]thiophene-2-carboxamide;
40) N-(3-chloro-5-(2-(4-fluorophenyl)propan-2-yl)phenyl)-5-(methylsulfonamido)benzo[b]thiophene-2-carboxamide;
41) N-(3-(difluoromethoxy)-5-(2-(3-methoxy-5-(trifluoromethoxy)phenyl)propan-2-yl)phenyl)-5-(methylsulfonamido)benzo[b]thiophene-2-carboxamide;

42) N-(3-chloro-5-(2-(3-methoxy-5-(trifluoromethoxy)phenyl)propan-2-yl)phenyl)-5-(methylsulfonamido)benzo[b]thiophene-2-carboxamide;
43) N-(3-(2-(3-(2-amino-2-oxoethoxy)phenyl)propan-2-yl)-5-bromophenyl)-5-(methylsulfonamido)benzo[b]thiophene-2-carboxamide;
44) N-(3-(2-(5-(2-amino-2-oxoethoxy)-2-fluorophenyl)propan-2-yl)-5-bromophenyl)-5-(methylsulfonamido)benzo[b]thiophene-2-carboxamide;
45) N-(3-(2-(3-((1-amino-2-methyl-1-oxopropan-2-yl)oxy)phenyl)propan-2-yl)-5-bromophenyl)-5-(methylsulfonamido)benzo[b]thiophene-2-carboxamide;
46) N-(3-bromo-5-(2-(3-(difluoromethoxy)phenyl)propan-2-yl)phenyl)-5-(methylsulfonamido)benzo[b]thiophene-2-carboxamide;
47) N-(3-bromo-5-(2-(2-fluoro-5-(trifluoromethoxy)phenyl)propan-2-yl)phenyl)-5-(methylsulfonamido)benzo[b]thiophene-2-carboxamide;
48) N-(3-bromo-5-(2-(3-ethoxy-5-(trifluoromethoxy)phenyl)propan-2-yl)phenyl)-5-(methylsulfonamido)benzo[b]thiophene-2-carboxamide;
49) N-(3-bromo-5-(2-(3-isopropoxy-5-(trifluoromethoxy)phenyl)propan-2-yl)phenyl)-5-(methylsulfonamido)benzo[b]thiophene-2-carboxamide;
50) N-(3-bromo-5-(2-(3-(morpholinomethyl)phenyl)propan-2-yl)phenyl)-5-(methylsulfonamido)benzo[b]thiophene-2-carboxamide;
51) N-(3-(2-(4-fluorophenyl)propan-2-yl)phenyl)-3-methyl-6-(methylsulfonamido)benzo[b]thiophene-2-carboxamide;
52) N-(3-(2-(4-fluorophenyl)propan-2-yl)phenyl)-3-methyl-5-(methylsulfonamido)benzo[b]thiophene-2-carboxamide;
53) N-(3-bromo-5-(3-(4-fluorophenyl)pentan-3-yl)phenyl)-5-(methylsulfonamido)benzo[b]thiophene-2-carboxamide;
54) N-(3-methoxy-5-(3-(3-methoxy-5-(trifluoromethoxy)phenyl)pentan-3-yl)phenyl)-5-(methylsulfonamido)benzo[b]thiophene-2-carboxamide;
55) N-(3-methoxy-5-(3-(3-methoxy-5-(trifluoromethoxy)phenyl)pentan-3-yl)phenyl)-6-(methylsulfonamido)-1H-indole-2-carboxamide;
56) N-(3-bromo-5-(2-(3-methoxy-5-(trifluoromethoxy)phenyl)propan-2-yl)phenyl)-5-(methylsulfonamido)thieno[2,3-b]pyridine-2-carboxamide;
57) N-(3-chloro-5-(2-(3-methoxy-5-(trifluoromethoxy)phenyl)propan-2-yl)phenyl)-5-(methylsulfonamido)thieno[2,3-b]pyridine-2-carboxamide;
58) N-(3-chloro-5-(2-(3-ethoxy-5-(trifluoromethoxy)phenyl)propan-2-yl)phenyl)-5-(methylsulfonamido)benzo[b]thiophene-2-carboxamide;
59) N-(3-chloro-5-(2-(3-ethoxy-5-(trifluoromethoxy)phenyl)propan-2-yl)phenyl)-6-(methylsulfonamido)-1H-indole-2-carboxamide;
60) N-(3-bromo-5-(2-(3-ethoxy-5-(trifluoromethoxy)phenyl)propan-2-yl)phenyl)-5-(methylsulfonamido)thieno[3,2-b]pyridine-2-carboxamide;
61) N-(3-bromo-5-(2-(3-ethoxy-5-(trifluoromethoxy)phenyl)propan-2-yl)phenyl)-5-(methylsulfonamido)thieno[2,3-c]pyridine-2-carboxamide;
62) N-(3-chloro-5-(2-(2-fluoro-5-(trifluoromethoxy)phenyl)propan-2-yl)phenyl)-5-(methylsulfonamido)benzo[b]thiophene-2-carboxamide;
63) N-(3-fluoro-5-(2-(3-methoxy-5-(trifluoromethoxy)phenyl)propan-2-yl)phenyl)-5-(methylsulfonamido)benzo[b]thiophene-2-carboxamide;
64) N-(3-chloro-5-(2-phenylpropan-2-yl)phenyl)-5-(methylsulfonamido)benzo[b]thiophene-2-carboxamide;
65) N-(3-chloro-5-(2-(3-fluorophenyl)propan-2-yl)phenyl)-5-(methylsulfonamido)benzo[b]thiophene-2-carboxamide;
66) N-(3-chloro-5-(2-(3-isopropoxy-5-(trifluoromethoxy)phenyl)propan-2-yl)phenyl)-5-(methylsulfonamido)-4-morpholinobenzo[b]thiophene-2-carboxamide;
67) N-(3-chloro-5-(2-(3-fluoro-5-methoxyphenyl)propan-2-yl)phenyl)-5-(methylsulfonamido)benzo[b]thiophene-2-carboxamide;
68) N-(3-chloro-5-(2-(3-isopropoxy-5-(trifluoromethoxy)phenyl)propan-2-yl)phenyl)-5-(methylsulfonamido)benzo[b]thiophene-2-carboxamide;
69) N-(3-chloro-5-(2-(3-isopropoxy-5-(trifluoromethoxy)phenyl)propan-2-yl)phenyl)-5-(methylsulfonamido)thieno[2,3-b]pyridine-2-carboxamide;
70) N-(3-chloro-5-(2-(3-isopropoxy-5-(trifluoromethoxy)phenyl)propan-2-yl)phenyl)-5-(methylsulfonamido)thieno[3,2-b]pyridine-2-carboxamide;
71) N-(3-chloro-5-(2-(3-isopropoxy-5-(trifluoromethoxy)phenyl)propan-2-yl)phenyl)-5-(methylsulfonamido)thieno[2,3-c]pyridine-2-carboxamide;
72) N-(3-chloro-5-(2-(3-isobutoxy-5-(trifluoromethoxy)phenyl)propan-2-yl)phenyl)-5-(methylsulfonamido)benzo[b]thiophene-2-carboxamide;
73) N-(3-chloro-5-(2-(3-propoxy-5-(trifluoromethoxy)phenyl)propan-2-yl)phenyl)-5-(methylsulfonamido)benzo[b]thiophene-2-carboxamide;
74) N-(3-chloro-5-(2-(3-isopropoxy-5-(trifluoromethoxy)phenyl)propan-2-yl)phenyl)-6-(methylsulfonamido)imidazo[1,2-a]pyridine-2-carboxamide;
75) N-(3-(2-(3-(but-2-yn-1-yloxy)-5-(trifluoromethoxy)phenyl)propan-2-yl)-5-chlorophenyl)-5-(methylsulfonamido)benzo[b]thiophene-2-carboxamide;
76) N-(3-chloro-5-(2-(3-(oxetan-3-yloxy)-5-(trifluoromethoxy)phenyl)propan-2-yl)phenyl)-5-(methylsulfonamido)benzo[b]thiophene-2-carboxamide;
77) N-(3-chloro-5-(2-(3-(cyanomethoxy)-5-(trifluoromethoxy)phenyl)propan-2-yl)phenyl)-5-(methylsulfonamido)benzo[b]thiophene-2-carboxamide;
78) N-(3-(2-(3-(allyloxy)-5-(trifluoromethoxy)phenyl)propan-2-yl)-5-chlorophenyl)-5-(methylsulfonamido)benzo[b]thiophene-2-carboxamide;
79) N-(3-chloro-5-(2-(3-cyclopropoxy-5-(trifluoromethoxy)phenyl)propan-2-yl)phenyl)-5-(methylsulfonamido)benzo[b]thiophene-2-carboxamide;
80) N-(3-chloro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;
81) N-(3-chloro-5-(2-(3-isopropoxy-5-(trifluoromethoxy)phenyl)propan-2-yl)phenyl)-5-(methylsulfonamido)benzo[d]thiazole-2-carboxamide;
82) N-(3-fluoro-5-(2-(3-isopropoxy-5-(trifluoromethoxy)phenyl)propan-2-yl)phenyl)-5-(methylsulfonamido)benzo[b]thiophene-2-carboxamide;
83) N-(3-chloro-5-(2-(3-(2,2-difluoroethoxy)-5-(trifluoromethoxy)phenyl)propan-2-yl)phenyl)-5-(methylsulfonamido)benzo[b]thiophene-2-carboxamide;
84) N-(3-chloro-5-(2-(3-isopropoxy-5-(trifluoromethoxy)phenyl)propan-2-yl)phenyl)-6-fluoro-5-(methylsulfonamido)benzo[b]thiophene-2-carboxamide;
85) N-(3-fluoro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;

86) N-(3-fluoro-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide;
87) N-(3-bromo-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;
88) N-(3-chloro-5-(2-(3-(2,2,2-trifluoroethoxy)-5-(trifluoromethoxy)phenyl)propan-2-yl)phenyl)-5-(methylsulfonamido)benzo[b]thiophene-2-carboxamide;
89) N-(3-bromo-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide;
90) N-(3-chloro-5-(2-(3-(2-morpholinoethoxy)-5-(trifluoromethoxy)phenyl)propan-2-yl)phenyl)-5-(methylsulfonamido)benzo[b]thiophene-2-carboxamide;
91) N-(3-(2-(3-bromo-5-isopropoxyphenyl)propan-2-yl)-5-chlorophenyl)-5-(methylsulfonamido)benzo[b]thiophene-2-carboxamide;
92) N-(3-chloro-5-(2-(3-chloro-5-isopropoxyphenyl)propan-2-yl)phenyl)-5-(methylsulfonamido)benzo[b]thiophene-2-carboxamide;
93) N-(3-chloro-5-(2-(3-isopropoxy-5-(trifluoromethoxy)phenyl)propan-2-yl)phenyl)-4-fluoro-5-(methylsulfonamido)benzo[b]thiophene-2-carboxamide;
94) N-(3-chloro-5-(2-(3-(2-(dimethyl amino)ethoxy)-5-(trifluoromethoxy)phenyl)propan-2-yl)phenyl)-5-(methylsulfonamido)benzo[b]thiophene-2-carboxamide;
95) tert-butyl 4-(3-(2-(3-chloro-5-(5-(methylsulfonamido)benzo[b]thiophene-2-carboxamido)phenyl)propan-2-yl)-5-(trifluoromethoxy)phenoxy)piperidine-1-carboxylate;
96) N-(3-chloro-5-(2-(3-(piperidin-4-yloxy)-5-(trifluoromethoxy)phenyl)propan-2-yl)phenyl)-5-(methylsulfonamido)benzo[b]thiophene-2-carboxamide;
97) N-(3-chloro-5-(2-(3-isopropoxy-5-(trifluoromethoxy)phenyl)propan-2-yl)phenyl)-5-(methylsulfonyl)-4,5,6,7-tetrahydrothieno[3,2-c]pyridine-2-carboxamide;
98) N-(3-bromo-5-(2-(3-methoxy-5-(trifluoromethoxy)phenyl)propan-2-yl)phenyl)-6-(methylsulfonamido)-1H-pyrrolo[3,2-c]pyridine-2-carboxamide;
99) N-(3-bromo-5-(2-(3-methoxy-5-(trifluoromethoxy)phenyl)propan-2-yl)phenyl)-5-(methylsulfonamido)-1H-pyrrolo[2,3-c]pyridine-2-carboxamide 2,2,2-trifluoroacetate;
100) N-(3-chloro-5-(2-(3-isopropoxy-5-(trifluoromethoxy)phenyl)propan-2-yl)phenyl)-6-(methylsulfonamido)-1H-pyrrolo[2,3-b]pyridine-2-carboxamide;
101) N-(3-chloro-5-(2-(3-isopropoxy-5-(trifluoromethoxy)phenyl)propan-2-yl)phenyl)-6-(methylsulfonamido)-1H-pyrrolo[3,2-c]pyridine-2-carboxamide;
102) N-(3-chloro-5-(2-(3-isopropoxy-5-(trifluoromethoxy)phenyl)propan-2-yl)phenyl)-4-(methylsulfonamido)thiophene-2-carboxamide;
103) N-(3-chloro-5-(2-(3-isopropoxy-5-(trifluoromethoxy)phenyl)propan-2-yl)phenyl)-5-(morpholine-4-sulfonamido)benzo[b]thiophene-2-carboxamide;
104) N-(3-chloro-5-(2-(3-isopropoxy-5-(trifluoromethoxy)phenyl)propan-2-yl)phenyl)-5-(methylsulfonamido)-4,5,6,7-tetrahydrothieno[3,2-c]pyridine-2-carboxamide;
105) 6-chloro-N-(3-chloro-5-(2-(3-isopropoxy-5-(trifluoromethoxy)phenyl)propan-2-yl)phenyl)-5-(methylsulfonamido)benzo[b]thiophene-2-carboxamide;
106) N-(3-chloro-5-(2-(3-methoxyphenyl)propan-2-yl)phenyl)-5-(methylsulfonamido)benzo[b]thiophene-2-carboxamide;
107) N-(3-ethynyl-5-(2-(4-fluorophenyl)propan-2-yl)phenyl)-6-(methylsulfonamido)-1H-indole-2-carboxamide;
108) N-(3-ethynyl-5-(2-(4-fluorophenyl)propan-2-yl)phenyl)-5-(methylsulfonamido)benzo[b]thiophene-2-carboxamide;
109) N-(3-(2-(2,4-difluorophenyl)propan-2-yl)-5-ethynylphenyl)-5-(methylsulfonamido)benzo[b]thiophene-2-carboxamide;
110) 3-chloro-N-(3-(2-(4-fluorophenyl)propan-2-yl)phenyl)-6-(methylsulfonamido)benzo[b]thiophene-2-carboxamide;
111) 3-chloro-N-(2',4'-difluoro-[1,1'-biphenyl]-3-yl)-6-(methylsulfonamido)benzo[b]thiophene-2-carboxamide;
112) N-(2',4'-difluoro-[1,1'-biphenyl]-3-yl)-7-methoxy-5-(methylsulfonamido)benzofuran-2-carboxamide;
113) N-(3-(2-(4-fluorophenyl)propan-2-yl)phenyl)-7-methoxy-5-(methylsulfonamido)benzofuran-2-carboxamide;
114) N-(3-chloro-5-(2-(3-(prop-1-yn-1-yl)-5-(trifluoromethoxy)phenyl)propan-2-yl)phenyl)-5-(methylsulfonamido)benzo[b]thiophene-2-carboxamide;
115) N-(3-bromo-5-(2-(3-((4-methylpiperazin-1-yl)methyl)phenyl)propan-2-yl)phenyl)-5-(methylsulfonamido)benzo[b]thiophene-2-carboxamide;
116) tert-butyl 4-(3-(2-(3-bromo-5-(5-(methylsulfonamido)benzo[b]thiophene-2-carboxamido)phenyl)propan-2-yl)benzyl)piperazine-1-carboxylate;
117) tert-butyl 4-(3-(2-(3-bromo-5-(6-(methylsulfonamido)-1H-indole-2-carboxamido)phenyl)propan-2-yl)benzyl)piperazine-1-carboxylate;
118) N-(3-bromo-5-(2-(3-(piperazin-1-ylmethyl)phenyl)propan-2-yl)phenyl)-5-(methylsulfonamido) benzo[b]thiophene-2-carboxamide;
119) N-(3-bromo-5-(2-(3-(piperazin-1-ylmethyl)phenyl)propan-2-yl)phenyl)-6-(methylsulfonamido)-1H-indole-2-carboxamide;
120) N-(3-(2-(3-((1H-imidazol-1-yl)methyl)phenyl)propan-2-yl)-5-bromophenyl)-5-(methylsulfonamido)benzo[b]thiophene-2-carboxamide;
121) N-(3-chloro-5-(2-(3-((2-hydroxyazetidin-1-yl)methyl)-5-isopropoxyphenyl)propan-2-yl)phenyl)-5-(methylsulfonamido)benzo[b]thiophene-2-carboxamide;
122) N-(3-bromo-5-(2-(3-isopropoxy-5-(morpholinomethyl)phenyl)propan-2-yl)phenyl)-5-(methylsulfonamido)benzo[b]thiophene-2-carboxamide;
123) tert-butyl 4-(3-(2-(3-bromo-5-(5-(methylsulfonamido)benzo[b]thiophene-2-carboxamido)phenyl)propan-2-yl)-5-isopropoxybenzyl)piperazine-1-carboxylate;
124) N-(3-bromo-5-(2-(3-isopropoxy-5-(piperazin-1-ylmethyl)phenyl)propan-2-yl)phenyl)-5-(methylsulfonamido)benzo[b]thiophene-2-carboxamide;
125) N-(3-chloro-5-(2-(3-isopropoxy-5-(pyrrolidin-1-ylmethyl)phenyl)propan-2-yl)phenyl)-5-(methylsulfonamido)benzo[b]thiophene-2-carboxamide;
126) N-(3-chloro-5-(2-(3-isopropoxy-5-(morpholinomethyl)phenyl)propan-2-yl)phenyl)-5-(methylsulfonamido)benzo[b]thiophene-2-carboxamide;
127) N-(3-chloro-5-(2-(3-isopropoxy-5-((4-pivaloylpiperazin-1-yl)methyl)phenyl)propan-2-yl)phenyl)-5-(methylsulfonamido)benzo[b]thiophene-2-carboxamide;
128) N-(3-chloro-5-(2-(3-isopropoxy-5-((4-(methylsulfonyl)piperazin-1-yl)methyl)phenyl)propan-2-yl)phenyl)-5-(methylsulfonamido)benzo[b]thiophene-2-carboxamide;
129) N-(3-chloro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide;

130) N-(3-chloro-5-(2-(3-isopropoxy-5-((4-(oxetan-3-yl)piperazin-1-yl)methyl)phenyl)propan-2-yl)phenyl)-5-(methylsulfonamido)benzo[b]thiophene-2-carboxamide;
131) N-(3-chloro-5-(2-(3-((4-(N,N-dimethylsulfamoyl)piperazin-1-yl)methyl)-5-isopropoxyphenyl)propan-2-yl)phenyl)-5-(methylsulfonamido)benzo[b]thiophene-2-carboxamide;
132) N-(3-chloro-5-(2-(3-((1,1-dioxidothiomorpholino)methyl)-5-isopropoxyphenyl)propan-2-yl)phenyl)-5-(methylsulfonamido)benzo[b]thiophene-2-carboxamide;
133) 4-(3-(2-(3-chloro-5-(5-(methylsulfonamido)benzo[b]thiophene-2-carboxamido)phenyl)propan-2-yl)-5-isopropoxybenzyl)-N,N-dimethylpiperazine-1-carboxamide;
134) N-(3-(2-(3-((2-oxa-7-azaspiro[3,5]nonan-7-yl)methyl)-5-isopropoxyphenyl)propan-2-yl)-5-chlorophenyl)-5-(methylsulfonamido)benzo[b]thiophene-2-carboxamide;
135) N-(3-chloro-5-(2-(3-isopropoxy-5-((4-(5-isopropyl-1,3,4-oxadiazol-2-yl)piperazin-1-yl)methyl)phenyl)propan-2-yl)phenyl)-5-(methylsulfonamido)benzo[b]thiophene-2-carboxamide;
136) N-(3-fluoro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide;
137) N-(3-fluoro-5-(2-(3-isopropoxy-5-(morpholinomethyl)phenyl)propan-2-yl)phenyl)-5-(methylsulfonamido)benzo[b]thiophene-2-carboxamide;
138) N-(3-chloro-5-(2-(3-((1-methyl-1H-pyrazol-4-yl)methyl)-5-(1,1,2,2-tetrafluoroethoxy)phenyl)propan-2-yl)phenyl)-5-(methylsulfonamido) benzo[b]thiophene-2-carboxamide;
139) N-(3-bromo-5-(2-(3-((4-(N,N-dimethylsulfamoyl)piperazin-1-yl)methyl)-5-(1,1,2,2-tetrafluoroethoxy)phenyl)propan-2-yl)phenyl)-5-(methylsulfonamido)benzo[b]thiophene-2-carboxamide;
140) N-(3-fluoro-5-(2-(3-(morpholinomethyl)-5-(1,1,2,2-tetrafluoroethoxy)phenyl)propan-2-yl)phenyl)-5-(methylsulfonamido)benzo[b]thiophene-2-carboxamide;
141) N-(3-bromo-5-(2-(3-((4-(oxetan-3-yl)piperazin-1-yl)methyl)-5-(1,1,2,2-tetrafluoroethoxy)phenyl)propan-2-yl)phenyl)-5-(methylsulfonamido)benzo[b]thiophene-2-carboxamide;
142) N-(3-chloro-5-(2-(3-isopropoxy-5-(1-methyl-1H-pyrazol-5-yl)phenyl)propan-2-yl)phenyl)-5-(methylsulfonamido)benzo[b]thiophene-2-carboxamide;
143) N-(3-chloro-5-(2-(3-isopropoxy-5-(1-methyl-1H-pyrazol-4-yl)phenyl)propan-2-yl)phenyl)-5-(methylsulfonamido)benzo[b]thiophene-2-carboxamide;
144) N-(3-chloro-5-(2-(3-(3-hydroxy-4-methylpiperazin-1-yl)-5-isopropoxyphenyl)propan-2-yl)phenyl)-5-(methylsulfonamido)benzo[b]thiophene-2-carboxamide;
145) N-(3-chloro-5-(2-(3-isopropoxy-5-morpholinophenyl)propan-2-yl)phenyl)-5-(methylsulfonamido)benzo[b]thiophene-2-carboxamide;
146) N-(3-chloro-5-(2-(3-isopropoxy-5-(pyrrolidin-1-yl)phenyl)propan-2-yl)phenyl)-5-(methylsulfonamido)benzo[b]thiophene-2-carboxamide;
147) N-(3-chloro-5-(2-(3-isopropoxy-5-(4-methylpiperazin-1-yl)phenyl)propan-2-yl)phenyl)-5-(methylsulfonamido)benzo[b]thiophene-2-carboxamide;
148) N-(6-chloro-4-(2-(3-methoxy-5-(trifluoromethoxy)phenyl)propan-2-yl)pyridin-2-yl)-5-(methylsulfonamido)benzo[b]thiophene-2-carboxamide;
149) N-(2-chloro-6-(2-(3-methoxy-5-(trifluoromethoxy)phenyl)propan-2-yl)pyridin-4-yl)-5-(methylsulfonamido)benzo[b]thiophene-2-carboxamide;
150) N-(4-chloro-6-(2-(3-methoxy-5-(trifluoromethoxy)phenyl)propan-2-yl)pyridin-2-yl)-5-(methylsulfonamido)benzo[b]thiophene-2-carboxamide;
151) N-(3-chloro-5-(2-(3-isopropoxy-5-(trifluoromethoxy)phenyl)propan-2-yl)phenyl)-2-(methylsulfonamido)thieno[2,3-b]pyrazine-6-carboxamide;
152) N-(3-(2-(4-bromophenyl)propan-2-yl)-5-chlorophenyl)-5-(methylsulfonamido)benzo[b]thiophene-2-carboxamide;
153) N-(3-chloro-5-(2-(3,4-dimethoxyphenyl)propan-2-yl)phenyl)-5-(methylsulfonamido)benzo[b]thiophene-2-carboxamide;
154) N-(3-chloro-5-(2-(2,4-dimethoxyphenyl)propan-2-yl)phenyl)-5-(methylsulfonamido)benzo[b]thiophene-2-carboxamide;
155) N-(3-chloro-5-(2-(4-methoxyphenyl)propan-2-yl)phenyl)-5-(methylsulfonamido)benzo[b]thiophene-2-carboxamide;
156) N-(3-chloro-5-(2-(2,5-dimethoxyphenyl)propan-2-yl)phenyl)-5-(methylsulfonamido)benzo[b]thiophene-2-carboxamide;
157) N-(3-chloro-5-(2-(4-(methylthio)phenyl)propan-2-yl)phenyl)-5-(methylsulfonamido)benzo[b]thiophene-2-carboxamide;
158) N-(3-chloro-5-(2-(4-chlorophenyl)propan-2-yl)phenyl)-5-(methylsulfonamido)benzo[b]thiophene-2-carboxamide;
159) N-(3-chloro-5-(2-(4-(1-methyl-1H-pyrazol-5-yl)phenyl)propan-2-yl)phenyl)-5-(methylsulfonamido)benzo[b]thiophene-2-carboxamide;
160) N-(3-chloro-5-(2-(4-(methylsulfinyl)phenyl)propan-2-yl)phenyl)-5-(methylsulfonamido)benzo[b]thiophene-2-carboxamide;
161) N-(3-chloro-5-(2-(4-(methylsulfonyl)phenyl)propan-2-yl)phenyl)-5-(methylsulfonamido)benzo[b]thiophene-2-carboxamide;
162) N-(3-chloro-5-(2-(3,4-difluorophenyl)propan-2-yl)phenyl)-5-(methylsulfonamido)benzo[b]thiophene-2-carboxamide;
163) N-(3-chloro-5-(2-(4-chlorophenyl)propan-2-yl)phenyl)-6-fluoro-5-(N-methylmethylsulfonamido)benzo[b]thiophene-2-carboxamide;
164) N-(3-chloro-5-(2-(piperidin-1-yl)propan-2-yl)phenyl)-5-(methylsulfonamido)benzo[b]thiophene-2-carboxamide;
165) 6-chloro-N-(3-chloro-5-(2-(piperidin-1-yl)propan-2-yl)phenyl)-5-(methylsulfonamido)benzo[b]thiophene-2-carboxamide;
166) N-(3-(2-(1H-pyrrol-2-yl)propan-2-yl)-5-chlorophenyl)-5-(methylsulfonamido)benzo[b]thiophene-2-carboxamide;
167) N-(3-(2-(1H-pyrrol-3-yl)propan-2-yl)-5-chlorophenyl)-5-(methylsulfonamido)benzo[b]thiophene-2-carboxamide;
168) N-(3-chloro-5-(2-(1-methyl-1H-pyrrol-3-yl)propan-2-yl)phenyl)-5-(methylsulfonamido)benzo[b]thiophene-2-carboxamide;
169) N-(3-chloro-5-(2-(1-methyl-1H-pyrrol-2-yl)propan-2-yl)phenyl)-5-(methylsulfonamido)benzo[b]thiophene-2-carboxamide;
170) N-(3-chloro-5-(2-(thiophen-2-yl)propan-2-yl)phenyl)-5-(methylsulfonamido)benzo[b]thiophene-2-carboxamide;

171) N-(3-chloro-5-(2-(thiophen-3-yl)propan-2-yl)phenyl)-5-(methylsulfonamido)benzo[b]thiophene-2-carboxamide;

172) 6-chloro-N-(3-chloro-5-(2-(4-chlorophenyl)propan-2-yl)phenyl)-5-(methylsulfonamido)benzo[b]thiophene-2-carboxamide;

173) 6-bromo-N-(3-chloro-5-(2-(4-chlorophenyl)propan-2-yl)phenyl)-5-(methylsulfonamido)benzo[b]thiophene-2-carboxamide;

174) N-(3-chloro-5-(2-(5-chlorothiophen-2-yl)propan-2-yl)phenyl)-5-(methylsulfonamido)benzo[b]thiophene-2-carboxamide;

175) 6-chloro-N-(3-chloro-5-(2-(5-chlorothiophen-2-yl)propan-2-yl)phenyl)-5-(methylsulfonamido)benzo[b]thiophene-2-carboxamide;

176) N-(3-chloro-5-(2-(2-methoxythiophen-3-yl)propan-2-yl)phenyl)-5-(methylsulfonamido)benzo[b]thiophene-2-arboxamide;

177) N-(3-chloro-5-(2-(5-methoxythiophen-2-yl)propan-2-yl)phenyl)-5-(methylsulfonamido)benzo[b]thiophene-2-carboxamide;

178) N-(3-chloro-5-(2-(5-methylthiophen-2-yl)propan-2-yl)phenyl)-5-(methylsulfonamido)benzo[b]thiophene-2-carboxamide;

179) 6-chloro-N-(3-chloro-5-(2-(5-methylthiophen-2-yl)propan-2-yl)phenyl)-5-(methylsulfonamido)benzo[b]thiophene-2-carboxamide;

180) 6-chloro-N-(3-chloro-5-(2-(5-isopropylthiophen-2-yl)propan-2-yl)phenyl)-5-(methylsulfonamido)benzo[b]thiophene-2-carboxamide;

181) 6-chloro-N-(3-chloro-5-(2-(4-methylthiophen-2-yl)propan-2-yl)phenyl)-5-(methylsulfonamido)benzo[b]thiophene-2-carboxamide;

182) 6-chloro-N-(3-chloro-5-(2-(4-fluorophenyl)propan-2-yl)phenyl)-5-(methylsulfonamido)benzo[b]thiophene-2-carboxamide;

183) 6-chloro-N-(3-chloro-5-(2-(4-methoxyphenyl)propan-2-yl)phenyl)-5-(methylsulfonamido)benzo[b]thiophene-2-carboxamide;

184) 5-chloro-N-(3-chloro-5-(2-(4-chlorophenyl)propan-2-yl)phenyl)-6-(methylsulfonamido)benzo[b]thiophene-2-carboxamide;

185) 6-chloro-N-(3-chloro-5-(2-(4-chlorophenyl)propan-2-yl)phenyl)-5-((2-methoxyethyl)sulfonamido)benzo[b]thiophene-2-carboxamide;

186) 6-chloro-N-(3-chloro-5-(2-(5-cyanothiophen-2-yl)propan-2-yl)phenyl)-5-(methylsulfonamido)benzo[b]thiophene-2-carboxamide;

187) N-(3-chloro-5-(2-(1-ethyl-1H-pyrrol-2-yl)propan-2-yl)phenyl)-5-(methylsulfonamido)benzo[b]thiophene-2-carboxamide;

188) 6-chloro-N-(3-chloro-5-(2-(4-chlorophenyl)propan-2-yl)phenyl)-5-((2-hydroxyethyl)sulfonamido)benzo[b]thiophene-2-carboxamide;

189) N-(3-chloro-5-(2-(pyrimidin-2-yloxy)propan-2-yl)phenyl)-5-(methylsulfonamido)benzo[b]thiophene-2-carboxamide;

190) N-(3-chloro-5-(2-(6-oxopyridazin-1(6H)-yl)propan-2-yl)phenyl)-5-(methylsulfonamido)benzo[b]thiophene-2-carboxamide;

191) N-(3-chloro-5-(2-(pyridin-4-yl)propan-2-yl)phenyl)-5-(methylsulfonamido)benzo[b]thiophene-2-carboxamide;

192) 2-((3-bromo-5-(2-(3-isopropoxy-5-(trifluoromethoxy)phenyl)propan-2-yl)phenyl)carbamoyl)benzo[b]thiophen-5-yl dihydrogen phosphate;

193) 2-((3-chloro-5-(2-(3-isopropoxy-5-(trifluoromethoxy)phenyl)propan-2-yl)phenyl)carbamoyl)benzo[b]thiophen-5-yl dihydrogen phosphate;

194) tert-butyl (2-((3-chloro-5-(2-(3-isopropoxy-5-(trifluoromethoxy)phenyl)propan-2-yl)phenyl)carbamoyl)benzo[b]thiophen-5-yl)carbamate;

195) N-(3-chloro-5-(2-(3-isopropoxy-5-(trifluoromethoxy)phenyl)propan-2-yl)phenyl)-5-((2-methoxyethyl)sulfonamido)benzo[b]thiophene-2-carboxamide;

196) N-(3-chloro-5-(2-(3-isopropoxy-5-(trifluoromethoxy)phenyl)propan-2-yl)phenyl)-5-(((tetrahydrofuran-3-yl)methyl)sulfonamido)benzo[b]thiophene-2-carboxamide;

197) N-(3-chloro-5-(2-(3-isopropoxy-5-(trifluoromethoxy)phenyl)propan-2-yl)phenyl)-5-(((tetrahydrofuran-2-yl)methyl)sulfonamido)benzo[b]thiophene-2-carboxamide;

198) N-(3-chloro-5-(2-(3-isopropoxy-5-(trifluoromethoxy)phenyl)propan-2-yl)phenyl)-5-(((tetrahydro-2H-pyran-4-yl)methyl)sulfonamido)benzo[b]thiophene-2-carboxamide;

199) N-(3-chloro-5-(2-(3-isopropoxy-5-(trifluoromethoxy)phenyl)propan-2-yl)phenyl)-5-((3,5-dimethylisoxazole)-4-sulfonamido)benzo[b]thiophene-2-carboxamide;

200) N-(3-chloro-5-(2-(3-isopropoxy-5-(trifluoromethoxy)phenyl)propan-2-yl)phenyl)-5-((1-methyl-1H-pyrazole)-3-sulfonamido)benzo[b]thiophene-2-carboxamide;

201) N-(3-chloro-5-(2-(3-isopropoxy-5-(trifluoromethoxy)phenyl)propan-2-yl)phenyl)-5-((1-methyl-1H-pyrazole)-4-sulfonamido)benzo[b]thiophene-2-carboxamide;

202) N-(3-chloro-5-(2-(3-isopropoxy-5-(trifluoromethoxy)phenyl)propan-2-yl)phenyl)-5-(ethylsulfonamido)benzo[b]thiophene-2-carboxamide;

203) N-(3-chloro-5-(2-(3-isopropoxy-5-(trifluoromethoxy)phenyl)propan-2-yl)phenyl)-5-((1-methylethyl)sulfonamido)benzo[b]thiophene-2-carboxamide;

204) N-(3-chloro-5-(2-(3-isopropoxy-5-(trifluoromethoxy)phenyl)propan-2-yl)phenyl)-5-((tetrahydrofuran)-3-sulfonamido)benzo[b]thiophene-2-carboxamide;

205) N-(3-chloro-5-(2-(3-isopropoxy-5-(trifluoromethoxy)phenyl)propan-2-yl)phenyl)-5-((1,1-dioxidotetrahydro-2H-thiopyran)-4-sulfonamido)benzo[b]thiophene-2-carboxamide;

206) 5-((1-acetylpiperidine)-4-sulfonamido)-N-(3-chloro-5-(2-(3-isopropoxy-5-(trifluoromethoxy)phenyl)propan-2-yl)phenyl)benzo[b]thiophene-2-carboxamide;

207) N-(3-chloro-5-(2-(3-isopropoxy-5-(trifluoromethoxy)phenyl)propan-2-yl)phenyl)-5-(vinylsulfonamido)benzo[b]thiophene-2-carboxamide;

208) N-(3-chloro-5-(2-(3-isopropoxy-5-(trifluoromethoxy)phenyl)propan-2-yl)phenyl)-5-((2-(dimethylamino)ethyl)sulfonamido)benzo[b]thiophene-2-carboxamide;

209) N-(3-chloro-5-(2-(3-isopropoxy-5-(trifluoromethoxy)phenyl)propan-2-yl)phenyl)-5-((2-morpholinoethyl)sulfonamido)benzo[b]thiophene-2-carboxamide;

210) N-(3-chloro-5-(2-(3-isopropoxy-5-(trifluoromethoxy)phenyl)propan-2-yl)phenyl)-5-((2-(hydroxy(methyl)amino)ethyl)sulfonamido)benzo[b]thiophene-2-carboxamide;

211) N-(3-chloro-5-(2-(3-isopropoxy-5-(trifluoromethoxy)phenyl)propan-2-yl)phenyl)-5-(1,1-dioxido-1,2-thiazinan-2-yl)benzo[b]thiophene-2-carboxamide;

212) N-(3-chloro-5-(2-(3-isopropoxy-5-(trifluoromethoxy)phenyl)propan-2-yl)phenyl)-5-(1,1-dioxidoisothiazolidin-2-yl)benzo[b]thiophene-2-carboxamide;

213) N-(3-iodo-5-(2-(3-isopropoxy-5-(trifluoromethoxy)phenyl)propan-2-yl)phenyl)-5-(methylsulfonamido)benzo[b]thiophene-2-carboxamide;

214) 3-iodo-N-(3-iodo-5-(2-(3-isopropoxy-5-(trifluoromethoxy)phenyl)propan-2-yl)phenyl)-5-(methylsulfonamido)benzo[b]thiophene-2-carboxamide;
215) N-(3-chloro-5-(2-(3-isopropoxy-5-(trifluoromethoxy)phenyl)propan-2-yl)phenyl)-6-fluoro-5-(N-methylmethylsulfonamido)benzo[b]thiophene-2-carboxamide;
216) N-(3-chloro-5-(2-(3-isopropoxy-5-(trifluoromethoxy)phenyl)propan-2-yl)phenyl)-6-fluoro-N-methyl-5-(N-methylmethylsulfonamido)benzo[b]thiophene-2-carboxamide;
217) N-(3-chloro-5-(2-(3-isopropoxy-5-(trifluoromethoxy)phenyl)propan-2-yl)phenyl)-6-fluoro-5-(N-(2-morpholinoethyl)methylsulfonamido)benzo[b]thiophene-2-carboxamide;
218) N-(3-chloro-5-(2-(3-isopropoxy-5-(trifluoromethoxy)phenyl)propan-2-yl)phenyl)-6-fluoro-N-(2-morpholinoethyl)-5-(N-(2-morpholinoethyl)methylsulfonamido)benzo[b]thiophene-2-carboxamide;
219) N-(3-chloro-5-(2-(3-isopropoxy-5-(trifluoromethoxy)phenyl)propan-2-yl)phenyl)-5-(N-(2-(dimethylamino)ethyl)methylsulfonamido)-6-fluorobenzo[b]thiophene-2-carboxamide;
220) N-(3-chloro-5-(4-chlorophenoxy)phenyl)-5-(N-methylmethylsulfonamido)benzo[b]thiophene-2-carboxamide;
221) N-(3-chloro-5-(2-(4-chlorophenyl)propan-2-yl)phenyl)-5-(N-methylmethylsulfonamido)benzo[b]thiophene-2-carboxamide;
222) N-(3-chloro-5-(2-(3-isopropoxy-5-(trifluoromethoxy)phenyl)propan-2-yl)phenyl)-5-(methylsulfonamido)benzo[b]thiophene-2-carboxamide 1,1-dioxide;
223) N-(3-chloro-5-(2-(3-isopropoxy-5-(trifluoromethoxy)phenyl)propan-2-yl)phenyl)-5-(methylsulfonamido)benzo[b]thiophene-2-carboxamide 1-oxide;
224) N-(3-(2-(3-cyanophenyl)propan-2-yl)phenyl)-5-(methylsulfonamido)benzo[b]thiophene-2-carboxamide;
225) N-(2',4'-difluoro-[1,1'-biphenyl]-3-yl)-6-nitro-1H-indole-2-carboxamide;
226) 6-nitro-N-(2'-(trifluoromethyl)-[1,1'-biphenyl]-3-yl)-1H-indole-2-carboxamide;
227) 5-nitro-N-(2'-(trifluoromethyl)-[1,1'-biphenyl]-3-yl)-1H-indole-2-carboxamide;
228) 3-methyl-5-nitro-N-(2'-(trifluoromethyl)-[1,1'-biphenyl]-3-yl)-1H-indole-2-carboxamide;
229) N-(4'-fluoro-2'-(trifluoromethyl)-[1,1'-biphenyl]-3-yl)-6-nitroindoline-2-carboxamide;
230) 6-nitro-N-(2'-(trifluoromethyl)-[1,1'-biphenyl]-3-yl)indoline-2-carboxamide;
231) N-(2',4'-difluoro-[1,1'-biphenyl]-3-yl)-6-nitroindoline-2-carboxamide;
232) 6-nitro-N-(2'-(trifluoromethyl)-[1,1'-biphenyl]-3-yl)benzo[d]thiazole-2-carboxamide;
233) N-(2',4'-difluoro-[1,1'-biphenyl]-3-yl)-5-nitro-1H-benzo[d]imidazole-2-carboxamide;
234) 5-nitro-N-(2'-(trifluoromethyl)-[1,1'-biphenyl]-3-yl)-1H-benzo[d]imidazole-2-carboxamide;
235) N-(4'-fluoro-2'-(trifluoromethyl)-[1,1'-biphenyl]-3-yl)-5-nitro-1H-benzo[d]imidazole-2-carboxamide;
236) N-(2',4'-difluoro-[1,1'-biphenyl]-3-yl)-5-methoxy-6-(methylsulfonamido)-1H-indole-2-carboxamide;
237) N-(2',4'-difluoro-[1,1'-biphenyl]-3-yl)-5-(methylsulfonamido)benzo[b]thiophene-2-carboxamide;
238) N-(2',4'-difluoro-[1,1'-biphenyl]-3-yl)-5-(methylsulfonamido)benzofuran-2-carboxamide;
239) N-(2',4'-difluoro-[1,1'-biphenyl]-3-yl)-5-(trifluoromethoxy)-1H-indole-2-carboxamide;
240) N-(2',4'-difluoro-[1,1'-biphenyl]-3-yl)-6-(methylsulfonyl)-1H-indole-2-carboxamide;
241) N-(2',4'-difluoro-[1,1'-biphenyl]-3-yl)-3-methyl-6-(methylsulfonamido)benzo[b]thiophene-2-carboxamide;
242) N-(2',4'-difluoro-[1,1'-biphenyl]-3-yl)-6-(methylsulfonamido)benzo[b]thiophene-2-carboxamide;
243) N-(2',4'-difluoro-[1,1'-biphenyl]-3-yl)-3-methyl-5-(methylsulfonamido)benzo[b]thiophene-2-carboxamide;
244) N-(4'-fluoro-2'-(trifluoromethyl)-[1,1'-biphenyl]-3-yl)-6-nitro-1H-indole-2-carboxamide;
245) N-(5-acetyl-2',4'-difluoro-[1,1'-biphenyl]-3-yl)-6-(methylsulfonamido)-1H-indole-2-carboxamide;
246) N-(4-(2,4-difluorophenyl)-1H-indazol-6-yl)-6-(methylsulfonamido)-1H-indole-2-carboxamide;
247) N-(2',4'-difluoro-[1,1'-biphenyl]-3-yl)-1-methyl-6-nitro-1H-indole-2-carboxamide;
248) N-(2',4'-difluoro-[1,1'-biphenyl]-3-yl)-1-methyl-6-(methylsulfonamido)-1H-indole-2-carboxamide;
249) 1-methyl-6-nitro-N-(2'-(trifluoromethyl)-[1,1'-biphenyl]-3-yl)-1H-indole-2-carboxamide;
250) 1-methyl-5-nitro-N-(2'-(trifluoromethyl)-[1,1'-biphenyl]-3-yl)-1H-indole-2-carboxamide;
251) 3-methyl-1-(2-morpholino ethyl)-5-nitro-N-(2'-(trifluoromethyl)-[1,1'-biphenyl]-3-yl)-1H-indole-2-carboxamide;
252) 1-(2-morpholinoethyl)-6-nitro-N-(2'-(trifluoromethyl)-[1,1'-biphenyl]-3-yl)-1H-indole-2-carboxamide;
253) 1-methyl-6-(methylsulfonamido)-N-(2'-(trifluoromethyl)-[1,1'-biphenyl]-3-yl)-1H-indole-2-carboxamide;
254) 2-((2-((2',4'-difluoro-[1,1'-biphenyl]-3-yl)carbamoyl)-1H-indol-6-yl)oxy)-2-methylpropanoic acid;
255) ethyl 2-((2-((2',4'-difluoro-[1,1'-biphenyl]-3-yl)carbamoyl)-1H-indol-6-yl)oxy)acetate;
256) 2-((2-((2',4'-difluoro-[1,1'-biphenyl]-3-yl)carbamoyl)-1H-indol-6-yl)oxy)acetic acid;
257) N-(2',4'-difluoro-[1,1'-biphenyl]-3-yl)-6-((N-methylsulfamoyl)amino)-1H-indole-2-carboxamide;
258) 5-amino-N-(2'-(trifluoromethyl)-[1,1'-biphenyl]-3-yl)-1H-indole-2-carboxamide;
259) 5-(methylsulfonamido)-N-(2'-(trifluoromethyl)-[1,1'-biphenyl]-3-yl)-1H-indole-2-carboxamide;
260) 6-(methylsulfonamido)-N-(2'-(trifluoromethyl)-[1,1'-biphenyl]-3-yl)-1H-indole-2-carboxamide;
261) N-(2',4'-difluoro-[1,1'-biphenyl]-3-yl)-6-(methylsulfonamido)indoline-2-carboxamide;
262) N-(4'-fluoro-2'-(trifluoromethyl)-[1,1'-biphenyl]-3-yl)-6-(methylsulfonamido)indoline-2-carboxamide;
263) tert-butyl 6-nitro-2-((2'-(trifluoromethyl)-[1,1'-biphenyl]-3-yl)carbamoyl)-1H-indole-1-carboxylate;
264) 6-(2,2,2-trifluoroethyl sulfonamido)-N-(2'-(trifluoromethyl)-[1,1'-biphenyl]-3-yl)-1H-indole-2-carboxamide;
265) 6-(sulfamoylamino)-N-(2'-(trifluoromethyl)-[1,1'-biphenyl]-3-yl)-1H-indole-2-carboxamide;
266) 6-(methylsulfonamido)-N-(2'-(trifluoromethyl)-[1,1'-biphenyl]-3-yl)-1H-indole-3-carboxamide;
267) 6-((N,N-dimethylsulfamoyl)amino)-N-(2'-(trifluoromethyl)-[1,1'-biphenyl]-3-yl)-1H-indole-2-carboxamide;
268) N-(2'-(trifluoromethyl)-[1,1'-biphenyl]-3-yl)-6-(trifluoromethylsulfonamido)-1H-indole-2-carboxamide;
269) 64N-methylsulfamoyl)amino)-N-(2'-(trifluoromethyl)-[1,1'-biphenyl]-3-yl)-1H-indole-2-carboxamide;
270) N-(2',4'-difluoro-[1,1'-biphenyl]-3-yl)-6-(methylsulfonamido)-1H-indole-2-carboxamide;
271) 6-amino-N-(2',4'-difluoro-[1,1'-biphenyl]-3-yl)-1H-indole-2-carboxamide;
272) N-(2',4'-difluoro-[1,1'-biphenyl]-3-yl)-5-(methylsulfonamido)-1H-indole-2-carboxamide;
273) N-(2',4'-difluoro-[1,1'-biphenyl]-3-yl)-6-(2,2,2-trifluoro ethylsulfonamido)-1H-indole-2-carboxamide;

274) N-(2',4'-difluoro-[1,1'-biphenyl]-3-yl)-6-(sulfamoylamino)-1H-indole-2-carboxamide;
275) N-(2',4'-difluoro-[1,1'-biphenyl]-3-yl)-6-(methylsulfonamido)-1H-indole-3-carboxamide;
276) N-(2',4'-difluoro-[1,1'-biphenyl]-3-yl)-6-((N,N-dimethylsulfamoyl)amino)-1H-indole-2-carboxamide;
277) N-(4'-fluoro-2'-(trifluoromethyl)-[1,1'-biphenyl]-3-yl)-6-(methylsulfonamido)-1H-indole-2-carboxamide;
278) 6-(cyclopropanesulfonamido)-N-(4-(2,4-difluorophenyl)pyridin-2-yl)-1H-indole-2-carboxamide;
279) N-(4-(2,4-difluorophenyl)pyridin-2-yl)-6-(methylsulfonamido)-1H-indole-2-carboxamide;
280) N-(2',4'-difluoro-[1,1'-biphenyl]-3-yl)-N-methyl-6-(methylsulfonamido)-1H-indole-2-carboxamide;
281) N-(5'-methoxy-2'-(trifluoromethyl)-[1,1'-biphenyl]-3-yl)-6-(methylsulfonamido)-1H-indole-2-carboxamide;
282) N-(5'-methoxy-2'-(trifluoromethyl)-[1,1'-biphenyl]-3-yl)-6-nitro-1H-indole-2-carboxamide;
283) 6-(methylsulfonamido)-N-(4'-sulfamoyl-2'-(trifluoromethyl)-[1,1'-biphenyl]-3-yl)-1H-indole-2-carboxamide;
284) N-(4'-cyano-2'-(trifluoromethyl)-[1,1'-biphenyl]-3-yl)-6-(methylsulfonamido)-1H-indole-2-carboxamide;
285) 6-(methylsulfonamido)-N-(4'-nitro-2'-(trifluoromethyl)-[1,1'-biphenyl]-3-yl)-1H-indole-2-carboxamide;
286) methyl 3'-(6-nitro-1H-indole-2-carboxamido)-6-(trifluoromethyl)-[1,1'-biphenyl]-3-carboxylate;
287) methyl 3'-(6-(methylsulfonamido)-1H-indole-2-carboxamido)-6-(trifluoromethyl)-[1,1'-biphenyl]-3-carboxylate;
288) methyl 4-methoxy-3'-(6-nitro-1H-indole-2-carboxamido)-6-(trifluoromethyl)-[1,1'-biphenyl]-3-carboxylate;
289) methyl 4-methoxy-3'-(6-(methylsulfonamido)-1H-indole-2-carboxamido)-6-(trifluoromethyl)-[1,1'-biphenyl]-3-carboxylate;
290) 6-(methylsulfonamido)-N-(3-(3-(trifluoromethyl)pyridin-2-yl)phenyl)-1H-indole-2-carboxamide;
291) 6-(methylsulfonamido)-N-(3-(4-(trifluoromethyl)pyridin-3-yl)phenyl)-1H-indole-2-carboxamide;
292) 6-nitro-N-(3-(2-(trifluoromethyl)pyridin-3-yl)phenyl)-1H-indole-2-carboxamide;
293) 6-(methylsulfonamido)-N-(3-(2-(trifluoromethyl)pyridin-3-yl)phenyl)-1H-indole-2-carboxamide;
294) N-(3-(6-chloro-4-(trifluoromethyl)pyridin-3-yl)phenyl)-6-(methylsulfonamido)-1H-indole-2-carboxamide;
295) N-(2'-fluoro-4'-methoxy-[1,1'-biphenyl]-3-yl)-6-nitro-1H-indole-2-carboxamide;
296) tert-butyl 2-((2'-fluoro-4'-methoxy-[1,1'-biphenyl]-3-yl)carbamoyl)-6-(methylsulfonamido)-1H-indole-1-carboxylate;
297) N-(4-(2-fluoro-5-methoxyphenyl)pyridin-2-yl)-6-nitro-1H-indole-2-carboxamide;
298) methyl 6-chloro-3'-(6-nitro-1H-indole-2-carboxamido)-[1,1'-biphenyl]-3-carboxylate;
299) methyl 6-chloro-3'-(6-(methylsulfonamido)-1H-indole-2-carboxamido)-[1,1'-biphenyl]-3-carboxylate;
300) methyl 4-chloro-3-(2-(6-(methylsulfonamido)-1H-indole-2-carboxamido)pyridin-4-yl)benzoate;
301) N-(5-cyano-2',4'-difluoro-[1,1'-biphenyl]-3-yl)-6-(methylsulfonamido)-1H-indole-2-carboxamide;
302) N-(5-bromo-2',4'-difluoro-[1,1'-biphenyl]-3-yl)-6-(methylsulfonamido)-1H-indole-2-carboxamide;
303) N-(5-bromo-2',4'-difluoro-[1,1'-biphenyl]-3-yl)-5-methoxy-6-(methylsulfonamido)-1H-indole-2-carboxamide;
304) N-(5-bromo-2',4'-difluoro-[1,1'-biphenyl]-3-yl)-6-(methylsulfonyl)-1H-indole-2-carboxamide;
305) N-(5-bromo-2',4'-difluoro-[1,1'-biphenyl]-3-yl)-5-(methylsulfonamido)benzo[b]thiophene-2-carboxamide;
306) N-(5-bromo-2',4'-difluoro-[1,1'-biphenyl]-3-yl)-5-(methylsulfonamido)benzofuran-2-carboxamide;
307) N-(5-bromo-2',4'-difluoro-[1,1'-biphenyl]-3-yl)-6-((N-methylsulfamoyl)amino)-1H-indole-2-carboxamide;
308) N-(5-bromo-2',4'-difluoro-[1,1'-biphenyl]-3-yl)-5-(trifluoromethoxy)-1H-indole-2-carboxamide;
309) N-(5-bromo-2',4'-difluoro-[1,1'-biphenyl]-3-yl)-3-methyl-6-(methylsulfonamido)benzo[b]thiophene-2-carboxamide;
310) N-(5-bromo-2',4'-difluoro-[1,1'-biphenyl]-3-yl)-6-(methylsulfonamido)benzo[b]thiophene-2-carboxamide;
311) N-(5-bromo-2',4'-difluoro-[1,1'-biphenyl]-3-yl)-3-methyl-5-(methylsulfonamido)benzo[b]thiophene-2-carboxamide;
312) 6-(methylsulfonamido)-N-(2',4',5-trifluoro-[1,1'-biphenyl]-3-yl)-1H-indole-2-carboxamide;
313) N-(2',4'-difluoro-5-(trifluoromethyl)-[1,1'-biphenyl]-3-yl)-6-(methylsulfonamido)-1H-indole-2-carboxamide;
314) N-(2',4'-difluoro-5-methoxy-[1,1'-biphenyl]-3-yl)-6-(methylsulfonamido)-1H-indole-2-carboxamide;
315) N-(5-cyano-4'-fluoro-2'-(trifluoromethyl)-[1,1'-biphenyl]-3-yl)-6-(methylsulfonamido)-1H-indole-2-carboxamide;
316) N-(2',4'-difluoro-5-methoxy-[1,1'-biphenyl]-3-yl)-3-methyl-6-(methylsulfonamido)benzo[b]thiophene-2-carboxamide;
317) N-(2',4'-difluoro-5-methoxy-[1,1'-biphenyl]-3-yl)-5-(methylsulfonamido)benzo[b]thiophene-2-carboxamide;
318) N-(2',4'-difluoro-5-(methylcarbamoyl)-[1,1'-biphenyl]-3-yl)-6-(methylsulfonamido)-1H-indole-2-carboxamide;
319) N-(5-(dimethylcarbamoyl)-2',4'-difluoro-[1,1'-biphenyl]-3-yl)-6-(methylsulfonamido)-1H-indole-2-carboxamide;
320) N-(2',4'-difluoro-5-(piperidine-1-carbonyl)-[1,1'-biphenyl]-3-yl)-6-(methylsulfonamido)-1H-indole-2-carboxamide;
321) N-(2',4'-difluoro-5-(morpholine-4-carbonyl)-[1,1'-biphenyl]-3-yl)-6-(methylsulfonamido)-1H-indole-2-carboxamide;
322) N-(5-chloro-2',4'-difluoro-[1,1'-biphenyl]-3-yl)-6-fluoro-5-(methylsulfonamido)benzo[b]thiophene-2-carboxamide;
323) N-(5-chloro-2',4'-difluoro-[1,1'-biphenyl]-3-yl)-5-(methylsulfonamido)benzo[b]thiophene-2-carboxamide;
324) N-(5-chloro-3'-methoxy-5'-(trifluoromethoxy)-[1,1'-biphenyl]-3-yl)-5-(methylsulfonamido)benzo[b]thiophene-2-carboxamide;
325) N-(5-chloro-3'-methoxy-5'-(trifluoromethoxy)-[1,1'-biphenyl]-3-yl)-6-fluoro-5-(methylsulfonamido)benzo[b]thiophene-2-carboxamide;
326) N-(5-chloro-3'-methoxy-5'-(trifluoromethoxy)-[1,1'-biphenyl]-3-yl)-6-fluoro-5-(N-methylmethylsulfonamido)benzo[b]thiophene-2-carboxamide;
327) N-(5-chloro-2',4'-difluoro-[1,1'-biphenyl]-3-yl)-5-((tetrahydrofuran)-3-sulfonamido)benzo[b]thiophene-2-carboxamide;
328) N-(5-chloro-3'-methoxy-5'-(trifluoromethoxy)-[1,1'-biphenyl]-3-yl)-5-((tetrahydrofuran)-3-sulfonamido)benzo[b]thiophene-2-carboxamide;
329) N-(5-chloro-2',4'-difluoro-[1,1'-biphenyl]-3-yl)-6-fluoro-5-(N-methylmethylsulfonamido)benzo[b]thiophene-2-carboxamide;

330) N-(5-chloro-2',4'-difluoro-[1,1'-biphenyl]-3-yl)-6-fluoro-5-((tetrahydrofuran)-3-sulfonamido)benzo[b]thiophene-2-carboxamide;
331) N-(4-chloro-6-(2,4-difluorophenyl)pyridin-2-yl)-5-(methylsulfonamido)benzo[b]thiophene-2-carboxamide;
332) N-(3-chloro-5-(thiophen-3-yl)phenyl)-5-(methylsulfonamido)benzo[b]thiophene-2-carboxamide;
333) 6-chloro-N-(5-chloro-2',4'-difluoro-[1,1'-biphenyl]-3-yl)-5-(methylsulfonamido)benzo[b]thiophene-2-carboxamide;
334) N-(3-chloro-5-(1-methyl-1H-pyrrol-2-yl)phenyl)-5-(methylsulfonamido)benzo[b]thiophene-2-carboxamide;
335) N-(5-chloro-2',4'-difluoro-[1,1'-biphenyl]-3-yl)-3-hydroxy-5-(methylsulfonamido)benzo[b]thiophene-2-carboxamide;
336) N-(3-chloro-5-(thiophen-2-yl)phenyl)-5-(methylsulfonamido)benzo[b]thiophene-2-carboxamide;
337) N-(6-chloro-4-(2,4-difluorophenyl)pyridin-2-yl)-5-(methylsulfonamido)benzo[b]thiophene-2-carboxamide;
338) N-(3-chloro-5-(pyrazin-2-yl)phenyl)-5-(methylsulfonamido)benzo[b]thiophene-2-carboxamide;
339) N-(3-chloro-5-(6-chloropyrazin-2-yl)phenyl)-5-(methylsulfonamido)benzo[b]thiophene-2-carboxamide;
340) N-(3-chloro-5-(1-methyl-1H-imidazol-5-yl)phenyl)-5-(methylsulfonamido)benzo[b]thiophene-2-carboxamide;
341) N-(5-bromo-2',4'-difluoro-[1,1'-biphenyl]-3-yl)-1-methyl-6-(N-methylmethylsulfonamido)-1H-indole-2-carboxamide;
342) N-(5-bromo-2',4'-difluoro-[1,1'-biphenyl]-3-yl)-6-(N-methylmethylsulfonamido)-1H-indole-2-carboxamide;
343) 1-methyl-6-(N-methylmethylsulfonamido)-N-(2'-(trifluoromethyl)-[1,1'-biphenyl]-3-yl)-1H-indole-2-carboxamide;
344) N-(2',4'-difluoro-[1,1'-biphenyl]-3-yl)-6-(N-methylmethylsulfonamido)-1H-indole-2-carboxamide;
345) N-(2',4'-difluoro-[1,1'-biphenyl]-3-yl)-1-methyl-6-(N-methylmethylsulfonamido)-1H-indole-2-carboxamide;
346) 6-(N-methylmethylsulfonamido)-N-(2'-(trifluoromethyl)-[1,1'-biphenyl]-3-yl)-1H-indole-2-carboxamide;
347) N-(2',4'-difluoro-5-methoxy-[1,1'-biphenyl]-3-yl)-6-(N-methylmethylsulfonamido)-1H-indole-2-carboxamide;
348) N-(2',4'-difluoro-5-methoxy-[1,1'-biphenyl]-3-yl)-1-methyl-6-(N-methylmethylsulfonamido)-1H-indole-2-carboxamide;
349) N-(2',4'-difluoro-5-(6-fluoropyridin-3-yl)-[1,1'-biphenyl]-3-yl)-6-(methylsulfonamido)-1H-indole-2-carboxamide;
350) tert-butyl 2-(2',4'-difluoro-5-(6-(methylsulfonamido)-1H-indole-2-carboxamido)-[1,1'-biphenyl]-3-yl)-1H-pyrrole-1-carboxylate;
351) N-(2',4'-difluoro-5-(1H-pyrazol-3-yl)-[1,1'-biphenyl]-3-yl)-6-(methylsulfonamido)-1H-indole-2-carboxamide;
352) N-(2',4'-difluoro-5-(1H-pyrrol-2-yl)-[1,1'-biphenyl]-3-yl)-6-(methylsulfonamido)-1H-indole-2-carboxamide;
353) N-(2',4'-difluoro-5-(1-methyl-1H-pyrrol-2-yl)-[1,1'-biphenyl]-3-yl)-6-(methylsulfonamido)-1H-indole-2-carboxamide;
354) N-(2',4'-difluoro-5-(thiophen-2-yl)-[1,1'-biphenyl]-3-yl)-6-(methylsulfonamido)-1H-indole-2-carboxamide;
355) N-(2',4'-difluoro-5-(thiophen-3-yl)-[1,1'-biphenyl]-3-yl)-6-(methylsulfonamido)-1H-indole-2-carboxamide;
356) N-(2',4'-difluoro-5-(pyridin-4-yl)-[1,1'-biphenyl]-3-yl)-6-(methylsulfonamido)-1H-indole-2-carboxamide;
357) N-(2',4'-difluoro-5-(pyridin-3-yl)-[1,1'-biphenyl]-3-yl)-6-(methylsulfonamido)-1H-indole-2-carboxamide;
358) N-(2',4'-difluoro-5-(6-(trifluoromethyl)pyridin-3-yl)-[1,1'-biphenyl]-3-yl)-6-(methylsulfonamido)-1H-indole-2-carboxamide;
359) N-(5-(6-cyanopyridin-3-yl)-2',4'-difluoro-[1,1'-biphenyl]-3-yl)-6-(methylsulfonamido)-1H-indole-2-carboxamide;
360) N-(2',4'-difluoro-5-(pyrimidin-5-yl)-[1,1'-biphenyl]-3-yl)-6-(methylsulfonamido)-1H-indole-2-carboxamide;
361) N-(5-(2-aminopyrimidin-5-yl)-2',4'-difluoro-[1,1'-biphenyl]-3-yl)-6-(methylsulfonamido)-1H-indole-2-carboxamide;
362) 6-(methylsulfonamido)-N-(2,2'',4,4''-tetrafluoro-[1,1':3',1''-terphenyl]-5'-yl)-1H-indole-2-carboxamide;
363) N-(5-(cyanomethyl)-2',4'-difluoro-[1,1'-biphenyl]-3-yl)-6-(methylsulfonamido)-1H-indole-2-carboxamide;
364) N-(2',4'-difluoro-5-(6-hydroxypyridin-3-yl)-[1,1'-biphenyl]-3-yl)-6-(methylsulfonamido)-1H-indole-2-carboxamide;
365) N-(5-ethynyl-2',4'-difluoro-[1,1'-biphenyl]-3-yl)-6-(methylsulfonamido)-1H-indole-2-carboxamide;
366) N-(5-(2,2-difluoroethoxy)-2',4'-difluoro-[1,1'-biphenyl]-3-yl)-6-(methylsulfonamido)-1H-indole-2-carboxamide;
367) N-(2',4'-difluoro-5-isobutoxy-[1,1'-biphenyl]-3-yl)-6-(methylsulfonamido)-1H-indole-2-carboxamide;
368) N-(5-(cyanomethoxy)-2',4'-difluoro-[1,1'-biphenyl]-3-yl)-6-(methylsulfonamido)-1H-indole-2-carboxamide;
369) N-(5-(difluoromethoxy)-2',4'-difluoro-[1,1'-biphenyl]-3-yl)-6-(methylsulfonamido)-1H-indole-2-carboxamide;
370) N-(5-(difluoromethoxy)-2',4'-difluoro-[1,1'-biphenyl]-3-yl)-5-(methylsulfonamido)benzo[b]thiophene-2-carboxamide;
371) N-(2',4'-difluoro-5-(piperidin-1-yl)-[1,1'-biphenyl]-3-yl)-6-(methylsulfonamido)-1H-indole-2-carboxamide;
372) N-(5-(dimethylamino)-2',4'-difluoro-[1,1'-biphenyl]-3-yl)-6-(methylsulfonamido)-1H-indole-2-carboxamide;
373) N-(2',4'-difluoro-5-(methylamino)-[1,1'-biphenyl]-3-yl)-6-(methylsulfonamido)-1H-indole-2-carboxamide;
374) N-(2',4'-difluoro-5-morpholino-[1,1'-biphenyl]-3-yl)-6-(methylsulfonamido)-1H-indole-2-carboxamide;
375) N-(5-(dimethylamino)-2',4'-difluoro-[1,1'-biphenyl]-3-yl)-5-(methylsulfonamido)benzo[b]thiophene-2-carboxamide;
376) N-(5-(dimethylamino)-2',4'-difluoro-[1,1'-biphenyl]-3-yl)-5-(methylsulfonamido)benzofuran-2-carboxamide;
377) N-(5'-carbamoyl-4'-methoxy-2'-(trifluoromethyl)-[1,1'-biphenyl]-3-yl)-6-(methylsulfonamido)-1H-indole-2-carboxamide;
378) N-(5'-carbamoyl-4'-hydroxy-2'-(trifluoromethyl)-[1,1'-biphenyl]-3-yl)-6-(methylsulfonamido)-1H-indole-2-carboxamide;
379) N-(5'-carbamoyl-2'-(trifluoromethyl)-[1,1'-biphenyl]-3-yl)-6-(methylsulfonamido)-1H-indole-2-carboxamide;
380) N-(5'-carbamoyl-2'-chloro-[1,1'-biphenyl]-3-yl)-6-(methylsulfonamido)-1H-indole-2-carboxamide;
381) N-(4-(5-carbamoyl-2-chlorophenyl)pyridin-2-yl)-6-(methylsulfonamido)-1H-indole-2-carboxamide;
382) N-(2',4'-difluoro-5-(6-methoxypyridin-3-yl)-[1,1'-biphenyl]-3-yl)-6-(methylsulfonamido)-1H-indole-2-carboxamide;
383) N-(2',4'-difluoro-5-(6-methoxypyridin-2-yl)-[1,1'-biphenyl]-3-yl)-6-(methylsulfonamido)-1H-indole-2-carboxamide;
384) N-(2',4'-difluoro-5-(6-hydroxypyridin-2-yl)-[1,1'-biphenyl]-3-yl)-6-(methylsulfonamido)-1H-indole-2-carboxamide;

385) N-(4'-amino-2'-(trifluoromethyl)-[1,1'-biphenyl]-3-yl)-6-(methylsulfonamido)-1H-indole-2-carboxamide;
386) N-(4'-(methylamino)-2'-(trifluoromethyl)-[1,1'-biphenyl]-3-yl)-6-(methylsulfonamido)-1H-indole-2-carboxamide;
387) N-(3-(difluoro(phenyl)methyl)phenyl)-6-(methylsulfonamido)-1H-indole-2-carboxamide;
388) N-(3-(difluoro(pyridin-4-yl)methyl)phenyl)-6-(methylsulfonamido)-1H-indole-2-carboxamide;
389) N-(3-(difluoro(pyridin-2-yl)methyl)phenyl)-6-(methylsulfonamido)-1H-indole-2-carboxamide;
390) N-(3-((3-cyanophenyl)difluoromethyl)phenyl)-6-(methylsulfonamido)-1H-indole-2-carboxamide;
391) N-(3-((3-cyanophenyl)difluoromethyl)-5-(2,2-difluoroethoxy)phenyl)-6-(methylsulfonamido)-1H-indole-2-carboxamide;
392) N-(3-((3-cyanophenyl)difluoromethyl)-5-isobutoxyphenyl)-6-(methylsulfonamido)-1H-indole-2-carboxamide;
393) N-(3-(cyanomethoxy)-5-((3-cyanophenyl)difluoromethyl)phenyl)-6-(methylsulfonamido)-1H-indole-2-carboxamide;
394) N-(3-((4-methoxyphenyl)sulfonyl)phenyl)-6-(methylsulfonamido)-1H-indole-2-carboxamide;
395) 6-(methylsulfonamido)-N-(3-(phenyl sulfonyl)phenyl)-1H-indole-2-carboxamide;
396) 6-(methylsulfonamido)-N-(3-(trifluoromethoxy)phenyl)sulfonyl)phenyl)-1H-indole-2-carboxamide;
397) N-(3-methoxy-5-((3-(trifluoromethoxy)phenyl)sulfonyl)phenyl)-6-(methylsulfonamido)-1H-indole-2-carboxamide;
398) 6-(methylsulfonamido)-N-(3-((3-(trifluoromethoxy)phenyl)sulfonyl)-5-(trifluoromethyl)phenyl)-1H-indole-2-carboxamide;
399) N-(3-cyano-5-((3-(trifluoromethoxy)phenyl)sulfonyl)phenyl)-6-(methylsulfonamido)-1H-indole-2-carboxamide;
400) N-(3-isobutoxy-5-((3-(trifluoromethoxy)phenyl)sulfonyl)phenyl)-6-(methylsulfonamido)-1H-indole-2-carboxamide;
401) N-(3-(2,2-difluoroethoxy)-5-((3-(trifluoromethoxy)phenyl)sulfonyl)phenyl)-6-(methylsulfonamido)-1H-indole-2-carboxamide;
402) N-(3-((3-cyanophenyl)sulfonyl)phenyl)-6-(methylsulfonamido)-1H-indole-2-carboxamide;
403) 6-(methylsulfonamido)-N-(3-(pyridin-2-ylsulfonyl)phenyl)-1H-indole-2-carboxamide;
404) 6-(methylsulfonamido)-N-(3-(pyridin-3-yl sulfonyl)phenyl)-1H-indole-2-carboxamide;
405) N-(3-((3-chlorophenyl)sulfonyl)phenyl)-6-(methylsulfonamido)-1H-indole-2-carboxamide;
406) N-(3-((6-cyanopyridin-2-yl)sulfonyl)phenyl)-6-(methylsulfonamido)-1H-indole-2-carboxamide;
407) N-(3-((5-methoxypyridin-3-yl)sulfonyl)phenyl)-6-(methylsulfonamido)-1H-indole-2-carboxamide;
408) N-(3-((6-methoxypyridin-2-yl)sulfonyl)phenyl)-6-(methylsulfonamido)-1H-indole-2-carboxamide;
409) N-(3-(benzo[b]thiophen-5-ylsulfonyl)phenyl)-6-(methylsulfonamido)-1H-indole-2-carboxamide;
410) N-(3-((2-methylbenzo[d]thiazol-6-yl)sulfonyl)phenyl)-6-(methylsulfonamido)-1H-indole-2-carboxamide;
411) N-(3-((3-cyano-5-methoxyphenyl)sulfonyl)phenyl)-6-(methylsulfonamido)-1H-indole-2-carboxamide;
412) N-(3-((3-(cyanomethyl)phenyl)sulfonyl)phenyl)-6-(methylsulfonamido)-1H-indole-2-carboxamide;
413) 6-(methylsulfonamido)-N-(3-((4-oxo-4H-chromen-7-yl)sulfonyl)phenyl)-1H-indole-2-carboxamide;
414) N-(3-((3-bromophenyl)sulfonyl)phenyl)-6-(methylsulfonamido)-1H-indole-2-carboxamide;
415) N-(3-((3-aminophenyl) sulfonyl)phenyl)-6-(methylsulfonamido)-1H-indole-2-carboxamide;
416) N-(3-ethynylphenyl)sulfonyl)phenyl)-6-(methylsulfonamido)-1H-indole-2-carboxamide;
417) N-(3-((3-cyano-5-hydroxyphenyl)sulfonyl)phenyl)-6-(methylsulfonamido)-1H-indole-2-carboxamide;
418) N-(3-bromo-5-((7-fluoro-3,4-dihydroisoquinolin-2 (1H)-yl)sulfonyl)phenyl)-5-(methylsulfonamido)benzo[b]thiophene-2-carboxamide;
419) N-(3-bromo-5-((5,7-difluoro-3,4-dihydroisoquinolin-2 (1H)-yl)sulfonyl)phenyl)-5-(methylsulfonamido)benzo[b]thiophene-2-carboxamide;
420) N-(3-bromo-5-((4,4-difluoropiperidin-1-yl)sulfonyl)phenyl)-5-(methylsulfonamido)benzo[b]thiophene-2-carboxamide;
421) 5-(methylsulfonamido)-N-(3-(1-phenylcyclopropyl)phenyl)benzo[b]thiophene-2-carboxamide;
422) 6-(methylsulfonamido)-N-(3-(1-phenylcyclopropyl)phenyl)-1H-indole-2-carboxamide;
423) 5-(methylsulfonamido)-N-(3-(1-phenylvinyl)phenyl)benzo[b]thiophene-2-carboxamide;
424) N-(3-(1-(4-fluorophenyl)cyclopropyl)phenyl)-5-(methylsulfonamido)benzo[b]thiophene-2-carboxamide;
425) N-(3-(1-(4-fluorophenyl)cyclopropyl)phenyl)-6-(methylsulfonamido)-1H-indole-2-carboxamide;
426) N-(3-bromo-5-(1-(2,4-difluorophenyl)cyclopropyl)phenyl)-5-(methylsulfonamido)benzo[b]thiophene-2-carboxamide;
427) N-(3-methoxy-5-(1-(3-methoxy-5-(trifluoromethoxy)phenyl)cyclopropyl)phenyl)-5-(methylsulfonamido)benzo[b]thiophene-2-carboxamide;
428) N-(3-(difluoromethoxy)-5-(1-(4-fluorophenyl) cyclopropyl)phenyl)-6-(methylsulfonamido)-1H-indole-2-carboxamide;
429) N-(3-(difluoromethoxy)-5-(1-(4-fluorophenyl)cyclopropyl)phenyl)-5-(methylsulfonamido)benzo[b]thiophene-2-carboxamide;
430) N-(3-chloro-5-(1-(3-isopropoxy-5-(trifluoromethoxy)phenyl)cyclopropyl)phenyl)-6-fluoro-5-(N-methylmethylsulfonamido)benzo[b]thiophene-2-carboxamide;
431) N-(3-chloro-5-(1-(3-isopropoxy-5-(trifluoromethoxy)phenyl)cyclopropyl)phenyl)-5-(methylsulfonamido)benzo[b]thiophene-2-carboxamide;
432) N-(3-chloro-5-(1-(4-chlorophenyl)cyclopropyl)phenyl)-5-(methylsulfonamido)benzo[b]thiophene-2-carboxamide;
433) 6-chloro-N-(3-chloro-5-(1-(4-chlorophenyl)cyclopropyl)phenyl)-5-(methylsulfonamido)benzo[b]thiophene-2-carboxamide;
434) N-(3-benzoylphenyl)-6-(methylsulfonamido)-1H-indole-2-carboxamide;
435) N-(3-(1-hydroxy-1-phenylethyl)phenyl)-6-(methylsulfonamido)-1H-indole-2-carboxamide;
436) 6-(N-(2-amino-2-oxoethyl)methylsulfonamido)-N-(3-(2-(3-hydroxy-5-(trifluoromethoxy)phenyl)propan-2-yl)phenyl)-1H-indole-2-carboxamide;
437) N-(3-(2-(3-(2-amino-2-oxoethoxy)-5-(trifluoromethoxy)phenyl)propan-2-yl)phenyl)-6-(N-(2-amino-2-oxoethyl)methylsulfonamido)-1H-indole-2-carboxamide;
438) N-(3-chloro-5-((2,4-difluorophenyl)amino)phenyl)-5-(methylsulfonamido)benzo[b]thiophene-2-carboxamide;
439) N-(3-chloro-5-((2,4-difluorophenyl)(methyl)amino) phenyl)-5-(methylsulfonamido)benzo[b]thiophene-2-carboxamide;

440) N-(3-chloro-5-((4-chlorophenyl)(methyl)amino)phenyl)-5-(methylsulfonamido)benzo[b]thiophene-2-carboxamide;
441) 6-chloro-N-(3-chloro-5-((4-chlorophenyl)(methyl)amino)phenyl)-5-(methylsulfonamido)benzo[b]thiophene-2-carboxamide;
442) 6-chloro-N-(3-chloro-5-((2,4-difluorophenyl)(methyl)amino)phenyl)-5-(methylsulfonamido)benzo[b]thiophene-2-carboxamide;
443) N-(3-chloro-5-((3-isopropoxy-5-(trifluoromethoxy)phenyl)(methyl)amino)phenyl)-5-(methylsulfonamido)benzo[b]thiophene-2-carboxamide;
444) N-(3-chloro-5-(2,4-difluorophenoxy)phenyl)-5-(methylsulfonamido)benzo[b]thiophene-2-carboxamide;
445) N-(3-chloro-5-(4-chlorophenoxy)phenyl)-5-(methylsulfonamido)benzo[b]thiophene-2-carboxamide;
446) N-(3-chloro-5-(4-fluorophenoxy)phenyl)-5-(methylsulfonamido)benzo[b]thiophene-2-carboxamide;
447) N-(3-chloro-5-(4-methoxyphenoxy)phenyl)-5-(methylsulfonamido)benzo[b]thiophene-2-carboxamide;
448) N-(3-chloro-5-(2,5-difluorophenoxy)phenyl)-5-(methylsulfonamido)benzo[b]thiophene-2-carboxamide;
449) 6-chloro-N-(3-chloro-5-(4-chlorophenoxy)phenyl)-5-(methylsulfonamido)benzo[b]thiophene-2-carboxamide;
450) N-(3-chloro-5-(3-(trifluoromethoxy)phenoxy)phenyl)-5-(methylsulfonamido)benzo[b]thiophene-2-carboxamide;
451) N-(3-chloro-5-(4-cyanophenoxy)phenyl)-5-(methylsulfonamido)benzo[b]thiophene-2-carboxamide;
452) N-(3-chloro-5-(3-isopropoxy-5-(trifluoromethoxy)phenoxy)phenyl)-5-(methylsulfonamido)benzo[b]thiophene-2-carboxamide;
453) 6-bromo-N-(3-chloro-5-(4-chlorophenoxy)phenyl)-5-(methylsulfonamido)benzo[b]thiophene-2-carboxamide;
454) N-(3-chloro-5-(4-(trifluoromethoxy)phenoxy)phenyl)-5-(methylsulfonamido)benzo[b]thiophene-2-carboxamide;
455) N-(3-chloro-5-(3-(trifluoromethyl)phenoxy)phenyl)-5-(methylsulfonamido)benzo[b]thiophene-2-carboxamide;
456) N-(3-chloro-5-(3-chlorophenoxy)phenyl)-5-(methylsulfonamido)benzo[b]thiophene-2-carboxamide;
457) N-(3-chloro-5-(3-methoxyphenoxy)phenyl)-5-(methylsulfonamido)benzo[b]thiophene-2-carboxamide;
458) N-(3-chloro-5-(3-chloro-5-cyanophenoxy)phenyl)-5-(methylsulfonamido)benzo[b]thiophene-2-carboxamide;
459) N-(3-chloro-5-(3-cyanophenoxy)phenyl)-5-(methylsulfonamido)benzo[b]thiophene-2-carboxamide;
460) N-(3-chloro-5-(3,4-difluorophenoxy)phenyl)-5-(methylsulfonamido)benzo[b]thiophene-2-carboxamide;
461) N-(3-chloro-5-(3-chloro-4-fluorophenoxy)phenyl)-5-(methylsulfonamido)benzo[b]thiophene-2-carboxamide;
462) N-(3-chloro-5-(2,4-dichlorophenoxy)phenyl)-5-(methylsulfonamido)benzo[b]thiophene-2-carboxamide;
463) N-(3-chloro-5-(3,5-difluorophenoxy)phenyl)-5-(methylsulfonamido)benzo[b]thiophene-2-carboxamide;
464) N-(3-chloro-5-(3,5-dichlorophenoxy)phenyl)-5-(methylsulfonamido)benzo[b]thiophene-2-carboxamide;
465) N-(3-chloro-5-(4-(trifluoromethyl)phenoxy)phenyl)-5-(methylsulfonamido)benzo[b]thiophene-2-carboxamide;
466) N-(3-chloro-5-(4-chloro-3-fluorophenoxy)phenyl)-5-(methylsulfonamido)benzo[b]thiophene-2-carboxamide;
467) N-(3-chloro-5-(3-chloro-5-(trifluoromethoxy)phenoxy)phenyl)-5-(methylsulfonamido)benzo[b]thiophene-2-carboxamide;
468) N-(3-chloro-5-(4-chloro-3-(trifluoromethoxy)phenoxy)phenyl)-5-(methylsulfonamido)benzo[b]thiophene-2-carboxamide;
469) N-(3-chloro-5-(3-chloro-5-fluorophenoxy)phenyl)-5-(methylsulfonamido)benzo[b]thiophene-2-carboxamide;
470) N-(3-chloro-5-(4-fluoro-3-(trifluoromethoxy)phenoxy)phenyl)-5-(methylsulfonamido)benzo[b]thiophene-2-carboxamide;
471) 6-chloro-N-(3-chloro-5-(thiazol-2-yloxy)phenyl)-5-(methylsulfonamido)benzo[b]thiophene-2-carboxamide;
472) 6-chloro-N-(3-chloro-5-(thiazol-5-yloxy)phenyl)-5-(methylsulfonamido)benzo[b]thiophene-2-carboxamide;
473) 6-chloro-N-(3-chloro-5-((5-chlorothiophen-2-yl)oxy)phenyl)-5-(methylsulfonamido)benzo[b]thiophene-2-carboxamide;
474) 6-chloro-N-(3-chloro-5-(3-chloro-5-methoxyphenoxy)phenyl)-5-(methylsulfonamido)benzo[b]thiophene-2-carboxamide;
475) 6-chloro-N-(3-chloro-5-(3-chloro-5-hydroxyphenoxy)phenyl)-5-(methylsulfonamido)benzo[b]thiophene-2-carboxamide;
476) 6-chloro-N-(3-chloro-5-(3-chloro-4-fluorophenoxy)phenyl)-5-(methylsulfonamido)benzo[b]thiophene-2-carboxamide;
477) 6-chloro-N-(3-chloro-5-(4-chloro-3-fluorophenoxy)phenyl)-5-(methylsulfonamido)benzo[b]thiophene-2-carboxamide;
478) 6-chloro-N-(3-chloro-5-(4-fluorophenoxy)phenyl)-5-(methylsulfonamido)benzo[b]thiophene-2-carboxamide;
479) 6-chloro-N-(3-chloro-5-(3-(trifluoromethoxy)phenoxy)phenyl)-5-(methylsulfonamido)benzo[b]thiophene-2-carboxamide;
480) 6-chloro-N-(3-chloro-5-(4-(trifluoromethoxy)phenoxy)phenyl)-5-(methylsulfonamido)benzo[b]thiophene-2-carboxamide;
481) 6-chloro-N-(3-chloro-5-(3,4-difluorophenoxy)phenyl)-5-(methylsulfonamido)benzo[b]thiophene-2-carboxamide;
482) 6-chloro-N-(3-chloro-5-(4-(trifluoromethyl)phenoxy)phenyl)-5-(methylsulfonamido)benzo[b]thiophene-2-carboxamide;
483) 6-chloro-N-(3-chloro-5-(3-chloro-5-fluorophenoxy)phenyl)-5-(methylsulfonamido)benzo[b]thiophene-2-carboxamide;
484) 6-chloro-N-(3-chloro-5-(3-fluoro-5-methoxyphenoxy)phenyl)-5-(methylsulfonamido)benzo[b]thiophene-2-carboxamide;
485) 5-chloro-N-(3-chloro-5-(4-chlorophenoxy)phenyl)-6-(methylsulfonamido)benzo[b]thiophene-2-carboxamide;
486) 6-chloro-N-(3-chloro-5-(cyclohexyloxy)phenyl)-5-(methylsulfonamido)benzo[b]thiophene-2-carboxamide;
487) 6-chloro-N-(3-chloro-5-((5-methylthiophen-2-yl)oxy)phenyl)-5-(methylsulfonamido)benzo[b]thiophene-2-carboxamide;
488) 4-bromo-N-(3-chloro-5-(2-(3-isopropoxy-5-methylphenyl)propan-2-yl)phenyl)-5-(methylsulfonamido)benzo[b]thiophene-2-carboxamide;
489) N-(2-chloro-6-(4-chlorophenoxy)pyridin-4-yl)-5-(methylsulfonamido)benzo[b]thiophene-2-carboxamide;
490) 6-chloro-N-(2-chloro-6-(4-chlorophenoxy)pyridin-4-yl)-5-(methylsulfonamido)benzo[b]thiophene-2-carboxamide;
491) N-(2-chloro-6-((6-chloropyridin-3-yl)oxy)pyridin-4-yl)-5-(methylsulfonamido)benzo[b]thiophene-2-carboxamide;
492) 6-chloro-N-(2-chloro-6-(6-chloropyridin-3-yl)oxy)pyridin-4-yl)-5-(methylsulfonamido)benzo[b]thiophene-2-carboxamide;

493) N-(2-chloro-6-((6-(trifluoromethyl)pyridin-3-yl)oxy)pyridin-4-yl)-5-(methylsulfonamido)benzo[b]thiophene-2-carboxamide;
494) 6-chloro-N-(2-chloro-6-((6-(trifluoromethyl)pyridin-3-yl)oxy)pyridin-4-yl)-5-(methylsulfonamido)benzo[b]thiophene-2-carboxamide;
495) N-(2-chloro-6-(4-(trifluoromethyl)phenoxy)pyridin-4-yl)-5-(methylsulfonamido)benzo[b]thiophene-2-carboxamide;
496) 6-chloro-N-(2-chloro-6-(4-(trifluoromethyl)phenoxy)pyridin-4-yl)-5-(methylsulfonamido)benzo[b]thiophene-2-carboxamide;
497) N-(3-chloro-5-(2-(4-chlorophenyl)propan-2-yl)phenyl)-6-methoxy-5-(methylsulfonamido)benzo[b]thiophene-2-carboxamide; and
498) N-(3-chloro-5-(4-chlorophenoxy)phenyl)-6-methoxy-5-(methylsulfonamido)benzo[b]thiophene-2-carboxamide.

The above-listed names of the compounds are described in accordance with the nomenclature method provided by ChemBioDraw Ultra software (Version 13.0.0.3015) of PerkinElmer.

The present invention provides a pharmaceutically acceptable salt of a heterocyclic derivative represented by formula (I) above. The pharmaceutically acceptable salt should have low toxicity to humans, and should not have any negative impact on the biological activities and physicochemical properties of parent compounds. Examples of the pharmaceutically acceptable salt may include an acid addition salt between a pharmaceutically usable free acid and a basic compound represented by formula (I), an alkaline metal salt (sodium salt, etc.) and an alkaline earth metal salt (potassium salt, etc.), an organic base addition salt between an organic base and carboxylic acid represented by formula (I), amino acid addition salt, etc.

Examples of a suitable form of salts according to the present invention may be a salt with an inorganic acid or organic acid, wherein the inorganic acid may be hydrochloric acid, sulfuric acid, nitric acid, phosphoric acid, perchloric acid, bromic acid, etc., and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc. The organic base which may be used for the preparation of the organic base addition salt may include tris(hydroxymethyl)methylamine, dicyclohexylamine, etc. Amino acids which may be used for the preparation of amino acid addition base may include natural amino acids such as alanine, and glycine.

The salts may be prepared using a conventional method. For example, the salts may be prepared by dissolving the compound represented by formula (I) in a water-miscible solvent such as methanol, ethanol, acetone, and 1,4-dioxane, adding a free acid or a free base, and then crystallizing the resultant thereafter.

Additionally, the compounds of the present invention may have a chiral carbon center, and thus they may be present in the form of an R or S isomer, a racemic compound, an individual enantiomer or a mixture, an individual diastereomer or a mixture, and all these stereoisomers and a mixture thereof may belong to the scope of the present invention.

Additionally, the compounds of the present invention may also include a hydrate or solvate of the heterocyclic derivative represented by formula (I). The hydrate or solvate may be prepared using a known method, and they are preferred to be non-toxic and water-soluble, and in particular, they are preferably water or a hydrate or solvate having 1-5 molecules of alcoholic solvent (especially ethanol, etc.) bound thereto.

The present invention also provides a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

Further, the present invention provides method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

Further, the present invention provides a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

Specifically, the diseases associated with the activation of STAT3 protein is selected from the group consisting of solid cancers, hematological or blood cancers, radio- or chemo-resistant cancers, metastatic cancers, inflammatory diseases, immunological diseases, diabetes, macular degeneration, human papillomavirus infection and tuberculosis.

More specifically, the diseases associated with the activation of STAT3 protein are selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, auto-immune diseases comprising rheumatoid arthritis, psoriasis, hepatitis, inflammatory bowel disease, Crohn's disease, diabetes, macular degeneration, human papillomavirus infection, and tuberculosis.

In particular, a heterocyclic derivative represented by formula (I) above, or a pharmaceutically acceptable salt or a stereoisomer thereof has an excellent inhibitory effect on the activation of STAT3 protein, and thus the present invention also provides a composition for the inhibition of STAT3 protein comprising the same as an active ingredient.

The pharmaceutical composition of the present invention, in addition to the heterocyclic derivative represented by formula (I) above, the pharmaceutically acceptable salt thereof, or the stereoisomer thereof, may further include as active ingredients, common and non-toxic pharmaceutically acceptable additives, for example, a carrier, an excipient, a diluent, an adjuvant, etc., to be formulated into a preparation according to a conventional method.

The pharmaceutical composition of the present invention may be formulated into various forms of preparations for oral administration such as tablets, pills, powders, capsules, syrups, or emulsions, or for parenteral administration such as intramuscular, intravenous or subcutaneous injections, etc., and preferably in the form of a preparation for oral administration.

Examples of the additives to be used in the pharmaceutical composition of the present invention may include sweeteners, binders, solvents, solubilization aids, wetting agents, emulsifiers, isotonic agents, absorbents, disintegrating agents, antioxidants, preservatives, lubricants, fillers, flavoring agents, etc. For example, they may include, lactose, dextrose, sucrose, mannitol, sorbitol, cellulose, glycine, silica, talc, stearic acid, stearin, magnesium stearate, magnesium alluminosilicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc.

The pharmaceutical composition of the present invention may be formulated into a preparation for oral administration by adding additives to active ingredients, wherein the additives may include cellulose, calcium silicate, corn starch, lactose, sucrose, dextrose, calcium phosphate, stearic acid, magnesium stearate, calcium stearate, gelatin, talc, surfactants, suspension agents, emulsifiers, diluents, etc.

The pharmaceutical composition of the present invention may be formulated into a preparation for injection by adding additives to the active ingredients, for example, water, a saline solution, a glucose solution, an aqueous glucose solution analog, alcohol, glycol, ether, oil, fatty acid, fatty acid ester, glyceride, surfactants, suspension agents, emulsifiers, etc.

The compound of the present invention may be administered preferably in an amount ranging from 0.1 to 2,000 mg/day based on an adult subject with 70 kg body weight. The compound of the present invention may be administered once daily or a few divided doses. The dosage of the compound of the present invention may vary depending on the health conditions, age, body weight, sex of the subject, administration route, severity of illness, etc., and the scope of the present invention will not be limited to the dose suggested above.

EXAMPLE

Hereinafter, the present invention is described more specifically by the following examples, but these are provided only for illustration purposes and the present invention is not limited thereto.

The definition of the abbreviations used in the following examples is as follows.

TABLE 1

| Abbreviation | Full name |
|---|---|
| Al(CH$_3$)$_3$ | Trimethyl aluminum |
| AlCl$_3$ | Aluminum chloride |
| AcOH | Acetic acid |
| AIBN | 2,2'-Azobis(2-methylpropionitrile) |
| BINAP | 2,2'-bis(diphenylphosphino)-1,1'-binaphthyl |
| rac-BINAP | rac-2,2'-bis(diphenylphosphino)-1,1'-binaphthyl |
| BBr$_3$ | Boron tribromide |
| Boc$_2$O | Di-tert-butyl dicarbonate |
| Brine | Brine is water saturated or nearly saturated with a brine salt (generally, sodium chloride) |
| n-BuLi | n-butyllithium |
| tert-BuLi | tert-butyllithium |
| CCl$_4$ | Carbon tetrachloride |
| CH$_3$CN | Acetonitrile |
| CHCl$_3$ | Chloroform |
| CHBr$_3$ | Bromoform |
| CDCl$_3$ | Deuterated chloroform |
| CD$_3$OD | Methanol-d$_4$ |
| CH$_2$Cl$_2$ | Dichloromethane |
| CH$_2$I$_2$ | Diiodomethane |
| CH$_3$I | Methyl iodide |
| (COCl)$_2$ | Oxalyl chloride |

TABLE 1-continued

| Abbreviation | Full name |
|---|---|
| Cs$_2$CO$_3$ | Cesium carbonate |
| CuCN | Copper (I) cyanide |
| CuI | Copper (I) iodide |
| Cu$_2$O | Copper (I) oxide |
| CuSO$_4$•5H$_2$O | Copper(II) sulfate pentahydrate |
| DEAD | Diethyl azodicarboxylate |
| Deoxo-Fluor | Bis(2-methoxyethyl)aminosulfur trifluoride |
| DIAD | Diisopropyl azodicarboxylate |
| DIBAL | Diisobutylaluminum hydride |
| DIPEA | N,N-Diisopropylethylamine |
| DMA | N,N-Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| DMSO-d$_6$ | Dimethylsulfoxide-d$_6$ |
| EDC | Ethyl-(N,N-dimethylamino)propylcarbodiimide |
| EtOAc | Ethyl acetate |
| EtOH | Ethyl alcohol |
| Et$_2$O | Diethyl ether |
| Et$_3$N | Triethylamine |
| Et$_2$Zn | Diethylzinc |
| Fe | Iron |
| HATU | 2-(7-Aza-1H-benzotriazol-1-yl)-1,1,3,3-tetramethyluronium hexafluorophosphate |
| HBr | Hydrogen bromide |
| HCl | Hydrogen chloride |
| H$_2$SO$_4$ | Sulfuric acid |
| n-Hex | n-Hexane |
| HMPA | Hexamethylphosphoramide |
| HNO$_3$ | Nitric acid |
| H$_2$O | Water |
| H$_2$O$_2$ | Hydrogen peroxide |
| HOBt | 1-Hydroxybenzotriazole |
| H-Gly-OEt•HCl | Glycine ethyl ester hydrochloride |
| i-Pr$_2$O | Diisopropyl ether |
| K$_2$CO$_3$ | Potassium carbonate |
| KMnO$_4$ | Potassium manganate(VII) |
| KOAc | Potassium acetate |
| KOH | Potassium hydroxide |
| K$_3$PO$_4$•H$_2$O | Tripotassium phosphate monohydrate |
| LiAlH$_4$ | Lithium aluminum hydride |
| LiOH•H$_2$O | Lithium hydroxide, monohydrate |
| LiOMe | Lithium methoxide |
| mCPBA | meta-Chloroperoxybenzoic acid |
| MeOH | Methyl alcohol |
| MnO$_2$ | Manganese dioxide |
| NaBH$_3$CN | Sodium cyanoborohydride |
| NBS | N-Bromosuccinimide |
| Na$_2$CO$_3$ | Sodium carbonate |
| Na$_2$SO$_4$ | Sodium sulfate |
| NaH | Sodium hydride |
| NaHCO$_3$ | Sodium bicarbonate |
| NaOAc | Sodium acetate |
| NaOH | Sodium hydroxide |
| NaOMe | Sodium methoxide |
| NaOt-Bu | Sodium tert-butoxide |
| NaBH$_4$ | Sodium borohydride |
| NaN$_3$ | Sodium azide |
| NaI | Sodium iodide |
| NH$_4$Cl | Ammonium chloride |
| NH$_4$OH | Ammonium hydroxide |
| NHMe$_2$ | Dimethylamine |
| Pd(dba)$_2$ | Bis(dibenzylideneacetone)palladium(0) |
| Pd$_2$(dba)$_3$ | Tris(dibenzylideneacetone)dipalladium(0) |
| Pd$_2$(dba)$_3$•CHCl$_3$ | Tris(dibenzylideneacetone)dipalladium(0), chloroform adduct |
| Pd(dppf)$_2$Cl$_2$•CH$_2$Cl$_2$ | [1,1'-bis(diphenylphosphino)ferrocene]dichloropalladium(II), dichloromethane adduct |
| Pd(dppf)$_2$Cl$_2$ | [1,1'-bis(diphenylphosphino)ferrocene]dichloropalladium(II) |
| Pd(PPh$_3$)$_4$ | Tetrakis(triphenylphosphine)palladium(0) |
| Pd(OAc)$_2$ | Palladium(II) acetate |
| Pd(t-bu$_3$P)$_2$ | Bis(tri-tert-butylphosphine)palladium(0) |
| PCl$_5$ | Phosphorus pentachloride |
| PPh$_3$ | Triphenylphosphine |
| POCl$_3$ | Phosphoryl chloride |
| Ra—Ni | Raney nickel |

TABLE 1-continued

| Abbreviation | Full name |
|---|---|
| (SnMe$_3$)$_2$ | Hexamethylditin |
| SOCl$_2$ | Thionyl chloride |
| TBAF | Tetra-n-butylammonium fluoride |
| Tf$_2$O | Trifluoromethanesulfonic anhydride |
| THF | Tetrahydrofuran |
| TiCl$_4$ | Titanium tetrachloride |
| TFA | Trifluoroacetic acid |
| Xantphos | 4,5-bis(diphenylphosphino)-9,9-dimethylxanthene |
| Zn | Zinc |
| ZnI$_2$ | Zinc iodide |

Intermediate 1) Synthesis of 6-(methylsulfonamido)-1H-indole-2-carboxylic acid hydrochloride

(a) Synthesis of methyl 6-nitro-1H-indole-2-carboxylate

6-Nitro-1H-indole-2-carboxylic acid (100.0 mg, 0.49 mmol) was dissolved in
MeOH (2.4 mL), and SOCl$_2$ (100.0 μL) was slowly added. The reaction mixture was refluxed for 4 hours and concentrated under reduced pressure, and the residue was purified by flash column chromatography (amine silica gel, CH$_2$Cl$_2$:MeOH=30:1) to obtain methyl 6-nitro-1H-indole-2-carboxylate (107.0 mg, 100%) as a yellow solid.
$^1$H-NMR (300MHz, DMSO-d$_6$): δ 12.64 (brs, 1H), 8.34 (s, 1H), 7.92 (m, 2H), 7.33 (s, 1H), 3.93 (s, 3H)

(b) Synthesis of methyl 6-amino-1H-indole-2-carboxylate

Methyl 6-nitro-1H-indole-2-carboxylate (4.3 g, 19.39 mmol) was dissolved in a mixture of THF/MeOH/H$_2$O (115.0 mL, 1/1/0.5 v/v), and Zn (12.7 g, 0.19 mmol) and NH$_4$Cl (3.1 g, 58.14 mmol) were added. The reaction mixture was ultrasonificated at 40° C. for 1 hour, filtered through Celite and concentrated under reduced pressure. The residue was recrystallized in a mixture of i-Pr$_2$O/MeOH/EtOAc (100.0 mL, 1/0.1/0.1 v/v) to obtain methyl 6-amino-1H-indole-2-carboxylate (3.2 g, 86%) as a yellow solid.
LC/MS (ESI+): 191 (M+1)

(c) Synthesis of methyl 6-(methylsulfonamido)-1H-indole-2-carboxylate

Methyl 6-amino-1H-indole-2-carboxylate (250.0 mg, 1.31 mmol) was dissolved in pyridine (10.0 mL), and methanesulfonyl chloride (107.0 μL, 1.38 mmol) was slowly added at 0° C. The reaction mixture was stirred at room temperature for 3 hours, extracted with EtOAc, washed with brine, dried over anhydrous Na$_2$SO$_4$, and concentrated under reduced pressure. The residue was recrystallized in a mixture of i-Pr$_2$O/MeOH (100.0 mL, 1/0.1 v/v) to obtain methyl 6-(methylsulfonamido)-1H-indole-2-carboxylate (280.0 mg, 80%) as a yellow solid.
$^1$H-NMR (300MHz, DMSO-d$_6$): δ 11.87 (brs, 1H), 9.69 (brs, 1H), 7.60 (d, 1H, J=9.0Hz), 7.37 (s, 1H), 7.11 (m, 1H), 6.98 (dd, 1H, J=8.4, 1.8Hz), 3.85 (s, 3H), 2.95 (s, 3H)

(d) Synthesis of 6-(methylsulfonamido)-1H-indole-2-carboxylic acid hydrochloride Methyl 6-(methylsulfonamido)-1H-indole-2-carboxylate (280.0 mg, 1.04 mmol) was dissolved in a mixture of THF/MeOH/H$_2$O (5.6 mL, 5/3/1 v/v), and LiOH·H$_2$O (125.0 mg, 5.22 mmol) was added. The reaction mixture was stirred at room temperature for 10 hours, concentrated under reduced pressure. The residue was diluted in H$_2$O (2.0 mL), acidified to pH 1-2 with 1 N HCl and extracted with EtOAc. The organic extract was washed with brine, dried over anhydrous Na$_2$SO$_4$, concentrated under reduced pressure. The residue was recrystallized with a mixture of i-Pr$_2$O/MeOH (10.0 mL, 1/0.1 v/v) to obtain 6-(methylsulfonamido)-1H-indole-2-carboxylic acid hydrochloride (136.0 mg, 45%) as an off-white solid.
$^1$H-NMR (300MHz, DMSO-d$_6$): δ 12.60 (brs, 1H), 11.48 (brs, 1H), 9.43 (brs, 1H), 7.36 (d, 1H, J=8.4Hz), 7.15 (s, 1H), 6.82 (m, 1H), 6.75 (dd, 1H, J=8.4, 1.8Hz), 2.73 (s, 3H)

Intermediate 2) Synthesis of 6-((N-methylsulfamoyl)amino)-1H-indole-2-carboxylic acid hydrochloride

(a) Synthesis of methyl 6-((N-methylsulfamoyl)amino)-1H-indole-2-carboxylate Methyl 6-amino-1H-indole-2-carboxylate (intermediate 1-b) (900.0 mg, 4.73 mmol) and DMAP (2.0 g, 16.60 mmol) were dissolved in CH$_3$CN (20.0 mL), and methylsulfamoyl chloride (644.0 mg, 4.97 mmol) was slowly added at 0° C. After refluxing for 1 hour, the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=4:1) to obtain methyl 6-((N-methylsulfamoyl)amino)-1H-indole-2-carboxylate (902.0 mg, 64%) as a brown solid.
LC/MS ESI (+): 284 (M+1)

(b) Synthesis of 6-((N-methylsulfamoyl)amino)-1H-indole-2-carboxylic acid hydrochloride Methyl 6-((N-methylsulfamoyl)amino)-1H-indole-2-carboxylate (900.0 mg, 3.18 mmol) was dissolved in a mixture of THF/MeOH/H$_2$O (18.0 mL, 5/10/3 v/v), and LiOH·H$_2$O (380.0 mg, 15.90 mmol) was added. After stirring at room temperature for 14 hours, the reaction mixture was concentrated under reduced pressure. The residue was diluted in H$_2$O (2.0 mL), acidified to pH 1-2 with 1 N HCl and extracted with EtOAc. The organic extract was washed with brine, dried over anhydrous Na$_2$SO$_4$, concentrated under reduced pressure. The residue was recrystallized using i-Pr$_2$O to obtain 6-((N-methylsulfamoyl)amino)-1H-indole-2-carboxylic acid hydrochloride (630.0 mg, 70%) as a brown solid.
LC/MS ESI (+): 270 (M+1)

Intermediate 3) Synthesis of 5-(methylsulfonamido)benzo[b]thiophene-2-carboxylic acid

(a) Synthesis of ethyl 5-(methylsulfonamido)benzo[b]thiophene-2-carboxylate Ethyl 5-amino-1-benzothiophene-2-carboxylate (300.0 mg, 1.36 mmol) was dissolved in pyridine (15.0 mL), and methanesulfonyl chloride (111.0 μL, 1.38 mmol) was slowly added at 0° C. The reaction mixture was stirred at room temperature for 3 hours, extracted with EtOAc. The organic extract was washed with brine, dried over anhydrous Na$_2$SO$_4$, concentrated under reduced pressure. The residue was recrystallized using a mixture of i-Pr$_2$O/MeOH (100.0 mL, 1/0.1 v/v) to obtain ethyl 5-(methylsulfonamido)benzo[b]thiophene-2-carboxylate (350.0 mg, 86%) as a yellow solid.

LC/MS ESI (+): 300 (M+1)

(b) Synthesis of 5-(methylsulfonamido)benzo[b]thiophene-2-carboxylic acid

Ethyl 5-(methylsulfonamido)benzo[b]thiophene-2-carboxylate (189.0 mg, 0.66 mmol) was dissolved in a mixture of THF/$H_2O$ (6.6 mL, 2/1 v/v), and LiOH·$H_2O$ (278.0 mg, 6.62 mmol) was added. The reaction mixture was stirred at room temperature for 10 hours, concentrated under reduced pressure. The residue was diluted in $H_2O$ (2.0 mL) and acidified to pH 1-2 with 1 N HCl. The precipitate was filtered, washed with i-$Pr_2O$ and dried under reduced pressure to obtain 5-(methylsulfonamido)benzo[b]thiophene-2-carboxylic acid (165.5 mg, 92%) as an off-white solid.

LC/MS ESI (+): 272 (M+1)

$^1$H-NMR (300MHz, DMSO-$d_6$): δ 13.50 (s, 1H), 9.88 (s, 1H), 8.08 (s, 1H), 8.00 (d, 1H, J=9.0Hz), 7.82 (d, 1H, J=1.8Hz), 7.35 (dd, 1H, J=9.0, 1.8Hz), 3.01 (s, 3H)

Intermediate 4) Synthesis of 5-(morpholine-4-sulfonamido)benzo[b]thiophene-2-carboxylic acid The synthesis procedure of Intermediate 3 was repeated except for using ethyl 5-amino-1-benzothiophene-2-carboxylate (100.0 mg, 0.45 mmol) to obtain 5-(morpholine-4-sulfonamido)benzo[b]thiophene-2-carboxylic acid (60.0 mg).

LC/MS ESI (+): 343 (M+1)

$^1$H-NMR (400MHz, DMSO-$d_6$): δ 13.40 (brs, 1H), 10.67 (s, 1H), 8.09 (s, 1H), 7.97 (d, 1H, J=8.8Hz), 7.81 (d, 1H, J=1.9Hz), 7.37 (dd, 1H, J=8.8, 2.1Hz), 3.50-3.52 (m, 4H), 3.07-3.09 (m, 4H)

Intermediate 5) Synthesis of 5-((tetrahydrofuran)-3-sulfonamido)benzo[b]thiophene-2-carboxylic acid The synthesis procedure of Intermediate 3 was repeated except for using ethyl 5-amino-1-benzothiophene-2-carboxylate (100.0 mg, 0.45 mmol) to obtain 5-((tetrahydrofuran)-3-sulfonamido)benzo[b]thiophene-2-carboxylic acid (16.0 mg).

LC/MS ESI (+): 328 (M+1)

$^1$H-NMR (400MHz, DMSO-$d_6$): δ 10.09 (s, 1H), 8.11 (s, 1H), 8.02 (d, 1H, J=8.8Hz), 7.86 (d, 1H, J=1.6Hz), 7.38 (dd, 1H, J=8.8, 1.6Hz), 3.90-4.01 (m, 2H), 3.79-3.87 (m, 2H), 3.61-3.66 (m, 1H), 2.12-2.18 (m, 2H)

Intermediate 6) Synthesis of 3-methyl-6-(methylsulfonamido)benzo[b]thiophene-2-carboxylic acid (a) Synthesis of ethyl 3-methyl-6-(methylsulfonamido)benzo[b]thiophene-2-carboxylate Ethyl 6-amino-3-methylbenzo[b]thiophene-2-carboxylate (300.0 mg, 1.27 mmol) was dissolved in pyridine (12.7 mL), and methanesulfonyl chloride (128.0 μL, 1.65 mmol) was slowed added at 0° C. The reaction mixture was stirred at room temperature for 1 hour, and extracted with EtOAc. The organic extract was washed with brine, dried over anhydrous $Na_2SO_4$, concentrated under reduced pressure. The residue was purified by flash column chromatography (amine silica gel, $CH_2Cl_2$:MeOH=20:1) to obtain ethyl 3-methyl-6-(methylsulfonamido)benzo[b]thiophene-2-carboxylate (394.0 mg, 99%) as a white solid.

LC/MS ESI (+): 314 (M+1)

$^1$H-NMR (300MHz, DMSO-$d_6$): δ 9.90 (s, 1H), 7.98 (d, 1H, J=8.8Hz), 7.72 (m, 1H), 7.42 (dd, 1H, J=8.8, 1.8Hz), 4.33 (q, 2H, J=7.2Hz), 3.01 (s, 3H), 2.68 (s, 3H), 1.33 (t, 3H, J=6.9Hz)

(b) Synthesis of 3-methyl-6-(methylsulfonamido)benzo[b]thiophene-2-carboxylic acid Ethyl 3-methyl-6-(methylsulfonamido)benzo[b]thiophene-2-carboxylate (390.0 mg, 1.24 mmol) was dissolved in a mixture of THF/$H_2O$ (24.8 mL, 2/1 v/v), and LiOH·$H_2O$ (261.0 mg, 6.22 mmol) was added. The reaction mixture was stirred at room temperature for 10 hours, concentrated under reduced pressure. The residue was diluted in $H_2O$ (2.0 mL), acidified to pH 1-2 with 1 N HCl, and extracted with EtOAc. The organic extract was washed with brine, dried over anhydrous $Na_2SO_4$, concentrated under reduced pressure to obtain 3-methyl-6-(methylsulfonamido)benzo[b]thiophene-2-carboxylic acid (354.0 mg, 100%) as a white solid.

$^1$H-NMR (300MHz, DMSO-$d_6$): δ 13.38 (brs, 1H), 9.87 (s, 1H), 7.96 (d, 1H, J=8.8Hz), 7.71 (m, 1H), 7.40 (dd, 1H, J=8.8, 1.8Hz), 3.01 (s, 3H), 2.66 (s, 3H)

Intermediate 7) Synthesis of 5-(methylsulfonamido)benzofuran-2-carboxylic acid (a) Synthesis of ethyl 5-(methylsulfonamido)benzofuran-2-carboxylate Ethyl 5-aminobenzofuran-2-carboxylate (300.0 mg, 1.46 mmol) was dissolved in pyridine (15.0 mL), and methanesulfonyl chloride (119.0 μL, 1.38 mmol) was slowly added at 0° C. The reaction mixture was stirred at room temperature for 3 hours, extracted with EtOAc. The organic extract was washed with brine, dried over anhydrous $Na_2SO_4$, concentrated under reduced pressure. The residue was recrystallized using a mixture of i-$Pr_2O$/MeOH (100.0 mL, 1/0.1 v/v) to obtain ethyl 5-(methylsulfonamido)benzofuran-2-carboxylate (300.0 mg, 72%) as an off-white solid.

LC/MS ESI (+): 284 (M+1)

(b) Synthesis of 5-(methylsulfonamido)benzofuran-2-carboxylic acid

Ethyl 5-(methylsulfonamido)benzofuran-2-carboxylate (180.0 mg, 0.71 mmol) was dissolved in a mixture of THF/$H_2O$ (6.6 mL, 2/1 v/v), and LiOH·$H_2O$ (299.0 mg, 6.62 mmol) was added. The reaction mixture was stirred at room temperature for 10 hours, concentrated under reduced pressure. The residue was diluted in $H_2O$ (2.0 mL) and acidified to pH 1-2 with 1 N HCl. The precipitate was filtered and washed with i-$Pr_2O$. The precipitate was dried under reduced pressure to obtain 5-(methylsulfonamido)benzofuran-2-carboxylic acid (170.0 mg, 94%) as an off-white solid.

LC/MS ESI (+): 256 (M+1)

Intermediate 8) Synthesis of 5-methoxy-6-(methylsulfonamido)-1H-indole-2-carboxylic acid (a) Synthesis of ethyl 5-methoxy-6-(methylsulfonamido)-1H-indole-2-carboxylate Ethyl 6-amino-5-methoxy-1H-indole-2-carboxylate (100.0 mg, 0.43 mmol) was dissolved in pyridine (4.3 mL), and methanesulfonyl chloride (39.8 μL, 0.51 mmol) was slowly added at 0° C. The reaction mixture was stirred at room temperature for 1 hour, extracted with EtOAc. The organic extract was washed with brine, dried over anhydrous $Na_2SO_4$, concentrated under reduced pressure. The residue was purified by flash column chromatography (amine silica gel, $CH_2Cl_2$:MeOH=20:1) to obtain ethyl 5-methoxy-6-(methylsulfonamido)-1H-indole-2-carboxylate (131.0 mg, 97%) as a white solid.

LC/MS ESI (+): 313 (M+1)

$^1$H-NMR (300MHz, DMSO-$d_6$): δ 11.71 (s, 1H), 8.90 (brs, 1H), 7.39 (s, 1H), 7.19 (s, 1H), 7.04 (m, 1H), 4.31 (q, 2H, J=7.2Hz), 3.83 (s, 3H), 2.91 (s, 3H), 1.32 (t, 3H, J=7.5Hz)

(b) Synthesis of 5-methoxy-6-(methylsulfonamido)-1H-indole-2-carboxylic acid

Ethyl 5-methoxy-6-(methylsulfonamido)-1H-indole-2-carboxylate (131.0 mg, 0.42 mmol) was dissolved in a mixture of THF/$H_2O$ (8.4 mL, 2/1 v/v), and LiOH·$H_2O$ (88.0 mg, 2.10 mmol) was added. The reaction mixture was stirred at room temperature for 10 hours, acidified to pH 1-2 with 1 N HCl, and extracted with EtOAc. The organic extract was washed with brine, dried over anhydrous $Na_2SO_4$, concentrated under reduced pressure to obtain 5-methoxy-6-(methylsulfonamido)-1H-indole-2-carboxylic acid (119.0 mg, 100%) as a white solid.

LC/MS ESI (+): 285 (M+1)

$^1$H-NMR (300MHz, DMSO-$d_6$); δ 12.88 (brs, 1H), 11.59 (s, 1H), 8.83 (s, 1H), 7.38 (s, 1H), 7.20 (s, 1H), 6.98 (s, 1H), 3.83 (s, 3H), 2.91 (s, 3H)

Intermediate 9) Synthesis of 6-(methylsulfonamido)-1H-pyrrolo[2,3-b]pyridine-2-carboxylic acid hydrochloride (a) Synthesis of 6-amino-1H-pyrrolo[2,3-b]pyridine-2-carboxylic acid In a sealed tube, 6-chloro-1H-pyrrolo[2,3-b]pyridine-2-carboxylic acid (500.0 mg, 2.53 mmol) was dissolved in 30% $NH_4OH$ (15.0 mL), and $CuSO_4$·$5H_2O$ (318.0 mg, 1.27 mmol) was added. The reaction mixture was refluxed at 150° C. for 48 hours, and concentrated under reduced pressure to obtain a mixture of a white solid of 6-chloro-1H-pyrrolo[2,3-b]pyridine-2-carboxylic acid and 6-amino-1H-pyrrolo[2,3-b]pyridine-2-carboxylic acid by 1:1.

LC/MS ESI (+): 178 (M+1)

(b) Synthesis of methyl 6-amino-1H-pyrrolo[2,3-b]pyridine-2-carboxylate

The mixture (500.0 mg) of 6-chloro-1H-pyrrolo[2,3-b]pyridine-2-carboxylic acid and 6-amino-1H-pyrrolo[2,3-b]pyridine-2-carboxylic acid was dissolved in MeOH (20.0 mL), and $SOCl_2$ (4.0 mL) was added. The reaction mixture was refluxed at 80° C. for 19 hours and concentrated under reduced pressure to obtain a mixture of a white solid of methyl 6-chloro-1H-pyrrolo[2,3-b]pyridine-2-carboxylate and methyl 6-amino-1H-pyrrolo[2,3-b]pyridine-2-carboxylate by 1:1.

LC/MS ESI (+): 192 (M+1)

(c) Synthesis of methyl 6-(methylsulfonamido)-1H-pyrrolo[2,3-b]pyridine-2-carboxylate The synthesis procedure of Intermediate 6-a was repeated except for using the mixture of methyl 6-chloro-1H-pyrrolo[2,3-b]pyridine-2-carboxylate and methyl 6-amino-1H-pyrrolo[2,3-b]pyridine-2-carboxylate to obtain methyl 6-(methylsulfonamido)-1H-pyrrolo[2,3-b]pyridine-2-carboxylate (76.0 mg, 3 step yield: 8%) as a white solid.

LC/MS ESI (+): 270 (M+1)

(d) Synthesis of 6-(methylsulfonamido)-1H-pyrrolo[2,3-b]pyridine-2-carboxylic acid hydrochloride The synthesis procedure of Intermediate 6-b was repeated except for using methyl 6-(methylsulfonamido)-1H-pyrrolo[2,3-b]pyridine-2-carboxylate (76.0 mg, 0.20 mmol) to obtain 6-(methylsulfonamido)-1H-pyrrolo[2,3-b]pyridine-2-carboxylic acid hydrochloride (30.0 mg, 60%).

LC/MS ESI (+): 256 (M+1)

Intermediate 10) Synthesis of 6-(methylsulfonamido)-1H-pyrrolo[3,2-c]pyridine-2-carboxylic acid hydrochloride The synthesis procedure of Intermediate 9 was repeated except for using 6-chloro-1H-pyrrolo[3,2-c]pyridine-2-carboxylic acid (300.0 mg) to obtain 6-(methylsulfonamido)-1H-pyrrolo[3,2-c]pyridine-2-carboxylic acid hydrochloride (30.0 mg).

LC/MS ESI (+): 256 (M+1)

Intermediate 11) Synthesis of 5-(methylsulfonamido)-1H-pyrrolo[2,3-c]pyridine-2-carboxylic acid hydrochloride The synthesis procedure of Intermediate 9 was repeated except for using ethyl 5-bromo-1H-pyrrolo[2,3-c]pyridine-2-carboxylate (200.0 mg, 0.74 mmol) to obtain 5-(methylsulfonamido)-1H-pyrrolo[2,3-c]pyridine-2-carboxylic acid hydrochloride (21.6 mg).

LC/MS ESI (+): 256 (M+1)

$^1$H-NMR (300MHz, DMSO-$d_6$): δ 13.48 (brs, 1H), 12.17 (s, 1H), 9.98 (s, 1H), 8.58 (s, 1H), 7.29 (s, 1H), 7.06 (s, 1H), 3.19 (s, 3H)

Intermediate 12) Synthesis of 4-(methylsulfonamido)thiophene-2-carboxylic acid (a) Synthesis of methyl 4-(methylsulfonamido)thiophene-2-carboxylate The synthesis procedure of Intermediate 1-c was repeated except for using methyl 4-aminothiophene-2-carboxylate (100.0 mg, 0.64 mmol) to obtain methyl 4-(methylsulfonamido)thiophene-2-carboxylate (110.0 mg, 73%).

LC/MS ESI (+): 236 (M+1)

$^1$H-NMR (400MHz, $CDCl_3$): δ 7.63 (d, 1H, J=1.6Hz), 7.31 (d, 1H, J=1.6Hz), 6.61 (s, 1H), 3.90 (s, 3H), 3.03 (s, 3H)

(b) Synthesis of 4-(methylsulfonamido)thiophene-2-carboxylic acid

The synthesis procedure of Intermediate 1-d was repeated except for using methyl 4-(methylsulfonamido)thiophene-2-carboxylate (110.0 mg, 0.47 mmol) to obtain 4-(methylsulfonamido)thiophene-2-carboxylic acid (95.0 mg, 91%).

¹H-NMR (400MHz, MeOH-d₄): δ 7.59 (d, 1H, J=1.7Hz), 7.30 (d, 1H, J=1.7Hz), 2.97 (s, 3H)

Intermediate 13) Synthesis of 6-(methylsulfonamido)benzo[b]thiophene-2-carboxylic acid (a) Synthesis of methyl 6-nitrobenzo[b]thiophene-2-carboxylate 2,4-Dinitrobenzaldehyde (1.2 g, 5.96 mmol) and Et₃N (2.0 mL, 14.40 mmol) were dissolved in DMSO (7.0 mL), and methyl-2-mercaptoacetate (0.6 mL, 6.00 mmol) was slowly added at room temperature. After stirring for 12 hours, the reaction mixture was heated at 110° C. for 2 hours. The reaction mixture was extracted with EtOAc, washed with brine, dried over anhydrous Na₂SO₄, concentrated under reduced pressure. The residue was washed with Et₂O to obtain methyl 6-nitrobenzo[b]thiophene-2-carboxylate (1.1 g, 78%) as a yellow solid.
¹H-NMR (300MHz, DMSO-d₆): δ 9.18 (s, 1H), 8.38 (s, 1H), 8.26-8.27 (m, 2H), 3.93 (s, 3H)

(b) Synthesis of methyl 6-aminobenzo[b]thiophene-2-carboxylate

Methyl 6-nitrobenzo[b]thiophene-2-carboxylate (500.0 mg, 2.11 mmol), Zn (2.1 g, 31.60 mmol), and NH₄Cl (564.0 mg, 10.60 mmol) were dissolved in a mixture of THF/MeOH/H₂O (42.0 mL, 1/0.5/0.5 v/v). The reaction mixture was ultrasonificated for 2 hours, filtered through Celite and concentrated under reduced pressure to obtain methyl 6-aminobenzo[b]thiophene-2-carboxylate (437.0 mg) as a white solid without purification.
LC/MS ESI (+): 208 (M+1)

(c) Synthesis of methyl 6-(methylsulfonamido)benzo[b]thiophene-2-carboxylate

Crude methyl 6-aminobenzo[b]thiophene-2-carboxylate (437.0 mg) was dissolved in pyridine (21.0 mL), and methanesulfonyl chloride (213.0 μL, 2.74 mmol) was slowly added at room temperature. After stirring for 2 hours, the reaction mixture was extracted with EtOAc. The organic extract was washed with brine, dried over anhydrous Na₂SO₄, concentrated under reduced pressure. The residue was purified by flash column chromatography (amine silica gel, n-Hex:EtOAc=1:1) to obtain methyl 6-(methylsulfonamido)benzo[b]thiophene-2-carboxylate (272.0 mg, 2 step yield: 45%) as a yellow solid.
¹H-NMR (300MHz, DMSO-d₆): δ 10.18 (s, 1H), 8.14 (s, 1H), 7.97 (d, 1H, J=8.8Hz), 7.83 (s, 1H), 7.30 (dd, 1H, J=9.2, 1.5Hz), 3.87 (s, 3H), 3.09 (s, 3H)

(d) Synthesis of 6-(methylsulfonamido)benzo[b]thiophene-2-carboxylic acid

Methyl 6-(methylsulfonamido)benzo[b]thiophene-2-carboxylate (270.0 mg, 0.95 mmol) and LiOH·H₂O (199.0 mg, 4.73 mmol) were dissolved in a mixture of THF/H₂O (9.5 mL, 4/1 v/v), followed by stirring at room temperature for 24 hours. The reaction mixture was acidified to pH 1-2 with 1 N HCl and then extracted with EtOAc. The organic extract was dried over anhydrous Na₂SO₄ and filtered to obtain 6-(methylsulfonamido)benzo[b]thiophene-2-carboxylic acid (257.0 mg, 100%) as a white solid.

¹H-NMR (300MHz, DMSO-d₆): δ 13.30 (brs, 1H), 10.11 (s, 1H), 8.03 (s, 1H), 7.94 (d, 1H, J=8.8Hz), 7.80 (s, 1H), 7.29 (dd, 1H, J=8.8, 2.3Hz), 3.07 (s, 3H)

Intermediate 14) Synthesis of 6-fluoro-5-(methylsulfonamido)benzo[b]thiophene-2-carboxylic acid (a) Synthesis of methyl 6-fluoro-5-nitrobenzo[b]thiophene-2-carboxylate The synthesis procedure of Intermediate 13-a was repeated except for using 2,4-difluoro-5-nitrobenzaldehyde (5.0 g, 26.70 mmol) to obtain methyl 6-fluoro-5-nitrobenzo[b]thiophene-2-carboxylate mixture (1.6 g).
¹H-NMR (300MHz, CDCl₃): δ 8.62 (d, 1H, J=7.2Hz), 8.13 (s, 1H), 7.77 (d, 1H, J=10.4Hz), 3.99 (s, 3H)

(b) Synthesis of methyl 5-amino-6-fluorobenzo[b]thiophene-2-carboxylate

The synthesis procedure of Intermediate 13-b was repeated except for using methyl 6-fluoro-5-nitrobenzo[b]thiophene-2-carboxylate mixture (1.6 g) to obtain methyl 5-amino-6-fluorobenzo[b]thiophene-2-carboxylate (853.0 mg, 2 step yield: 14%).
LC/MS ESI (+): 226 (M+1)
¹H-NMR (300MHz, CDCl₃): δ 7.86 (s, 1H), 7.45 (d, 1H, J=10.8Hz), 7.21 (d, 1H, J=8.4Hz), 3.92 (s, 3H), 3.86 (s, 2H)

(c) Synthesis of methyl 6-fluoro-5-(methylsulfonamido)benzo[b]thiophene-2-carboxylate The synthesis procedure of Intermediate 13-c was repeated except for using methyl 5-amino-6-fluorobenzo[b]thiophene-2-carboxylate (530.0 mg, 2.35 mmol) to obtain methyl 6-fluoro-5-(methylsulfonamido)benzo[b]thiophene-2-carboxylate (663.0 mg, 93%).
LC/MS ESI (+): 304 (M+1)
¹H-NMR (400MHz, CDCl₃): δ 9.78 (s, 1H), 8.23 (s, 1H), 8.12 (d, 1H, J=10.3Hz), 8.06 (d, 1H, J=7.7Hz), 3.89 (s, 3H), 3.06 (s, 3H)

(d) Synthesis of 6-fluoro-5-(methylsulfonamido)benzo[b]thiophene-2-carboxylic acid The synthesis procedure of Intermediate 13-d was repeated except for using methyl 6-fluoro-5-(methylsulfonamido)benzo[b]thiophene-2-carboxylate (134.6 mg, 0.44 mmol) to obtain 6-fluoro-5-(methylsulfonamido)benzo[b]thiophene-2-carboxylic acid (118.0 mg, 92%).
LC/MS ESI (+): 290 (M+1)
¹H-NMR (400MHz, DMSO-d₆): δ 13.56 (brs, 1H), 9.75 (s, 1H), 8.11 (s, 1H), 8.08 (d, 1H, J=10.4Hz), 8.02 (d, 1H, J=7.7Hz), 3.06 (s, 3H)

Intermediate 15) Synthesis of 6-fluoro-5-(N-methylmethylsulfonamido)benzo[b]thiophene-2-carboxylic acid (a) Synthesis of methyl 6-fluoro-5-(N-methylmethylsulfonamido)benzo[b]thiophene-2-carboxylate Methyl 6-fluoro-5-(methylsulfonamido)benzo[b]thiophene-2-carboxylate (intermediate 14-c) (663.0 mg, 2.19 mmol) was dissolved in anhydrous DMF (22.0 mL), and CH₃I (272.0 μL, 4.37 mmol) and K₂CO₃ (906.4 mg, 6.56 mmol) were added at room temperature. The reaction mixture was heated at 60° C. for 14 hours and cooled to room temperature, followed by adding water and extracting with EtOAc. The organic extract was washed with brine, dried over anhydrous $Na_2SO_4$, concentrated under reduced pressure. The residue was purified by flash column chromatography (silica gel, n-Hex:EtOAc=1:1) to obtain methyl 6-fluoro-5-(N-methylmethylsulfonamido)benzo[b]thiophene-2-carboxylate (672.8 mg, 97%) as an off-white solid.

LC/MS ESI (+): 318 (M+1)
$^1$H-NMR (400MHz, DMSO-$d_6$): δ 8.22 (d, 1H, J=7.6Hz), 8.20 (s, 1H), 8.16 (d, 1H, J=10.6Hz), 3.89 (s, 3H), 3.26 (s, 3H), 3.12 (s, 3H)

(b) Synthesis of 6-fluoro-5-(N-methylmethylsulfonamido)benzo[b]thiophene-2-carboxylic acid The synthesis procedure of Intermediate 13-d was repeated except for using methyl 6-fluoro-5-(N-methylmethylsulfonamido)benzo[b]thiophene-2-carboxylate (672.8 mg, 2.12 mmol) to obtain 6-fluoro-5-(N-methylmethylsulfonamido)benzo[b]thiophene-2-carboxylic acid (596.8 mg, 93%).

LC/MS ESI (+): 304 (M+1)
$^1$H-NMR (400MHz, DMSO-$d_6$): δ 13.65 (brs, 1H), 8.20 (d, 1H, J=7.5Hz), 8.20 (d, 1H, J=10.5Hz), 8.08 (s, 1H), 3.26 (s, 3H), 3.12 (s, 3H)

Intermediate 16) Synthesis of 4-fluoro-5-(methylsulfonamido)benzo[b]thiophene-2-carboxylic acid The synthesis procedure of Intermediate 13 was repeated except for using 2,6-difluoro-3-nitrobenzaldehyde (300.0 mg, 1.60 mmol) to obtain 4-fluoro-5-(methylsulfonamido)benzo[b]thiophene-2-carboxylic acid (14.7 mg).

LC/MS ESI (+): 290 (M+1)
$^1$H-NMR (300MHz, DMSO-$d_6$): δ 13.83 (brs, 1H), 9.77 (s, 1H), 8.03 (m, 1H), 7.88 (d, 1H, J=8.4Hz), 7.48-7.50 (m, 1H), 3.04 (s, 3H)

Intermediate 17) Synthesis of 5-(methylsulfonamido)-4-morpholinobenzo[b]thiophene-2-carboxylic acid hydrochloride (a) Synthesis of methyl 4-fluoro-5-nitrobenzo[b]thiophene-2-carboxylate The synthesis procedure of Intermediate 13-a was repeated except for using 2,6-difluoro-3-nitrobenzaldehyde (300.0 mg, 1.60 mmol) to obtain regioisomers (84.0 mg) including methyl 4-fluoro-5-nitrobenzo[b]thiophene-2-carboxylate.

$^1$H-NMR (300MHz, CDCl$_3$): δ 8.30 (s, 1H), 8.13-8.17 (m, 1H), 7.74 (d, 1H, J=8.8Hz), 4.00 (s, 3H)

(b) Synthesis of methyl 4-morpholino-5-nitrobenzo[b]thiophene-2-carboxylate

The regioisomers of methyl 4-fluoro-5-nitrobenzo[b]thiophene-2-carboxylate (82.0 mg, 0.32 mmol), morpholine (55.5 μL, 0.64 mmol), and $K_2CO_3$ (88.7 mg, 0.64 mmol) were dissolved in DMSO (2.6 mL). The reaction mixture was heated at 100° C. for 5 hours. The reaction mixture was extracted with EtOAc, washed with brine, dried over anhydrous $Na_2SO_4$, concentrated under reduced pressure. The residue was purified by flash column chromatography (silica gel, n-Hex:EtOAc=1:1), to obtain methyl 4-morpholino-5-nitrobenzo[b]thiophene-2-carboxylate (20.5 mg, 2 step yield: 4%) as a yellow solid.

LC/MS ESI (+): 323 (M+1)
$^1$H-NMR (300MHz, CDCl$_3$): δ 8.24 (s, 1H), 7.70 (d, 1H, J=8.8Hz), 7.60 (d, 1H, J=8.8Hz), 3.99 (s, 3H), 3.30-3.90 (m, 4H), 3.28-3.30 (m, 4H)

(c) Synthesis of methyl 5-amino-4-morpholinobenzo[b]thiophene-2-carboxylate

The synthesis procedure of Intermediate 13-b was repeated except for using methyl 4-morpholino-5-nitrobenzo[b]thiophene-2-carboxylate (19.0 mg, 0.06 mmol) to obtain methyl 5-amino-4-morpholinobenzo[b]thiophene-2-carboxylate (22.0 mg, quant.).

LC/MS ESI (+): 293 (M+1)
$^1$H-NMR (300MHz, CDCl$_3$): δ 8.25 (s, 1H), 7.50 (d, 1H, J=8.8Hz), 7.00 (d, 1H, J=8.4Hz), 4.36 (brs, 2H), 3.97-4.03 (m, 2H), 3.95 (s, 3H), 3.76-3.82 (m, 2H), 3.55-3.62 (m, 2H), 2.83-2.86 (m, 2H)

(d) Synthesis of methyl 5-(methylsulfonamido)-4-morpholinobenzo[b]thiophene-2-carboxylate The synthesis procedure of Intermediate 13-c was repeated except for using methyl 5-amino-4-morpholinobenzo[b]thiophene-2-carboxylate (20.0 mg, 0.07 mmol) to obtain methyl 5-(methylsulfonamido)-4-morpholinobenzo[b]thiophene-2-carboxylate (16.8 mg, 66%).

LC/MS ESI (+): 371 (M+1)
$^1$H-NMR (300MHz, CDCl$_3$): δ 8.33 (s, 1H), 8.31 (s, 1H), 7.77 (s, 2H), 4.02-4.07 (m, 2H), 3.98 (s, 3H), 3.81-3.85 (m, 2H), 3.66-3.69 (m, 2H), 3.05 (s, 3H), 2.73-2.77 (m, 2H)

(e) Synthesis of 5-(methylsulfonamido)-4-morpholinobenzo[b]thiophene-2-carboxylic acid hydrochloride The synthesis procedure of Intermediate 13-d was repeated except for using methyl 5-(methylsulfonamido)-4-morpholinobenzo[b]thiophene-2-carboxylate (15.0 mg, 0.04 mmol) to obtain 5-(methylsulfonamido)-4-morpholinobenzo[b]thiophene-2-carboxylic acid hydrochloride (10.2 mg, 71%).

LC/MS ESI (+): 357 (M+1)
$^1$H-NMR (300MHz, DMSO-$d_6$): δ 13.68 (brs, 1H), 8.84 (s, 1H), 8.05 (brs, 1H), 7.83 (d, 1H, J=8.8Hz), 7.50 (d, 1H, J=8.8Hz), 3.80-3.82 (m, 4H), 3.18-3.20 (m, 4H), 3.07 (s, 3H)

Intermediate 18) Synthesis of 5-(methylsulfonamido)thieno[3,2-b]pyridine-2-carboxylic acid hydrochloride (a) Synthesis of methyl 5-bromothieno[3,2-b]pyridine-2-carboxylate The synthesis procedure of Intermediate 13-a was repeated except for using 6-bromo-3-fluoropicolinaldehyde (300.0 mg, 1.47 mmol) to obtain methyl 5-bromothieno[3,2-b]pyridine-2-carboxylate (368.0 mg, 92%).

LC/MS ESI (+): 272 (M+1)
$^1$H-NMR (300MHz, DMSO-$d_6$): δ 8.57 (d, 1H, J=8.8Hz), 8.20 (s, 1H), 7.75 (d, 1H, J=8.4Hz), 3.93 (s, 3H)

(b) Synthesis of 5-bromothieno[3,2-b]pyridine-2-carboxylic acid

The synthesis procedure of Intermediate 13-d was repeated except for using methyl 5-bromothieno[3,2-b]pyridine-2-carboxylate (368.0 mg, 1.35 mmol) to obtain 5-bromothieno[3,2-b]pyridine-2-carboxylic acid without purification.

LC/MS ESI (+): 258 (M+1)
$^1$H-NMR (300MHz, DMSO-$d_6$): δ 8.53 (d, 1H, J=8.8Hz), 8.10 (s, 1H), 7.72 (d, 1H, J=8.4Hz)

(c) Synthesis of 5-aminothieno[3,2-b]pyridine-2-carboxylic acid

The synthesis procedure of Intermediate 9-a was repeated except for using 5-bromothieno[3,2-b]pyridine-2-carboxylic acid to obtain 5-aminothieno[3,2-b]pyridine-2-carboxylic acid without purification.

LC/MS ESI (+): 195 (M+1)

(d) Synthesis of methyl 5-aminothieno[3,2-b]pyridine-2-carboxylate

The synthesis procedure of Intermediate 9-b was repeated except for using 5-aminothieno[3,2-b]pyridine-2-carboxylic acid to obtain methyl 5-aminothieno[3,2-b]pyridine-2-carboxylate (259.0 mg, 3 step yield: 92%).

LC/MS ESI (+): 209 (M+1)

(e) Synthesis of methyl 5-(methylsulfonamido)thieno[3,2-b]pyridine-2-carboxylate The synthesis procedure of Intermediate 9-c was repeated except for using methyl 5-aminothieno[3,2-b]pyridine-2-carboxylate (288.0 mg, 1.38 mmol) to obtain methyl 5-(methylsulfonamido)thieno[3,2-b]pyridine-2-carboxylate (159.0 mg, 40%).

$^1$H-NMR (300MHz, DMSO-$d_6$): δ 10.93 (s, 1H), 8.48 (d, 1H, J=8.8Hz), 8.06 (s, 1H), 7.12 (d, 1H, J=8.8Hz), 3.92 (s, 3H), 3.42 (s, 3H)

(f) Synthesis of 5-(methylsulfonamido)thieno[3,2-b]pyridine-2-carboxylic acid hydrochloride The synthesis procedure of Intermediate 9-d was repeated except for using methyl 5-(methylsulfonamido)thieno[3,2-b]pyridine-2-carboxylate (159.0 mg, 0.56 mmol) to obtain 5-(methylsulfonamido)thieno[3,2-b]pyridine-2-carboxylic acid hydrochloride (93.5 mg, 54%).

LC/MS ESI (+): 273 (M+1)
$^1$H-NMR (300MHz, DMSO-$d_6$): δ 13.75 (brs, 1H), 10.87 (s, 1H), 8.45 (d, 1H, J=8.8Hz), 7.95 (s, 1H), 7.09 (d, 1H, J=8.8Hz), 3.41 (s, 3H)

Intermediate 19) Synthesis of 5-(methylsulfonamido)thieno[2,3-c]pyridine-2-carboxylic acid hydrochloride The synthesis procedure of Intermediate 18 was repeated except for using 2-chloro-5-fluoroisonicotinaldehyde (500.0 mg, 3.13 mmol) to obtain 5-(methylsulfonamido)thieno[2,3-c]pyridine-2-carboxylic acid hydrochloride (94.0 mg).

LC/MS ESI (+): 273 (M+1)
$^1$H-NMR (300MHz, DMSO-$d_6$): δ 13.93 (brs, 1H), 10.58 (brs, 1H), 9.09 (s, $^1$H), 8.11 (s, 1H), 7.55 (s, 1H), 3.30 (s, 3H)

Intermediate 20) Synthesis of 5-(methylsulfonamido)thieno[2,3-b]pyridine-2-carboxylic acid

(a) Synthesis of methyl thieno[2,3-b]pyridine-2-carboxylate

2-Chloronicotinaldehyde (300.0 mg, 2.12 mmol) was dissolved in anhydrous DMF (2.1 mL) and $H_2O$ (210.0 μL), and methyl-2-mercaptoacetate (0.2 mL, 2.37 mmol) and $K_2CO_3$ (327.0 mg, 2.37 mmol) were slowly added at room temperature. The reaction mixture was heated at 35° C. for 12 hours. The reaction mixture was extracted with EtOAc, washed with brine, dried over anhydrous $Na_2SO_4$, concentrated under reduced pressure. The residue was purified by flash column chromatography (silica gel, n-Hex:EtOAc=1:5) to obtain methyl thieno[2,3-b]pyridine-2-carboxylate (288.0 mg, 70%) as an off-white oil.

LC/MS ESI (+): 194 (M+1)
$^1$H-NMR (400MHz, $CDCl_3$): δ 8.70 (dd, 1H, J=4.8, 1.6Hz), 8.17 (dd, 1H, J=8.4, 1.6Hz), 8.02 (s, 1H), 7.38 (dd, 1H, J=8.0, 4.8Hz), 3.98 (s, 3H)

(b) Synthesis of 2-(methoxycarbonyl)thieno[2,3-b]pyridine 7-oxide

Methyl thieno[2,3-b]pyridine-2-carboxylate (112.0 mg, 0.58 mmol) was dissolved in 35% $H_2O_2$ (190 μL) and AcOH (170.0 μL), and the reaction temperature was raised to 55° C. The reaction mixture was heated for 2 hours, water was added to quench the reaction, extracted with $CH_2Cl_2$. The reaction mixture was washed with brine, dried over anhydrous $Na_2SO_4$, concentrated under reduced pressure. The residue was purified by flash column chromatography (silica gel, n-Hex:EtOAc=1:1) to obtain 2-(methoxycarbonyl)thieno[2,3-b]pyridine 7-oxide (80.0 mg, 66%) as a white solid.

LC/MS ESI (+): 210 (M+1)
$^1$H-NMR (400MHz, $CDCl_3$): δ 8.40 (d, 1H, J=6.0Hz), 8.05 (s, 1H), 7.81 (d, 1H, J=8.4Hz), 7.39 (dd, 1H, J=8.0, 6.4Hz), 3.99 (s, 3H)

(c) Synthesis of 2-(methoxycarbonyl)-5-nitrothieno[2,3-b]pyridine 7-oxide 2-(Methoxycarbonyl)thieno[2,3-b]pyridine 7-oxide (1.5 g, 7.21 mmol) was dissolved in AcOH (9.8 mL), and $HNO_3$ (430.0 μL 6.85 mmol) was slowly added. The reaction mixture was heated at 120° C. for 8 hours, cooled to room temperature. And the reaction mixture was concentrated under reduced pressure. The residue was purified by flash column chromatography (silica gel, n-Hex:EtOAc=1:3) to obtain 2-(methoxycarbonyl)-5-nitrothieno[2,3-b]pyridine 7-oxide (478.0 mg, 26%) as a white solid.

LC/MS ESI (+): 255 (M+1)
$^1$H-NMR (400MHz, $CDCl_3$): δ 9.20 (d, 1H, J=1.6Hz), 8.61 (d, 1H, J=1.6Hz), 8.18 (s, 1H), 4.02 (s, 3H)

(d) Synthesis of methyl 5-aminothieno[2,3-b]pyridine-2-carboxylate 2-(Methoxycarbonyl)-5-nitrothieno[2,3-b]pyridine 7-oxide (478.0 mg, 1.88 mmol) was dissolved in THF, (40.0 mL). Under an atmosphere of hydrogen gas, Ra—Ni was added, and the reaction mixture was stirred at room temperature for 12 hours, filtered through Celite and concentrated under reduced pressure. The residue was purified by flash column chromatography (silica gel, n-Hex:EtOAc=1:1) to obtain methyl 5-aminothieno[2,3-b]pyridine-2-carboxylate (175.0 mg, 45%) as an off-white oil.

LC/MS ESI (+): 209 (M+1)

$^1$H-NMR (400MHz, CDCl$_3$): δ 8.25 (brs, 1H), 7.84 (s, 1H), 7.38 (d, 1H, J=2.4Hz), 3.95 (s, 3H), 3.80 (brs, 2H)

(e) Synthesis of methyl 5-(methylsulfonamido)thieno[2,3-b]pyridine-2-carboxylate The synthesis procedure of Intermediate 13-c was repeated except for using methyl 5-aminothieno[2,3-b]pyridine-2-carboxylate (175.0 mg, 0.84 mmol) to obtain methyl 5-(methylsulfonamido)thieno[2,3-b]pyridine-2-carboxylate (234.0 mg, 93%).

LC/MS ESI (+): 287 (M+1)

$^1$H-NMR (400MHz, CDCl$_3$): δ 8.51 (d, 1H, J=2.4Hz), 8.19 (d, 1H, J=2.4Hz), 7.99 (s, 1H), 5.03 (s, 1H), 3.98 (s, 3H), 3.07 (s, 3H)

(f) Synthesis of 5-(methylsulfonamido)thieno[2,3-b]pyridine-2-carboxylic acid

The synthesis procedure of Intermediate 13-d was repeated except for using methyl 5-(methylsulfonamido)thieno[2,3-b]pyridine-2-carboxylate (234.0 mg, 0.82 mmol) to obtain 5-(methylsulfonamido)thieno[2,3-b]pyridine-2-carboxylic acid (188.0 mg, 74%).

LC/MS ESI (+): 273 (M+1)

$^1$H-NMR (400MHz, CDCl$_3$): δ 10.17 (s, 1H) 8.56 (d, 1H, J=2.4Hz), 8.25 (d, 1H, J=2.4Hz), 8.14 (s, 1H), 3.09 (s, 3H)

Intermediate 21) Synthesis of 6-nitrobenzo[d]thiazole-2-carboxylic acid

A mixture of 2-methyl-6-nitrobenzo[d]thiazole (50.0 mg, 0.26 mmol), KMnO$_4$ (81.0 mg, 0.51 mmol), and H$_2$O (1.0 mL) was heated at 105° C. for 1 hour, and KMnO$_4$ (81.0 mg, 0.51 mmol) was added twice with time interval of 1 hour, followed by stirring for 2 hours. The reaction temperature was cooled to room temperature, and the reaction mixture was filtered through Celite and concentrated under reduced pressure to obtain 6-nitrobenzo[d]thiazole-2-carboxylic acid (40.0 mg, 70%) as a brown solid.

LC/MS ESI (+): 225 (M+1)

Intermediate 22) Synthesis of 5-nitro-1H-benzo[d]imidazole-2-carboxylic acid

4-Nitrobenzene-1,2-diamine (2.0 g, 13.1 mmol) was dissolved in AcOH (40.0 mL), and methyl 2,2,2-trichloroacetimidate (1.8 mL, 14.4 mmol), NH$_4$Cl (310.0 mg, 5.88 mmol) and DIPEA (2.1 mL, 11.8 mmol) were added at 0° C., followed by stirring at room temperature for 2 hours. The reaction mixture was extracted using CH$_2$Cl$_2$, and the organic extract was washed with brine, dried over anhydrous Na$_2$SO$_4$, concentrated under reduced pressure. The residue was dissolved in THF (30.0 mL), and 1 N NaOH aqueous solution (100.0 mL) was added, followed by stirring at room temperature for 2 hours. The reaction mixture was neutralized by adding 1 N HCl aqueous solution (pH 7), and the precipitate was filtered and washed with water to obtain 5-nitro-1H-benzo[d]imidazole-2-carboxylic acid (820.0 mg, 30%) as a white solid.

LC/MS ESI (+): 208 (M+1)

Intermediate 23) Synthesis of 6-(methylsulfonamido)imidazo[1,2-a]pyridine-2-carboxylic acid hydrochloride (a) Synthesis of ethyl 6-nitroimidazo[1,2-a]pyridine-2-carboxylate 5-Nitropyridine-2-amine (1.5 g, 10.80 mmol) and ethyl 3-bromo-2-oxopropanoate (1.6 mL, 13.00 mmol) were dissolved in EtOH (15.0 mL), followed by refluxing for 16 hours. After completing the reaction, the reaction mixture was filtered to obtain a pale yellow solid. The filtrate was extracted with EtOAc, washed with sat. NaHCO$_3$ aqueous solution and brine, dried over anhydrous Na$_2$SO$_4$, concentrated under reduced pressure. The residue was purified by flash column chromatography (silica gel, n-Hex:EtOAc=2:1) to obtain ethyl 6-nitroimidazo[1,2-a]pyridine-2-carboxylate (2.3 g, 90%) as a yellow solid.

LC/MS ESI (+): 236 (M+1)

$^1$H-NMR (300MHz, CDCl$_3$): δ 9.30 (s, 1H), 8.38 (s, 1H), 8.06 (d, 1H, J=10.0Hz), 7.84 (d, 1H, J=10.4Hz), 4.50 (q, 2H, J=7.2Hz), 1.46 (t, 3H, J=7.2Hz)

(b) Synthesis of methyl 6-aminoimidazo[1,2-a]pyridine-2-carboxylate

The synthesis procedure of Intermediate 13-b was repeated except for using ethyl 6-nitroimidazo[1,2-a]pyridine-2-carboxylate (300.0 mg, 1.28 mmol) to obtain methyl 6-aminoimidazo[1,2-a]pyridine-2-carboxylate (67.1 mg, 27%).

LC/MS ESI (+): 192 (M+1)

$^1$H-NMR (300MHz, CDCl$_3$): δ 8.02 (s, 1H), 7.54 (s, 1H), 7.51 (d, 1H, J=9.6Hz), 6.87 (d, 1H, J=9.6Hz), 3.96 (s, 3H), 3.53 (brs, 2H)

(c) Synthesis of methyl 6-(methylsulfonamido)imidazo[1,2-a]pyridine-2-carboxylate The synthesis procedure of Intermediate 13-c was repeated except for using methyl 6-aminoimidazo[1,2-a]pyridine-2-carboxylate (67.0 mg, 0.35 mmol) to obtain methyl 6-(methylsulfonamido)imidazo[1,2-a]pyridine-2-carboxylate (72.4 mg, 77%).

LC/MS ESI (+): 270 (M+1)

$^1$H-NMR (300MHz, DMSO-d$_6$): δ 9.82 (s, 1H), 8.60 (s, 1H), 8.50 (s, 1H), 7.62 (d, 1H, J=9.2Hz), 7.24 (d, 1H, J=9.6Hz), 3.82 (s, 3H), 3.04 (s, 3H)

(d) Synthesis of 6-(methylsulfonamido)imidazo[1,2-a]pyridine-2-carboxylic acid hydrochloride The synthesis procedure of Intermediate 13-d was repeated except for using methyl 6-(methylsulfonamido)imidazo[1,2-a]pyridine-2-carboxylate (71.0 mg, 0.26 mmol) to obtain 6-(methylsulfonamido)imidazo[1,2-a]pyridine-2-carboxylic acid hydrochloride (48.5 mg, 63%).

LC/MS ESI (+): 256 (M+1)

$^1$H-NMR (300MHz, DMSO-d$_6$): δ 9.81 (s, 1H), 8.55 (s, 1H), 8.51 (s, 1H), 7.63 (d, 1H, J=9.6Hz), 7.24 (d, 1H, J=9.6Hz), 3.05 (s, 3H)

Intermediate 24) Synthesis of 5-(methylsulfonyl)-4,5,6,7-tetrahydrothieno[3,2-c]pyridine-2-carboxylic acid (a) Synthesis of tert-butyl 4-chloro-5-formyl-3,6-dihydropyridine-1(2H)-carboxylate DMF (387.0 μL, 5.02 mmol) was cooled to 0° C., and POCl$_3$ (374.0 μL, 4.02 mmol) was slowly added. The resultant was diluted with CH$_2$Cl$_2$ (1.0 mL), and the reaction mixture was stirred at room temperature for 2 hours. The reaction mixture was cooled again to 0° C., and a solution of tert-butyl 4-oxopiperidine-1-carboxylate (500.0 mg, 2.51 mmol) in CH$_2$Cl$_2$ (5.0 mL) was slowly added. After stirring at room temperature for 2 hours, the reaction mixture was poured into the solution of NaOAc in ice water. The reaction mixture was extracted again with CH$_2$Cl$_2$, washed with distilled water, dried over anhydrous Na$_2$SO$_4$, concentrated under reduced pressure. The residue was not purified to obtain tert-butyl 4-chloro-5-formyl-3,6-dihydropyridine-1(2H)-carboxylate as a colorless liquid.

(b) Synthesis of 5-(tert-butyl) 2-methyl 6,7-dihydrothieno[3,2-c]pyridine-2,5(4H)-dicarboxylate The synthesis procedure of Intermediate 13-a was repeated except for using tert-butyl 4-chloro-5-formyl-3,6-dihydropyridine-1(2H)-carboxylate to obtain 5-(tert-butyl) 2-methyl 6,7-dihydrothieno[3,2-c]pyridine-2,5(4H)-dicarboxylate (165.0 mg, 2 step yield: 22%).
$^1$H-NMR (300MHz, CDCl$_3$): δ 7.50 (s, 1H), 4.49 (s, 2H), 3.87 (s, 3H), 3.73 (m, 2H), 2.87 (m, 2H), 1.49 (s, 9H)

(c) Synthesis of methyl 4,5,6,7-tetrahydrothieno[3,2-c]pyridine-2-carboxylate 5-(tert-Butyl) 2-methyl 6,7-dihydrothieno[3,2-c]pyridine-2,5(4H)-dicarboxylate (163.0 mg, 0.55 mmol) was dissolved in CH$_2$Cl$_2$ (2.7 mL), and TFA (0.5 mL) was slowly added, followed by stirring at room temperature for 3 hours. The reaction mixture was extracted with EtOAc, washed with sat. NaHCO$_3$ aqueous solution and brine, dried over anhydrous Na$_2$SO$_4$, concentrated under reduced pressure. The residue was dried to obtain methyl 4,5,6,7-tetrahydrothieno[3,2-c]pyridine-2-carboxylate (96.0 mg, 89%) as a yellow solid.
LC/MS ESI (+): 198 (M+1)
$^1$H-NMR (300MHz, CDCl$_3$): δ 7.45 (s, 1H), 3.93 (s, 2H), 3.86 (s, 3H), 3.16-3.19 (m, 2H), 2.83-2.88 (m, 2H), 1.88 (brs, 1H)

(d) Synthesis of methyl 5-(methylsulfonyl)-4,5,6,7-tetrahydrothieno[3,2-c]pyridine-2-carboxylate The synthesis procedure of Intermediate 13-c was repeated except for using methyl 4,5,6,7-tetrahydrothieno[3,2-c]pyridine-2-carboxylate (94.0 mg, 0.48 mmol) to obtain methyl 5-(methylsulfonyl)-4,5,6,7-tetrahydrothieno[3,2-e]pyridine-2-carboxylate (92.6 mg, 71%).
LC/MS ESI (+): 276 (M+1)
$^1$H-NMR (300MHz, CDCl$_3$): δ 7.49 (s, 1H), 4.40 (s, 2H), 3.88 (s, 3H), 3.63-3.65 (m, 2H), 3.01-3.03 (m, 2H), 2.87 (s, 3H)

(e) Synthesis of 5-(methylsulfonyl)-4,5,6,7-tetrahydrothieno[3,2-c]pyridine-2-carboxylic acid The synthesis procedure of Intermediate 13-d was repeated except for using methyl 5-(methylsulfonyl)-4,5,6,7-tetrahydrothieno[3,2-c]pyridine-2-carboxylate (91.0 mg, 0.33 mmol) to obtain 5-(methylsulfonyl)-4,5,6,7-tetrahydrothieno[3,2-c]pyridine-2-carboxylic acid (80.7 mg, 94%).
LC/MS ESI (+): 262 (M+1)
$^1$H-NMR (300MHz, DMSO-d$_6$): δ 13.03 (s, 1H), 7.56 (s, 1H), 4.32 (s, 2H), 3.49-3.51 (m, 2H), 2.97-2.99 (m, 5H)

Intermediate 25) Synthesis of 5-(methylsulfonamido)-4,5,6,7-tetrahydrothieno[3,2-c]pyridine-2-carboxylic acid (a) Synthesis of ethyl 5-amino-4,5,6,7-tetrahydrothieno[3,2-c]pyridine-2-carboxylate Ethyl 4,5,6,7-tetrahydrothieno[3,2-c]pyridine-2-carboxylate (340.0 mg, 1.61 mmol) was dissolved in a mixture of EtOH/H$_2$O (6.0 mL/12.0 mL), and aminosulfuric acid (182.0 mg, 1.61 mmol) and K$_2$CO$_3$ (444.8 mg, 3.22 mmol) were added, followed by stirring at room temperature for 13 hours. EtOH was evaporated under reduced pressure. The reaction mixture was extracted with EtOAc, washed with brine, dried over anhydrous Na$_2$SO$_4$, concentrated under reduced pressure. The residue was purified by flash column chromatography (silica gel, CH$_2$Cl$_2$:MeOH=9:1) to obtain ethyl 5-amino-4,5,6,7-tetrahydrothieno[3,2-c]pyridine-2-carboxylate (95.9 mg, 26%) as a yellow liquid.
LC/MS ESI (+): 227 (M+1)
$^1$H-NMR (400MHz, DMSO-d$_6$): δ 7.50 (s, 1H), 4.25 (q, 2H, J=7.1Hz), 3.73 (brs, 2H), 3.57 (s, 2H), 2.82-2.91 (m, 4H), 1.27 (t, 3H, J=7.1Hz)

(b) Synthesis of ethyl 5-(methylsulfonamido)-4,5,6,7-tetrahydrothieno[3,2-c]pyridine-2-carboxylate The synthesis procedure of Intermediate 6-a was repeated except for using ethyl 5-amino-4,5,6,7-tetrahydrothieno[3,2-c]pyridine-2-carboxylate (95.0 mg, 0.42 mmol) to obtain ethyl 5-(methylsulfonamido)-4,5,6,7-tetrahydrothieno[3,2-c]pyridine-2-carboxylate (53.0 mg, 42%).
LC/MS ESI (+): 305 (M+1)
$^1$H-NMR (400MHz, DMSO-d$_6$): δ 8.56 (s, 1H), 7.54 (s, 1H), 4.26 (q, 2H, J=7.1Hz), 3.92 (s, 2H), 3.11-3.15 (m, 2H), 2.96-3.00 (m, 5H), 1.27 (t, 3H, J=7.1Hz)

(c) Synthesis of 5-(methylsulfonamido)-4,5,6,7-tetrahydrothieno[3,2-c]pyridine-2-carboxylic acid The synthesis procedure of Intermediate 6-b was repeated except for using ethyl 5-(methylsulfonamido)-4,5,6,7-tetrahydrothieno[3,2-c]pyridine-2-carboxylate (53.0 mg, 0.17 mmol) to obtain 5-(methylsulfonamido)-4,5,6,7-tetrahydrothieno[3,2-c]pyridine-2-carboxylic acid (39.0 mg, 81%).
LC/MS ESI (+): 277 (M+1)
$^1$H-NMR (400MHz, DMSO-d$_6$): δ 12.95 (brs, 1H), 8.55 (s, 1H), 7.44 (s, 1H), 3.90 (s, 2H), 3.10-3.14 (m, 2H), 2.96-2.97 (m, 5H)

Intermediate 26) Synthesis of 6-chloro-5-(methylsulfonamido)benzo[b]thiophene-2-carboxylic acid (a) Synthesis of methyl 6-chloro-5-nitrobenzo[b]thiophene-2-carboxylate 4-Chloro-2-fluoro-5-nitrobenzaldehyde (9.6 g, 47.16 mmol) was dissolved in anhydrous DMF (100.0 mL), and methyl 2-mercaptoacetate (4.0 mL, 44.73 mmol) and K$_2$CO$_3$ (13.0 g, 94.06 mmol) were added, followed by stirring at room temperature for 3 hours and heated at 50° C. for 2 hours. The reaction mixture was poured into ice water, and a brown solid was filtered and extracted with $CH_2Cl_2$. The organic extract was washed with brine, dried over anhydrous $Na_2SO_4$ and concentrated under reduced pressure to obtain methyl 6-chloro-5-nitrobenzo[b]thiophene-2-carboxylate (10.2 g) as a yellow compound without purification.

(b) Synthesis of methyl 5-amino-6-chlorobenzo[b]thiophene-2-carboxylate

The synthesis procedure of Intermediate 13-b was repeated except for using crude methyl 6-chloro-5-nitrobenzo[b]thiophene-2-carboxylate (10.2 g) to obtain methyl 5-amino-6-chlorobenzo[b]thiophene-2-carboxylate (9.0 g, 2 step yield: 79%).

$^1$H-NMR (400MHz, DMSO-$d_6$): δ 7.98 (s, 1H), 7.96 (s, 1H), 7.30 (s, 1H), 5.49 (brs, 2H), 3.85 (s, 3H)

(c) Synthesis of methyl 6-chloro-5-(methylsulfonamido)benzo[b]thiophene-2-carboxylate The synthesis procedure of Intermediate 6-a was repeated except for using methyl 5-amino-6-chlorobenzo[b]thiophene-2-carboxylate (4.0 g, 16.55 mmol) to obtain methyl 6-chloro-5-(methylsulfonamido)benzo[b]thiophene-2-carboxylate (3.2 g, 60%).

$^1$H-NMR (400MHz, DMSO-$d_6$): δ 9.62 (s, 1H), 8.37 (s, 1H), 8.23 (s, 1H), 8.11 (s, 1H), 3.90 (s, 3H), 3.07 (s, 3H).

(d) Synthesis of 6-chloro-5-(methylsulfonamido)benzo[b]thiophene-2-carboxylic acid The synthesis procedure of Intermediate 6-b was repeated except for using methyl 6-chloro-5-(methylsulfonamido)benzo[b]thiophene-2-carboxylate (3.2 g, 9.85 mmol) to obtain 6-chloro-5-(methylsulfonamido)benzo[b]thiophene-2-carboxylic acid (3.0 g, 100%).

$^1$H-NMR (400MHz, DMSO-$d_6$): δ 13.62 (brs, 1H), 9.61 (s, 1H), 8.34 (s, 1H), 8.13 (s, 1H), 8.09 (s, 1H), 3.07 (s, 3H).

Intermediate 27) Synthesis of 3-hydroxy-5-(methylsulfonamido)benzo[b]thiophene-2-carboxylic acid

(a) Synthesis of methyl 3-hydroxy-5-nitrobenzo[b]thiophene-2-carboxylate

Methyl 2-chloro-5-nitrobenzoate (1.0 g, 4.64 mmol) was dissolved in anhydrous DMF (23.0 mL), and methyl 2-mercaptoacetate (390.0 mg, 4.41 mmol) and $K_2CO_3$ (1920.0 mg, 13.89 mmol) were added, followed by heating at 80° C. for 2 hours. The reaction mixture was cooled to room temperature and extracted with EtOAc. The organic extract was washed with brine, dried over anhydrous $Na_2SO_4$, concentrated under reduced pressure. The residue was purified by flash column chromatography (silica gel, n-Hex:EtOAc=1:1), $CH_2Cl_2$ (10.0 mL) was added and stirred for 10 minutes. Insoluble solid was filtered to obtain methyl 3-hydroxy-5-nitrobenzo[b]thiophene-2-carboxylate (1.2 g, 97%) as a brown solid.

$^1$H-NMR (400MHz, DMSO-$d_6$): δ 8.33 (s, 1H), 8.06 (d, 1H, J=8.7Hz), 7.75 (d, 1H, J=8.7Hz), 3.59 (s, 3H)

(b) Synthesis of methyl 5-amino-3-hydroxybenzo[b]thiophene-2-carboxylate

The synthesis procedure of Intermediate 13-b was repeated except for using methyl 3-hydroxy-5-nitrobenzo[b]thiophene-2-carboxylate (160.0 mg, 0.64 mmol) to obtain methyl 5-amino-3-hydroxybenzo[b]thiophene-2-carboxylate (220.0 mg, 100%).

LC/MS ESI (+): 224 (M+1)

(c) Synthesis of methyl 3-hydroxy-5-(methylsulfonamido)benzo[b]thiophene-2-carboxylate The synthesis procedure of Intermediate 6-a was repeated except for using methyl 5-amino-3-hydroxybenzo[b]thiophene-2-carboxylate (50.0 mg, 0.24 mmol) to obtain methyl 3-hydroxy-5-(methylsulfonamido)benzo[b]thiophene-2-carboxylate (70.0 mg, 97%).

$^1$H-NMR (400MHz, DMSO-$d_6$): δ 10.57 (brs, 1H), 9.93 (s, 1H), 7.89 (d, 1H, J=8.7Hz), 7.41 (dd, 1H, J=8.7, 2.1Hz), 3.85 (s, 3H), 3.00 (s, 3H)

(d) Synthesis of 3-hydroxy-5-(methylsulfonamido)benzo[b]thiophene-2-carboxylic acid The synthesis procedure of Intermediate 6-b was repeated except for using methyl 3-hydroxy-5-(methylsulfonamido)benzo[b]thiophene-2-carboxylate (57.0 mg, 0.19 mmol) to obtain 3-hydroxy-5-(methylsulfonamido)benzo[b]thiophene-2-carboxylic acid (35.0 mg, 61%) as a yellow solid.

LC/MS ESI (+): 288 (M+1)

$^1$H-NMR (400MHz, DMSO-$d_6$): δ 10.60 (brs, 1H), 9.92 (s, 1H), 7.90 (d, 1H, J=8.7Hz), 7.71 (d, 1H, J=1.9Hz), 7.42 (dd, 1H, J=8.7, 2.1Hz), 3.01 (s, 3H)

Intermediate 28) Synthesis of 5-chloro-6-(methylsulfonamido)benzo[b]thiophene-2-carboxylic acid

(a) Synthesis of 1-bromo-4-(bromomethyl)-2-chloro-5-fluorobenzene

1-Bromo-2-chloro-5-fluoro-4-methylbenzene (1.0 g, 4.48 mmol) was dissolved in 1,2-dichloroethane (45.0 mL), and NBS (955.8 mg, 4.48 mmol) and AIBN (73.6 mg, 0.45 mmol) were added, followed by heating at 90° C. for 15 hours. The reaction mixture was extracted with $CH_2Cl_2$, washed with brine, dried over anhydrous $Na_2SO_4$, concentrated under reduced pressure. The residue was purified by flash column chromatography (silica gel, n-Hex:EtOAc=9:1) to obtain 1-bromo-4-(bromomethyl)-2-chloro-5-fluorobenzene (880.0 mg, 65%) as a colorless liquid.

$^1$H-NMR (400MHz, CDCl$_3$): δ 7.51 (d, 1H, J=7.1Hz), 7.40 (d, 1H, J=8.8Hz), 4.42 (s, 2H)

(b) Synthesis of 4-bromo-5-chloro-2-fluorobenzaldehyde

1-Bromo-4-(bromomethyl)-2-chloro-5-fluorobenzene (780.0 mg, 2.58 mmol) was dissolved in anhydrous $CH_3CN$ (25.8 mL), and N-methylmorpholine-N-oxide (604.5 mg, 5.16 mmol) and molecular sieve (2.0 g, 4 Å) were added, followed by stirring at room temperature for 5 hours. The reaction mixture was extracted with EtOAc, washed with brine, dried over anhydrous $Na_2SO_4$, concentrated under reduced pressure. The residue was purified by flash column chromatography (silica gel, n-Hex:EtOAc=9:1) to obtain 4-bromo-5-chloro-2-fluorobenzaldehyde (404.8 mg, 66%) as a white solid.

$^1$H-NMR (400MHz, CDCl$_3$): δ 10.26 (s, 1H), 7.94 (d, 1H, J=6.6Hz), 7.54 (d, 1H, J=9.2Hz)

(c) Synthesis of methyl 6-bromo-5-chlorobenzo[b]
thiophene-2-carboxylate

The synthesis procedure of Intermediate 26-a was repeated except for using 4-bromo-5-chloro-2-fluorobenzaldehyde (404.8 mg, 1.71 mmol) to obtain methyl 6-bromo-5-chlorobenzo[b]thiophene-2-carboxylate (311.7 mg, 60%).

$^1$H-NMR (400MHz, CDCl$_3$): δ 8.14 (s, 1H), 7.97 (s, 1H), 7.94 (s, 1H), 3.95 (s, 3H)

(d) Synthesis of methyl 5-chloro-6-(methylsulfonamido)benzo[b]thiophene-2-carboxylate Methyl 6-bromo-5-chlorobenzo[b]thiophene-2-carboxylate (311.7 mg, 1.02 mmol) and methanesulfonamide (145.5 mg, 1.53 mmol) were dissolved in 1,4-dioxane (20.0 mL), and Pd$_2$(bda)$_3$(0) (93.4 mg, 0.10 mmol), Xantphos (177.1 mg, 0.31 mmol) and Cs$_2$CO$_3$ (664.7 mg, 2.04 mmol) were added, followed by refluxing at 100° C. for 2 hours. The reaction mixture was cooled to room temperature, extracted with EtOAc, washed with brine, dried over anhydrous Na$_2$SO$_4$, concentrated under reduced pressure. The residue was purified by flash column chromatography (silica gel, n-Hex:EtOAc=2:1), followed by adding EtOH (5.0 mL) and stirring for 10 minutes. The resultant was filtered to obtain methyl 5-chloro-6-(methylsulfonamido)benzo[b]thiophene-2-carboxylate (165.7 mg, 51%) as a yellow solid.

LC/MS ESI (+): 320 (M+1)

$^1$H-NMR (400MHz, DMSO-d$_6$): δ 9.70 (s, 1H), 8.22 (s, 1H), 8.16 (s, 1H), 8.14 (s, 1H), 3.89 (s, 3H), 3.11 (s, 3H)

(e) Synthesis of 5-chloro-6-(methylsulfonamido)
benzo[b]thiophene-2-carboxylic acid The synthesis procedure of Intermediate 6-b was repeated except for using methyl 5-chloro-6-(methylsulfonamido)benzo[b]thiophene-2-carboxylate (195.0 mg, 0.61 mmol) to obtain 5-chloro-6-(methylsulfonamido)benzo[b]thiophene-2-carboxylic acid (160.7 mg, 86%).

$^1$H-NMR (400MHz, DMSO-d$_6$): δ 13.62 (brs, 1H), 9.67 (brs, 1H), 8.20 (s, 1H), 8.14 (s, 1H), 8.03 (s, 1H), 3.12 (s, 3H)

Intermediate 29) Synthesis of 6-bromo-5-(methylsulfonamido)benzo[b]thiophene-2-carboxylic acid (a) Synthesis of
4-bromo-2-fluoro-5-nitrobenzaldehyde 4-Bromo-2-fluorobenzaldehyde (2.0 g, 9.85 mmol) was dissolved in concentrated sulfuric acid (5.2 mL, 98.50 mmol), and 60% HNO$_3$ (1.0 mL, 12.80 mmol) was added at 0° C. The reaction mixture was stirred at room temperature for 4 hours, and extracted with CH$_2$Cl$_2$. The organic extract was washed with brine, dried over anhydrous Na$_2$SO$_4$ and concentrated under reduced pressure. The residue was recrystallized using i-Pr$_2$O to obtain 4-bromo-2-fluoro-5-nitrobenzaldehyde (900.0 mg, 37%) as a white solid.

$^1$H-NMR (400MHz, CDCl$_3$): δ 10.31 (s, 1H), 8.42 (d, 1H, J=6.4Hz), 7.67 (d, 1H, J=9.0Hz).

(b) Synthesis of methyl 6-bromo-5-nitrobenzo[b]
thiophene-2-carboxylate

The synthesis procedure of Intermediate 26-a was repeated except for using 4-bromo-2-fluoro-5-nitrobenzaldehyde (500 mg, 2.02 mmol) to obtain a yellow compound of methyl 6-bromo-5-nitrobenzo[b]thiophene-2-carboxylate (550.0 mg).

(c) Synthesis of methyl 5-amino-6-bromobenzo[b]
thiophene-2-carboxylate

The synthesis procedure of Intermediate 13-b was repeated except for using crude methyl 6-bromo-5-nitrobenzo[b]thiophene-2-carboxylate (550.0 mg) to obtain methyl 5-amino-6-bromobenzo[b]thiophene-2-carboxylate (180.0 mg, 2 step yield: 31%).

LC/MS ESI (+): 286 (M+1)

(d) Synthesis of methyl 6-bromo-5-(methylsulfonamido)benzo[b]thiophene-2-carboxylate The synthesis procedure of Intermediate 6-a was repeated except for using methyl 5-amino-6-bromobenzo[b]thiophene-2-carboxylate (180.0 mg, 0.63 mmol) to obtain methyl 6-bromo-5-(methylsulfonamido)benzo[b]thiophene-2-carboxylate (185.7 mg, 81%).

$^1$H-NMR (400MHz, CDCl$_3$): δ 8.08 (s, 1H), 8.06 (s, 1H), 7.94 (s, 1H), 6.76 (s, 1H), 3.89 (s, 3H), 2.95 (s, 3H).

(e) Synthesis of 6-bromo-5-(methylsulfonamido)
benzo[b]thiophene-2-carboxylic acid The synthesis procedure of Intermediate 6-b was repeated except for using methyl 6-bromo-5-(methylsulfonamido)benzo[b]thiophene-2-carboxylate (185.7 mg, 0.51 mmol) to obtain 6-bromo-5-(methylsulfonamido)benzo[b]thiophene-2-carboxylic acid (200.0 mg, 74%).

$^1$H-NMR (400MHz, DMSO-d$_6$): δ 9.52 (s, 1H), 8.48 (s, 1H), 8.05-8.07 (m, 2H), 3.08 (s, 3H)

Intermediate 30) Synthesis of 6-fluoro-5-((tetrahydrofuran)-3-sulfonamido)benzo[b]thiophene-2-carboxylic acid (a) Synthesis of methyl 5-[bis(tetrahydrofuran-3-ylsulfonyl)amino]-6-fluoro-benzothiophene-2-carboxylate Methyl 5-amino-6-fluorobenzo[b]thiophene-2-carboxylate (120.0 mg, 0.53 mmol) was dissolved in CH$_2$Cl$_2$ (5.3 mL), and tetrahydrofuran-3-sulfonyl chloride (180.4 mg, 1.06 mmol) and DIPEA (0.2 mL, 1.17 mmol) were added. The reaction mixture was stirred for 15 hours, water was added to quench the reaction. The reaction mixture was extracted with EtOAc. The organic extract was washed with brine, dried over anhydrous Na$_2$SO$_4$ and concentrated under reduced pressure to obtain methyl 5-[bis(tetrahydrofuran-3-ylsulfonyl)amino]-6-fluoro-benzothiophene-2-carboxylate (109.0 mg).

LC/MS ESI (+): 494 (M+1)

(b) Synthesis of 6-fluoro-5-((tetrahydrofuran)-3-sulfonamido)benzo[b]thiophene-2-carboxylic acid The synthesis procedure of Intermediate 6-b was repeated except for using crude methyl 5-[bis(tetrahydrofuran-3-ylsulfonyl)amino]-6-fluoro-benzothiophene-2-carboxylate (109.0 mg) to obtain 6-fluoro-5-((tetrahydrofuran)-3-sulfonamido)benzo[b]thiophene-2-carboxylic acid (90.0 mg, 2 step yield: 49%).

LC/MS ESI (+): 346 (M+1)

¹H-NMR (400MHz, DMSO-d₆): δ 12.07 (s, 1H), 9.97 (s, 1H), 8.13 (s, 1H), 8.06-8.11 (m, 2H), 3.87 (m, 4H), 3.68 (m, 1H), 2.18-2.22 (m, 2H)

Intermediate 31) Synthesis of 6-chloro-5-(2-methoxyethyl)sulfonamido)benzo[b]thiophene-2-carboxylic acid (a) Synthesis of methyl 5-[bis(2-methoxyethylsulfony)amino]-6-chloro-benzothiophene-2-carboxylate Methyl 5-amino-6-chlorobenzo[b]thiophene-2-carboxylate (400.0 mg, 1.65 mmol) was dissolved in CH₂Cl₂ (6.0 mL), and 2-methoxyethane-1-sulfonyl chloride (0.4 mL, 3.64 mmol) and DIPEA (0.9 mL, 4.95 mmol) were added. The reaction mixture was stirred for 1 hour, water was added to quench the reaction, and then extracted with EtOAc. The organic extract was washed with brine, dried over anhydrous Na₂SO₄, concentrated under reduced pressure. The residue was purified by flash column chromatography (silica gel, n-Hex:EtOAc=1:1) to obtain methyl 5-[bis(2-methoxyethylsulfonyl)amino]-6-chloro-benzothiophene-2-carboxylate (350.0 mg, 43%) as an off-white oil.

LC/MS ESI (+): 486 (M+1)
¹H-NMR (400MHz, CDCl₃): δ 8.08 (s, 1H), 8.04 (s, 1H), 8.02 (s, 1H), 4.09-4.16 (m, 2H), 3.97 (s, 3H), 3.89-3.92 (m, 4H), 3.81-3.87 (m, 2H), 3.40 (s, 6H)

(b) Synthesis of 6-chloro-5-((2-methoxyethyl)sulfonamido)benzo[b]thiophene-2-carboxylic acid The synthesis procedure of Intermediate 6-b was repeated except for using methyl 5-[bis(2-methoxyethylsulfonyl)amino]-6-chloro-benzothiophene-2-carboxylate (350.0 mg, 0.72 mmol) to obtain 6-chloro-5-(2-methoxyethyl)sulfonamido)benzo[b]thiophene-2-carboxylic acid (220.0 mg, 87%).

LC/MS ESI (+): 350 (M+1)
¹H-NMR (400MHz, DMSO-d₆): δ 9.64 (s, 1H), 8.33 (s, 1H), 8.07-8.11 (m, 2H), 3.74 (t, 2H, J=6.4Hz), 3.46 (t, 2H, J=6.4Hz), 3.24 (s, 3H)

Intermediate 32) Synthesis of (3-methoxy-5-nitrophenyl)(3-(trifluoromethoxy)phenyl)methanone (a) Synthesis of 3-methoxy-5-nitrobenzoic acid To a mixture of LiOMe (3.6 g, 94.28 mmol) and HMPA (100.0 mL), 3,5-dinitrobenzoic acid (5.0 g, 23.57 mmol) was added at room temperature. The reaction mixture was stirred for 17 hours and heated at 80° C. for 17 hours, and then cooled to room temperature. The reaction mixture was poured into a mixture of 6M H₂SO₄ and ice water, and extracted with Et₂O. The organic extract was washed with 1 N HCl and brine, dried over anhydrous Na₂SO₄, concentrated under reduced pressure to obtain 3-methoxy-5-nitrobenzoic acid (4.0 g, 86%) as a yellow solid.

¹H-NMR (300MHz, DMSO-d₆): δ 13.76 (brs, 1H), 8.21 (m, 1H), 7.95 (t, 1H, J=2.7Hz), 7.82 (dd, 1H, J=2.7, 1.1Hz), 3.94 (s, 3H)

(b) Synthesis of 3-methoxy-5-nitrobenzoyl chloride

3-Methoxy-5-nitrobenzoic acid (6.8 g, 34.34 mmol) was dissolved in anhydrous CH₂Cl₂ (10.0 mL), and (COCl)₂ (6.0 mL, 68.68 mmol) and a catalytic amount of anhydrous DMF were added. Stirring was performed at room temperature for 3 hours, and the reaction mixture was concentrated under reduced pressure, followed by adding i-Pr₂O, stirring for 30 minutes and then filtering. The filtrate was concentrated under reduced pressure to obtain 3-methoxy-5-nitrobenzoyl chloride (7.0 g, 95%) as an off-white solid.

(c) Synthesis of (3-methoxy-5-nitrophenyl)(3-(trifluoromethoxy)phenyl)methanone

3-Methoxy-5-nitrobenzoyl chloride (350.0 mg, 1.62 mmol) and (3-(trifluoromethoxy)phenyl)boronic acid (257.0 mg, 1.25 mmol) were dissolved in anhydrous toluene (12.0 mL), and Pd(dppf)₂Cl₂·CH₂Cl₂ (51.0 mg, 0.06 mmol) and K₃PO₄·H₂O (575.0 mg, 2.50 mmol) were added. The reaction mixture was heated at 110° C. for 2 hours, and the reaction temperature was cooled to room temperature. Water was added to the reaction mixture, followed by extraction with EtOAc. The organic extract was washed with sat. NaHCO₃ aqueous solution and brine, dried over anhydrous Na₂SO₄, concentrated under reduced pressure. The residue was purified by flash column chromatography (silica gel, n-Hex:EtOAc=5:1) to obtain (3-methoxy-5-nitrophenyl)(3-(trifluoromethoxy)phenyl)methanone (232.4 mg, 55%) as an off-white oil.

¹H-NMR (300MHz, DMSO-d₆): δ 8.00-8.03 (m, 2H), 7.83 (m, 1H), 7.71-7.79 (m, 3H), 7.69 (m, 1H), 3.95 (s, 3H)

Intermediate 33) Synthesis of 3-(difluoromethoxy)-5-nitrobenzoic acid (a) Synthesis of methyl 3-hydroxy-5-nitrobenzoate To a solution of 3-hydroxy-5-nitrobenzoic acid (3.7 g, 20.00 mmol) in MeOH (70.0 mL), SOCl₂ (12.0 mL) was added at 0° C. The reaction mixture was stirred at 6° C. for 3 hours, and concentrated under reduced pressure. Water was added to the residue, followed by extracting with EtOAc. The organic extract was washed with brine, dried over anhydrous Na₂SO₄, concentrated under reduced pressure to obtain methyl 3-hydroxy-5-nitrobenzoate (3.9 g) as an off-white solid without purification.

¹H-NMR (300MHz, DMSO-d₆): δ 10.96 (s, 1H), 8.08 (m, 1H), 7.78 (m, 1H), 7.70 (m, 1H), 3.90 (s, 3H)

(b) Synthesis of methyl 3-(difluoromethoxy)-5-nitrobenzoate

To a solution of crude methyl 3-hydroxy-5-nitrobenzoate (3.9 g) in anhydrous DMF (150.0 mL), sodium 2-chloro-2,2-difluoroacetate (5.0 g, 33.30 mmol) and Na₂CO₃ (1.8 g, 165.00 mmol) were added at room temperature. The reaction mixture was heated at 100° C. for 30 minutes and cooled to room temperature. Water was added to the reaction mixture, followed by extracting with EtOAc. The organic extract was washed with brine, dried over anhydrous Na₂SO₄, concentrated under reduced pressure. The residue was purified by flash column chromatography (silica gel, n-Hex:EtOAc=5: 95 to 30:70) to obtain methyl 3-(difluoromethoxy)-5-nitrobenzoate (2.5 g, 2 step yield: 61%) as a white solid.

¹H-NMR (300MHz, CDCl₃): δ 8.73 (m, 1H), 8.19 (t, 1H, J=2.1Hz), 8.13 (s, 1H), 6.65 (t, 1H, J=71.7Hz), 4.00 (s, 3H)

(c) Synthesis of 3-(difluoromethoxy)-5-nitrobenzoic acid

Methyl-3-(difluoromethoxy)-5-nitrobenzoate (2.5 g, 10.10 mmol) was dissolved in a mixture of THF/H₂O (50.0 mL, 4/1 v/v), and LiOH·H$_2$O (485.0 mg, 20.20 mmol) was added at 0° C. The reaction mixture was stirred at 5° C. for 12 hours and concentrated under reduced pressure. The residue was acidified to pH 3-4 with 1 N HCl aqueous solution and extracted with EtOAc. The organic extract was washed with brine, dried over anhydrous Na$_2$SO$_4$, concentrated under reduced pressure to obtain 3-(difluoromethoxy)-5-nitrobenzoic acid (2.4 g, 100%) as a white solid.

$^1$H-NMR (300MHz, DMSO-d$_6$): δ 14.25 (brs, 1H), 8.47 (s, 1H), 8.22 (s, 1H), 8.06 (s, 1H), 7.53 (t, 1H, J=72.9Hz)

Intermediate 34) Synthesis of (2-fluorophenyl)(3-nitrophenyl)methanone

To a solution of 1-bromo-2-fluorobenzene (1.0 g, 5.71 mmol) in anhydrous THF (15.0 mL), 1.7 M solution of tert-BuLi in pentane (3.5 mL, 6.00 mmol) was added at −78° C., followed by stirring for 30 minutes. ZnI$_2$ (1.9 g, 6.00 mmol) was dissolved in anhydrous THF (10.0 mL), and was added to the reaction mixture, followed by stirring at 0° C. for 30 minutes. The reaction mixture was added to a solution of 3-nitrobenzoyl chloride (1.1 g, 5.71 mmol) and Pd$_2$(dba)$_3$·CHCl$_3$ (296.0 mg, 0.29 mmol) in anhydrous THF (15.0 mL) at 0° C., followed by stirring at room temperature for 12 hours. Water was added to the reaction mixture to quench the reaction, followed by extracting with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=5:1) to obtain (2-fluorophenyl)(3-nitrophenyl)methanone (490.0 mg, 35%) as an off-white oil.

$^1$H-NMR (300MHz, CDCl$_3$): δ 8.63 (s, 1H), 8.45 (d, 1H, J=8.0Hz), 8.17 (d, 1H, J=8.0Hz), 7.59-7.73 (m, 3H), 7.34 (t, 1H, J=7.6Hz), 7.20 (t, 1H, J=8.0Hz)

Intermediate 35) Synthesis of (3-bromo-5-nitrophenyl)(3-methoxyphenyl)methanone

3-Bromo-5-nitrobenzoyl chloride (2.7 g, 10.06 mmol) was dissolved in anhydrous Et$_2$O (100.0 mL), and (3-methoxyphenyl)boronic acid (1.5 g, 10.06 mmol), Pd(dba)$_2$ (289.0 mg, 0.50 mmol), PPh$_3$ (264.0 mg, 1.01 mmol), and copper thiophene-2-carboxylate (1.9 g, 10.06 mmol) were added. The reaction mixture was stirred at room temperature for 12 hours, filtered through Celite and concentrated under reduced pressure. The residue was purified by flash column chromatography (amine silica gel, n-Hex:EtOAc=9:1) to obtain (3-bromo-5-nitrophenyl)(3-methoxyphenyl)methanone (1.2 g, 35%) as an off-white oil.

$^1$H-NMR (300MHz, CDCl$_3$): δ 8.58 (t, 1H, J=1.9Hz), 8.54 (m, 1H), 8.25 (t, 1H, J=1.9Hz), 7.44 (t, 1H, J=8.0Hz), 7.35 (m, 1H), 7.29 (d, 1H, J=7.6Hz), 7.22 (dd, 1H, J=9.2, 2.7Hz), 3.88 (s, 3H)

Intermediate 36) Synthesis of (3-bromo-5-nitrophenyl)(4-fluorophenyl)methanone

To a mixture solution of 3-bromo-5-nitrobenzoyl chloride (1.1 g, 4.15 mmol) and fluorobenzene (8.0 mL), AlCl$_3$ (1.7 g, 12.50 mmol) was added at 0° C. The reaction mixture was heated at 50° C. for 5 hours, cooled to room temperature and poured into ice water, followed by extracting with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=5:1) to obtain (3-bromo-5-nitrophenyl)(4-fluorophenyl)methanone (1.2 g, 86%) as a colorless oil.

$^1$H-NMR (300MHz, CDCl$_3$): δ 8.59 (t, 1H, J=1.9Hz), 8.50 (dd, 1H, J=2.3, 1.5Hz), 8.22 (t, 1H, J=1.5Hz), 7.85 (dd, 2H, J=8.8, 5.3Hz), 7.24 (t, 2H, J=8.8Hz)

Intermediate 37) Synthesis of 1-(dichloro(3-(trifluoromethoxy)phenyl)methyl)-3-methoxy-5-nitrobenzene (3-Methoxy-5-nitrophenyl)(3-(trifluoromethoxy)phenyl)methanone (264.0 mg, 0.77 mmol) was dissolved in 1,2-dibromoethane (7.0 mL), and PCl$_5$ (805.9 mg, 3.87 mmol) was added. The reaction mixture was heated at 110° C. for 24 hours and cooled to room temperature. The reaction mixture was poured into NaHCO$_3$ dissolved in ice water, followed by vigorous stirring. The reaction mixture was extracted with CH$_2$Cl$_2$, and the organic extract was dried over anhydrous Na$_2$SO$_4$, concentrated under reduced pressure. The residue was purified by flash column chromatography (amine silica gel, n-Hex:EtOAc=5:1) to obtain 1-(dichloro(3-(trifluoromethoxy)phenyl)methyl)-3-methoxy-5-nitrobenzene (243.2 mg, 79%) as an off-white oil.

$^1$H-NMR (300MHz, DMSO-d$_6$): δ 7.94 (t, 1H, J=1.9Hz), 7.85 (t, 1H, J=1.9Hz), 7.61-7.68 (m, 3H), 7.55 (brs, 1H), 7.50 (t, 1H, J=1.9Hz), 3.91 (s, 3H)

Intermediate 38) Synthesis of 1-methoxy-3-nitro-5-(2-(3-(trifluoromethoxy)phenyl)propan-2-yl)benzene In CH$_2$Cl$_2$ (3.0 mL), 1.0 M solution of TiCl$_4$ in CH$_2$Cl$_2$ (123.0 μL, 0.12 mmol) and 1.0 M solution of dimethylzinc in heptane (1.8 mL, 1.84 mmol) were added at −40° C., followed by stirring for 30 minutes. A solution of 1-(dichloro(3-(trifluoromethoxy)phenyl)methyl)-3-methoxy-5-nitrobenzene (243.2 mg, 0.61 mmol) in CH$_2$Cl$_2$ (3.0 mL) was slowly added at −40° C. The reaction mixture was stirred at 0° C. for 2 hours, water was added to quench the reaction, and then extracted with CH$_2$Cl$_2$. The organic extract was dried over anhydrous Na$_2$SO$_4$, concentrated under reduced pressure. The residue was purified by flash column chromatography (amine silica gel, n-Hex:EtOAc=9:1) to obtain 1-methoxy-3-nitro-5-(2-(3-(trifluoromethoxy)phenyl)propan-2-yl)benzene (164.0 mg, 75%) as an off-white oil.

$^1$H-NMR (300MHz, DMSO-d$_6$): δ 7.58-7.60 (m, 2H), 7.45 (m, 1H), 7.29 (dt, 1H, J=8.0, 1.1Hz), 7.21-7.25 (m, 3H), 3.84 (s, 3H), 1.70 (s, 6H)

Intermediate 39) Synthesis of 3-methoxy-5-(2-(3-(trifluoromethoxy)phenyl)propan-2-yl)aniline 1-Methoxy-3-nitro-5-(2-(3-(trifluoromethoxy)phenyl)propan-2-yl)benzene (164.0 mg, 0.46 mmol) was dissolved in MeOH (4.0 mL). Under an atmosphere of hydrogen gas, Ra—Ni was added, and a reaction was performed at room temperature for 12 hours. The reaction mixture was filtered through Celite and concentrated under reduced pressure. The residue was purified by flash column chromatography (silica gel, n-Hex:EtOAc=4:1) to obtain 3-methoxy-5-(2-(3-(trifluoromethoxy)phenyl)propan-2-yl)aniline (121.7 mg, 81%) as an off-white oil.

LC/MS ESI (+): 326 (M+1)

$^1$H-NMR (300MHz, DMSO-d$_6$): δ 7.40 (t, 1H, J=8.0Hz), 7.23 (d, 1H, J=8.0Hz), 7.15 (d, 1H, J=8.0Hz), 7.10 (s, 1H), 5.98-6.00 (m, 2H), 5.92 (t, 1H, J=1.9Hz), 5.01 (s, 2H), 3.60 (s, 3H), 1.55 (s, 6H)

Intermediate 40) Synthesis of 3-bromo-5-(2-(3-(difluoromethoxy)phenyl)propan-2-yl)aniline 1-Bromo-3-(2-(3-(difluoromethoxy)phenyl)propan-2-yl)-5-nitrobenzene (106.6 mg, 0.28 mmol) was dissolved in a mixture of MeOH/H$_2$O (3.0 mL, 9/1 v/v), and Zn (270.7 mg, 4.14 mmol) and NH$_4$Cl (73.8 mg, 1.38 mmol) were added at room temperature. The reaction mixture was ultrasonificated at 40° C. for 40 minutes, and then cooled to room temperature, filtered through Celite and concentrated under reduced pressure. The residue was purified by flash column chromatography (amine silica gel, n-Hex:EtOAc=4:1) to obtain 3-bromo-5-(2-(3-(difluoromethoxy)phenyl)propan-2-yl)aniline (91.5 mg, 93%) as an off-white oil.

LC/MS ESI (+): 356 (M+1)

Intermediate 41) Synthesis of 3-(2-(3-bromo-5-nitrophenyl)propan-2-yl)phenol To a solution of 1-bromo-3-(2-(3-methoxyphenyl)propan-2-yl)-5-nitrobenzene (602.0 mg, 1.72 mmol) in anhydrous CH$_2$Cl$_2$ (8.0 mL), 1.0 M solution of BBr$_3$ in CH$_2$Cl$_2$ (8.6 mL, 8.60 mmol) was added at 0° C., followed by stirring at room temperature for 3.5 hours. Water was added at 0° C. to quench the reaction, followed by extraction with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=4:1) to obtain 3-(2-(3-bromo-5-nitrophenyl)propan-2-yl)phenol (570.0 mg, 98%) as an off-white oil.

$^1$H-NMR (300MHz, DMSO-d$_6$): δ 9.31 (s, 1H), 8.22 (t, 1H, J=1.9Hz), 7.95 (t, 1H, J=1.9Hz), 7.82 (t, 1H, J=1.9Hz), 7.11 (t, 1H, J=8.4Hz), 6.68 (d, 1H, J=8.4Hz), 6.61-6.63 (m, 2H), 1.65 (s, 6H)

Intermediate 42) Synthesis of 2-(3-(2-(3-bromo-5-nitrophenyl)propan-2-yl)phenoxy)acetamide 3-(2-(3-Bromo-5-nitrophenyl)propan-2-yl)phenol (123.0 mg, 0.37 mmol) was dissolved in anhydrous DMF (3.5 mL), and K$_2$CO$_3$ (152.0 mg, 1.10 mmol) and 2-iodoacetamide (135.0 mg, 0.73 mmol) were added. The reaction mixture was stirred at 30° C. for 76 hours, water was added, and then extracted with EtOAc. The organic extract was washed with brine, dried over anhydrous Na$_2$SO$_4$, concentrated under reduced pressure. The residue was purified by flash column chromatography (silica gel, n-Hex:EtOAc=1:2) to obtain 2-(3-(2-(3-bromo-5-nitrophenyl)propan-2-yl)phenoxy)acetamide (129.1 mg, 83%) as a white solid.

LC/MS ESI (+): 393 (M+1)

$^1$H-NMR (300MHz, DMSO-d$_6$): δ 8.22 (m, 1H), 7.96 (m, 1H), 7.83 (m, 1H), 7.51 (brs, 1H), 7.36 (brs, 1H), 7.25 (td, 1H, J=8.4, 3.1Hz), 6.78-6.89 (m, 3H), 4.38 (s, 2H), 1.68 (s, 6H)

Intermediate 43) Synthesis of 1-bromo-3-(2-(3-(difluoromethoxy)phenyl)propan-2-yl)-5-nitrobenzene 3-(2-(3-Bromo-5-nitrophenyl)propan-2-yl)phenol (122.2 mg, 0.36 mmol) was dissolved in a mixture of CH$_3$CN/H$_2$O (3.6 mL, 1/1 v/v), and KOH (407.0 mg, 7.26 mmol) and diethyl (bromodifluoromethyl)phosphonate (129.0 µL, 0.73 mmol) were added. The reaction mixture was heated at 40° C. for 5 hours, and water was added to quench the reaction, followed by extracting with EtOAc. The organic extract was washed with brine, dried over anhydrous Na$_2$SO$_4$, concentrated under reduced pressure. The residue was purified by flash column chromatography (silica gel, n-Hex:EtOAc=9:1) to obtain 1-bromo-3-(2-(3-(difluoromethoxy)phenyl)propan-2-yl)-5-nitrobenzene (106.6 mg, 70%) as an off-white oil.

$^1$H-NMR (300MHz, DMSO-d$_6$): δ 8.24 (m, 1H), 7.98 (m, 1H), 7.86 (m, 1H), 7.38 (t, 1H, J=7.6Hz), 7.25 (t, 1H, J=74.4Hz), 7.12 (d, 1H, J=7.6Hz), 7.08 (s, 1H), 7.05 (d, 1H, J=8.0Hz), 1.71 (s, 6H)

Intermediate 44) Synthesis of 4-(3-(2-(3-chloro-5-nitrophenyl)propan-2-yl)-5-(1,1,2,2-tetrafluoroethoxy)benzyl)-1-methyl-1H-pyrazole 1-(Bromomethyl)-3-(2-(3-chloro-5-nitrophenyl)propan-2-yl)-5-(1,1,2,2-tetrafluoroethoxy)benzene (150.0 mg, 0.24 mmol), 1-methyl-4-(4,4,5,5-tetramethyl-1,3,2-dioxaborolan-2-yl)-1H-pyrazole (54.5 mg, 0.26 mmol), Pd(PPh$_3$)$_4$ (27.5 mg, 0.02 mmol) and Na$_2$CO$_3$ (75.4 mg, 0.71 mmol) were added to a mixture of DME/H$_2$O (4.5 mL, 2/1 v/v) in a sealed tube. The reaction mixture was heated at 100° C. for 4 hours and cooled to room temperature, followed by extracting with EtOAc. The organic extract was washed with brine, dried over anhydrous Na$_2$SO$_4$, concentrated under reduced pressure. The residue was purified by flash column chromatography (silica gel, n-Hex:EtOAc=1:1) to obtain 4-(3-(2-(3-chloro-5-nitrophenyl)propan-2-yl)-5-(1,1,2,2-tetrafluoro ethoxy)benzyl)-1-methyl-1H-pyrazole (25.9 mg, 22%) as a yellow oil.

LC/MS ESI (+): 486 (M+1)

$^1$H-NMR (400MHz, CDCl$_3$): δ 8.07 (m, 1H), 7.97 (m, 1H), 7.48 (m, 1H), 7.28 (s, 1H), 7.04 (s, 1H), 6.94 (s, 1H), 6.92 (s, 1H), 6.89 (s, 1H), 5.87 (tt, 1H, J=53.1, 2.7Hz), 3.85 (s, 3H), 3.79 (s, 2H), 1.70 (s, 6H)

Example 1

Synthesis of N-(3-(2-(4-fluorophenyl)propan-2-yl)phenyl)-6-(methylsulfonamido)-1H-indole-2-carboxamide 3-(2-(4-fluorophenyl)propan-2-yl)aniline (36.0 mg, 0.16 mmol), 6-(methylsulfonamido)-1H-indole-2-carboxylic acid hydrochloride (50.0 mg, 0.17 mmol) and HATU (66.0 mg, 0.17 mmol) were dissolved in anhydrous DMF (1.6 mL), and DIPEA (84.0 µL, 0.48 mmol) was added. The reaction mixture was stirred at room temperature for 15 hours and then extracted with CH$_2$Cl$_2$. The organic extract was washed with brine, dried over anhydrous Na$_2$SO$_4$, concentrated under reduced pressure. The residue was purified by flash column chromatography (amine silica gel, CH$_2$Cl$_2$:MeOH=95:5) to obtain N-(3-(2-(4-fluorophenyl)propan-2-yl)phenyl)-6-(methylsulfonamido)-1H-indole-2-carboxamide (37.0 mg, 50%) as a white solid.

LC/MS ESI (+): 466 (M+1)

$^1$H-NMR (300MHz, DMSO-d$_6$): δ 11.68 (s, 1H), 10.08 (s, 1H), 9.60 (s, 1H), 7.73 (d, 1H, J=8.4Hz), 7.58-7.62 (m, 2H), 7.36 (s, 2H), 7.24-7.30 (m, 3H), 7.10 (t, 2H, J=8.8 Hz), 6.97 (dd, 2H J=8.8, 1.9Hz), 2.93 (s, 3H), 1.65 (s, 6H)

Through the synthetic method according to Example 1, compounds from Example 2 to Example 106 were synthesized, and the data of each example are as follows.

TABLE 2

| Ex. | Compound | Analysis data |
|---|---|---|
| 2 | 6-(methylsulfonamido)-N-(3-(2-phenylpropan-2-yl)phenyl)-1H-indole-2-carboxamide | LC/MS ESI (+): 448 (M + 1)<br>$^1$H-NMR(300 MHz, DMSO-$d_6$): δ 11.69 (s, 1H), 10.09 (s, 1H), 9.60 (s, 1H), 7.73 (d, 1H, J = 8.0 Hz), 7.58~7.64 (m, 2H), 7.36 (s, 2H), 7.22~7.32 (m, 5H), 7.16 (t, 1H, J = 6.9 Hz), 6.95~6.99 (m, 2H), 2.93 (s, 3H), 1.66 (s, 6H) |
| 3 | N-(3-(2-(4-fluorophenyl)propan-2-yl)phenyl)-5-methoxy-6-(methylsulfonamido)-1H-indole-2-carboxamide | LC/MS ESI (+): 496 (M + 1)<br>$^1$H-NMR (300 MHz, DMSO-$d_6$): δ 11.58 (s, 1H), 10.08 (s, 1H), 8.86 (brs, 1H), 7.72 (d, 1H, J = 8.4 Hz), 7.62 (s, 1H), 7.38 (s, 1H), 7.21~7.30 (m, 5H), 7.07~7.13 (m, 2H), 6.96 (d, 1H, J = 8.0 Hz), 3.85 (s, 3H), 2.90 (s, 3H), 1.65 (s, 6H) |
| 4 | N-(3-methoxy-5-(2-(3-(trifluoromethoxy)phenyl)propan-2-yl)phenyl)-6-(methylsulfonamido)-1H-indole-2-carboxamide | LC/MS ESI (+): 562 (M + 1)<br>$^1$H-NMR (300 MHz, DMSO-$d_6$): δ 11.68 (s, 1H), 10.08 (s, 1H), 9.61 (s, 1H), 7.60 (d, 1H, J = 8.8 Hz), 7.41~7.47 (m, 2H), 7.36 (s, 2H), 7.17~7.28 (m, 4H), 6.97 (dd, 1H, J = 8.8, 1.9 Hz), 6.51 (s, 1H), 3.73 (s, 3H), 2.93 (s, 3H), 1.65 (s, 6H) |
| 5 | N-(3-(2-(4-fluorophenyl)propan-2-yl)phenyl)-6-((N-methylsulfamoyl)amino)-1H-indole-2-carboxamide | LC/MS ESI (+): 481 (M + 1)<br>$^1$H-NMR (300 MHz, DMSO-$d_6$): δ 11.61 (s, 1H), 10.05 (s, 1H), 9.55 (s, 1H), 7.72 (d, 1H, J = 8.0 Hz), 7.62 (s, 1H), 7.54 (d, 1H, J = 8.8 Hz), 7.33 (s, 2H), 7.24~7.29 (m, 3H), 7.07~7.13 (m, 3H), 6.95~6.98 (m, 2H), 2.47 (s, 3H), 1.65 (s, 6H) |
| 6 | N-(3-(2-(4-fluorophenyl)propan-2-yl)phenyl)-6-(methylsulfonyl)-1H-indole-2-carboxamide | LC/MS ESI (+): 451 (M + 1)<br>$^1$H-NMR (300 MHZ, DMSO-$d_6$): δ 12.39 (s, 1H), 10.35 (s, 1H), 8.00 (s, 1H), 7.93 (d, 1H, J = 8.8 Hz), 7.75 (dd, 1H, J = 8.8, 1.1 Hz), 7.64 (s, 1H), 7.61 (dd, 1H, J = 9.2, 1.5 Hz), 7.58 (s, 1H), 7.25~7.33 (m, 3H), 7.08~7.14 (m, 2H), 7.01 (dd, 1H, J = 8.0, 1.1 Hz), 3.20 (s, 3H), 1.66 (s, 6H) |
| 7 | N-(3-(2-(2-fluorophenyl)propan-2-yl)phenyl)-6-(methylsulfonamido)-1H-indole-2-carboxamide | LC/MS ESI (+): 466 (M + 1)<br>$^1$H-NMR(300 MHz, DMSO-$d_6$): δ 11.67 (s, 1H), 10.07 (s, 1H), 9.60 (s, 1H), 7.70 (d, 1H, J = 8.8 Hz), 7.52~7.60 (m, 3H), 7.36 (s, 2H), 7.21~7.33 (m, 3H), 7.04 (dd, 1H J = 12.2, 8.0 Hz), 6.96 (d, 1H, J = 8.8 Hz), 6.89 (d, 1H, J = 7.3 Hz), 2.92 (s, 3H), 1.66 (s, 6H) |
| 8 | 6-(methylsulfonamido)-N-(3-(2-(3-(trifluoromethoxy)phenyl)propan-2-yl)phenyl)-1H-indole-2-carboxamide | LC/MS ESI (+): 532 (M + 1)<br>$^1$H-NMR (300 MHz, DMSO-$d_6$): δ 11.68 (s, 1H), 10.10 (s, 1H), 9.61 (brs, 1H), 7.76 (d, 1H, J = 7.4 Hz), 7.65 (s, 1H), 7.60 (d, 1H, J = 8.8 Hz), 7.43 (t, 1H, J = 7.9 Hz), 7.36 (s, 2H), 7.25~7.32 (m, 2H), 7.15~7.20 (m, 2H), 6.96 (d, 2H, J = 7.9 Hz), 2.93 (s, 3H), 1.67 (s, 6H) |
| 9 | N-(3-(2-(3-methoxy-5-(trifluoromethoxy)phenyl)propan-2-yl)phenyl)-6-(methylsulfonamido)-1H-indole-2-carboxamide | LC/MS ESI (+): 562 (M + 1)<br>$^1$H-NMR (300 MHz, DMSO-$d_6$): δ 11.69 (s, 1H), 10.11 (s, 1H), 9.61 (s, 1H), 7.76 (d, 1H, J = 8.4 Hz), 7.60~7.64 (m, 2H), 7.37 (s, 2H), 7.29 (t, 1H, J = 8.0 Hz), 6.97 (d, 2H, J = 8.4 Hz), 6.79 (d, 2H, J = 6.5 Hz), 6.70 (s, 1H), 3.75 (s, 3H), 2.93 (s, 3H), 1.65 (s, 6H) |
| 10 | N-(3-(1-(3-methoxy-5-(trifluoromethoxy)phenyl)ethyl)phenyl)-6-(methylsulfonamido)-1H-indole-2-carboxamide | LC/MS ESI (+): 548 (M + 1)<br>$^1$H-NMR (300 MHz, DMSO-$d_6$): δ 11.70 (s, 1H), 10.13 (s, 1H), 9.62 (s, 1H), 7.60~7.71 (m, 3H), 7.38 (s, 2H), 7.30 (t, 1H, J = 7.7 Hz), 7.04 (d, 1H, J = 7.7 Hz), 6.98 (d, 1H, J = 8.5 Hz), 6.90 (s, 1H), 6.81 (s, 1H), 6.76 (s, 1H), 4.16~4.24 (m, 1H), 3.77 (s, 3H), 2.94 (s, 3H), 1.58 (d, 3H, J = 7.4 Hz) |
| 11 | N-(3-(2-(2,4-difluorophenyl)propan-2-yl)phenyl)-6-(methylsulfonamido)-1H-indole-2-carboxamide | LC/MS ESI (+): 484 (M + 1)<br>$^1$H-NMR(300 MHz, DMSO-$d_6$): δ 11.68 (s, 1H), 10.07 (s, 1H), 9.60 (s, 1H), 7.70 (d, 1H, J = 8.0 Hz), 7.54~7.61 (m, 3H), 7.36 (s, 2H), 7.25 (t, 1H, J = 8.1 Hz), 7.04~7.14 (m, 2H), 6.97 (dd, 1H J = 8.5, 1.8 Hz), 6.91 (d, 1H, J = 8.1 Hz), 2.93 (s, 3H), 1.65 (s, 6H) |
| 12 | N-(3-(2-(3-methoxyphenyl)propan-2-yl)phenyl)-6-(methylsulfonamido)-1H-indole-2-carboxamide | LC/MS ESI (+): 478 (M + 1)<br>$^1$H-NMR(300 MHz, DMSO-$d_6$): δ 11.68 (s, 1H), 10.09 (s, 1H), 9.61 (s, 1H), 7.74 (d, 1H, J = 8.1 Hz), 7.58~7.62 (m, 2H), 7.37 (s, 2H), 7.27 (t, 1H, J = 7.3 Hz), 7.20 (dd, 1H J = 8.8, 7.7 Hz), 6.97 (dd, 2H J = 8.8, 1.9 Hz), 6.74~6.81 (m, 3H), 3.70 (s, 3H), 2.93 (s, 3H), 1.64 (s, 6H) |
| 13 | N-(3-methoxy-5-(2-(3-methoxy-5-(trifluoromethoxy)phenyl)propan-2-yl)phenyl)-6-(methylsulfonamido)-1H-indole-2-carboxamide | LC/MS ESI (+): 592 (M + 1)<br>$^1$H-NMR (300 MHz, DMSO-$d_6$): δ 11.68 (s, 1H), 10.08 (s, 1H), 9.62 (s, 1H), 7.61 (d, 1H, J = 8.8 Hz), 7.47 (s, 1H), 7.37 (s, 2H), 7.22 (s, 1H), 6.97 (d, 1H, J = 8.8 Hz), 6.81 (s, 1H), 6.78 (s, 1H), 6.72 (s, 1H), 6.52 (s, 1H), 3.76 (s, 3H), 3.73 (s, 3H), 2.93 (s, 3H), 1.63 (s, 6H) |

TABLE 2-continued

| Ex. | Compound | Analysis data |
|---|---|---|
| 14 | N-(3-bromo-5-(2-(4-fluorophenyl)propan-2-yl)phenyl)-6-(methylsulfonamido)-1H-indole-2-carboxamide | LC/MS ESI (+): 544 (M + 1)<br>$^1$H-NMR(300 MHz, DMSO-$d_6$): δ 11.71 (s, 1H), 10.22 (s, 1H), 9.64 (s, 1H), 8.04 (s, 1H), 7.58~7.63 (m, 2H), 7.37 (s, 2H), 7.28 (dd, 2H J = 8.8, 5.3 Hz), 7.09~7.16 (m, 3H), 6.98 (dd, 1H J = 8.8, 1.5 Hz), 2.93 (s, 3H), 1.64 (s, 6H) |
| 15 | N-(3-bromo-5-(2-(2,4-difluorophenyl)propan-2-yl)phenyl)-6-(methylsulfonamido)-1H-indole-2-carboxamide | LC/MS ESI (+): 562 (M + 1)<br>$^1$H-NMR(300 MHz, DMSO-$d_6$): δ 11.71 (s, 1H), 10.21 (s, 1H), 9.64 (s, 1H), 8.04 (s, 1H), 7.53~7.64 (m, 3H), 7.36 (s, 2H), 7.10~7.16 (m, 2H), 7.06 (s, 1H), 6.97 (dd, 1H J = 8.8, 1.9 Hz), 2.93 (s, 3H), 1.64 (s, 6H) |
| 16 | N-(3-bromo-5-(2-(3-methoxy-5-(trifluoromethoxy)phenyl)propan-2-yl)phenyl)-6-(methylsulfonamido)-1H-indole-2-carboxamide | LC/MS ESI (+): 640 (M + 1)<br>$^1$H-NMR(300 MHz, DMSO-$d_6$): δ 11.73 (s, 1H), 10.24 (s, 1H), 9.65 (s, 1H), 8.09 (s, 1H), 7.59~7.64 (m, 2H), 7.38 (s, 2H), 7.12 (s, 1H), 6.98 (dd, 1H J = 8.8, 1.8 Hz), 6.80~6.82 (m, 2H), 6.73 (s, 1H), 3.77 (s, 3H), 2.94 (s, 3H), 1.64 (s, 6H) |
| 17 | N-(3-(difluoromethoxy)-5-(2-(4-fluorophenyl)propan-2-yl)phenyl)-6-(methylsulfonamido)-1H-indole-2-carboxamide | LC/MS ESI (+): 532 (M + 1)<br>$^1$H-NMR(300 MHz, DMSO-$d_6$): δ 11.75 (s, 1H), 10.25 (s, 1H), 9.65 (s, 1H), 7.72 (s, 1H), 7.62 (d, 1H, J = 8.6 Hz), 7.46 (m, 1H), 7.36~7.38 (m, 2H), 7.28 (dd, 2H, J = 8.8, 5.5 Hz), 7.23 (t, 1H, J = 74.0 Hz), 7.09~7.17 (m, 2H), 6.98 (dd, 1H, J = 8.4, 1.7 Hz), 6.76 (m, 1H), 2.94 (s, 3H), 1.65 (s, 6H) |
| 18 | N-(3-(2-(3-(2-amino-2-oxoethoxy)phenyl)propan-2-yl)-5-bromophenyl)-6-(methylsulfonamido)-1H-indole-2-carboxamide | LC/MS ESI (+): 599 (M + 1)<br>$^1$H-NMR (300 MHz, DMSO-$d_6$): δ 11.68 (s, 1H), 10.21 (s, 1H), 9.60 (s, 1H), 8.06 (s, 1H), 7.60~7.63 (m, 2H), 7.51 (s, 1H), 7.38 (s, 1H), 7.37 (s, 1H), 7.34 (s, 1H), 7.24 (t, 1H, J = 8.0 Hz), 7.08 (s, 1H), 6.99 (dd, 1H, J = 9.2, 1.9 Hz), 6.90 (s, 1H), 6.83 (d, 1H, J = 8.0 Hz), 6.77 (d, 1H, J = 8.4 Hz), 4.38 (s, 2H), 2.94 (s, 3H), 1.64 (s, 6H) |
| 19 | N-(3-bromo-5-(2-(4-fluorophenyl)propan-2-yl)phenyl)-5-methoxy-6-(methylsulfonamido)-1H-indole-2-carboxamide | LC/MS ESI (+): 574 (M + 1)<br>$^1$H-NMR (300 MHz, DMSO-d6): δ 11.58 (s, 1H), 10.19 (s, 1H), 8.77 (s, 1H), 8.04 (s, 1H), 7.61 (s, 1H), 7.41 (s, 1H), 7.26~7.31 (m, 3H), 7.23 (s, 1H), 7.09~7.16 (m, 3H), 3.86 (s, 3H), 2.92 (s, 3H), 1.65 (s, 6H) |
| 20 | N-(3-bromo-5-(2-(3-(difluoromethoxy)phenyl)propan-2-yl)phenyl)-6-(methylsulfonamido)-1H-indole-2-carboxamide | LC/MS ESI (+): 592 (M + 1)<br>$^1$H-NMR (300 MHz, DMSO-$d_6$): δ 11.68 (s, 1H), 10.21 (s, 1H), 9.61 (s, 1H), 8.07 (s, 1H), 7.60~7.63 (m, 2H), 7.34~7.39 (m, 3H), 7.23 (t, 1H, J = 74.4 Hz), 7.08~7.11 (m, 2H), 6.97~7.05 (m, 3H), 2.94 (s, 3H), 1.65 (s, 6H) |
| 21 | N-(3-chloro-5-(2-(4-fluorophenyl)propan-2-yl)phenyl)-6-(methylsulfonamido)-1H-indole-2-carboxamide | LC/MS ESI (+): 500 (M + 1)<br>$^1$H-NMR (300 MHz, DMSO-$d_6$): δ 11.68 (s, 1H), 10.21 (s, 1H), 9.59 (s, 1H), 7.92~7.93 (m, 1H), 7.60 (d, 1H, J = 8.4 Hz), 7.54 (s, 1H), 7.36~7.38 (m, 2H), 7.26~7.30 (m, 2H), 7.09~7.15 (m, 2H), 6.96~7.00 (m, 2H), 2.93 (s, 3H), 1.64 (s, 6H) |
| 22 | N-(3-bromo-5-(2-(3-ethoxy-5-(trifluoromethoxy)phenyl)propan-2-yl)phenyl)-6-(methylsulfonamido)-1H-indole-2-carboxamide | LC/MS ESI (+): 654 (M + 1)<br>$^1$H-NMR (300 MHz, DMSO-$d_6$): δ 11.73 (s, 1H), 10.25 (s, 1H), 9.64 (s, 1H), 8.09 (s, 1H), 7.57~7.65 (m, 2H), 7.37 (s, 2H), 7.12 (s, 1H), 6.98 (dd, 1H, J = 8.4, 1.7 Hz), 6.75~6.80 (m, 2H), 6.73 (s, 1H), 4.02 (q, 2H, J = 7.0 Hz), 2.94 (s, 3H), 1.64 (s, 6H), 1.30 (t, 3H, J = 7.0 Hz) |
| 23 | N-(3-bromo-5-(2-(2-fluoro-5-(trifluoromethoxy)phenyl)propan-2-yl)phenyl)-6-(methylsulfonamido)-1H-indole-2-carboxamide | LC/MS ESI (+): 628 (M + 1)<br>$^1$H-NMR (300 MHz, DMSO-$d_6$): δ 11.67 (s, 1H), 10.20 (s, 1H), 9.59 (s, 1H), 8.04 (m, 1H), 7.61 (d, 1H, J = 8.4 Hz), 7.56 (m, 1H), 7.49 (m, 1H), 7.35~7.38 (m, 3H), 7.24 (dd, 1H, J = 11.1, 8.8 Hz), 7.06 (m, 1H), 6.99 (dd, 1H, J = 8.8, 1.9 Hz), 2.94 (s, 3H), 1.66 (s, 6H) |
| 24 | N-(3-chloro-5-(2-(3-methoxy-5-(trifluoromethoxy)phenyl)propan-2-yl)phenyl)-6-(methylsulfonamido)-1H-indole-2-carboxamide | LC/MS ESI (+): 596 (M + 1)<br>$^1$H-NMR (400 MHz, DMSO-$d_6$): δ 11.73 (s, 1H), 10.26 (s, 1H), 9.65 (s, 1H), 7.96 (s, 1H), 7.63 (d, 1H, J = 8.8 Hz), 7.55 (s, 1H), 7.38 (s, 2H), 7.00 (s, 1H), 6.99 (d, 1H, J = 8.8 Hz), 6.81 (s, 2H), 6.73 (s, 1H), 3.77 (s, 3H), 2.94 (s, 3H), 1.65 (s, 6H) |
| 25 | N-(3-(2-(4-fluorophenyl)propan-2-yl)phenyl)-5-(trifluoromethoxy)-1H-indole-2-carboxamide | LC/MS ESI (+): 457 (M + 1)<br>$^1$H-NMR (300 MHz, DMSO-$d_6$): δ 12.01 (s, 1H), 10.25 (s, 1H), 7.74 (d, 1H, J = 8.4 Hz), 7.70 (s, 1H), 7.62 (s, 1H), 7.52 (d, 1H, J = 8.8 Hz), 7.46 (s, 1H), 7.24~7.31 (m, 3H), 7.20 (dd, 1H, J = 9.2, 1.5 Hz), 7.07~7.13 (m, 2H), 6.99 (d, 1H, J = 8.4 Hz), 1.65 (s, 6H) |
| 26 | N-(3-(2-(4-fluorophenyl)propan-2-yl)phenyl)-5-(methylsulfonamido)benzo[b]thiophene-2-carboxamide | LC/MS ESI (+): 483 (M + 1)<br>$^1$H-NMR(300 MHz, DMSO-$d_6$): δ 10.39 (brs, 1H), 9.92 (m, 1H), 8.29 (s, 1H), 8.01 (d, 1H, J = 8.8 Hz), 7.98 (m, 1H), 7.70 (m, 1H), 7.61 (m, 1H), 7.25~7.37 (m, 4H), 7.08~7.16 (m, 2H), 7.01 (d, 1H, J = 8.8 Hz), 3.01 (s, 3H), 1.66 (s, 6H) |

TABLE 2-continued

| Ex. | Compound | Analysis data |
|---|---|---|
| 27 | N-(3-(2-(2,4-difluorophenyl)propan-2-yl)phenyl)-5-(methylsulfonamido)benzo[b]thiophene-2-carboxamide | LC/MS ESI (+): 501 (M + 1)<br>$^1$H-NMR (300 MHz, DMSO-$d_6$): δ 10.37 (s, 1H), 9.86 (s, 1H), 8.28 (s, 1H), 8.01 (d, 1H, J = 8.8 Hz), 7.78 (d, 1H, J = 1.9 Hz), 7.68 (dd, 1H, J = 7.6, 1.5 Hz), 7.56~7.63 (m, 1H), 7.53~7.54 (m, 1H), 7.35 (dd, 1H, J = 8.8, 2.2 Hz), 7.27 (t, 1H, J = 8.0 Hz), 7.05~7.15 (m, 2H), 6.93 (d, 1H, J = 8.8 Hz), 3.01 (s, 3H), 1.65 (s, 6H) |
| 28 | N-(3-(2-(4-fluorophenyl)propan-2-yl)phenyl)-5-(methylsulfonamido)benzofuran-2-carboxamide | LC/MS ESI (+): 467 (M + 1)<br>$^1$H-NMR (300 MHz, DMSO-$d_6$): δ 10.44 (s, 1H), 9.74 (brs, 1H), 7.62~7.75 (m, 5H), 7.23~7.36 (m, 4H), 7.07~7.13 (m, 2H), 7.00 (d, 1H, J = 8.0 Hz), 2.97(s, 3H), 1.64(s, 6H) |
| 29 | N-(3-(2-(2,4-difluorophenyl)propan-2-yl)phenyl)-5-(methylsulfonamido)benzofuran-2-carboxamide | LC/MS ESI (+): 485 (M + 1)<br>$^1$H-NMR (300 MHz, DMSO-$d_6$): δ 10.44 (s, 1H), 9.74 (s, 1H), 7.54~7.74 (m, 6H), 7.34 (dd, 1H, J = 8.8, 2.3 Hz), 7.26 (t, 1H, J = 8.0 Hz), 7.04~7.11 (m, 2H), 6.93 (d, 1H, J = 8.4 Hz), 2.97 (s, 3H), 1.64 (s, 6H) |
| 30 | N-(3-(2-(4-fluorophenyl)propan-2-yl)phenyl)-6-(methylsulfonamido)benzo[b]thiophene-2-carboxamide | LC/MS ESI (+): 483 (M + 1)<br>$^1$H-NMR (300 MHz, DMSO-$d_6$): δ 10.38 (s, 1H), 10.07 (s, 1H), 8.27 (s, 1H), 7.94 (d, 1H, J = 8.8 Hz), 7.81 (d, 1H, J = 1.5 Hz), 7.68 (d, 1H, J = 8.0 Hz), 7.59~7.60 (m, 1H), 7.22~7.32 (m, 4H), 7.07~7.14 (m, 2H), 6.99 (d, 1H, J = 8.0 Hz), 3.07 (s, 3H), 1.64 (s, 6H) |
| 31 | N-(3-(2-(2-fluorophenyl)propan-2-yl)phenyl)-5-(methylsulfonamido)benzo[b]thiophene-2-carboxamide | LC/MS ESI (+): 483 (M + 1)<br>$^1$H-NMR(300 MHz, DMSO-$d_6$): δ 10.38 (s, 1H), 9.87 (s, 1H), 8.28 (s, 1H), 8.01 (d, 1H, J = 8.8 Hz), 7.78 (d, 1H, J = 1.9 Hz), 7.66 (d, 1H, J = 8.4 Hz), 7.52~7.58 (m, 2H), 7.21~7.36 (m, 4H), 7.02 (dd, 1H, J = 12.2, 8.4 Hz), 6.93 (d, 1H, J = 8.0 Hz), 3.01 (s, 3H), 1.66 (s, 6H) |
| 32 | N-(3-bromo-5-(2-(4-fluorophenyl)propan-2-yl)phenyl)-5-(methylsulfonamido)benzo[b]thiophene-2-carboxamide | LC/MS ESI (+): 561 (M + 1)<br>$^1$H-NMR(300 MHz, DMSO-$d_6$): δ 10.53 (s, 1H), 9.88 (s, 1H), 8.28 (s, 1H), 8.00~8.03 (m, 2H), 7.79 (d, 1H, J = 2.3 Hz), 7.55 (t, 1H, J = 1.9 Hz), 7.35 (dd, 1H, J = 8.8, 2.3 Hz), 7.25~7.30 (m, 2H), 7.10~7.16 (m, 3H), 3.01 (s, 3H), 1.66 (s, 6H) |
| 33 | N-(3-(2-(3-methoxy-5-(trifluoromethoxy)phenyl)propan-2-yl)phenyl)-5-(methylsulfonamido)benzo[b]thiophene-2-carboxamide | LC/MS ESI (+): 579 (M + 1)<br>$^1$H-NMR (300 MHz, DMSO-$d_6$): δ 10.33 (s, 1H), 9.77 (s, 1H), 8.27 (s, 1H), 8.00 (d, 1H, J = 8.8 Hz), 7.79 (d, 1H, J = 1.9 Hz), 7.70 (d, 1H, J = 7.9 Hz), 7.63 (s, 1H), 7.36 (dd, 1H, J = 8.8, 2.3 Hz), 7.31 (t, 1H, J = 7.9 Hz), 7.10 (d, 1H, J = 7.9 Hz), 6.80 (s, 1H), 6.76 (s, 1H), 6.70 (s, 1H), 3.76 (s, 3H), 3.00 (s, 3H), 1.66 (s, 6H) |
| 34 | N-(3-methoxy-5-(2-(3-methoxy-5-(trifluoromethoxy)phenyl)propan-2-yl)phenyl)-5-(methylsulfonamido)benzo[b]thiophene-2-carboxamide | LC/MS ESI (+): 609 (M + 1)<br>$^1$H-NMR (300 MHz, DMSO-$d_6$): δ 10.31 (s, 1H), 9.78 (s, 1H), 8.27 (s, 1H), 7.99 (d, 1H, J = 8.8 Hz), 7.78 (d, 1H, J = 1.9 Hz), 7.42 (s, 1H), 7.36 (dd, 1H, J = 8.8, 2.3 Hz), 7.21 (s, 1H), 6.81 (s, 1H), 6.76 (s, 1H), 6.71 (s, 1H), 6.56 (s, 1H), 3.76 (s, 3H), 3.74 (s, 3H), 3.00 (s, 3H), 1.64 (s, 6H) |
| 35 | N-(3-bromo-5-(2-(2,4-difluorophenyl)propan-2-yl)phenyl)-5-(methylsulfonamido)benzo[b]thiophene-2-carboxamide | LC/MS ESI (+): 579 (M + 1)<br>$^1$H-NMR(300 MHz, DMSO-$d_6$): δ 10.51 (s, 1H), 9.88 (s, 1H), 8.27 (s, 1H), 8.00~8.03 (m, 2H), 7.78 (d, 1H, J = 2.2 Hz), 7.57~7.65 (m, 1H), 7.48 (s, 1H), 7.35 (dd, 1H, J = 8.5, 2.2 Hz), 7.09~7.17 (m, 3H), 3.01 (s, 3H), 1.64 (s, 6H) |
| 36 | N-(3-bromo-5-(2-(3-methoxy-5-(trifluoromethoxy)phenyl)propan-2-yl)phenyl)-5-(methylsulfonamido)benzo[b]thiophene-2-carboxamide | LC/MS ESI (+): 657 (M + 1)<br>$^1$H-NMR(300 MHz, DMSO-$d_6$): δ 10.54 (s, 1H), 9.88 (s, 1H), 8.28 (s, 1H), 8.00~8.03 (m, 2H), 7.79 (d, 1H, J = 2.2 Hz), 7.57 (s, 1H), 7.35 (dd, 1H, J = 8.8, 2.2 Hz), 7.16 (s, 1H), 6.81 (s, 2H), 6.72 (s, 1H), 3.77 (s, 3H), 3.01 (s, 3H), 1.64 (s, 6H) |
| 37 | 5-(methylsulfonamido)-N-(3-(2-(3-(trifluoromethoxy)phenyl)propan-2-yl)phenyl)benzo[b]thiophene-2-carboxamide | LC/MS ESI (+): 549 (M + 1)<br>$^1$H-NMR (300 MHz, DMSO-$d_6$): δ 10.41 (s, 1H), 9.88 (s, 1H), 8.28 (s, 1H), 8.00 (d, 1H, J = 8.5 Hz), 7.78 (d, 1H, J = 1.8 Hz), 7.71 (d, 1H, J = 8.1 Hz), 7.63 (s, 1H), 7.44 (t, 1H, J = 8.1 Hz), 7.34 (dd, 1H, J = 8.8, 2.2 Hz), 7.31 (t, 1H, J = 8.1 Hz), 7.25 (d, 1H, J = 7.7 Hz), 7.19 (d, 1H, J = 8.1 Hz), 7.15 (s, 1H), 7.00 (d, 1H, J = 7.7 Hz), 3.00 (s, 3H), 1.67 (s, 6H) |
| 38 | N-(3-(2-(3-methoxyphenyl)propan-2-yl)phenyl)-5-(methylsulfonamido)benzo[b]thiophene-2-carboxamide | LC/MS ESI (+): 495 (M + 1)<br>$^1$H-NMR (300 MHz, DMSO-$d_6$): δ 10.39 (s, 1H), 9.87 (s, 1H), 8.29 (s, 1H), 8.00 (d, 1H, J = 8.5 Hz), 7.77 (d, 1H, J = 2.2 Hz), 7.69 (d, 1H, J = 8.1 Hz), 7.60 (s, 1H), 7.34 (dd, 1H, J = 8.8, 2.2 Hz), 7.28 (t, 1H, J = 8.1 Hz), 7.21 (t, 1H, J = 7.7 Hz), 7.00 (d, 1H, J = 8.5 Hz), 6.75~6.80 (m, 3H), 3.70 (s, 3H), 3.00 (s, 3H), 1.64 (s, 6H) |

TABLE 2-continued

| Ex. | Compound | Analysis data |
|---|---|---|
| 39 | N-(3-(difluoromethoxy)-5-(2-(4-fluorophenyl)propan-2-yl)phenyl)-5-(methylsulfonamido)benzo[b]thiophene-2-carboxamide | LC/MS ESI (+): 549 (M + 1)<br>$^1$H-NMR(300 MHz, DMSO-$d_6$): δ 10.55 (s, 1H), 9.89 (s, 1H), 8.29 (s, 1H), 8.02 (d, 1H, J = 8.6 Hz), 7.79 (d, 1H, J = 2.1 Hz), 7.66 (m, 1H), 7.43 (s, 1H), 7.36 (dd, 1H, J = 8.6, 2.1 Hz), 7.28 (dd, 2H, J = 8.8, 5.5 Hz), 7.23 (t, 1H, J = 74.0 Hz), 7.13 (t, 2H, J = 8.9 Hz), 6.80 (m, 1H), 3.02 (s, 3H), 1.65 (s, 6H) |
| 40 | N-(3-chloro-5-(2-(4-fluorophenyl)propan-2-yl)phenyl)-5-(methylsulfonamido)benzo[b]thiophene-2-carboxamide | LC/MS ESI (+): 517 (M + 1)<br>$^1$H-NMR (300 MHz, DMSO-$d_6$): δ 10.52 (s, 1H), 9.84 (s, 1H), 8.28 (s, 1H), 8.02 (d, 1H, J = 8.8 Hz), 7.87 (t, 1H, J = 1.5 Hz), 7.79 (d, 1H, J = 1.9 Hz), 7.51 (s, 1H), 7.36 (dd, 1H, J = 8.8, 1.9 Hz), 7.26~7.31 (m, 2H), 7.10~7.16 (m, 2H), 7.00 (t, 1H, J = 1.9 Hz), 3.01 (s, 3H), 1.65 (s, 6H) |
| 41 | N-(difluoromethoxy)-5-(2-(3-methoxy-5-(trifluoromethoxy)phenyl)propan-2-yl)phenyl)-5-(methylsulfonamido)benzo[b]thiophene-2-carboxamide | LC/MS ESI (+): 645 (M + 1)<br>$^1$H-NMR(300 MHz, DMSO-$d_6$): δ 10.50 (s, 1H), 9.84 (s, 1H), 8.29 (s, 1H), 8.02 (d, 1H, J = 8.5 Hz), 7.79 (s, 1H), 7.68 (s, 1H), 7.47 (s, 1H), 7.36 (d, 1H, J = 8.6 Hz), 7.22 (t, 1H, J = 74.0 Hz), 6.70~6.83 (m, 4H), 3.77 (s, 3H), 3.01 (s, 3H), 1.65 (s, 6H) |
| 42 | N-(3-chloro-5-(2-(3-methoxy-5-(trifluoromethoxy)phenyl)propan-2-yl)phenyl)-5-(methylsulfonamido)benzo[b]thiophene-2-carboxamide | LC/MS ESI (+): 613 (M + 1)<br>$^1$H-NMR (400 MHz, DMSO-$d_6$): δ 10.51 (s, 1H), 9.82 (s, 1H), 8.23 (s, 1H), 7.96 (d, 1H, J = 8.8 Hz), 7.84 (s, 1H), 7.74 (d, 1H, J = 1.6 Hz), 7.46 (s, 1H), 7.30 (dd, 1H, J = 8.8, 2.2 Hz), 6.98 (s, 1H), 6.74 (s, 2H), 6.67 (s, 1H), 3.71 (s, 3H), 2.96 (s, 3H), 1.58 (s, 6H) |
| 43 | N-(3-(2-(3-(2-amino-2-oxoethoxy)phenyl)propan-2-yl)-5-bromophenyl)-5-(methylsulfonamido)benzo[b]thiophene-2-carboxamide | LC/MS ESI (+): 616 (M + 1)<br>$^1$H-NMR (300 MHz, DMSO-$d_6$): δ 10.51 (s, 1H), 9.84 (s, 1H), 8.28 (s, 1H), 8.01~8.03 (m, 2H), 7.79 (s, 1H), 7.58 (s, 1H), 7.52 (s, 1H), 7.33~7.38 (m, 2H) 7.24 (t, 1H, J = 8.0 Hz), 7.13 (s, 1H), 6.89 (s, 1H), 6.76~6.84 (m, 2H), 4.38 (s, 2H), 3.01 (s, 3H), 1.64 (s, 6H) |
| 44 | N-(3-(2-(5-(2-amino-2-oxoethoxy)-2-fluorophenyl)propan-2-yl)-5-bromophenyl)-5-(methylsulfonamido)benzo[b]thiophene-2-carboxamide | LC/MS ESI (+): 634 (M + 1)<br>$^1$H-NMR (400 MHz, DMSO-$d_6$): δ 10.53 (s, 1H), 9.88 (brs, 1H), 8.28 (s, 1H), 8.01~8.03 (m, 2H), 7.79 (m, 1H), 7.64 (s, 1H), 7.52 (s, 1H), 7.45 (s, 1H), 7.36 (m, 1H), 7.18 (m, 1H), 7.08 (s, 1H), 7.02 (dd, 1H, J = 11.3, 9.0 Hz), 6.86 (m, 1H), 4.45 (s, 2H), 3.01 (s, 3H), 1.63 (s, 6H) |
| 45 | N-(3-(2-(3-((1-amino-2-methyl-1-oxopropan-2-yl)oxy)phenyl)propan-2-yl)-5-bromophenyl)-5-(methylsulfonamido)benzo[b]thiophene-2-carboxamide | LC/MS ESI (+): 644 (M + 1)<br>$^1$H-NMR (300 MHz, DMSO-$d_6$): δ 10.55 (s, 1H), 9.89 (s, 1H), 8.29 (s, 1H), 7.99~8.03 (m, 2H), 7.78 (d, 1H, J = 1.9 Hz), 7.61 (m, 1H), 7.52 (s, 1H), 7.35 (dd, 1H, J = 8.8, 1.9 Hz), 7.25 (s, 1H), 7.21 (t, 1H, J = 8.0 Hz), 7.10 (m, 1H), 6.87 (m, 1H), 6.78 (m, 1H), 6.70 (m, 1H), 3.01 (s, 3H), 1.62 (s, 6H), 1.38 (s, 6H) |
| 46 | N-(3-bromo-5-(2-(3-(difluoromethoxy)phenyl)propan-2-yl)phenyl)-5-(methylsulfonamido)benzo[b]thiophene-2-carboxamide | LC/MS ESI (+): 609 (M + 1)<br>$^1$H-NMR (300 MHz, DMSO-$d_6$): δ 10.52 (s, 1H), 9.85 (s, 1H), 8.28 (s, 1H), 8.00~8.03 (m, 2H), 7.79 (d, 1H, J = 1.9 Hz), 7.59 (s, 1H), 7.34~7.39 (m, 2H) 7.24 (t, 1H, J = 74.0 Hz), 7.15 (s, 1H), 7.09 (d, 1H, J = 8.0 Hz), 7.01~7.04 (m, 2H), 3.01 (s, 3H), 1.65 (s, 6H) |
| 47 | N-(3-bromo-5-(2-(2-fluoro-5-(trifluoromethoxy)phenyl)propan-2-yl)phenyl)-5-(methylsulfonamido)benzo[b]thiophene-2-carboxamide | LC/MS ESI (+): 645 (M + 1)<br>$^1$H-NMR (400 MHz, DMSO-$d_6$): δ 10.53 (s, 1H), 9.88 (s, 1H), 8.27 (s, 1H), 8.01~8.03 (m, 2H), 7.79 (m, 1H), 7.51 (s, 2H), 7.34~7.41 (m, 2H), 7.25 (dd, 1H, J = 11.1, 9.3 Hz), 7.10 (s, 1H), 3.01 (s, 3H), 1.66 (s, 6H) |
| 48 | N-(3-bromo-5-(2-(3-ethoxy-5-(trifluoromethoxy)phenyl)propan-2-yl)phenyl)-5-(methylsulfonamido)benzo[b]thiophene-2-carboxamide | LC/MS ESI (+): 671 (M + 1)<br>$^1$H-NMR(300 MHz, DMSO-$d_6$): δ 10.55 (s, 1H), 9.88 (brs, 1H), 8.28 (s, 1H), 8.00~8.06 (m, 2H), 7.79 (d, 1H, J = 2.0 Hz), 7.57 (s, 1H), 7.35 (dd, 1H, J = 8.8, 2.1 Hz), 7.16 (s, 1H), 6.75~6.80 (m, 2H), 6.72 (s, 1H), 4.02 (q, 2H, J = 7.0 Hz), 3.01 (s, 3H), 1.63 (s, 6H), 1.30 (t, 3H, J = 6.9 Hz) |
| 49 | N-(3-bromo-5-(2-(3-isopropoxy-5-(trifluoromethoxy)phenyl)propan-2-yl)phenyl)-5-(methylsulfonamido)benzo[b]thiophene-2-carboxamide | LC/MS ESI (+): 685 (M + 1)<br>$^1$H-NMR(300 MHz, DMSO-$d_6$): δ 10.56 (s, 1H), 9.86 (brs, 1H), 8.29 (s, 1H), 8.00~8.07 (m, 2H), 7.79 (d, 1H, J = 2.1 Hz), 7.58 (s, 1H), 7.36 (dd, 1H, J = 8.7, 2.1 Hz), 7.17 (s, 1H), 6.78 (s, 1H), 6.69~6.74 (m, 2H), 4.63 (m, 1H), 3.01 (s, 3H), 1.63 (s, 6H), 1.23 (d, 6H, J = 6.0 Hz) |
| 50 | N-(3-bromo-5-(2-(3-(morpholinomethyl)phenyl)propan-2-yl)phenyl)-5-(methylsulfonamido)benzo[b]thiophene-2-carboxamide | LC/MS ESI (+): 642 (M + 1)<br>$^1$H-NMR(400 MHz, DMSO-$d_6$): δ 10.53 (s, 1H), 9.89 (s, 1H), 8.28 (s, 1H), 8.02 (d, 1H, J = 8.8 Hz), 7.98 (s, 1H), 7.79 (d, 1H, J = 1.8 Hz), 7.59 (s, 1H), 7.36 (dd, 1H, J = 8.8, 2.0 Hz), 7.28 (t, 1H, J = 7.7 Hz), 7.18 (d, 1H, J = 7.7 Hz), 7.09~7.12 (m, 3H), 3.51 (s, 4H), 3.42 (s, 2H), 3.01 (s, 3H), 2.29 (s, 4H), 1.64 (s, 6H) |

TABLE 2-continued

| Ex. | Compound | Analysis data |
|---|---|---|
| 51 | N-(3-(2-(4-fluorophenyl)propan-2-yl)phenyl)-3-methyl-6-(methylsulfonamido)benzo[b]thiophene-2-carboxamide | LC/MS ESI (+): 497 (M + 1)<br>$^{1}$H-NMR (300 MHz, DMSO-$d_6$): δ 10.26 (s, 1H), 9.87 (s, 1H), 8.00 (d, 1H, J = 8.4 Hz), 7.68 (d, 1H, J = 1.9 Hz), 7.57~7.60 (m, 2H), 7.37 (dd, 1H, J = 8.8, 1.9 Hz), 7.23~7.30 (m, 3H), 7.07~7.13 (m, 2H), 6.97 (d, 1H, J = 8.0 Hz), 3.01 (s, 3H), 2.54 (s, 3H), 1.63 (s, 6H) |
| 52 | N-(3-(2-(4-fluorophenyl)propan-2-yl)phenyl)-3-methyl-5-(methylsulfonamido)benzo[b]thiophene-2-carboxamide | LC/MS ESI (+): 497 (M + 1)<br>$^{1}$H-NMR (300 MHz, DMSO-$d_6$): δ 10.25 (s, 1H), 9.86 (s, 1H), 7.99 (d, 1H, J = 8.4 Hz), 7.68 (d, 1H, J = 1.9 Hz), 7.57~7.60 (m, 2H), 7.37 (dd, 1H, J = 8.4, 2.2 Hz), 7.23~7.30 (m, 3H), 7.07~7.13 (m, 2H), 6.97 (d, 1H, J = 7.6 Hz), 3.01 (s, 3H), 2.54 (s, 3H), 1.63 (s, 6H) |
| 53 | N-(3-bromo-5-(3-(4-fluorophenyl)pentan-3-yl)phenyl)-5-(methylsulfonamido)benzo[b]thiophene-2-carboxamide | LC/MS ESI (+): 589 (M + 1)<br>$^{1}$H-NMR (300 MHz, DMSO-$d_6$): δ 10.47 (s, 1H), 9.83 (s, 1H), 8.27 (s, 1H), 7.98~8.02 (m, 2H), 7.78 (d, 1H, J = 2.0 Hz), 7.53 (s, 1H), 7.35 (dd, 1H, J = 8.7, 2.1 Hz), 7.19~7.23 (m, 2H), 7.09~7.15 (m, 2H), 7.05 (s, 1H), 3.00 (s, 3H), 2.08 (q, 4H, J = 7.5 Hz), 0.59 (t, 6H, J = 7.2 Hz) |
| 54 | N-(3-methoxy-5-(3-(3-methoxy-5-(trifluoromethoxy)phenyl)pentan-3-yl)phenyl)-5-(methylsulfonamido)benzo[b]thiophene-2-carboxamide | LC/MS ESI (+): 637 (M + 1)<br>$^{1}$H-NMR (300 MHz, DMSO-$d_6$): δ 10.33 (s, 1H), 9.80 (brs, 1H), 8.28 (s, 1H), 8.01 (d, 1H, J = 8.8 Hz), 7.79 (d, 1H, J = 1.9 Hz), 7.42 (s, 1H), 7.35 (dd, 1H, J = 8.8, 2.3 Hz), 7.15 (s, 1H), 6.77 (s, 1H), 6.75 (s, 1H), 6.66 (s, 1H), 6.50 (s, 1H), 3.75 (s, 3H), 3.73 (s, 3H), 3.01 (s, 3H), 2.05 (q, 4H, J = 7.3 Hz), 0.60 (t, 6H, J = 7.3 Hz) |
| 55 | N-(3-methoxy-5-(3-(3-methoxy-5-(trifluoromethoxy)phenyl)pentan-3-yl)phenyl)-6-(methylsulfonamido)-1H-indole-2-carboxamide | LC/MS ESI (+): 620 (M + 1)<br>$^{1}$H-NMR(300 MHz, DMSO-$d_6$): δ 11.65 (s, 1H), 10.04 (s, 1H), 9.59 (brs, 1H), 7.60 (d, 1H, J = 8.8 Hz), 7.48 (s, 1H), 7.38 (d, 1H, J = 1.9 Hz), 7.35 (d, 1H, J = 1.9 Hz), 7.18 (s, 1H), 6.98 (dd, 1H, J = 8.4, 1.9 Hz), 6.76 (s, 2H), 6.66 (s, 1H), 6.47 (s, 1H), 3.75 (s, 3H), 3.73 (s, 3H), 2.93 (s, 3H), 2.07 (q, 4H, J = 7.3 Hz), 0.61 (t, 6H, J = 7.3 Hz) |
| 56 | N-(3-bromo-5-(2-(3-methoxy-5-(trifluoromethoxy)phenyl)propan-2-yl)phenyl)-5-(methylsulfonamido)thieno[2,3-b]pyridine-2-carboxamide | LC/MS ESI (+): 658 (M + 1)<br>$^{1}$H-NMR(400 MHz, DMSO-$d_6$): δ 10.66 (s, 1H), 10.17 (s, 1H), 8.53 (s, 1H), 8.28 (s, 1H), 8.20 (s, 1H), 8.03 (s, 1H), 7.58 (s, 1H), 7.19 (s, 1H), 6.82 (s, 2H), 6.74 (s, 1H), 3.78 (s, 3H), 3.08 (s, 3H), 1.65 (s, 6H) |
| 57 | N-(3-chloro-5-(2-(3-methoxy-5-(trifluoromethoxy)phenyl)propan-2-yl)phenyl)-5-(methylsulfonamido)thieno[2,3-b]pyridine-2-carboxamide | LC/MS ESI (+): 614 (M + 1)<br>$^{1}$H-NMR(400 MHz, DMSO-$d_6$): δ 10.68 (s, 1H), 10.14 (s, 1H), 8.54 (s, 1H), 8.29 (s, 1H), 8.21 (s, 1H), 7.90 (s, 1H), 7.53 (s, 1H), 7.07 (s, 1H), 6.82 (s, 2H), 6.74 (s, 1H), 3.78 (s, 3H), 3.09 (s, 3H), 1.66 (s, 6H) |
| 58 | N-(3-chloro-5-(2-(3-ethoxy-5-(trifluoromethoxy)phenyl)propan-2-yl)phenyl)-5-(methylsulfonamido)benzo[b]thiophene-2-carboxamide | LC/MS ESI (+): 627 (M + 1)<br>$^{1}$H-NMR (400 MHz, DMSO-$d_6$): δ 10.55 (s, 1H), 9.87 (brs, 1H), 8.28 (s, 1H), 8.02 (d, 1H, J = 8.6 Hz), 7.90 (s, 1H), 7.79 (s, 1H), 7.52 (s, 1H), 7.35 (d, 1H, J = 8.6 Hz), 7.04 (s, 1H), 6.72~6.78 (m, 3H), 4.01 (q, 2H, J = 6.8 Hz), 3.01 (s, 3H), 1.64 (s, 6H), 1.30 (t, 3H, J = 6.8 Hz) |
| 59 | N-(3-chloro-5-(2-(3-ethoxy-5-(trifluoromethoxy)phenyl)propan-2-yl)phenyl)-6-(methylsulfonamido)-1H-indole-2-carboxamide | LC/MS ESI (+): 610 (M + 1)<br>$^{1}$H-NMR (400 MHz, DMSO-$d_6$): δ 11.72 (s, 1H), 10.25 (s, 1H), 9.64 (s, 1H), 7.96 (s, 1H), 7.62 (d, 1H, J = 8.6 Hz), 7.55 (s, 1H), 7.37~7.39 (m, 2H), 6.97~7.00 (m, 2H), 6.73~6.78 (m, 3H), 4.03 (q, 2H, J = 6.8 Hz), 2.94 (s, 3H), 1.64 (s, 6H), 1.30 (t, 3H, J = 6.8 Hz) |
| 60 | N-(3-bromo-5-(2-(3-ethoxy-5-(trifluoromethoxy)phenyl)propan-2-yl)phenyl)-5-(methylsulfonamido)thieno[3,2-b]pyridine-2-carboxamide | LC/MS ESI (+): 672 (M + 1)<br>$^{1}$H-NMR(400 MHz, DMSO-$d_6$): δ 10.90 (s, 1H), 10.55 (s, 1H), 8.44 (d, 1H, J = 8.9 Hz), 8.40 (s, 1H), 8.05 (m, 1H), 7.60 (m, 1H), 7.17 (m, 1H), 7.04 (d, 1H, J = 8.8 Hz), 6.77 (s, 2H), 6.72 (s, 1H), 4.02 (q, 2H, J = 7.0 Hz), 3.42 (s, 3H), 1.64 (s, 6H), 1.30 (t, 3H, J = 7.0 Hz) |
| 61 | N-(3-bromo-5-(2-(3-ethoxy-5-(trifluoromethoxy)phenyl)propan-2-yl)phenyl)-5-(methylsulfonamido)thieno[2,3-c]pyridine-2-carboxamide | LC/MS ESI (+): 672 (M + 1)<br>$^{1}$H-NMR(400 MHz, DMSO-$d_6$): δ 10.70 (s, 1H), 10.54 (brs, 1H), 9.09 (s, 1H), 8.26 (s, 1H), 8.03 (m, 1H), 7.55 (s, 1H), 7.51 (s, 1H), 7.20 (m, 1H), 6.78 (s, 2H), 6.72 (s, 1H), 4.02 (q, 2H, J = 7.2 Hz), 3.30 (s, 3H), 1.64 (s, 6H), 1.30 (t, 3H, J = 6.8 Hz) |
| 62 | N-(3-chloro-5-(2-(2-fluoro-5-(trifluoromethoxy)phenyl)propan-2-yl)phenyl)-5-(methylsulfonamido)benzo[b]thiophene-2-carboxamide | LC/MS ESI (+): 601 (M + 1)<br>$^{1}$H-NMR(400 MHz, DMSO-$d_6$): δ 10.54 (s, 1H), 9.86 (brs, 1H), 8.26 (s, 1H), 8.01 (d, 1H, J = 8.7 Hz), 7.87 (m, 1H), 7.79 (d, 1H, J = 1.9 Hz), 7.49~7.52 (m, 1H), 7.47 (s, 1H), 7.34~7.39 (m, 2H), 7.25 (dd, 1H, J = 11.1, 9.0 Hz), 6.97 (m, 1H), 3.00 (s, 3H), 1.66 (s, 6H) |

TABLE 2-continued

| Ex. | Compound | Analysis data |
|---|---|---|
| 63 | N-(3-fluoro-5-(2-(3-methoxy-5-(trifluoromethoxy)phenyl)propan-2-yl)phenyl)-5-(methylsulfonamido)benzo[b]thiophene-2-carboxamide | LC/MS ESI (+): 597 (M + 1)<br>$^1$H-NMR(400 MHz, DMSO-d$_6$); 10.56 (s, 1H), 9.86 (s, 1H), 8.28 (s, 1H), 8.02 (d, 1H, J = 8.7 Hz), 7.79 (s, 1H), 7.68 (d, 1H, J = 11.0 Hz), 7.35~7.38 (m, 2H), 6.79~6.86 (m, 3H), 6.72 (s, 1H), 3.76 (s, 3H), 3.01 (s, 3H), 1.65 (s, 6H) |
| 64 | N-(3-chloro-5-(2-phenylpropan-2-yl)phenyl)-5-(methylsulfonamido)benzo[b]thiophene-2-carboxamide | LC/MS ESI (+): 499 (M + 1)<br>$^1$H-NMR(400 MHz, DMSO-d$_6$): δ 10.54 (s, 1H), 9.86 (brs, 1H), 8.28 (s, 1H), 8.02 (d, 1H, J = 8.7 Hz), 7.87 (s, 1H), 7.79 (s, 1H), 7.54 (s, 1H), 7.20~7.37 (m, 6H), 7.00 (s, 1H), 3.01 (s, 3H), 1.65 (s, 6H) |
| 65 | N-(3-chloro-5-(2-(3-fluorophenyl)propan-2-yl)phenyl)-5-(methylsulfonamido)benzo[b]thiophene-2-carboxamide | LC/MS ESI (+): 517 (M + 1)<br>$^1$H-NMR(400 MHz, DMSO-d$_6$): δ 10.56 (s, 1H), 9.90 (s, 1H), 8.29 (s, 1H), 8.03 (d, 1H, J = 8.8 Hz), 7.90 (t, 1H, J = 2.0 Hz), 7.80 (d, 1H, J = 2.0 Hz), 7.52 (t, 1H, J = 1.6 Hz), 7.34~7.40 (m, 2H), 7.07~7.11 (m, 2H), 7.05~7.06 (m, 2H), 3.02 (s, 3H), 1.67 (s, 6H) |
| 66 | N-(3-chloro-5-(2-(3-isopropoxy-5-(trifluoromethoxy)phenyl)propan-2-yl)phenyl)-5-(methylsulfonamido)-4-morpholinobenzo[b]thiophene-2-carboxamide | LC/MS ESI (+): 726 (M + 1)<br>$^1$H-NMR(400 MHz, DMSO-d$_6$): δ 10.74 (brs, 1H), 8.82 (brs, 1H), 8.50 (s, 1H), 7.84 (m, 2H), 7.55 (d, 1H, J = 8.8 Hz), 7.52 (s, 1H), 7.06 (s, 1H), 6.77 (s, 1H), 6.74 (m, 1H), 6.72 (s, 1H), 4.60~4.66 (m, 1H), 3.84 (m, 4H), 3.22~3.26 (brs, 3H), 3.02~3.05 (m, 4H), 1.66 (s, 6H), 1.24 (d, 6H, J = 6.0 Hz) |
| 67 | N-(3-chloro-5-(2-(3-fluoro-5-methoxyphenyl)propan-2-yl)phenyl)-5-(methylsulfonamido)benzo[b]thiophene-2-carboxamide | LC/MS ESI (+): 547 (M + 1)<br>$^1$H-NMR(400 MHz, DMSO-d$_6$): δ 10.53 (s, 1H), 9.86 (brs, 1H), 8.27 (s, 1H), 8.00 (d, 1H, J = 8.7 Hz), 7.87 (s, 1H), 7.77 (d, 1H, J = 2.0 Hz), 7.48 (s, 1H), 7.33 (dd, 1H, J = 8.7, 2.0 Hz), 7.03 (s, 1H), 6.60~6.70 (m, 1H), 6.58~6.61 (m, 2H), 3.72 (s, 3H), 2.99 (s, 3H), 1.61 (s, 6H) |
| 68 | N-(3-chloro-5-(2-(3-isopropoxy-5-(trifluoromethoxy)phenyl)propan-2-yl)phenyl)-5-(methylsulfonamido)benzo[b]thiophene-2-carboxamide | LC/MS ESI (+): 641 (M + 1)<br>$^1$H-NMR(400 MHz, DMSO-d$_6$): δ 10.56 (s, 1H), 9.89 (s, 1H), 8.28 (s, 1H), 8.02 (d, 1H, J = 8.0 Hz), 7.91 (s, 1H), 7.79 (s, 1H), 7.54 (s, 1H), 7.36 (d, 1H, J = 8.0 Hz), 7.06 (s, 1H), 6.78 (s, 1H), 6.74 (s, 1H), 6.72 (s, 1H), 4.59~4.68 (m, 1H), 3.01 (s, 3H), 1.65 (s, 6H), 1.25 (d, 6H, J = 6.0 Hz) |
| 69 | N-(3-chloro-5-(2-(3-isopropoxy-5-(trifluoromethoxy)phenyl)propan-2-yl)phenyl)-5-(methylsulfonamido)thieno[2,3-b]pyridine-2-carboxamide | LC/MS ESI (+): 642 (M + 1)<br>$^1$H-NMR(400 MHz, DMSO-d$_6$): δ 10.68 (s, 1H), 10.14 (s, 1H), 8.54 (s, 1H), 8.28 (s, 1H), 8.20 (s, 1H), 7.90 (s, 1H), 7.54 (s, 1H), 7.08 (s, 1H), 6.78 (s, 1H), 6.74 (s, 1H), 6.72 (s, 1H), 4.61~4.67 (m, 1H), 3.07 (s, 3H), 1.65 (s, 6H), 1.25 (d, 6H, J = 5.9 Hz) |
| 70 | N-(3-chloro-5-(2-(3-isopropoxy-5-(trifluoromethoxy)phenyl)propan-2-yl)phenyl)-5-(methylsulfonamido)thieno[3,2-b]pyridine-2-carboxamide | LC/MS ESI (+): 642 (M + 1)<br>$^1$H-NMR(400 MHz, DMSO-d$_6$): δ 10.89 (s, 1H), 10.57 (s, 1H), 8.45 (d, 1H, J = 8.9 Hz), 8.41 (s, 1H), 7.92 (m, 1H), 7.56 (m, 1H), 7.03~7.06 (m, 2H), 6.77 (s, 1H), 6.72 (m, 1H), 6.71 (s, 1H), 4.60~4.66 (m, 1H), 3.42 (s, 3H), 1.64 (s, 6H), 1.23 (d, 6H, J = 6.0 Hz) |
| 71 | N-(3-chloro-5-(2-(3-isopropoxy-5-(trifluoromethoxy)phenyl)propan-2-yl)phenyl)-5-(methylsulfonamido)thieno[2,3-c]pyridine-2-carboxamide | LC/MS ESI (+): 642 (M + 1)<br>$^1$H-NMR(400 MHz, DMSO-d$_6$): δ 10.73 (s, 1H), 10.54 (brs, 1H), 9.10 (s, 1H), 8.27 (s, 1H), 7.90 (m, 1H), 7.52 (s, 2H), 7.08 (m, 1H), 6.77 (s, 1H), 6.73 (s, 1H), 6.71 (s, 1H), 4.60~4.66 (m, 1H), 3.31 (s, 3H), 1.64 (s, 6H), 1.24 (d, 6H, J = 6.0 Hz) |
| 72 | N-(3-chloro-5-(2-(3-isobutoxy-5-(trifluoromethoxy)phenyl)propan-2-yl)phenyl)-5-(methylsulfonamido)benzo[b]thiophene-2-carboxamide | LC/MS ESI (+): 655 (M + 1)<br>$^1$H-NMR (400 MHz, DMSO-d$_6$): δ 10.55 (s, 1H), 9.87 (brs, 1H), 8.28 (s, 1H), 8.02 (d, 1H, J = 8.6 Hz), 7.90 (s, 1H), 7.80 (s, 1H), 7.52 (s, 1H), 7.36 (d, 1H, J = 8.8 Hz), 7.04 (s, 1H), 6.71~6.80 (m, 3H), 3.75 (d, 2H, J = 6.4 Hz), 3.01 (s, 3H), 1.93~2.04 (m, 1H), 1.64 (s, 6H), 0.96 (d, 6H, J = 6.6 Hz) |
| 73 | N-(3-chloro-5-(2-(3-propoxy-5-(trifluoromethoxy)phenyl)propan-2-yl)phenyl)-5-(methylsulfonamido)benzo[b]thiophene-2-carboxamide | LC/MS ESI (+): 641 (M + 1)<br>$^1$H-NMR(400 MHz, DMSO-d$_6$): δ 10.56 (s, 1H), 9.89 (s, 1H), 8.29 (s, 1H), 8.03 (d, 1H, J = 8.8 Hz), 7.91 (s, 1H), 7.81 (s, 1H), 7.53 (s, 1H), 7.37 (d, 1H, J = 8.8 Hz), 7.05 (s, 1H), 6.80 (s, 2H), 6.73 (s, 1H), 3.94 (t, 2H, J = 6.4 Hz), 3.03 (s, 3H), 1.69~1.74 (m, 2H), 1.65 (s, 6H), 0.97 (t, 3H, J = 7.2 Hz) |
| 74 | N-(3-chloro-5-(2-(3-isopropoxy-5-(trifluoromethoxy)phenyl)propan-2-yl)phenyl)-6-(methylsulfonamido)imidazo[1,2-a]pyridine-2-carboxamide | LC/MS ESI (+): 625 (M + 1)<br>$^1$H-NMR(400 MHz, DMSO-d$_6$): δ 10.43 (s, 1H), 9.83 (brs, 1H), 8.57 (s, 1H), 8.54 (s, 1H), 8.04 (m, 1H), 7.80 (m, 1H), 7.64 (d, 1H, J = 9.6 Hz), 7.27 (dd, 1H, J = 9.6, 1.6 Hz), 6.96 (m, 1H), 6.69 (s, 1H), 6.67 (m, 1H), 6.64 (s, 1H), 4.53~4.59 (m, 1H), 3.00 (s, 3H), 1.63 (s, 6H), 1.23 (d, 6H, J = 6.0 Hz) |

TABLE 2-continued

| Ex. | Compound | Analysis data |
|---|---|---|
| 75 | N-(3-(2-(3-(but-2-yn-1-yloxy)-5-(trifluoromethoxy)phenyl)propan-2-yl)-5-chlorophenyl)-5-(methylsulfonamido)benzo[b]thiophene-2-carboxamide | LC/MS ESI (+): 651 (M + 1)<br>$^1$H-NMR(400 MHz, DMSO-d$_6$): δ 10.57 (s, 1H), 9.88 (s, 1H), 8.29 (s, 1H), 8.03 (d, 1H, J = 8.8 Hz), 7.91 (s, 1H), 7.80 (d, 1H, J = 2.0 Hz), 7.55 (s, 1H), 7.37 (dd, 1H, J = 8.8, 2.0 Hz), 7.05 (s, 1H), 6.84 (s, 2H), 6.80 (s, 1H), 4.78 (d, 2H, J = 2.4 Hz), 3.02 (s, 3H), 1.80 (s, 3H) 1.66 (s, 6H) |
| 76 | N-(3-chloro-5-(2-(3-(oxetan-3-yloxy)-5-(trifluoromethoxy)phenyl)propan-2-yl)phenyl)-5-(methylsulfonamido)benzo[b]thiophene-2-carboxamide | LC/MS ESI (+): 655 (M + 1)<br>$^1$H-NMR(400 MHz, DMSO-d$_6$): δ 10.55 (s, 1H), 9.86 (brs, 1H), 8.28(s, 1H), 8.02 (d, 1H, J = 8.7 Hz), 7.90 (s, 1H), 7.80 (s, 1H), 7.53 (s, 1H), 7.36(d, 1H, J = 8.7 Hz), 7.05 (s, 1H), 6.79 (s, 1H), 6.68 (s, 1H), 6.62 (s, 1H), 5.30~5.35 (m, 1H), 4.87 (dd, 2H, J = 6.8, 6.4 Hz), 4.51 (dd, 2H, J = 7.2, 4.8 Hz), 3.01 (s, 3H), 1.65 (s, 6H) |
| 77 | N-(3-chloro-5-(2-(3-(cyanomethoxy)-5-(trifluoromethoxy)phenyl)propan-2-yl)phenyl)-5-(methylsulfonamido)benzo[b]thiophene-2-carboxamide | LC/MS ESI (+): 638 (M + 1)<br>$^1$H-NMR(400 MHz, DMSO-d$_6$): δ 10.55 (s, 1H), 9.85 (brs, 1H), 8.28 (s, 1H), 8.02 (d, 1H, J = 8.7 Hz), 7.91 (s, 1H), 7.79 (s, 1H), 7.54 (s, 1H), 7.36 (d, 1H, J = 8.7 Hz), 7.04 (s, 1H), 7.00 (s, 1H), 6.96 (s, 1H), 6.87 (s, 1H), 5.23 (s, 2H), 3.01 (s, 3H), 1.66 (s, 6H) |
| 78 | N-(3-(2-(3-(allyloxy)-5-(trifluoromethoxy)phenyl)propan-2-yl)-5-chlorophenyl)-5-(methylsulfonamido)benzo[b]thiophene-2-carboxamide | LC/MS ESI (+): 639 (M + 1)<br>$^1$H-NMR(400 MHz, DMSO-d$_6$): δ 10.55 (s, 1H), 9.87 (brs, 1H), 8.29 (s, 1H), 8.02 (d, 1H, J = 8.4 Hz), 7.91 (m, 1H), 7.79 (s, 1H), 7.54 (s, 1H), 7.36 (d, 1H, J = 8.7 Hz), 7.05 (m, 1H), 6.83 (s, 2H), 6.75 (s, 1H), 5.96~6.06 (m, 1H), 5.40 (dd, 1H, J = 17.3, 1.6 Hz), 5.27 (dd, 1H, J = 10.8, 1.7 Hz), 4.60 (d, 2H, J = 5.4 Hz), 3.01 (s, 3H), 1.66 (s, 6H) |
| 79 | N-(3-chloro-5-(2-(3-cyclopropoxy-5-(trifluoromethoxy)phenyl)propan-2-yl)phenyl)-5-(methylsulfonamido)benzo[b]thiophene-2-carboxamide | LC/MS ESI (+): 639 (M + 1)<br>$^1$H-NMR(400 MHz, DMSO-d$_6$): δ 10.55 (s, 1H), 9.88 (brs, 1H), 8.29 (s, 1H), 8.03 (d, 1H, J = 8.4 Hz), 7.91 (m, 1H), 7.80 (m, 1H), 7.55 (s, 1H), 7.37 (dd, 1H, J = 8.8, 2.4 Hz), 7.06 (m, 1H), 6.95 (s, 1H), 6.87 (m, 1H), 6.78 (s, 1H), 3.86~3.91 (m, 1H), 3.02 (s, 3H), 1.66 (s, 6H), 0.78 (m, 2H), 0.67 (m, 2H) |
| 80 | N-(3-chloro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide | LC/MS ESI (+): 699 (M + 1)<br>$^1$H-NMR(400 MHz, DMSO-d$_6$): δ 10.57 (s, 1H), 9.88 (s, 1H), 8.28 (s, 1H), 8.03 (d, 1H, J = 8.4 Hz), 7.93 (s, 1H), 7.80 (s, 1H), 7.56 (s, 1H), 7.37 (d, 1H, J = 8.8 Hz), 7.27 (s, 1H), 7.24 (s, 1H), 7.14 (s, 1H), 7.07 (s, 1H), 6.82 (tt, 1H, J = 56.0, 3.2 Hz), 3.02 (s, 3H), 1.69 (s, 6H) |
| 81 | N-(3-chloro-5-(2-(3-isopropoxy-5-(trifluoromethoxy)phenyl)propan-2-yl)phenyl)-5-(methylsulfonamido)benzo[d]thiazole-2-carboxamide | LC/MS ESI(+): 642 (M + 1)<br>$^1$H-NMR(400 MHz, DMSO-d$_6$): δ 11.21 (s, 1H), 10.19 (brs, 1H), 8.26 (d, 1H, J = 8.7 Hz), 8.10 (s, 1H), 8.05 (s, 1H), 7.86 (s, 1H), 7.51 (dd, 1H, J = 8.7, 2.0 Hz), 7.13 (s, 1H), 6.83 (s, 1H), 6.79 (s, 1H), 6.77 (s, 1H), 4.67~4.70 (m, 1H), 3.11 (s, 3H), 1.70 (s, 6H), 1.29 (d, 6H, J = 6.0 Hz) |
| 82 | N-(3-fluoro-5-(2-(3-isopropoxy-5-(trifluoromethoxy)phenyl)propan-2-yl)phenyl)-5-(methylsulfonamido)benzo[b]thiophene-2-carboxamide | LC/MS ESI (+): 625 (M + 1)<br>$^1$H-NMR(400 MHz, DMSO-d$_6$): δ 10.57 (s, 1H), 9.87 (s, 1H), 8.29 (s, 1H), 8.02 (d, 1H, J = 8.8 Hz), 7.80 (s, 1H), 7.68 (d, 1H, J = 10.8 Hz), 7.40 (s, 1H), 7.36 (d, 1H, J = 8.8 Hz), 6.85 (d, 1H, J = 10.4 Hz), 6.76 (s, 1H), 6.73 (s, 1H), 6.70 (s, 1H), 4.59~4.65 (m, 1H), 3.01 (s, 3H), 1.64 (s, 6H), 1.23 (d, 6H, J = 6.0 Hz) |
| 83 | N-(3-chloro-5-(2-(3-(2,2-difluoroethoxy)-5-(trifluoromethoxy)phenyl)propan-2-yl)phenyl)-5-(methylsulfonamido)benzo[b]thiophene-2-carboxamide | LC/MS ESI (+): 663 (M + 1)<br>$^1$H-NMR (400 MHz, DMSO-d$_6$): δ 10.55 (s, 1H), 9.87 (brs, 1H), 8.28 (s, 1H), 8.02 (d, 1H, J = 8.7 Hz), 7.90 (s, 1H), 7.79 (s, 1H), 7.53 (s, 1H), 7.36 (d, 1H, J = 8.7 Hz), 7.04 (s, 1H), 6.92 (s, 1H), 6.89 (s, 1H), 6.80 (s, 1H), 6.37 (tt, 1H, J = 54.3, 3.3 Hz), 4.37 (td, 2H, J = 14.7, 3.3 Hz), 3.01 (s, 3H), 1.65 (s, 6H) |
| 84 | N-(3-chloro-5-(2-(3-isopropoxy-5-(trifluoromethoxy)phenyl)propan-2-yl)phenyl)-6-fluoro-5-(methylsulfonamido)benzo[b]thiophene-2-carboxamide | LC/MS ESI (+): 659 (M + 1)<br>$^1$H-NMR(400 MHz, DMSO-d$_6$): δ 10.61 (s, 1H), 9.77 (brs, 1H), 8.29 (s, 1H), 8.09 (d, 1H, J = 10.4 Hz), 7.99 (d, 1H, J = 7.6 Hz), 7.90 (m, 1H), 7.53 (s, 1H), 7.06 (m, 1H), 6.78 (s, 1H), 6.74 (m, 1H), 6.72 (s, 1H), 4.62~4.65 (m, 1H), 3.06 (s, 3H), 1.65 (s, 6H), 1.25 (d, 6H, J = 6.0 Hz) |
| 85 | N-(3-fluoro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide | LC/MS ESI (+): 683 (M + 1)<br>$^1$H-NMR(400 MHz, DMSO-d$_6$): δ 10.59 (s, 1H), 9.88 (brs, 1H), 8.29 (s, 1H), 8.03 (d, 1H, J = 8.8 Hz), 7.80 (m, 1H), 7.71 (d, 1H, J = 10.9 Hz), 7.42 (s, 1H), 7.37 (dd, 1H, J = 8.7, 2.1 Hz), 7.26 (s, 1H), 7.23 (s, 1H), 7.13 (s, 1H), 6.89 (d, 1H, J = 10.2 Hz), 6.81 (tt, 1H, J = 51.9, 3.0 Hz), 3.02 (s, 3H), 1.69 (s, 6H) |

TABLE 2-continued

| Ex. | Compound | Analysis data |
|---|---|---|
| 86 | N-(3-fluoro-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide | LC/MS ESI (+): 684 (M + 1)<br>$^1$H-NMR(400 MHz, DMSO-d$_6$): δ 10.76 (s, 1H), 10.54 (s, 1H), 9.10 (s, 1H), 8.27 (s, 1H), 7.70 (d, 1H, J = 10.9 Hz), 7.52 (s, 1H), 7.41 (s, 1H), 7.26 (s, 1H), 7.23 (s, 1H), 7.13 (s, 1H), 6.93 (d, 1H, J = 10.4 Hz), 6.81 (tt, 1H, J = 51.9, 3.0 Hz), 3.31 (s, 3H), 1.69 (s, 6H) |
| 87 | N-(3-bromo-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide | LC/MS ESI (+): 743 (M + 1)<br>$^1$H-NMR(400 MHz, DMSO-d$_6$): δ 10.55 (s, 1H), 9.88 (s, 1H), 8.28 (s, 1H), 8.06 (s, 1H), 8.03 (d, 1H, J = 8.8 Hz), 7.80 (s, 1H), 7.60 (s, 1H), 7.36 (dd, 1H, J = 8.8, 1.6 Hz), 7.27 (s, 1H), 7.24 (s, 1H), 7.19 (s, 1H), 7.14 (s, 1H), 6.82 (tt, 1H, J = 52.0, 3.2 Hz), 3.02 (s, 3H), 1.69 (s, 6H) |
| 88 | N-(3-chloro-5-(2-(3-(2,2,2-trifluoroethoxy)-5-(trifluoromethoxy)phenyl)propan-2-yl)phenyl)-5-(methylsulfonamido)benzo[b]thiophene-2-carboxamide | LC/MS ESI (+): 681 (M + 1)<br>$^1$H-NMR (400 MHz, DMSO-d$_6$): δ 10.55 (s, 1H), 9.85 (brs, 1H), 8.28 (s, 1H), 8.02 (d, 1H, J = 8.5 Hz), 7.90 (s, 1H), 7.79 (s, 1H), 7.55 (s, 1H), 7.36 (d, 1H, J = 8.7 Hz), 7.05 (s, 1H), 7.00 (s, 1H), 6.98 (s, 1H), 6.84 (s, 1H), 4.85 (q, 2H, J = 8.8 Hz), 3.00 (s, 3H), 1.67 (s, 6H) |
| 89 | N-(3-bromo-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide | LC/MS ESI (+): 744 (M + 1)<br>$^1$H-NMR(400 MHz, DMSO-d$_6$): δ 10.71 (s, 1H), 10.53 (brs, 1H), 9.10 (s, 1H), 8.26 (s, 1H), 8.04 (s, 1H), 7.57 (s, 1H), 7.52 (s, 1H), 7.26 (s, 1H), 7.22 (s, 2H), 7.12 (s, 1H), 6.80 (t, 1H, J = 52.0 Hz), 3.33 (s, 3H), 1.68 (s, 6H) |
| 90 | N-(3-chloro-5-(2-(3-(2-morpholinoethoxy)-5-(trifluoromethoxy)phenyl)propan-2-yl)phenyl)-5-(methylsulfonamido)benzo[b]thiophene-2-carboxamide | LC/MS ESI (+): 712 (M + 1)<br>$^1$H-NMR(400 MHz, DMSO-d$_6$): δ 10.57 (s, 1H), 9.91 (brs, 1H), 8.28 (s, 1H), 8.01 (d, 1H, J = 8.9 Hz), 7.91 (s, 1H), 7.78 (s, 1H), 7.54 (s, 1H), 7.34 (d, 1H, J = 8.9 Hz), 7.05 (s, 1H), 6.84 (s, 1H), 6.80 (s, 1H), 6.75 (s, 1H), 4.10 (t, 2H, J = 5.5 Hz), 3.54~3.57 (m, 4H), 3.05 (s, 3H), 2.65 (t, 2H, J = 5.5 Hz), 2.41~2.46 (m, 4H), 1.65 (s, 6H) |
| 91 | N-(3-(2-(3-bromo-5-isopropoxyphenyl)propan-2-yl)-5-chlorophenyl)-5-(methylsulfonamido)benzo[b]thiophene-2-carboxamide | LC/MS ESI (+): 636 (M + 1)<br>$^1$H-NMR(400 MHz, DMSO-d$_6$): δ 10.57 (s, 1H), 9.90 (brs, 1H), 8.28 (s, 1H), 8.01 (d, 1H, J = 8.7 Hz), 7.91 (s, 1H), 7.77 (s, 1H), 7.49 (s, 1H), 7.34 (d, 1H, J = 8.7 Hz), 7.06 (s, 1H), 6.98 (s, 1H), 6.91 (s, 1H), 6.68 (s, 1H), 4.52~4.64 (m, 1H), 2.99 (s, 3H), 1.64 (s, 6H), 1.21 (d, 6H, J = 6.0 Hz) |
| 92 | N-(3-chloro-5-(2-(3-chloro-5-isopropoxyphenyl)propan-2-yl)phenyl)-5-(methylsulfonamido)benzo[b]thiophene-2-carboxamide | LC/MS ESI (+): 591 (M + 1)<br>$^1$H-NMR(400 MHz, DMSO-d$_6$): δ 10.57 (s, 1H), 9.88 (brs, 1H), 8.28 (s, 1H), 8.01 (d, 1H, J = 8.7 Hz), 7.91 (s, 1H), 7.77 (s, 1H), 7.49 (s, 1H), 7.34 (d, 1H, J = 8.7 Hz), 7.07 (s, 1H), 6.87 (s, 1H), 6.79 (s, 1H), 6.65 (s, 1H), 4.59~4.63 (m, 1H), 3.00 (s, 3H), 1.62 (s, 6H), 1.22 (d, 6H, J = 6.0 Hz) |
| 93 | N-(3-chloro-5-(2-(3-isopropoxy-5-(trifluoromethoxy)phenyl)propan-2-yl)phenyl)-4-fluoro-5-(methylsulfonamido)benzo[b]thiophene-2-carboxamide | LC/MS ESI (+): 659 (M + 1)<br>$^1$H-NMR(400 MHz, DMSO-d$_6$): δ 10.67 (s, 1H), 9.75 (brs, 1H), 8.46 (s, 1H), 7.89~7.92 (m, 2H), 7.49~7.53 (m, 2H), 7.06 (m, 1H), 6.78 (s, 1H), 6.71~6.72 (m, 2H), 4.60~4.66 (m, 1H), 3.05 (s, 3H), 1.64 (s, 6H), 1.23 (d, 6H, J = 6.0 Hz) |
| 94 | N-(3-chloro-5-(2-(3-(2-(dimethylamino)ethoxy)-5-(trifluoromethoxy)phenyl)propan-2-yl)phenyl)-5-(methylsulfonamido)benzo[b]thiophene-2-carboxamide | LC/MS ESI (+): 670 (M + 1)<br>$^1$H-NMR(400 MHz, DMSO-d$_6$): δ 10.57 (s, 1H), 9.88 (s, 1H), 8.28 (s, 1H), 8.02 (d, 1H, J = 8.8 Hz), 7.90 (s, 1H), 7.79 (d, 1H J = 2.0 Hz), 7.52 (s, 1H), 7.35 (dd, 1H, J = 8.8, 2.0 Hz), 7.05 (s, 1H), 6.82 (s, 1H), 6.78 (s, 1H), 6.73 (s, 1H), 4.04 (t, 2H J = 5.6 Hz), 3.01 (s, 3H), 2.57 (t, 2H J = 5.6 Hz), 2.17 (s, 6H), 1.64 (s, 6H) |
| 95 | tert-butyl 4-(3-(2-(3-chloro-5-(5-(methylsulfonamido)benzo[b]thiophene-2-carboxamido)phenyl)propan-2-yl)-5-(trifluoromethoxy)phenoxy)piperidine-1-carboxylate | LC/MS ESI (+): 782 (M + 1)<br>$^1$H-NMR(400 MHz, DMSO-d$_6$): δ 10.57 (s, 1H), 9.90 (s, 1H), 8.29 (s, 1H), 8.03 (d, 1H, J = 8.8 Hz), 7.90 (s, 1H), 7.80 (s, 1H), 7.55 (s, 1H), 7.36 (d, 1H, J = 8.8 Hz), 7.07 (s, 1H), 6.90 (s, 1H), 6.80 (s, 1H), 6.75 (s, 1H), 4.60~4.62 (m, 1H), 3.64~3.67 (m, 2H), 3.10~3.20 (m, 2H), 3.02 (s, 3H), 1.86~1.91 (m, 2H), 1.65 (s, 6H), 1.53~1.44 (m, 2H), 1.39 (s, 9H) |
| 96 | N-(3-chloro-5-(2-(3-(piperidin-4-yloxy)-5-(trifluoromethoxy)phenyl)propan-2-yl)phenyl)-5-(methylsulfonamido)benzo[b]thiophene-2-carboxamide | LC/MS ESI (+): 682 (M + 1)<br>$^1$H-NMR(400 MHz, DMSO-d$_6$): δ 10.54 (s, 1H), 8.26 (s, 1H), 7.99 (d, 1H, J = 8.8 Hz), 7.90 (s, 1H), 7.76 (s, 1H), 7.53 (s, 1H), 7.33 (d, 1H, J = 8.8 Hz), 7.05 (s, 1H), 6.82 (s, 1H), 6.74 (s, 1H), 6.71 (s, 1H), 4.37~4.46 (m, 1H), 2.98 (s, 3H), 2.88~2.92 (m, 2H), 2.53~2.57 (m, 2H), 1.84~1.89 (m, 2H), 1.64 (s, 6H), 1.38~1.42 (m, 2H) |

TABLE 2-continued

| Ex. | Compound | Analysis data |
|---|---|---|
| 97 | N-(3-chloro-5-(2-(3-isopropoxy-5-(trifluoromethoxy)phenyl)propan-2-yl)phenyl)-5-(methylsulfonyl)-4,5,6,7-tetrahydrothieno[3,2-c]pyridine-2-carboxamide | LC/MS ESI (+): 631 (M + 1)<br>¹H-NMR(400 MHz, DMSO-d₆): δ 10.29 (s, 1H), 7.86 (m, 1H), 7.76 (s, 1H), 7.45 (s, 1H), 7.01 (m, 1H), 6.77 (s, 1H), 6.71 (s, 1H), 6.69 (s, 1H), 4.59~4.65 (m, 1H), 4.32 (s, 2H), 3.49~3.52 (m, 2H), 2.98 (s, 5H), 1.62 (s, 6H), 1.23 (d, 6H, J = 6.0 Hz) |
| 98 | N-(3-bromo-5-(2-(3-methoxy-5-(trifluoromethoxy)phenyl)propan-2-yl)phenyl)-6-(methylsulfonamido)-1H-pyrrolo[3,2-c]pyridine-2-carboxamide | LC/MS ESI (+): 641(M + 1)<br>¹H-NMR(400 MHz, DMSO-d₆): δ 11.97 (s, 1H), 10.40 (brs, 2H), 8.75 (s, 1H), 8.07 (s, 1H), 7.59 (s, 1H), 7.49 (s, 1H), 7.15 (s, 1H), 7.07 (s, 1H), 6.82 (s, 1H), 6.80 (s, 1H), 6.73 (s, 1H), 3.78 (s, 3H), 3.24 (s, 3H), 1.64 (s, 6H) |
| 99 | N-(3-bromo-5-(2-(3-methoxy-5-(trifluoromethoxy)phenyl)propan-2-yl)phenyl)-5-(methylsulfonamido)-1H-pyrrolo[2,3-c]pyridine-2-carboxamide 2,2,2-trifluoroacetate | LC/MS ESI (+): 641 (M + 1)<br>¹H-NMR(400 MHz, DMSO-d₆): δ 12.18 (s, 1H), 10.49 (s, 1H), 9.95 (s, 1H), 8.60 (s, 1H), 8.07 (s, 1H), 7.59 (s, 1H), 7.34 (s, 1H), 7.32 (s, 1H), 7.18 (s, 1H), 6.81 (s, 2H), 6.73 (s, 1H), 3.77 (s, 3H), 3.19 (s, 3H), 1.65 (s, 6H) |
| 100 | N-(3-chloro-5-(2-(3-isopropoxy-5-(trifluoromethoxy)phenyl)propan-2-yl)phenyl)-6-(methylsulfonamido)-1H-pyrrolo[2,3-b]pyridine-2-carboxamide | LC/MS ESI (+): 625 (M + 1)<br>¹H-NMR(400 MHz, DMSO-d₆): δ 12.12 (s, 1H), 10.63 (brs, 1H), 10.22 (s, 1H), 8.04 (d, 1H, J = 8.4 Hz), 7.95 (s, 1H), 7.53 (s, 1H), 7.31 (s, 1H), 7.00 (s, 1H), 6.71~6.77 (m, 4H), 4.61~4.64 (m, 1H), 3.43 (s, 3H), 1.64 (s, 6H), 1.23 (d, 6H, J = 5.9 Hz) |
| 101 | N-(3-chloro-5-(2-(3-isopropoxy-5-(trifluoromethoxy)phenyl)propan-2-yl)phenyl)-6-(methylsulfonamido)-1H-pyrrolo[3,2-c]pyridine-2-carboxamide | LC/MS ESI (+): 625 (M + 1)<br>¹H-NMR(400 MHz, DMSO-d₆): δ 11.98 (brs, 1H), 10.41 (brs, 2H), 8.75 (s, 1H), 7.94(s, 1H), 7.54 (s, 1H), 7.48 (s, 1H), 7.07 (s, 1H), 7.03(s, 1H), 6.77 (s, 1H), 6.73 (s, 1H), 6.71 (s, 1H), 4.61~4.64 (m, 1H), 3.23 (s, 3H), 1.64 (s, 6H), 1.23 (d, 6H, J = 5.5 Hz) |
| 102 | N-(3-chloro-5-(2-(3-isopropoxy-5-(trifluoromethoxy)phenyl)propan-2-yl)phenyl)-4-(methylsulfonamido)thiophene-2-carboxamide | LC/MS ESI (+): 591 (M + 1)<br>¹H-NMR (400 MHz, DMSO-d₆): δ 10.43 (s, 1H), 9.98 (brs, 1H), 7.85 (s, 2H), 7.50 (s, 1H), 7.33 (s, 1H), 7.01 (s, 1H), 6.69~6.76 (m, 2H), 4.60~4.66 (m, 2H), 3.02 (s, 3H), 1.64 (s, 6H), 1.24 (d, 6H, J = 5.9 Hz) |
| 103 | N-(3-chloro-5-(2-(3-isopropoxy-5-(trifluoromethoxy)phenyl)propan-2-yl)phenyl)-5-(morpholine-4-sulfonamido)benzo[b]thiophene-2-carboxamide | LC/MS ESI (+): 712 (M + 1)<br>¹H-NMR(400 MHz, DMSO-d₆): δ 10.56 (s, 1H), 10.19 (brs, 1H), 8.27 (s, 1H), 8.00 (d, 1H, J = 8.8 Hz), 7.91 (s, 1H), 7.78 (s, 1H), 7.53 (s, 1H), 7.36 (dd, 1H, J = 8.7, 2.1 Hz), 7.05 (s, 1H), 6.77 (s, 1H), 6.72 (s, 1H), 6.71 (s, 1H), 4.60~4.66 (m, 1H), 3.51~3.54 (m, 4H), 3.07~3.10 (m, 4H), 1.64 (s, 6H), 1.23 (d, 6H, J = 6.0 Hz) |
| 104 | N-(3-chloro-5-(2-(3-isopropoxy-5-(trifluoromethoxy)phenyl)propan-2-yl)phenyl)-5-(methylsulfonamido)-4,5,6,7-tetrahydrothieno[3,2-c]pyridine-2-carboxamide | LC/MS ESI (+): 646 (M + 1)<br>¹H-NMR(400 MHz, DMSO-d₆): δ 10.21 (s, 1H), 8.55 (s, 1H), 7.86 (m, 1H), 7.68 (s, 1H), 7.48 (m, 1H), 6.99 (m, 1H), 6.76 (s, 1H), 6.71 (m, 1H), 6.69 (s, 1H), 4.62 (m, 1H), 3.93 (s, 2H), 3.12~3.15 (m, 2H), 2.97~3.00 (m, 5H), 1.62 (s, 6H), 1.23 (d, 6H, J = 6.0 Hz) |
| 105 | 6-chloro-N-(3-chloro-5-(2-(3-isopropoxy-5-(trifluoromethoxy)phenyl)propan-2-yl)phenyl)-5-(methylsulfonamido)benzo[b]thiophene-2-carboxamide | LC/MS ESI (+): 675 (M + 1)<br>¹H-NMR (400 MHz, DMSO-d₆): δ 10.64 (s, m), 9.68 (brs, 1H), 8.34 (s, 1H), 8.29 (s, 1H), 8.03 (s, 1H), 7.89 (s, 1H), 7.52 (s, 1H), 7.05 (s, 1H), 6.77 (s, 1H), 6.72 (s, 1H), 6.70 (s, 1H), 4.60 (m, 1H), 3.05 (s, 3H), 1.64 (s, 6H), 1.23 (d, 6H, J = 5.9 Hz) |
| 106 | N-(3-chloro-5-(2-(3-methoxyphenyl)propan-2-yl)phenyl)-5-(methylsulfonamido)benzo[b]thiophene-2-carboxamide | LC/MS ESI (+): 529 (M + 1)<br>¹H-NMR(400 MHz, DMSO-d₆): δ 10.46 (s, 1H), 9.79 (brs, 1H), 8.21 (s, 1H), 7.95 (d, 1H, J = 8.8 Hz), 7.81 (s, 1H), 7.72 (s, 1H), 7.46 (s, 1H), 7.29 (dd, 1H, J = 8.8, 2.0 Hz), 7.16 (t, 1H, J = 8.8 Hz), 6.94 (s, 1H), 6.10~6.73 (m, 3H), 3.66 (s, 3H), 2.94 (s, 3H), 1.57 (s, 6H) |

Example 107

Synthesis of N-(3-ethynyl-5-(2-(4-fluorophenyl)propan-2-yl)phenyl)-6-(methylsulfonamido)-1H-indole-2-carboxamide

(a) Synthesis of N-(3-(2-(4-fluorophenyl)propan-2-yl)-5-((trimethylsilyl)ethynyl)phenyl)-6-(methylsulfonamido)-1H-indole-2-carboxamide N-(3-bromo-5-(2-(4-fluorophenyl)propan-2-yl)phenyl)-6-(methylsulfonamido)-1H-indole-2-carboxamide (56.0 mg, 0.10 mmol), CuI (12.0 mg, 0.06 mmol), and Pd(t-Bu$_3$P)$_2$ (31.0 mg, 0.06 mmol) were dried under reduced pressure, and dissolved in anhydrous 1,4-dioxane (1.0 mL) in a sealed tube. Ethynyltrimethylsilane (189.0 μL, 1.34 mmol), Et$_3$N (186.0 μL, 1.34 mmol) were added, followed by heating at 130° C. for 14 hours, and the reaction mixture was cooled to room temperature. Water was added to the reaction mixture, and then extracted with EtOAc. The organic extract was washed with brine, dried over anhydrous Na$_2$SO$_4$, concentrated under reduced pressure. The residue was purified by flash column chromatography (amine silica gel, CH$_2$Cl$_2$:MeOH=20:1) to obtain N-(3-(2-(4-fluorophenyl)propan-2-yl)-5-((trimethylsilyl)ethynyl)phenyl)-6-(methylsulfonamido)-1H-indole-2-carboxamide (30.0 mg, 50%) as an off-white solid.

LC/MS ESI (+): 562 (M+1)

(b) Synthesis of N-(3-ethynyl-5-(2-(4-fluorophenyl)propan-2-yl)phenyl)-6-(methylsulfonamido)-1H-indole-2-carboxamide To a solution of N-(3-(2-(4-fluorophenyl)propan-2-yl)-5-((trimethylsilyl)ethynyl)phenyl)-6-(methylsulfonamido)-1H-indole-2-carboxamide (30.0 mg, 0.05 mmol) in anhydrous THF (1.0 mL), 1 N solution of TBAF in THF (106.0 μL, 0.10 mol) was added, followed by stirring at room temperature for 1 hour. Water was added, and then extracted with EtOAc. The organic extract was washed with brine, dried over anhydrous Na$_2$SO$_4$, concentrated under reduced pressure. The residue was purified by flash column chromatography (amine silica gel, CH$_2$Cl$_2$:MeOH=20:1) to obtain N-(3-ethynyl-5-(2-(4-fluorophenyl)propan-2-yl)phenyl)-6-(methylsulfonamido)-1H-indole-2-carboxamide (10.0 mg, 38%) as an off-white solid.

LC/MS ESI (+): 490 (M+1)

$^1$H-NMR (300MHz, DMSO-d$_6$): 0.3-11.68 (s, 1H), 10.15 (s, 1H), 9.58 (brs, 1H), 7.92 (s, 1H), 7.60-7.64 (m, 2H), 7.38 (d, 1H, J=1.3Hz), 7.36 (d, 1H, J=1.3Hz), 7.24-7.30 (m, 2H), 7.09-7.16 (m, 2H), 7.03 (s, 1H), 6.98 (dd, 1H, J=8.2, 1.5Hz), 4.15 (s, 1H), 2.84 (s, 3H), 1.65 (s, 6H)

Through the synthetic method according to Example 107, compounds of Example 108 and Example 109 were synthesized, and the data of each example are as follows.

TABLE 3

| Ex. | Compound | Analysis data |
|---|---|---|
| 108 | N-(3-ethynyl-5-(2-(4-fluorophenyl)propan-2-yl)phenyl)-5-(methylsulfonamido)benzo[b]thiophene-2-carboxamide | LC/MS ESI (+): 507 (M + 1)<br>$^1$H-NMR (300 MHz, DMSO-d$_6$): δ 10.48 (s, 1H), 9.88 (brs, 1H), 8.28 (s, 1H), 8.02 (d, 1H, J = 8.8 Hz), 7.87 (s, 1H), 7.78 (d, 1H, J = 1.9 Hz), 7.61 (s, 1H), 7.35 (dd, 1H, J = 8.8, 1.9 Hz), 7.25~7.29 (m, 2H), 7.07~7.15 (m, 3H), 4.20 (s, 1H), 3.00 (s, 3H), 1.64 (s, 6H) |
| 109 | N-(3-(2-(2,4-difluorophenyl)propan-2-yl)-5-ethynylphenyl)-5-(methylsulfonamido)benzo[b]thiophene-2-carboxamide | LC/MS ESI (+): 525 (M + 1)<br>$^1$H-NMR (300 MHz, DMSO-d$_6$): δ 10.43 (s, 1H), 9.83 (brs, 1H), 8.26 (s, 1H), 8.01 (d, 1H, J = 8.6 Hz), 7.86 (t, 1H, J = 1.5 Hz), 7.78 (d, 1H, J = 1.9 Hz), 7.56~7.64 (m, 2H), 7.35 (dd, 1H, J = 8.8, 2.1 Hz), 7.06~7.16 (m, 2H), 7.02 (s, 1H), 4.15 (s, 1H), 3.01 (s, 3H), 1.65 (s, 6H) |

Example 110

Synthesis of 3-chloro-N-(3-(2-(4-fluorophenyl)propan-2-yl)phenyl)-6-(methylsulfonamido)benzo[b]thiophene-2-carboxamide

(a) Synthesis of 3-chloro-N-(3-(2-(4-fluorophenyl)propan-2-yl)phenyl)-6-nitrobenzo[b]thiophene-2-carboxamide 3-Chloro-6-nitrobenzo[b]thiophene-2-carboxylic acid (50.0 mg, 0.19 mmol), 3-(2-(4-fluorophenyl)propan-2-yl)aniline (49.0 mg, 0.21 mmol), HATU (81.0 mg, 0.21 mmol), and DIPEA (51.0 μL, 0.29 mmol) were dissolved in anhydrous DMF (4.0 mL), followed by heating at 40° C. for 24 hours. The reaction mixture was extracted with EtOAc, dried over anhydrous Na$_2$SO$_4$, concentrated under reduced pressure. The residue was purified by flash column chromatography (amine silica gel, n-Hex:EtOAc=4:1) to obtain 3-chloro-N-(3-(2-(4-fluorophenyl)propan-2-yl)phenyl)-6-nitrobenzo[b]thiophene-2-carboxamide (37.0 mg, 41%) as a yellowish brown solid.

$^1$H-NMR (300MHz, DMSO-d$_6$): δ 10.69 (s, 1H), 9.28 (s, 1H), 8.39 (dd, 1H, J=8.8, 2.2Hz), 8.13 (d, 1H, J=8.8Hz), 7.57-7.61 (m, 2H), 7.10-7.34 (m, 3H), 6.34-6.39 (m, 3H), 1.64 (s, 6H)

(b) Synthesis of 6-amino-3-chloro-N-(3-(2-(4-fluorophenyl)propan-2-yl)phenyl)benzo[b]thiophene-2-carboxamide 3-Chloro-N-(3 fluorophenyl)propan-2-yl)phenyl)-6-nitrobenzo[b]thiophene-2-carboxamide (35.0 mg, 0.08 mmol), Zn (73.6 mg, 1.13 mmol), and NH$_4$Cl (20.0 mg, 0.38 mmol) were dissolved in a mixture of THF/MeOH/H$_2$O (3.0 mL, 1/0.5/0.5 v/v), and ultrasonificated for 1.5 hours. Through filtering and concentration under reduced pressure, 6-amino-3-chloro-N-(3-(2-(4-fluorophenyl)propan-2-yl)phenyl)benzo[b]thiophene-2-carboxamide was obtained as a white solid.

LC/MS ESI (+): 439 (M+1)

(c) Synthesis of 3-chloro-N-(3-(2-(4-fluorophenyl)propan-2-yl)phenyl)-6-(methylsulfonamido)benzo[b]thiophene-2-carboxamide 6-Amino-3-chloro-N-(3-(2-(4-fluorophenyl)propan-2-yl)phenyl)benzo[b]thiophene-2-carboxamide was dissolved in pyridine (1.0 mL), and methanesulfonyl chloride (7.6 μL, 0.10 mmol) was slowly added at 0° C. The reaction mixture was stirred at room temperature for 2 hours and extracting with EtOAc. The organic extract was washed with brine, dried over anhydrous Na$_2$SO$_4$, concentrated under reduced pressure. The residue was purified by flash column chromatography (amine silica gel, CH$_2$Cl$_2$:MeOH=20:1) to obtain 3-chloro-N-(3-(2-(4-fluorophenyl)propan-2-yl)phenyl)-6-(methylsulfonamido)benzo[b]thiophene-2-carboxamide (20.9 mg, 2 step yield: 54%) as a white solid.

LC/MS ESI (+): 517 (M+1)

$^1$H-NMR (300MHz, DMSO-d$_6$): δ 10.40 (s, 1H), 10.24 (s, 1H), 7.90 (m, 1H), 7.88 (d, 1H, J=8.8Hz), 7.56-7.60 (m, 2H), 7.42 (dd, 1H, J=8.8, 1.9Hz), 7.23-7.31 (m, 3H), 7.07-7.13 (m, 2H), 7.00 (d, 1H, J=7.6Hz), 3.11 (s, 3H), 1.63 (s, 6H)

Through the synthetic method according to Example 110, compounds from Example 111 to Example 113 were synthesized, and the data of each example are as follows.

Example 114

Synthesis of N-(3-chloro-5-(2-(3-(prop-1-yn-1-yl)-5-(trifluoromethoxy)phenyl)propan-2-yl)phenyl)-5-(methylsulfonamido)benzo[b]thiophene-2-carboxamide (a) Synthesis of 3-(2-(3-chloro-5-nitrophenyl)propan-2-yl)-5-(trifluoromethoxy)phenyl trifluoromethanesulfonate 3-(2-(3-Chloro-5-nitrophenyl)propan-2-yl)-5-(trifluoromethoxy)phenol (100.0 mg, 0.27 mmol) was dissolved in CH$_2$Cl$_2$ (2.7 mL), and pyridine (109.0 μL, 1.35 mmol) and Tf$_2$O (45.0 μL, 0.27 mmol) were slowly added at 0° C. The mixture was stirred at 0° C. for 2 hours and then extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=9:1) to obtain 3-(2-(3-chloro-5-nitrophenyl)propan-2-yl)-5-(trifluoromethoxy)phenyl trifluoromethanesulfonate (120.0 mg, 88%) as a colorless liquid.

$^1$H-NMR (400MHz, CDCl$_3$): δ 8.13 (t, 1H, J=1.9Hz), 7.99 (t, 1H, J=1.9Hz), 7.45 (t, 1H, J=1.8Hz), 7.08-7.10 (m, 2H), 7.04 (t, 1H, J=1.9Hz), 1.75 (s, 6H)

(b) Synthesis of 1-chloro-3-nitro-5-(2-(3-(prop-1-yn-1-yl)-5-(trifluoromethoxy)phenyl)propan-2-yl)benzene 3-(2-(3-Chloro-5-nitrophenyl)propan-2-yl)-5-(trifluoromethoxy)phenyl trifluoromethanesulfonate (280.0 mg, 0.55 mmol) was dissolved in anhydrous DMF (5.5 mL), and 1-(trimethylsilyl)-1-propyne (123.0 μL, 0.83 mmol), Pd(PPh$_3$)$_4$ (64.0 mg, 0.06 mmol), CuI (21.0 mg, 0.11 mmol), and DIPEA (480.0 μL, 2.75 mmol) were added at room temperature. The mixture was heated at 90° C. for 15 hours and then extracted with CH$_2$Cl$_2$. The organic extract was washed with brine, dried over anhydrous Na$_2$SO$_4$, concentrated under reduced pressure. The residue was purified by flash column chromatography (silica gel, n-Hex:CH$_2$Cl$_2$=4:

TABLE 4

| Ex. | Compound | Analysis data |
| --- | --- | --- |
| 111 | 3-chloro-N-(2',4'-difluoro-[1,1'-biphenyl]-3-yl)-6-(methylsulfonamido)benzo[b]thiophene-2-carboxamide | LC/MS ESI (+): 493 (M + 1)<br>$^1$H-NMR (300 MHz, DMSO-d$_6$): δ 10.56 (s, 1H), 10.28 (s, 1H), 7.88~7.93 (m, 3H), 7.75 (d, 1H, J = 8.5 Hz), 7.56~7.64 (m, 1H), 7.50 (t, 1H, J = 7.7 Hz), 7.36~7.44 (m, 2H), 7.31 (d, 1H, J = 7.7 Hz), 7.19~7.25 (m, 1H), 3.10 (s, 3H) |
| 112 | N-(2',4'-difluoro-[1,1'-biphenyl]-3-yl)-7-methoxy-5-(methylsulfonamido)benzofuran-2-carboxamide | LC/MS ESI (+): 473 (M + 1)<br>$^1$H-NMR (300 MHz, DMSO-d$_6$): δ 10.59 (s, 1H), 9.72 (brs, 1H), 7.99 (s, 1H), 7.87 (d, 1H, J = 8.1 Hz), 7.75 (s, 1H), 7.56~7.64 (m, 1H), 7.48 (t, 1H, J = 8.1 Hz), 7.36~7.44 (m, 1H), 7.28~7.30 (m, 1H), 7.22~7.26 (m, 1H), 7.20 (s, 1H), 6.90 (s, 1H), 3.97 (s, 3H), 3.00 (s, 3H) |
| 113 | N-(3-(2-(4-fluorophenyl)propan-2-yl)phenyl)-7-methoxy-5-(methylsulfonamido)benzofuran-2-carboxamide | LC/MS ESI (+): 497 (M + 1)<br>$^1$H-NMR (300 MHz, DMSO-d$_6$): δ 10.39 (s, 1H), 9.71 (brs, 1H), 7.73 (d, 1H, J = 7.6 Hz), 7.70 (s, 1H), 7.63 (s, 1H), 7.23~7.30 (m, 3H), 7.18 (m, 1H), 7.07~7.13 (m, 2H), 6.98 (d, 1H, J = 8.0 Hz), 6.94 (s, 1H), 3.95 (s, 3H), 2.99 (s, 3H), 1.64 (s, 6H) |

1) to obtain 1-chloro-3-nitro-5-(2-(3-(prop-1-yn-1-yl)-5-(trifluoromethoxy)phenyl)propan-2-yl)benzene (120.0 mg, 55%) as a colorless liquid.

$^1$H-NMR (400MHz, CDCl$_3$): δ 8.08 (t, 1H, J=1.9Hz), 7.99 (t, 1H, J=1.9Hz), 7.46 (t, 1H, J=1.8Hz), 7.11-7.13 (m, 2H), 6.94 (s, 1H), 2.04 (s, 3H), 1.70 (s, 6H)

(c) Synthesis of 3-chloro-5-(2-(3-(prop-1-yn-1-yl)-5-(trifluoromethoxy)phenyl)propan-2-yl)aniline The synthesis procedure of Intermediate 40 was repeated except for using 1-chloro-3-nitro-5-(2-(3-(prop-1-yn-1-yl)-5-(trifluoromethoxy)phenyl)propan-2-yl)benzene (120.0 mg, 0.30 mmol) to obtain 3-chloro-5-(2-(3-(prop-1-yn-1-yl)-5-(trifluoromethoxy)phenyl)propan-2-yl)aniline (93.0 mg, 84%).

LC/MS ESI (+): 368 (M+1)

(d) Synthesis of N-(3-chloro-5-(2-(3-(prop-1-yn-1-yl)-5-(trifluoromethoxy)phenyl)propan-2-yl)phenyl)-5-(methylsulfonamido)benzo[b]thiophene-2-carboxamide The synthesis procedure of Example 1 was repeated except for using 3-chloro-5-(2-(3-(prop-1-yn-1-yl)-5-(trifluoromethoxy)phenyl)propan-2-yl)aniline (55.0 mg, 0.15 mmol) to obtain N-(3-chloro-5-(2-(3-(prop-1-yn-1-yl)-5-(trifluoromethoxy)phenyl)propan-2-yl)phenyl)-5-(methylsulfonamido)benzo[b]thiophene-2-carboxamide (40.0 mg, 43%).

LC/MS ESI (+): 621 (M+1)

$^1$H-NMR (400MHz, DMSO-d$_6$): δ 10.55 (s, 1H), 9.90 (brs, 1H), 8.27 (s, 1H), 8.01 (d, 1H, J=8.6Hz), 7.92 (s, 1H), 7.78 (s, 1H), 7.52 (s, 1H), 7.35 (d, 1H, J=8.6Hz), 7.20-7.36 (m, 3H), 7.07 (s, 1H), 2.99 (s, 3H), 2.04 (s, 3H), 1.67 (s, 6H)

Example 115

Synthesis of N-(3-bromo-5-(2-(3-((4-methylpiperazin-1-yl)methyl)phenyl)propan-2-yl)phenyl)-5-(methylsulfonamido)benzo[b]thiophene-2-carboxamide

(a) Synthesis of (3-(2-(3-bromo-5-nitrophenyl)propan-2-yl)phenyl)methanol

Methyl 3-(2-(3-bromo-5-nitrophenyl)propan-2-yl)benzoate (100.0 mg, 0.26 mmol) was dissolved in anhydrous THF (2.6 mL), and LiAlH$_4$ (15.0 mg, 0.40 mmol) or 1.0 M solution of DIBAL in THF (400.0 μL, 0.40 mmol) was added at 0° C. The mixture was stirred at 0° C. for 1 hour and then extracted with EtOAc. The organic extract was washed with brine, dried over anhydrous Na$_2$SO$_4$, concentrated under reduced pressure. The residue was purified by flash column chromatography (silica gel, n-Hex:EtOAc=2:1) to obtain (3-(2-(3-bromo-5-nitrophenyl)propan-2-yl)phenyl)methanol (52.0 mg, 56%) as a white solid.

$^1$H-NMR (400MHz, CDCl$_3$): δ 8.21 (s, 1H), 8.05 (s, 1H), 7.65 (s, 1H), 7.32 (t, 1H, J=7.6Hz), 7.21-7.26 (m, 2H), 7.10 (d, 1H, J=7.8Hz), 4.89 (d, 2H, J=5.9Hz), 1.73 (s, 6H)

(b) Synthesis of 3-(2-(3-bromo-5-nitrophenyl)propan-2-yl)benzyl methanesulfonate (3-(2-(3-Bromo-5-nitrophenyl)propan-2-yl)phenyl)methanol (40.0 mg, 0.11 mmol) was dissolved in anhydrous CH$_2$Cl$_2$ (1.1 mL), and methanesulfonyl chloride (10.0 μL, 0.13 mmol) and DIPEA (40.0 μL, 0.23 mmol) were added at room temperature. The mixture was stirred at room temperature for 3 hours and then extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=4:1) to obtain 3-(2-(3-bromo-5-nitrophenyl)propan-2-yl)benzyl methanesulfonate (20.0 mg, 41%) as a white solid.

$^1$H-NMR (400MHz, CDCl$_3$): δ 8.22 (s, 1H), 8.01 (s, 1H), 7.64 (s, 1H), 7.37 (t, 1H, J=7.6Hz), 7.31 (d, 1H, J=7.6Hz), 7.25 (s, 1H), 7.22 (d, 1H, J=7.7Hz), 4.89 (s, 2H), 2.92 (s, 3H), 1.73 (s, 6H)

(c) Synthesis of 1-(3-(2-(3-bromo-5-nitrophenyl)propan-2-yl)benzyl)-4-methylpiperazine 3-(2-(3-Bromo-5-nitrophenyl)propan-2-yl)benzyl methanesulfonate (20.0 mg, 0.05 mmol) was dissolved in anhydrous CH$_2$Cl$_2$ (0.5 mL), and 1-methylpiperazine (10.0 μL, 0.09 mmol) and DIPEA (24.0 μL, 0.14 mmol) were added at room temperature. The mixture was stirred at room temperature for 15 hours and extracted with CH$_2$Cl$_2$. The organic extract was washed with brine, dried over anhydrous Na$_2$SO$_4$, concentrated under reduced pressure. The residue was purified by flash column chromatography (silica gel, CH$_2$Cl$_2$:MeOH=20:1) to obtain 1-(3-(2-(3-bromo-5-nitrophenyl)propan-2-yl)benzyl)-4-methylpiperazine (22.0 mg, quant.) as a colorless liquid.

$^1$H-NMR (400MHz, CDCl$_3$): δ 8.20 (s, 1H), 8.04 (s, 1H), 7.64 (s, 1H), 7.26 (t, 1H, J=7.6Hz), 7.19 (d, 1H, J=7.6Hz), 7.07-7.11 (m, 2H), 3.48 (s, 2H), 2.43 (brs, 8H), 2.28 (s, 3H), 1.72 (s, 6H)

(d) Synthesis of 3-bromo-5-(2-(3-((4-methylpiperazin-1-yl)methyl)phenyl)propan-2-yl)aniline The synthesis procedure of Intermediate 40 was repeated except for using 1-(3-(2-(3-bromo-5-nitrophenyl)propan-2-yl)benzyl)-4-methylpiperazine (35.0 mg, 0.08 mmol) to obtain 3-bromo-5-(2-(3-((4-methylpiperazin-1-yl)methyl)phenyl)propan-2-yl)aniline (30.0 mg, 92%).

LC/MS ESI (+): 402 (M+1)

(e) Synthesis of N-(3-bromo-5-(2-(3-((4-methylpiperazin-1-yl)methyl)phenyl)propan-2-yl)phenyl)-5-(methylsulfonamido)benzo[b]thiophene-2-carboxamide The synthesis procedure of Example 1 was repeated except for using 3-bromo-5-(2-(3-((4-methylpiperazin-1-yl)methyl)phenyl)propan-2-yl)aniline (30.0 mg, 0.07 mmol) to obtain N-(3-bromo-5-(2-(3-((4-methylpiperazin-1-yl)methyl)phenyl)propan-2-yl)phenyl)-5-(methylsulfonamido)benzo[b]thiophene-2-carboxamide (2.5 mg, 6%).

LC/MS ESI (+): 655 (M+1)

$^1$H-NMR (400MHz, DMSO-d$_6$): δ 10.55 (s, 1H), 9.89 (s, 1H), 8.29 (s, 1H), 8.04 (d, 1H, J=8.7Hz), 7.96 (s, 1H), 7.79 (d, 1H, J=1.6Hz), 7.62 (s, 1H), 7.36 (dd, 1H, J=8.7, 1.9Hz), 7.30 (t, 1H, J=7.2Hz), 7.10-7.19 (m, 4H), 3.51 (s, 2H), 3.02 (s, 3H), 2.70 (brs, 4H), 2.26 (brs, 4H), 1.65 (s, 3H), 1.23 (s, 6H)

Through the synthetic method according to Example 115, compounds from Example 116 to Example 125 were synthesized, and the data of each example are as follows.

TABLE 5

| Ex. | Compound | Analysis data |
|---|---|---|
| 116 | tert-butyl 4-(3-(2-(3-bromo-5-(5-(methylsulfonamido)benzo[b]thiophene-2-carboxamido)phenyl)propan-2-yl)benzyl)piperazine-1-carboxylate | LC/MS ESI (+): 741 (M + 1)<br>$^1$H-NMR (400 MHz, DMSO-$d_6$): δ 10.50 (s, 1H), 9.34 (brs, 1H), 8.24 (s, 1H), 7.98 (s, 1H), 7.94 (d, 1H, J = 8.8 Hz), 7.72 (s, 1H), 7.61 (s, 1H), 7.38~7.45 (m, 1H), 7.26~7.31 (m, 2H), 7.09~7.19 (m, 3H), 3.46 (s, 2H), 3.25 (brs, 4H), 2.94 (s, 3H), 2.25 (brs, 4H), 1.64 (s, 6H), 1.34 (s, 9H) |
| 117 | tert-butyl 4-(3-(2-(3-bromo-5-(6-(methylsulfonamido)-1H-indole-2-carboxamido)phenyl)propan-2-yl)benzyl)piperazine-1-carboxylate | LC/MS ESI (+): 724 (M + 1)<br>$^1$H-NMR (400 MHz, DMSO-$d_6$): δ 11.72 (s, 1H), 10.24 (s, 1H), 9.65 (brs, 1H), 8.06 (s, 1H), 7.60~7.62 (m, 2H), 7.31~7.43 (m, 6H), 7.05 (s, 1H), 6.97 (d, 1H, J = 8.6 Hz), 3.71 (s, 2H), 3.24 (brs, 4H), 2.93 (s, 3H), 2.67 (brs, 4H), 1.65 (s, 6H), 1.35 (s, 9H) |
| 118 | N-(3-bromo-5-(2-(3-(piperazin-1-ylmethyl)phenyl)propan-2-yl)phenyl)-5-(methylsulfonamido)benzo[b]thiophene-2-carboxamide | LC/MS ESI (+): 641 (M + 1)<br>$^1$H-NMR (400 MHz, DMSO-$d_6$): δ 10.54 (s, 1H), 8.28 (s, 1H), 7.99~8.03 (m, 2H), 7.78 (s, 1H), 7.59 (s, 1H), 7.35 (dd, 1H, J = 8.8, 1.9 Hz), 7.27 (t, 1H, J = 7.8 Hz), 7.16 (d, 1H, J = 7.8 Hz), 7.09~7.12 (m, 3H), 3.50 (s, 2H), 3.00 (s, 3H), 2.66 (brs, 4H), 2.24 (brs, 4H), 1.64 (s, 6H) |
| 119 | N-(3-bromo-5-(2-(3-(piperazin-1-ylmethyl)phenyl)propan-2-yl)phenyl)-6-(methylsulfonamido)-1H-indole-2-carboxamide | LC/MS ESI (+): 624 (M + 1)<br>$^1$H-NMR (400 MHz, DMSO-$d_6$): δ 11.70 (s, 1H), 10.22 (s, 1H), 9.65 (brs, 1H), 8.04 (s, 1H), 7.57~7.66 (m, 2H), 7.36~7.39 (m, 2H), 6.96~7.28 (m, 6H), 3.44 (s, 2H), 2.93 (s, 3H), 2.81 (brs, 4H), 2.30 (brs, 4H), 1.64 (s, 6H) |
| 120 | N-(3-(2-(3-((1H-imidazol-1-yl)methyl)phenyl)propan-2-yl)-5-bromophenyl)-5-(methylsulfonamido)benzo[b]thiophene-2-carboxamide | LC/MS ESI (+): 623 (M + 1)<br>$^1$H-NMR(400 MHz, DMSO-$d_6$): δ 10.53 (s, 1H), 9.82 (brs, 1H), 8.28 (s, 1H), 8.00~8.03 (m, 2H), 7.79 (d, 1H, J = 1.9 Hz), 7.73 (s, 1H), 7.58 (s, 1H), 7.35 (dd, 1H, J = 8.7, 2.1 Hz), 7.29 (t, 1H, J = 7.1 Hz), 7.25 (s, 1H), 7.16~7.17 (m, 2H), 7.10 (s, 1H), 7.02 (d, 1H, J = 7.6 Hz), 6.88 (s, 1H), 5.17 (s, 2H), 3.00 (s, 3H), 1.63 (s, 6H) |
| 121 | N-(3-chloro-5-(2-(3-((2-hydroxyazetidin-1-yl)methyl)-5-isopropoxyphenyl)propan-2-yl)phenyl)-5-(methylsulfonamido)benzo[b]thiophene-2-carboxamide | LC/MS ESI (+): 642 (M + 1)<br>$^1$H-NMR(400 MHz, DMSO-$d_6$): δ 10.55 (s, 1H), 10.19 (brs, 1H), 8.27 (s, 1H), 7.90 (d, 1H, J = 8.7 Hz), 7.86 (s, 1H), 7.76 (s, 1H), 7.55 (s, 1H), 7.33 (dd, 1H, J = 8.7, 2.0 Hz), 7.07 (s, 1H), 6.98~7.90 (m, 2H), 6.72 (s, 1H), 4.48~4.54 (m, 1H), 4.21~4.27 (m, 3H), 3.70~3.78 (m, 2H), 2.97 (s, 3H), 1.90~2.30 (m, 3H), 1.62 (s, 6H), 1.20 (d, 6H, J = 6.0 Hz) |
| 122 | N-(3-bromo-5-(2-(3-isopropoxy-5-(morpholinomethyl)phenyl)propan-2-yl)phenyl)-5-(methylsulfonamido)benzo[b]thiophene-2-carboxamide | LC/MS ESI (+): 700 (M + 1)<br>$^1$H-NMR(400 MHz, DMSO-$d_6$): δ 10.51 (s, 1H), 9.87 (brs, 1H), 8.27 (s, 1H), 8.01 (d, 1H, J = 8.7 Hz), 7.98 (m, 1H), 7.78 (d, 1H, J = 2.0 Hz), 7.58 (m, 1H), 7.35 (dd, 1H, J = 8.7, 2.1 Hz), 7.11 (m, 1H), 6.66~6.68 (m, 2H), 6.62 (m, 1H), 4.55 (m, 1H), 3.50~3.52 (m, 4H), 3.37 (s, 2H), 3.00 (s, 3H), 2.29 (brs, 4H), 1.61 (s, 6H), 1.23 (d, 6H, J = 6.0 Hz) |
| 123 | tert-butyl 4-(3-(2-(3-bromo-5-(5-(methylsulfonamido)benzo[b]thiophene-2-carboxamido)phenyl)propan-2-yl)-5-isopropoxybenzyl)piperazine-1-carboxylate | LC/MS ESI (+): 799 (M + 1)<br>$^1$H-NMR(400 MHz, DMSO-$d_6$): δ 10.51 (s, 1H), 9.97 (brs, 1H), 8.26 (s, 1H), 7.97~7.99 (m, 2H), 7.75 (s, 1H), 7.60 (s, 1H), 7.33 (d, 1H, J = 8.9 Hz), 7.11 (s, 1H), 6.66~6.68 (m, 2H), 6.63 (s, 1H), 4.56 (m, 1H), 3.41 (s, 2H), 3.26 (brs, 4H), 2.97 (s, 3H), 2.25 (brs, 4H), 1.61 (s, 6H), 1.34 (s, 9H), 1.24 (d, 6H, J = 5.8 Hz) |
| 124 | N-(3-bromo-5-(2-(3-isopropoxy-5-(piperazin-1-ylmethyl)phenyl)propan-2-yl)phenyl)-5-(methylsulfonamido)benzo[b]thiophene-2-carboxamide | LC/MS ESI (+): 699 (M + 1)<br>$^1$H-NMR(400 MHz, DMSO-$d_6$): δ 10.52 (s, 1H), 8.28 (s, 1H), 8.02 (d, 1H, J = 8.7 Hz), 7.99 (m, 1H), 7.79 (d, 1H, J = 1.9 Hz), 7.59 (m, 1H), 7.36 (dd, 1H, J = 8.7, 2.1 Hz), 7.10 (m, 1H), 6.66~6.68 (m, 2H), 6.62 (m, 1H), 4.55 (m, 1H), 3.51 (s, 1H), 3.38 (s, 2H), 3.01 (s, 3H), 2.71~2.74 (m, 4H), 2.29 (brs, 4H), 1.61 (s, 6H), 1.24 (d, 6H, J = 5.9 Hz) |
| 125 | N-(3-chloro-5-(2-(3-isopropoxy-5-(pyrrolidin-1-ylmethyl)phenyl)propan-2-yl)phenyl)-5-(methylsulfonamido)benzo[b]thiophene-2-carboxamide | LC/MS ESI (+): 640 (M + 1)<br>$^1$H-NMR(400 MHz, DMSO-$d_6$): δ 10.54 (s, 1H), 9.86 (brs, 1H), 8.28 (s, 1H), 8.02 (d, 1H, J = 8.8 Hz), 7.86 (s, 1H), 7.79 (s, 1H), 7.55 (s, 1H), 7.36 (dd, 1H, J = 8.4, 1.6 Hz), 6.99 (s, 1H), 6.70 (m, 2H), 6.61 (m, 1H), 4.54~4.57 (m, 1H), 3.48~3.52 (m, 4H), 3.02 (s, 3H), 2.38~2.40 (m, 2H), 1.62~1.66 (m, 10H), 1.24 (d, 6H, J = 5.6 Hz) |

Example 126

Synthesis of N-(3-chloro-5-(2-(3-isopropoxy-5-(morpholinomethyl)phenyl)propan-2-yl)phenyl)-5-(methylsulfonamido)benzo[b]thiophene-2-carboxamide (a) Synthesis of 1-(bromomethyl)-3-(2-(3-chloro-5-nitrophenyl)propan-2-yl)-5-isopropoxybenzene 1-Chloro-3-(2-(3-isopropoxy-5-methylphenyl)propan-2-yl)-5-nitrobenzene (500.0 mg, 1.44 mmol) was dissolved in anhydrous CCl$_4$ (15.0 mL), and NBS (256.0 mg, 1.44 mmol) and AIBN (24.0 mg, 0.14 mmol) were added at room temperature. The mixture was refluxed at 90° C. for 3 hours, followed by cooling to room temperature and extracting with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=9:1) to obtain 1-(bromomethyl)-3-(2-(3-chloro-5-nitrophenyl)propan-2-yl)-5-isopropoxybenzene (310.0 mg, 51%) as a yellow liquid.

$^1$H-NMR (400MHz, CDCl$_3$): δ 8.05 (t, 1H, J=1.9Hz), 8.00 (t, 1H, J=1.9Hz), 7.49 (t, 1H, J=1.8Hz), 6.79 (s, 1H), 6.75 (s, 1H), 6.62 (s, 1H), 4.48-4.55 (m, 1H), 4.42 (s, 2H), 1.69 (s, 6H), 1.32 (d, 6H, J=6.0Hz)

(b) Synthesis of 4-(3-(2-(3-chloro-5-nitrophenyl)propan-2-yl)-5-isopropoxybenzyl)morpholine 1-(Bromomethyl)-3-(2-(3-chloro-5-nitrophenyl)propan-2-yl)-5-isopropoxybenzene (86.0 mg, 0.20 mmol) was dissolved in anhydrous CH$_2$Cl$_2$ (3.1 mL), and morpholine (54.0 μL, 0.62 mmol) and DIPEA (162.0 μL, 0.93 mmol) were added at room temperature. The mixture was stirred at room temperature for 2 hours and extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=7:3) to obtain 4-(3-(2-(3-chloro-5-nitrophenyl)propan-2-yl)-5-isopropoxybenzyl)morpholine (66.0 mg, 76%) as a colorless liquid.

$^1$H-NMR (400MHz, CDCl$_3$): δ 8.04 (t, 1H, J=1.9Hz), 7.99 (t, 1H, J=1.9Hz), 7.49 (t, 1H, J=1.8Hz), 6.76 (s, 1H), 6.66 (s, 1H), 6.62 (s, 1H), 4.48-4.58 (m, 1H), 3.68 (t, 4H, J=4.6Hz), 3.43 (s, 2H), 2.40 (t, 4H, J=4.3Hz), 1.69 (s, 6H), 1.32 (d, 6H, J=6.0Hz)

(c) Synthesis of 3-chloro-5-(2-(3-isopropoxy-5-(morpholinomethyl)phenyl)propan-2-yl)aniline The synthesis procedure of Intermediate 40 was repeated except for using 4-(3-(2-(3-chloro-5-nitrophenyl)propan-2-yl)-5-isopropoxybenzyl)morpholine (66.0 mg, 0.15 mmol) to obtain 3-chloro-5-(2-(3-isopropoxy-5-(morpholinomethyl)phenyl)propan-2-yl)aniline (61.0 mg, quant.).

LC/MS ESI (+): 403 (M+1)

(d) Synthesis of N-(3-chloro-5-(2-(3-isopropoxy-5-(morpholinomethyl)phenyl)propan-2-yl)phenyl)-5-(methylsulfonamido)benzo[b]thiophene-2-carboxamide The synthesis procedure of Example 1 was repeated except for using 3-chloro-5-(2-(3-isopropoxy-5-(morpholinomethyl)phenyl)propan-2-yl)aniline (61.0 mg, 0.15 mmol) to obtain N-(3-chloro-5-(2-(3-isopropoxy-5-(morpholinomethyl)phenyl)propan-2-yl)phenyl)-5-(methylsulfonamido)benzo[b]thiophene-2-carboxamide (35.0 mg, 36%).

LC/MS ESI (+): 656 (M+1)

$^1$H-NMR (400MHz, DMSO-d$_6$): δ 10.53 (s, 1H), 9.89 (brs, 1H), 8.28 (s, 1H), 8.01 (d, 1H, J=8.7Hz), 7.87 (s, 1H), 7.78 (s, 1H), 7.54 (s, 1H), 7.35 (d, 1H, J=8.7Hz), 7.00 (s, 1H), 6.63-6.69 (m, 3H), 4.54-4.59 (m, 1H), 3.53 (brs, 4H), 3.40 (s, 2H), 3.00 (s, 3H), 2.30 (brs, 4H), 1.63 (s, 6H), 1.24 (d, 6H, J=6.0Hz)

Through the synthetic method according to Example 126, compounds from Example 127 to Example 141 were synthesized, and the data of each example are as follows.

TABLE 6

| Ex. | Compound | Analysis data |
|---|---|---|
| 127 | N-(3-chloro-5-(2-(3-isopropoxy-5-((4-pivaloylpiperazin-1-yl)methyl)phenyl)propan-2-yl)phenyl)-5-(methylsulfonamido)benzo[b]thiophene-2-carboxamide | LC/MS ESI (+): 739 (M + 1)<br>$^1$H-NMR (400 MHz, DMSO-d$_6$): δ 10.45 (s, 1H), 9.88 (brs, 1H), 8.21 (s, 1H), 7.93 (d, 1H, J = 8.7 Hz), 7.79 (s, 1H), 7.70 (s, 1H), 7.47 (s, 1H), 7.27 (d, 1H, J = 8.7 Hz), 6.94 (s, 1H), 6.57~6.60 (m, 3H), 4.48~4.51 (m, 1H), 3.40 (brs, 4H), 3.33 (s, 2H), 2.92 (s, 3H), 2.22 (brs, 4H), 1.55 (s, 6H), 1.17 (d, 6H, J = 6.0 Hz), 1.04 (s, 9H) |
| 128 | N-(3-chloro-5-(2-(3-isopropoxy-5-((4-(methylsulfonyl)piperazin-1-yl)methyl)phenyl)propan-2-yl)phenyl)-5-(methylsulfonamido)benzo[b]thiophene-2-carboxamide | LC/MS ESI (+): 733 (M + 1)<br>$^1$H-NMR(400 MHz, DMSO-d$_6$): δ 10.46 (s, 1H), 9.85 (brs, 1H), 8.19 (s, 1H), 7.92 (d, 1H, J = 8.6 Hz), 7.79 (s, 1H), 7.69 (s, 1H), 7.48 (s, 1H), 7.27 (d, 1H, J = 8.9 Hz), 6.93 (s, 1H), 6.56~6.63 (m, 3H), 4.46~4.50 (m, 1H), 3.39 (s, 2H), 3.00 (brs, 4H), 2.91 (s, 3H), 2.76 (s, 3H), 2.35 (brs, 4H), 1.56 (s, 6H), 1.17 (d, 6H, J = 6.0 Hz) |
| 129 | N-(3-chloro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide | LC/MS ESI (+): 765 (M + 1)<br>$^1$H-NMR(400 MHz, DMSO-d$_6$): δ 10.53 (s, 1H), 9.86 (brs, 1H), 8.28 (s, 1H), 8.01 (d, 1H, J = 8.7 Hz), 7.85 (s, 1H), 7.79 (s, 1H), 7.56 (s, 1H), 7.36 (d, 1H, J = 8.7 Hz), 7.00 (s, 1H), 6.70 (s, 2H), 6.63 (s, 1H), 4.56 (m, 1H), 3.45 (s, 2H), 3.28 (brs, 4H), 3.05 (m, 1H), 3.01 (s, 3H), 2.40 (brs, 4H), 1.62 (s, 6H), 1.21~1.25 (m, 12H) |

TABLE 6-continued

| Ex. | Compound | Analysis data |
|---|---|---|
| 130 | N-(3-chloro-5-(2-(3-isopropoxy-5-((4-(oxetan-3-yl)piperazin-1-yl)methyl)phenyl)propan-2-yl)phenyl)-5-(methylsulfonamido)benzo[b]thiophene-2-carboxamide | LC/MS ESI (+): 711 (M + 1)<br>$^1$H-NMR(400 MHz, DMSO-d$_6$): δ 10.51 (s, 1H), 9.86 (s, 1H), 8.28 (s, 1H), 8.02 (d, 1H, J = 8.8 Hz), 7.86 (s, 1H), 7.79 (m, 1H), 7.51 (s, 1H), 7.36 (dd, 1H, J = 8.7, 1.6 Hz), 7.02 (s, 1H), 6.64~6.66 (m, 3H), 4.55 (m, 1H), 4.40 (t, 2H, J = 6.4 Hz), 4.31 (t, 2H, = 6.0 Hz), 3.39 (s, 2H), 3.28 (m, 1H), 3.01 (s, 3H), 2.33 (brs, 4H), 2.18 (brs, 4H), 1.62 (s, 6H), 1.24 (d, 6H, J = 5.9 Hz) |
| 131 | N-(3-chloro-5-(2-(3-((4-(N,N-dimethylsulfamoyl)piperazin-1-yl)methyl)-5-isopropoxyphenyl)propan-2-yl)phenyl)-5-(methylsulfonamido)benzo[b]thiophene-2-carboxamide | LC/MS ESI (+): 762 (M + 1)<br>$^1$H-NMR(400 MHz, DMO-d$_6$): δ 10.53 (s, 1H), 9.86 (brs, 1H), 8.28 (s, 1H), 8.01 (d, 1H, J = 8.7 Hz), 7.86 (s, 1H), 7.79 (s, 1H), 7.54 (s, 1H), 7.36 (d, 1H, J = 8.9 Hz), 7.00 (s, 1H), 6.63~6.68 (m, 3H), 4.52~4.57 (m, 1H), 3.43 (s, 2H), 3.10 (brs, 4H), 3.01 (s, 3H), 2.70 (s, 6H), 2.36 (brs, 4H), 1.62 (s, 6H), 1.24 (d, 6H, J = 5.9 Hz) |
| 132 | N-(3-chloro-5-(2-(3-((1,1-dioxidothiomorpholino)methyl)-5-isopropoxyphenyl)propan-2-yl)phenyl)-5-(methylsulfonamido)benzo[b]thiophene-2-carboxamide | LC/MS ESI (+): 704 (M + 1)<br>$^1$H-NMR(400 MHz, DMSO-d$_6$): δ 10.53 (s, 1H), 9.86 (s, 1H), 8.28 (s, 1H), 8.02 (d, 1H, J = 8.8 Hz), 7.84 (s, 1H), 7.79 (d, 1H, J = 1.6 Hz), 7.55 (s, 1H), 7.36 (dd, 1H, J = 8.8, 2.0 Hz), 7.01 (s, 1H), 6.73 (s, 2H), 6.62 (s, 1H), 4.51~4.61 (m, 1H), 3.60 (s, 2H), 3.07 (brs, 4H), 3.01 (s, 3H), 2.84 (brs, 4H), 1.63 (s, 6H), 1.23 (d, 6H, J = 2.0 Hz) |
| 133 | 4-(3-(2-(3-chloro-5-(5-(methylsulfonamido)benzo[b]thiophene-2-carboxamido)phenyl)propan-2-yl)-5-isopropoxybenzyl)-N,N-dimethylpiperazine-1-carboxamide | LC/MS ESI (+): 726 (M + 1)<br>$^1$H-NMR(400 MHz, DMSO-d$_6$): δ 10.53 (s, 1H), 9.85 (brs, 1H), 8.27 (s, 1H), 8.00 (d, 1H, J = 8.7 Hz), 7.85 (s, 1H), 7.78 (s, 1H), 7.54 (s, 1H), 7.35 (d, 1H, J = 8.8 Hz), 7.00 (s, 1H), 6.62~6.68 (m, 3H), 4.53~4.57 (m, 1H), 3.37 (s, 2H), 3.04 (brs, 4H), 3.00 (s, 3H), 2.64 (s, 6H), 2.29 (brs, 4H), 1.62 (s, 6H), 1.23 (d, 6H, J = 5.9 Hz) |
| 134 | N-(3-(2-(3-((2-oxa-7-azaspiro[3,5]nonan-7-yl)methyl)-5-isopropoxyphenyl)propan-2-yl)-5-chlorophenyl)-5-(methylsulfonamido)benzo[b]thiophene-2-carboxamide | LC/MS ESI (+): 696 (M + 1)<br>$^1$H-NMR(400 MHz, DMSO-d$_6$): δ 10.53 (s, 1H), 9.86 (brs, 1H), 8.28 (s, 1H), 8.02 (d, 1H, J = 8.7 Hz), 7.86 (s, 1H), 7.79 (s, 1H), 7.53 (s, 1H), 7.36 (d, 1H, J = 8.8 Hz), 6.98 (s, 1H), 6.65 (s, 2H), 6.61 (s, 1H), 4.54 (m, 1H), 4.20 (s, 4H), 3.45 (brs, 2H), 3.01 (s, 3H), 2.18 (brs, 4H), 1.69 (brs, 4H), 1.61 (s, 6H), 1.23 (d, 6H, J = 5.9 Hz) |
| 135 | N-(3-chloro-5-(2-(3-isopropoxy-5-((4-(5-isopropyl-1,3,4-oxadiazol-2-yl)piperazin-1-yl)methyl)phenyl)propan-2-yl)phenyl)-5-(methylsulfonamido)benzo[b]thiophene-2-carboxamide | LC/MS ESI (+): 765 (M + 1)<br>$^1$H-NMR(400 MHz, DMSO-d$_6$): δ 10.53 (s, 1H), 9.86 (brs, 1H), 8.28 (s, 1H), 8.01 (d, 1H, J = 8.7 Hz), 7.84(s, 1H), 7.80 (s, 1H), 7.55 (s, 1H), 7.35 (d, 1H, J = 8.6 Hz), 7.01 (s, 1H), 6.64~6.70 (m, 3H), 4.53~4.59 (m, 1H), 3.46 (s, 2H), 3.32 (brs, 4H), 3.00 (s, 3H), 2.90~2.97 (m, 1H), 2.42 (brs, 4H), 1.63 (s, 6H), 1.24 (d, 6H, J = 5.9 Hz), 1.18 (d, 6H, J = 6.9 Hz) |
| 136 | N-(3-fluoro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide | LC/MS ESI (+): 749 (M + 1)<br>$^1$H-NMR(400 MHz, DMSO-d$_6$): δ 10.54 (s, 1H), 9.86 (brs, 1H), 8.28 (s, 1H), 8.01 (d, 1H, J = 8.7 Hz), 7.78 (d, 1H, J = 1.9 Hz), 7.63 (d, 1H, J = 11.1 Hz), 7.41 (s, 1H), 7.35 (dd, 1H, J = 8.7, 2.1 Hz), 6.82 (d, 1H, J = 10.3 Hz), 6.71 (s, 2H), 6.62 (s, 1H), 4.55 (m, 1H), 3.45 (s, 2H), 3.27~3.29 (m, 4H), 3.05 (m, 1H), 3.01 (s, 3H), 2.39~2.41 (m, 4H), 1.62 (s, 6H), 1.21~1.24 (m, 12H) |
| 137 | N-(3-fluoro-5-(2-(3-isopropoxy-5-(morpholinomethyl)phenyl)propan-2-yl)phenyl)-5-(methylsulfonamido)benzo[b]thiophene-2-carboxamide | LC/MS ESI (+): 640 (M + 1)<br>$^1$H-NMR (400 MHz, DMSO-d$_6$): δ 10.54 (s, 1H), 9.86 (brs, 1H), 8.28 (s, 1H), 8.01 (d, 1H, J = 8.7 Hz), 7.78 (s, 1H), 7.63 (d, 1H, J = 10.9 Hz), 7.34~7:38 (m, 2H), 6.82 (d, 1H, J = 10.4 Hz), 6.61~6.82 (m, 3H), 4.51~4.57 (m, 1H), 3.51 (brs, 4H), 3.38 (s, 2H), 3.01 (s, 3H), 2.30 (brs, 4H), 1.62 (s, 6H), 1.23 (d, 6H, J = 6.0 Hz) |
| 138 | N-(3-chloro-5-(2-(3-((1-methyl-1H-pyrazol-4-yl)methyl)-5-(1,1,2,2-tetrafluoroethoxy)phenyl)propan-2-yl)phenyl)-5-(methylsulfonamido)benzo[b]thiophene-2-carboxamide | LC/MS ESI (+): 709 (M + 1)<br>$^1$H-NMR(400 MHz, DMSO-d$_6$): δ 10.55 (s, 1H), 9.87 (brs, 1H), 8.28 (s, 1H), 8.00 (d, 1H, J = 8.7 Hz), 7.90 (m, 1H), 7.78 (d, 1H, J = 2.0 Hz), 7.53 (m, 1H), 7.42 (s, 1H), 7.35 (dd, 1H, J = 8.7, 2.1 Hz), 7.23 (s, 1H), 7.15 (s, 1H), 7.01 (m, 1H), 6.93 (s, 1H), 6.87 (s, 1H), 6.61~6.87 (m, 1H), 3.78 (s, 2H), 3.75 (s, 3H), 2.99 (s, 3H), 1.64 (s, 6H) |
| 139 | N-(3-bromo-5-(2-(3-((4-(N,N-dimethylsulfamoyl)piperazin-1-yl)methyl)-5-(1,1,2,2-tetrafluoroethoxy)phenyl)propan-2-yl)phenyl)-5-(methylsulfonamido)benzo[b]thiophene-2-carboxamide | LC/MS ESI (+): 864 (M + 1)<br>$^1$H-NMR(400 MHz, DMSO-d$_6$): δ 10.54 (s, 1H), 9.87 (s, 1H), 8.28 (s, 1H), 8.02 (s, 1H), 8.01 (d, 1H, J = 8.7 Hz), 7.80 (s, 1H), 7.60 (s, 1H), 7.36 (d, 1H, J = 8.8 Hz), 7.15 (s, 1H), 7.13 (s, 1H), 7.09 (s, 1H), 7.02 (s, 1H), 6.78 (t, 1H, J = 52.0 Hz), 3.54 (s, 2H), 3.11~3.18 (m, 4H), 3.05 (s, 3H), 2.71 (s, 6H), 2.38~2.53 (m, 4H), 1.66 (s, 6H) |

TABLE 6-continued

| Ex. | Compound | Analysis data |
|---|---|---|
| 140 | N-(3-fluoro-5-(2-(3-(morpholinomethyl)-5-(1,1,2,2-tetrafluoroethoxy)phenyl)propan-2-yl)phenyl)-5-(methylsulfonamido)benzo[b]thiophene-2-carboxamide; | LC/MS ESI (+): 698 (M + 1)<br>$^1$H-NMR (400 MHz, DMSO-d$_6$): δ 10.55 (s, 1H), 9.85 (brs, 1H), 8.28 (s, 1H), 8.02 (d, 1H, J = 8.7 Hz), 7.79 (s, 1H), 7.65 (d, 1H, J = 11.0 Hz), 7.40 (s, 1H), 7.36 (d, 1H, J = 10.4 Hz), 7.14 (s, 1H), 7.07 (s, 1H), 6.97 (s, 1H), 6.83 (d, 1H, J = 10.4 Hz), 6.77 (t, 1H, J = 2.0 Hz), 3.53 (brs, 4H), 3.48 (s, 2H), 3.01 (s, 3H), 2.31 (brs, 4H), 1.66 (s, 6H) |
| 141 | N-(3-bromo-5-(2-(3-((4-(oxetan-3-yl)piperazin-1-yl)methyl)-5-(1,1,2,2-tetrafluoroethoxy)phenyl)propan-2-yl)phenyl)-5-(methylsulfonamido)benzo[b]thiophene-2-carboxamide | LC/MS ESI (+): 813 (M + 1)<br>$^1$H-NMR(400 MHz, DMSO-d$_6$): δ 10.50 (s, 1H), 9.87 (s, 1H), 8.26 (s, 1H), 8.02 (s, 1H), 8.01 (d, 1H, J = 8.8 Hz), 7.78 (s, 1H), 7.57 (s, 1H), 7.35 (d, 1H, J = 8.4 Hz), 7.16 (s, 1H), 7.09 (s, 1H), 7.05 (s, 1H), 7.01 (s, 1H), 6.77 (t, 1H, J = 52.0 Hz), 4.40 (t, 2H, J = 6.0 Hz), 4.32 (t, 2H, J = 6.0 Hz), 3.48 (s, 2H), 3.26~3.28 (m, 1H), 3.00 (s, 3H) 2.34 (s, 4H) 2.18 (s, 4H), 1.65 (s, 6H) |

Example 142

Synthesis of N-(3-chloro-5-(2-(3-isopropoxy-5-(1-methyl-1H-pyrazol-5-yl)phenyl)propan-2-yl)phenyl)-5-(methylsulfonamido)benzo[b]thiophene-2-carboxamide (a) Synthesis of 5-(3-(2-(3-chloro-5-nitrophenyl)propan-2-yl)-5-isopropoxyphenyl)-1-methyl-1H-pyrazole The synthesis procedure of Intermediate 44 was repeated except for using 1-bromo-3-(2-(3-chloro-5-nitrophenyl)propan-2-yl)-5-isopropoxybenzene (50.0 mg, 0.12 mmol) to obtain 5-(3-(2-(3-chloro-5-nitrophenyl)propan-2-yl)-5-isopropoxyphenyl)-1-methyl-1H-pyrazole (32.0 mg, 64%).

LC/MS ESI (+): 414 (M+1)
$^1$H-NMR (400MHz, CDCl$_3$): δ 8.07 (s, 1H), 8.03 (s, 1H), 7.54 (s, 1H), 7.54 (s, 1H), 7.50 (s, 1H), 6.78 (s, 1H), 6.74 (s, 1H), 6.27 (s, 1H), 4.53-4.56 (m, 1H), 3.83 (s, 3H), 1.73 (s, 6H), 1.34 (d, 6H, J=6.0Hz)

(b) Synthesis of 3-chloro-5-(2-(3-isopropoxy-5-(1-methyl-1H-pyrazol-5-yl)phenyl)propan-2-yl)aniline The synthesis procedure of Intermediate 40 was repeated except for using 5-(3-(2-(3-chloro-5-nitrophenyl)propan-2-yl)-5-isopropoxyphenyl)-1-methyl-1H-pyrazole (32.0 mg, 0.08 mmol) to obtain 3-chloro-5-(2-(3-isopropoxy-5-(1-methyl-1H-pyrazol-5-yl)phenyl)propan-2-yl)aniline (22.0 mg, 76%).

LC/MS ESI (+): 384 (M+1)

(c) Synthesis of N-(3-chloro-5-(2-(3-isopropoxy-5-(1-methyl-1H-pyrazol-5-yl)phenyl)propan-2-yl)phenyl)-5-(methylsulfonamido)benzo[b]thiophene-2-carboxamide The synthesis procedure of Example 1 was repeated except for using 3-chloro-5-(2-(3-isopropoxy-5-(1-methyl-1H-pyrazol-5-yl)phenyl)propan-2-yl)aniline (16.0 mg, 0.06 mmol) to obtain N-(3-chloro-5-(2-(3-isopropoxy-5-(1-methyl-1H-pyrazol-5-yl)phenyl)propan-2-yl)phenyl)-5-(methylsulfonamido)benzo[b]thiophene-2-carboxamide (15.0 mg, 42%).

LC/MS ESI (+): 637 (M+1)
$^1$H-NMR (400MHz, DMSO-d$_6$): δ 10.56 (s, 1H), 9.88 (brs, 1H), 8.28 (s, 1H), 8.02 (d, 1H, J=8.7Hz), 7.89 (s, 1H), 7.79 (s, 1H), 7.58 (s, 1H), 7.44 (s, 1H), 7.35 (d, 1H, J=8.7Hz), 7.10 (s, 1H), 6.88 (s, 2H), 6.75 (s, 1H), 6.39 (s, 1H), 4.63-4.69 (m, 1H), 3.80 (s, 3H), 3.01 (s, 3H), 1.68 (s, 6H), 1.25 (d, 6H, J=6.0Hz)

Through the synthetic method according to Example 142, compounds from Example 143 to Example 147 were synthesized, and the data of each example are as follows.

TABLE 7

| Ex. | Compound | Analysis data |
|---|---|---|
| 143 | N-(3-chloro-5-(2-(3-isopropoxy-5-(1-methyl-1H-pyrazol-4-yl)phenyl)propan-2-yl)phenyl)-5-(methylsulfonamido)benzo[b]thiophene-2-carboxamide | LC/MS ESI (+): 637 (M + 1)<br>$^1$H-NMR(400 MHz, DMSO-d$_6$): δ 10.56 (s, 1H), 9.88 (brs, 1H), 8.28 (s, 1H), 8.13 (s, 1H), 8.01 (d, 1H, J = 8.7 Hz), 7.89 (s, 1H), 7.84 (s, 1H), 7.78 (s, 1H), 7.54 (s, 1H), 7.35 (d, 1H, J = 8.7 Hz), 7.05 (s, 1H), 7.11 (s, 1H), 6.95 (s, 1H), 6.47 (s, 1H), 4.60~4.66 (m, 1H), 3.83 (s, 3H), 3.01 (s, 3H), 1.66 (s, 6H), 1.23 (d, 6H, J = 6.0 Hz) |
| 144 | N-(3-chloro-5-(2-(3-(3-hydroxy-4-methylpiperazin-1-yl)-5-isopropoxyphenyl)propan-2-yl)phenyl)-5-(methylsulfonamido)benzo[b]thiophene-2-carboxamide | LC/MS ESI (+): 671 (M + 1)<br>$^1$H-NMR(400 MHz, DMSO-d$_6$): δ 10.58 (s, 1H), 8.28 (s, 1H), 7.98 (d, 1H, J = 8.8 Hz), 7.86 (s, 1H), 7.76 (s, 1H), 7.54 (s, 1H), 7.34 (dd, 1H, J = 8.8, 1.6 Hz), 7.00 (s, 1H), 6.43 (s, 1H), 6.34 (s, 1H), 6.16 (s, 1H), 4.48~4.60 (m, 1H), 3.40~3.46 (m, 5H), 3.13 (s, 3H), 2.99~3.05 (m, 2H), 3.00 (s, 3H), 1.61 (s, 6H), 1.20 (d, 6H, J = 6.0 Hz) |
| 145 | N-(3-chloro-5-(2-(3-isopropoxy-5-morpholinophenyl)propan-2-yl)phenyl)-5-(methylsulfonamido)benzo[b]thiophene-2-carboxamide | LC/MS ESI (+): 642 (M + 1)<br>$^1$H-NMR(400 MHz, DMSO-d$_6$): δ 10.53 (s, 1H), 9.86 (brs, 1H), 8.23 (s, 1H), 7.98 (d, 1H, J = 8.9 Hz), 7.82 (s, 1H), 7.72 (s, 1H), 7.40 (s, 1H), 7.29 (d, 1H, J = 8.7 Hz), 6.94 (s, 1H), 6.33 (s, 1H), 6.22 (s, 1H), 6.07 (s, 1H), 4.46~4.48 (m, 1H), 3.62(brs, 4H), 2.98 (s, 3H), 2.94 (brs, 4H), 1.54 (s, 6H), 1.17 (d, 6H, J = 6.0 Hz) |

TABLE 7-continued

| Ex. | Compound | Analysis data |
|---|---|---|
| 146 | N-(3-chloro-5-(2-(3-isopropoxy-5-(pyrrolidin-1-yl)phenyl)propan-2-yl)phenyl)-5-(methylsulfonamido)benzo[b]thiophene-2-carboxamide | LC/MS ESI (+): 626 (M + 1)<br>$^1$H-NMR(400 MHz, DMSO-d$_6$): δ 10.57 (s, 1H), 9.90 (s, 1H), 8.31 (s, 1H), 8.04 (d, 1H, J = 8.8 Hz), 7.89 (s, 1H), 7.80 (s, 1H), 7.54 (s, 1H), 7.37 (dd, 1H, J = 8.8, 2.0 Hz), 7.02 (s, 1H), 5.98 (s, 1H), 5.95 (s, 1H), 5.89 (s, 1H), 4.48~4.54 (m, 1H), 3.15~3.18 (m, 4H), 3.03 (s, 3H), 1.90~1.93 (m, 4H), 1.61 (s, 6H), 1.21 (d, 6H, J = 6.0 Hz) |
| 147 | N-(3-chloro-5-(2-(3-isopropoxy-5-(4-methylpiperazin-1-yl)phenyl)propan-2-yl)phenyl)-5-(methylsulfonamido)benzo[b]thiophene-2-carboxamide | LC/MS ESI (+): 655 (M + 1)<br>$^1$H-NMR(400 MHz, DMSO-d$_6$): δ 10.45 (s, 1H), 9.81 (brs, 1H), 8.22 (s, 1H), 7.95 (d, 1H, J = 8.8 Hz), 7.81 (s, 1H), 7.73 (s, 1H), 7.45 (s, 1H), 7.29 (dd, 1H, J = 8.8, 2.2 Hz), 6.94 (s, 1H), 6.32 (s, 1H), 6.20 (s, 1H), 6.04 (s, 1H), 4.44~4.46 (m, 1H), 2.99~3.00 (m, 4H), 2.94 (s, 3H), 2.30~2.35 (m, 4H), 2.13 (s, 3H), 1.53 (s, 6H), 1.13 (d, 6H, J = 6.0 Hz) |

Example 148

Synthesis of N-(6-chloro-4-(2-(3-methoxy-5-(trifluoromethoxy)phenyl)propan-2-yl)pyridin-2-yl)-5-(methylsulfonamido)benzo[b]thiophene-2-carboxamide (a) Synthesis of 2,6-dichloro-N-methoxy-N-methylisonicotinamide 2,6-Dichloroisonicotinic acid (192.0 mg, 1.00 mmol) was dissolved in anhydrous CH$_2$Cl$_2$ (10.0 mL), and (COCl)$_2$ (130.0 μL, 1.50 mmol) and a catalytic amount of anhydrous DMF were added. The mixture was stirred at 0° C. for 1 hour and dried for 1 hour under reduced pressure. The residue was dissolved in anhydrous CH$_2$Cl$_2$ (10.0 mL), and N,O-dimethylhydroxylamine (292.0 mg, 3.00 mmol) and pyridine (480.0 μL, 6.00 mmol) were added at 0° C. The reaction mixture was extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=1:4) to obtain 2,6-dichloro-N-methoxy-N-methylisonicotinamide (220.0 mg, 94%) as a white solid.

LC/MS ESI (+): 235 (M+1)
$^1$H-NMR (400MHz, CDCl$_3$): δ 7.50 (s, 2H), 3.58 (s, 3H), 3.38 (s, 3H)

(b) Synthesis of (2,6-dichloropyridin-4-yl)(3-methoxy-5-(trifluoromethoxy)phenyl)methanone 1-Bromo-3-methoxy-5-(trifluoromethoxy)benzene (5.0 g, 18.72 mmol) was dissolved in THF (70.0 mL), and tert-BuLi (11.9 mL, 20.16 mmol) was slowly added at −78° C., followed by stirring for 2 hours. 2,6-Dichloro-N-methoxy-N-methylisonicotinamide (3.4 g, 14.40 mmol) was dissolved in THF (7.6 mL) and added to the reaction mixture, followed by stirring at 0° C. for 2 hours. The reaction mixture was extracted with EtOAc. The organic extract was washed with brine, dried over anhydrous Na$_2$SO$_4$, concentrated under reduced pressure. The residue was purified by flash column chromatography (silica gel, n-Hex:CH$_2$Cl$_2$=1:10) to obtain (2,6-dichloropyridin-4-yl)(3-methoxy-5-(trifluoromethoxy)phenyl)methanone (2.8 g, 55%) as a yellow solid.

LC/MS ESI (+): 366 (M+1)
$^1$H-NMR (400MHz, CDCl$_3$): δ 7.53 (s, 2H) 7.24 (s, 1H), 7.19 (s, 1H), 7.06 (s, 1H), 3.89 (s, 3H)

(c) Synthesis of 2,6-dichloro-4-(dichloro(3-methoxy-5-(trifluoromethoxy)phenyl)methyl)pyridine The synthesis procedure of Intermediate 37 was repeated except for using (2,6-dichloropyridin-4-yl)(3-methoxy-5-(trifluoromethoxy)phenyl)methanone (2.8 g, 7.64 mmol) to obtain 2,6-dichloro-4-(dichloro(3-methoxy-5-(trifluoromethoxy)phenyl)methyl)pyridine (1.9 g, 60%).

LC/MS ESI (+): 420 (M+1)
$^1$H-NMR (400MHz, CDCl$_3$): δ 7.45 (s, 2H) 7.05 (s, 1H), 7.03 (s, 1H), 6.82 (s, 1H), 3.85 (s, 3H)

(d) Synthesis of 2,6-dichloro-4-(2-(3-methoxy-5-(trifluoromethoxy)phenyl)propan-2-yl)pyridine In CH$_2$Cl$_2$ (30.0 mL), 1.0 M solution of TiCl$_4$ in CH$_2$Cl$_2$ (9.0 mL, 9.00 mmol) and 1.2 M solution of dimethylzinc in toluene (22.6 mL, 27.06 mmol) were added at −40° C., followed by stirring for 30 minutes. A solution of 2,6-dichloro-4-(dichloro(3-methoxy-5-(trifluoromethoxy)phenyl)methyl)pyridine (1.9 g, 5.0 mmol) in CH$_2$Cl$_2$ (15.0 mL) was slowly added at −40° C., and the reaction mixture was heated to room temperature, followed by stirring for 12 hours. Water was added to quench the reaction, and then extracted with CH$_2$Cl$_2$. The organic extract was dried over anhydrous Na$_2$SO$_4$, concentrated under reduced pressure. The residue was purified by flash column chromatography (amine silica gel, n-Hex:EtOAc=1:1) to obtain 2,6-dichloro-4-(2-(3-methoxy-5-(trifluoromethoxy)phenyl)propan-2-yl)pyridine (540.0 mg, 31%) as an off-white oil.

LC/MS ESI (+): 380 (M+1)
$^1$H-NMR (400MHz, CDCl$_3$): δ 7.07 (s, 2H) 6.66 (s, 1H), 6.62 (s, 2H), 3.79 (s, 3H), 1.64 (s, 6H)

(e-I) Synthesis of 6-chloro-4-(2-(3-methoxy-5-(trifluoromethoxy)phenyl)propan-2-yl)pyridin-2-amine (method I)

In 2,6-dichloro-4-(2-(3-methoxy-5-(trifluoromethoxy)phenyl)propan-2-yl)pyridine (70.0 mg, 0.18 mmol), 35% solution of NH$_4$OH in H$_2$O (3.0 mL) and 1,4-dioxane (1.0 mL) were added. The mixture was stirred at 160° C. for 12 hours, and then, cooled to room temperature and concentrated under reduced pressure. The residue was purified by flash column chromatography (amine silica gel, n-Hex:EtOAc=1:9) to obtain 6-chloro-4-(2-(3-methoxy-5-(trifluoromethoxy)phenyl)propan-2-yl)pyridin-2-amine (40.0 mg, 60%) as an off-white oil.

LC/MS ESI (+): 361 (M+1)

$^1$H-NMR (400MHz, CDCl$_3$): δ 6.66 (s, 2H), 6.63 (s, 1H), 6.50 (s, 1H), 6.18 (s, 1H), 4.48 (brs, 2H), 3.78 (s, 3H), 1.58 (s, 6H)

(e-II) Synthesis of 6-chloro-4-(2-(3-methoxy-5-(trifluoromethoxy)phenyl)propan-2-yl)pyridin-2-amine (method II)

2,6-Dichloro-4-(2-(3-methoxy-5-(trifluoromethoxy)phenyl)propan-2-yl)pyridine (50.0 mg, 0.13 mmol), NaN$_3$ (17.0 mg, 0.26 mmol), Cu$_2$O (18.7 mg, 0.13 mmol), and L-proline (19.5 mg, 0.17 mmol) were dissolved in DMSO (1.0 mL), followed by stirring at 100° C. for 12 hours. The reaction mixture was cooled to room temperature and extracted with EtOAc, dried over anhydrous Na$_2$SO$_4$, concentrated under reduced pressure. The residue was purified by flash column chromatography (amine silica gel, n-Hex:EtOAc=9:1) to obtain 6-chloro-4-(2-(3-methoxy-5-(trifluoromethoxy)phenyl)propan-2-yl)pyridin-2-amine (18.0 mg, 38%) as an off-white oil.

(f) Synthesis of N-(6-chloro-4-(2-(3-methoxy-5-(trifluoromethoxy)phenyl)propan-2-yl)pyridin-2-yl)-5-nitrobenzo[b]thiophene-2-carboxamide 5-Nitrobenzo[b]thiophene-2-carboxylic acid (13.3 mg, 0.06 mmol) was dissolved in anhydrous CH$_2$Cl$_2$ (1.0 mL), and (COCl)$_2$ (5.3 μL, 0.06 mmol) and a catalytic amount of anhydrous DMF were added. The mixture was stirred at 0° C. for 1 hour and dried for 1 hour under reduced pressure. The residue was dissolved in anhydrous pyridine (1.0 mL), and, 6-chloro-4-(2-(3-methoxy-5-(trifluoromethoxy)phenyl)propan-2-yl)pyridin-2-amine (10.0 mg, 0.03 mmol) was added at 0° C. The reaction mixture was extracted with EtOAc. The organic extract was washed with brine, dried over anhydrous Na$_2$SO$_4$, concentrated under reduced pressure. The residue was purified by flash column chromatography (amine silica gel, n-Hex:EtOAc=1:4) to obtain N-(6-chloro-4-(2-(3-methoxy-5-(trifluoromethoxy)phenyl)propan-2-yl)pyridin-2-yl)-5-nitrobenzo[b]thiophene-2-carboxamide (11.0 mg, 72%) as a yellow solid.

LC/MS ESI (+): 566 (M+1)

$^1$H-NMR (400MHz, CDCl$_3$): δ 8.81 (d, 1H, J=2.0Hz), 8.55 (s, 1H), 8.33 (dd, 1H, J=8.8, 2.0Hz), 8.27 (d, 1H, J=1.2Hz), 8.04 (d, 1H, J=8.8Hz), 8.03 (s, 1H), 6.90 (d, 1H, J=1.2Hz), 6.69 (t, 1H, J=2.0Hz), 6.67 (s, 1H), 6.05 (s, 1H), 3.79 (s, 3H), 1.70 (s, 6H)

(g) Synthesis of 5-amino-N-(6-chloro-4-(2-(3-methoxy-5-(trifluoromethoxy)phenyl)propan-2-yl)pyridin-2-yl)benzo[b]thiophene-2-carboxamide The synthesis procedure of Intermediate 40 was repeated except for using N-(6-chloro-4-(2-(3-methoxy-5-(trifluoromethoxy)phenyl)propan-2-yl)pyridin-2-yl)-5-nitrobenzo[b]thiophene-2-carboxamide (10.0 mg, 0.02 mmol) to obtain 5-amino-N-(6-chloro-4-(2-(3-methoxy-5-(trifluoromethoxy)phenyl)propan-2-yl)pyridin-2-yl)benzo[b]thiophene-2-carboxamide (9.0 mg, 91%).

LC/MS ESI (+): 536 (M+1)

$^1$H-NMR (400MHz, CDCl$_3$): δ 8.46 (s, 1H), 8.31 (d, 1H, J=1.2Hz), 7.72 (s, 1H), 7.65 (d, 1H, J=8.8Hz), 7.13 (d, 1H, J=2.0Hz), 6.91 (dd, 1H, J=8.8, 2.0Hz), 6.83 (d, 1H, J=1.6Hz), 6.66-6.68 (m, 2H), 6.63-6.64 (m, 1H), 3.80-3.82 (m, 2H), 3.78 (s, 3H), 1.69 (s, 6H)

(h) Synthesis of N-(6-chloro-4-(2-(3-methoxy-5-(trifluoromethoxy)phenyl)propan-2-yl)pyridin-2-yl)-5-(methylsulfonamido)benzo[b]thiophene-2-carboxamide The synthesis procedure of Intermediate 6-a was repeated except for using 5-amino-N-(6-chloro-4-(2-(3-methoxy-5-(trifluoromethoxy)phenyl)propan-2-yl)pyridin-2-yl)benzo[b]thiophene-2-carboxamide (9.0 mg, 0.02 mmol) to obtain N-(6-chloro-4-(2-(3-methoxy-5-(trifluoromethoxy)phenyl)propan-2-yl)pyridin-2-yl)-5-(methylsulfonamido)benzo[b]thiophene-2-carboxamide (1.7 mg, 17%).

LC/MS ESI (+): 614 (M+1)

$^1$H-NMR (400MHz, DMSO-d$_6$): δ 11.42 (s, 1H), 9.88 (s, 1H), 8.50 (s, 1H), 8.10 (s, 1H), 7.98 (d, 1H, J=8.4Hz), 7.70 (s, 1H), 7.32 (d, 1H, J=8.4Hz), 7.12 (s, 1H), 6.85 (s, 2H), 6.78 (s, 1H), 3.78 (s, 3H), 2.97 (s, 3H), 1.66 (s, 6H)

Example 149

Synthesis of N-(2-chloro-6-(2-(3-methoxy-5-(trifluoromethoxy)phenyl)propan-2-yl)pyridin-4-yl)-5-(methylsulfonamido)benzo[b]thiophene-2-carboxamide The synthesis procedure of Example 148 was repeated except for using 4,6-dichloropicolinic acid (3.0 g, 15.63 mmol) to obtain N-(2-chloro-6-(2-(3-methoxy-5-(trifluoromethoxy)phenyl)propan-2-yl)pyridin-4-yl)-5-(methylsulfonamido)benzo[b]thiophene-2-carboxamide (49.6 mg).

LC/MS ESI (+): 614 (M+1)

$^1$H-NMR (400MHz, DMSO-d$_6$): δ 10.86 (s, 1H), 9.96 (s, 1H), 8.31 (s, 1H), 8.02 (d, 1H, J=8.8Hz), 7.88 (s, 1H), 7.80 (s, 1H), 7.54 (s, 1H), 7.36 (d, 1H, J=8.8Hz), 6.82 (s, 2H), 6.75 (s, 1H), 3.77 (s, 3H), 3.00 (s, 3H), 1.66 (s, 6H)

Example 150

Synthesis of N-(4-chloro-6-(2-(3-methoxy-5-(trifluoromethoxy)phenyl)propan-2-yl)pyridin-2-yl)-5-(methylsulfonamido)benzo[b]thiophene-2-carboxamide The synthesis procedure of Example 148 was repeated except for using 4,6-dichloropicolinic acid (3.0 g, 15.63 mmol) to obtain N-(4-chloro-6-(2-(3-methoxy-5-(trifluoromethoxy)phenyl)propan-2-yl)pyridin-2-yl)-5-(methylsulfonamido)benzo[b]thiophene-2-carboxamide (5.7 mg).

LC/MS ESI (+): 614 (M+1)

$^1$H-NMR (400MHz, DMSO-d$_6$): δ 11.05 (s, 1H), 9.91 (s, 1H), 8.57 (s, 1H), 8.09 (d, 1H, J=1.6Hz), 8.03 (d, 1H, J=8.8Hz), 7.78 (s, 1H), 7.37 (dd, 1H, J=8.8, 1.6Hz), 7.19 (d, 1H, J=1.6Hz), 6.86 (t, 1H, J=2.0Hz), 6.80 (s, 2H), 3.77 (s, 3H), 3.02 (s, 3H), 1.75 (s, 6H)

Example 151

Synthesis of N-(3-chloro-5-(2-(3-isopropoxy-5-(trifluoromethoxy)phenyl)propan-2-yl)phenyl)-2-(methylsulfonamido)thieno[2,3-b]pyrazine-6-carboxamide

(a) Synthesis of methyl 5-chloro-4-nitrothiophene-2-carboxylate

5-Chloro-4-nitrothiophene-2-carboxylic acid (1.0 g, 4.82 mmol) was dissolved in MeOH (50.0 mL), and SOCl$_2$ (699.0 μL, 9.63 mmol) was slowly added. After refluxing for 20 hours, the reaction mixture was concentrated under reduced pressure. The residue was purified by flash column chromatography (silica gel, n-Hex:EtOAc=4:1) to obtain methyl 5-chloro-4-nitrothiophene-2-carboxylate (797.5 mg, 75%) as a white solid.

$^1$H-NMR (400MHz, CDCl$_3$): δ 8.18 (s, 1H), 3.94 (s, 3H)

(b) Synthesis of methyl 5-((2-ethoxy-2-oxoethyl)amino)-4-nitrothiophene-2-carboxylate Methyl 5-chloro-4-nitrothiophene-2-carboxylate (697.5 mg, 3.15 mmol) was dissolved in anhydrous CH$_3$CN (31.0 mL), and H-Gly-OEt.HCl (483.2 mg, 3.46 mmol) and K$_2$CO$_3$ (1.1 g, 7.87 mmol) were added at room temperature. The mixture was refluxed at 70° C. for 3 hours and then cooled to room temperature. The reaction mixture was poured into ice water. The resulting solid was filtered to obtain methyl 5-((2-ethoxy-2-oxoethyl)amino)-4-nitrothiophene-2-carboxylate (713.2 mg, 79%) as a yellow solid.

LC/MS ESI (+): 289 (M+1)

$^1$H-NMR (400MHz, CDCl$_3$): δ 8.74 (s, 1H), 8.04 (s, 1H), 4.33 (q, 2H, J=7.1Hz), 4.10 (d, 2H, J=5.4Hz), 3.87 (s, 3H), 1.34 (t, 3H, J=7.1Hz)

(c) Synthesis of methyl 2-oxo-1,2,3,4-tetrahydrothieno[2,3-b]pyrazine-6-carboxylate Methyl 5-((2-ethoxy-2-oxoethyl)amino)-4-nitrothiophene-2-carboxylate (713.2 mg, 2.47 mmol) was dissolved in a mixture of AcOH/H$_2$O (14.3 mL, 20/3 v/v), and Fe (414.4 mg, 7.42 mmol) was added at room temperature. The mixture was refluxed at 70° C. for 24 hours and then cooled to room temperature. The reaction mixture was poured into ice water, and the resulting solid was filtered to obtain methyl 2-oxo-1,2,3,4-tetrahydrothieno[2,3-b]pyrazine-6-carboxylate (415.0 mg, 79%) as a green solid.

LC/MS ESI (+): 213 (M+1)

$^1$H-NMR (400MHz, DMSO-d$_6$): δ 10.26 (s, 1H), 7.20 (s, 1H), 7.06 (s, 1H), 3.87-3.89 (m, 2H), 3.69 (s, 3H)

(d) Synthesis of methyl 2-oxo-1,2-dihydrothieno[2,3-b]pyrazine-6-carboxylate

Methyl 2-oxo-1,2,3,4-tetrahydrothieno[2,3-b]pyrazine-6-carboxylate (415.0 mg, 1.96 mmol) was dissolved in anhydrous THF (20.0 mL), and MnO$_2$ (849.8 mg, 9.78 mmol) was added at room temperature, followed by stirring for 10 days. The reaction mixture was filtered through Celite and concentrated under reduced pressure to obtain methyl 2-oxo-1,2-dihydrothieno[2,3-b]pyrazine-6-carboxylate (220.5 mg, 54%) as a brown solid.

LC/MS ESI (+): 211 (M+1)

$^1$H-NMR (400MHz, DMSO-d$_6$): δ 12.76 (brs, 1H), 8.13 (brs, 1H), 7.62 (brs, 1H), 3.89 (s, 3H)

(e) Synthesis of methyl 2-chlorothieno[2,3-b]pyrazine-6-carboxylate

A mixture of methyl 2-oxo-1,2-dihydrothieno[2,3-b]pyrazine-6-carboxylate (220.5 mg, 1.05 mmol) and POCl$_3$ (5.9 mL, 62.94 mmol) was refluxed at 110° C. for 15 hours, and the reaction mixture was concentrated under reduced pressure. The residue was dissolved in EtOAc, washed with sat. NaHCO$_3$ aqueous solution and brine, dried over anhydrous Na$_2$SO$_4$, concentrated under reduced pressure to obtain methyl 2-chlorothieno[2,3-b]pyrazine-6-carboxylate (205.2 mg, 86%) as a brown solid.

LC/MS ESI (+): 229 (M+1)

$^1$H-NMR (400MHz, CDCl$_3$): δ 8.61 (s, 1H), 8.10 (s, 1H), 4.01 (s, 3H)

(f) Synthesis of 2-chlorothieno[2,3-b]pyrazine-6-carboxylic acid

Methyl 2-chlorothieno[2,3-b]pyrazine-6-carboxylate (298.0 mg, 1.30 mmol) was dissolved in a mixture of THF/EtOH (10.0 mL, 1/1 v/v), and 2.0 N NaOH aqueous solution (3.26 mL, 6.52 mmol) was added at room temperature, followed by stirring at room temperature for 7 hours. The reaction mixture was concentrated under reduced pressure, and the resulting residue was dissolved in water. 1 N HCl aqueous solution was added for acidification to pH 1-2. The resulting solid precipitate was filtered and dried under reduced pressure to obtain 2-chlorothieno[2,3-b]pyrazine-6-carboxylic acid (179.8 mg, 64%) as a brown solid.

LC/MS ESI (+): 215 (M+1)

$^1$H-NMR (400MHz, DMSO-d$_6$): δ 8.89 (s, 1H), 8.14 (s, 1H)

(g) Synthesis of 2-chloro-N-(3-chloro-5-(2-(3-isopropoxy-5-(trifluoromethoxy)phenyl)propan-2-yl)phenyl)thieno[2,3-b]pyrazine-6-carboxamide The synthesis procedure of Example 1 was repeated except for using 2-chlorothieno[2,3-b]pyrazine-6-carboxylic acid (179.8 mg, 0.84 mmol) to obtain 2-chloro-N-(3-chloro-5-(2-(3-isopropoxy-5-(trifluoromethoxy)phenyl)propan-2-yl)phenyl)thieno[2,3-b]pyrazine-6-carboxamide (295.4 mg, 60%) as a yellow solid.

LC/MS ESI (+): 584 (M+1)

$^1$H-NMR (400MHz, CDCl$_3$): 0.3-8.60 (s, 1H), 7.88 (s, 1H), 7.83 (s, 1H), 7.75 (m, 1H), 7.22 (m, 1H), 7.07 (m, 1H), 6.64-6.66 (m, 2H), 6.59 (m, 1H), 4.48 (m, 1H), 1.66 (s, 6H), 1.32 (d, 6H, J=6.0Hz)

(h) Synthesis of N-(3-chloro-5-(2-(3-isopropoxy-5-(trifluoromethoxy)phenyl)propan-2-yl)phenyl)-2-((4-methoxybenzyl)amino)thieno[2,3-b]pyrazine-6-carboxamide To a solution of 2-chloro-N-(3-chloro-5-(2-(3-isopropoxy-5-(trifluoromethoxy)phenyl)propan-2-yl)phenyl)thieno[2,3-b]pyrazine-6-carboxamide (295.4 mg, 0.51 mmol) in anhydrous 1,4-dioxane (10.0 mL), (4-methoxyphenyl)methaneamine (99.0 μL, 0.76 mmol), Pd(OAc)$_2$ (11.3 mg, 0.05 mmol), Xantphos (40.9 mg, 0.07 mmol) and Cs$_2$CO$_3$ (493.6 mg, 1.52 mmol) were added. The mixture was reacted in a microwave with 100 W, at 120° C. for 30 minutes and cooled to room temperature. Water was added, followed by extracting with EtOAc. The organic extract was washed with brine, dried over anhydrous Na$_2$SO$_4$, concentrated under reduced pressure. The residue was purified by flash column chromatography (silica gel, n-Hex:EtOAc=1:1) to obtain N-(3-chloro-5-(2-(3-isopropoxy-5-(trifluoromethoxy)phenyl)propan-2-yl)phenyl)-2-((4-methoxybenzyl)amino)thieno[2,3-b]pyrazine-6-carboxamide (112.5 mg, 33%) as a yellow solid.

LC/MS ESI (+): 685 (M+1)

$^1$H-NMR (400MHz, CDCl$_3$): δ 7.95 (s, 1H), 7.72-7.74 (m, 3H), 7.32 (d, 2H, J=8.3Hz), 7.21 (s, 1H), 7.02 (s, 1H), 6.90 (d, 2H, J=8.1Hz), 6.65 (s, 2H), 6.59 (s, 1H), 4.99 (m, 1H), 4.58 (d, 2H, J=5.4Hz), 4.48 (m, 1H), 3.81 (s, 3H), 1.65 (s, 6H), 1.32 (d, 6H, J=6.0Hz)

(i) Synthesis of 2-amino-N-(3-chloro-5-(2-(3-isopropoxy-5-(trifluoromethoxy)phenyl)propan-2-yl)phenyl)thieno[2,3-b]pyrazine-6-carboxamide N-(3-chloro-5-(2-(3-isopropoxy-5-(trifluoromethoxy)phenyl)propan-2-yl)phenyl)-2-((4-methoxybenzyl)amino)thieno[2,3-b]pyrazine-6-carboxamide (112.5 mg, 0.16 mmol) was dissolved in anhydrous $CH_2Cl_2$ (3.2 mL), and TFA (1.6 mL) was added at room temperature. The mixture was stirred at 40° C. for 19 hours and then concentrated under reduced pressure. The residue was basified with sat. $NaHCO_3$ aqueous solution (pH 9) and extracted with EtOAc. The organic extract was washed with brine, dried over anhydrous $Na_2SO_4$, concentrated under reduced pressure. The residue was purified by flash column chromatography (silica gel, n-Hex:EtOAc=1:2) to obtain 2-amino-N-(3-chloro-5-(2-(3-isopropoxy-5-(trifluoromethoxy)phenyl)propan-2-yl)phenyl)thieno[2,3-b]pyrazine-6-carboxamide (80.0 mg, 86%) as a yellow solid.

LC/MS ESI (+): 565 (M+1)

$^1$H-NMR (400MHz, $CDCl_3$): δ 8.06 (s, 1H), 7.72-7.73 (m, 2H), 7.67 (s, 1H), 7.23 (s, 1H), 7.03 (s, 1H), 7.65 (s, 2H), 6.59 (s, 1H), 4.75 (s, 2H), 4.47 (m, 1H), 1.66 (s, 6H), 1.32 (d, 6H, J=6.0Hz)

(j) Synthesis of 2-[bis(methylsulfonyl)amino]-N-[3-chloro-5-[1-[3-isopropoxy-5-(trifluoromethoxy)phenyl]-1-methyl-ethyl]phenyl]thieno[2,3-b]pyrazine-6-carboxamide 2-Amino-N-(3-chloro-5-(2-(3-isopropoxy-5-(trifluoromethoxy)phenyl)propan-2-yl)phenyl)thieno[2,3-b]pyrazine-6-carboxamide (20.0 mg, 0.04 mmol) was dissolved in anhydrous $CH_2Cl_2$ (0.7 mL), and DIPEA (12.3 μL, 0.07 mmol) and methanesulfonyl chloride (4.1 μL, 0.05 mmol) were added at room temperature. The mixture was stirred at room temperature for 16 hours, and water was added, followed by extracting with $CH_2Cl_2$. The organic extract was washed with brine, dried over anhydrous $Na_2SO_4$, concentrated under reduced pressure. The residue was purified by flash column chromatography (silica gel, n-Hex:EtOAc=1:1) to obtain 2-[bis(methylsulfonyl)amino]-N-[3-chloro-5-[1-[3-isopropoxy-5-(trifluoromethoxy)phenyl]-1-methyl-ethyl]phenyl]thieno[2,3-b]pyrazine-6-carboxamide (9.2 mg, 36%) as a yellow solid.

LC/MS ESI (+): 721 (M+1)

$^1$H-NMR (400MHz, $CDCl_3$): δ 8.61 (s, 1H), 7.94 (s, 1H), 7.92 (s, 1H), 7.73 (s, 1H), 7.21 (s, 1H), 7.06 (s, 1H), 6.64-6.65 (m, 2H), 6.59 (s, 1H), 4.48 (m, 1H), 3.64 (s, 6H), 1.65 (s, 6H), 1.32 (d, 6H, J=6.0Hz)

(k) Synthesis of N-(3-chloro-5-(2-(3-isopropoxy-5-(trifluoromethoxy)phenyl)propan-2-yl)phenyl)-2-(methylsulfonamido)thieno[2,3-b]pyrazine-6-carboxamide N-(3-chloro-5-(2-(3-isopropoxy-5-(trifluoromethoxy)phenyl)propan-2-yl)phenyl)-2-(N-(methylsulfonyl)methylsulfonamido)thieno[2,3-b]pyrazine-6-carboxamide (9.2 mg, 0.01 mmol) was dissolved in THF (0.2 mL), and 1.0 N KOH aqueous solution (38.2 μL, 0.04 mmol) was added at room temperature. The mixture was stirred at room temperature for 3 hours, and water was added, followed by extracting with $CH_2Cl_2$. The organic extract was washed with brine, dried over anhydrous $Na_2SO_4$, concentrated under reduced pressure. The residue was purified by flash column chromatography (silica gel, n-Hex:EtOAc=1:2) to obtain N-(3-chloro-5-(2-(3-isopropoxy-5-(trifluoromethoxy)phenyl)propan-2-yl)phenyl)-2-(methylsulfonamido)thieno[2,3-b]pyrazine-6-carboxamide (4.0 mg, 50%) as a white solid.

LC/MS ESI (+): 643 (M+1)

$^1$H-NMR (400MHz, DMSO-$d_6$): δ 11.40 (s, 1H), 10.64 (s, 1H), 8.41 (s, 1H), 8.32 (s, 1H), 7.91 (s, 1H), 7.55 (s, 1H), 7.08 (s, 1H), 6.77 (s, 1H), 6.73 (s, 1H), 6.71 (s, 1H), 4.63 (m, 1H), 3.39 (s, 3H), 1.64 (s, 6H), 1.23 (d, 6H, J=5.5Hz)

Example 152

Synthesis of N-(3-(2-(4-bromophenyl)propan-2-yl)-5-chlorophenyl)-5-(methylsulfonamido)benzo[b]thiophene-2-carboxamide

(a) Synthesis of 1-(2-(4-bromophenyl)propan-2-yl)-3-chloro-5-nitrobenzene 1-(2-Bromopropan-2-yl)-3-chloro-5-nitrobenzene (Example 166-b) (200.0 mg, 0.72 mmol) and bromobenzene (1.1 mL, 10.77 mmol) were dissolved in 1,2-dichloroethane (7.0 mL), and $AlCl_3$ (287.2 mg, 2.15 mmol) was added at room temperature. The mixture was stirred at room temperature for 12 hours, and water was added, followed by extracting with $CH_2Cl_2$. The organic extract was washed with brine, dried over anhydrous $Na_2SO_4$, concentrated under reduced pressure. The residue was purified by flash column chromatography (silica gel, n-Hex:EtOAc=9:1) to obtain 1-(2-(4-bromophenyl)propan-2-yl)-3-chloro-5-nitrobenzene (255.4 mg, 100%) as a yellow solid.

$^1$H-NMR (400MHz, $CDCl_3$): δ 8.06 (s, 1H), 8.00 (s, 1H), 7.46 (s, 1H), 7.44 (d, 2H, J=8.6Hz), 7.07 (d, 2H, J=8.6Hz), 1.70 (s, 6H)

(b) Synthesis of 3-(2-(4-bromophenyl)propan-2-yl)-5-chloroaniline

The synthesis procedure of Intermediate 40 was repeated except for using 1-(2-(4-Bromophenyl)propan-2-yl)-3-chloro-5-nitrobenzene (84.2 mg, 0.24 mmol) to obtain 3-(2-(4-bromophenyl)propan-2-yl)-5-chloroaniline (67.1 mg, 87%).

LC/MS ESI (+): 324 (M+1)

$^1$H-NMR (400MHz, $CDCl_3$): δ 7.38 (d, 1H, J=8.6Hz), 7.09 (d, 1H, J=8.6Hz), 6.60 (m, 1H), 6.51 (m, 1H), 6.32 (m, 1H), 3.65 (s, 2H), 1.59 (s, 6H)

(c) Synthesis of N-(3-(2-(4-bromophenyl)propan-2-yl)-5-chlorophenyl)-5-(methylsulfonamido)benzo[b]thiophene-2-carboxamide The synthesis procedure of Example 1 was repeated except for using 3-(2-(4-bromophenyl)propan-2-yl)-5-chloroaniline (67.1 mg, 0.21 mmol) to obtain N-(3-(2-(4-bromophenyl)propan-2-yl)-5-chlorophenyl)-5-(methylsulfonamido)benzo[b]thiophene-2-carboxamide (40.4 mg, 34%).

LC/MS ESI (+): 577 (M+1)

$^1$H-NMR (400MHz, DMSO-$d_6$): δ 10.53 (s, 1H), 9.87 (s, 1H), 8.27 (s, 1H), 8.02 (d, 1H, J=8.7Hz), 7.89 (s, 1H), 7.79 (s, 1H), 7.49-7.51 (m, 3H), 7.36 (d, 1H, J=8.7Hz), 7.21 (d, 2H, J=8.0Hz), 7.03 (s, 1H), 3.01 (s, 3H), 1.64 (s, 6H)

Through the synthetic method according to Example 152, compounds from Example 153 to Example 163 were synthesized, and the data of each example are as follows.

TABLE 8

| Ex. | Compound | Analysis data |
|---|---|---|
| 153 | N-(3-chloro-5-(2-(3,4-dimethoxyphenyl)propan-2-yl)phenyl)-5-(methylsulfonamido)benzo[b]thiophene-2-carboxamide | LC/MS ESI (+): 559 (M + 1)<br>$^1$H-NMR(400 MHz, DMSO-$d_6$): δ 10.55 (s, 1H), 9.89 (s, 1H), 8.28 (s, 1H), 8.02 (d, 1H, J = 9.0 Hz), 7.87 (s, 1H), 7.78 (s, 1H), 7.51 (s, 1H), 7.36 (d, 1H, J = 9.0 Hz), 7.00 (s, 1H), 6.76~6.87 (m, 3H), 3.72 (s, 3H), 3.69 (s, 3H), 3.01 (s, 3H), 1.63 (s, 6H) |
| 154 | N-(3-chloro-5-(2-(2,4-dimethoxyphenyl)propan-2-yl)phenyl)-5-(methylsulfonamido)benzo[b]thiophene-2-carboxamide | LC/MS ESI (+): 559 (M + 1)<br>$^1$H-NMR (400 MHz, DMSO-$d_6$): δ 10.50 (s, 1H), 9.88 (s, 1H), 8.29 (s, 1H), 8.02 (d, 1H, J = 8.7 Hz), 7.81 (s, 1H), 7.78 (s, 1H), 7.39 (s, 1H), 7.33~7.36 (m, 2H), 6.85 (t, 1H, J = 1.7 Hz), 6.55 (dd, 1H, J = 8.6, 2.5 Hz), 6.49 (d, 1H, J = 2.5 Hz), 3.75 (s, 3H), 3.40 (s, 3H), 3.01 (s, 3H), 1.58 (s, 6H) |
| 155 | N-(3-chloro-5-(2-(4-methoxyphenyl)propan-2-yl)phenyl)-5-(methylsulfonamido)benzo[b]thiophene-2-carboxamide | LC/MS ESI (+): 529 (M + 1)<br>$^1$H-NMR (400 MHz, DMSO-$d_6$): δ 10.55 (s, 1H), 9.87 (s, 1H), 8.29 (s, 1H), 8.02 (d, 1H, J = 8.7 Hz), 7.86 (s, 1H), 7.78 (s, 1H), 7.51 (s, 1H), 7.35 (d, 1H, J = 8.7 Hz), 7.16 (d, 2H, J = 8.8 Hz), 6.99 (s, 1H), 6.87 (d, 2H, J = 8.8 Hz), 3.72 (s, 3H), 3.01 (s, 3H), 1.62 (s, 6H) |
| 156 | N-(3-chloro-5-(2-(2,5-dimethoxyphenyl)propan-2-yl)phenyl)-5-(methylsulfonamido)benzo[b]thiophene-2-carboxamide | LC/MS ESI (+): 559 (M + 1)<br>$^1$H-NMR (400 MHz, DMSO-$d_6$): δ 10.51 (s, 1H), 9.89 (s, 1H), 8.30 (s, 1H), 8.03 (d, 1H, J = 8.7 Hz), 7.85 (s, 1H), 7.80 (s, 1H), 7.39 (s, 1H), 7.36 (d, 1H, J = 8.7 Hz), 7.00 (s, 1H), 6.84~6.90 (m, 3H), 3.77 (s, 3H), 3.31 (s, 3H), 3.02 (s, 3H), 1.61 (s, 6H) |
| 157 | N-(3-chloro-5-(2-(4-(methylthio)phenyl)propan-2-yl)phenyl)-5-(methylsulfonamido)benzo[b]thiophene-2-carboxamide | LC/MS ESI (+): 545 (M + 1)<br>$^1$H-NMR(400 MHz, DMSO-$d_6$): δ 10.54 (s, 1H), 9.87 (s, 1H), 8.28 (s, 1H), 8.02 (d, 1H, J = 8.7 Hz), 7.88 (s, 1H), 7.79 (s, 1H), 7.51 (s, 1H), 7.36 (d, 1H, J = 8.6 Hz), 7.17~7.22 (m, 4H), 7.00 (s, 1H), 3.01 (s, 3H), 2.45 (s, 3H), 1.63 (s, 6H) |
| 158 | W-(3-chloro-5-(2-(4-chlorophenyl)propan-2-yl)phenyl)-5-(methylsulfonamido)benzo[b]thiophene-2-carboxamide | LC/MS ESI (+): 533 (M + 1)<br>$^1$H-NMR(400 MHz, DMSO-$d_6$): δ 10.53 (s, 1H), 9.87 (s, 1H), 8.27 (s, 1H), 8.02 (d, 1H, J = 8.7 Hz), 7.88 (s, 1H), 7.79 (s, 1H), 7.49 (s, 1H), 7.34~7.38 (m, 3H), 7.27 (d, 2H, J = 8.0 Hz), 7.03 (s, 1H), 3.01 (s, 3H), 1.64 (s, 6H) |
| 159 | N-(3-chloro-5-(2-(4-(1-methyl-1H-pyrazol-5-yl)phenyl)propan-2-yl)phenyl)-5-(methylsulfonamido)benzo[b]thiophene-2-carboxamide | LC/MS ESI (+): 579 (M + 1)<br>$^1$H-NMR(400 MHz, DMSO-$d_6$): δ 10.57 (s, 1H), 9.88 (brs, 1H), 8.29 (s, 1H), 8.02 (d, 1H, J = 8.8 Hz), 7.90 (s, 1H), 7.79 (d, 1H, J = 1.6 Hz), 7.58 (s, 1H), 7.49 (d, 2H, J = 8.3 Hz), 7.48 (s, 1H), 7.34~7.38 (m, 3H), 7.08 (s, 1H), 6.39 (d, 1H, J = 1.7 Hz), 3.85 (s, 3H), 3.01 (s, 3H), 1.70 (s, 6H) |
| 160 | N-(3-chloro-5-(2-(4-(methylsulfinyl)phenyl)propan-2-yl)phenyl)-5-(methylsulfonamido)benzo[b]thiophene-2-carboxamide | LC/MS ESI (+): 561 (M + 1)<br>$^1$H-NMR(400 MHz, DMSO-$d_6$): δ 10.55 (s, 1H), 9.87 (s, 1H), 8.28 (s, 1H), 8.01 (d, 1H, J = 8.7 Hz), 7.90 (s, 1H), 7.78 (s, 1H), 7.64 (d, 2H, J = 8.0 Hz), 7.55 (s, 1H), 7.47 (d, 2H, J = 8.0 Hz), 7.36 (d, 1H, J = 8.7 Hz), 7.06 (s, 1H), 3.02 (s, 3H), 2.75 (s, 3H), 1.70 (s, 6H) |
| 161 | N-(3-chloro-5-(2-(4-(methylsulfonyl)phenyl)propan-2-yl)phenyl)-5-(methylsulfonamido)benzo[b]thiophene-2-carboxamide | LC/MS ESI (+): 577 (M + 1)<br>$^1$H-NMR (400 MHz, DMSO-$d_6$): δ 10.56 (s, 1H), 9.87 (brs, 1H), 8.27 (s, 1H), 8.01 (d, 1H, J = 8.7 Hz), 7.91 (s, 1H), 7.87 (d, 2H, J = 7.9 Hz), 7.78 (s, 1H), 7.51~7.54 (m, 3H), 7.35 (d, 1H, J = 8.8 Hz), 7.06 (s, 1H), 3.20 (s, 3H), 3.00 (s, 3H), 1.69 (s, 6H) |
| 162 | N-(3-chloro-5-(2-(3,4-difluorophenyl)propan-2-yl)phenyl)-5-(methylsulfonamido)benzo[b]thiophene-2-carboxamide | LC/MS ESI (+): 535 (M + 1)<br>$^1$H-NMR(400 MHz, DMSO-$d_6$): δ 10.54 (s, 1H), 9.88 (s, 1H), 8.28 (s, 1H), 8.02 (d, 1H, J = 8.7 Hz), 7.89 (s, 1H), 7.80 (s, 1H), 7.48 (s, 1H), 7.34~7.37 (m, 3H), 7.05~7.06 (m, 2H), 3.01 (s, 3H), 1.65 (s, 6H) |
| 163 | N-(3-chloro-5-(2-(4-chlorophenyl)propan-2-yl)phenyl)-6-fluoro-5-(N-methylmethylsulfonamido)benzo[b]thiophene-2-carboxamide | LC/MS ESI (+): 565 (M + 1)<br>$^1$H-NMR(400 MHz, DMSO-$d_6$): δ 10.66 (s, 1H), 8.30 (s, 1H), 8.18 (d, 1H, J = 7.4 Hz), 8.14 (d, 1H, J = 10.5 Hz), 7.87 (s, 1H), 7.49 (s, 1H), 7.37 (d, 2H, J = 8.7 Hz), 7.27 (d, 2H, J = 8.7 Hz), 7.04 (s, 1H), 3.28 (s, 3H), 3.12 (s, 3H), 1.64 (s, 6H) |

Example 164

Synthesis of N-(3-chloro-5-(2-(piperidin-1-yl)propan-2-yl)phenyl)-5-(methylsulfonamido)benzo[b]thiophene-2-carboxamide

(a) Synthesis of 1-(2-(3-chloro-5-nitrophenyl)propan-2-yl)piperidine 1-(2-Bromopropan-2-yl)-3-chloro-5-nitrobenzene (Example 166-b) (30.0 mg, 0.11 mmol) was dissolved in piperidine (183.0 mg, 2.14 mmol), followed by stirring at room temperature for 2 days. The reaction mixture was extracted with $CH_2Cl_2$, and the organic extract was washed with brine, dried over anhydrous $Na_2SO_4$, concentrated under reduced pressure. The residue was purified by flash column chromatography (silica gel, n-Hex:EtOAc=9:1) to obtain 1-(2-(3-chloro-5-nitrophenyl)propan-2-yl)piperidine (35.0 mg, quant.) as a colorless liquid.

$^1$H-NMR (400MHz, $CDCl_3$): δ 8.31 (s, 1H), 8.20 (s, 1H), 7.90 (s, 1H), 2.37 (t, 4H, J=4.3Hz), 1.55 (t, 4H, J=5.2Hz), 1.42-1.46 (m, 2H), 1.33 (s, 6H)

(b) Synthesis of 3-chloro-5-(2-(piperidin-1-yl)propan-2-yl)aniline

The synthesis procedure of Intermediate 40 was repeated except for using 1-(2-(3-chloro-5-nitrophenyl)propan-2-yl)piperidine (35.0 mg, 0.11 mmol) to obtain 3-chloro-5-(2-(piperidin-1-yl)propan-2-yl)aniline (25.0 mg, 90%).

LC/MS ESI (+): 253 (M+1)

$^1$H-NMR (400MHz, $CDCl_3$): δ 6.90 (s, 1H), 6.79 (s, 1H), 6.52 (s, 1H), 3.67 (brs, 2H), 2.38 (brs, 4H), 1.48-1.54 (m, 4H), 1.40-1.43 (m, 2H), 1.25 (s, 6H)

(c) Synthesis of N-(3-chloro-5-(2-(piperidin-1-yl)propan-2-yl)phenyl)-5-(methylsulfonamido)benzo[b]thiophene-2-carboxamide The synthesis procedure of Example 1 was repeated except for using 3-chloro-5-(2-(piperidin-1-yl)propan-2-yl)aniline (25.0 mg, 0.10 mmol) to obtain N-(3-chloro-5-(2-(piperidin-1-yl)propan-2-yl)phenyl)-5-(methylsulfonamido)benzo[b]thiophene-2-carboxamide (27.0 mg, 53%).

LC/MS ESI (+): 506 (M+1)

$^1$H-NMR (400MHz, DMSO-$d_6$): δ 10.53 (s, 1H), 9.83 (s, 1H), 8.28 (s, 1H), 7.97 (d, 1H, J=8.7Hz), 7.82 (s, 1H), 7.73-7.75 (m, 2H), 7.30 (d, 1H, J=8.7Hz), 7.20 (s, 1H), 2.96 (s, 3H), 2.31 (brs, 4H), 1.44 (brs, 4H), 1.33 (brs, 2H), 1.21 (s, 6H)

Through the synthetic method according to Example 164, a compound of Example 165 was synthesized, and the data is as follows.

Example 166

Synthesis of N-(3-(2-(1H-pyrrol-2-yl)propan-2-yl)-5-chlorophenyl)-5-(methylsulfonamido)benzo[b]thiophene-2-carboxamide

(a) Synthesis of 1-chloro-3-nitro-5-(prop-1-en-2-yl)benzene

1-Bromo-3-chloro-5-nitrobenzene (5.0 g, 21.15 mmol), 4,4,5,5-tetramethyl-2-(prop-1-en-2-yl)-1,3,2-dioxaborolan (4.0 mL, 21.15 mmol), $Pd(PPh_3)_4$ (1.2 g, 1.06 mmol) and $Na_2CO_3$ (6.7 g, 63.44 mmol) were added to a mixture of $DME/H_2O$ (105.0 mL, 2/1 v/v), followed by refluxing at 80° C. for 7 hours. The reaction mixture was cooled to room temperature and then extracted with EtOAc. The organic extract was washed with brine, dried over anhydrous $Na_2SO_4$, concentrated under reduced pressure. The residue was purified by flash column chromatography (silica gel, n-Hex:EtOAc=9:1) to obtain a mixture of 1-chloro-3-nitro-5-(prop-1-en-2-yl)benzene and 1-bromo-3-chloro-5-nitrobenzene (4.2 g) as a yellow oil.

$^1$H-NMR (400MHz, $CDCl_3$): δ 8.20 (m, 1H), 8.11 (m, 1H), 7.74 (m, 1H), 5.52 (s, 1H), 5.30 (m, 1H), 2.18-2.19 (m, 3H)

(b) Synthesis of 1-(2-bromopropan-2-yl)-3-chloro-5-nitrobenzene

A mixture of 1-chloro-3-nitro-5-(prop-1-en-2-yl)benzene and 1-bromo-3-chloro-5-nitrobenzene (4.2 g) was dissolved in anhydrous $Et_2O$ (50.0 mL), and 33% solution of HBr in AcOH (25.9 mL, 147.76 mmol) was added at 0° C., followed by stirring at room temperature for 12 hours. A large amount of $Et_2O$ was added, and an organic layer was washed with $H_2O$, sat. $NaHCO_3$ aqueous solution, and brine, dried over anhydrous $Na_2SO_4$, concentrated under reduced pressure. The residue was purified by flash column chromatography (silica gel, n-Hex:EtOAc=20:1) to obtain 1-(2-bromopropan-2-yl)-3-chloro-5-nitrobenzene (3.0 g, 2 step yield: 51%) as a yellow oil.

$^1$H-NMR (400MHz, $CDCl_3$): δ 8.34 (m, 1H), 8.14 (m, 1H), 7.93 (m, 1H), 2.21 (s, 6H)

(c) Synthesis of 2-(2-(3-chloro-5-nitrophenyl)propan-2-yl)-1H-pyrrole and 3-(2-(3-chloro-5-nitrophenyl)propan-2-yl)-1H-pyrrole 1-(2-Bromopropan-2-yl)-3-chloro-5-nitrobenzene (150 mg, 0.43 mmol) and pyrrole (1.1 mL, 16.17 mmol) were dissolved in 1,2-dichloroethane (5.4 mL), and $AlCl_3$ (215.6 mg, 1.62 mmol) was added at room temperature. The mixture was heated at 30° C. for 4 days, and water was added. The resulting reaction mixture was filtered through Celite and extracted with $CH_2Cl_2$. The organic extract was washed with brine, dried over anhydrous $Na_2SO_4$, concen-

TABLE 9

| Ex. | Compound | Analysis data |
| --- | --- | --- |
| 165 | 6-chloro-N-(3-chloro-5-(2-(piperidin-1-yl)propan-2-yl)phenyl)-5-(methylsulfonamido)benzo[b]thiophene-2-carboxamide | LC/MS ESI (+): 540 (M + 1)<br>$^1$H-NMR (400 MHz, DMSO-$d_6$): δ 10.60 (s, 1H), 9.58 (brs, 1H), 8.26~8.28 (m, 2H), 7.97 (s, 1H), 7.80 (s, 1H), 7.73 (s, 1H), 7.21 (s, 1H), 2.98 (s, 3H), 2.27~2.34 (m, 4H), 1.39~1.46 (m, 4H), 1.32~1.34 (m, 2H), 1.21 (s, 6H) | trated under reduced pressure. The residue was purified by flash column chromatography (silica gel, n-Hex:EtOAc=9:1) to obtain 2-(2-(3-chloro-5-nitrophenyl)propan-2-yl)-1H-pyrrole (166-c-1) (37.2 mg, 33%) as a yellow oil and 3-(2-(3-chloro-5-nitrophenyl)propan-2-yl)-1H-pyrrole (166-c-2) (20.0 mg, 18%) as a yellow solid.

(166-c-1) 2-(2-(3-Chloro-5-nitrophenyl)propan-2-yl)-1H-pyrrole

LC/MS ESI (+): 265 (M+1)

$^1$H-NMR (400MHz, CDCl$_3$): δ 8.05, (m, 1H), 8.01 (m, 1H), 7.74 (brs, 1H), 7.47 (m, 1H), 6.73 (m, 1H), 6.18 (m, 1H), 6.13 (m, 1H), 1.72 (s, 6H)

(166-c-2) 3-(2-(3-Chloro-5-nitrophenyl)propan-2-yl)-1H-pyrrole

LC/MS ESI (+): 265 (M+1)

$^1$H-NMR (400MHz, CDCl$_3$): δ 8.08-8.13 (m, 2H), 8.01 (m, 1H), 7.61 (m, 1H), 6.78 (m, 1H), 6.63 (m, 1H), 5.99 (m, 1H), 1.67 (s, 6H)

(d) Synthesis of 3-(2-(1H-pyrrol-2-yl)propan-2-yl)-5-chloroaniline

The synthesis procedure of Intermediate 40 was repeated except for using 2-(2-(3-chloro-5-nitrophenyl)propan-2-yl)-1H-pyrrole (44.2 mg, 0.17 mmol) to obtain 3-(2-(1H-pyrrol-2-yl)propan-2-yl)-5-chloroaniline (35.0 mg, 89%).

LC/MS ESI (+): 235 (M+1)

$^1$H-NMR (400MHz, CDCl$_3$): δ 7.69 (brs, 1H), 6.65-6.67 (m, 2H), 6.51 (m, 1H), 6.34 (m, 1H), 6.14 (m, 1H), 6.09 (m, 1H), 3.65 (s, 2H), 1.61 (s, 6H)

(e) Synthesis of N-(3-(2-(1H-pyrrol-2-yl)propan-2-yl)-5-chlorophenyl)-5-(methylsulfonamido)benzo[b]thiophene-2-carboxamide The synthesis procedure of Example 1 was repeated except for using 3-(2-(1H-pyrrol-2-yl)propan-2-yl)-5-chloroaniline (35.0 mg, 0.15 mmol) to obtain N-(3-(2-(1H-pyrrol-2-yl)propan-2-yl)-5-chlorophenyl)-5-(methylsulfonamido)benzo[b]thiophene-2-carboxamide (35.1 mg, 56%).

LC/MS ESI (+): 488 (M+1)

$^1$H-NMR (400MHz, DMSO-d$_6$): δ 10.57 (s, 1H), 10.48 (s, 1H), 9.89 (s, 1H), 8.30 (s, 1H), 8.02 (d, 1H, J=8.7Hz), 7.84 (m, 1H), 7.80 (d, 1H, J=2.0Hz), 7.53 (m, 1H), 7.36 (dd, 1H, J=8.7, 2.1Hz), 6.89 (m, 1H), 6.63 (m, 1H), 5.91-5.94 (m, 2H), 3.01 (s, 3H), 1.61 (s, 6H)

Example 167

Synthesis of N-(3-(2-(1H-pyrrol-3-yl)propan-2-yl)-5-chlorophenyl)-5-(methylsulfonamido)benzo[b]thiophene-2-carboxamide (a) Synthesis of 3-(2-(1H-pyrrol-3-yl)propan-2-yl)-5-chloroaniline The synthesis procedure of Intermediate 13-c was repeated except for using 3-(2-(3-Chloro-5-nitrophenyl)propan-2-yl)-1H-pyrrole (Example 166-c-2) (20.0 mg, 0.08 mmol) to obtain 3-(2-(1H-pyrrol-3-yl)propan-2-yl)-5-chloroaniline (14.3 mg, 81%).

LC/MS ESI (+): 235 (M+1)

$^1$H-NMR (400MHz, CDCl$_3$): δ 8.00 (brs, 1H), 6.72-6.75 (m, 2H), 6.58 (m, 1H), 6.47-6.50 (m, 2H), 6.04 (m, 1H), 3.62 (s, 2H), 1.58 (s, 6H)

(b) Synthesis of N-(3-(2-(1H-pyrrol-3-yl)propan-2-yl)-5-chlorophenyl)-5-(methylsulfonamido)benzo[b]thiophene-2-carboxamide The synthesis procedure of Example 1 was repeated except for using 3-(2-(1H-pyrrol-3-yl)propan-2-yl)-5-chloroaniline (14.3 mg, 0.06 mmol) to obtain N-(3-(2-(1H-pyrrol-3-yl)propan-2-yl)-5-chlorophenyl)-5-(methylsulfonamido)benzo[b]thiophene-2-carboxamide (13.7 mg, 46%).

LC/MS ESI (+): 488 (M+1)

$^1$H-NMR (400MHz, DMSO-d$_6$): δ 10.54-10.55 (m, 2H), 9.89 (s, 1H), 8.31 (s, 1H), 8.02 (d, 1H, J=8.7Hz), 7.81 (m, 1H), 7.79 (d, 1H, J=2.0Hz), 7.62 (m, 1H), 7.36 (dd, 1H, J=8.7, 2.1Hz), 7.01 (m, 1H), 6.67 (m, 1H), 6.59 (m, 1H), 5.86 (m, 1H), 3.02 (s, 3H), 1.57 (s, 6H)

Through the synthetic method according to Examples 166 and 167, compounds from Example 168 to Example 185 were synthesized, and the data of each example are as follows.

TABLE 10

| Ex. | Compound | Analysis data |
|-----|----------|---------------|
| 168 | N-(3-chloro-5-(2-(1-methyl-1H-pyrrol-3-yl)propan-2-yl)phenyl)-5-(methylsulfonamido)benzo[b]thiophene-2-carboxamide | LC/MS ESI (+): 502 (M + 1) <br> $^1$H-NMR(400 MHz, DMSO-d$_6$): δ 10.54 (s, 1H), 9.89 (s, 1H), 8.31 (s, 1H), 8.02 (d, 1H, J = 8.8 Hz), 7.83 (s, 1H), 7.80 (s, 1H), 7.60 (s, 1H), 7.36 (d, 1H, J = 8.8 Hz), 7.02 (s, 1H), 6.60 (s, 1H), 6.53 (s, 1H), 5.81 (s, 1H), 3.56 (s, 3H), 3.02 (s, 3H), 1.55 (s, 6H) |
| 169 | N-(3-chloro-5-(2-(1-methyl-1H-pyrrol-2-yl)propan-2-yl)phenyl)-5-(methylsulfonamido)benzo[b]thiophene-2-carboxamide | LC/MS ESI (+): 502 (M + 1) <br> $^1$H-NMR(400 MHz, DMSO-d$_6$): δ 10.59 (s, 1H), 9.87 (s, 1H), 8.29 (s, 1H), 8.02 (d, 1H, J = 8.7 Hz), 7.88 (s, 1H), 7.79 (s, 1H), 7.49 (s, 1H), 7.36 (d, 1H, J = 8.7 Hz), 6.88 (s, 1H), 6.61 (s, 1H), 6.10 (s, 1H), 5.94 (s, 1H), 3.09 (s, 3H), 3.01 (s, 3H), 1.61 (s, 6H) |
| 170 | N-(3-chloro-5-(2-(thiophen-2-yl)propan-2-yl)phenyl)-5-(methylsulfonamido)benzo[b]thiophene-2-carboxamide | LC/MS ESI (+): 505 (M + 1) <br> $^1$H-NMR(400 MHz, DMSO-d$_6$): δ 10.57 (s, 1H), 9.86 (s, 1H), 8.30 (s, 1H), 8.02 (d, 1H, J = 8.7 Hz), 7.88 (s, 1H), 7.80 (s, 1H), 7.65 (s, 1H), 7.35~7.40 (m, 2H), 7.08 (s, 1H), 6.97~6.99 (m, 2H), 3.02 (s, 3H), 1.74 (s, 6H) |
| 171 | N-(3-chloro-5-(2-(thiophen-3-yl)propan-2-yl)phenyl)-5-(methylsulfonamido)benzo[b]thiophene-2-carboxamide | LC/MS ESI (+): 505 (M + 1) <br> $^1$H-NMR(400 MHz, DMSO-d$_6$): δ 10.55 (s, 1H), 9.87 (brs, 1H), 8.29 (s, 1H), 8.02 (d, 1H, J = 8.7 Hz), 7.85 (s, 1H), 7.79 (m, 1H), 7.57 (s, 1H), 7.46 (dd, 1H, J = 4.9, 2.9 Hz), 7.36 (dd, 1H, J = 8.8, 1.5 Hz), 7.31 (m, 1H), 6.99 (s, 1H), 6.90 (d, 1H, J = 4.9 Hz), 3.01 (s, 3H), 1.65 (s, 6H) |

TABLE 10-continued

| Ex. | Compound | Analysis data |
|---|---|---|
| 172 | 6-chloro-N-(3-chloro-5-(2-(4-chlorophenyl)propan-2-yl)phenyl)-5-(methylsulfonamido)benzo[b]thiophene-2-carboxamide | LC/MS ESI (+): 567 (M + 1)<br>$^1$H-NMR (400 MHz, DMSO-d$_6$): δ 10.63 (s, 1H), 9.62 (s, 1H), 8.35 (s, 1H), 8.29 (s, 1H), 8.03 (s, 1H), 7.87 (s, 1H), 7.48 (s, 1H), 7.37 (d, 2H, J = 8.6 Hz), 7.27(d, 2H, J = 8.6 Hz), 7.03 (s, 1H), 3.06 (s, 3H), 1.64 (s, 6H) |
| 173 | 6-bromo-N-(3-chloro-5-(2-(4-chlorophenyl)propan-2-yl)phenyl)-5-(methylsulfonamido)benzo[b]thiophene-2-carboxamide | LC/MS ESI (+): 611 (M + 1)<br>$^1$H-NMR(400 MHz, DMSO-d$_6$): δ 10.63 (s, 1H), 9.55 (s, 1H), 8.50 (s, 1H), 8.27 (s, 1H), 8.02 (s, 1H), 7.87 (s, 1H), 7.48 (s, 1H), 7.37 (d, 2H, J = 8.6 Hz), 7.27(d, 2H, J = 8.6 Hz), 7.04 (s, 1H), 3.07 (s, 3H), 1.64 (s, 6H) |
| 174 | N-(3-chloro-5-(2-(5-chlorothiophen-2-yl)propan-2-yl)phenyl)-5-(methylsulfonamido)benzo[b]thiophene-2-carboxamide | LC/MS ESI(+): 539 (M + 1)<br>$^1$H-NMR (400 MHz, DMSO-d$_6$): δ 10.58 (s, m), 9.90 (s, 1H), 8.29 (s, 1H), 8.01 (d, 1H, J = 8.7 Hz), 7.90 (s, 1H), 7.78 (s, 1H), 7.63 (s, 1H), 7.34 (d, 1H, J = 8.7 Hz), 7.12 (s, 1H), 6.98 (d, 1H, J = 3.9 Hz), 6.85 (d, 1H, J = 3.9 Hz), 3.00 (s, 3H), 1.70 (s, 6H) |
| 175 | 6-chloro-N-(3-chloro-5-(2-(5-chlorothiophen-2-yl)propan-2-yl)phenyl)-5-(methylsulfonamido)benzo[b]thiophene-2-carboxamide | LC/MS ESI (+): 573 (M + 1)<br>$^1$H-NMR (400 MHz, DMSO-d$_6$): δ 10.63 (s, 1H), 9.69 (s, 1H), 8.26 (s, 2H), 7.98 (s, 1H), 7.90 (s, 1H), 7.62 (s, 1H), 7.13 (s, 1H), 6.98 (d, 1H, J = 3.8 Hz), 6.85 (d, 1H, J = 3.8 Hz), 2.98 (s, 3H), 1.70 (s, 6H) |
| 176 | N-(3-chloro-5-(2-(2-methoxythiophen-3-yl)propan-2-yl)phenyl)-5-(methylsulfonamido)benzo[b]thiophene-2-carboxamide | LC/MS ESI (+): 535 (M + 1)<br>$^1$H-NMR(400 MHz, DMSO-d$_6$): δ 10.55 (s, 1H), 9.89 (brs, 1H), 8.30 (s, 1H), 8.01 (d, 1H, J = 8.7 Hz), 7.84 (s, 1H), 7.79 (s, 1H), 7.55 (s, 1H), 7.35 (dd, 1H, J = 8.7, 1.5 Hz), 6.97 (s, 1H), 6.78~6.82 (m, 2H), 3.63 (s, 3H), 3.01 (s, 3H), 1.62 (s, 6H) |
| 177 | N-(3-chloro-5-(2-(5-methoxythiophen-2-yl)propan-2-yl)phenyl)-5-(methylsulfonamido)benzo[b]thiophene-2-carboxamide | LC/MS ESI (+): 535 (M + 1)<br>$^1$H-NMR(400 MHz, DMSO-d$_6$): δ 10.57 (s, 1H), 9.88 (brs, 1H), 8.29 (s, 1H), 8.00 (d, 1H, J = 8.8 Hz), 7.87 (s, 1H), 7.78 (s, 1H), 7.62 (s, 1H), 7.34 (dd, 1H, J = 8.7, 2.1 Hz), 7.06 (s, 1H), 6.57 (d, 1H, J = 3.9 Hz), 6.10 (d, 1H, J = 3.9 Hz), 3.78 (s, 3H), 3.00 (s, 3H), 1.65 (s, 6H) |
| 178 | N-(3-chloro-5-(2-(5-methylthiophen-2-yl)propan-2-yl)phenyl)-5-(methylsulfonamido)benzo[b]thiophene-2-carboxamide | LC/MS ESI (+): 519 (M + 1)<br>$^1$H-NMR(400 MHz, DMSO-d$_6$): δ 10.57 (s, 1H), 9.89 (brs, 1H), 8.30 (s, 1H), 8.02 (d, 1H, J = 8.7 Hz), 7.88 (m, 1H), 7.80 (m, 1H), 7.64 (m, 1H), 7.36 (dd, 1H, J = 8.7, 2.1 Hz), 7.07 (m, 1H), 6.74 (d, 1H, J = 3.4 Hz), 6.63 (m, 1H), 3.01 (s, 3H), 2.37 (s, 3H), 1.69 (s, 6H) |
| 179 | 6-chloro-N-(3-chloro-5-(2-(5-methylthiophen-2-yl)propan-2-yl)phenyl)-5-(methylsulfonamido)benzo[b]thiophene-2-carboxamide | LC/MS ESI (+): 553 (M + 1)<br>$^1$H-NMR(400 MHz, DMSO-d$_6$): δ 10.66 (s, 1H), 9.64 (s, 1H), 8.34 (s, 1H), 8.31 (s, 1H), 8.03 (s, 1H), 7.87 (m, 1H), 7.62 (m, 1H), 7.08 (m, 1H), 6.74 (d, 1H, J = 3.5 Hz), 6.63 (m, 1H), 3.05 (s, 3H), 2.37 (s, 3H), 1.69 (s, 6H) |
| 180 | 6-chloro-N-(3-chloro-5-(2-(5-isopropylthiophen-2-yl)propan-2-yl)phenyl)-5-(methylsulfonamido)benzo[b]thiophene-2-carboxamide | LC/MS ESI (+): 581 (M + 1)<br>$^1$H-NMR(400 MHz, DMSO-d$_6$): δ 10.69 (s, 1H), 9.64 (s, 1H), 8.36 (s, 1H), 8.32 (s, 1H), 8.05 (s, 1H), 7.88 (m, 1H), 7.64 (m, 1H), 7.09 (m, 1H), 6.74 (d, 1H, J = 3.5 Hz), 6.67 (dd, 1H, J = 3.5, 0.8 Hz), 3.02~3.09 (m, 4H), 1.70 (s, 6H), 1.22 (d, 6H, J = 6.8 Hz) |
| 181 | 6-chloro-N-(3-chloro-5-(2-(4-methylthiophen-2-yl)propan-2-yl)phenyl)-5-(methylsulfonamido)benzo[b]thiophene-2-carboxamide | LC/MS ESI (+): 553 (M + 1)<br>$^1$H-NMR(400 MHz, DMSO-d$_6$): δ 10.66 (s, 1H), 9.64 (s, 1H), 8.33 (s, 1H), 8.30 (s, 1H), 8.02 (s, 1H), 7.88 (m, 1H), 7.62 (m, 1H), 7.09 (m, 1H), 6.95 (m, 1H), 6.77 (d, 1H, J = 1.3 Hz), 3.04 (s, 3H), 2.17 (d, 3H, J = 0.9 Hz), 1.70 (s, 6H) |
| 182 | 6-chloro-N-(3-chloro-5-(2-(4-fluorophenyl)propan-2-yl)phenyl)-5-(methylsulfonamido)benzo[b]thiophene-2-carboxamide | LC/MS ESI (+): 551 (M + 1)<br>$^1$H-NMR(400 MHz, DMSO-d$_6$): δ 10.64 (s, 1H), 9.64 (brs, 1H), 8.35 (s, 1H), 8.29 (s, 1H), 8.04 (s, 1H), 7.87 (s, 1H), 7.49 (s, 1H), 7.28 (dd, 2H, J = 8.4, 5.7 Hz), 7.13 (t, 2H, J = 8.8 Hz), 7.03 (s, 1H), 3.06 (s, 3H), 1.64 (s, 6H) |
| 183 | 6-chloro-N-(3-chloro-5-(2-(4-methoxyphenyl)propan-2-yl)phenyl)-5-(methylsulfonamido)benzo[b]thiophene-2-carboxamide | LC/MS ESI (+): 563 (M + 1)<br>$^1$H-NMR (400 MHz, DMSO-d$_6$): δ 10.64 (s, 1H), 9.65 (brs, 1H), 8.35 (s, 1H), 8.30 (s, 1H), 8.03 (s, 1H), 7.87 (s, 1H), 7.51 (s, 1H), 7.17 (d, 2H, J = 8.8 Hz), 7.00 (s, 1H), 6.88 (d, 2H, J = 8.8 Hz), 3.74 (s, 3H), 3.06 (s, 3H), 1.63 (s, 6H) |
| 184 | 5-chloro-N-(3-chloro-5-(2-(4-chlorophenyl)propan-2-yl)phenyl)-6-(methylsulfonamido)benzo[b]thiophene-2-carboxamide | LC/MS ESI (+): 567 (M + 1)<br>$^1$H-NMR(400 MHz, DMSO-d$_6$): δ 10.65 (s, 1H), 9.68 (brs, 1H), 8.23 (s, 1H), 8.19 (s, 1H), 8.12 (s, 1H), 7.88 (m, 1H), 7.49 (m, 1H), 7.37 (d, 2H, J = 8.7 Hz), 7.27 (d, 2H, J = 8.7 Hz), 7.03 (m, 1H), 3.09 (s, 3H), 1.64 (s, 6H) |

TABLE 10-continued

| Ex. | Compound | Analysis data |
|---|---|---|
| 185 | 6-chloro-N-(3-chloro-5-(2-(4-chlorophenyl)propan-2-yl)phenyl)-5-((2-methoxyethyl)sulfonamido)benzo[b]thiophene-2-carboxamide | LC/MS ESI (+): 611 (M + 1)<br>$^1$H-NMR (400 MHz, DMSO-$d_6$): δ 10.63 (s, 1H), 9.67 (brs, 1H), 8.34 (s, 1H), 8.30 (s, 1H), 8.05 (s, 1H), 7.89 (s, 1H), 7.49 (s, 1H), 7.39 (d, 2H, J = 8.8 Hz), 7.28 (d, 2H, J = 8.8 Hz), 7.05 (s, 1H), 3.74 (t, 2H, J = 6.4 Hz), 3.47~3.41 (m, 2H), 3.24 (s, 3H), 1.65 (s, 6H) |

Example 186

Synthesis of 6-chloro-N-(3-chloro-5-(2-(5-cyanothiophen-2-yl)propan-2-yl)phenyl)-5-(methylsulfonamido)benzo[b]thiophene-2-carboxamide (a) Synthesis of 5-(2-(3-chloro-5-nitrophenyl)propan-2-yl)thiophene-2-carbonitrile 2-Bromo-5-(2-(3-chloro-5-nitrophenyl)propan-2-yl)thiophene (250.0 mg, 0.69 mmol) and CuCN (62.0 mg, 0.69 mmol) were dissolved in anhydrous DMF (1.0 mL), and the reaction temperature was increased to 140° C., followed by stirring for 5 hours. The reaction mixture was cooled to room temperature and concentrated under reduced pressure. The residue was purified by flash column chromatography (silica gel, n-Hex:EtOAc=7:1) to obtain 5-(2-(3-chloro-5-nitrophenyl)propan-2-yl)thiophene-2-carbonitrile (56.0 mg, 26%) as a yellow liquid.

$^1$H-NMR (400MHz, CDCl$_3$): δ 8.21 (s, 1H), 8.07 (s, 1H), 7.56 (s, 1H), 7.51 (d, 1H, J=4.0Hz), 6.85 (d, 1H, J=4.0Hz), 1.84 (s, 6H)

(b) Synthesis of 5-(2-(3-amino-5-chlorophenyl)propan-2-yl)thiophene-2-carbonitrile The synthesis procedure of Intermediate 40 was repeated except for using 5-(2-(3-chloro-5-nitrophenyl)propan-2-yl)thiophene-2-carbonitrile (54.0 mg, 0.18 mmol) to obtain 5-(2-(3-amino-5-chlorophenyl)propan-2-yl)thiophene-2-carbonitrile (35.0 mg, 72%).

LC/MS ESI (+): 277 (M+1)

$^1$H-NMR (400MHz, CDCl$_3$): δ 7.45 (d, 1H, J=4.0Hz), 6.81 (d, 1H, J=4.0Hz), 6.65 (s, 1H), 6.56 (s, 1H), 6.41 (s, 1H), 3.72 (brs, 2H), 1.72 (s, 6H)

(c) Synthesis of 6-chloro-N-(3-chloro-5-(2-(5-cyanothiophen-2-yl)propan-2-yl)phenyl)-5-(methylsulfonamido)benzo[b]thiophene-2-carboxamide The synthesis procedure of Example 1 was repeated except for using 5-(2-(3-Amino-5-chlorophenyl)propan-2-yl)thiophene-2-carbonitrile (35.0 mg, 0.13 mmol) to obtain 6-chloro-N-(3-chloro-5-(2-(5-cyanothiophen-2-yl)propan-2-yl)phenyl)-5-(methylsulfonamido)benzo[b]thiophene-2-carboxamide (10.0 mg, 14%).

LC/MS ESI (+): 564 (M+1)

$^1$H-NMR (400MHz, DMSO-$d_6$): δ 10.59 (s, 1H), 9.59 (brs, 1H), 8.24 (s, 1H), 8.21 (s, 1H), 7.95 (s, 1H), 7.84 (s, 1H), 7.80 (d, 1H, J=3.6Hz), 7.54 (s, 1H), 7.11-7.12 (m, 2H), 2.95 (s, 3H), 1.71 (s, 6H)

Example 187

Synthesis of N-(3-chloro-5-(2-(1-ethyl-1H-pyrrol-2-yl)propan-2-yl)phenyl)-5-(methylsulfonamido)benzo[b]thiophene-2-carboxamide (a) Synthesis of 2-(2-(3-chloro-5-nitrophenyl)propan-2-yl)-1-ethyl-1H-pyrrole 2-(2-(3-Chloro-5-nitrophenyl)propan-2-yl)-1H-pyrrole (66.0 mg, 0.25 mmol) was dissolved in anhydrous DMF (5.0 mL), and 60% NaH in mineral oil (11.0 mg, 0.28 mmol) was added at 0° C. The reaction mixture was stirred at 0° C. for 30 minutes, and ethyl iodide (57.0 mg, 0.37 mmol) was added. The reaction mixture was stirred at room temperature for 1 hours and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain 2-(2-(3-chloro-5-nitrophenyl)propan-2-yl)-1-ethyl-1H-pyrrole (47.0 mg, 64%) as a yellow liquid.

$^1$H-NMR (400MHz, CDCl$_3$): δ 8.05 (s, 1H), 8.00 (s, 1H), 7.43 (s, 1H), 6.67 (t, 1H, J=2.4Hz), 6.17 (d, 2H, J=2.4Hz), 3.37 (q, 2H, J=7.2Hz), 1.70 (s, 6H), 1.08 (t, 3H, J=7.2Hz)

(b) Synthesis of 3-chloro-5-(2-(1-ethyl-1H-pyrrol-2-yl)propan-2-yl)aniline

The synthesis procedure of Intermediate 40 was repeated except for using 2-(2-(3-Chloro-5-nitrophenyl)propan-2-yl)-1-ethyl-1H-pyrrole (47.0 mg, 0.16 mmol) to obtain 3-chloro-5-(2-(1-ethyl-1H-pyrrol-2-yl)propan-2-yl)aniline (31.0 mg, 73%).

LC/MS ESI (+): 263 (M+1)

$^1$H-NMR (400MHz, CDCl$_3$): δ 6.62-6.64 (m, 2H), 6.50 (s, 1H), 6.29 (s, 1H), 6.13 (t, 1H, J=2.8Hz), 6.10 (m, 1H), 3.64 (brs, 2H), 3.45 (q, 2H, J=7.2Hz), 1.60 (s, 6H), 1.09 (t, 3H, J=7.2Hz)

(c) Synthesis of N-(3-chloro-5-(2-(1-ethyl-1H-pyrrol-2-yl)propan-2-yl)phenyl)-5-(methylsulfonamido)benzo[b]thiophene-2-carboxamide The synthesis procedure of Example 1 was repeated except for using 3-chloro-5-(2-(1-ethyl-1H-pyrrol-2-yl)propan-2-yl)aniline (31.0 mg, 0.12 mmol) to obtain N-(3-chloro-5-(2-(1-ethyl-1H-pyrrol-2-yl)propan-2-yl)phenyl)-5-(methylsulfonamido)benzo[b]thiophene-2-carboxamide (30.0 mg, 50%).

LC/MS ESI (+): 516 (M+1)

$^1$H-NMR (400MHz, DMSO-$d_6$): δ 10.60 (s, 1H), 9.87 (brs, 1H), 8.31 (s, 1H), 8.03 (d, 1H, J=8.8Hz), 7.89 (s, 1H), 7.80 (s, 1H), 7.52 (s, 1H), 7.37 (d, 1H, J=8.8Hz), 6.90 (s, 1H), 6.74 (s, 1H), 6.05 (m, 1H), 6.02 (m, 1H), 3.42 (q, 2H, J=7.2Hz), 3.02 (s, 3H), 1.62 (s, 6H), 0.98 (t, 3H, J=7.2Hz)

Example 188

Synthesis of 6-chloro-N-(3-chloro-5-(2-(4-chlorophenyl)propan-2-yl)phenyl)-5-((2-hydroxyethyl)sulfonamido)benzo[b]thiophene-2-carboxamide 6-Chloro-N-(3-chloro-5-(2-(4-chlorophenyl)propan-2-yl)phenyl)-5-((2-methoxyethyl)sulfonamido)benzo[b]thiophene-2-carboxamide (63.0 mg, 0.10 mmol) was dissolved in toluene (1.0 mL), and 1.0M BBr$_3$ dissolved in CH$_2$Cl$_2$ (30.6 μL, 0.31 mmol) was slowly added at 0° C. The reaction temperature was increased to room temperature, and the reaction mixture was stirred for 15 hours and extracted with EtOAc. The organic extract was washed with water, dried over anhydrous Na$_2$SO$_4$, concentrated under reduced pressure. The residue was purified by reversed-phase column chromatography (C18-silica gel, 0.1% formic acid in CH$_3$CN:0.1% formic acid in H$_2$O=7:3) to obtain 6-chloro-N-(3-chloro-5-(2-(4-chlorophenyl)propan-2-yl)phenyl)-5-((2-hydroxyethyl)sulfonamido)benzo[b]thiophene-2-carboxamide (34.0 mg, 56%) as a white solid.

LC/MS ESI (+): 597 (M+1)

$^1$H-NMR (400MHz, DMSO-d$_6$): δ 10.63 (s, 1H), 9.62 (brs, 1H), 8.35 (s, 1H), 8.29 (s, 1H), 8.06 (s, 1H), 7.89 (s, 1H), 7.49 (s, 1H), 7.39 (d, 2H, J=8.8Hz), 7.28 (d, 2H, J=8.8Hz), 7.05 (s, 1H), 5.04 (brs, 1H), 3.80-3.84 (m, 2H), 3.30-3.32 (m, 2H), 1.65 (s, 6H)

Example 189

Synthesis of N-(3-chloro-5-(2-(pyrimidin-2-yloxy)propan-2-yl)phenyl)-5-(methylsulfonamido)benzo[b]thiophene-2-carboxamide (a) Synthesis of 2-((2-(3-chloro-5-nitrophenyl)propan-2-yl)oxy)pyrimidine 1-(2-Bromopropan-2-yl)-3-chloro-5-nitrobenzene (Example 166-b) (24.0 mg, 0.09 mmol) was dissolved in anhydrous DMF (0.9 mL), and K$_2$CO$_3$ (24.0 mg, 0.17 mmol) and pyrimidine-4(3H)-one (17.0 mg, 0.17 mmol) were added at room temperature. The mixture was stirred at room temperature for 15 hours, and the reaction mixture was extracted with EtOAc. The organic extract was washed with brine, dried over anhydrous Na$_2$SO$_4$, concentrated under reduced pressure. The residue was purified by flash column chromatography (silica gel, EtOAc) to obtain 2-((2-(3-chloro-5-nitrophenyl)propan-2-yl)oxy)pyrimidine (11.0 mg, 44%) as a colorless liquid.

$^1$H-NMR (400MHz, CDCl$_3$): δ 8.57 (s, 1H), 8.11 (s, 1H), 7.92-7.97 (m, 2H), 7.47 (s, 1H), 6.34 (d, 1H, J=6.5Hz), 1.99 (s, 6H)

(b) Synthesis of 3-chloro-5-(2-(pyrimidin-2-yloxy)propan-2-yl)aniline

The synthesis procedure of Intermediate 40 was repeated except for using 2-((2-(3-chloro-5-nitrophenyl)propan-2-yl)oxy)pyrimidine (11.0 mg, 0.04 mmol) to obtain 3-chloro-5-(2-(pyrimidin-2-yloxy)propan-2-yl)aniline (4.0 mg, 38%).

LC/MS ESI (+): 264 (M+1)

(c) Synthesis of N-(3-chloro-5-(2-(pyrimidin-2-yloxy)propan-2-yl)phenyl)-5-(methylsulfonamido)benzo[b]thiophene-2-carboxamide The synthesis procedure of Example 1 was repeated except for using 3-chloro-5-(2-(pyrimidin-2-yloxy)propan-2-yl)aniline (4.0 mg, 0.01 mmol) to obtain N-(3-chloro-5-(2-(pyrimidin-2-yloxy)propan-2-yl)phenyl)-5-(methylsulfonamido)benzo[b]thiophene-2-carboxamide (2.0 mg, 35%).

LC/MS ESI (+): 517 (M+1)

$^1$H-NMR (400MHz, DMSO-d$_6$): δ 10.51 (s, 1H), 9.85 (brs, 1H), 8.75 (s, 1H), 8.21 (s, 1H), 7.97 (d, 1H, J=6.5Hz), 7.87-7.90 (m, 2H), 7.68 (s, 1H), 7.43 (s, 1H), 7.26 (d, 1H, J=8.1Hz), 7.01 (s, 1H), 6.29 (d, 1H, J=6.5Hz), 2.89 (s, 3H), 1.89 (s, 6H)

Example 190

Synthesis of N-(3-chloro-5-(2-(6-oxopyridazin-1(6H)-yl)propan-2-yl)phenyl)-5-(methylsulfonamido)benzo[b]thiophene-2-carboxamide (a) Synthesis of 2-(2-(3-chloro-5-nitrophenyl)propan-2-yl)pyridazin-3(2H)-one 1-(2-Bromopropan-2-yl)-3-chloro-5-nitrobenzene (Example 166-b) (24.0 mg, 0.09 mmol) was dissolved in anhydrous DMF (0.9 mL), and K$_2$CO$_3$ (24.0 mg, 0.17 mmol) and pyridazin-3(2H)-one (17.0 mg, 0.17 mmol) were added at room temperature. The mixture was stirred at room temperature for 15 hours, and the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=1:1) to obtain 2-(2-(3-chloro-5-nitrophenyl)propan-2-yl)pyridazin-3(2H)-one (13.0 mg, 51%) as a colorless liquid.

$^1$H-NMR (400MHz, CDCl$_3$): δ 8.07 (s, 1H), 7.94 (s, 1H), 7.89 (s, 1H), 7.50 (s, 1H), 7.24 (d, 1H, J=3.7Hz), 6.80 (d, 1H, J=9.3Hz), 1.93 (s, 6H)

(b) Synthesis of 2-(2-(3-amino-5-chlorophenyl)propan-2-yl)pyridazin-3(2H)-one

The synthesis procedure of Intermediate 40 was repeated except for using 2-(2-(3-chloro-5-nitrophenyl)propan-2-yl)pyridazin-3(2H)-one (13.0 mg, 0.05 mmol) to obtain 2-(2-(3-amino-5-chlorophenyl)propan-2-yl)pyridazin-3(2H)-one (2.0 mg, 15%).

LC/MS ESI (+): 264 (M+1)

(c) Synthesis of N-(3-chloro-5-(2-(6-oxopyridazin-1(6H)-yl)propan-2-yl)phenyl)-5-(methylsulfonamido)benzo[b]thiophene-2-carboxamide The synthesis procedure of Example 1 was repeated except for using 2-(2-(3-amino-5-chlorophenyl)propan-2-yl)pyridazin-3(2H)-one (2.0 mg, 0.01 mmol) to obtain N-(3-chloro-5-(2-(6-oxopyridazin-1(6H)-yl)propan-2-yl)phenyl)-5-(methylsulfonamido)benzo[b]thiophene-2-carboxamide (3.0 mg, 72%).

LC/MS ESI (+): 517 (M+1)

$^1$H-NMR (400MHz, DMSO-d$_6$): δ 10.54 (s, 1H), 9.87 (brs, 1H), 8.27 (s, 1H), 8.06 (s, 1H), 8.01 (d, 1H, J=8.7Hz), 7.87 (s, 1H), 7.78 (s, 1H), 7.48 (dd, 1H, J=9.3, 3.8Hz), 7.40

(s, 1H), 7.35 (d, 1H, J=8.7Hz), 6.96 (s, 1H), 6.83 (d, 1H, J=9.3Hz), 3.00 (s, 3H), 1.83 (s, 6H)

Example 191

Synthesis of N-(3-chloro-5-(2-(pyridin-4-yl)propan-2-yl)phenyl)-5-(methylsulfonamido)benzo[b]thiophene-2-carboxamide (a) Synthesis of 3-chloro-5-methoxybenzonitrile 3,5-Dichlorobenzonitrile (1.5 g, 8.72 mmol) was dissolved in anhydrous DMF (10.0 mL), and 35% solution of NaOMe in MeOH (4.0 mL) was slowly added, followed by stirring for 72 hours. The reaction mixture was extracted with EtOAc, washed with brine, dried over anhydrous $Na_2SO_4$, concentrated under reduced pressure. The residue was purified by flash column chromatography (silica gel, n-Hex:EtOAc=1:3) to obtain 3-chloro-5-methoxybenzonitrile (970.0 mg, 63%) as a white solid.
$^1$H-NMR (400MHz, $CDCl_3$): δ 7.23 (t, 1H, J=1.6Hz), 7.12 (t, 1H, J=2.0Hz), 7.05 (dd, 1H, J=2.4, 1.2Hz), 3.84 (s, 3H)

(b) Synthesis of (3-chloro-5-methoxyphenyl)(pyridin-4-yl)methanone

4-Bromopyridine (1.8 g, 11.4 mmol) was dissolved in $Et_2O$ (7.5 mL), and n-BuLi (9.8 mL, 15.7 mmol) was slowly added at −78° C. and stirred for 1 hour. 3-Chloro-5-methoxybenzonitrile (1.2 g, 7.16 mmol) was dissolved in $Et_2O$ (10.0 mL) and added to the reaction mixture, followed by stirring at 0° C. for 12 hours. The reaction was quenched with 1 N HCl, and the reaction mixture was extracted with EtOAc. The organic extract was washed with brine, dried over anhydrous $Na_2SO_4$, concentrated under reduced pressure. The residue was purified by flash column chromatography (amine silica gel, n-Hex:$CH_2Cl_2$=1:1) to obtain (3-chloro-5-methoxyphenyl)(pyridin-4-yl)methanone (950.0 mg, 56%) as an off-white oil.
LC/MS ESI (+): 248 (M+1)
$^1$H-NMR (400MHz, $CDCl_3$): δ 8.83 (d, 2H, J=5.2Hz), 7.58 (d, 2H, J=6.0Hz), 7.32 (t, 1H, J=1.6Hz), 7.24 (s, 1H), 7.17 (t, 1H, J=2.0Hz), 3.86 (s, 3H)

(c) Synthesis of 4-(dichloro(3-chloro-5-methoxyphenyl)methyl)pyridine

The synthesis procedure of Intermediate 37 was repeated except for using (3-chloro-5-methoxyphenyl)(pyridin-4-yl)methanone (950.0 mg, 2.55 mmol) to obtain 4-(dichloro(3-chloro-5-methoxyphenyl)methyl)pyridine (510.0 mg, 43%).
LC/MS ESI (+): 302 (M+1)
$^1$H-NMR (400MHz, $CDCl_3$): δ 8.68 (d, 2H, J=6.0Hz), 7.51 (d, 2H, J=6.0Hz), 7.15 (s, 1H), 7.02 (t, 1H, J=2.0Hz), 6.91 (t, 1H, J=2.0Hz), 3.80 (s, 3H)

(d) Synthesis of 4-(2-(3-chloro-5-methoxyphenyl)propan-2-yl)pyridine

The synthesis procedure of Intermediate 38 was repeated except for using 4-(dichloro(3-chloro-5-methoxyphenyl)methyl)pyridine (200.0 mg, 0.66 mmol) to obtain 4-(2-(3-chloro-5-methoxyphenyl)propan-2-yl)pyridine (71.4 mg, 41%).
LC/MS ESI (+): 262 (M+1)

$^1$H-NMR (400MHz, $CDCl_3$): δ 8.52 (brs, 2H), 7.13 (brs, 2H), 6.78 (t, 1H, J=1.6Hz), 6.75 (t, 1H, J=2.0Hz), 6.61 (t, 1H, J=2.0Hz), 3.75 (s, 3H), 1.64 (s, 6H)

(f) Synthesis of 3-chloro-5-(2-(pyridin-4-yl)propan-2-yl)phenol

The synthesis procedure of Intermediate 41 was repeated except for using 4-(2-(3-chloro-5-methoxyphenyl)propan-2-yl)pyridine (183.0 mg, 0.49 mmol) to obtain 3-chloro-5-(2-(pyridin-4-yl)propan-2-yl)phenol (157.0 mg, 91%).
LC/MS ESI (+): 248 (M+1)
$^1$H-NMR (400MHz, $CDCl_3$): δ 8.37 (d, 2H, J=5.2Hz), 7.15 (d, 2H, J=5.2Hz), 6.87 (s, 1H), 6.76 (s, 1H), 6.30 (s, 1H), 1.63 (s, 6H)

(g) Synthesis of 3-chloro-5-(2-(pyridin-4-yl)propan-2-yl)phenyl trifluoromethanesulfonate The synthesis procedure of Example 114-a was repeated except for using 3-chloro-5-(2-(pyridin-4-yl)propan-2-yl)phenol (80.0 mg, 0.32 mmol) to obtain 3-chloro-5-(2-(pyridin-4-yl)propan-2-yl)phenyl trifluoromethanesulfonate (40.0 mg, 33%).
LC/MS ESI (+): 380 (M+1)
$^1$H-NMR (400MHz, $CDCl_3$): δ 8.55 (d, 2H, J=5.2Hz), 7.21 (s, 1H), 7.18 (s, 1H), 7.10 (d, 2H, J=5.2Hz), 6.99 (s, 1H), 1.68 (s, 6H)

(h) Synthesis of 3-chloro-5-(2-(pyridin-4-yl)propan-2-yl)aniline

3-Chloro-5-(2-(pyridin-4-yl)propan-2-yl)phenyl trifluoromethanesulfonate (40.0 mg, 0.11 mmol), benzophenone imine (21.0 μL, 0.13 mmol), $Pd_2dba_3CHCl_3$ (11.0 mg, 0.01 mmol), rac-BINAP (13.7 mg, 0.02 mmol), and $Cs_2CO_3$ (51.3 mg, 0.16 mmol) were dissolved in THF (3.0 mL), followed by refluxing for 2 days. The reaction mixture was extracted with EtOAc, washed with brine, dried over anhydrous $Na_2SO_4$, and concentrated under reduced pressure. The residue was dissolved in THF (2.0 mL), and 2 N HCl aqueous solution (0.5 mL) was added, followed by stirring at room temperature for 3 hours. The reaction mixture was extracted with $CH_2Cl_2$, washed with sat. $NaHCO_3$ aqueous solution, dried over anhydrous $Na_2SO_4$ and concentrated under reduced pressure. The residue was purified by flash column chromatography (amine silica gel, $CH_2Cl_2$:MeOH=20:1) to obtain 3-chloro-5-(2-(pyridin-4-yl)propan-2-yl)aniline (6.8 mg, 2 step yield: 26%) as a yellow liquid.
LC/MS ESI (+): 247 (M+1)
$^1$H-NMR (300MHz, $CDCl_3$): δ 8.50 (m, 2H), 7.13 (d, 2H, J=5.6Hz), 6.60 (m, 1H), 6.54 (m, 1H), 6.31 (m, 1H), 3.68 (brs, 2H), 1.61 (s, 6H)

(i) Synthesis of N-(3-chloro-5-(2-(pyridin-4-yl)propan-2-yl)phenyl)-5-(methylsulfonamido)benzo[b]thiophene-2-carboxamide The synthesis procedure of Example 1 was repeated except for using 3-Chloro-5-(2-(pyridin-4-yl)propan-2-yl)aniline (6.0 mg, 0.02 mmol) to obtain N-(3-chloro-5-(2-(pyridin-4-yl)propan-2-yl)phenyl)-5-(methylsulfonamido)benzo[b]thiophene-2-carboxamide (3.3 mg, 28%).
LC/MS ESI (+): 500 (M+1)
$^1$H-NMR (400MHz, DMSO-$d_6$): δ 10.56 (s, 1H), 9.88 (brs, 1H), 8.51 (d, 2H, J=5.6Hz), 8.29 (s, 1H,), 8.03 (d, 1H, J=8.4Hz), 7.91 (s, 1H), 7.80 (s, 1H), 7.52 (s, 1H), 7.37 (dd, 1H, J=8.8, 2.0Hz), 7.27 (d, 2H, J=6.4Hz), 7.07 (s, 1H), 3.02 (s, 3H), 1.67 (s, 6H)

Example 192

Synthesis of 2-((3-bromo-5-(2-(3-isopropoxy-5-(trifluoromethoxy)phenyl)propan-2-yl)phenyl)carbamoyl)benzo[b]thiophen-5-yl dihydrogen phosphate (a) Synthesis of methyl 5-methoxybenzo[b]thiophene-2-carboxylate The synthesis procedure of Intermediate 14-1 was repeated except for using 2-fluoro-5-methoxybenzaldehyde (900.0 mg, 5.84 mmol) to obtain methyl 5-methoxybenzo[b]thiophene-2-carboxyle (270.0 mg, 21%).

LC/MS ESI (+): 223 (M+1)
$^1$H-NMR (400MHz, CDCl$_3$): δ 7.96 (s, 1H), 7.69 (d, 1H, J=8.9Hz), 7.25 (d, 1H, J=2.4Hz), 7.09 (dd, 1H, J=8.9, 2.4Hz), 3.92 (s, 3H), 3.86 (s, 3H)

(b) Synthesis of methyl 5-hydroxybenzo[b]thiophene-2-carboxylate

The synthesis procedure of Intermediate 42 was repeated except for using methyl 5-methoxybenzo[b]thiophene-2-carboxylate (261.0 mg, 1.17 mmol) to obtain methyl 5-hydroxybenzo[b]thiophene-2-carboxylate (192.0 mg, 79%).

LC/MS ESI (+): 209 (M+1)

(c) Synthesis of 5-hydroxybenzo[b]thiophene-2-carboxylic acid

The synthesis procedure of Intermediate 13-d was repeated except for using methyl 5-hydroxybenzo[b]thiophene-2-carboxylate (191.0 mg, 0.92 mmol) to obtain 5-hydroxybenzo[b]thiophene-2-carboxylic acid (180.0 mg, 99%).

LC/MS ESI (+): 195 (M+1)
$^1$H-NMR (400MHz, CDCl$_3$): δ 13.28 (brs, 1H), 9.62 (s, 1H), 7.79 (d, 1H, J=8.8Hz), 7.30 (s, 1H), 7.00 (d, 1H, J=8.8Hz)

(d) Synthesis of N-(3-bromo-5-(2-(3-isopropoxy-5-(trifluoromethoxy)phenyl)propan-2-yl)phenyl)-5-hydroxybenzo[b]thiophene-2-carboxamide The synthesis procedure of Intermediate 13-d was repeated except for using 5-hydroxybenzo[b]thiophene-2-carboxylic acid (30 mg, 0.15 mmol) to obtain N-(3-bromo-5-(2-(3-isopropoxy-5-(trifluoromethoxy)phenyl)propan-2-yl)phenyl)-5-hydroxybenzo[b]thiophene-2-carboxamide (15.0 mg, 16%).

LC/MS ESI (+): 608 (M+1)
$^1$H-NMR (400MHz, CDCl$_3$): δ 7.65-7.79 (m, 3H), 7.22-7.24 (m, 2H), 7.18-7.19 (m, 1H), 7.00-7.04 (m, 1H), 6.98-6.99 (m, 1H), 6.61-6.63 (m, 2H), 6.55-6.59 (m, 1H), 5.50 (brs, 1H), 4.40-4.49 (m, 1H), 1.60 (s, 6H), 1.29 (d, 6H, J=6.0Hz)

(e) Synthesis of 2-((3-bromo-5-(2-(3-isopropoxy-5-(trifluoromethoxy)phenyl)propan-2-yl)phenyl)carbamoyl)benzo[b]thiophen-5-yl dihydrogen phosphate N-(3-bromo-5-(2-(3-isopropoxy-5-(trifluoromethoxy)phenyl)propan-2-yl)phenyl)-5-hydroxybenzo[b]thiophene-2-carboxamide (13.9 mg, 0.02 mmol) was dissolved in anhydrous THF (1.5 mL), and Et$_3$N (38.0 μL, 0.23 mmol) and POCl$_3$ (22.0 μL, 0.23 mmol) were added. After stirring at room temperature for 2 hours, cold H$_2$O (1.0 mL) was added, followed by stirring at room temperature for 1 hour. The reaction mixture was concentrated under reduced pressure. The residue was purified by reversed-phase column chromatography (C18-silica gel, CH$_3$CN:H$_2$O=4:6) to obtain 2-((3-bromo-5-(2-(3-isopropoxy-5-(trifluoromethoxy)phenyl)propan-2-yl)phenyl)carbamoyl)benzo[b]thiophen-5-yl dihydrogen phosphate (2.0 mg, 13%) as a white solid.

LC/MS ESI (+): 688 (M+1)
$^1$H-NMR (400MHz, DMSO-d$_6$): δ 10.55 (s, 1H), 8.20 (s, 1H), 8.02 (s, 1H), 7.84 (d, 1H, J=8.7Hz), 7.72 (s, 1H), 7.60 (s, 1H), 7.32 (d, 1H, J=8.7Hz), 7.13 (s, 1H), 6.76 (s, 1H), 6.71 (s, 1H), 6.70 (s, 1H), 4.55-4.68 (m, 1H), 1.63 (s, 6H), 1.22 (d, 6H, J=5.5Hz)

Example 193

Synthesis of 2-((3-chloro-5-(2-(3-isopropoxy-5-(trifluoromethoxy)phenyl)propan-2-yl)phenyl)carbamoyl)benzo[b]thiophen-5-yl dihydrogen phosphate The synthesis procedure of Example 192 was repeated except for using methyl 5-hydroxybenzo[b]thiophene-2-carboxylate (86.7 mg, 0.45 mmol) to obtain 2-((3-chloro-5-(2-(3-isopropoxy-5-(trifluoromethoxy)phenyl)propan-2-yl)phenyl)carbamoyl)benzo[b]thiophen-5-yl dihydrogen phosphate (5.0 mg).

LC/MS ESI (+): 644 (M+1)
$^1$H-NMR (400MHz, DMSO-d$_6$): δ 10.59 (s, 1H), 8.26 (s, 1H), 8.00 (d, 1H, J=8.7Hz), 7.90 (s, 1H), 7.74 (s, 1H), 7.54 (s, 1H), 7.32 (d, 1H, J=8.7Hz), 7.03 (s, 1H), 6.75 (s, 1H), 6.72 (s, 1H), 6.71 (s, 1H), 4.59-4.65 (m, 1H), 1.64 (s, 6H), 1.23 (d, 6H, J=5.5Hz)

Example 194

Synthesis of tert-butyl (2-((3-chloro-5-(2-(3-isopropoxy-5-(trifluoromethoxy)phenyl)propan-2-yl)phenyl)carbamoyl)benzo[b]thiophen-5-yl)carbamate (a) Synthesis of ethyl 5-((tert-butoxycarbonyl)amino)benzo[b]thiophene-2-carboxylate Ethyl 5-aminobenzo[b]thiophene-2-carboxylate (500.0 mg, 2.26 mmol), Boc$_2$O (592.0 mg, 2.71 mmol) was dissolved in THF (45.0 mL), followed by refluxing for 18 hours. The reaction mixture was extracted with EtOAc, washed with 1 N HCl aqueous solution, dried over anhydrous Na$_2$SO$_4$ and concentrated under reduced pressure. The residue was purified by flash column chromatography (silica gel, n-Hex:EtOAc=4:1) to obtain ethyl 5-((tert-butoxycarbonyl)amino)benzo[b]thiophene-2-carboxylate (684.8 mg, 94%) as a red solid.

$^1$H-NMR (400MHz, CDCl$_3$): δ 8.04 (s, 1H), 7.97 (s, 1H), 7.74 (d, 1H, J=8.8Hz), 7.33 (dd, 1H, J=8.8, 2.4Hz), 6.57 (s, 1H), 4.40 (q, 2H, J=7.2Hz), 1.54 (s, 9H), 1.41 (t, 3H, J=7.2Hz)

(b) Synthesis of 5-((tert-butoxycarbonyl)amino)benzo[b]thiophene-2-carboxylic acid Ethyl 5-((tert-butoxycarbonyl)amino)benzo[b]thiophene-2-carboxylate (684.0 mg, 2.13 mmol) was dissolved in MeOH (3.0 mL), and 2 N NaOH aqueous solution (2.13 mL) was added, followed by heating at 60° C. for 2 hours and 30 minutes. The reaction mixture was concentrated under reduced pressure. H₂O was added to the resulting residue to dilute, and 1 N HCl aqueous solution was added for acidification to pH 1-2. The precipitate was filtered. The pale red solid was dried to obtain 5-((tert-butoxycarbonyl)amino)benzo[b]thiophene-2-carboxylic acid (603.0 mg, 97%).

¹H-NMR (400MHz, DMSO-$d_6$): δ 9.53 (s, 1H), 8.19 (s, 1H), 7.99 (s, 1H), 7.88 (d, 1H, J=8.8Hz), 7.46 (dd, 1H, J=8.8, 2.0Hz), 1.49 (s, 9H)

(c) Synthesis of tert-butyl (2-((3-chloro-5-(2-(3-isopropoxy-5-(trifluoromethoxy)phenyl)propan-2-yl)phenyl)carbamoyl)benzo[b]thiophen-5-yl)carbamate The synthesis procedure of Intermediate 13-c was repeated except for using 5-((tert-butoxycarbonyl)amino)benzo[b]thiophene-2-carboxylic acid (603.0 mg, 2.06 mmol) to obtain tert-butyl (2-((3-chloro-5-(2-(3-isopropoxy-5-(trifluoromethoxy)phenyl)propan-2-yl)phenyl)carbamoyl)benzo[b]thiophen-5-yl)carbamate (1.1 g, 77%).

LC/MS ESI (+): 663 (M+1)

¹H-NMR (400MHz, DMSO-$d_6$): δ 10.54 (s, 1H), 9.54 (s, 1H), 8.23 (s, 1H), 8.13 (s, 1H), 7.91-7.93 (m, 2H), 7.54-7.56 (m, 2H), 7.05 (s, 1H), 6.78 (s, 1H), 6.73 (s, 1H), 6.72 (s, 1H), 4.61-4.67 (m, 1H), 1.65 (s, 6H), 1.51 (s, 9H), 1.25 (d, 6H, J=6.0Hz)

Example 195

Synthesis of N-(3-chloro-5-(2-(3-isopropoxy-5-(trifluoromethoxy)phenyl)propan-2-yl)phenyl)-5-((2-methoxyethyl)sulfonamido)benzo[b]thiophene-2-carboxamide (a) Synthesis of 5-amino-N-(3-chloro-5-(2-(3-isopropoxy-5-(trifluoromethoxy)phenyl)propan-2-yl)phenyl)benzo[b]thiophene-2-carboxamide tert-Butyl (2-((3-chloro-5-(2-(3-isopropoxy-5-(trifluoromethoxy)phenyl)propan-2-yl)phenyl)carbamoyl)benzo[b]thiophen-5-yl)carbamate (Example 194) (930.0 mg, 1.40 mmol) was dissolved in CH₂Cl₂ (14.0 mL), and TFA (1.4 mL) was added, followed by stirring at room temperature for 2 hours. The reaction mixture was extracted with CH₂Cl₂, washed with sat. NaHCO₃ aqueous solution and brine, dried over anhydrous Na₂SO₄, concentrated under reduced pressure. The residue was purified by flash column chromatography (silica gel, n-Hex:EtOAc=1:1) to obtain 5-amino-N-(3-chloro-5-(2-(3-isopropoxy-5-(trifluoromethoxy)phenyl)propan-2-yl)phenyl)benzo[b]thiophene-2-carboxamide (734.0 mg, 93%) as a yellow liquid.

¹H-NMR (400MHz, CDCl₃): δ 7.74-7.75 (m, 1H), 7.70 (s, 1H), 7.67 (brs, 1H), 7.63 (d, 1H, J=8.4Hz), 7.19-7.20 (m, 1H), 7.11 (d, 1H, J=2.0Hz), 7.00-7.01 (m, 1H), 6.90 (dd, 1H, J=8.4, 2.0Hz), 6.65 (d, 2H, J=2.4Hz), 6.59 (s, 1H), 4.44-4.51 (m, 1H), 3.79 (s, 2H), 1.65 (s, 6H), 1.31 (d, 6H, J=6.0Hz)

(b) Synthesis of N-(3-chloro-5-(2-(3-isopropoxy-5-(trifluoromethoxy)phenyl)propan-2-yl)phenyl)-5-((2-methoxyethyl)sulfonamido)benzo[b]thiophene-2-carboxamide The synthesis procedure of Intermediate 13-c was repeated except for using 5-amino-N-(3-chloro-5-(2-(3-isopropoxy-5-(trifluoromethoxy)phenyl)propan-2-yl)phenyl)benzo[b]thiophene-2-carboxamide (40.0 mg, 0.07 mmol) to obtain N-(3-chloro-5-(2-(3-isopropoxy-5-(trifluoromethoxy)phenyl)propan-2-yl)phenyl)-5-((2-methoxyethyl)sulfonamido)benzo[b]thiophene-2-carboxamide (36.6 mg, 75%).

LC/MS ESI (+): 685 (M+1)

¹H-NMR (400MHz, DMSO-$d_6$): δ 10.55 (s, 1H), 9.93 (s, 1H), 8.29 (s, 1H), 8.02 (d, 1H, J=8.8Hz), 7.91 (m, 1H), 7.80 (m, 1H), 7.55 (s, 1H), 7.36 (dd, 1H, J=8.8, 2.1Hz), 7.06 (m, 1H), 6.78 (s, 1H), 6.73 (s, 1H), 6.72 (s, 1H), 4.62-4.65 (m, 1H), 3.68 (t, 2H, J=6.0Hz), 3.38 (t, 2H, J=6.1Hz), 3.19 (s, 3H), 1.65 (s, 6H), 1.25 (d, 6H, J=6.0Hz)

Through the synthetic method according to Example 195, compounds from Example 196 to Example 206 were synthesized, and the data of each example are as follows.

TABLE 11

| Ex. | Compound | Analysis data |
|---|---|---|
| 196 | N-(3-chloro-5-(2-(3-isopropoxy-5-(trifluoromethoxy)phenyl)propan-2-yl)phenyl)-5-(((tetrahydrofuran-3-yl)methyl)sulfonamido)benzo[b]thiophene-2-carboxamide | LC/MS ESI (+): 711 (M + 1)<br>¹H-NMR(400 MHz, DMSO-$d_6$): δ 10.55 (s, 1H), 10.03 (brs, 1H), 8.29 (s, 1H), 8.02 (d, 1H, J = 8.7 Hz), 7.92 (m, 1H), 7.79 (m, 1H), 7.54 (s, 1H), 7.36 (dd, 1H, J = 8.8, 2.1 Hz), 7.06 (m, 1H), 6.78 (s, 1H), 6.74 (m, 1H), 6.72 (s, 1H), 4.61~4.67 (m, 1H), 3.84~3.88 (m, 1H), 3.58~3.71 (m, 2H), 3.33~3.37 (m, 1H), 3.25~3.28 (m, 2H), 2.56~2.63 (m, 1H), 2.05~2.13 (m, 1H), 1.65 (s, 6H), 1.57~1.64 (m, 1H), 1.25 (d, 6H, J = 6.0 Hz) |
| 197 | N-(3-chloro-5-(2-(3-isopropoxy-5-(trifluoromethoxy)phenyl)propan-2-yl)phenyl)-5-(((tetrahydrofuran-2-yl)methyl)sulfonamido)benzo[b]thiophene-2-carboxamide | LC/MS ESI (+): 711 (M + 1)<br>¹H-NMR(400 MHz, DMSO-$d_6$): δ 10.56 (s, 1H), 9.94 (brs, 1H), 8.28 (s, 1H), 8.00 (d, 1H, J = 9.1 Hz), 7.92 (s, 1H), 7.79 (s, 1H), 7.54 (s, 1H), 7.35 (d, 1H, J = 8.5 Hz), 7.06 (s, 1H), 6.79 (m, 1H), 6.74 (m, 1H), 6.72 (s, 1H), 4.62~4.66 (m, 1H), 4.19~4.22 (m, 1H), 3.58~3.72 (m, 2H), 3.29~3.30 (m, 2H), 2.02~2.07 (m, 1H), 1.78~1.81 (m, 2H), 1.58~1.65 (m, 7H), 1.25 (d, 6H, J = 5.5 Hz) |
| 198 | N-(3-chloro-5-(2-(3-isopropoxy-5-(trifluoromethoxy)phenyl)propan-2-yl)phenyl)-5-(((tetrahydro-2H-pyran-4-yl)methyl)sulfonamido)benzo[b]thiophene-2-carboxamide | LC/MS ESI (+): 725 (M + 1)<br>¹H-NMR(400 MHz, DMSO-$d_6$): δ 10.56 (s, 1H), 9.99 (brs, 1H), 8.28 (s, 1H), 8.01 (d, 1H, J = 8.7 Hz), 7.92 (s, 1H), 7.78 (s, 1H), 7.54 (s, 1H), 7.34 (d, 1H, J = 8.3 Hz), 7.06 (s, 1H), 6.79 (s, 1H), 6.74 (s, 1H), 6.72 (s, 1H), 4.61~4.67 (m, 1H), 3.80 (d, 2H, J = 10.7 Hz), 3.26~3.32 (m, 2H), 3.07 (m, 2H), 2.09~2.13 (m, 1H), 1.75 (m, 1H), 1.71 (m, 1H), 1.65 (s, 6H), 1.22~1.34 (m, 8H) |

TABLE 11-continued

| Ex. | Compound | Analysis data |
|---|---|---|
| 199 | N-(3-chloro-5-(2-(3-isopropoxy-5-(trifluoromethoxy)phenyl)propan-2-yl)phenyl)-5-((3,5-dimethylisoxazole)-4-sulfonamido)benzo[b]thiophene-2-carboxamide | LC/MS ESI (+): 722 (M + 1)<br>¹H-NMR(400 MHz, DMSO-d₆): δ 10.63 (brs, 1H), 10.55 (s, 1H), 8.22 (s, 1H), 7.95~7.98 (m, 1H), 7.90 (s, 1H), 7.61~7.62 (m, 1H), 7.51 (s, 1H), 7.18~7.20 (m, 1H), 7.04 (s, 1H), 6.77 (s, 1H), 6.70~6.72 (m, 2H), 4.61~4.64 (m, 1H), 2.45 (s, 3H), 2.22 (s, 3H), 1.63 (s, 6H), 1.23 (d, 6H, J = 5.7 Hz) |
| 200 | N-(3-chloro-5-(2-(3-isopropoxy-5-(trifluoromethoxy)phenyl)propan-2-yl)phenyl)-5-((1-methyl-1H-pyrazole)-3-sulfonamido)benzo[b]thiophene-2-carboxamide | LC/MS ESI (+): 707 (M + 1)<br>¹H-NMR(400 MHz, DMSO-d₆): δ 10.53 (s, 1H), 10.29 (brs, 1H), 8.21 (s, 1H), 8.17 (brs, 1H), 7.90 (s, 2H), 7.67 (s, 2H), 7.51 (s, 1H), 7.20~7.24 (m, 1H), 7.04 (s, 1H), 6.77 (s, 1H), 6.71~6.72 (m, 2H), 4.60~4.66 (m, 1H), 3.79 (s, 3H), 1.63 (s, 6H), 1.23 (d, 6H, J = 5.7 Hz) |
| 201 | N-(3-chloro-5-(2-(3-isopropoxy-5-(trifluoromethoxy)phenyl)propan-2-yl)phenyl)-5-((1-methyl-1H-pyrazole)-4-sulfonamido)benzo[b]thiophene-2-carboxamide | LC/MS ESI (+): 707 (M + 1)<br>¹H-NMR(400 MHz, DMSO-d₆): δ 10.53~10.57 (m, 2H), 8.22 (s, 1H), 7.91 (s, 2H), 7.82 (s, 1H), 7.70 (s, 1H), 7.53 (s, 1H), 7.26 (d, 1H, J = 8.9 Hz), 7.05 (s, 1H), 6.79 (s, 1H), 6.72 (m, 2H), 6.62 (s, 1H), 4.61~4.67 (m, 1H), 3.87 (s, 3H), 1.65 (s, 6H), 1.25 (d, 6H, J = 5.7 Hz) |
| 202 | N-(3-chloro-5-(2-(3-isopropoxy-5-(trifluoromethoxy)phenyl)propan-2-yl)phenyl)-5-(ethylsulfonamido)benzo[b]thiophene-2-carboxamide | LC/MS ESI (+): 655 (M + 1)<br>¹H-NMR(400 MHz, DMSO-d₆): δ 10.55 (s, 1H), 9.99 (brs, 1H), 8.27 (s, 1H), 7.99 (d, 1H, J = 8.4 Hz), 7.92 (s, 1H), 7.78 (s, 1H), 7.54 (s, 1H), 7.36 (d, 1H, J = 8.6 Hz), 7.06 (s, 1H), 6.79 (s, 1H), 6.72~6.73 (m, 2H), 4.61~4.67 (m, 1H), 3.07~3.13 (m, 2H), 1.65 (s, 6H), 1.19~1.25 (m, 9H) |
| 203 | N-(3-chloro-5-(2-(3-isopropoxy-5-(trifluoromethoxy)phenyl)propan-2-yl)phenyl)-5-((1-methylethyl)sulfonamido)benzo[b]thiophene-2-carboxamide | LC/MS ESI (+): 669 (M + 1)<br>¹H-NMR(400 MHz, DMSO-d₆): δ 10.53 (s, 1H), 9.97 (brs, 1H), 8.25 (s, 1H), 7.96 (d, 1H, J = 8.5 Hz), 7.90 (s, 1H), 7.78 (s, 1H), 7.53 (s, 1H), 7.36 (d, 1H, J = 8.3 Hz), 7.04 (s, 1H), 6.77 (s, 1H), 6.71~6.72 (m, 2H), 4.60~4.66 (m, 1H), 3.19~3.27 (m, 1H), 1.64 (s, 6H), 1.23 (d, 12H, J = 5.9 Hz) |
| 204 | N-(3-chloro-5-(2-(3-isopropoxy-5-(trifluoromethoxy)phenyl)propan-2-yl)phenyl)-5-((tetrahydrofuran)-3-sulfonamido)benzo[b]thiophene-2-carboxamide | LC/MS ESI (+): 697 (M + 1)<br>¹H-NMR (400 MHz, DMSO-d₆): δ 10.56 (s, 1H), 10.08 (s, 1H), 8.28 (s, 1H), 8.02 (d, 1H, J = 8.7 Hz), 7.90 (s, 1H), 7.81 (s, 1H), 7.53 (s, 1H), 7.36 (d, 1H, J = 8.7 Hz), 7.05 (s, 1H), 6.70~6.78 (m, 3H), 4.59~4.66 (m, 1H), 3.89~4.00 (m, 2H), 3.77~3.86 (m, 2H), 3.59~3.65 (m, 1H), 2.07~2.17 (m, 2H), 1.64 (s, 6H), 1.23 (d, 6H, J = 6.0 Hz) |
| 205 | N-(3-chloro-5-(2-(3-isopropoxy-5-(trifluoromethoxy)phenyl)propan-2-yl)phenyl)-5-((1,1-dioxidotetrahydro-2H-thiopyran)-4-sulfonamido)benzo[b]thiophene-2-carboxamide | LC/MS ESI (+): 759 (M + 1)<br>¹H-NMR(400 MHz, DMSO-d₆): 5 10.55 (s, 1H), 10.26 (brs, 1H), 8.28 (s, 1H), 8.03 (d, 1H, J = 8.8 Hz), 7.91 (m, 1H), 7.81 (d, 1H, J = 1.9 Hz), 7.53 (s, 1H), 7.38 (dd, 1H, J = 8.7, 2.0 Hz), 7.05 (s, 1H), 6.78 (s, 1H), 6.71~6.72 (m, 2H), 4.63 (m, 1H), 3.51 (m, 1H), 3.14~3.25 (m, 4H), 2.40~2.42 (m, 2H), 2.04~2.14 (m, 2H), 1.64 (s, 6H), 1.24 (d, 6H, J = 6.0 Hz) |
| 206 | 5-((1-acetylpiperidine)-4-sulfonamido)-N-(3-chloro-5-(2-(3-isopropoxy-5-(trifluoromethoxy)phenyl)propan-2-yl)phenyl)benzo[b]thiophene-2-carboxamide | LC/MS ESI (+): 752 (M + 1)<br>¹H-NMR(400 MHz, CDCl₃): δ 8.09 (s, 1H), 7.83~7.85 (m, 2H), 7.77 (s, 2H), 7.32 (d, 1H, J = 8.9 Hz), 7.02 (s, 1H), 6.90 (s, 1H), 6.65 (s, 2H), 6.58 (s, 1H), 4.74 (m, 1H), 4.47 (m, 1H), 3.94 (m, 1H), 3.26 (m, 1H), 3.05 (m, 1H), 2.54 (m, 1H), 2.12~2.21 (m, 2H), 2.07 (s, 3H), 1.78~1.88 (m, 2H), 1.65 (s, 6H), 1.31 (d, 6H, J = 6.0 Hz) |

Example 207

Synthesis of N-(3-chloro-5-(2-(3-isopropoxy-5-(trifluoromethoxy)phenyl)propan-2-yl)phenyl)-5-(vinylsulfonamido)benzo[b]thiophene-2-carboxamide The synthesis procedure of Example 195-a was repeated except for using 5-amino-N-(3-chloro-5-(2-(3-isopropoxy-5-(trifluoromethoxy)phenyl)propan-2-yl)phenyl)benzo[b]thiophene-2-carboxamide (20.0 mg, 0.04 mmol) to obtain N-(3-chloro-5-(2-(3-isopropoxy-5-(trifluoromethoxy)phenyl)propan-2-yl)phenyl)-5-(vinylsulfonamido)benzo[b]thiophene-2-carboxamide (14.0 mg, 59%).

LC/MS ESI (+): 653 (M+1)

$^1$H-NMR (400MHz, DMSO-d$_6$): δ 10.55 (s, 1H), 10.16 (brs, 1H), 8.26 (s, 1H), 7.99 (d, 1H, J=8.1Hz), 7.91 (s, 1H), 7.72 (s, 1H), 7.54 (s, 1H), 7.29 (d, 1H, J=8.6Hz), 7.05 (s, 1H), 6.81-6.84 (m, 1H), 6.78 (s, 1H), 6.74 (s, 1H), 6.72 (s, 1H), 6.12 (d, 1H, J=16.6Hz), 6.03 (d, 1H, J=9.4Hz), 4.62-4.67 (m, 1H), 1.65 (s, 6H), 1.25 (d, 6H, J=5.9Hz)

Example 208

Synthesis of N-(3-chloro-5-(2-(3-isopropoxy-5-(trifluoromethoxy)phenyl)propan-2-yl)phenyl)-5-((2-(dimethylamino)ethyl)sulfonamido)benzo[b]thiophene-2-carboxamide N-(3-chloro-5-(2-(3-isopropoxy-5-(trifluoromethoxy)phenyl)propan-2-yl)phenyl)-5-(vinylsulfonamido)benzo[b]thiophene-2-carboxamide (Example 207) (10.0 mg, 0.02 mmol) was dissolved in THF (0.5 mL), and 2.0 M solution of NHMe$_2$ in THF (76.5 μL, 0.15 mmol) was added. The mixture was stirred at room temperature for 17 hours, and the reaction mixture was concentrated under reduced pressure. The residue was purified by flash column chromatography (amine silica gel, CH$_2$Cl$_2$:MeOH=20:1) to obtain N-(3-chloro-5-(2-(3-isopropoxy-5-(trifluoromethoxy)phenyl)propan-2-yl)phenyl)-5-((2-(dimethylamino)ethyl)sulfonamido)benzo[b]thiophene-2-carboxamide (10.0 mg, 93%) as a white solid.

LC/MS ESI (+): 698 (M+1)

$^1$H-NMR (400MHz, DMSO-d$_6$): δ 10.54 (s, 1H), 9.94 (brs, 1H), 8.27 (s, 1H), 8.00 (d, 1H, J=7.6Hz), 7.91 (s, 1H), 7.78 (s, 1H), 7.54 (s, 1H), 7.36 (d, 1H, J=6.8Hz), 7.05 (s, 1H), 6.78 (s, 1H), 6.74 (s, 1H), 6.72 (s, 1H), 4.61-4.67 (m, 1H), 3.22-3.26 (m, 2H), 2.63-2.68 (m, 2H), 2.08 (s, 6H), 1.65 (s, 6H), 1.25 (d, 6H, J=6.0Hz)

Through the synthetic method according to Example 208, compounds of Example 209 and Example 210 were synthesized, and the data of each example are as follows.

Example 211

Synthesis of N-(3-chloro-5-(2-(3-isopropoxy-5-(trifluoromethoxy)phenyl)propan-2-yl)phenyl)-5-(1,1-dioxido-1,2-thiazinan-2-yl)benzo[b]thiophene-2-carboxamide (a) Synthesis of N-(3-chloro-5-(2-(3-isopropoxy-5-(trifluoromethoxy)phenyl)propan-2-yl)phenyl)-5-((4-chlorobutyl)sulfonamido)benzo[b]thiophene-2-carboxamide The synthesis procedure of Example 195-a was repeated except for using 5-amino-N-(3-chloro-5-(2-(3-isopropoxy-5-(trifluoromethoxy)phenyl)propan-2-yl)phenyl)benzo[b]thiophene-2-carboxamide (50.0 mg, 0.09 mmol) to obtain N-(3-chloro-5-(2-(3-isopropoxy-5-(trifluoromethoxy)phenyl)propan-2-yl)phenyl)-5-((4-chlorobutyl)sulfonamido)benzo[b]thiophene-2-carboxamide (46.9 mg, 74%).

LC/MS ESI (+): 717 (M+1)

$^1$H-NMR (400MHz, CDCl$_3$): δ 10.57 (s, 1H), 10.00 (s, 1H), 8.29 (s, 1H), 8.03 (d, 1H, J=3.2Hz), 7.92 (s, 1H), 7.80 (s, 1H), 7.54 (s, 1H), 7.37 (d, 1H, J=8.8Hz), 7.06 (s, 1H), 6.79 (s, 1H), 6.73 (d, 2H, J=6.0Hz), 4.63-4.66 (m, 1H), 3.63-3.65 (m, 2H), 3.17-3.20 (m, 2H), 1.81 (m, 4H), 1.65 (s, 6H), 1.25 (d, 6H, J=5.6Hz)

(b) Synthesis of N-(3-chloro-5-(2-(3-isopropoxy-5-(trifluoromethoxy)phenyl)propan-2-yl)phenyl)-5-(1,1-dioxido-1,2-thiazinan-2-yl)benzo[b]thiophene-2-carboxamide N-(3-chloro-5-(2-(3-isopropoxy-5-(trifluoromethoxy)phenyl)propan-2-yl)phenyl)-5-((4-chlorobutyl)sulfonamido)benzo[b]thiophene-2-carboxamide (43.0 mg, 0.06 mmol), and K$_2$CO$_3$ (16.6 mg, 0.12 mmol) were dissolved in anhydrous DMF (1.2 mL), followed by heating at 50° C. for 13 hours. The reaction mixture was extracted with EtOAc, washed with brine, dried over anhydrous Na$_2$SO$_4$ and concentrated under reduced pressure. The residue was purified by flash column chromatography (amine silica gel, CH$_2$Cl$_2$:MeOH=20:1) to obtain N-(3-chloro-5-(2-(3-isopropoxy-5-(trifluoromethoxy)phenyl)propan-2-yl)phenyl)-5-(1,1-dioxido-1,2-thiazinan-2-yl)benzo[b]thiophene-2-carboxamide (33.5 mg, 82%) as a white solid.

LC/MS ESI (+): 681 (M+1)

$^1$H-NMR (400MHz, DMSO-d$_6$): δ 10.68 (s, 1H), 8.32 (s, 1H), 8.08 (d, 1H, J=8.7Hz), 7.94 (s, 1H), 7.92 (s, 1H), 7.54

TABLE 12

| Ex. | Compound | Analysis data |
|---|---|---|
| 209 | N-(3-chloro-5-(2-(3-isopropoxy-5-(trifluoromethoxy)phenyl)propan-2-yl)phenyl)-5-((2-morpholinoethyl)sulfonamido)benzo[b]thiophene-2-carboxamide | LC/MS ESI (+): 740 (M + 1)<br>$^1$H-NMR(400 MHz, DMSO-d$_6$): δ 10.54 (s, 1H), 9.95 (brs, 1H), 8.28 (s, 1H), 8.01 (d, 1H, J = 8.8 Hz), 7.91 (s, 1H), 7.80 (m, 1H), 7.54 (s, 1H), 7.37 (dd, 1H, J = 9.1, 1.9 Hz), 7.06 (s, 1H), 6.78 (s, 1H), 6.74 (s, 1H), 6.72 (s, 1H), 4.61~4.67 (m, 1H), 3.46~3.48 (m, 4H), 3.29~3.30 (m, 2H), 2.68~2.72 (m, 2H), 2.29~2.30 (m, 4H), 1.65 (s, 6H), 1.25 (d, 6H, J = 6.0 Hz) |
| 210 | N-(3-chloro-5-(2-(3-isopropoxy-5-(trifluoromethoxy)phenyl)propan-2-yl)phenyl)-5-((2-(hydroxy(methyl)amino)ethyl)sulfonamido)benzo[b]thiophene-2-carboxamide | LC/MS ESI (+): 700 (M + 1)<br>$^1$H-NMR(400 MHz, DMSO-d$_6$): δ 10.54 (s, 1H), 9.98 (brs, 1H), 8.28 (s, 1H), 8.02 (d, 1H, J = 8.6 Hz), 7.96 (brs, 1H), 7.91 (s, 1H), 7.80 (s, 1H), 7.55 (s, 1H), 7.37 (d, 1H, J = 8.4 Hz), 7.05 (s, 1H), 6.78 (s, 1H), 6.74 (s, 1H), 6.72 (s, 1H), 4.61~4.67 (m, 1H), 3.26~3.30 (m, 2H), 2.88~2.92 (m, 2H), 2.47 (s, 3H), 1.65 (s, 6H), 1.25 (d, 6H, J = 6.0 Hz) |

(s, 1H), 7.47 (d, 1H, J=9.0Hz), 7.07 (s, 1H), 6.79 (s, 1H), 6.73 (m, 2H), 4.61-4.67 (m, 1H), 3.74 (m, 2H), 3.35-3.38 (m, 2H), 2.20 (m, 2H), 1.86 (m, 2H), 1.65 (s, 6H), 1.25 (d, 6H, J=5.8Hz)

Example 212

Synthesis of N-(3-chloro-5-(2-(3-isopropoxy-5-(trifluoromethoxy)phenyl)propan-2-yl)phenyl)-5-(1,1-dioxidoisothiazolidin-2-yl)benzo[b]thiophene-2-carboxamide The synthesis procedure of Example 211 was repeated except for using 5-amino-N-(3-chloro-5-(2-(3-isopropoxy-5-(trifluoromethoxy)phenyl)propan-2-yl)phenyl)benzo[b]thiophene-2-carboxamide (50.0 mg, 0.09 mmol) to obtain N-(3-chloro-5-(2-(3-isopropoxy-5-(trifluoromethoxy)phenyl)propan-2-yl)phenyl)-5-(1,1-dioxidoisothiazolidin-2-yl)benzo[b]thiophene-2-carboxamide (36.0 mg, 68%).

LC/MS ESI (+): 667 (M+1)

$^1$H-NMR (400MHz, DMSO-$d_6$): δ 10.64 (s, 1H), 8.29 (s, 1H), 8.08 (d, 1H, J=9.0Hz), 7.91 (s, 1H), 7.74 (s, 1H), 7.54 (s, 1H), 7.48 (d, 1H, J=8.8Hz), 7.06 (s, 1H), 6.79 (s, 1H), 6.72-6.74 (m, 2H), 4.61-4.67 (m, 1H), 3.85 (m, 2H), 3.57 (m, 2H), 2.44-2.47 (m, 2H), 1.65 (s, 6H), 1.25 (d, 6H, J=5.8Hz)

Example 213

Synthesis of N-(3-iodo-5-(2-(3-isopropoxy-5-(trifluoromethoxy)phenyl)propan-2-yl)phenyl)-5-(methylsulfonamido)benzo[b]thiophene-2-carboxamide (a) Synthesis of 1-iodo-3-(2-(3-methoxy-5-(trifluoromethoxy)phenyl)propan-2-yl)-5-nitrobenzene 1-Bromo-3-(2-(3-methoxy-5-(trifluoromethoxy)phenyl)propan-2-yl)-5-nitrobenzene (370.0 mg, 0.85 mmol), NaI (255.0 mg, 1.70 mmol), CuI (8.1 mg, 0.04 mmol), and trans-N,N'-dimethylcyclohexane-1,2-diamine (13.4 μL, 0.09 mmol) were dissolved in 1,4-dioxane (2.0 mL), followed by refluxing at 110° C. overnight. Sat. NaHCO$_3$ aqueous solution was added to quench the reaction, and the reaction mixture was extracted with EtOAc, washed with brine, dried over anhydrous Na$_2$SO$_4$ and concentrated under reduced pressure. The residue was purified by flash column chromatography (silica gel, n-Hex:EtOAc=4:1) to obtain 1-iodo-3-(2-(3-methoxy-5-(trifluoromethoxy)phenyl)propan-2-yl)-5-nitrobenzene (362.0 mg, 88%) as a yellow liquid.

$^1$H-NMR (400MHz, CDCl$_3$): δ 8.41 (s, 1H), 8.05 (s, 1H), 7.82 (s, 1H), 6.64 (s, 2H), 6.62 (s, 1H), 3.78 (s, 3H), 1.68 (s, 6H)

(b) Synthesis of 3-(2-(3-iodo-5-nitrophenyl)propan-2-yl)-5-(trifluoromethoxy)phenol The synthesis procedure of Intermediate 41 was repeated except for using 1-iodo-3-(2-(3-methoxy-5-(trifluoromethoxy)phenyl)propan-2-yl)-5-nitrobenzene (360.0 mg, 0.75 mmol) to obtain 3-(2-(3-iodo-5-nitrophenyl)propan-2-yl)-5-(trifluoromethoxy)phenol (279.0 mg, 80%).

$^1$H-NMR (400MHz, CDCl$_3$): δ 8.41 (s, 1H), 8.05 (s, 1H), 7.82 (s, 1H), 6.62 (d, 2H, J=6.0Hz), 6.55 (s, 1H), 5.05 (s, 1H), 1.68 (s, 6H)

(c) Synthesis of 1-iodo-3-(2-(3-isopropoxy-5-(trifluoromethoxy)phenyl)propan-2-yl)-5-nitrobenzene The synthesis procedure of Intermediate 42 was repeated except for using 3-(2-(3-iodo-5-nitrophenyl)propan-2-yl)-5-(trifluoromethoxy)phenol (279.0 mg, 0.60 mmol) to obtain 1-iodo-3-(2-(3-isopropoxy-5-(trifluoromethoxy)phenyl)propan-2-yl)-5-nitrobenzene (286.0 mg, 94%).

$^1$H-NMR (400MHz, CDCl$_3$): δ 8.40 (s, 1H), 8.05 (s, 1H), 7.83 (s, 1H), 6.59-6.61 (m, 3H), 4.45-4.51 (m, 1H), 1.68 (s, 6H), 1.32 (d, 6H, J=6.4Hz)

(d) Synthesis of 3-iodo-5-(2-(3-isopropoxy-5-(trifluoromethoxy)phenyl)propan-2-yl)aniline The synthesis procedure of Intermediate 40 was repeated except for using 1-iodo-3-(2-(3-isopropoxy-5-(trifluoromethoxy)phenyl)propan-2-yl)-5-nitrobenzene (260.0 mg, 0.51 mmol) to obtain 3-iodo-5-(2-(3-isopropoxy-5-(trifluoromethoxy)phenyl)propan-2-yl)aniline (247.0 mg, quant.).

$^1$H-NMR (400MHz, CDCl$_3$): δ 6.97 (s, 1H), 6.88 (s, 1H), 6.63 (s, 2H), 6.56 (s, 1H), 6.39 (s, 1H), 4.45-4.48 (m, 1H), 3.59 (s, 2H), 1.57 (s, 6H), 1.27 (d, 6H, J=6.4Hz)

(e) Synthesis of N-(3-iodo-5-(2-(3-isopropoxy-5-(trifluoromethoxy)phenyl)propan-2-yl)phenyl)-5-(methylsulfonamido)benzo[b]thiophene-2-carboxamide The synthesis procedure of Example 1 was repeated except for using 3-Iodo-5-(2-(3-isopropoxy-5-(trifluoromethoxy)phenyl)propan-2-yl)aniline (211.0 mg, 0.43 mmol) to obtain N-(3-iodo-5-(2-(3-isopropoxy-5-(trifluoromethoxy)phenyl)propan-2-yl)phenyl)-5-(methylsulfonamido)benzo[b]thiophene-2-carboxamide (200.0 mg, 64%).

LC/MS ESI (+): 733 (M+1)

$^1$H-NMR (400MHz, DMSO-$d_6$): δ 10.49 (s, 1H), 9.88 (brs, 1H), 8.28 (s, 1H), 8.20 (s, 1H), 8.03 (d, 1H, J=8.8Hz), 7.80 (s, 1H), 7.62 (s, 1H), 7.37 (d, 1H, J=8.6Hz), 7.34 (s, 1H), 6.78 (s, 1H), 6.72 (s, 1H), 6.71 (s, 1H), 4.61-4.67 (m, 1H), 3.02 (s, 3H), 1.63 (s, 6H), 1.25 (d, 6H, J=5.7Hz)

Example 214

Synthesis of 3-iodo-N-(3-iodo-5-(2-(3-isopropoxy-5-(trifluoromethoxy)phenyl)propan-2-yl)phenyl)-5-(methylsulfonamido)benzo[b]thiophene-2-carboxamide (a) Synthesis of N-(3-(2-(3-isopropoxy-5-(trifluoromethoxy)phenyl)propan-2-yl)-5-(trimethylstannyl)phenyl)-5-(methylsulfonamido)benzo[b]thiophene-2-carboxamide N-(3-iodo-5-(2-(3-isopropoxy-5-(trifluoromethoxy)phenyl)propan-2-yl)phenyl)-5-(methylsulfonamido)benzo[b]thiophene-2-carboxamide (Example 213) (20.0 mg, 0.03 mmol), (SnMe$_3$)$_2$ (11.0 mg, 0.03 mmol), and Pd(PPh$_3$)$_4$ (3.1 mg, 3.0 μM) were dissolved in toluene (1.0 mL), followed by heating at 105° C. for 1 hour and 30 minutes. The reaction mixture was concentrated under reduced pressure, and the residue was purified by flash column chromatography (silica gel, n-Hex:EtOAc=2:1) to obtain N-(3-(2-(3-isopropoxy-5-(trifluoromethoxy)phenyl)propan-2-yl)-5-(trimethylstannyl)phenyl)-5-(methylsulfonamido)benzo[b]thiophene-2-carboxamide (19.8 mg, 95%) as a white solid.

$^1$H-NMR (400MHz, CDCl$_3$): δ 7.87 (d, 1H, J=7.6Hz), 7.83 (s, 1H), 7.79 (s, 1H), 7.71 (s, 1H), 7.65 (s, 1H), 7.40 (s, 1H), 7.28 (d, 1H, J=8.8Hz), 7.10 (s, 1H), 6.70 (s, 1H), 6.67 (s, 1H), 6.58 (s, 1H), 6.40 (s, 1H), 4.44-4.51 (m, 1H), 3.04 (s, 3H), 1.60 (s, 6H), 1.31 (d, 6H, J=6.0Hz), 0.28 (t, 9H, J=27.2Hz)

(b) Synthesis of 3-iodo-N-(3-iodo-5-(2-(3-isopropoxy-5-(trifluoromethoxy)phenyl)propan-2-yl)phenyl)-5-(methylsulfonamido)benzo[b]thiophene-2-carboxamide N-(3-(2-(3-isopropoxy-5-(trifluoromethoxy)phenyl)propan-2-yl)-5-(trimethylstannyl)phenyl)-5-(methylsulfonamido)benzo[b]thiophene-2-carboxamide (17.4 mg, 0.02 mmol), NaI (17.2 mg, 0.12 mmol), N-chlorosuccinimide (24.6 mg, 0.18 mmol), and AcOH (5.0 μL) were dissolved in MeOH (0.5 mL), followed by stirring at room temperature overnight. The reaction mixture was concentrated under reduced pressure. The residue was purified by flash column chromatography (amine silica gel, $CH_2Cl_2$MeOH=20:1) to obtain 3-iodo-N-(3-iodo-5-(2-(3-isopropoxy-5-(trifluoromethoxy)phenyl)propan-2-yl)phenyl)-5-(methylsulfonamido)benzo[b]thiophene-2-carboxamide (1.4 mg, 7%) as a white solid.

$^1$H-NMR (400MHz, DMSO-$d_6$): δ 10.66 (s, 1H), 9.71 (s, 1H), 8.48 (s, 1H), 8.19 (s, 1H), 8.03 (m, 1H), 7.64 (s, 1H), 7.57 (d, 1H, J=8.9Hz), 7.33 (s, 1H), 6.77 (s, 1H), 6.71 (m, 2H), 4.60-4.66 (m, 1H), 3.05 (s, 3H), 1.63 (s, 6H), 1.24 (d, 6H, J=5.9Hz)

Example 215 and Example 216

Synthesis of N-(3-chloro-5-(2-(3-isopropoxy-5-(trifluoromethoxy)phenyl)propan-2-yl)phenyl)-6-fluoro-5-(N-methylmethylsulfonamido)benzo[b]thiophene-2-carboxamide and N-(3-chloro-5-(2-(3-isopropoxy-5-(trifluoromethoxy)phenyl)propan-2-yl)phenyl)-6-fluoro-N-methyl-5-(N-methylmethylsulfonamido)benzo[b]thiophene-2-carboxamide N-(3-chloro-5-(2-(3-isopropoxy-5-(trifluoromethoxy)phenyl)propan-2-yl)phenyl)-6-fluoro-5-(methylsulfonamido)benzo[b]thiophene-2-carboxamide (Example 84) (30.0 mg, 0.05 mmol), $CH_3I$ (8.4 μL, 0.14 mmol), and $K_2CO_3$ (12.6 mg, 0.09 mmol) were dissolved in anhydrous DMF (1.0 mL), followed by stirring at room temperature for 14 hours. The reaction mixture was extracted with EtOAc, washed with brine, dried over anhydrous $Na_2SO_4$ and concentrated under reduced pressure. The residue was purified by flash column chromatography (silica gel, n-Hex: EtOAc=1:1) to obtain white solid compounds of N-(3-chloro-5-(2-(3-isopropoxy-5-(trifluoromethoxy)phenyl)propan-2-yl)phenyl)-6-fluoro-5-(N-methylmethylsulfonamido)benzo[b]thiophene-2-carboxamide (20.2 mg, 66%) and N-(3-chloro-5-(2-(3-isopropoxy-5-(trifluoromethoxy)phenyl)propan-2-yl)phenyl)-6-fluoro-N-methyl-5-(N-methylmethylsulfonamido)benzo[b]thiophene-2-carboxamide (10.6 mg, 34%).

Example 215

LC/MS ESI (+): 673 (M+1)
$^1$H-NMR (400MHz, DMSO-$d_6$): δ 10.70 (s, 1H), 8.31 (s, 1H), 8.20 (d, 1H, J=7.4Hz), 8.16 (d, 1H, J=10.5Hz), 7.90 (m, 1H), 7.53 (s, 1H), 7.07 (m, 1H), 6.79 (s, 1H), 6.74 (m, 1H), 6.72 (s, 1H), 4.61-4.67 (m, 1H), 3.29 (s, 3H), 3.14 (s, 3H), 1.65 (s, 6H), 1.25 (d, 6H, J=6.0Hz)

Example 216

LC/MS ESI (+): 687 (M+1)
$^1$H-NMR (400MHz, DMSO-$d_6$): δ 7.97 (d, 1H, J=7.4Hz), 7.92 (d, 1H, J=10.5Hz), 7.49 (m, 1H), 7.31 (m, 1H), 7.21 (m, 2H), 6.76 (m, 1H), 6.69 (s, 1H), 6.61 (s, 1H), 4.57-4.63 (m, 1H), 3.36 (s, 3H), 3.23 (s, 3H), 3.08 (s, 3H), 1.55 (s, 6H), 1.21 (d, 6H, J=6.0Hz)

Through the synthetic method according to Examples 215 and 216, compounds from Example 217 to Example 221 were synthesized, and the data of each example are as follows.

TABLE 13

| Ex. | Compound | Analysis data |
|---|---|---|
| 217 | N-(3-chloro-5-(2-(3-isopropoxy-5-(trifluoromethoxy)phenyl)propan-2-yl)phenyl)-6-fluoro-5-(N-(2-morpholinoethyl)methylsulfonamido)benzo[b]thiophene-2-carboxamide | LC/MS ESI (+): 772 (M + 1)<br>$^1$H-NMR(400 MHz, DMSO-$d_6$): δ 10.69 (s, 1H), 8.32 (s, 1H), 8.18 (d, 1H, J = 7.3 Hz), 8.14 (d, 1H, J = 10.2 Hz), 7.90 (m, 1H), 7.53 (s, 1H), 7.07 (m, 1H), 6.79 (s, 1H), 6.74 (m, 1H), 6.72 (s, 1H), 4.61~4.67 (m, 1H), 3.75 (m, 2H), 3.42 (m, 4H), 3.19 (s, 3H), 2.40~2.43 (m, 2H), 2.30 (m, 4H), 1.65 (s, 6H), 1.25 (d, 6H, J = 6.0 Hz) |
| 218 | N-(3-chloro-5-(2-(3-isopropoxy-5-(trifluoromethoxy)phenyl)propan-2-yl)phenyl)-6-fluoro-N-(2-morpholinoethyl)-5-(N-(2-morpholinoethyl)methylsulfonamido)benzo[b]thiophene-2-carboxamide | LC/MS ESI (+): 885 (M + 1)<br>$^1$H-NMR(400 MHz, DMSO-$d_6$): δ 7.97~7.99 (m, 1H), 7.92 (d, 1H, J = 10.3 Hz), 7.54 (s, 1H), 7.38 (s, 1H), 7.16 (s, 1H), 7.04 (s, 1H), 6.71 (s, 2H), 6.59 (s, 1H), 4.59 (m, 1H), 3.94 (brs, 2H), 3.68 (s, 2H), 3.41 (m, 8H), 3.13 (s, 3H), 2.34 (s, 4H), 2.25 (s, 8H), 1.50 (s, 6H), 1.21 (m, 6H) |
| 219 | N-(3-chloro-5-(2-(3-isopropoxy-5-(trifluoromethoxy)phenyl)propan-2-yl)phenyl)-5-(N-(2-(dimethylamino)ethyl)methylsulfonamido)-6-fluorobenzo[b]thiophene-2-carboxamide | LC/MS ESI (+): 730 (M + 1)<br>$^1$H-NMR(400 MHz, DMSO-$d_6$): δ 10.70 (s, 1H), 8.31 (s, 1H), 8.14~8.17 (m, 2H), 7.90 (m, 1H), 7.52 (s, 1H), 7.06 (m, 1H), 6.78 (s, 1H), 6.72 (m, 1H), 6.71 (s, 1H), 4.60~4.66 (m, 1H), 3.69~3.71 (m, 2H), 3.16 (s, 3H), 2.29~2.32 (m, 2H), 2.10 (s, 6H), 1.64 (s, 6H), 1.23 (d, 6H, J = 6.0 Hz) |
| 220 | N-(3-chloro-5-(4-chlorophenoxy)phenyl)-5-(N-methylmethylsulfonamido)benzo[b]thiophene-2-carboxamide | LC/MS ESI (+): 521 (M + 1)<br>$^1$H-NMR(400 MHz, DMSO-$d_6$);<br>d 10.71 (s, 1H), 8.30 (s, 1H), 8.10 (d, 1H, J = 8.7 Hz), 8.03 (d, 1H, J = 2.0 Hz), 7.76 (t, 1H, J = 1.8 Hz), 7.56 (dd, 1H, J = 8.7, 2.1 Hz), 7.51 (d, 2H, J = 8.9 Hz), 7.36 (t, 1H, J = 2.0 Hz), 7.18 (d, 2H, J = 8.9 Hz), 6.93 (t, 1H, J = 2.0 Hz), 3.32 (s, 3H), 2.99 (s, 3H) |

| Ex. | Compound | Analysis data |
|---|---|---|
| 221 | N-(3-chloro-5-(2-(4-chlorophenyl)propan-2-yl)phenyl)-5-(N-methylmethylsulfonamido)benzo[b]thiophene-2-carboxamide | LC/MS ESI (+): 547 (M + 1)<br>$^1$H-NMR(400 MHz, DMSO-d$_6$): δ 10.65 (s, 1H), 8.32 (s, 1H), 8.11 (d, 1H, J = 8.7 Hz), 8.03 (d, 1H, J = 2.0 Hz), 7.89 (t, 1H, J = 1.8 Hz), 7.56 (dd, 1H, J = 8.7, 2.1 Hz), 7.51 (s, 1H), 7.38 (d, 2H, J = 8.7 Hz), 7.28 (d, 2H, J = 8.7 Hz), 7.05 (s, 1H), 3.33 (s, 3H), 3.00 (s, 3H), 1.65 (s, 6H) |

Example 222 and Example 223

Synthesis of N-(3-chloro-5-(2-(3-isopropoxy-5-(trifluoromethoxy)phenyl)propan-2-yl)phenyl)-5-(methylsulfonamido)benzo[b]thiophene-2-carboxamide 1,1-dioxide and N-(3-chloro-5-(2-(3-isopropoxy-5-(trifluoromethoxy)phenyl)propan-2-yl)phenyl)-5-(methylsulfonamido)benzo[b]thiophene-2-carboxamide 1-oxide N-(3-chloro-5-(2-(3-isopropoxy-5-(trifluoromethoxy)phenyl)propan-2-yl)phenyl)-5-(methylsulfonamido)benzo[b]thiophene-2-carboxamide (Example 68) (10.0 mg, 0.02 mmol), and mCPBA (10.8 mg, 0.05 mmol) were dissolved in CH$_2$Cl$_2$ (1.0 mL), followed by stirring at room temperature for 7 hours. The reaction mixture was extracted with CH$_2$Cl$_2$, washed with sat. NaHCO$_3$ aqueous solution and brine, dried over anhydrous Na$_2$SO$_4$ and concentrated under reduced pressure. The residue was purified by flash column chromatography (silica gel, n-Hex:EtOAc=1:1) to obtain white solid compounds of N-(3-chloro-5-(2-(3-isopropoxy-5-(trifluoromethoxy)phenyl)propan-2-yl)phenyl)-5-(methylsulfonamido)benzo[b]thiophene-2-carboxamide 1,1-dioxide (1.2 mg, 11%) and N-(3-chloro-5-(2-(3-isopropoxy-5-(trifluoromethoxy)phenyl)propan-2-yl)phenyl)-5-(methylsulfonamido)benzo[b]thiophene-2-carboxamide 1-oxide (0.7 mg, 7%).

Example 222

LC/MS ESI (+): 673 (M+1)
$^1$H-NMR (400MHz, DMSO-d$_6$): δ 10.61 (brs, 1H), 10.53 (s, 1H), 8.32 (s, 1H), 7.87 (d, 1H, J=8.3Hz), 7.81 (m, 1H), 7.50 (m, 1H), 7.39-7.41 (m, 2H), 7.08 (m, 1H), 6.77 (s, 1H), 6.71 (m, 1H), 6.70 (s, 1H), 4.60-4.66 (m, 1H), 3.15 (s, 3H), 1.63 (s, 6H), 1.23 (d, 6H, J=6.0Hz)

Example 223

LC/MS ESI (+): 657 (M+1)
$^1$H-NMR (400MHz, DMSO-d$_6$): δ 10.64 (s, 1H), 10.43 (brs, 1H), 8.11 (s, 1H), 7.98 (d, 1H, J=8.2Hz), 7.84 (m, 1H), 7.57 (m, 1H), 7.44 (s, 1H), 7.36 (dd, 1H, J=8.3, 1.6Hz), 7.07 (s, 1H), 6.77 (s, 1H), 6.70-6.72 (m, 2H), 4.60-4.66 (m, 1H), 3.12 (s, 3H), 1.63 (s, 6H), 1.23 (d, 6H, J=5.9Hz)

Example 224

Synthesis of N-(3-(2-(3-cyanophenyl)propan-2-yl)phenyl)-5-(methylsulfonamido)benzo[b]thiophene-2-carboxamide (a) Synthesis of 3-(3-methoxybenzoyl)benzonitrile In 3-methoxybenzoyl chloride (540.0 mg, 3.16 mmol) and Pd$_2$dba$_3$·CHCl$_3$ (164.0 mg, 0.16 mmol), 0.5 M solution of (3-cyanophenyl)zinc(II) iodide in THF (6.3 mL, 6.30 mmol) was added at 0° C. The mixture was stirred at room temperature for 3 hours, and sat. NH$_4$Cl aqueous solution (15.0 mL) was added, followed by extracting with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=4:1) to obtain 3-(3-methoxybenzoyl)benzonitrile (450.0 mg, 57%) as a white solid.
$^1$H-NMR (300MHz, CDCl$_3$): δ 8.08 (s, 1H), 8.04 (d, 1H, J=7.8Hz), 7.87 (d, 1H, J=7.8Hz), 7.84 (t, 1H, J=7.8Hz), 7.42 (t, 1H, J=7.8Hz), 7.34 (s, 1H), 7.28 (d, 1H, J=7.8Hz), 7.19 (d, 1H, J=8.2Hz), 3.88 (s, 3H)

(b) Synthesis of 3-(2-(3-methoxyphenyl)propan-2-yl)benzonitrile 3-(3-Methoxybenzoyl)benzonitrile (350.0 mg, 1.47 mmol) was dissolved in dibromoethane (10.0 mL), and PCl$_5$ (1.5 g, 6.96 mmol) was added. The reaction mixture was stirred at 110° C. for 7 hours, ice water was added, and extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=1:4) to obtain 3-(dichloro(3-methoxyphenyl)methyl)benzonitrile (258.0 mg) as a yellow oil. CH$_2$Cl$_2$ (9.0 mL) was cooled to −40° C., and 1.0 M solution of TiCl$_4$ in CH$_2$Cl$_2$ (0.2 mL, 0.17 mmol) and 1.0 M solution of dimethylzinc in n-heptane (2.6 mL, 2.64 mmol) were added. After stirring for 30 minutes, separated 3-(dichloro(3-methoxyphenyl)methyl)benzonitrile (258.0 mg, 0.88 mmol) dissolved in CH$_2$Cl$_2$ (2.2 mL) was added at −40° C. After stirring at 0° C. for 2 hours, the reaction mixture was extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=4:1) to obtain 3-(2-(3-methoxyphenyl)propan-2-yl)benzonitrile (156.0 mg, 42%) as a colorless oil.
$^1$H-NMR (300MHz, CDCl$_3$): δ 7.53 (s, 1H), 7.43-7.48 (m, 2H), 7.35 (t, 1H, J=7.5Hz), 7.22 (t, 1H, J=7.6Hz), 6.74-6.77 (m, 3H), 3.78 (s, 3H), 1.67 (s, 6H)

(c) Synthesis of 3-(2-(3-hydroxyphenyl)propan-2-yl)benzonitrile 3-(2-(3-Methoxyphenyl)propan-2-yl)benzonitrile (156.0 mg, 0.62 mmol) was dissolved in CH$_2$Cl$_2$ (6.0 mL), and 1.0 M solution of BBr$_3$ in CH$_2$Cl$_2$ (1.9 mL, 1.86 mmol) was slowly added at 0° C. The reaction mixture was heated to room temperature, followed by stirring for 1 hour, and the reaction mixture was extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=4:6) to obtain 3-(2-(3-hydroxyphenyl)propan-2-yl)benzonitrile (90.0 mg, 61%) as a colorless oil.

$^1$H-NMR (300MHz, CDCl$_3$): δ 7.54 (s, 1H), 7.46 (t, 2H, J=7.3Hz), 7.36 (t, 1H, J=7.5Hz), 7.17 (t, 1H, J=7.8Hz), 6.76 (d, 1H, J=7.8Hz), 6.65-6.70 (m, 2H), 4.78 (s, 1H), 1.66 (s, 6H)

(d) Synthesis of 3-(2-(3-cyanophenyl)propan-2-yl) phenyl trifluoromethanesulfonate 3-(2-(3-Hydroxyphenyl)propan-2-yl)benzonitrile (90.0 mg, 0.38 mmol) was dissolved in CH$_2$Cl$_2$ (4.0 mL), and Tf$_2$O (96.0 μL, 0.57 mmol) was added at 0° C. The reaction mixture was heated to room temperature, followed by stirring for 3 hours, and the reaction mixture was extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=4:1) to obtain 3-(2-(3-cyanophenyl)propan-2-yl)phenyl trifluoromethanesulfonate (110.0 mg, 78%) as a colorless oil.

$^1$H-NMR (300MHz, CDCl$_3$): δ 7.48-7.54 (m, 2H), 7.35-7.43 (m, 3H), 7.19 (d, 1H, J=7.9Hz), 7.14 (d, 1H, J=8.2Hz), 7.08 (t, 1H, J=2.0Hz), 1.70 (s, 6H)

(e) Synthesis of 3-(2-(3-aminophenyl)propan-2-yl) benzonitrile 3-(2-(3-Cyanophenyl)propan-2-yl)phenyl trifluoromethanesulfonate (110.0 mg, 0.30 mmol) was dissolved in anhydrous THF (12.0 mL), and Pd$_2$(dba)$_3$ (32.0 mg, 0.03 mmol), rac-BINAP (28.0 mg, 0.05 mmol), and benzophenoneimine (60.0 μL, 0.36 mmol) were added. The mixture was refluxed at 100° C. for 5 hours. The reaction mixture was cooled to room temperature. The reaction mixture was extracted with CH$_2$Cl$_2$, washed with brine, dried over anhydrous Na$_2$SO$_4$, concentrated under reduced pressure. The residue was dissolved in anhydrous THF (12.0 mL), and 2 N HCl aqueous solution (1.6 mL, 3.00 mmol) was added. The mixture was stirred at room temperature for 5 hours, and the reaction mixture was extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=4:1) to obtain 3-(2-(3-aminophenyl)propan-2-yl)benzonitrile (30.0 mg, 42%) as a yellow oil.

LC/MS ESI (+): 237 (M+1)

$^1$H-NMR (300MHz, CDCl$_3$): δ 7.54 (t, 1H, J=1.5Hz), 7.43-7.48 (m, 2H), 7.34 (t, 1H, J=7.5Hz), 7.08 (t, 1H, J=7.6Hz), 6.59 (d, 1H, J=7.7Hz), 6.54 (d, 1H, J=8.0Hz), 6.48 (t, 1H, J=2.0Hz), 3.61 (brs, 2H), 1.64 (s, 6H)

(f) Synthesis of N-(3-(2-(3-cyanophenyl)propan-2-yl)phenyl)-5-(methylsulfonamido)benzo[b]thiophene-2-carboxamide 5-(Methylsulfonamido)benzo[b]thiophene-2-carboxylic acid (36.0 mg, 0.13 mmol), 3-(2-(3-aminophenyl)propan-2-yl)benzonitrile (30.0 mg, 0.13 mmol), and HATU (53.0 mg, 0.14 mmol) were dissolved in anhydrous DMF (1.3 mL), and DIPEA (44.0 μL, 0.24 mmol) was added. The mixture was stirred at 40° C. for 3 hours, and the reaction mixture was extracted with CH$_2$Cl$_2$. The organic extract was washed with brine, dried over anhydrous Na$_2$SO$_4$, concentrated under reduced pressure. The residue was purified by flash column chromatography (amine silica gel, CH$_2$Cl$_2$:MeOH=95:5) to obtain N-(3-(2-(3-cyanophenyl)propan-2-yl)phenyl)-5-(methylsulfonamido)benzo[b]thiophene-2-carboxamide (35.0 mg, 56%) as a white solid.

LC/MS ESI (+): 490 (M+1)

$^1$H-NMR (300MHz, DMSO-d$_6$): δ 10.40 (s, 1H), 9.87 (s, 1H), 8.28 (s, 1H), 8.01 (d, 1H, J=9.2Hz), 7.67-7.78 (m, 4H), 7.59 (s, 1H), 7.47-7.55 (m, 2H), 7.28-7.36 (m, 2H), 7.00 (d, 1H, J=8.4Hz), 3.00 (s, 3H), 1.66 (s, 6H)

Example 225

Synthesis of N-(2',4'-difluoro-[1,1'-biphenyl]-3-yl)-6-nitro-1H-indole-2-carboxamide (a) Synthesis of 2',4'-difluoro-[1,1'-biphenyl]-3-amine 3-Bromoaniline (2.0 g, 11.60 mmol), (2,4-difluorophenyl) boronic acid (1.9 g, 12.20 mmol), Pd(PPh$_3$)$_4$ (1.3 g, 1.16 mmol) and Na$_2$CO$_3$ (3.7 g, 34.90 mmol) were dissolved in a mixture of DME/H$_2$O (150.0 mL, 4/1 v/v), followed by stirring at 85° C. for 4 hours. The reaction mixture was cooled to room temperature and extracted with EtOAc. The organic extract was washed with brine, dried over anhydrous Na$_2$SO$_4$, concentrated under reduced pressure. The residue was purified by flash column chromatography (silica gel, n-Hex:EtOAc=2:1) to obtain 2',4'-difluoro-[1,1'-biphenyl]-3-amine (1.6 g, 67%) as a colorless oil.

LC/MS ESI (+): 206 (M+1)

$^1$H-NMR (300MHz, CDCl$_3$): δ 7.36-7.42 (m, 1H), 7.22 (t, 1H, J=7.8Hz), 6.82-6.96 (m, 3H), 6.81 (d, 1H, J=1.7Hz), 6.69 (d, 1H, J=8.0Hz), 3.68 (brs, 2H)

(b) Synthesis of N-(2',4'-difluoro-[1,1'-biphenyl]-3-yl)-6-nitro-1H-indole-2-carboxamide 6-Nitro-1H-indole-2-carboxylic acid (100.0 mg, 0.49 mmol), 2',4'-difluoro-[1,1'-biphenyl]-3-amine (109.0 mg, 0.53 mmol), EDC (186.0 mg, 0.97 mmol), HOBt (131.0 mg, 0.97 mmol), and DIPEA (422.0 μL, 2.43 mmol) were dissolved in anhydrous DMF (4.0 mL), followed by stirring at 10° C. for 24 hours. The reaction mixture was extracted with EtOAc, and the organic extract was washed with brine, dried over anhydrous Na$_2$SO$_4$, concentrated under reduced pressure. The residue was purified by flash column chromatography (silica gel, n-Hex:EtOAc=2:1) to obtain N-(2',4'-difluoro-[1,1'-biphenyl]-3-yl)-6-nitro-1H-indole-2-carboxamide (110.0 mg, 58%) as a yellow solid.

LC/MS ESI (+): 394 (M+1)

$^1$H-NMR (300MHz, DMSO-d$_6$): δ 12.50 (brs, 1H), 10.70 (s, 1H), 8.38 (s, 1H), 8.02 (d, 1H, J=1.5Hz), 7.91-7.94 (m, 3H), 7.57-7.65 (m, 2H), 7.51 (t, 1H, J=7.8Hz), 7.37-7.44 (m, 1H), 7.20-7.31 (m, 2H)

Through the synthetic method according to Example 225, compounds from Example 226 to Example 246 were synthesized, and the data of each example are illustrated as follows.

TABLE 14

| Ex. | Compound | Analysis data |
|---|---|---|
| 226 | 6-nitro-N-(2'-(trifluoromethyl)-[1,1'-biphenyl]-3-yl)-1H-indole-2-carboxamide | LC/MS ESI (+): 426 (M + 1)<br>¹H-NMR (300 MHz, DMSO-d₆): δ 12.50 (brs, 1H), 10.61 (brs, 1H), 8.37 (s, 1H), 7.85~7.93 (m, 5H), 7.76 (t, 1H, J = 7.4 Hz), 7.64 (t, 1H, J = 7.4 Hz), 7.59 (s, 1H), 7.10~7.47 (m, 2H), 7.09 (d, 1H, J = 7.6 Hz) |
| 227 | 5-nitro-N-(2'-(trifluoromethyl)-[1,1'-biphenyl]-3-yl)-1H-indole-2-carboxamide | LC/MS ESI (+): 426 (M + 1)<br>¹H-NMR (300 MHz, DMSO-d₆): δ 12.50 (s, 1H), 10.61 (s, 1H), 8.79 (s, 1H), 8.11 (dd, 1H, J = 9.0, 2.3 Hz), 7.84~7.91 (m, 3H), 7.76 (t, 2H, J = 7.4 Hz), 7.64 (t, 1H, J = 7.8 Hz), 7.62 (d, 1H, J = 9.2 Hz), 7.44~7.49 (m, 2H), 7.08 (d, 1H, J = 7.6 Hz) |
| 228 | 3-methyl-5-nitro-N-(2'-(trifluoromethyl)-[1,1'-biphenyl]-3-yl)-1H-indole-2-carboxamide | LC/MS ESI (+): 440 (M + 1)<br>¹H-NMR (300 MHz, DMSO-d₆): δ 12.39 (brs, 1H), 10.25 (s, 1H), 8.67 (d, 1H, J = 2.3 Hz), 8.11 (dd, 1H, J = 9.2, 2.3 Hz), 7.85 (d, 1H, J = 7.3 Hz), 7.72~7.87 (m, 3H), 7.64 (d, 1H, J = 6.5 Hz), 7.58 (d, 1H, J = 9.2 Hz), 7.43~7.48 (m, 2H), 7.08 (d, 1H, J = 8.0 Hz), 2.60 (s, 3H) |
| 229 | N-(4'-fluoro-2'-(trifluoromethyl)-[1,1'-biphenyl]-3-yl)-6-nitroindoline-2-carboxamide | LC/MS ESI (+): 446 (M + 1)<br>¹H-NMR (300 MHz, DMSO-d₆): δ 8.83 (s, 1H), 7.75 (dd, 1H, J = 8.1, 2.1 Hz), 7.64 (dd, 1H, J = 8.1, 1.2 Hz), 7.61 (d, 1H, J = 2.1 Hz), 7.56 (s, 1H), 7.22~7.47 (m, 5H), 7.07 (d, 1H, J = 7.2 Hz), 4.59~4.70 (m, 2H), 3.71 (dd, 1H, J = 18.3, 10.8 Hz), 3.28 (m, 1H) |
| 230 | 6-nitro-N-(2'-(trifluoromethyl)-[1,1'-biphenyl]-3-yl)indoline-2-carboxamide | LC/MS ESI (+): 428 (M + 1)<br>¹H-NMR (300 MHz, DMSO-d₆): δ 8.82 (s, 1H), 7.31~7.78 (m, 9H), 7.23 (s, 1H), 7.10 (d, 1H, J = 2.1 Hz), 4.59~4.70 (m, 2H), 3.71 (dd, 1H, J = 17.7, 10.5 Hz), 3.28 (dd, 1H, J = 17.7, 8.1 Hz) |
| 231 | N-(2',4'-difluoro-[1,1'-biphenyl]-3-yl)-6-nitroindoline-2-carboxamide | LC/MS ESI (+): 396 (M + 1)<br>¹H-NMR (300 MHz, DMSO-d₆): δ 8.85 (s, 1H), 7.76 (dd, 1H, J = 8.1, 1.8 Hz), 7.72 (d, 1H, J = 1.5 Hz), 7.63~7.65 (m, 2H), 7.40 (t, 2H, J = 7.8 Hz), 7.29 (s, 1H), 7.24 (s, 1H), 6.87~6.98 (m, 2H), 4.62~4.73 (m, 2H), 3.72 (dd, 1H, J = 17.7, 10.8 Hz), 3.28 (dd, 1H, J = 17.7, 8.4 Hz), |
| 232 | 6-nitro-N-(2'-(trifluoromethyl)-[1,1'-biphenyl]-3-yl)benzo[d]thiazole-2-carboxamide | LC/MS ESI (+): 444 (M + 1)<br>¹H-NMR (300 MHz, DMSO-d₆): δ 11.41 (s, 1H), 9.34 (s, 1H), 8.38~8.44 (m, 2H), 7.96~8.00 (m, 2H), 7.86 (d, 1H, J = 7.2 Hz), 7.65~7.76 (m, 2H), 7.43~7.50 (m, 2H), 7.13 (d, 1H, J = 8.1 Hz) |
| 233 | N-(2',4'-difluoro-[1,1'-biphenyl]-3-yl)-5-nitro-1H-benzo[d]imidazole-2-carboxamide | LC/MS ESI (+): 395 (M + 1)<br>¹H-NMR (300 MHz, DMSO-d₆): δ 14.11 (brs, 1H), 11.19 (s, 1H), 8.56 (s, 1H), 8.22 (dd, 1H, J = 9.0, 2.2 Hz), 8.14 (s, 1H), 7.98 (d, 1H, J = 8.0 Hz), 7.84 (d, 1H, J = 9.0 Hz), 7.60 (m, 1H), 7.50 (t, 1H, J = 7.9 Hz), 7.40 (m, 1H), 7.31 (d, 1H, J = 8.1 Hz), 7.24 (dt, 1H, J = 8.6, 2.4 Hz) |
| 234 | 5-nitro-N-(2'-(trifluoromethyl)-[1,1'-biphenyl]-3-yl)-1H-benzo[d]imidazole-2-carboxamide | LC/MS ESI (+): 427 (M + 1)<br>¹H-NMR (300 MHz, DMSO-d₆): δ 14.07 (brs, 1H), 11.19 (s, 1H), 8.55 (s, 1H), 8.21 (dd, 1H, J = 9.1, 2.2 Hz), 7.96~8.02 (m, 2H), 7.82~7.87 (m, 2H), 7.75 (t, 1H, J = 7.3 Hz), 7.64 (t, 1H, J = 7.4 Hz), 7.43~7.49 (m, 2H), 7.10 (d, 1H, J = 7.6 Hz) |
| 235 | N-(4'-fluoro-2'-(trifluoromethyl)-[1,1'-biphenyl]-3-yl)-5-nitro-1H-benzo[d]imidazole-2-carboxamide | LC/MS ESI (+): 445 (M + 1)<br>¹H-NMR (300 MHz, DMSO-d₆): δ 14.12 (brs, 1H), 11.27 (s, 1H), 8.59 (brs, 1H), 8.24 (d, 1H, J = 8.8 Hz), 7.95~8.04 (m, 2H), 7.75~7.91 (m, 2H), 7.64 (dt, 1H, J = 8.4, 2.3 Hz), 7.44~7.54 (m, 2H), 7.10 (d, 1H, J = 7.3 Hz) |
| 236 | N-(2',4'-difluoro-[1,1'-biphenyl]-3-yl)-5-methoxy-6-(methylsulfonamido)-1H-indole-2-carboxamide | LC/MS ESI (+): 472 (M + 1)<br>¹H-NMR (300 MHz, DMSO-d₆): δ 11.62 (s, 1H), 10.27 (s, 1H), 8.83 (s, 1H), 7.97 (s, 1H), 7.88 (d, 1H, J = 8.0 Hz), 7.56~7.64 (m, 1H), 7.47 (t, 1H, J = 8.4 Hz), 7.40~7.44 (m, 2H), 7.36 (s, 1H), 7.19~7.25 (m, 3H), 3.86 (s, 3H), 2.92 (s, 3H) |
| 237 | N-(2',4'-difluoro-[1,1'-biphenyl]-3-yl)-5-(methylsulfonamido)benzo[b]thiophene-2-carboxamide | LC/MS ESI (+): 459 (M + 1)<br>¹H-NMR (300 MHz, DMSO-d₆): δ 10.59 (s, 1H), 9.89 (brs, 1H), 8.35 (s, 1H), 8.03 (d, 2H, J = 8.8 Hz), 7.81~7.84 (m, 2H), 7.20~7.65 (m, 6H), 3.03 (s, 3H) |
| 238 | N-(2',4'-difluoro-[1,1'-biphenyl]-3-yl)-5-(methylsulfonamido)benzofuran-2-carboxamide | LC/MS ESI (+): 443 (M + 1)<br>¹H-NMR(300 MHz, DMSO-d₆): δ 10.64 (s, 1H), 9.76 (brs, 1H), 8.02 (brs, 1H), 7.86 (m, 1H), 7.20~7.76 (m, 9H), 2.97 (s, 3H) |
| 239 | N-(2',4'-difluoro-[1,1'-biphenyl]-3-yl)-5-(trifluoromethoxy)-1H-indole-2-carboxamide | LC/MS ESI (+): 433 (M + 1)<br>¹H-NMR (300 MHz, DMSO-d₆): δ 12.04 (s, 1H), 10.43 (s, 1H), 7.98 (s, 1H), 7.89 (d, 1H, J = 8.0 Hz), 7.74 (s, 1H), 7.47~7.65 (m, 4H), 7.36~7.40 (m, 1H), 7.20~7.28 (m, 3H) |

TABLE 14-continued

| Ex. | Compound | Analysis data |
|---|---|---|
| 240 | N-(2',4'-difluoro-[1,1'-biphenyl]-3-yl)-6-(methylsulfonyl)-1H-indole-2-carboxamide | LC/MS ESI (+): 427 (M + 1)<br>$^1$H-NMR (300 MHz, DMSO-$d_6$): δ 12.40 (s, 1H), 10.54 (s, 1H), 8.03 (s, 1H), 7.99 (s, 1H), 7.96 (d, 1H, J = 8.8 Hz), 7.90 (dd, 1H, J = 8.0, 1.9 Hz), 7.57~7.65 (m, 3H), 7.51 (t, 1H, J = 8.0 Hz), 7.37~7.44 (m, 1H), 7.20~7.30 (m, 2H), 3.21 (s, 3H) |
| 241 | N-(2',4'-difluoro-[1,1'-biphenyl]-3-yl)-3-methyl-6-(methylsulfonamido)benzo[b]thiophene-2-carboxamide | LC/MS ESI (+): 473 (M + 1)<br>$^1$H-NMR (300 MHz, DMSO-$d_6$): δ 10.44 (s, 1H), 9.88 (s, 1H), 8.02 (d, 1H, J = 8.8 Hz), 7.93 (s, 1H), 7.75 (d, 1H, J = 8.0 Hz), 7.70 (d, 1H, J = 1.9 Hz), 7.55~7.63 (m, 1H), 7.48 (t, 1H, J = 8.0 Hz), 7.36~7.43 (m, 2H), 7.29 (d, 1H, J = 7.6 Hz), 7.19~7.26 (m, 1H), 3.01 (s, 3H), 2.58 (s, 3H) |
| 242 | N-(2',4'-difluoro-[1,1'-biphenyl]-3-yl)-6-(methylsulfonamido)benzo[b]thiophene-2-carboxamide | LC/MS ESI (+): 459 (M + 1)<br>$^1$H-NMR (300 MHz, DMSO-$d_6$): δ 10.58 (s, 1H), 10.07 (s, 1H), 8.33 (s, 1H), 7.96~7.98 (m, 2H), 7.80~7.83 (m, 2H), 7.56~7.64 (m, 1H), 7.49 (t, 1H, J = 8.0 Hz), 7.36~7.44 (m, 1H), 7.19~7.33 (m, 3H), 3.08 (s, 3H) |
| 243 | N-(2',4'-difluoro-[1,1'-biphenyl]-3-yl)-3-methyl-5-(methylsulfonamido)benzo[b]thiophene-2-carboxamide | LC/MS ESI (+): 473 (M + 1)<br>$^1$H-NMR (300 MHz, DMSO-$d_6$): δ 10.44 (s, 1H), 9.88 (s, 1H), 8.02 (d, 1H, J = 8.8 Hz), 7.93 (s, 1H), 7.75 (d, 1H, J = 8.4 Hz), 7.70 (d, 1H, J = 1.9 Hz), 7.55~7.63 (m, 1H), 7.48 (t, 1H, J = 8.0 Hz), 7.35~7.43 (m, 2H), 7.29 (d, 1H, J = 8.0 Hz), 7.19~7.26 (m, 1H), 3.02 (s, 3H), 2.58 (s, 3H) |
| 244 | N-(4'-fluoro-2'-(trifluoromethyl)-[1,1'-biphenyl]-3-yl)-6-nitro-1H-indole-2-carboxamide | LC/MS ESI (+): 444 (M + 1)<br>$^1$H-NMR (300 MHz, DMSO-$d_6$): δ 12.50 (s, 1H), 10.61 (s, 1H), 8.38 (s, 1H), 7.85~7.97 (m, 4H), 7.88 (dd, 1H, J = 9.5, 2.7 Hz), 7.61~7.68 (m, 2H), 7.55 (d, 1H, J = 5.7 Hz), 7.48 (t, 1H, J = 7.8 Hz), 7.09 (d, 1H, J = 7.4 Hz) |
| 245 | N-(5-acetyl-2',4'-difluoro-[1,1'-biphenyl]-3-yl)-6-(methylsulfonamido)-1H-indole-2-carboxamide | LC/MS ESI (+): 484 (M + 1)<br>$^1$H-NMR (300 MHz, DMSO-$d_6$): δ 11.73 (s, 1H), 10.47 (s, 1H), 9.63 (brs, 1H), 8.43 (t, 1H, J = 1.7 Hz), 8.31 (m, 1H), 7.82 (m, 1H), 7.63~7.74 (m, 2H), 7.40~7.48 (m, 3H), 7.27 (dt, 1H, J = 8.6, 2.4 Hz), 6.99 (dd, 1H, J = 8.6, 2.0 Hz), 2.94 (s, 3H), 2.65 (s, 3H) |
| 246 | N-(4-(2,4-difluorophenyl)-1H-indazol-6-yl)-6-(methylsulfonamido)-1H-indole-2-carboxamide | LC/MS ESI (+): 482 (M + 1)<br>$^1$H-NMR (300 MHz, DMSO-$d_6$): δ 13.16 (s, 1H), 11.75 (s, 1H), 10.36 (s, 1H), 9.61 (brs, 1H), 8.36 (s, 1H), 7.86 (s, 1H), 7.63~7.75 (m, 2H), 7.41~7.54 (m, 4H), 7.29 (dt, 1H, J = 8.4, 2.7 Hz), 6.99 (dd, 1H, J = 8.6, 1.7 Hz), 2.95 (s, 3H) |

Example 247

Synthesis of N-(2',4'-difluoro-[1,1'-biphenyl]-3-yl)-1-methyl-6-nitro-1H-indole-2-carboxamide N-(2',4'-difluoro-[1,1'-biphenyl]-3-yl)-6-nitro-1H-indole-2-carboxamide (266.0 mg, 0.68 mmol) was dissolved in anhydrous DMF (6.0 mL), and $K_2CO_3$ (207.0 mg, 1.50 mmol) and $CH_3I$ (47.0 μL, 0.75 mmol) were added, followed by stirring at room temperature for 3 hours. The reaction mixture was extracted with EtOAc, and the organic extract was washed with brine, dried over anhydrous $Na_2SO_4$, concentrated under reduced pressure. The residue was recrystallized with a mixture of EtOAc/i-$Pr_2$O/MeOH and filtered to obtain N-(2',4'-difluoro-[1,1'-biphenyl]-3-yl)-1-methyl-6-nitro-1H-indole-2-carboxamide (163.0 mg, 59%) as a yellow solid.

LC/MS ESI (+): 408 (M+1)

$^1$H-NMR (300MHz, DMSO-$d_6$): δ 10.70 (s, 1H), 8.63 (s, 1H), 7.92-8.02 (m, 3H), 7.83 (m, 1H), 7.55-7.64 (m, 1H), 7.37-7.52 (m, 3H), 7.21-7.31 (m, 2H), 4.13 (s, 3H)

Example 248

Synthesis of N-(2',4'-difluoro-[1,1'-biphenyl]-3-yl)-1-methyl-6-(methylsulfonamido)-1H-indole-2-carboxamide (a) Synthesis of 6-amino-N-(2',4'-difluoro-[1,1'-biphenyl]-3-yl)-1-methyl-1H-indole-2-carboxamide N-(2',4'-difluoro-[1,1'-biphenyl]-3-yl)-1-methyl-6-nitro-1H-indole-2-carboxamide (Example 247) (150.0 mg, 0.37 mmol) was dissolved in a mixture of MeOH/$H_2O$ (4.0 mL, 9/1 v/v), and Zn (242.0 mg, 3.70 mmol) and $NH_4Cl$ (60.0 mg, 1.12 mmol) were added, and ultrasonificated at 40° C. for 2 hours. The reaction mixture was filtered through Celite and concentrated under reduced pressure. The residue was purified by flash column chromatography (amine silica gel, EtOAc:n-Hex=30:70) to obtain 6-amino-N-(2',4'-difluoro-[1,1'-biphenyl]-3-yl)-1-methyl-1H-indole-2-carboxamide (40.0 mg, 29%) as a gray solid.

LC/MS ESI (+): 378 (M+1)

¹H-NMR (300MHz, DMSO-d₆): δ 10.13 (s, 1H), 7.98 (s, 1H), 7.79 (d, 1H, J=5.4Hz), 7.58 (t, 1H, J=2.4Hz), 7.32-7.45 (m, 3H), 7.20-7.22 (m, 2H), 6.90 (brs, 1H), 6.51 (m, 2H), 5.22 (brs, 2H), 3.85 (s, 3H)

(b) Synthesis of N-(2',4'-difluoro-[1,1'-biphenyl]-3-yl)-1-methyl-6-(methylsulfonamido)-1H-indole-2-carboxamide 6-Amino-N-(2',4'-difluoro-[1,1'-biphenyl]-3-yl)-1-methyl-1H-indole-2-carboxamide (40.0 mg, 0.11 mmol) was dissolved in pyridine (2.0 mL), and methanesulfonyl chloride (9.4 μL, 0.12 mmol) was slowly added at 0° C. The reaction mixture was heated to room temperature, followed by stirring for 15 hours, and the reaction mixture was extracted with EtOAc. The organic extract was washed with brine, dried over anhydrous Na₂SO₄, concentrated under reduced pressure. The residue was purified by flash column chromatography (amine silica gel, EtOAc:n-Hex=60:40) to obtain N-(2',4'-difluoro-[1,1'-biphenyl]-3-yl)-1-methyl-6-(methylsulfonamido)-1H-indole-2-carboxamide (23.4 mg, 47%) as a white solid.

LC/MS ESI (+): 456 (M+1)

¹H-NMR (300MHz, DMSO-d₆): δ 10.40 (s, 1H), 9.74 (s, 1H), 8.00 (m, 1H), 7.83 (m, 1H), 7.66 (d, 1H, J=8.4Hz), 7.55-7.61 (m, 1H), 7.33-7.49 (m, 4H), 7.22-7.26 (m, 2H), 7.03 (dd, 1H, J=8.4, 1.5Hz), 3.97 (s, 3H), 2.99 (s, 3H)

Through the synthetic method according to Examples 247 and 248, compounds from Example 249 to Example 253 were synthesized, and the data of each example are as follows.

Example 254

Synthesis of 2-((2-(2',4'-difluoro-[1,1'-biphenyl]-3-yl)carbamoyl)-1H-indol-6-yl)oxy)-2-methylpropanoic acid (a) Synthesis of N-(2',4'-difluoro-[1,1'-biphenyl]-3-yl)-6-methoxy-1H-indole-2-carboxamide 6-Methoxy-1H-indole-2-carboxylic acid (69.0 mg, 0.36 mmol), 2',4'-difluoro-[1,1'-biphenyl]-3-amine (70.0 mg, 0.34 mmol), HATU (155.0 mg, 0.41 mmol), and DIPEA (89.0 μL, 0.51 mmol) were dissolved in anhydrous DMF (1.0 mL), followed by stirring at 40° C. for 12 hours. The reaction mixture was extracted with EtOAc, dried over anhydrous Na₂SO₄, concentrated under reduced pressure. The residue was purified by flash column chromatography (amine silica gel, n-Hex:EtOAc=3:1) to obtain N-(2',4'-difluoro-[1,1'-biphenyl]-3-yl)-6-methoxy-1H-indole-2-carboxamide (118.0 mg, 92%) as an off-white solid.

LC/MS ESI (+): 379 (M+1)

(b) Synthesis of N-(2',4'-difluoro-[1,1'-biphenyl]-3-yl)-6-hydroxy-1H-indole-2-carboxamide To a solution of N-(2',4'-difluoro-[1,1'-biphenyl]-3-yl)-6-methoxy-1H-indole-2-carboxamide (118.0 mg, 0.31 mmol) in CH₂Cl₂, 1.0 M solution of BBr₃ in CH₂Cl₂ (3.1 mL, 3.10 mmol) was slowly added at 0° C. The reaction mixture was extracted with EtOAc, dried over anhydrous Na₂SO₄, concentrated under reduced pressure. The residue was purified by flash column chromatography (silica gel, n-Hex:

TABLE 15

| Ex. | Compound | Analysis data |
|---|---|---|
| 249 | 1-methyl-6-nitro-N-(2'-(trifluoromethyl)-[1,1'-biphenyl]-3-yl)-1H-indole-2-carboxamide | LC/MS ESI (+): 440 (M + 1)<br>¹H-NMR (300 MHz, DMSO-d₆): δ 8.42 (s, 1H), 8.07 (dd, 1H, J = 9.0, 1.5 Hz), 7.96 (s, 1H), 7.77 (d, 1H, J = 7.4 Hz), 7.75 (d, 1H, J = 8.8 Hz), 7.70 (d, 1H, J = 8.8 Hz), 7.62 (s, 1H), 7.58 (d, 1H, J = 7.8 Hz), 7.45 (m, 3H), 7.19 (d, 1H, J = 7.3 Hz), 7.08 (s, 1H), 4.18 (s, 3H) |
| 250 | 1-methyl-5-nitro-N-(2'-(trifluoromethyl)-[1,1'-biphenyl]-3-yl)-1H-indole-2-carboxamide | LC/MS ESI (+): 440 (M + 1)<br>¹H-NMR (300 MHz, DMSO-d₆): δ 8.66 (d, 1H, J = 1.9 Hz), 8.25 (dd, 1H, J = 9.2, 2.1 Hz), 7.97 (s, 1H), 7.77 (d, 1H, J = 7.6 Hz), 7.70 (dd, 1H, J = 8.0, 1.1 Hz), 7.62 (s, 1H), 7.58 (d, 1H, J = 7.8 Hz), 7.45 (m, 4H), 7.18 (m, 2H), 4.14 (s, 3H) |
| 251 | 3-methyl-1-(2-morpholinoethyl)-5-nitro-N-(2'-(trifluoromethyl)-[1,1'-biphenyl]-3-yl)-1H-indole-2-carboxamide | LC/MS ESI (+): 553 (M + 1)<br>¹H-NMR (300 MHz, DMSO-d₆): δ 10.69 (s, 1H), 8.66 (d, 1H, J = 2.2 Hz), 8.13 (dd, 1H, J = 9.2, 2.2 Hz), 7.78~7.86 (m, 5H), 7.63 (t, 1H, J = 7.7 Hz), 7.45 (t, 2H, J = 7.7 Hz), 7.08 (d, 1H, J = 7.4 Hz), 4.55 (t, 2H, J = 5.5 Hz), 3.38 (t, 4H, J = 4.4 Hz), 2.56 (t, 2H, y = 5.9 Hz), 2.51 (s, 3H), 2.31 (t, 4H, J = 4.4 Hz) |
| 252 | 1-(2-morpholinoethyl)-6-nitro-N-(2'-(trifluoromethyl)-[1,1'-biphenyl]-3-yl)-1H-indole-2-carboxamide | LC/MS ESI (+): 539 (M + 1)<br>¹H-NMR (300 MHz, DMSO-d₆): δ 10.76 (s, 1H), 8.66 (d, 1H, J = 2.2 Hz), 7.98~8.01 (m, 1H), 7.93 (s, 1H), 7.81~7.90 (m, 4H), 7.78 (t, 1H, J = 7.6 Hz), 7.42~7.48 (m, 2H), 7.33 (s, 1H), 7.07 (d, 1H, J = 8.4 Hz), 4.80 (t, 2H, J = 5.5 Hz), 3.35 (t, 4H, J = 4.4 Hz), 2.53~2.58 (m, 2H), 2.27~2.36 (m, 4H) |
| 253 | 1-methyl-6-(methylsulfonamido)-N-(2'-(trifluoromethyl)-[1,1'-biphenyl]-3-yl)-1H-indole-2-carboxamide | LC/MS ESI (+): 488 (M + 1)<br>¹H-NMR (300 MHz, DMSO-d₆): δ 10.39 (s, 1H), 9.71 (s, 1H), 7.81~7.87 (m, 3H), 7.74 (t, 1H, J = 7.3 Hz), 7.66 (d, 1H, J = 8.6 Hz), 7.64 (t, 1H, J = 7.4 Hz), 7.40~7.45 (m, 2H), 7.31~7.34 (m, 2H), 7.01~7.06 (m, 2H), 3.95 (s, 3H), 2.99 (s, 3H) |

EtOAc=2:1) to obtain N-(2',4'-difluoro-[1,1'-biphenyl]-3-yl)-6-hydroxy-1H-indole-2-carboxamide (21.0 mg, 19%) as an off-white solid.

LC/MS ESI (+): 365 (M+1)

$^1$H-NMR (300MHz, DMSO-$d_6$): δ 11.34 (s, 1H), 10.14 (s, 1H), 9.29 (s, 1H), 7.96 (d, 1H, J=1.2Hz), 7.87 (m, 1H), 7.55-7.64 (m, 1H), 7.33-7.54 (m, 4H), 7.19-7.26 (m, 2H), 6.81 (d, 1H, J=1.8Hz), 6.60 (dd, 1H, J=8.7, 2.1Hz)

(c) Synthesis of ethyl 2-((2-((2',4'-difluoro-[1,1'-biphenyl]-3-yl)carbamoyl)-1H-indol-6-yl)oxy)-2-methylpropanoate N-(2',4'-difluoro-[1,1'-biphenyl]-3-yl)-6-hydroxy-1H-indole-2-carboxamide (30.0 mg, 0.08 mmol) was dissolved in DMSO (5.0 mL), and KOH (7.0 mg, 0.12 mmol) was added, followed by stirring at room temperature for 10 minutes. Ethyl α-bromoisobutyrate (13.2 μL, 0.09 mmol) was added at room temperature, followed by stirring for 12 hours. The reaction mixture was extracted with EtOAc, dried over anhydrous $Na_2SO_4$, concentrated under reduced pressure. The residue was purified by flash column chromatography (silica gel, n-Hex:EtOAc=2:1) to obtain ethyl 2-((2-((2',4'-difluoro-[1,1'-biphenyl]-3-yl)carbamoyl)-1H-indol-6-yl)oxy)-2-methylpropanoate (20.0 mg, 51%) as an off-white solid.

LC/MS ESI (+): 479 (M+1)

(d) Synthesis of 2-((2-((2',4'-difluoro-[1,1'-biphenyl]-3-yl)carbamoyl)-1H-indol-6-yl)oxy)-2-methylpropanoic acid Ethyl 2-((2-((2',4'-difluoro-[1,1'-biphenyl]-3-yl)carbamoyl)-1H-indol-6-yl)oxy)-2-methyl propanoate (26.0 mg, 0.05 mmol) was dissolved in a mixture of THF/MeOH/$H_2O$ (4.0 mL, 1/2.4/0.6 v/v), and LiOH·$H_2O$ (3.0 mg, 0.13 mmol) was added. After stirring at room temperature for 12 hours, and after the reaction was complete, the reaction mixture was concentrated under reduced pressure. The residue was dissolved in $H_2O$ (1.0 mL) and acidified to pH 1-2 with 1 N HCl. The precipitate was filtered and dried under reduced pressure to obtain 2-((2-((2',4'-difluoro-[1,1'-biphenyl]-3-yl)carbamoyl)-1H-indol-6-yl)oxy)-2-methylpropanoic acid (7.7 mg, 35%) as a white solid.

LC/MS ESI (+): 451 (M+1)

$^1$H-NMR (300MHz, DMSO-$d_6$): 0.3-13.0 (brs, 1H), 11.57 (s, 1H), 10.22 (s, 1H), 7.97 (s, 1H), 7.94 (m, 1H), 7.25-7.63 (m, 5H), 7.19-7.23 (m, 2H), 6.91 (d, 1H, J=2.4Hz), 6.68 (dd, 1H, J=8.7, 2.4Hz), 1.53 (s, 6H)

Through the synthetic method according to Example 254, compounds of Example 255 and Example 256 were synthesized, and the data of each example are as follows.

Example 257

Synthesis of N-(2',4'-difluoro-[1,1'-biphenyl]-3-yl)-6-((N-methylsulfamoyl)amino)-1H-indole-2-carboxamide (a) Synthesis of N-(2',4'-difluoro-[1,1'-biphenyl]-3-yl)-6-nitro-1H-indole-2-carboxamide 6-Nitro-1H-indole-2-carboxylic acid (300.0 mg, 1.46 mmol), 2',4'-difluoro-[1,1'-biphenyl]-3-amine (328.0 mg, 1.60 mmol), EDC (556.0 mg, 2.91 mmol), HOBt (393.0 mg, 2.91 mmol), and DIPEA (1.3 mL, 7.28 mmol) were dissolved in anhydrous DMF (15.0 mL), followed by stirring at 10° C. for 24 hours. The reaction mixture was extracted with EtOAc, washed with brine, dried over anhydrous $Na_2SO_4$, concentrated under reduced pressure. The residue was purified by flash column chromatography (silica gel, n-Hex:EtOAc=2:1) to obtain N-(2',4'-difluoro-[1,1'-biphenyl]-3-yl)-6-nitro-1H-indole-2-carboxamide (392.0 mg, 69%) as a yellow solid.

LC/MS ESI (+): 394 (M+1)

(b) Synthesis of tert-butyl 2-((2',4'-difluoro-[1,1'-biphenyl]-3-yl)carbamoyl)-6-nitro-1H-indole-1-carboxylate N-(2',4'-difluoro-[1,1'-biphenyl]-3-yl)-6-nitro-1H-indole-2-carboxamide (392.0 mg, 1.00 mmol), $Boc_2O$ (239.0 mg, 1.10 mmol), and $Et_3N$ (278.0 μL, 1.99 mmol) were dissolved in anhydrous DMF (4.0 mL), followed by stirring at room temperature for 24 hours. The reaction mixture was extracted with EtOAc, and the organic extract was washed with brine, dried over anhydrous $Na_2SO_4$, concentrated under reduced pressure. The residue was purified by flash column chromatography (silica gel, n-Hex:EtOAc=2:1) to obtain tert-butyl 2-((2',4'-difluoro-[1,1'-biphenyl]-3-yl)carbamoyl)-6-nitro-1H-indole-1-carboxylate (302.0 mg, 62%) as a yellow solid.

LC/MS ESI (+): 494 (M+1)

(c) Synthesis of tert-butyl 6-amino-2-((2',4'-difluoro-[1,1-biphenyl]-3-yl)carbamoyl)-1H-indole-1-carboxylate tert-Butyl 2-((2',4'-difluoro-[1,1'-biphenyl]-3-yl)carbamoyl)-6-nitro-1H-indole-1-carboxylate (302.0 mg, 0.61 mmol), Zn (600.0 mg, 9.18 mmol), and $NH_4Cl$ (164.0 mg, 3.06 mmol) were dissolved in a mixture of MeOH/$H_2O$ (2.5 mL, 4/1 v/v), and ultrasonificated for 2 hours. The reaction mixture was extracted with $CH_2Cl_2$, dried over anhydrous $Na_2SO_4$, concentrated under reduced pressure. The residue was purified by flash column chromatography (silica gel, $CH_2Cl_2$:MeOH=99:1) to obtain tert-butyl 6-amino-2-((2',4'-

TABLE 16

| Ex. | Compound | Analysis data |
| --- | --- | --- |
| 255 | ethyl 2-((2-((2',4'-difluoro-[1,1'-biphenyl]-3-yl)carbamoyl)-1H-indol-6-yl)oxy)acetate | LC/MS ESI (+): 451 (M + 1)<br>$^1$H-NMR (300 MHz, DMSO-$d_6$): δ 9.13 (brs, 1H), 7.80 (d, 2H, J = 11.4 Hz), 7.68 (m, 1H), 7.57 (d, 1H, J = 8.7 Hz), 7.41~7.49 (m, 2H), 7.30 (m, 1H), 6.86~6.90 (m, 5H), 4.68 (s, 2H), 4.29 (q, 2H, J = 7.2 Hz), 1.32 (t, 3H, J = 7.2 Hz) |
| 256 | 2-((2-((2',4'-difluoro-[1,1'-biphenyl]-3-yl)carbamoyl)-1H-indol-6-yl)oxy)acetic acid | LC/MS ESI(+): 423 (M + 1)<br>$^1$H-NMR (300 MHz, DMSO-$d_6$): δ 13.13 (brs, 1H), 11.56 (brs, 1H), 10.22 (brs, 1H), 7.97 (m, 1H), 7.87 (d, 1H, J = 8.0 Hz), 7.56~7.64 (m, 2H), 7.36~7.49 (m, 3H), 7.20~7.25 (m, 2H), 6.85 (m, 1H), 6.75 (dd, 1H, J = 8.8, 2.3 Hz), 4.68 (s, 2H) | difluoro-[1,1'-biphenyl]-3-yl)carbamoyl)-1H-indole-1-carboxylate (218.0 mg, 77%) as a white solid.

LC/MS ESI (+): 464 (M+1)

(d) Synthesis of tert-butyl 2-((2',4'-difluoro-[1,1'-biphenyl]-3-yl)carbamoyl)-6-((N-methylsulfamoyl)amino)-1H-indole-1-carboxylate tert-Butyl 6-amino-2-((2',4'-difluoro-[1,1'-biphenyl]-3-yl)carbamoyl)-1H-indole-1-carboxylate (35.0 mg, 0.08 mmol), and DMAP (32.0 mg, 0.26 mmol) were dissolved in $CH_3CN$ (3.0 mL), and methylsulfamoyl chloride (11.0 mg, 0.08 mmol) was slowly added at 0° C., followed by refluxing at 100° C. for 48 hours. The reaction mixture was extracted with EtOAc, washed with brine, dried over anhydrous $Na_2SO_4$, concentrated under reduced pressure to obtain tert-butyl 2-((2',4'-difluoro-[1,1'-biphenyl]-3-yl)carbamoyl)-6-((N-methylsulfamoyl)amino)-1H-indole-1-carboxylate (44.5 mg) as a white solid.

LC/MS ESI (+): 557 (M+1)

(e) Synthesis of N-(2',4'-difluoro-[1,1'-biphenyl]-3-yl)-6-((N-methylsulfamoyl)amino)-1H-indole-2-carboxamide Crude tert-butyl 2-((2',4'-difluoro-[1,1'-biphenyl]-3-yl)carbamoyl)-6-((N-methylsulfamoyl)amino)-1H-indole-1-carboxylate (44.5 mg) was dissolved in $CH_2Cl_2$ (2.0 mL), and TFA (0.5 mL) was slowly added. After stirring at room temperature for 1 hour, 1 N NaOH aqueous solution was added to quench the reaction. The reaction mixture was extracted with EtOAc, washed with brine, dried over anhydrous $Na_2SO_4$, concentrated under reduced pressure. The residue was purified by flash column chromatography (silica gel, $CH_2Cl_2$:MeOH=99:1) to obtain N-(2',4'-difluoro-[1,1'-biphenyl]-3-yl)-6-((N-methylsulfamoyl)amino)-1H-indole-2-carboxamide (14.3 mg, 2 step yield: 41%) as an off-white solid.

LC/MS ESI (+): 457 (M+1)

$^1$H-NMR (300MHz, DMSO-$d_6$): δ 11.65 (s, 1H), 10.23 (s, 1H), 9.60 (s, 1H), 7.98 (m, 1H), 7.86-7.89 (m, 1H), 7.56-7.64 (m, 2H), 7.47 (t, 1H, J=7.8Hz), 7.35-7.43 (m, 3H), 7.19-7.26 (m, 2H), 7.16 (d, 1H, J=5.1Hz), 6.98 (dd, 1H, J=9.0, 1.7Hz), 2.47 (d, 3H, J=5.0Hz)

Through the synthetic method according to Example 257, compounds from Example 258 to Example 279 were synthesized, and the data of each example are as follows.

TABLE 17

| Ex. | Compound | Analysis data |
|---|---|---|
| 258 | 5-amino-N-(2'-(trifluoromethyl)-[1,1'-biphenyl]-3-yl)-1H-indole-2-carboxamide | LC/MS ESI (+): 396 (M + 1)<br>$^1$H-NMR (300 MHz, DMSO-$d_6$): δ 9.17 (s, 1H), 7.86 (s, 1H), 7.70~7.77 (m, 2H), 7.55~7.61 (m, 2H), 7.36~7.51 (m, 3H), 7.25 (d, 1H, J = 7.4 Hz), 7.13 (d, 1H, J = 7.4 Hz), 6.93 (d, 1H, J = 1.9 Hz), 6.81 (d, 1H, J = 1.5 Hz), 6.78 (dd, 1H, J = 8.6, 2.1 Hz), 3.60 (s, 2H) |
| 259 | 5-(methylsulfonamido)-N-(2'-(trifluoromethyl)-[1,1'-biphenyl]-3-yl)-1H-indole-2-carboxamide | LC/MS ESI (+): 474 (M + 1)<br>$^1$H-NMR (300 MHz, DMSO-$d_6$): δ 11.80 (s, 1H), 10.30 (s, 1H), 9.38 (s, 1H), 7.83~7.89 (m, 3H), 7.75 (t, 1H, J = 7.8 Hz), 7.64 (t, 1H, J = 7.8 Hz), 7.52 (d, 1H, J = 1.7 Hz), 7.39~7.47 (m, 4H), 7.13 (dd, 1H, J = 8.5, 1.9 Hz), 7.05 (d, 1H, J = 7.6 Hz), 2.90 (s, 3H) |
| 260 | 6-(methylsulfonamido)-N-(2'-(trifluoromethyl)-[1,1'-biphenyl]-3-yl)-1H-indole-2-carboxamide | LC/MS ESI (+): 474 (M + 1)<br>$^1$H-NMR (300 MHz, DMSO-$d_6$): δ 9.35 (s, 1H), 7.87 (s, 1H), 7.73 (m, 2H), 7.60~7.65 (m, 2H), 7.57 (d, 1H, J = 7.3 Hz), 7.51 (d, 1H, J = 7.6 Hz), 7.41~7.46 (m, 2H), 7.37 (d, 1H, J = 7.4 Hz), 7.16 (d, 1H, J = 8.2 Hz), 6.98 (m, 2H), 6.57 (s, 1H), 3.02 (s, 3H) |
| 261 | N-(2',4'-difluoro-[1,1'-biphenyl]-3-yl)-6-(methylsulfonamido)indoline-2-carboxamide | LC/MS ESI (+): 444 (M + 1)<br>$^1$H-NMR (300 MHz, DMSO-$d_6$): δ 9.99 (s, 1H), 9.35 (brs, 1H), 7.86 (s, 1H), 7.69 (dd, 1H, J = 7.8, 2.0 Hz), 7.51~7.57 (m, 1H), 7.33~7.44 (m, 2H), 7.16~7.22 (m, 2H), 6.91 (d, 1H, J = 7.8 Hz), 6.51 (s, 1H), 6.41 (d, 1H, J = 7.8 Hz), 6.21 (s, 1H), 4.37~4.44 (m, 1H), 3.24~3.27 (m, 1H), 2.97~3.06 (m, 1H), 2.89 (s, 3H) |
| 262 | N-(4'-fluoro-2'-(trifluoromethyl)-[1,1'-biphenyl]-3-yl)-6-(methylsulfonamido)indoline-2-carboxamide | LC/MS ESI (+): 494 (M + 1)<br>$^1$H-NMR (300 MHz, DMSO-$d_6$): δ 10.00 (s, 1H), 9.35 (brs, 1H), 7.68~7.75 (m, 3H), 7.56~7.60 (m, 1H), 7.34~7.48 (m, 2H), 6.89~7.00 (m, 2H), 6.49 (s, 1H), 6.38~6.42 (m, 1H), 6.15~6.20 (m, 1H), 4.39~4.43 (m, 1H), 3.24~3.27 (m, 1H), 2.97~3.07 (m, 1H), 2.87 (s, 3H) |
| 263 | tert-butyl 6-nitro-2-((2'-(trifluoromethyl)-[1,1'-biphenyl]-3-yl)carbamoyl)-1H-indole-1-carboxylate | LC/MS ESI (+): 526 (M + 1)<br>$^1$H-NMR (300 MHz, DMSO-$d_6$): δ 10.94 (s, 1H), 8.97 (d, 1H, J = 2.1 Hz), 8.20 (dd, 1H, J = 8.8, 2.1 Hz), 7.96 (d, 1H, J = 8.6 Hz), 7.83~7.86 (m, 2H), 7.72~7.78 (m, 2H), 7.64 (t, 1H, J = 7.6 Hz), 7.44 (q, 2H, J = 7.8 Hz), 7.28 (d, 1H, J = 0.8 Hz), 7.07 (d, 1H, J = 7.4 Hz), 1.47 (s, 9H) |
| 264 | 6-(2,2,2-trifluoroethylsulfonamido)-N-(2'-(trifluoromethyl)-[1,1'-biphenyl]-3-yl)-1H-indole-2-carboxamide | LC/MS ESI (+): 542 (M + 1)<br>$^1$H-NMR (300 MHz, DMSO-$d_6$): δ 11.78 (s, 1H), 10.36 (s, 1H), 10.28 (s, 1H), 7.84~7.89 (m, 3H), 7.75 (t, 1H, J = 7.8 Hz), 7.61~7.67 (m, 2H), 7.42~7.46 (m, 4H), 7.05 (d, 1H, J = 7.6 Hz), 6.99 (dd, 1H, 7 = 8.4, 1.5 Hz), 4.42 (q, 2H, J = 9.7 Hz) |

TABLE 17-continued

| Ex. | Compound | Analysis data |
|---|---|---|
| 265 | 6-(sulfamoylamino)-N-(2'-(trifluoromethyl)-[1,1'-biphenyl]-3-yl)-1H-indole-2-carboxamide | LC/MS ESI (+): 475 (M + 1)<br>$^1$H-NMR (300 MHz, DMSO-$d_6$): δ 11.63 (s, 1H), 10.21 (s, 1H), 9.33 (brs, 1H), 7.83~7.88 (m, 3H), 7.72 (t, 1H, J = 7.6 Hz), 7.64 (t, 1H, J = 8.0 Hz), 7.56 (d, 1H, J = 8.8 Hz), 7.40~7.47 (m, 2H), 7.33~7.36 (m, 2H), 6.94~6.99 (m, 4H) |
| 266 | 6-(methylsulfonamido)-N-(2'-(trifluoromethyl)-[1,1'-biphenyl]-3-yl)-1H-indole-3-carboxamide | LC/MS ESI (+): 474 (M + 1)<br>$^1$H-NMR (300 MHz, DMSO-$d_6$): δ 11.73 (s, 1H), 9.83 (s, 1H), 9.59 (s, 1H), 8.27 (d, 1H, J = 2.6 Hz), 8.09 (d, 1H, J = 8.5 Hz), 7.74~7.86 (m, 3H), 7.74 (t, 1H, J = 7.4 Hz), 7.63 (t, 1H, J = 7.2 Hz), 7.36~7.46 (m, 3H), 7.03 (dd, 1H, J = 8.5, 1.1 Hz), 6.98 (d, 1H, J = 7.5 Hz), 2.92 (s, 3H) |
| 267 | 6-((N,N-dimethylsulfamoyl)amino)-N-(2'-(trifluoromethyl)-[1,1'-biphenyl]-3-yl)-1H-indole-2-carboxamide | LC/MS ESI (+): 503 (M + 1)<br>$^1$H-NMR (300 MHz, DMSO-$d_6$): δ 11.64 (s, 1H), 10.22 (s, 1H), 9.82 (s, 1H), 7.81~7.88 (m, 3H), 7.75 (t, 1H, J = 7.6 Hz), 7.55~7.66 (m, 2H), 7.45 (dd, 1H, J = 7.4, 2.3 Hz), 7.42 (d, 1H, J = 8.0 Hz), 7.38 (d, 2H, J = 1.5 Hz), 7.04 (d, 1H, J = 7.4 Hz), 6.98 (dd, 1H, J = 9.0, 1.9 Hz), 2.69 (s, 6H) |
| 268 | N-(2'-(trifluoromethyl)-[1,1'-biphenyl]-3-yl)-6-(trifluoromethylsulfonamido)-1H-indole-2-carboxamide | LC/MS ESI (+): 528 (M + 1)<br>$^1$H-NMR (300 MHz, DMSO-$d_6$): δ 11.87 (s, 1H), 11.81 (brs, 1H), 10.34 (s, 1H), 7.83~7.89 (m, 3H), 7.70~7.77 (m, 2H), 7.64 (t, 1H, y = 7.6 Hz), 7.41~7.47 (m, 4H), 7.05 (d, 1H, J = 7.6 Hz), 6.98 (dd, 1H, J = 8.6, 1.7 Hz) |
| 269 | 6-((N-methylsulfamoyl)amino)-N-(2'-(trifluoromethyl)-[1,1'-biphenyl]-3-yl)-1H-indole-2-carboxamide | LC/MS ESI (+): 489 (M + 1)<br>$^1$H-NMR (300 MHz, DMSO-$d_6$): δ 11.65 (s, 1H), 10.21 (s, 1H), 9.57 (brs, 1H), 7.83~7.88 (m, 3H), 7.75 (t, 1H, J = 7.4 Hz), 7.64 (t, 1H, J = 7.4 Hz), 7.57 (d, 1H, J = 8.6 Hz), 7.34~7.46 (m, 4H), 7.13 (m, 1H), 7.03 (m, 1H), 6.97 (dd, 1H, J = 8.6, 1.7 Hz), 2.47 (d, 3H, J = 5.0 Hz) |
| 270 | N-(2',4'-difluoro-[1,1'-biphenyl]-3-yl)-6-(methylsulfonamido)-1H-indole-2-carboxamide | LC/MS ESI (+): 442 (M + 1)<br>$^1$H-NMR (300 MHz, DMSO-$d_6$): δ 11.7 (s, 1H), 10.3 (s, 1H), 9.63 (s, 1H), 7.98 (d, 1H, J = 1.5 Hz), 7.88 (dd, 1H, J = 8.2, 1.5 Hz), 7.56~7.74 (m, 2H), 7.48 (t, 1H, 7 = 8.0 Hz), 7.36~7.44 (m, 3H), 7.20~7.26 (m, 2H), 6.99 (dd, 1H, J = 8.6, 1.7 Hz), 2.94 (s, 3H) |
| 271 | 6-amino-N-(2',4'-difluoro-[1,1'-biphenyl]-3-yl)-1H-indole-2-carboxamide | LC/MS ESI (+): 364 (M + 1)<br>$^1$H-NMR (300 MHz, DMSO-$d_6$): δ 8.97 (s, 1H), 7.79~7.90 (m, 2H), 7.65~7.68 (m, 1H), 7.41~7.49 (m, 3H), 7.28~7.30 (m, 1H), 6.89~7.00 (m, 3H), 6.65~6.68 (m, 1H), 6.62 (dd, 1H, J = 8.6, 2.1 Hz), 3.80 (brs, 2H) |
| 272 | N-(2',4'-difluoro-[1,1'-biphenyl]-3-yl)-5-(methylsulfonamido)-1H-indole-2-carboxamide | LC/MS ESI (+): 442 (M + 1)<br>$^1$H-NMR (300 MHz, DMSO-$d_6$): δ 11.81 (s, 1H), 10.33 (s, 1H), 9.39 (brs, 1H), 7.98 (d, 1H, J = 1.4 Hz), 7.88 (d, 1H, J = 7.9 Hz), 7.57~7.65 (m, 1H), 7.37~7.52 (m, 5H), 7.20~7.28 (m, 2H), 7.13 (dd, 1H, J = 8.8, 2.3 Hz), 2.90 (s, 3H) |
| 273 | N-(2',4'-difluoro-[1,1'-biphenyl]-3-yl)-6-(2,2,2-trifluoroethylsulfonamido)-1H-indole-2-carboxamide | LC/MS ESI (+): 510 (M + 1)<br>$^1$H-NMR (300 MHz, DMSO-$d_6$);<br>d 11.79 (s, 1H), 10.36 (s, 1H), 10.31 (s, 1H), 7.99 (m, 1H), 7.88 (d, 1H, J = 8.2 Hz), 7.67 (d, 1H, J = 8.8 Hz), 7.56~7.62 (m, 1H), 7.48 (t, 1H, J = 8.0 Hz), 7.37~7.44 (m, 3H), 7.20~7.27 (m, 2H), 6.99 (dd, 1H, J = 8.6, 1.9 Hz), 4.42 (q, 2H, J = 9.7 Hz) |
| 274 | N-(2',4'-difluoro-[1,1'-biphenyl]-3-yl)-6-(sulfamoylamino)-1H-indole-2-carboxamide | LC/MS ESI (+): 443 (M + 1)<br>$^1$H-NMR (300 MHz, DMSO-$d_6$): δ 11.65 (s, 1H), 10.24 (s, 1H), 9.33 (s, 1H), 7.98 (m, 1H), 7.86~7.89 (m, 1H), 7.55~7.64 (m, 2H), 7.40~7.50 (m, 2H), 7.34~7.38 (m, 2H), 7.20~7.26 (m, 2H), 6.96~7.00 (m, 3H) |
| 275 | N-(2'4'-difluoro-[1,1'-biphenyl]-3-yl)-6-(methylsulfonamido)-1H-indole-3-carboxamide | LC/MS ESI (+): 442 (M + 1)<br>$^1$H-NMR (300 MHz, DMSO-$d_6$): δ 11.74 (s, 1H), 9.85 (s, 1H), 9.60 (s, 1H), 8.28 (d, 1H, J = 2.4 Hz), 8.11 (d, 1H, J = 8.5 Hz), 7.99 (s, 1H), 7.81 (d, 1H, J = 8.3 Hz), 7.59 (m, 1H), 7.36~7.46 (m, 3H), 7.17~7.26 (m, 2H), 7.04 (d, 1H, J = 8.1 Hz), 2.93 (s, 3H) |
| 276 | N-(2',4'-difluoro-[1,1'-biphenyl]-3-yl)-6-((N,N-dimethylsulfamoyl)amino)-1H-indole-2-carboxamide | LC/MS ESI (+): 471 (M + 1)<br>$^1$H-NMR (300 MHz, DMSO-$d_6$); d11.64 (s, 1H), 10.25 (s, 1H), 9.82 (brs, 1H), 7.97 (m, 1H), 7.87 (m, 1H), 7.56~7.64 (m, 2H), 7.50 (t, 1H, J = 7.8 Hz), 7.36~7.44 (m, 3H), 7.20~7.26 (m, 2H), 6.98 (dd, 1H, J = 8.6, 1.7 Hz), 2.69 (s, 6H) |
| 277 | N-(4'-fluoro-2'-(trifluoromethyl)-[1,1'-biphenyl]-3-yl)-6-(methylsulfonamido)-1H-indole-2-carboxamide | LC/MS ESI (+): 492 (M + 1)<br>$^1$H-NMR (300 MHz, DMSO-$d_6$): δ 9.29 (s, 1H), 7.86 (s, 1H), 7.61~7.71 (m, 3H), 7.43~7.49 (m, 3H), 7.34~7.41 (m, 1H), 7.27~7.31 (m, 1H), 7.12 (d, 1H, J = 7.8 Hz), 6.99~7.00 (m, 1H), 6.91 (d, 1H, J = 2.0 Hz), 6.52 (s, 1H), 3.03 (s, 3H) |

TABLE 17-continued

| Ex. | Compound | Analysis data |
|---|---|---|
| 278 | 6-(cyclopropanesulfon-amido)-N-(4-(2,4-difluorophenyl)pyridin-2-yl)-1H-indole-2-carboxamide | LC/MS ESI (+): 469 (M + 1)<br>$^1$H-NMR (300 MHz, DMSO-d$_6$): δ 11.72 (s, 1H), 10.95 (s, 1H), 9.68 (s, 1H), 8.49 (d, 1H, J = 5.1 Hz), 8.44 (s, 1H), 7.74 (m, 1H), 7.58~7.62 (m, 2H), 7.42~7.52 (m, 2H), 7.26~7.36 (m, 2H), 7.01 (m, 1H), 2.58 (m, 1H), 0.89~0.91 (m, 4H) |
| 279 | N-(4-(2,4-difluorophenyl)pyridin-2-yl)-6-(methylsulfonamido)-1H-indole-2-carboxamide | LC/MS ESI (+): 443 (M + 1)<br>$^1$H-NMR(300 MHz) DMSO-d$_6$): δ 11.74 (s, 1H), 10.95 (s, 1H), 9.67 (s, 1H), 8.49 (d, 1H, J = 5.1 Hz), 8.44 (s, 1H), 7.69~7.77 (m, 1H), 7.60~7.62 (m, 2H), 7.44~7.49 (m, 1H), 7.40 (s, 1H), 7.26~7.35 (m, 2H), 6.96~7.00 (m, 1H), 2.95 (s, 3H), |

Example 280

Synthesis of N-(2',4'-difluoro-[1,1'-biphenyl]-3-yl)-N-methyl-6-(methylsulfonamido)-1H-indole-2-carboxamide (a) Synthesis of 2',4'-difluoro-N-methyl-[1,1'-biphenyl]-3-amine To a mixture of 2',4'-difluoro-[1,1'-biphenyl]-3-amine (150.0 mg, 0.73 mmol), and triethylorthoformate (3.0 mL), a catalytic amount of TFA was added, followed by refluxing for 5 hours. The reaction mixture was concentrated under reduced pressure, and the residue was dissolved in EtOH (2.0 mL). NaBH$_4$ (276.0 mg, 7.30 mmol) was slowly added at 0° C., followed by refluxing for 2 hours. Water was added to quench the reaction, and the reaction mixture was extracted with EtOAc. The organic extract was washed with brine, dried over anhydrous Na$_2$SO$_4$, concentrated under reduced pressure. The residue was purified by flash column chromatography (amine silica gel, n-Hex:EtOAc=9:1) to obtain 2',4'-difluoro-N-methyl-[1,1'-biphenyl]-3-amine (140.0 mg, 88%) as a colorless oil.

$^1$H-NMR (300MHz, CDCl$_3$): δ 7.36-7.44 (m, 1H), 7.23-7.28 (m, 1H), 6.82-6.96 (m, 3H), 6.72 (d, 1H, J=1.8Hz), 6.63 (dd, 1H, J=7.5, 2.4Hz), 4.02 (brs, 1H), 2.88 (s, 3H)

(b) Synthesis of N-(2',4'-difluoro-[1,1'-biphenyl]-3-yl)-N-methyl-6-nitro-1H-indole-2-carboxamide 6-Nitro-1H-indole-2-carboxylic acid (51.0 mg, 0.25 mmol), 2',4'-difluoro-N-methyl-[1,1'-biphenyl]-3-amine (60.0 mg, 0.27 mmol), EDC (58.0 mg, 0.30 mmol), and HOBt (41.0 mg, 0.30 mmol) were dissolved in anhydrous DMF (2.5 mL), and DIPEA (65.0 μL, 0.37 mmol) was added, followed by stirring at room temperature for 24 hours. The reaction mixture was extracted with EtOAc, and the organic extract was washed with brine, dried over anhydrous Na$_2$SO$_4$, concentrated under reduced pressure. The residue was purified by flash column chromatography (silica gel, n-Hex:EtOAc=9:1) to obtain N-(2',4'-difluoro-[1,1'-biphenyl]-3-yl)-N-methyl-6-nitro-1H-indole-2-carboxamide (30.0 mg, 30%) as a yellow solid.

LC/MS ESI (+): 394 (M+1)

(c) Synthesis of N-(2',4'-difluoro-[1,1'-biphenyl]-3-yl)-N-methyl-6-(methylsulfonamido)-1H-indole-2-carboxamide The synthesis procedure of Example 257 was repeated except for using N-(2',4'-difluoro-[1,1'-biphenyl]-3-yl)-N-methyl-6-nitro-1H-indole-2-carboxamide (45.0 mg, 0.11 mmol) to obtain N-(2',4'-difluoro-[1,1'-biphenyl]-3-yl)-N-methyl-6-(methylsulfonamido)-1H-indole-2-carboxamide (5.0 mg, 4 step yield: 10%) as a white solid.

LC/MS ESI (+): 456 (M+1)

$^1$H-NMR (300MHz, DMSO-d$_6$): δ 11.60 (s, 1H), 9.55 (s, 1H), 7.55-7.63 (m, 5H), 7.37-7.43 (m, 2H), 7.33 (m, 1H), 7.25 (d, 1H, J=8.4Hz), 7.19-7.25 (m, 1H), 6.82 (dd, 1H, J=8.4, 1.8Hz), 3.42 (s, 3H), 2.89 (s, 3H)

Example 281

Synthesis of N-(5'-methoxy-2'-(trifluoromethyl)-[1,1'-biphenyl]-3-yl)-6-(methylsulfonamido)-1H-indole-2-carboxamide (a) Synthesis of 5'-methoxy-2'-(trifluoromethyl)-[1,1'-biphenyl]-3-amine (3-Aminophenyl)boronic acid hydrochloride (324.0 mg, 1.87 mmol), and 2-bromo-4-methoxy-1-(trifluoromethyl)benzene (500.0 mg, 1.96 mmol) were dissolved in a mixture of DME/H$_2$O (25.0 mL, 4/1 v/v), and Pd(PPh$_3$)$_4$ (216.0 mg, 0.19 mmol) and Na$_2$CO$_3$ (1.2 g, 11.20 mmol) were added, followed by stirring at 85° C. for 2 hours. The reaction mixture was cooled to room temperature and extracted with EtOAc. The organic extract was washed with brine, dried over anhydrous Na$_2$SO$_4$, concentrated under reduced pressure. The residue was purified by flash column chromatography (silica gel, n-Hex:EtOAc=2:1) to obtain 5'-methoxy-2'-(trifluoromethyl)-[1,1'-biphenyl]-3-amine (334.0 mg, 67%) as a colorless oil.

LC/MS ESI (+): 268 (M+1)

(b) Synthesis of N-(5'-methoxy-2'-(trifluoromethyl)-[1,1'-biphenyl]-3-yl)-6-nitro-1H-indole-2-carboxamide 5'-Methoxy-2'-(trifluoromethyl)-[1,1'-biphenyl]-3-amine (200.0 mg, 0.75 mmol), 6-nitro-1H-indole-2-carboxylic acid (154.0 mg, 0.75 mmol), and HATU (341.0 mg, 0.90 mmol) were dissolved in anhydrous DMF (3.0 mL), and DIPEA (196.0 μL, 1.12 mmol) was slowed added. After stirring at 18° C. for 3 hours, the reaction mixture was extracted with EtOAc, and the organic extract was washed with brine, dried over anhydrous Na$_2$SO$_4$, concentrated under reduced pressure. The residue was purified by column chromatography (n-Hex:EtOAc=2:1) to obtain N-(5'-methoxy-2'-(trifluoromethyl)-[1,1'-biphenyl]-3-yl)-6-nitro-1H-indole-2-carboxamide (320.0 mg, 94%) as a yellow solid.

LC/MS ESI (+): 456 (M+1)

¹H-NMR (300MHz, DMSO-d₆): δ 12.56 (s, 1H), 10.58 (s, 1H), 8.37 (s, 1H), 7.94 (d, 2H, J=1.3Hz), 7.84-7.91 (m, 2H), 7.78 (d, 1H, J=8.8Hz), 7.61 (d, 1H, J=1.1Hz), 7.46 (t, 1H, J=7.8Hz), 7.16 (dd, 1H, J=8.2, 2.9Hz), 7.10 (d, 1H, J=8.2Hz), 6.94 (d, 1H, J=2.5Hz), 3.87 (s, 3H)

(c) Synthesis of tert-butyl 2-((5'-methoxy-2'-(trifluoromethyl)-[1,1'-biphenyl]-3-yl)carbamoyl)-6-nitro-1H-indole-1-carboxylate N-(5'-methoxy-T-(trifluoromethyl)-[1,1'-biphenyl]-3-yl)-6-nitro-1H-indole-2-carboxamide (320.0 mg, 0.70 mmol), Boc₂O (169.0 mg, 0.77 mmol), and Et₃N (294.0 μL, 2.11 mmol) were dissolved in anhydrous DMF (4.0 mL), followed by stirring at 17° C. for 24 hours. The reaction mixture was extracted with EtOAc, and the organic extract was washed with brine, dried over anhydrous Na₂SO₄, concentrated under reduced pressure. The residue was purified by flash column chromatography (silica gel, n-Hex:EtOAc=2:1) to obtain tert-butyl 2-((5'-methoxy-2'-(trifluoromethyl)-[1,1'-biphenyl]-3-yl)carbamoyl)-6-nitro-1H-indole-1-carboxylate (163.0 mg, 42%) as a yellow solid.
LC/MS ESI (+): 556 (M+1)

(d) Synthesis of tert-butyl 2-((5'-methoxy-2'-(trifluoromethyl)-[1,1'-biphenyl]-3-yl)carbamoyl)-6-(methylsulfonamido)-1H-indole-1-carboxylate tert-Butyl 2-((5'-methoxy-2'-(trifluoromethyl)-[1,1'-biphenyl]-3-yl)carbamoyl)-6-nitro-1H-indole-1-carboxylate (163.0 mg, 0.29 mmol) was dissolved in a mixture of MeOH/H₂O (5.0 mL, 9/1 v/v), and Zn (288.0 mg, 4.40 mmol) and NH₄Cl (78.0 mg, 1.47 mmol) were added. The reaction mixture was ultrasonificated for 1 hour, filtered through Celite and concentrated under reduced pressure. The residue was extracted with EtOAc, and the organic extract was washed with brine, dried over anhydrous Na₂SO₄, concentrated under reduced pressure. The residue was dissolved in pyridine (3.0 mL), and methanesulfonyl chloride (25.0 μL, 0.32 mmol) was slowly added at 0° C. The reaction mixture was extracted with EtOAc, and the organic extract was washed with brine, dried over anhydrous Na₂SO₄. The residue was purified by flash column chromatography (silica gel, n-Hex:EtOAc=2:1) to obtain tert-butyl 2-((5'-methoxy-2'-(trifluoromethyl)-[1,1'-biphenyl]-3-yl)carbamoyl)-6-(methylsulfonamido)-1H-indole-1-carboxylate (143.0 mg, 2 step yield: 81%) as a white solid.
LC/MS ESI (+): 604 (M+1)

(e) Synthesis of N-(5'-methoxy-2'-(trifluoromethyl)-[1,1'-biphenyl]-3-yl)-6-(methylsulfonamido)-1H-indole-2-carboxamide tert-Butyl 2-((5'-methoxy-2'-(trifluoromethyl)-[1,1'-biphenyl]-3-yl)carbamoyl)-6-(methylsulfonamido)-1H-indole-1-carboxylate (143.0 mg, 0.24 mmol) was dissolved in CH₂Cl₂ (2.0 mL), and TFA (0.5 mL) was added at 15° C. After stirring for 1 hour, the reaction was quenched with 1 N NaOH aqueous solution. The reaction mixture was extracted with EtOAc, and the organic extract was washed with brine, dried over anhydrous Na₂SO₄ and concentrated under reduced pressure. The residue was purified by flash column chromatography (silica gel, n-Hex:EtOAc=2:1) to obtain N-(5'-methoxy-2'-(trifluoromethyl)-[1,1'-biphenyl]-3-yl)-6-(methylsulfonamido)-1H-indole-2-carboxamide (26.0 mg, 22%) as a white solid.
LC/MS ESI (+): 504 (M+1)
¹H-NMR (300MHz, DMSO-d₆): δ 11.73 (s, 1H), 10.30 (s, 1H), 9.63 (s, 1H), 7.85 (m, 2H), 7.77 (d, 1H, J=9.2Hz), 7.63 (d, 1H, J=8.6Hz), 7.39-7.45 (m, 3H), 7.13-7.17 (m, 1H), 7.05 (d, 1H, J=8.0Hz), 6.98 (dd, 1H, J=8.4, 1.1Hz), 6.93 (d, 1H, J=2.3Hz), 3.86 (s, 3H), 2.94 (s, 3H)

Example 282

Synthesis of N-(5'-methoxy-2'-(trifluoromethyl)-[1,1'-biphenyl]-3-yl)-6-nitro-1H-indole-2-carboxamide Through the synthetic method according to Example 281-b, N-(5'-methoxy-2'-(trifluoromethyl)-[1,1'-biphenyl]-3-yl)-6-nitro-1H-indole-2-carboxamide was synthesized.
LC/MS ESI (+): 456 (M+1)
¹H-NMR (300MHz, DMSO-d₆): δ 12.56 (s, 1H), 10.58 (s, 1H), 8.37 (s, 1H), 7.94 (d, 2H, J=1.3Hz), 7.84-7.91 (m, 2H), 7.78 (d, 1H, J=8.8Hz), 7.61 (d, 1H, J=1.1Hz), 7.46 (t, 1H, J=7.8Hz), 7.16 (dd, 1H, J=8.2, 2.9Hz), 7.10 (d, 1H, J=8.2Hz), 6.94 (d, 1H, J=2.5Hz), 3.87 (s, 3H)

Through the synthetic method according to Example 280 or Examples 281 and 282, compounds from Example 283 to Example 300 were synthesized, and the data of each example are as follows.

TABLE 18

| Ex. | Compound | Analysis data |
| --- | --- | --- |
| 283 | 6-(methylsulfonamido)-N-(4'-sulfamoyl-2'-(trifluoromethyl)-[1,1'-biphenyl]-3-yl)-1H-indole-2-carboxamide | LC/MS ESI (+): 553 (M + 1)<br>¹H-NMR (300 MHz, DMSO-d₆): δ 11.74 (s, 1H), 10.31 (s, 1H), 9.64 (s, 1H), 8.26 (s, 1H), 8.15 (d, 1H, J = 7.6 Hz), 7.88~7.93 (m, 2H), 7.62~7.71 (m, 4H), 7.48 (t, 1H, J = 8.0 Hz), 7.38~7.42 (m, 2H), 7.07 (d, 1H, J = 8.4 Hz), 6.98 (dd, 1H, J = 8.4, 1.9 Hz), 2.94 (s, 3H) |
| 284 | N-(4'-cyano-2'-(trifluoromethyl)-[1,1'-biphenyl]-3-yl)-6-(methylsulfonamido)-1H-indole-2-carboxamide | LC/MS ESI (+): 499 (M + 1)<br>¹H-NMR (300 MHz, DMSO-d₆): δ 11.74 (s, 1H), 10.32 (s, 1H), 9.66 (brs, 1H), 8.43 (s, 1H), 8.23 (d, 1H, J = 7.7 Hz), 7.87~7.91 (m, 2H), 7.68 (d, 1H, J = 8.8 Hz), 7.63 (d, 1H, J = 8.5 Hz), 7.47 (t, 1H, J = 7.7 Hz), 7.39 (d, 2H, J = 6.3 Hz), 7.06 (d, 1H, J = 7.7 Hz), 6.98 (dd, 1H, J = 8.5, 1.8 Hz), 2.94 (s, 3H) |
| 285 | 6-(methylsulfonamido)-N-(4'-nitro-2'-(trifluoromethyl)-[1,1'-biphenyl]-3-yl)-1H-indole-2-carboxamide | LC/MS ESI (+): 519 (M + 1)<br>¹H-NMR (300 MHz, DMSO-d₆): δ 11.73 (s, 1H), 10.33 (s, 1H), 9.62 (brs, 1H), 8.54~8.60 (m, 2H), 7.90~7.94 (m, 2H), 7.78 (d, 1H, J = 8.8 Hz), 7.63 (d, 1H, J = 8.4 Hz), 7.50 (t, 1H, J = 8.8 Hz), 7.38~7.40 (m, 2H), 7.10 (d, 1H, J = 8.8 Hz), 6.98 (dd, 1H, J = 8.8, 1.5 Hz), 2.93 (s, 3H) |

TABLE 18-continued

| Ex. | Compound | Analysis data |
|---|---|---|
| 286 | methyl 3'-(6-nitro-1H-indole-2-carboxamido)-6-(trifluoromethyl)-[1,1'-biphenyl]-3-carboxylate | LC/MS ESI (+): 484 (M + 1)<br>$^1$H-NMR (300 MHz, DMSO-$d_6$): δ 12.56 (s, 1H), 10.62 (s, 1H), 8.37 (s, 1H), 8.17~8.20 (m, 1H), 8.05 (d, 1H, J = 8.2 Hz), 7.87~7.94 (m, 5H), 7.61 (m, 1H), 7.51 (t, 1H, J = 7.8 Hz), 7.14 (d, 1H, J = 7.8 Hz), 3.91 (s, 3H) |
| 287 | methyl 3'-(6-(methylsulfonamido)-1H-indole-2-carboxamido)-6-(trifluoromethyl)-[1,1'-biphenyl]-3-carboxylate | LC/MS ESI (+): 532 (M + 1)<br>$^1$H-NMR (300 MHz, DMSO-$d_6$): δ 11.73 (s, 1H), 10.30 (s, 1H), 9.63 (s, 1H), 8.18 (d, 1H, J = 8.8 Hz), 8.05 (d, 1H, J = 8.0 Hz), 7.86~7.92 (m, 3H), 7.63 (d, 1H, J = 8.6 Hz), 7.47 (t, 1H, J = 7.8 Hz), 7.37~7.41 (m, 2H), 7.09 (d, 1H, J = 7.8 Hz), 6.98 (dd, 1H, J = 8.4, 1.9 Hz), 3.91 (s, 3H), 2.94 (s, 3H) |
| 288 | methyl 4-methoxy-3'-(6-nitro-1H-indole-2-carboxamido)-6-(trifluoromethyl)-[1,1'-biphenyl]-3-carboxylate | LC/MS ESI (+): 514 (M + 1)<br>$^1$H-NMR (300 MHz, DMSO-$d_6$): δ 12.56 (s, 1H), 10.59 (s, 1H), 8.37 (s, 1H), 7.89~7.96 (m, 3H), 7.82 (s, 1H), 7.59~7.65 (m, 2H), 7.44~7.53 (m, 2H), 7.07~7.11 (m, 1H), 3.98 (s, 3H), 3.82 (s, 3H) |
| 289 | methyl 4-methoxy-3'-(6-(methylsulfonamido)-1H-indole-2-carboxamido)-6-(trifluoromethyl)-[1,1'-biphenyl]-3-carboxylate | LC/MS ESI (+): 562 (M + 1)<br>$^1$H-NMR (300 MHz, DMSO-$d_6$): δ 11.72 (s, 1H), 10.27 (s, 1H), 9.64 (s, 1H), 7.88 (dd, 1H, J = 8.0, 1.1 Hz), 7.81 (s, 1H), 7.62~7.64 (m, 2H), 7.51 (s, 1H), 7.39~7.46 (m, 3H), 7.04 (d, 1H, J = 7.6 Hz), 6.98 (dd, 1H, J = 8.6, 1.9 Hz), 3.98 (s, 3H), 3.82 (s, 3H), 2.94 (s, 3H) |
| 290 | 6-(methylsulfonamido)-N-(3-(3-(trifluoromethyl)pyridin-2-yl)phenyl)-1H-indole-2-carboxamide | LC/MS ESI (+): 475 (M + 1)<br>$^1$H-NMR (300 MHz, DMSO-$d_6$): δ 11.73 (s, 1H), 10.29 (s, 1H), 9.63 (brs, 1H), 8.93 (d, 1H, J = 5.7 Hz), 8.33 (dd, 1H, J = 7.6, 1.5 Hz), 7.99 (s, 1H), 7.92 (d, 1H, J = 8.8 Hz), 7.68~7.71 (m, 1H), 7.63 (d, 1H, J = 8.4 Hz), 7.37~7.50 (m, 3H), 7.16~7.19 (m, 1H), 6.98 (dd, 1H, J = 8.4, 1.5 Hz), 2.94 (s, 3H) |
| 291 | 6-(methylsulfonamido)-N-(3-(4-(trifluoromethyl)pyridm-3-yl)phenyl)-1H-indole-2-carboxamide | LC/MS ESI (+): 475 (M + 1)<br>$^1$H-NMR (300 MHz, DMSO-$d_6$): δ 11.75 (s, 1H), 10.33 (s, 1H), 9.66 (s, 1H), 8.90 (d, 1H, J = 5.9 Hz), 8.74 (s, 1H), 7.88~7.94 (m, 3H), 7.64 (d, 1H, J = 8.5 Hz), 7.49 (t, 1H, J = 7.7 Hz), 7.40 (dd, 2H, J = 8.5, 1.1 Hz), 7.72 (d, 1H, J = 7.7 Hz), 6.98 (dd, 1H, J = 8.5, 1.8 Hz), 2.94 (s, 3H) |
| 292 | 6-nitro-N-(3-(2-(trifluoromethyl)pyridin-3-yl)phenyl)-1H-indole-2-carboxamide | LC/MS ESI (+): 427 (M + 1)<br>$^1$H-NMR (300 MHz, DMSO-$d_6$): δ 12.54 (s, 1H), 10.63 (s, 1H), 8.81 (d, 1H, J = 4.6 Hz), 8.37 (s, 1H), 7.80~8.02 (m, 5H), 7.82 (dd, 1H, J = 7.6, 4.6 Hz), 7.62 (s, 1H), 7.52 (t, 1H, J = 8.0 Hz), 7.14 (d, 1H, J = 7.6 Hz) |
| 293 | 6-(methylsulfonamido)-N-(3-(2-(trifluoromethyl)pyridin-3-yl)phenyl)-1H-indole-2-carboxamide | LC/MS ESI (+): 475 (M + 1)<br>$^1$H-NMR (300 MHz, DMSO-$d_6$): δ 11.75 (s, 1H), 10.32 (s, 1H), 9.66 (brs, 1H), 8.80 (d, 1H, J = 5.5 Hz), 7.98 (d, 1H, J = 7.7 Hz), 7.89~7.91 (m, 2H), 7.81 (dd, 1H, J = 7.7, 4.8 Hz), 7.63 (d, 1H, J = 8.5 Hz), 7.48 (t, 1H, J = 7.7 Hz), 7.40 (d, 2H, J = 8.1 Hz), 7.09 (d, 1H, J = 7.4 Hz), 6.98 (dd, 1H, J = 8.5, 1.8 Hz), 2.50 (s, 3H) |
| 294 | N-(3-(6-chloro-4-(trifluoromethyl)pyridin-3-yl)phenyl)-6-(methylsulfonamido)-1H-indole-2-carboxamide | LC/MS ESI (+): 509 (M + 1)<br>$^1$H-NMR (300 MHz, DMSO-$d_6$): δ 11.73 (s, 1H), 10.33 (s, 1H), 9.64 (brs, 1H), 8.59 (s, 1H), 8.08 (s, 1H), 7.90~7.93 (m, 2H), 7.63 (d, 1H, J = 8.8 Hz), 7.50 (t, 1H, J = 8.4 Hz), 7.39 (d, 2H, J = 6.5 Hz), 7.11 (d, 1H, J = 8.0 Hz), 6.98 (dd, 1H, J = 8.4, 1.9 Hz), 2.94 (s, 3H) |
| 295 | N-(2'-fluoro-4'-methoxy-[1,1'-biphenyl]-3-yl)-6-nitro-1H-indole-2-carboxamide | LC/MS ESI (+): 406 (M + 1)<br>$^1$H-NMR (300 MHz, DMSO-$d_6$): δ 12.57 (s, 1H), 10.60 (s, 1H), 8.38 (s, 1H), 8.00 (s, 1H), 7.95 (s, 2H), 7.90 (d, 1H, J = 9.0 Hz), 7.64 (s, 1H), 7.49 (t, 1H, J = 8.1 Hz), 7.25~7.36 (m, 2H), 6.98~7.07 (m, 2H), 3.82 (s, 3H) |
| 296 | tert-butyl 2-((2'-fluoro-4'-methoxy-[1,1'-biphenyl]-3-yl)carbamoyl)-6-(methylsulfonamido)-1H-indole-1-carboxylate | LC/MS ESI (+): 554 (M + 1)<br>$^1$H-NMR (300 MHz, CDCl$_3$): δ 8.08 (s, 1H), 7.93 (s, 1H), 7.77 (brs, 2H), 7.57 (d, 1H, J = 8.4 Hz), 7.44 (t, 1H, J = 8.4 Hz), 7.15~7.39 (m, 2H), 7.05 (t, 1H, J = 9.6 Hz), 6.97 (s, 2H), 6.85 (s, 1H), 6.45 (s, 1H), 3.83 (s, 3H), 3.04 (s, 3H), 1.30 (s, 9H) |
| 297 | N-(4-(2-fluoro-5-methoxyphenyl)pyridin-2-yl)-6-nitro-1H-indole-2-carboxamide | LC/MS ESI (+): 407 (M + 1)<br>$^1$H-NMR (300 MHz, DMSO-$d_6$): δ 12.58 (s, 1H), 11.32 (s, 1H), 8.52 (d, 1H, J = 5.1 Hz) 8.47 (s, 1H), 8.38 (s, 1H), 7.92 (s, 2H), 7.82 (s, 1H), 7.42 (d, 1H, J = 5.1 Hz), 7.31 (t, 1H, J = 9.0 Hz), 7.06~7.18 (m, 2H), 3.82 (s, 3H) |
| 298 | methyl 6-chloro-3'-(6-nitro-1H-indole-2-carboxamido)-[1,1'-biphenyl]-3-carboxylate | LC/MS ESI (+): 450 (M + 1)<br>$^1$H-NMR (300 MHz, DMSO-$d_6$): δ 12.57 (s, 1H), 10.63 (s, 1H), 8.37 (s, 1H), 7.93~8.00 (m, 6H), 7.77 (d, 1H, J = 8.1 Hz), 7.62 (s, 1H), 7.51 (t, 1H, J = 8.1 Hz), 7.26 (d, 1H, J = 7.8 Hz), 3.88 (s, 3H) |

TABLE 18-continued

| Ex. | Compound | Analysis data |
|---|---|---|
| 299 | methyl 6-chloro-3'-(6-(methylsulfonamido)-1H-indole-2-carboxamido)-[1,1'-biphenyl]-3-carboxylate | LC/MS ESI (+): 498 (M + 1)<br>$^1$H-NMR (300 MHz, DMSO-$d_6$): δ 11.74 (s, 1H), 10.31 (s, 1H), 9.64 (s, 1H), 7.90~8.00 (m, 4H), 7.76 (d, 1H, J = 8.4 Hz), 7.62 (d, 1H, J = 8.4 Hz), 7.46 (t, 1H, J = 8.7 Hz), 7.39 (d, 2H, J = 4.8 Hz), 7.20 (d, 1H, J = 8.1 Hz), 6.97 (dd, 1H, J = 8.7, 1.8 Hz), 3.88 (s, 3H), 2.94 (s, 3H) |
| 300 | methyl 4-chloro-3-(2-(6-(methylsulfonamido)-1H-indole-2-carboxamido)pyridin-4-yl)benzoate | LC/MS ESI (+): 499 (M + 1)<br>$^1$H-NMR (300 MHz, DMSO-$d_6$): δ 11.75 (s, 1H), 11.01 (s, 1H), 9.68 (s, 1H), 8.51 (d, 1H, J = 5.1 Hz), 8.36 (s, 1H), 8.03 (dd, 1H, J = 8.4, 2.1 Hz), 8.00 (d, 1H, J = 2.1 Hz), 7.81 (d, 1H, J = 8.4 Hz), 7.63 (d, 1H, J = 2.1 Hz), 7.60 (d, 1H, J = 9.0 Hz), 7.39 (s, 1H), 7.29 (dd, 1H, J = 5.1, 1.5 Hz), 6.97 (d, 1H, J = 8.4 Hz), 3.89 (s, 3H), 2.95 (s, 3H) |

Example 301

Synthesis of N-(5-cyano-2',4'-difluoro-[1,1'-biphenyl]-3-yl)-6-(methylsulfonamido)-1H-indole-2-carboxamide (a) Synthesis of 2',4'-difluoro-5-nitro-[1,1'-biphenyl]-3-carbonitrile 3-Bromo-5-nitrobenzonitrile (200.0 mg, 0.89 mmol), (2,4-difluorophenyl)boronic acid (167.0 mg, 1.06 mmol), Pd(PPh$_3$)$_4$ (102.0 mg, 0.09 mmol) and Na$_2$CO$_3$ (280.0 mg, 2.64 mmol) were added to a mixture of DME/H$_2$O (9.0 mL, 4/1 v/v), followed by stirring at 90° C. for 3 hours. The reaction mixture was cooled to room temperature and extracted with EtOAc, and the organic extract was washed with brine, dried over anhydrous Na$_2$SO$_4$, concentrated under reduced pressure. The residue was purified by flash column chromatography (silica gel, n-Hex:EtOAc=4:1) to obtain 2',4'-difluoro-5-nitro-[1,1'-biphenyl]-3-carbonitrile (187.0 mg, 82%) as a white solid.

$^1$H-NMR (300MHz, CDCl$_3$): δ 8.60 (s, 1H), 8.52 (s, 1H), 8.13 (s, 1H), 7.44-7.52 (m, 1H), 6.99-7.11 (m, 2H)

(b) Synthesis of 5-amino-2',4'-difluoro-[1,1'-biphenyl]-3-carbonitrile

2',4'-Difluoro-5-nitro-[1,1'-biphenyl]-3-carbonitrile (184.0 mg, 0.89 mmol) was dissolved in a mixture of MeOH/H$_2$O (7.0 mL, 9/1 v/v), and Zn (693.0 mg, 10.60 mmol) and NH$_4$Cl (189.0 mg, 3.54 mmol) were added. The reaction mixture was ultrasonificated for 2 hours, filtered through Celite and concentrated under reduced pressure. The residue was extracted with EtOAc, and the organic extract was washed with brine, dried over anhydrous Na$_2$SO$_4$, concentrated under reduced pressure. The residue was purified by flash column chromatography (amine silica gel, n-Hex:EtOAc=1:1) to obtain 5-amino-2',4'-difluoro-[1,1'-biphenyl]-3-carbonitrile (160.0 mg, 99%) as a colorless oil.

LC/MS ESI (+): 231 (M+1)

(c) Synthesis of N-(5-cyano-2',4'-difluoro-[1,1'-biphenyl]-3-yl)-6-(methylsulfonamido)-1H-indole-2-carboxamide 5-Amino-2',4'-difluoro-[1,1'-biphenyl]-3-carbonitrile (70.0 mg, 0.28 mmol), 6-(methylsulfonamido)-1H-indole-2-carboxylic acid hydrochloride (70.0 mg, 0.30 mmol), and HATU (115.0 mg, 0.30 mmol) were dissolved in anhydrous DMF (2.8 mL), and DIPEA (72.0 μL, 0.41 mmol) was slowly added. After stirring at room temperature for 72 hours, the reaction mixture was extracted with EtOAc, and the organic extract was washed with brine, dried over anhydrous Na$_2$SO$_4$, concentrated under reduced pressure. The residue was purified by flash column chromatography (amine silica gel, CH$_2$Cl$_2$:MeOH=40:1) to obtain N-(5-cyano-2',4'-difluoro-[1,1'-biphenyl]-3-yl)-6-(methylsulfonamido)-1H-indole-2-carboxamide (5.8 mg, 5%) as a white solid.

LC/MS ESI (+): 467 (M+1)

$^1$H-NMR (300MHz, DMSO-$d_6$): δ 11.80 (s, 1H), 10.57 (s, 1H), 9.67 (s, 1H), 8.35 (s, 1H), 8.23 (s, 1H), 7.75 (s, 1H), 7.65-7.72 (m, 2H), 7.46-7.51 (m, 1H), 7.40-7.43 (m, 2H), 7.28 (td, 1H, J=8.8, 2.3Hz), 7.00 (dd, 1H, J=8.8, 1.9Hz), 2.95 (s, 3H)

Through the synthetic method according to Example 301, compounds from Example 302 to Example 336 were synthesized, and the data of each example are as follows.

TABLE 19

| Ex. | Compound | Analysis data |
|---|---|---|
| 302 | N-(5-bromo-2',4'-difluoro-[1,1'-biphenyl]-3-yl)-6-(methylsulfonamido)-1H-indole-2-carboxamide | LC/MS ESI (+): 520 (M + 1)<br>$^1$H-NMR (300 MHz, DMSO-$d_6$): δ 11.74 (s, 1H), 10.40 (s, 1H), 9.65 (s, 1H), 8.19 (s, 1H), 7.96 (s, 1H), 7.60~7.68 (m, 2H), 7.40~7.47 (m, 4H), 7.24 (td, 1H, J = 8.8, 2.3 Hz), 6.99 (dd, 1H, J = 8.8, 1.5 Hz), 2.94 (s, 3H) |
| 303 | N-(5-bromo-2',4'-difluoro-[1,1'-biphenyl]-3-yl)-5-methoxy-6-(methylsulfonamido)-1H-indole-2-carboxamide | LC/MS ESI (+): 550 (M + 1)<br>$^1$H-NMR (300 MHz, DMSO-$d_6$): δ 11.64 (s, 1H), 10.39 (s, 1H), 8.84 (s, 1H), 8.19 (s, 1H), 7.96 (s, 1H), 7.60~7.68 (m, 1H), 7.36~7.47 (m, 4H), 7.21~7.28 (m, 2H), 3.86 (s, 3H), 2.93 (s, 3H) |
| 304 | N-(5-bromo-2',4'-difluoro-[1,1'-biphenyl]-3-yl)-6-(methylsulfonyl)-1H-indole-2-carboxamide | $^1$H-NMR (300 MHz, DMSO-$d_6$): δ 12.47 (brs, 1H), 10.71 (brs, 1H), 8.20 (s, 1H), 8.04 (s, 1H), 7.96~7.99 (m, 2H), 7.58~7.69 (m, 3H), 7.39~7.48 (m, 2H), 7.25 (td, 1H, J = 9.2, 2.3 Hz), 3.21 (s, 3H) |

TABLE 19-continued

| Ex. | Compound | Analysis data |
|---|---|---|
| 305 | N-(5-bromo-2',4'-difluoro-[1,1'-biphenyl]-3-yl)-5-(methylsulfonamido)benzo[b]thiophene-2-carboxamide | LC/MS ESI (+): 537 (M + 1)<br>$^1$H-NMR (300 MHz, DMSO-d$_6$): δ 10.71 (brs, 1H), 9.93 (brs, 1H), 8.34 (s, 1H), 8.14 (m, 1H), 8.03 (d, 1H, J = 8.7 Hz), 7.95 (m, 1H), 7.83 (m, 1H), 7.61~7.69 (m, 1H), 7.36~7.50 (m, 3H), 7.22~7.28 (m, 1H), 3.03 (s, 3H) |
| 306 | N-(5-bromo-2',4'-difluoro-[1,1'-biphenyl]-3-yl)-5-(methylsulfonamido)benzofuran-2-carboxamide | LC/MS ESI (+): 521 (M + 1)<br>$^1$H-NMR (300 MHz, DMSO-d$_6$): δ 10.79 (brs, 1H), 9.78 (brs, 1H), 8.17 (m, 1H), 8.00 (s, 1H), 7.79 (s, 1H), 7.59~7.72 (m, 3H), 7.26~7.48 (m, 3H), 7.23 (m, 1H), 2.98 (s, 3H) |
| 307 | N-(5-bromo-2',4'-difluoro-[1,1'-biphenyl]-3-yl)-6-((N-methylsulfamoyl)amino)-1H-indole-2-carboxamide | LC/MS ESI (+): 535 (M + 1)<br>$^1$H-NMR (300 MHz, DMSO-d$_6$): δ 11.68 (s, 1H), 10.37 (s, 1H), 9.60 (s, 1H), 8.19 (s, 1H), 7.96 (s, 1H), 7.62~7.68 (m, 1H), 7.58 (d, 1H, J = 8.8 Hz), 7.43~7.46 (m, 2H), 7.36~7.40 (m, 2H), 7.24 (td, 1H, J = 8.4, 2.3 Hz), 7.12 (brs, 1H), 6.98 (dd, 1H, J = 8.8, 1.9 Hz), 2.47 (s, 3H)) |
| 308 | N-(5-bromo-2',4'-difluoro-[1,1'-biphenyl]-3-yl)-5-(trifluoromethoxy)-1H-indole-2-carboxamide | LC/MS ESI (+): 511 (M + 1)<br>$^1$H-NMR (300 MHz, DMSO-d$_6$): δ 12.07 (s, 1H), 10.55 (s, 1H), 8.19 (s, 1H), 7.97 (s, 1H), 7.75 (s, 1H), 7.60~7.68 (m, 1H), 7.56 (d, 1H, J = 8.8 Hz), 7.52 (s, 1H), 7.39~7.46 (m, 2H), 7.21~7.27 (m, 2H) |
| 309 | N-(5-bromo-2',4'-difluoro-[1,1'-biphenyl]-3-yl)-3-methyl-6-(methylsulfonamido)benzo[b]thiophene-2-carboxamide | LC/MS ESI (+): 551 (M + 1)<br>$^1$H-NMR (300 MHz, DMSO-d$_6$): δ 10.58 (s, 1H), 9.96 (brs, 1H), 8.07 (s, 1H), 8.01 (d, 1H, J = 8.4 Hz), 7.90 (s, 1H), 7.69 (s, 1H), 7.59~7.67 (m, 1H), 7.48 (s, 1H), 7.36~7.46 (m, 2H), 7.20~7.27 (m, 1H), 3.00 (s, 3H), 2.58 (s, 3H) |
| 310 | N-(5-bromo-2',4'-difluoro-[1,1'-biphenyl]-3-yl)-6-(methylsulfonamido)benzo[b]thiophene-2-carboxamide | LC/MS ESI (+): 537 (M + 1)<br>$^1$H-NMR (300 MHz, DMSO-d$_6$): δ 10.70 (s, 1H), 10.09 (s, 1H), 8.32 (s, 1H), 8.12 (s, 1H), 7.98 (d, 1H, J = 8.8 Hz), 7.94 (s, 1H), 7.83 (s, 1H), 7.60~7.68 (m, 1H), 7.39~7.47 (m, 2H), 7.32 (dd, 1H, J = 8.8, 1.9 Hz), 7.21~7.27 (m, 1H), 3.08 (s, 3H) |
| 311 | N-(5-bromo-2',4'-difluoro-[1,1'-biphenyl]-3-yl)-3-methyl-5-(methylsulfonamido)benzo[b]thiophene-2-carboxamide | LC/MS ESI (+): 551 (M + 1)<br>$^1$H-NMR (300 MHz, DMSO-d$_6$): δ 10.59 (s, 1H), 9.87 (s, 1H), 8.06 (s, 1H), 8.02 (d, 1H, J = 8.4 Hz), 7.89 (s, 1H), 7.70 (d, 1H, J = 1.9 Hz), 7.59~7.67 (m, 1H), 7.48 (s, 1H), 7.37~7.46 (m, 2H), 7.20~7.26 (m, 1H), 3.02 (s, 3H), 2.58 (s, 3H) |
| 312 | 6-(methylsulfonamido)-N-(2',4',5-trifluoro-[1,1'-biphenyl]-3-yl)-1H-indole-2-carboxamide | LC/MS ESI (+): 460 (M + 1)<br>$^1$H-NMR (300 MHz, DMSO-d$_6$): δ 11.79 (s, 1H), 10.46 (s, 1H), 9.68 (brs, 1H), 7.86~7.88 (m, 1H), 7.77 (d, 1H, J = 1.1 Hz), 7.60~7.71 (m, 2H), 7.38~7.45 (m, 3H), 7.24 (dt, 1H, J = 8.8, 1.9 Hz), 7.12 (d, 1H, J = 9.5 Hz), 7.00 (dd, 1H, J = 8.8, 1.9 Hz), 2.95 (s, 3H) |
| 313 | N-(2',4'-difluoro-5-(trifluoromethyl)-[1,1'-biphenyl]-3-yl)-6-(methylsulfonamido)-1H-indole-2-carboxamide | LC/MS ESI (+): 510 (M + 1)<br>$^1$H-NMR (300 MHz, DMSO-d$_6$): δ 11.77 (s, 1H), 10.57 (s, 1H), 9.68 (s, 1H), 8.32 (s, 1H), 8.27 (s, 1H), 7.65~7.74 (m, 2H), 7.57 (s, 1H), 7.41~7.50 (m, 3H), 7.27 (dt, 1H, J = 8.8, 2.7 Hz), 7.02 (dd, 1H, J = 8.4, 1.9 Hz), 2.95 (s, 3H) |
| 314 | N-(2',4'-difluoro-5-methoxy-[1,1'-biphenyl]-3-yl)-6-(methylsulfonamido)-1H-indole-2-carboxamide | LC/MS ESI (+): 472 (M + 1)<br>$^1$H-NMR (300 MHz, DMSO-d$_6$): δ 11.72 (s, 1H), 10.24 (s, 1H), 9.64 (s, 1H), 7.57~7.65 (m, 4H), 7.36~7.43 (m, 3H), 7.22 (td, 1H, J = 7.6, 1.9 Hz), 6.99 (dd, 1H, J = 8.8, 1.5 Hz), 6.81 (s, 1H), 3.82 (s, 3H), 2.95 (s, 3H) |
| 315 | N-(5-cyano-4'-fluoro-2'-(trifluoromethyl)-[1,1'-biphenyl]-3-yl)-6-(methylsulfonamido)-1H-indole-2-carboxamide | LC/MS ESI (+): 517 (M + 1)<br>$^1$H-NMR (300 MHz, DMSO-d$_6$): δ 11.80 (s, 1H), 10.56 (s, 1H), 9.68 (brs, 1H), 8.35 (s, 1H), 8.07 (s, 1H), 7.83 (dd, 1H, J = 9.5, 2.7 Hz), 7.64~7.72 (m, 2H), 7.55~7.62 (m, 2H), 7.40 (d, 2H, J = 6.1 Hz), 7.00 (dd, 1H, J = 8.4, 1.5 Hz), 2.93 (s, 3H) |
| 316 | N-(2',4'-difluoro-5-methoxy-[1,1'-biphenyl]-3-yl)-3-methyl-6-(methylsulfonamido)benzo[b]thiophene-2-carboxamide | LC/MS ESI (+): 503 (M + 1)<br>$^1$H-NMR (300 MHz, DMSO-d$_6$): δ 10.41 (s, 1H), 9.88 (s, 1H), 8.02 (d, 1H, J = 8.4 Hz), 7.70 (d, 1H, J = 2.3 Hz), 7.56~7.64 (m, 1H), 7.50 (s, 1H), 7.45 (s, 1H), 7.35~7.42 (m, 2H), 7.18~7.24 (m, 1H), 6.84 (s, 1H), 3.81 (s, 3H), 3.01 (s, 3H), 2.57 (s, 3H) |
| 317 | N-(2',4'-difluoro-5-methoxy-[1,1'-biphenyl]-3-yl)-5-(methylsulfonamido)benzo[b]thiophene-2-carboxamide | LC/MS ESI (+): 489 (M + 1)<br>$^1$H-NMR (300 MHz, DMSO-d$_6$): δ 10.55 (s, 1H), 9.90 (brs, 1H), 8.34 (s, 1H), 8.03 (d, 1H, J = 8.8 Hz), 7.81 (s, 1H), 7.52~7.65 (m, 1H), 7.56 (d, 1H, J = 2.3 Hz), 7.52 (d, 1H, J = 2.3 Hz), 7.35~7.43 (m, 2H), 7.21 (dt, 1H, J = 8.8, 1.9 Hz), 6.85 (s, 1H), 3.82 (s, 3H), 3.02 (s, 3H) |

TABLE 19-continued

| Ex. | Compound | Analysis data |
|---|---|---|
| 318 | N-(2',4'-difluoro-5-(methylcarbamoyl)-[1,1'-biphenyl]-3-yl)-6-(methylsulfonamido)-1H-indole-2-carboxamide | LC/MS ESI (+): 499 (M + 1)<br>¹H-NMR (300 MHz, DMSO-d₆): δ 11.71 (s, 1H), 10.42 (s, 1H), 9.62 (brs, 1H), 8.53~8.56 (m, 1H), 8.31 (s, 1H), 8.20 (s, 1H), 7.63~7.72 (m, 3H), 7.39~7.47 (m, 3H), 7.27 (dt, 1H, J = 8.4, 2.7 Hz), 6.99 (dd, 1H, J = 8.8, 1.9 Hz), 2.95 (s, 3H), 2.81 (d, 3H, J = 4.6 Hz), |
| 319 | N-(5-(dimethylcarbamoyl)-2',4'-difluoro-[1,1'-biphenyl]-3-yl)-6-(methylsulfonamido)-1H-indole-2-carboxamide | LC/MS ESI (+): 513 (M + 1)<br>¹H-NMR (300 MHz, DMSO-d₆): δ 11.73 (s, 1H), 10.38 (s, 1H), 9.64 (brs, 1H), 8.04 (s, 1H), 7.94 (s, 1H), 7.60~7.68 (m, 2H), 7.38~7.45 (m, 3H), 7.21~7.27 (m 2H), 7.00 (dd, 1H, J = 8.4, 1.5 Hz), 3.00 (s, 6H), 2.95 (s, 3H) |
| 320 | N-(2',4'-difluoro-5-(piperidine-1-carbonyl)-[1,1'-biphenyl]-3-yl)-6-(methylsulfonamido)-1H-indole-2-carboxamide | LC/MS ESI (+): 553 (M + 1)<br>¹H-NMR (300 MHz, DMSO-d₆): δ 11.73 (s, 1H), 10.39 (s, 1H), 9.64 (brs, 1H), 8.04 (s, 1H), 7.94 (s, 1H), 7.60~7.68 (m, 2H), 7.37~7.45 (m, 3H), 7.22~7.27 (m 2H), 7.00 (dd, 1H, J = 8.4, 1.9 Hz), 3.38~3.67 (m, 4H), 2.95 (s, 3H), 1.46~1.70 (m, 6H) |
| 321 | N-(2',4'-difluoro-5-(morpholine-4-carbonyl)-[1,1'-biphenyl]-3-yl)-6-(methylsulfonamido)-1H-indole-2-carboxamide | LC/MS ESI (+): 555 (M + 1)<br>¹H-NMR (300 MHz, DMSO-d₆): δ 11.74 (s, 1H), 10.41 (s, 1H), 9.65 (brs, 1H), 8.07 (s, 1H), 7.97 (s, 1H), 7.61~7.70 (m, 2H), 7.39~7.47 (m, 3H), 7.23~7.28 (m 2H), 7.01 (dd, 1H, J = 8.8, 1.9 Hz), 3.35~3.72 (m, 8H), 2.96 (s, 3H) |
| 322 | N-(5-chloro-2',4'-difluoro-[1,1'-biphenyl]-3-yl)-6-fluoro-5-(methylsulfonamido)benzo[b]thiophene-2-carboxamide | LC/MS ESI (+): 511 (M + 1)<br>¹H-NMR (400 MHz, DMSO-d₆): δ 10.75 (s, 1H), 9.74 (s, 1H), 8.34 (s, 1H), 8.10 (d, 1H, J = 10.3 Hz), 7.99~8.02 (m, 2H), 7.90 (s, 1H), 7.65 (m, 1H), 7.42 (m, 1H), 7.36 (s, 1H), 7.24 (m, 1H), 3.07 (s, 3H) |
| 323 | N-(5-chloro-2',4'-difluoro-[1,1'-biphenyl]-3-yl)-5-(methylsulfonamido)benzo[b]thiophene-2-carboxamide | LC/MS ESI (+): 493 (M + 1)<br>¹H-NMR (400 MHz, DMSO-d₆): δ 10.73 (s, 1H), 9.90 (s, 1H), 8.34 (s, 1H), 8.04 (d, 1H, J = 8.7 Hz), 8.00 (s, 1H), 7.90 (s, 1H), 7.82 (s, 1H), 7.65 (dd, 1H, J = 15.6, 8.8 Hz), 7.44 (t, 1H, J = 11.1 Hz), 7.36~7.39 (m, 2H), 7.25 (t, 1H, J = 8.3 Hz), 3.03 (s, 3H) |
| 324 | N-(5-chloro-3'-methoxy-5'-(trifluoromethoxy)-[1,1'-biphenyl]-3-yl)-5-(methylsulfonamido)benzo[b]thiophene-2-carboxamide | LC/MS ESI (+): 571 (M + 1)<br>¹H-NMR (400 MHz, DMSO-d₆): δ 10.72 (s, 1H), 9.90 (s, 1H), 8.34 (s, 1H), 8.03~8.06 (m, 2H), 7.98 (s, 1H), 7.83 (s, 1H), 7.60 (s, 1H), 7.37 (d, 1H, J = 8.7 Hz), 7.29 (s, 1H), 7.22 (s, 1H), 7.02 (s, 1H), 3.80 (s, 3H), 3.03 (s, 3H) |
| 325 | N-(5-chloro-3'-methoxy-5'-(trifluoromethoxy)-[1,1'-biphenyl]-3-yl)-6-fluoro-5-(methylsulfonamido)benzo[b]thiophene-2-carboxamide | LC/MS ESI (+): 589 (M + 1)<br>¹H-NMR (400 MHz, DMSO-d₆): δ 10.77 (s, 1H), 9.79 (s, 1H), 8.34 (s, 1H), 8.11 (d, 1H, J = 10.3 Hz), 8.01~8.03 (m, 2H), 7.97 (s, 1H), 7.60 (s, 1H), 7.29 (s, 1H), 7.22 (s, 1H), 7.02 (s, 1H), 3.89 (s, 3H), 3.07 (s, 3H) |
| 326 | N-(5-chloro-3'-methoxy-5'-(trifluoromethoxy)-[1,1'-biphenyl]-3-yl)-6-fluoro-5-(N-methylmethylsulfonamido)benzo[b]thiophene-2-carboxamide | LC/MS ESI (+): 603 (M + 1)<br>¹H-NMR (400 MHz, DMSO-d₆): δ 10.86 (s, 1H), 8.36 (s, 1H), 8.24 (d, 1H, J = 7.6 Hz), 8.17 (d, 1H, J = 10.4 Hz), 8.02 (t, 1H, J = 2.0 Hz), 7.98 (s, 1H), 7.60 (s, 1H), 7.31 (t, 1H, J = 2.0 Hz), 7.24 (s, 1H), 7.03 (s, 1H), 3.91 (s, 3H), 3.31 (s, 3H), 3.15 (s, 3H) |
| 327 | N-(5-chloro-2',4'-difluoro-[1,1'-biphenyl]-3-yl)-5-((tetrahydrofuran)-3-sulfonamido)benzo[b]thiophene-2-carboxamide | LC/MS ESI (+): 549 (M + 1)<br>¹H-NMR (400 MHz, DMSO-d₆): δ 10.73 (s, 1H), 10.10 (s, 1H), 8.34 (s, 1H), 8.05 (d, 1H, J = 8.4 Hz), 8.01 (s, 1H), 7.91 (s, 1H), 7.84 (s, 1H), 7.63~7.69 (m, 1H), 7.42~7.48 (m, 1H), 7.38~7.40 (m, 2H), 7.24~7.29 (m, 1H), 3.91~4.02 (m, 2H), 3.80~3.88 (m, 2H), 3.64 (q, 1H, J = 6.4 Hz) 2.13~2.19 (m, 2H) |
| 328 | N-(5-chloro-3'-methoxy-5'-(trifluoromethoxy)-[1,1'-biphenyl]-3-yl)-5-((tetrahydrofuran)-3-sulfonamido)benzo[b]thiophene-2-carboxamide | LC/MS ESI (+): 627 (M + 1)<br>¹H-NMR (400 MHz, DMSO-d₆): δ 10.71 (s, 1H), 10.11 (s, 1H), 8.34 (s, 1H), 8.04~8.06 (m, 2H), 7.99 (s, 1H), 7.85 (s, 1H), 7.61 (s, 1H), 7.40 (d, 1H, J = 8.4 Hz), 7.30 (s, 1H), 7.23 (s, 1H), 7.03 (s, 1H), 3.93~4.01 (m, 2H), 3.91 (s, 3H), 3.79~3.88 (m, 2H), 3.64 (q, 1H, J = 6.8 Hz) 2.13~2.16 (m, 2H) |
| 329 | N-(5-chloro-2',4'-difluoro-[1,1'-biphenyl]-3-yl)-6-fluoro-5-(N-methylmethylsulfonamido)benzo[b]thiophene-2-carboxamide | LC/MS ESI (+): 525 (M + 1)<br>¹H-NMR (400 MHz, DMSO-d₆): δ 10.85 (s, 1H), 8.36 (s, 1H), 8.24 (d, 1H, J = 7.2 Hz), 8.17 (d, 1H, J = 10.4 Hz), 8.00 (t, 1H, J = 2.0 Hz), 7.91 (s, 1H), 7.59~7.70 (m, 1H), 7.45 (td, 1H, J = 10.2, 2.0 Hz), 7.38 (s, 1H), 7.26 (td, 1H, J = 8.0, 2.4 Hz), 3.30 (s, 3H), 3.15 (s, 3H) |
| 330 | N-(5-chloro-2',4'-difluoro-[1,1'-biphenyl]-3-yl)-6-fluoro-5-((tetrahydrofuran)-3-sulfonamido)benzo[b]thiophene-2-carboxamide | LC/MS ESI (+): 567 (M + 1)<br>¹H-NMR (400 MHz, DMSO-d₆): δ 10.71 (s, 1H), 9.95 (s, 1H), 8.27 (s, 1H), 7.97~8.00 (m, 3H), 7.89 (s, 1H), 7.65 (m, 1H), 7.45 (m, 1H), 7.36 (s, 1H), 7.25 (m, 1H), 3.80~3.96 (m, 4H), 3.66 (m, 1H), 2.16~2.18 (m, 2H) |

TABLE 19-continued

| Ex. | Compound | Analysis data |
|---|---|---|
| 331 | N-(4-chloro-6-(2,4-difluorophenyl)pyridin-2-yl)-5-(methylsulfonamido)benzo[b]thiophene-2-carboxamide | LC/MS ESI (+): 494 (M + 1)<br>$^1$H-NMR (400 MHz, DMSO-$d_6$): δ 11.33 (brs, 1H), 9.81 (brs, 1H), 8.50 (s, 1H), 8.19 (s, 1H), 8.02 (m, 1H), 7.96 (d, 1H, J = 8.8 Hz), 7.71 (d, 1H, J = 2.0 Hz), 7.58 (s, 1H), 7.40 (m, 1H), 7.31 (dd, 1H, J = 8.8, 2.0 Hz), 7.24 (td, 1H, J = 8.8, 3.0 Hz), 2.94 (s, 3H) |
| 332 | N-(3-chloro-5-(thiophen-3-yl)phenyl)-5-(methylsulfonamido)benzo[b]thiophene-2-carboxamide | LC/MS ESI (+): 463 (M + 1)<br>$^1$H-NMR (400 MHz, DMSO-$d_6$): δ 10.66 (s, 1H), 9.91 (brs, 1H), 8.33 (s, 1H), 8.03 (d, 1H, J = 8.7 Hz), 8.01 (s, 1H), 7.96 (s, 1H), 7.87 (s, 1H), 7.83 (s, 1H), 7.70 (m, 1H), 7.58 (s, 1H), 7.54 (m, 1H), 7.37 (dd, 1H, J = 8.7, 2.0 Hz), 3.02 (s, 3H) |
| 333 | 6-chloro-N-(5-chloro-2',4'-difluoro-[1,1'-biphenyl]-3-yl)-5-(methylsulfonamido)benzo[b]thiophene-2-carboxamide | LC/MS ESI (+): 527 (M + 1)<br>$^1$H-NMR (400 MHz, DMSO-$d_6$): δ 10.81 (s, 1H), 9.65 (s, 1H), 8.36 (s, 1H), 8.34 (s, 1H), 8.07 (s, 1H), 7.98 (s, 1H), 7.89 (s, 1H), 7.65 (dd, 1H, J = 15.4, 8.7 Hz), 7.43 (td, 1H, J = 10.2, 2.3 Hz), 7.37 (s, 1H), 7.24 (td, 1H, J = 8.4, 2.3 Hz), 3.07 (s, 3H) |
| 334 | N-(3-chloro-5-(1-methyl-1H-pyrrol-2-yl)phenyl)-5-(methylsulfonamido)benzo[b]thiophene-2-carboxamide | LC/MS ESI (+): 460 (M + 1)<br>$^1$H-NMR (400 MHz, DMSO-$d_6$): δ 10.63 (s, 1H), 9.88 (brs, 1H), 8.32 (s, 1H), 8.03 (d, 1H, J = 8.7 Hz), 7.86 (s, 1H), 7.83 (s, 1H), 7.79 (s, 1H), 7.37 (dd, 1H, J = 8.7, 1.8 Hz), 7.26 (s, 1H), 6.90 (s, 1H), 6.28 (m, 1H), 6.10 (m, 1H), 3.72 (s, 3H), 3.02 (s, 3H) |
| 335 | N-(5-chloro-2',4'-difluoro-[1,1'-biphenyl]-3-yl)-3-hydroxy-5-(methylsulfonamido)benzo[b]thiophene-2-carboxamide | LC/MS ESI (+): 509 (M + 1)<br>$^1$H-NMR (400 MHz, DMSO-$d_6$): δ 12.21 (brs, 1H), 10.35 (brs, 1H), 9.89 (s, 1H), 7.96 (s, 1H), 7.89~7.91 (m, 2H), 7.81 (s, 1H), 7.65 (dd, 1H, J = 15.6, 8.7 Hz), 7.32~7.44 (m, 3H), 7.23 (t, 1H, J = 8.3 Hz), 3.03 (s, 3H) |
| 336 | N-(3-chloro-5-(thiophen-2-yl)phenyl)-5-(methylsulfonamido)benzo[b]thiophene-2-carboxamide | LC/MS ESI (+): 463 (M + 1)<br>$^1$H-NMR (400 MHz, DMSO-$d_6$): δ 10.67 (s, 1H), 9.89 (brs, 1H), 8.33 (s, 1H), 8.03 (d, 1H, J = 8.7 Hz), 7.99 (s, 1H), 7.91 (s, 1H), 7.82 (s, 1H), 7.61~7.66 (m, 2H), 7.56 (s, 1H), 7.37 (dd, 1H, J = 8.7, 2.1 Hz), 7.18 (m, 1H), 3.02 (s, 3H) |

Example 337

Synthesis of N-(6-chloro-4-(2,4-difluorophenyl)pyridin-2-yl)-5-(methylsulfonamido)benzo[b]thiophene-2-carboxamide (a) Synthesis of 2,6-dichloro-4-(2,4-difluorophenyl)pyridine The synthesis procedure of Example 301-a was repeated except for using 2,6-dichloro-4-iodopyridine (100.0 mg, 0.37 mmol) to obtain 2,6-dichloro-4-(2,4-difluorophenyl)pyridine (90.0 mg, 95%).

LC/MS ESI (+): 260 (M+1)
$^1$H-NMR (400MHz, CDCl$_3$): δ 7.46 (m, 1H), 7.43 (s, 1H), 7.42 (s, 1H), 6.96-7.06 (m, 2H)

(b) Synthesis of 6-chloro-4-(2,4-difluorophenyl)pyridin-2-amine 2,6-Dichloro-4-(2,4-difluorophenyl)pyridine (70.0 mg, 0.27 mmol), NaN$_3$ (34.9 mg, 0.54 mmol), Cu$_2$O (38.4 mg, 0.27 mmol), and L-proline (30.9 mg, 0.27 mmol) were dissolved in DMSO (2.0 mL), followed by stirring at 100° C. for 2 hours. After cooling to room temperature, the reaction mixture was extracted with EtOAc, dried over anhydrous Na$_2$SO$_4$, concentrated under reduced pressure. The residue was purified by flash column chromatography (amine silica gel, n-Hex:EtOAc=9:1) to obtain 6-chloro-4-(2,4-difluorophenyl)pyridin-2-amine (20.0 mg, 31%).

LC/MS ESI (+): 241 (M+1)

(c) Synthesis of N-(6-chloro-4-(2,4-difluorophenyl)pyridin-2-yl)-5-(methylsulfonamido)benzo[b]thiophene-2-carboxamide The synthesis procedure of Example 1 was repeated except for using 6-chloro-4-(2,4-difluorophenyl)pyridin-2-amine (5.0 mg, 0.02 mmol) to obtain N-(6-chloro-4-(2,4-difluorophenyl)pyridin-2-yl)-5-(methylsulfonamido)benzo[b]thiophene-2-carboxamide (520.0 μg, 5%).

LC/MS ESI (+): 494 (M+1)
$^1$H-NMR (400MHz, DMSO-$d_6$): δ 11.52 (s, 1H), 8.51 (s, 1H), 8.38 (s, 1H), 7.94 (m, 1H), 7.78 (m, 1H), 7.69 (s, 1H), 7.47-7.52 (m, 2H), 7.27-7.32 (m, 2H), 2.93 (s, 3H)

Example 338

Synthesis of N-(3-chloro-5-(pyrazin-2-yl)phenyl)-5-(methylsulfonamido)benzo[b]thiophene-2-carboxamide (a) Synthesis of 2-(3-chloro-5-nitrophenyl)-4,4,5,5-tetramethyl-1,3,2-dioxaborolane 1-Bromo-3-chloro-5-nitrobenzene (236.5 mg, 1.00 mmol) and 4,4,4',4',5,5,5',5'-octamethyl-2,2'-bi(1,3,2-dioxaborolane) (279.0 mg, 1.10 mmol) were dissolved in anhydrous DMSO (2.0 mL), and Pd(dppf)$_2$Cl$_2$·CH$_2$Cl$_2$ (40.8 mg, 0.05 mmol) and KOAc (294.0 mg, 3.00 mmol) were added. The reaction mixture was stirred at 120° C. for 30 minutes and cooled to room temperature. After adding water, the reaction mixture was extracted with EtOAc. The organic extract was washed with a saturated NaHCO$_3$ aqueous solution and brine, dried over anhydrous Na$_2$SO$_4$ and concentrated under reduced pressure to obtain 2-(3-chloro-5-nitrophenyl)-4,4,5,5-tetramethyl-1,3,2-dioxaborolane (280.0 mg).

LC/MS ESI (+): 202 (M+1): boronic acid confirmed by mass (b) Synthesis of 2-(3-chloro-5-nitrophenyl)pyrazine The synthesis procedure of Example 301-a was repeated except for using crude 2-(3-chloro-5-nitrophenyl)-4,4,5,5-tetramethyl-1,3,2-dioxaborolane (100.0 mg) to obtain 2-(3-chloro-5-nitrophenyl)pyrazine (44.0 mg, 53%).

LC/MS ESI (+): 236 (M+1)
$^1$H-NMR (400MHz, CDCl$_3$): δ 9.12 (s, 1H), 8.81 (s, 1H), 8.72 (s, 1H), 8.66 (s, 1H), 8.40 (s, 1H), 8.32 (s, 1H)

(c) Synthesis of 3-chloro-5-(pyrazin-2-yl)aniline

The synthesis procedure of Intermediate 39 was repeated except for using 2-(3-chloro-5-nitrophenyl)pyrazine (44.0 mg, 0.19 mmol) to obtain 3-chloro-5-(pyrazin-2-yl)aniline (35.0 mg, 92%).

LC/MS ESI (+): 206 (M+1)
$^1$H-NMR (400MHz, CDCl$_3$): δ 8.96 (s, 1H), 8.62 (s, 1H), 8.53 (s, 1H), 7.36 (s, 1H), 7.23 (s, 1H), 6.78 (s, 1H), 3.90 (brs, 2H)

(d) Synthesis of N-(3-chloro-5-(pyrazin-2-yl)phenyl)-5-(methylsulfonamido)benzo[b]thiophene-2-carboxamide The synthesis procedure of Example 1 was repeated except for using 3-chloro-5-(pyrazin-2-yl)aniline (35.0 mg, 0.17 mmol) to obtain N-(3-chloro-5-(pyrazin-2-yl)phenyl)-5-(methylsulfonamido)benzo[b]thiophene-2-carboxamide (10.0 mg, 13%).

LC/MS ESI (+): 459 (M+1)
$^1$H-NMR (400MHz, DMSO-d$_6$): δ 10.73 (s, 1H), 9.85 (brs, 1H), 9.24 (s, 1H), 8.71 (s, 1H), 8.63 (s, 1H), 8.44 (s, 1H), 8.29 (s, 1H), 8.06 (s, 1H), 7.95 (d, 1H, J=8.8Hz), 7.93 (s, 1H), 7.73 (s, 1H), 7.29 (d, 1H, J=8.8Hz), 2.93 (s, 3H)

Through the synthetic method according to Example 338, compounds of Example 339 and Example 340 were synthesized, and the data of each example are as follows.

Example 341 and Example 342

Synthesis of N-(5-bromo-2',4'-difluoro-[1,1'-biphenyl]-3-yl)-1-methyl-6-(N-methylmethylsulfonamido)-1H-indole-2-carboxamide and N-(5-bromo-2',4'-difluoro-[1,1-biphenyl]-3-yl)-6-(N-methylmethylsulfonamido)-1H-indole-2-carboxamide N-(5-bromo-2',4'-difluoro-[1,1'-biphenyl]-3-yl)-6-(methylsulfonamido)-1H-indole-2-carboxamide (Example 302) (26.5 mg, 0.05 mmol), MeI (3.8 μL, 0.06 mmol), and K$_2$CO$_3$ (10.6 mg, 0.08 mmol) were dissolved in anhydrous DMF (1.0 mL), followed by stirring at room temperature for 1 hour. The reaction mixture was extracted with EtOAc, and the organic extract was washed with brine, dried over anhydrous Na$_2$SO$_4$, concentrated under reduced pressure. The residue was purified by flash column chromatography (amine silica gel, n-Hex:EtOAc=2:1) to obtain white solid compounds of N-(5-bromo-2',4'-difluoro-[1,1'-biphenyl]-3-yl)-1-methyl-6-(N-methylmethylsulfonamido)-1H-indole-2-carboxamide (8.8 mg, 31%) and N-(5-bromo-2',4'-difluoro-[1,1'-biphenyl]-3-yl)-6-(N-methylmethylsulfonamido)-1H-indole-2-carboxamide (16.0 mg, 59%).

Example 341

LC/MS (ESI)+: 548 (M+1)
$^1$H-NMR (300MHz, DMSO-d$_6$): δ 10.58 (s, 1H), 8.16 (s, 1H), 7.98 (s, 1H), 7.73 (d, 1H, J=8.4Hz), 7.59-7.66 (m, 2H), 7.39-7.46 (m, 3H), 7.26 (dd, 1H, J=8.0, 3.1Hz), 7.18 (d, 1H, J=8.8Hz), 4.03 (s, 3H), 3.32 (s, 3H), 2.99 (s, 3H)

Example 342

$^1$H-NMR (300MHz, DMSO-d$_6$): δ 12.34 (s, 1H), 10.47 (s, 1H), 8.08 (s, 1H), 7.94 (s, 1H), 7.60-7.70 (m, 1H), 7.39-7.48 (m, 5H), 7.21-7.30 (m, 2H), 3.30 (s, 3H), 2.95 (s, 3H)

Through the synthetic methods according to Examples 341 and 342, compounds from Example 343 to Example 348 were synthesized, and the data of each example are as follows.

TABLE 20

| Ex. | Compound | Analysis data |
| --- | --- | --- |
| 339 | N-(3-chloro-5-(6-chloropyrazin-2-yl)phenyl)-5-(methylsulfonamido)benzo[b]thiophene-2-carboxamide | LC/MS ESI (+): 493 (M + 1)<br>$^1$H-NMR (400 MHz, DMSO-d$_6$): δ 10.86 (s, 1H), 9.90 (brs, 1H), 9.35 (s, 1H), 8.85 (s, 1H), 8.45 (s, 1H), 8.39 (s, 1H), 8.22 (s, 1H), 8.03~8.06 (m, 2H), 7.83 (s, 1H), 7.37 (d, 1H, J = 8.8 Hz), 3.02 (s, 3H) |
| 340 | N-(3-chloro-5-(1-methyl-1H-imidazol-5-yl)phenyl)-5-(methylsulfonamido)benzo[b]thiophene-2-carboxamide | LC/MS ESI (+): 461 (M + 1)<br>$^1$H-NMR (400 MHz, DMSO-d$_6$): δ 10.68 (s, 1H), 9.88 (brs, 1H), 8.32 (s, 1H), 8.04 (d, 1H, J = 8.7 Hz), 7.93 (s, 1H), 7.83 (s, 1H), 7.82 (s, 1H), 7.76 (s, 1H), 7.37 (dd, 1H, J = 8.7, 1.8 Hz), 7.36 (s, 1H), 7.17 (s, 1H), 3.74 (s, 3H), 3.02 (s, 3H) |

TABLE 21

| Ex. | Compound | Analysis data |
|---|---|---|
| 343 | 1-methyl-6-(N-methylmethylsulfonamido)-N-(2'-(trifluoromethyl)-[1,1'-biphenyl]-3-yl)-1H-indole-2-carboxamide | LC/MS ESI (+): 502 (M + 1)<br>$^1$H-NMR (300 MHz, DMSO-d$_6$): δ 10.47 (s, 1H), 7.82~7.87 (m, 3H), 7.73~7.77 (m, 2H), 7.61~7.67 (m, 2H), 7.40~7.46 (m, 2H), 7.35 (s, 1H), 7.18 (dd, 1H, J = 8.6, 1.7 Hz), 7.05 (d, 1H, J = 7.8 Hz), 4.01 (s, 3H), 3.31 (s, 3H), 2.99 (s, 3H) |
| 344 | N-(2',4'-difluoro-[1,1'-biphenyl]-3-yl)-6-(N-methylmethylsulfonamido)-1H-indole-2-carboxamide | LC/MS ESI (+): 456 (M + 1)<br>$^1$H-NMR (300 MHz, DMSO-d$_6$): δ 11.90 (s, 1H), 10.37 (s, 1H), 7.99 (d, 1H, J = 1.5 Hz), 7.89 (d, 1H, J = 8.0 Hz), 7.72 (d, 1H, J = 8.4 Hz), 7.57~7.65 (m, 1H), 7.36~7.51 (m, 4H), 7.21~7.28 (m, 2H), 7.16 (dd, 1H, J = 8.4, 1.9 Hz), 3.28 (s, 3H), 2.95 (s, 3H) |
| 345 | N-(2',4'-difluoro-[1,1'-biphenyl]-3-yl)-1-methyl-6-(N-methylmethylsulfonamido)-1H-indole-2-carboxamide | LC/MS ESI (+): 470 (M + 1)<br>$^1$H-NMR (300 MHz, DMSO-d$_6$): δ 10.47 (s, 1H), 8.02 (d, 1H, J = 1.5 Hz), 7.84 (dd, 1H, J = 8.0, 1.6 Hz), 7.72 (d, 1H, J = 8.4 Hz), 7.66 (d, 1H, J = 1.5 Hz), 7.50~7.64 (m, 1H), 7.40~7.47 (m, 2H), 7.39 (s, 1H), 7.19~7.25 (m, 2H), 7.19 (dd, 1H, J = 8.4, 1.9 Hz), 4.03 (s, 3H), 3.32 (s, 3H), 2.99 (s, 3H) |
| 346 | 6-(N-methylmethylsulfonamido)-N-(2'-(trifluoromethyl)-[1,1'-biphenyl]-3-yl)-1H-indole-2-carboxamide | LC/MS ESI (+): 488 (M + 1)<br>$^1$H-NMR (300 MHz, CDCl$_3$ + DMSO-d$_6$): δ 10.74 (s, 1H), 9.46 (s, 1H), 7.83~7.87 (m, 1H), 7.75~7.77 (m, 2H), 7.67 (d, 1H, J = 8.6 Hz), 7.59 (t, 1H, J = 7.3 Hz), 7.47~7.52 (m, 2H), 7.36~7.42 (m, 3H), 7.08~7.15 (m, 2H), 3.38 (s, 3H), 2.88 (s, 3H) |
| 347 | N-(2',4'-difluoro-5-methoxy-[1,1'-biphenyl]-3-yl)-6-(N-methylmethylsulfonamido)-1H-indole-2-carboxamide | $^1$H-NMR (300 MHz, DMSO-d$_6$): δ 12.33 (s, 1H), 10.27 (s, 1H), 7.57~7.65 (m, 1H), 7.36~7.51 (m, 6H), 7.19~7.29 (m, 2H), 6.85 (s, 1H), 3.83 (s, 3H), 3.30 (s, 3H), 2.95 (s, 3H) |
| 348 | N-(2',4'-difluoro-5-methoxy-[1,1'-biphenyl]-3-yl)-1-methyl-6-(N-methylmethylsulfonamido)-1H-indole-2-carboxamide | LC/MS ESI (+): 500 (M + 1)<br>$^1$H-NMR (300 MHz, DMSO-d$_6$): δ 10.43 (s, 1H), 7.71 (d, 1H, J = 9.2 Hz), 7.65 (s, 1H), 7.58~7.65 (m, 2H), 7.53 (s, 1H), 7.38~7.43 (m, 1H), 7.36 (s, 1H), 7.16~7.22 (m, 2H), 6.82 (s, 1H), 4.02 (s, 3H), 3.82 (s, 3H), 3.32 (s, 3H), 2.99 (s, 3H) |

Example 349

Synthesis of N-(2',4'-difluoro-5-(6-fluoropyridin-3-yl)-[1,1'-biphenyl]-3-yl)-6-(methylsulfonamido)-1H-indole-2-carboxamide (a) Synthesis of 5-bromo-2',4'-difluoro-[1,1'-biphenyl]-3-amine 3,5-Dibromoaniline (2.3 g, 9.06 mmol), (2,4-difluorophenyl)boronic acid (1.4 g, 9.06 mmol), Pd(PPh$_3$)$_4$ (1.0 g, 0.91 mmol) and Na$_2$CO$_3$ (2.9 g, 27.18 mmol) were added to a mixture of DME/H$_2$O (85.0 mL, 4/1 v/v), followed by stirring at 85° C. for 4 hours. The reaction mixture was cooled to room temperature and extracted with EtOAc. The organic extract was washed with brine, dried over anhydrous Na$_2$SO$_4$, concentrated under reduced pressure. The residue was purified by flash column chromatography (silica gel, n-Hex:EtOAc=4:1) to obtain 5-bromo-2',4'-difluoro-[1,1'-biphenyl]-3-amine (1.1 g, 43%) as a yellow solid.

LC/MS ESI (+): 284 (M+1)
$^1$H-NMR (300MHz, DMSO-d$_6$): δ 7.50 (td, 1H, J=8.8, 6.9Hz), 7.33 (ddd, 1H, J=11.1, 9.5, 2.7Hz), 7.15 (m, 1H), 6.77 (m, 1H), 6.73 (m, 1H), 6.66 (m, 1H), 5.56 (s, 2H)

(b) Synthesis of 2',4'-difluoro-5-(6-fluoropyridin-3-yl)-[1,1'-biphenyl]-3-amine 5-Bromo-2',4'-difluoro-[1,1'-biphenyl]-3-amine (50.0 mg, 0.76 mmol), (6-fluoropyridin-3-yl)boronic acid (50.0 mg, 0.35 mmol), Pd(dppf)Cl$_2$ (14.0 mg, 0.02 mmol) and K$_2$CO$_3$ (49.0 mg, 0.35 mmol) were added to a mixture of DMA/H$_2$O (2.2 mL, 9/1 v/v). The reaction was performed in a microwave with 100 W, at 100° C. for 30 minutes. The reaction mixture was cooled to room temperature and then extracted with EtOAc. The organic extract was washed with brine, dried over anhydrous Na$_2$SO$_4$, concentrated under reduced pressure. The residue was purified by flash column chromatography (silica gel, n-Hex:EtOAc=2:1) to obtain 2',4'-difluoro-5-(6-fluoropyridin-3-yl)-[1,1'-biphenyl]-3-amine (32.0 mg, 61%) as a colorless oil.

LC/MS ESI (+): 301 (M+1)
$^1$H-NMR (300MHz, CDCl$_3$): δ 8.42 (m, 1H), 7.97 (td, 1H, J=8.4, 2.5Hz), 7.44 (m, 1H), 6.89-7.02 (m, 4H), 6.84-6.85 (m, 2H), 3.89 (brs, 2H)

(c) Synthesis of N-(2',4'-difluoro-5-(6-fluoropyridin-3-yl)-[1,1'-biphenyl]-3-yl)-6-(methylsulfonamido)-1H-indole-2-carboxamide 6-(Methylsulfonamido)-1H-indole-2-carboxylic acid hydrochloride (29.0 mg, 0.10 mmol), 2',4'-difluoro-5-(6-fluoropyridin-3-yl)[1,1'-biphenyl]-3-amine (30.0 mg, 0.10 mmol), and HATU (42.0 mg, 0.11 mmol) were dissolved in anhydrous DMF (2.0 mL), and DIPEA (26.0 μL, 0.15 mmol) was added. The reaction mixture was stirred at 40° C. for 14 hours, and the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=2:3) to obtain N-(2',4'-difluoro-5-(6-fluoropyridin-3-yl)-[1,1'-biphenyl]-3-yl)-6-(methylsulfonamido)-1H-indole-2-carboxamide (22.0 mg, 40%) as a white solid.

LC/MS ESI (+): 537 (M+1)
$^1$H-NMR (300MHz, DMSO-d$_6$): δ 11.74 (s, 1H), 10.41 (s, 1H), 9.66 (s, 1H), 8.61 (d, 1H, J=1.9Hz), 8.35 (dt, 1H, J=8.4, 2.7Hz), 8.17 (m, 1H), 8.08 (m, 1H), 7.76 (m, 1H), 7.66 (d, 1H, J=8.6Hz), 7.57 (brs, 1H), 7.41-7.48 (m, 3H), 7.35 (dd, 1H, J=8.6, 2.9Hz), 7.26 (dt, 1H, J=8.6, 2.9Hz), 6.99 (dd, 1H, J=8.6, 1.5Hz), 2.95 (s, 3H)

Through the synthetic method according to Example 349, compounds from Example 350 to Example 363 were synthesized, and the data of each example are as follows.

TABLE 22

| Ex. | Compound | Analysis data |
|---|---|---|
| 350 | tert-butyl 2-(2',4'-difluoro-5-(6-(methylsulfonamido)-1H-indole-2-carboxamido)-[1,1'-biphenyl]-3-yl)-1H-pyrrole-1-carboxylate | LC/MS ESI (+): 607 (M + 1)<br>$^1$H-NMR (300 MHz, DMSO-d$_6$): δ 11.71 (s, 1H), 10.29 (s, 1H), 9.64 (brs, 1H), 7.90~7.94 (m, 2H), 7.59~7.67 (m, 2H), 7.31~7.45 (m, 4H), 7.19~7.27 (m, 2H), 6.98 (dd, 1H, J = 8.8, 1.9 Hz), 6.36~6.37 (m, 1H), 6.31~6.33 (m, 1H), 2.94 (s, 3H), 1.30 (s, 9H) |
| 351 | N-(2',4'-difluoro-5-(1H-pyrazol-3-yl)-[1,1'-biphenyl]-3-yl)-6-(methylsulfonamido)-1H-indole-2-carboxamide | LC/MS ESI (+): 508 (M + 1)<br>$^1$H-NMR (300 MHz, DMSO-d$_6$): δ 13.02 (brs, 1H), 11.71 (s, 1H), 10.27 (s, 1H), 9.63 (brs, 1H), 8.22~8.24 (m, 1H), 8.01~8.04 (m, 1H), 7.91~7.93 (m, 1H), 7.83 (s, 1H), 7.63~7.76 (m, 2H), 7.48 (s, 1H), 7.35~7.45 (m, 3H), 7.25 (dt, 1H, J = 7.7, 1.8 Hz), 6.98 (dd, 1H, J = 8.5, 1.8 Hz), 2.95 (s, 3H) |
| 352 | N-(2',4'-difluoro-5-(1H-pyrrol-2-yl)-[1,1'-biphenyl]-3-yl)-6-(methylsulfonamido)-1H-indole-2-carboxamide | LC/MS ESI (+): 507 (M + 1)<br>$^1$H-NMR (300 MHz, DMSO-d$_6$): δ 11.73 (s, 1H), 11.41 (brs, 1H), 10.27 (s, 1H), 9.64 (brs, 1H), 8.07 (s, 1H), 7.77 (s, 1H), 7.63~7.71 (m, 2H), 7.53 (s, 1H), 7.38~7.46 (m, 3H), 7.26 (dt, 1H, J = 8.4, 2.3 Hz), 7.00 (dd, 1H, J = 8.8, 1.9 Hz), 6.88 (s, 1H), 6.52 (s, 1H), 6.16 (dd, 1H, J = 5.3, 2.3 Hz), 2.95 (s, 3H) |
| 353 | N-(2',4'-difluoro-5-(1-methyl-1H-pyrrol-2-yl)-[1,1'-biphenyl]-3-yl)-6-(methylsulfonamido)-1H-indole-2-carboxamide | LC/MS ESI (+): 521 (M + 1)<br>$^1$H-NMR (300 MHz, DMSO-d$_6$): δ 11.76 (s, 1H), 10.33 (s, 1H), 9.65 (brs, 1H), 7.98 (s, 1H), 7.91 (s, 1H), 7.63~7.71 (m, 2H), 7.38~7.45 (m, 3H), 7.29 (d, 1H, J = 1.5 Hz), 7.24 (dt, 1H, J = 9.6, 2.6 Hz), 6.99 (dd, 1H, J = 8.5, 1.8 Hz), 6.89 (t, 1H, J = 2.6 Hz), 6.27 (dd, 1H, J = 3.7, 1.8 Hz), 6.10 (dd, 1H, J = 3.7, 2.6 Hz), 3.74 (s, 3H), 2.94 (s, 3H) |
| 354 | N-(2',4'-difluoro-5-(thiophen-2-yl)-[1,1'-biphenyl]-3-yl)-6-(methylsulfonamido)-1H-indole-2-carboxamide | LC/MS ESI (+): 524 (M + 1)<br>$^1$H-NMR (300 MHz, DMSO-d$_6$): δ 11.74 (s, 1H), 10.37 (s, 1H), 9.64 (brs, 1H), 8.19 (s, 1H), 7.97 (s, 1H), 7.53~7.74 (m, 5H), 7.39~7.47 (m, 3H), 7.26 (dt, 1H, J = 8.8, 1.9 Hz), 7.19 (dd, 1H, J = 5.3, 3.8 Hz), 7.00 (dd, 1H, J = 8.4, 1.9 Hz), 2.95 (s, 3H) |
| 355 | N-(2',4'-difluoro-5-(thiophen-3-yl)-[1,1'-biphenyl]-3-yl)-6-(methylsulfonamido)-1H-indole-2-carboxamide | LC/MS ESI (+): 524 (M + 1)<br>$^1$H-NMR (300 MHz, DMSO-d$_6$): δ 11.75 (s, 1H), 10.35 (s, 1H), 9.66 (brs, 1H), 8.16 (s, 1H), 7.95 (d, 1H, J = 1.5 Hz), 7.92 (dd, 1H, J = 3.1, 1.5 Hz), 7.64~7.74 (m, 3H), 7.57~7.58 (m, 2H), 7.39~7.47 (m, 3H), 7.25 (dt, 1H, J = 8.8, 1.9 Hz), 7.00 (dd, 1H, J = 8.4, 1.9 Hz), 2.95 (s, 3H) |
| 356 | N-(2',4'-difluoro-5-(pyridin-4-yl)-[1,1'-biphenyl]-3-yl)-6-(methylsulfonamido)-1H-indole-2-carboxamide | LC/MS ESI (+): 519 (M + 1)<br>$^1$H-NMR (300 MHz, DMSO-d$_6$): δ 11.74 (s, 1H), 10.44 (s, 1H), 9.56 (brs, 1H), 8.70 (d, 2H, J = 6.1 Hz), 8.27 (s, 1H), 8.12 (s, 1H), 7.65~7.73 (m, 1H), 7.73 (d, 2H, J = 6.1 Hz), 7.57~7.60 (m, 2H), 7.35~7.42 (m, 3H), 7.26 (dt, 1H, J = 8.4, 1.9 Hz), 7.00 (dd, 1H, J = 8.8, 1.9 Hz), 2.95 (s, 3H) |
| 357 | N-(2',4'-difluoro-5-(pyridin-3-yl)-[1,1'-biphenyl]-3-yl)-6-(methylsulfonamido)-1H-indole-2-carboxamide | LC/MS ESI (+): 519 (M + 1)<br>$^1$H-NMR (300 MHz, DMSO-d$_6$): δ 11.74 (s, 1H), 10.41 (s, 1H), 9.64 (brs, 1H), 8.94 (s, 1H), 8.61 (d, 1H, J = 5.0 Hz), 8.05~8.20 (m, 3H), 7.74~7.78 (m, 1H), 7.63~7.67 (m, 1H), 7.51~7.58 (m, 2H), 7.36~7.47 (m, 3H), 7.26 (dt, 1H, J = 8.4, 1.9 Hz), 6.99 (dd, 1H, J = 8.4, 1.9 Hz), 2.94 (s, 3H) |
| 358 | N-(2',4'-difluoro-5-(6-(trifluoromethyl)pyridin-3-yl)-[1,1'-biphenyl]-3-yl)-6-(methylsulfonamido)-1H-indole-2-carboxamide | LC/MS ESI (+): 587 (M + 1)<br>$^1$H-NMR (300 MHz, DMSO-d$_6$): δ 11.76 (s, 1H), 10.47 (s, 1H), 9.67 (brs, 1H), 9.15 (s, 1H), 8.42 (d, 1H, J = 8.0 Hz), 8.28 (s, 1H), 8.13 (s, 1H), 8.04 (d, 1H, J = 8.4 Hz), 7.72~7.80 (m, 1H), 7.65~7.77 (m, 2H), 7.39~7.46 (m, 3H), 7.25 (dt, 1H, J = 8.8, 2.3 Hz), 7.00 (dd, 1H, J = 8.4, 1.9 Hz), 2.96 (s, 3H) |
| 359 | N-(5-(6-cyanopyridin-3-yl)-2',4'-difluoro-[1,1'-biphenyl]-3-yl)-6-(methylsulfonamido)-1H-indole-2-carboxamide | LC/MS ESI (+): 544 (M + 1)<br>$^1$H-NMR (300 MHz, DMSO-d$_6$): δ 11.75 (s, 1H), 10.46 (s, 1H), 9.66 (brs, 1H), 9.15 (s, 1H), 8.41 (dd, 1H, J = 8.0, 2.3 Hz), 8.27 (s, 1H), 8.15~8.18 (m, 2H), 7.64~7.82 (m, 3H), 7.39~7.47 (m, 3H), 7.27 (dt, 1H, J = 8.8, 2.3 Hz), 7.00 (dd, 1H, J = 8.8, 1.9 Hz), 2.95 (s, 3H) |
| 360 | N-(2',4'-difluoro-5-(pyrimidin-5-yl)-[1,1'-biphenyl]-3-yl)-6-(methylsulfonamido)-1H-indole-2-carboxamide | LC/MS ESI (+): 520 (M + 1)<br>$^1$H-NMR (300 MHz, DMSO-d$_6$): δ 11.76 (s, 1H), 10.45 (s, 1H), 9.67 (brs, 1H), 9.25 (s, 1H), 9.19 (s, 2H), 8.23 (s, 1H), 8.13 (s, 1H), 7.73~7.81 (m, 1H), 7.65~7.68 (m, 2H), 7.41~7.46 (m, 3H), 7.27 (dt, 1H, J = 8.8, 1.9 Hz), 7.00 (dd, 1H, J = 8.4, 1.9 Hz), 2.96 (s, 3H) |

TABLE 22-continued

| Ex. | Compound | Analysis data |
|---|---|---|
| 361 | N-(5-(2-aminopyrimidin-5-yl)-2',4'-difluoro-[1,1'-biphenyl]-3-yl)-6-(methylsulfonamido)-1H-indole-2-carboxamide | LC/MS ESI (+): 535 (M + 1)<br>$^1$H-NMR (300 MHz, DMSO-d$_6$): δ 11.72 (s, 1H), 10.33 (s, 1H), 9.64 (brs, 1H), 8.62 (s, 2H), 8.05 (s, 1H), 7.99 (s, 1H), 7.71~7.74 (m, 1H), 7.64 (d, 1H, J = 8.5 Hz), 7.48 (s, 1H), 7.34~7.45 (m, 3H), 7.25 (dt, 1H, J = 7.7, 1.8 Hz), 7.00 (dd, 1H, J = 8.8, 1.8 Hz), 6.87 (s, 2H), 2.94 (s, 3H) |
| 362 | 6-(methylsulfonamido)-N-(2,2'',4,4''-tetrafluoro-[1,1':3',1''-terphenyl]-5'-yl)-1H-indole-2-carboxamide | LC/MS ESI (+): 554 (M + 1)<br>$^1$H-NMR (300 MHz, DMSO-d$_6$): δ 11.70 (s, 1H), 10.38 (s, 1H), 9.68 (s, 1H), 8.07 (s, 2H), 7.62~7.73 (m, 3H), 7.37~7.46 (m, 5H), 7.25 (td, 2H, J = 8.4, 2.7 Hz), 6.98 (dd, 1H, J = 8.8, 1.9 Hz), 2.93 (s, 3H) |
| 363 | N-(5-(cyanomethyl)-2',4'-difluoro-[1,1'-biphenyl]-3-yl)-6-(methylsulfonamido)-1H-indole-2-carboxamide | LC/MS ESI (+): 481 (M + 1)<br>$^1$H-NMR (300 MHz, DMSO-d$_6$): δ 11.72 (s, 1H), 10.38 (s, 1H), 9.65 (brs, 1H), 7.97 (s, 1H), 7.94 (s, 1H), 7.64 (d, 1H, J = 8.4 Hz), 7.56~7.66 (m, 1H), 7.38~7.46 (m, 3H), 7.21~7.28 (m, 2H), 6.99 (dd, 1H, J = 8.4, 1.5 Hz), 4.16 (s, 2H), 2.94 (s, 3H) |

Example 364

Synthesis of N-(2',4'-difluoro-5-(6-hydroxypyridin-3-yl)-[1,1'-biphenyl]-3-yl)-6-(methylsulfonamido)-1H-indole-2-carboxamide

(a) Synthesis of 5-(5-amino-2',4'-difluoro-[1,1'-biphenyl]-3-yl)pyridin-2-ol 2',4'-Difluoro-5-(6-fluoropyridin-3-yl)[1,1'-biphenyl]-3-amine (32.0 mg, 0.11 mmol) was dissolved in 1,4-dioxane (2.0 mL), and a mixture of 6 N HCl/1,4-dioxane (444.0 µL) was slowly added at 0° C. The mixture was stirred at 100° C. for 2 hours, and then basified with sat. NaHCO$_3$ aqueous solution (pH 9), and the reaction mixture was extracted with EtOAc. The organic extract was washed with brine, dried over anhydrous Na$_2$SO$_4$, concentrated under reduced pressure. The residue was purified by flash column chromatography (amine silica gel, n-Hex:EtOAc=1:1) to obtain 5-(5-amino-2',4'-difluoro-[1,1'-biphenyl]-3-yl)pyridin-2-ol (20.0 mg, 63%) as a yellow solid.

LC/MS ESI (+): 299 (M+1)

(b) Synthesis of N-(2',4'-difluoro-5-(6-hydroxypyridin-3-yl)-[1,1'-biphenyl]-3-yl)-6-(methylsulfonamido)-1H-indole-2-carboxamide 6-(methylsulfonamido)-1H-indole-2-carboxylic acid (29.0 mg, 0.10 mmol), 5-(5-amino-2',4'-difluoro-[1,1'-biphenyl]-3-yl)pyridin-2-ol (30.0 mg, 0.10 mmol), HATU (42.0 mg, 0.11 mmol), and DIPEA (26.0 µL, 0.15 mmol) were dissolved in anhydrous DMF (2.0 mL), followed by stirring at 40° C. for 12 hours. The reaction mixture was extracted with EtOAc, and the organic extract was washed with brine, dried over anhydrous Na$_2$SO$_4$, concentrated under reduced pressure. The residue was firstly purified by flash column chromatography, and the residue was purified by flash column chromatography (amine silica gel, n-Hex:EtOAc=1:1) to obtain N-(2',4'-difluoro-5-(6-hydroxypyridin-3-yl)-[1,1'-biphenyl]-3-yl)-6-(methylsulfonamido)-1H-indole-2-carboxamide (7.6 mg, 14%) as a white solid.

LC/MS ESI (+): 535 (M+1)

$^1$H-NMR (300MHz, DMSO-d$_6$): δ 11.82 (brs, 1H), 11.65 (s, 1H), 10.25 (s, 1H), 9.57 (s, 1H), 7.95-8.00 (m, 2H), 7.86 (dd, 1H, J=9.5, 3.0Hz), 7.63-7.77 (m, 3H), 7.34-7.42 (m, 4H), 7.23 (dt, 1H, J=8.3, 2.8Hz), 7.00 (dd, 1H, J=8.6, 1.9Hz), 6.49 (d, 1H, J=9.3Hz), 2.95 (s, 3H)

Example 365

Synthesis of N-(5-ethynyl-2',4'-difluoro-[1,1'-biphenyl]-3-yl)-6-(methylsulfonamido)-1H-indole-2-carboxamide

(a) Synthesis of 2',4'-difluoro-5-((trimethylsilyl)ethynyl)-[1,1'-biphenyl]-3-amine 5-Bromo-2',4'-difluoro-[1,1'-biphenyl]-3-amine (100.0 mg, 0.35 mmol), ethynyltrimethylsilane (149.0 µL, 1.06 mmol), Pd(t-Bu$_3$P)$_2$ (180.0 mg, 0.04 mmol), CuI (67.0 mg, 0.04 mmol), and Et$_3$N (147.0 µL, 1.06 mmol) were added to 1,4-dioxane (3.0 mL), followed by stirring at 40° C. for 17 minutes, and the reaction mixture was cooled to room temperature and then extracted with EtOAc. The organic extract was washed with brine, dried over anhydrous Na$_2$SO$_4$, concentrated under reduced pressure. The residue was purified by flash column chromatography (silica gel, n-Hex:EtOAc=2:1) to obtain 2',4'-difluoro-5-((trimethylsilyl)ethynyl)-[1,1'-biphenyl]-3-amine (75.0 mg, 71%) as a white solid.

LC/MS ESI (+): 302 (M+1)

$^1$H-NMR (300MHz, CDCl$_3$): δ 7.36 (m, 1H), 7.00 (m, 1H), 6.84-6.95 (m, 2H), 6.76-6.80 (m, 2H), 3.72 (brs, 2H), 1.57 (s, 9H)

(b) Synthesis of 5-ethynyl-2',4'-difluoro-[1,1'-biphenyl]-3-amine

2',4'-Difluoro-5-((trimethylsilyl)ethynyl)-[1,1'-biphenyl]-3-amine (71.0 mg, 0.24 mmol) was dissolved in anhydrous MeOH (2.0 mL), and K$_2$CO$_3$ (33.0 mg, 0.24 mmol) was added. The reaction mixture was stirred at 17° C. for 3 hours, and the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=20:1) to obtain 5-ethynyl-2',4'-difluoro-[1,1'-biphenyl]-3-amine (45.0 mg, 83%) as a yellow solid.

LC/MS ESI (+): 230 (M+1)

$^1$H-NMR (300MHz, CDCl$_3$): δ 7.36 (m, 1H), 7.00 (m, 1H), 6.86-6.96 (m, 2H), 6.80-6.83 (m, 2H), 3.72 (brs, 2H), 3.04 (s, 1H)

(c) Synthesis of N-(5-ethynyl-2',4'-difluoro-[1,1'-biphenyl]-3-yl)-6-(methylsulfonamido)-1H-indole-2-carboxamide 6-(Methylsulfonamido)-1H-indole-2-carboxylic acid hydrochloride (57.0 mg, 0.20 mmol), 5-ethynyl-2',4'-difluoro-[1,1'-biphenyl]-3-amine (45.0 mg, 0.20 mmol), HATU (82.0 mg, 0.22 mmol), and DIPEA (51.0 μL, 0.29 mmol) were dissolved in anhydrous DMF (2.0 mL), followed by stirring at 16° C. for 16 hours. The reaction mixture was extracted with EtOAc, and the organic extract was washed with brine, dried over anhydrous $Na_2SO_4$, concentrated under reduced pressure. The residue was purified by flash column chromatography (silica gel, n-Hex:EtOAc=1:1) to obtain N-(5-ethynyl-2',4'-difluoro-[1,1'-biphenyl]-3-yl)-6-(methylsulfonamido)-1H-indole-2-carboxamide (28.9 mg, 32%) as a white solid.

LC/MS ESI (+): 466 (M+1)

$^1$H-NMR (300MHz, DMSO-$d_6$): δ 11.74 (s, 1H), 10.35 (s, 1H), 9.65 (s, 1H), 8.05 (m, 1H), 8.00 (m, 1H), 7.60-7.68 (m, 2H), 7.39-7.46 (m, 3H), 7.34 (m, 1H), 7.24 (dt, 1H, J=8.4, 2.5Hz), 6.99 (dd, 1H, J=8.6, 1.9Hz), 4.30 (s, 1H), 2.95 (s, 3H)

Example 366

Synthesis of N-(5-(2,2-difluoroethoxy)-2',4'-difluoro-[1,1'-biphenyl]-3-yl)-6-(methylsulfonamido)-1H-indole-2-carboxamide (a) Synthesis of 2',4'-difluoro-5-nitro-[1,1'-biphenyl]-3-ol 2,4-Difluoro-3'-methoxy-5'-nitro-1,1'-biphenyl (753.0 mg, 2.84 mmol) was dissolved in anhydrous $CH_2Cl_2$ (28.4 mL), and 1.0 M solution of $BBr_3$ in $CH_2Cl_2$ (11.4 mL) was slowly added at 0° C. The mixture was stirred at 0° C. for 10 hours, MeOH was slowly added. The reaction mixture was extracted with EtOAc. The organic extract was washed with brine, dried over anhydrous $Na_2SO_4$, concentrated under reduced pressure. The residue was purified by flash column chromatography (silica gel, n-Hex:EtOAc=4:1) to obtain 2',4'-difluoro-5-nitro-[1,1'-biphenyl]-3-ol (187.0 mg, 82%) as a yellow solid.

$^1$H-NMR (300MHz, CDCl$_3$): δ 7.96 (s, 1H), 7.69-7.71 (m, 1H), 7.32-7.49 (m, 1H), 7.32-7.33 (m, 1H), 6.93-7.04 (m, 2H), 5.48 (s, 1H)

(b) Synthesis of 3'-(2,2-difluoroethoxy)-2,4-difluoro-5'-nitro-1,1'-biphenyl

2',4'-Difluoro-5-nitro-[1,1'-biphenyl]-3-ol (100.0 mg, 0.40 mmol) was dissolved in anhydrous DMF (2.0 mL), and $K_2CO_3$ (110.0 mg, 0.80 mmol) and 2-iodo-1,1-difluoroethane (42.0 μL, 0.48 mmol) were added. The reaction mixture was stirred at room temperature for 24 hours, and the reaction mixture was extracted with EtOAc. The organic extract was washed with brine, dried over anhydrous $Na_2SO_4$, concentrated under reduced pressure. The residue was purified by flash column chromatography (silica gel, n-Hex:EtOAc=3:1) to obtain 3'-(2,2-difluoroethoxy)-2,4-difluoro-5'-nitro-1,1'-biphenyl (107.0 mg, 91%) as a white solid.

$^1$H-NMR (300MHz, CDCl$_3$): δ 8.05 (s, 1H), 7.76-7.78 (m, 1H), 7.41-7.49 (m, 2H), 6.95-7.04 (m, 2H), 6.14 (tt, 1H, J=54.6, 3.8Hz), 4.32 (td, 2H, J=12.6, 3.8Hz)

(c) Synthesis of 5-(2,2-difluoroethoxy)-2',4'-difluoro-[1,1'-biphenyl]-3-amine

3'-(2,2-Difluoro ethoxy)-2,4-difluoro-5'-nitro-1,1'-biphenyl (107.0 mg, 0.34 mmol) was dissolved in a mixture of MeOH/$H_2O$ (3.4 mL, 8/1 v/v), and Zn (333.0 mg, 5.09 mmol) and $NH_4Cl$ (91.0 mg, 1.70 mmol) were added. The reaction mixture was ultrasonificated for 2 hours, filtered through Celite and concentrated under reduced pressure. The residue was extracted with EtOAc, and the organic extract was washed with brine, dried over anhydrous $Na_2SO_4$, concentrated under reduced pressure. The residue was purified by flash column chromatography (amine silica gel, n-Hex:EtOAc=1:1) to obtain 5-(2,2-difluoroethoxy)-2',4'-difluoro-[1,1'-biphenyl]-3-amine (96.0 mg, 99%) as a colorless oil.

LC/MS ESI (+): 286 (M+1)

(d) Synthesis of N-(5-(2,2-difluoroethoxy)-2',4'-difluoro-[1,1'-biphenyl]-3-yl)-6-(methylsulfonamido)-1H-indole-2-carboxamide 6-(Methylsulfonamido)-1H-indole-2-carboxylic acid hydrochloride (44.8 mg, 0.15 mmol), 5-(2,2-difluoroethoxy)-2',4'-difluoro-[1,1'-biphenyl]-3-amine (48.5 mg, 0.17 mmol), and HATU (64.6 mg, 0.17 mmol) were dissolved in anhydrous DMF (3.0 mL). DIPEA (40.0 μL, 0.23 mmol) was slowly added, followed by stirring at room temperature for 24 hours. The reaction mixture was extracted with EtOAc, and the organic extract was washed with brine, dried over anhydrous $Na_2SO_4$, concentrated under reduced pressure. The residue was purified by flash column chromatography (amine silica gel, $CH_2Cl_2$:MeOH=30:1) to obtain N-(5-(2,2-difluoroethoxy)-2',4'-difluoro-[1,1'-biphenyl]-3-yl)-6-(methylsulfonamido)-1H-indole-2-carboxamide (8.7 mg, 11%) as a white solid.

LC/MS ESI (+): 522 (M+1)

$^1$H-NMR (300MHz, DMSO-$d_6$): δ 11.73 (s, 1H), 10.27 (s, 1H), 9.64 (s, 1H), 7.60-7.68 (m, 4H), 7.36-7.44 (m, 3H), 7.23 (td, 1H, J=8.4, 1.9Hz), 6.99 (dd, 1H, J=8.4, 1.9Hz), 6.91 (s, 1H), 6.44 (tt, 1H, J=54.6, 3.4Hz), 4.39 (td, 2H, J=14.9, 3.4Hz), 2.94 (s, 3H)

Through the synthetic method according to Example 366, compounds from Example 367 to Example 370 were synthesized, and the data of each example are as follows.

TABLE 23

| Ex. | Compound | Analysis data |
| --- | --- | --- |
| 367 | N-(2',4'-difluoro-5-isobutoxy-[1,1'-biphenyl]-3-yl)-6-(methylsulfonamido)-1H-indole-2-carboxamide | LC/MS ESI (+): 514 (M + 1)<br>$^1$H-NMR (300 MHz, DMSO-$d_6$): δ 11.70 (s, 1H), 10.21 (s, 1H), 9.64 (s, 1H), 7.56~7.65 (m, 4H), 7.34~7.42 (m, 3H), 7.21 (td, 1H, J = 8.4, 2.3 Hz), 6.99 (dd, 1H, J = 8.8, 1.5 Hz), 6.80 (s, 1H), 3.81 (d, 2H, J = 6.5 Hz), 2.94 (s, 3H), 1.98~2.11 (m, 1H), 1.01 (d, 6H, J = 6.9 Hz) |
| 368 | N-(5-(cyanomethoxy)-2',4'-difluoro-[1,1'-biphenyl]-3-yl)-6-(methylsulfonamido)-1H-indole-2-carboxamide | LC/MS ESI (+): 497 (M + 1)<br>$^1$H-NMR (300 MHz, DMSO-$d_6$): δ 11.74 (s, 1H), 10.34 (s, 1H), 9.64 (s, 1H), 7.59~7.71 (m, 4H), 7.39~7.46 (m, 3H), 7.22~7.29 (m, 1H), 6.97~7.00 (m, 2H), 5.24 (s, 2H), 2.94 (s, 3H) |

TABLE 23-continued

| Ex. | Compound | Analysis data |
|---|---|---|
| 369 | N-(5-(difluoromethoxy)-2',4'-difluoro-[1,1'-biphenyl]-3-yl)-6-(methylsulfonamido)-1H-indole-2-carboxamide | LC/MS ESI (+): 508 (M + 1)<br>$^1$H-NMR (300 MHz, DMSO-$d_6$): δ 11.75 (s, 1H), 10.42 (s, 1H), 9.65 (s, 1H), 7.84~7.85 (m, 2H), 7.60~7.69 (m, 2H), 7.40~7.47 (m, 3H), 7.32 (t, 1H, J = 74.0 Hz), 7.26 (dt, 1H, J = 8.8, 2.3 Hz), 7.07 (brs, 1H), 6.99 (dd, 1H, J = 8.6, 1.9 Hz), 2.94 (s, 3H) |
| 370 | N-(5-(difluoromethoxy)-2',4'-difluoro-[1,1'-biphenyl]-3-yl)-5-(methylsulfonamido)benzo[b]thiophene-2-carboxamide | LC/MS ESI (+): 525 (M + 1)<br>$^1$H-NMR (300 MHz, DMSO-$d_6$): δ 10.73 (s, 1H), 9.80 (s, 1H), 8.33 (s, 1H), 8.03 (d, 1H, J = 8.8 Hz), 7.81~7.84 (m, 2H), 7.77 (s, 1H), 7.64 (m, 1H), 7.35~7.48 (m, 2H), 7.33 (t, 1H, J = 73.8 Hz), 7.26 (t, 1H, J = 8.1 Hz), 7.10 (s, 1H), 3.02 (s, 3H) |

Example 371

Synthesis of N-(2',4'-difluoro-5-(piperidin-1-yl)-[1,1'-biphenyl]-3-yl)-6-(methylsulfonamido)-1H-indole-2-carboxamide (a) Synthesis of 1-(3-iodo-5-nitrophenyl)piperidine 1-Fluoro-3-iodo-5-nitrobenzene (500.0 mg, 1.87 mmol) was dissolved in anhydrous DMF (10.0 mL), and K$_2$CO$_3$ (518.0 mg, 3.75 mmol) and piperidine (185.0 μL, 1.87 mmol) were added. The mixture was stirred at 130° C. for 16 hours, and the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=10:1) to obtain 1-(3-iodo-5-nitrophenyl)piperidine (330.0 mg, 53%) as a white solid.

LC/MS ESI (+): 333 (M+1)

$^1$H-NMR (300MHz, DMSO-$d_6$): δ 7.73 (s, 1H), 7.59-7.63 (m, 2H), 3.28-3.32 (m, 4H), 1.53-1.64 (m, 6H)

(b) Synthesis of 1-(2',4'-difluoro-5-nitro-[1,1'-biphenyl]-3-yl)piperidine 1-(3-Iodo-5-nitrophenyl)piperidine (250.0 mg, 0.75 mmol), (2,4-difluorophenyl)boronic acid (125.0 mg, 0.79 mmol), Pd(PPh$_3$)$_4$ (87.0 mg, 0.09 mmol) and Na$_2$CO$_3$ (239.0 mg, 2.26 mmol) were added to a mixture of DME/H$_2$O (7.5 mL, 4/1 v/v), followed by stirring at 85° C. for 4 hours. The reaction mixture was cooled to room temperature and extracted with EtOAc. The organic extract was washed with brine, dried over anhydrous Na$_2$SO$_4$, concentrated under reduced pressure. The residue was purified by flash column chromatography (silica gel, n-Hex:EtOAc=4:1) to obtain 1-(2',4'-difluoro-5-nitro-[1,1'-biphenyl]-3-yl)piperidine (260.0 mg, 100%) as a white solid.

LC/MS ESI (+): 319 (M+1)

(c) Synthesis of 2',4'-difluoro-5-(piperidin-1-yl)-[1,1'-biphenyl]-3-amine 1-(2',4'-Difluoro-5-nitro-[1,1'-biphenyl]-3-yl)piperidine (260.0 mg, 0.82 mmol) was dissolved in a mixture of THF/MeOH/H$_2$O (10.0 mL, 1/2/0.5 v/v), and Zn (534.0 mg, 8.17 mmol) and NH$_4$Cl (131.0 mg, 2.45 mmol) were added at room temperature. The reaction mixture was ultrasonificated for 1 hour, cooled to room temperature, filtered through Celite and concentrated under reduced pressure. The residue was purified by flash column chromatography (silica gel, CH$_2$Cl$_2$:MeOH=97:3) to obtain 2',4'-difluoro-5-(piperidin-1-yl)-[1,1'-biphenyl]-3-amine (98.0 mg, 42%) as an off-white solid.

LC/MS ESI (+): 289 (M+1)

$^1$H-NMR (300MHz, DMSO-$d_6$): δ 7.46 (td, 1H, J=9.0, 6.9Hz), 7.23-7.30 (m, 1H), 7.11 (m, 1H), 6.18-6.19 (m, 2H), 6.14 (m, 1H), 4.99 (s, 2H), 3.05-3.19 (m, 4H), 1.51-1.59 (m, 6H)

(d) Synthesis of N-(2',4'-difluoro-5-(piperidin-1-yl)-[1,1'-biphenyl]-3-yl)-6-(methylsulfonamido)-1H-indole-2-carboxamide 6-(Methylsulfonamido)-1H-indole-2-carboxylic acid hydrochloride (50.0 mg, 0.17 mmol), 2',4'-difluoro-5-(piperidin-1-yl)-[1,1'-biphenyl]-3-amine (50.0 mg, 0.17 mmol), HATU (72.0 mg, 0.19 mmol), and DIPEA (45.0 μL, 0.26 mmol) were dissolved in anhydrous DMF (3.0 mL), followed by stirring at 40° C. for 14 hours. The reaction mixture was extracted with EtOAc, and the organic extract was washed with brine, dried over anhydrous Na$_2$SO$_4$, concentrated under reduced pressure. The residue was purified by flash column chromatography (silica gel, CH$_2$Cl$_2$:MeOH=30:1) to obtain N-(2',4'-difluoro-5-(piperidin-1-yl)-[1,1'-biphenyl]-3-yl)-6-(methylsulfonamido)-1H-indole-2-carboxamide (23.0 mg, 26%) as a white solid.

LC/MS ESI (+): 525 (M+1)

$^1$H-NMR (300MHz, DMSO-$d_6$): δ 11.65 (s, 1H), 10.06 (s, 1H), 9.61 (brs, 1H), 7.54-7.64 (m, 2H), 7.44-7.46 (m, 2H), 7.31-7.39 (m, 3H), 7.19 (dt, 1H, J=8.4, 2.5Hz), 6.98 (d, 1H, J=8.4Hz), 6.76 (brs, 1H), 3.20-3.23 (m, 4H), 2.94 (s, 3H), 1.57-1.65 (m, 6H)

Through the synthetic method according to Example 371, compounds from Example 372 to Example 376 were synthesized, and the data of each example are as follows.

TABLE 24

| Ex. | Compound | Analysis data |
|---|---|---|
| 372 | N-(5-(dimethylamino)-2',4'-difluoro-[1,1'-biphenyl]-3-yl)-6-(methylsulfonamido)-1H-indole-2-carboxamide | LC/MS ESI (+): 485 (M + 1)<br>$^1$H-NMR (300 MHz, DMSO-$d_6$): δ 11.67 (s, 1H), 10.07 (s, 1H), 9.63 (brs, 1H), 7.55~7.65 (m, 2H), 7.30~7.40 (m, 5H), 7.20 (dt, 1H, J = 8.8, 2.5 Hz), 6.99 (dd, 1H, J = 8.6, 1.5 Hz), 6.56 (brs, 1H), 2.97 (s, 6H), 2.95 (s, 3H) |

TABLE 24-continued

| Ex. | Compound | Analysis data |
|---|---|---|
| 373 | N-(2',4'-difluoro-5-(methylamino)-[1,1'-biphenyl]-3-yl)-6-(methylsulfonamido)-1H-indole-2-carboxamide | LC/MS ESI (+): 471 (M + 1)<br>$^1$H-NMR (300 MHz, DMSO-$d_6$): δ 11.6 (s, 1H), 10.0 (s, 1H), 9.55 (brs, 1H), 7.62 (d, 1H, J = 8.6 Hz), 7.54 (m, 1H), 7.35 (m, 3H), 7.18 (m, 3H), 6.98 (dd, 1H, J = 8.6, 1.5 Hz), 6.40 (m, 1H), 5.90 (m, 1H), 2.93 (s, 3H), 2.72 (d, 3H, J = 5.0 Hz) |
| 374 | N-(2',4'-difluoro-5-morpholine-[1,1'-biphenyl]-3-yl)-6-(methylsulfonamido)-1H-indole-2-carboxamide | LC/MS ESI (+): 527 (M + 1)<br>$^1$H-NMR (300 MHz, DMSO-$d_6$): δ 11.66 (s, 1H), 10.11 (s, 1H), 9.61 (brs, 1H), 7.55~7.64 (m, 2H), 7.46~7.50 (m, 2H), 7.32~7.39 (m, 3H), 7.20 (dt, 1H, J = 8.8, 2.5 Hz), 6.98 (dd, 1H, J = 8.8, 1.5 Hz), 6.80 (brs, 1H), 3.77 (t, 4H, J = 4.6 Hz), 3.17 (t, 4H, J = 4.6 Hz), 2.94 (s, 3H) |
| 375 | N-(5-(dimethylamino)-2',4'-difluoro-[1,1'-biphenyl]-3-yl)-5-(methylsulfonamido)benzo[b]thiophene-2-carboxamide | LC/MS ESI (+): 502 (M + 1)<br>$^1$H-NMR (300 MHz, DMSO-$d_6$): δ 10.37 (s, 1H), 9.87 (s, 1H), 8.33 (s, 1H), 8.02 (d, 1H, J = 8.4 Hz), 7.80 (d, 1H, J = 1.9 Hz), 7.54~7.62 (m, 1H), 7.30~7.39 (m, 3H), 7.16~7.25 (m, 2H), 6.58 (s, 1H), 3.02 (s, 3H), 2.96 (s, 6H) |
| 376 | N-(5-(dimethylamino)-2',4'-difluoro-[1,1'-biphenyl]-3-yl)-5-(methylsulfonamido)benzofuran-2-carboxamide | LC/MS ESI (+): 486 (M + 1)<br>$^1$H-NMR (300 MHz, DMSO-$d_6$): δ 10.41 (s, 1H), 9.75 (s, 1H), 7.74 (s, 1H), 7.70 (d, 1H, J = 8.8 Hz), 7.65 (s, 1H), 7.53~7.61 (m, 1H), 7.31~7.38 (m, 3H), 7.28 (s, 1H), 7.19 (td, 1H, J = 8.4, 2.7 Hz), 6.58 (s, 1H), 2.98 (s, 3H), 2.95 (s, 6H) |

Example 377

Synthesis of N-(5'-carbamoyl-4'-methoxy-2'-(trifluoromethyl)-[1,1'-biphenyl]-3-yl)-6-(methylsulfonamido)-1H-indole-2-carboxamide (a) Synthesis of 4-methoxy-3'46-(methylsulfonamido)-1H-indole-2-carboxamido)-6-(trifluoromethyl)-[1,1'-biphenyl]-3-carboxylic acid Methyl 4-methoxy-3'(6-(methylsulfonamido)-1H-indole-2-carboxamido)-6-(trifluoromethyl)-[1,1'-biphenyl]-3-carboxylate (30.0 mg, 0.05 mmol) was dissolved in MeOH (1.0 mL), and 1 N NaOH aqueous solution (300.0 µL) was added. The reaction mixture was stirred at 10° C. for 17 hours, acidified to pH 3 with 1 N HCl aqueous solution and extracted with EtOAc. The organic extract was washed with brine, dried over anhydrous $Na_2SO_4$, concentrated under reduced pressure to obtain 4-methoxy-3'-(6-(methylsulfonamido)-1H-indole-2-carboxamido)-6-(trifluoromethyl)-[1,1'-biphenyl]-3-carboxylic acid (29.0 mg, 99%) as a white solid.

LC/MS ESI (+): 548 (M+1)

(b) Synthesis of N-(5'-carbamoyl-4'-methoxy-2'-(trifluoromethyl)-[1,1'-biphenyl]-3-yl)-6-(methylsulfonamido)-1H-indole-2-carboxamide 4-Methoxy-3'-(6-(methylsulfonamido)-1H-indole-2-carboxamido)-6-(trifluoromethyl)-[1,1'-biphenyl]-3-carboxylic acid (29.0 mg, 0.05 mmol), $NH_4Cl$ (14.0 mg, 0.27 mmol), EDC (15.0 mg, 0.08 mmol), and HOBt (11.0 mg, 0.08 mmol) were dissolved in anhydrous DMF (3.0 mL), and DIPEA (28.0 µL, 0.20 mmol) was added. After stirring at 7° C. for 16 hours, the reaction mixture was extracted with EtOAc. The organic extract was washed with brine, dried over anhydrous $Na_2SO_4$, concentrated under reduced pressure. The residue was purified by flash column chromatography (silica gel, $CH_2Cl_2$:MeOH=20:1) to obtain N-(5'-carbamoyl-4'-methoxy-2'-(trifluoromethyl)-[1,1'-biphenyl]-3-yl)-6-(methylsulfonamido)-1H-indole-2-carboxamide (3.0 mg, 10%) as a white solid.

LC/MS ESI (+): 547 (M+1)

$^1$H-NMR (300MHz, DMSO-$d_6$): δ 11.73 (s, 1H), 10.26 (s, 1H), 9.63 (s, 1H), 7.77-7.88 (m, 4H), 7.68 (s, 1H), 7.63 (d, 1H, J=8.6Hz), 7.37-7.48 (m, 4H), 6.96-7.04 (m, 2H), 4.02 (s, 3H), 2.94 (s, 3H)

Example 378

Synthesis of N-(5'-carbamoyl-4'-hydroxy-T-(trifluoromethyl)-[1,1'-biphenyl]-3-yl)-6-(methylsulfonamido)-1H-indole-2-carboxamide N-(5'-carbamoyl-4'-methoxy-2'-(trifluoromethyl)-[1,1'-biphenyl]-3-yl)-6-(methylsulfonamido)-1H-indole-2-carboxamide (25.0 mg, 0.05 mmol) was dissolved in anhydrous $CH_2Cl_2$ (2.0 mL), and 1.0 M solution of $BBr_3$ in $CH_2Cl_2$ (229.0 µL) was slowly added at 0° C. After stirring at 7° C. for 17 hours, MeOH was slowly added, followed by extracting with EtOAc. The organic extract was washed with brine, dried over anhydrous $Na_2SO_4$, concentrated under reduced pressure. The residue was purified by flash column chromatography (silica gel, $CH_2Cl_2$:MeOH=20:1) to obtain N-(5'-carbamoyl-4'-hydroxy-2'-(trifluoromethyl)-[1,1'-biphenyl]-3-yl)-6-(methylsulfonamido)-1H-indole-2-carboxamide (2.0 mg, 8%) as a white solid.

LC/MS ESI (+): 533 (M+1)

$^1$H-NMR (300MHz, DMSO-$d_6$): δ 13.26 (s, 1H), 11.73 (s, 1H), 10.26 (s, 1H), 9.64 (s, 1H), 8.61 (brs, 1H), 8.17 (brs, 1H), 7.97 (s, 1H), 7.86-7.89 (m, 1H), 7.80 (m, 1H), 7.63 (d, 1H, J=8.6Hz), 7.39-7.45 (m, 3H), 7.31 (s, 1H), 7.03-7.06 (m, 1H), 6.98 (dd, 1H, J=8.8, 1.7Hz), 2.94 (s, 3H)

Through the synthetic method according to Example 377, compounds from Example 379 to Example 381 were synthesized, and the data of each example are as follows.

TABLE 25

| Ex. | Compound | Analysis data |
|---|---|---|
| 379 | N-(5'-carbamoyl-2'-(trifluoromethyl)-[1,1'-biphenyl]-3-yl)-6-(methylsulfonamido)-1H-indole-2-carboxamide | LC/MS ESI (+): 517 (M + 1)<br>$^1$H-NMR (500 MHz, DMSO-$d_6$): δ 11.71 (s, 1H), 10.26 (s, 1H), 9.62 (s, 1H), 8.24 (s, 1H), 8.09 (d, 1H, J = 8.1 Hz), 7.97 (d, 1H, J = 8.6 Hz) 7.94 (s, 1H), 7.90 (d, 1H, J = 7.0 Hz), 7.86 (s, 1H), 7.62~7.66 (m, 2H), 7.47 (t, 1H, J = 8.0 Hz), 7.40 (m, 2H), 7.09 (d, 1H, J = 7.3 Hz), 6.99 (d, 1H, J = 9.0 Hz), 2.94 (s, 3H) |
| 380 | N-(5'-carbamoyl-2'-chloro-[1,1'-biphenyl]-3-yl)-6-(methylsulfonamido)-1H-indole-2-carboxamide | LC/MS ESI (+): 483 (M + 1)<br>$^1$H-NMR (300 MHz, DMSO-$d_6$): δ 11.74 (s, 1H), 10.30 (s, 1H), 9.94 (s, 1H), 8.14 (s, 1H), 7.89~7.97 (m, 4H), 7.67 (d, 1H, J = 8.1 Hz), 7.62 (d, 1H, J = 8.7 Hz), 7.46~7.52 (m, 2H), 7.40 (d, 2H, J = 5.4 Hz), 7.20 (d, 1H, J = 7.2 Hz), 6.97 (dd, 1H, J = 8.7, 1.8 Hz), 2.94 (s, 3H) |
| 381 | N-(4-(5-carbamoyl-2-chlorophenyl)pyridin-2-yl)-6-(methylsulfonamido)-1H-indole-2-carboxamide | LC/MS ESI (+): 484 (M + 1)<br>$^1$H-NMR (300 MHz, DMSO-$d_6$): δ 11.75 (s, 1H), 10.99 (s, 1H), 9.67 (s, 1H), 8.50 (d, 1H, J = 5.4 Hz), 8.37 (s, 1H), 8.17 (s, 1H), 7.95~8.00 (m, 2H), 7.73 (d, 1H, J = 8.4 Hz), 7.56~7.62 (m, 3H), 7.39 (s, 1H), 7.29 (dd, 1H, J = 3.6, 1.2 Hz), 6.96 (dd, 1H, J = 8.4, 1.5 Hz), 2.94 (s, 3H) |

Example 382

Synthesis of N-(2',4'-difluoro-5-(6-methoxypyridin-3-yl)-[1,1'-biphenyl]-3-yl)-6-(methylsulfonamido)-1H-indole-2-carboxamide N-(5-bromo-2',4'-difluoro-[1,1'-biphenyl]-3-yl)-6-(methylsulfonamido)-1H-indole-2-carboxamide (30.0 mg, 0.06 mmol), (6-methoxypyridin-3-yl)boronic acid (11.0 mg, 0.07 mmol), Pd(PPh$_3$)$_4$ (20.0 mg, 0.02 mmol) and Na$_2$CO$_3$ (18.0 mg, 0.17 mmol) were added to a mixture of DME/H$_2$O (0.6 mL, 5/1 v/v), followed by stirring at 80° C. for 14 hours. The reaction mixture was cooled to room temperature and then extracted with EtOAc. The organic extract was washed with brine, dried over anhydrous Na$_2$SO$_4$, concentrated under reduced pressure. The residue was purified by flash column chromatography (silica gel, n-Hex:EtOAc=1:1) to obtain N-(2',4'-difluoro-5-(6-methoxypyridin-3-yl)-[1,1'-biphenyl]-3-yl)-6-(methylsulfonamido)-1H-indole-2-carboxamide (4.0 mg, 13%) as a white solid.

LC/MS ESI (+): 549 (M+1)

$^1$H-NMR (300MHz, DMSO-$d_6$): δ 11.71 (s, 1H), 10.37 (s, 1H), 9.64 (brs, 1H), 8.51 (d, 1H, J=2.4Hz), 8.09 (s, 1H), 8.05 (dd, 1H, J=8.3, 2.4Hz), 8.01 (s, 1H), 7.69-7.73 (m, 1H), 7.62 (d, 1H, J=8.8Hz), 7.48 (s 1H), 7.37-7.42 (m, 3H), 7.24 (dt, 1H, J=8.3, 2.4Hz), 6.97 (dd, 1H, J=8.8, 2.0Hz), 6.95 (d, 1H, J=8.8Hz), 3.90 (s, 3H), 2.93 (s, 3H)

Through the synthetic method according to Example 382, compound of Example 383 was synthesized, and the data of the example are as follows.

TABLE 26

| Ex. | Compound | Analysis data |
|---|---|---|
| 383 | N-(2',4'-difluoro-5-(6-methoxypyridin-2-yl)-[1,1'-biphenyl]-3-yl)-6-(methylsulfonamido)-1H-indole-2-carboxamide | LC/MS ESI (+): 549 (M + 1)<br>$^1$H-NMR (300 MHz, DMSO-$d_6$):<br>δ 11.75 (s, 1H), 10.40 (s, 1H), 9.63 (brs, 1H), 8.62 (s, 1H), 8.08 (s, 1H), 7.92 (s, 1H), 7.84 (t, 1H, J = 7.9 Hz), 7.57~7.77 (m, 4H), 7.40~7.47 (m, 2H), 7.27 (t, 1H, J = 8.8 Hz), 6.98 (dd, 1H, J = 8.3, 1.9 Hz), 6.84 (d, 1H, J = 8.3 Hz), 3.99 (s, 3H), 2.94 (s, 3H) |

Example 384

Synthesis of N-(2',4'-difluoro-5-(6-hydroxypyridin-2-yl)-[1,1'-biphenyl]-3-yl)-6-(methylsulfonamido)-1H-indole-2-carboxamide N-(2',4'-difluoro-5-(6-methoxypyridin-2-yl)-[1,1'-biphenyl]-3-yl)-6-(methylsulfonamido)-1H-indole-2-carboxamide (13.0 mg, 0.02 mmol) was dissolved in anhydrous CH$_2$Cl$_2$ (28.4 mL), and 1.0 M solution of BBr$_3$ in CH$_2$Cl$_2$ (118.0 µL) was slowly added at 0° C. The reaction mixture was stirred at 25° C. for 17 hours, and MeOH was slowly added. The reaction mixture was extracted with EtOAc and the organic extract was washed with brine, dried over anhydrous Na$_2$SO$_4$, concentrated under reduced pressure. The residue was purified by flash column chromatography (silica gel, n-Hex:EtOAc=3:1) to obtain N-(2',4'-difluoro-5-(6-hydroxypyridin-2-yl)-[1,1'-biphenyl]-3-yl)-6-(methylsulfonamido)-1H-indole-2-carboxamide (3.0 mg, 24%) as a white solid.

LC/MS ESI (+): 535 (M+1)

$^1$H-NMR (300MHz, CD$_3$OD): δ 8.14 (t, 1H, J=1.9Hz), 8.00 (m, 1H), 7.63-7.72 (m, 3H), 7.58 (m, 1H), 7.47 (m, 1H), 7.36 (d, 1H, J=0.9Hz), 7.09-7.16 (m, 2H), 7.01 (dd, 1H, J=8.6, 1.9Hz), 6.73 (m, 1H), 6.57 (m, 1H), 2.96 (s, 3H)

Example 385

Synthesis of N-(4'-amino-2'-(trifluoromethyl)-[1,1'-biphenyl]-3-yl)-6-(methylsulfonamido)-1H-indole-2-carboxamide 6-(Methyl sulfonamido)-N-(4'-nitro-2'-(trifluoromethyl)-[1,1'-biphenyl]-3-yl)-1H-indole-2-carboxamide (48.0 mg, 0.09 mmol) was dissolved in a mixture of MeOH/H$_2$O (10.0 mL, 9/1 v/v), and Zn (90.0 mg, 1.38 mmol) and NH$_4$Cl (25.0 mg, 0.46 mmol) were added. The reaction mixture was ultrasonificated for 2 hours, filtered through Celite and concentrated under reduced pressure. The residue was extracted with EtOAc. The organic extract was washed with brine, dried over anhydrous Na$_2$SO$_4$, concentrated under reduced pressure. The residue was purified by flash column chromatography (amine silica gel, CH$_2$Cl$_2$:MeOH=20:1) to obtain N-(4'-amino-2'-(trifluoromethyl)-[1,1'-biphenyl]-3-yl)-6-(methylsulfonamido)-1H-indole-2-carboxamide (30.0 mg, 67%) as a colorless oil.

LC/MS ESI (+): 489 (M+1)
¹H-NMR (300MHz, DMSO-d₆): δ 11.72 (s, 1H), 10.19 (s, 1H), 9.63 (brs, 1H), 7.79 (d, 1H, J=9.5Hz), 7.73 (s, 1H), 7.62 (d, 1H, J=8.4Hz), 7.33-7.41 (m, 3H), 7.04 (d, 1H, J=8.4Hz), 6.94-7.00 (m, 3H), 6.82 (dd, 1H, J=7.3, 1.5Hz), 5.66 (brs, 2H), 2.93 (s, 3H)

Example 386

Synthesis of N-(4'-(methylamino)-2'-(trifluoromethyl]-[1,1'-biphenyl]-3-yl)-6-(methylsulfonamido)-1H-indole-2-carboxamide N-(4'-amino-2'-(trifluoromethyl)-[1,1'-biphenyl]-3-yl)-6-(methylsulfonamido)-1H-indole-2-carboxamide (30.0 mg, 0.06 mmol) was dissolved in triethoxymethane (2.0 mL), and a catalytic amount of TFA was added. After stirring at 80° C. for 4 hours, the reaction mixture was concentrated under reduced pressure. The residue was dissolved in EtOH (2.0 mL), and NaBH₄ (23.0 mg, 0.61 mmol) was added. After stirring at 70° C. for 2 hours, the reaction mixture was concentrated under reduced pressure, and the residue was extracted with EtOAc. The organic extract was washed with brine, dried over anhydrous Na₂SO₄, concentrated under reduced pressure. The residue was purified by flash column chromatography (silica gel, CH₂Cl₂:MeOH=20:1) to obtain N-(4'-(methylamino)-2'-(trifluoromethyl)-[1,1'-biphenyl]-3-yl)-6-(meth yl sulfonamido)-1H-indole-2-carboxamide (6.0 mg, 20%) as a white solid.
LC/MS ESI (+): 503 (M+1)
¹H-NMR (300MHz, CDCl₃): δ 11.71 (s, 1H), 10.19 (s, 1H), 9.63 (brs, 1H), 7.80 (d, 1H, J=8.8Hz), 7.74 (s, 1H), 7.62 (d, 1H, J=8.4Hz), 7.33-7.41 (m, 3H), 7.13 (d, 1H, J=8.4Hz), 6.97 (d, 1H, J=1.5Hz), 6.96 (d, 1H, J=1.9Hz), 6.90 (d, 1H, J=2.3Hz), 6.81 (dd, 1H, J=8.4, 1.9Hz), 6.25 (q, 1H, J=5.0Hz), 2.93 (s, 3H), 2.75 (d, 3H, J=5.0Hz)

Example 387

Synthesis of N-(3-(difluoro(phenyl)methyl)phenyl)-6-(methylsulfonamido)-1H-indole-2-carboxamide (a) Synthesis of 1-(difluoro(phenyl)methyl)-3-nitrobenzene (3-Nitrophenyl)(phenyl)methanone (0.3 g, 1.32 mmol) was dissolved in CH₂Cl₂ (2.0 mL) in a sealed tube, and 50% solution of Deoxo-Fluor in THF (7.9 mL, 3.96 mmol) was added. THF was distilled under reduced pressure, followed by stirring at 90° C. for 8 hours. The reaction mixture was cooled to room temperature and extracted with CH₂Cl₂. The organic extract was washed with brine, dried over anhydrous Na₂SO₄, concentrated under reduced pressure. The residue was purified by flash column chromatography (silica gel, n-Hex:EtOAc=4:1) to obtain 1-(difluoro(phenyl)methyl)-3-nitrobenzene (280.0 mg, 85%) as a yellow oil.
¹H-NMR (300MHz, CDCl₃): δ 8.39 (s, 1H), 8.31 (d, 1H, J=8.0Hz), 7.85 (d, 1H, J=7.6Hz), 7.63 (t, 1H, J=8.0Hz), 7.44-7.53 (m, 5H)

(b) Synthesis of 3-(difluoro(phenyl)methyl)aniline 1-(Difluoro(phenyl)methyl)-3-nitrobenzene (280.0 mg, 1.12 mmol) was dissolved in MeOH (5.0 mL). Under an atmosphere of hydrogen gas, Ra—Ni (100.0 mg, 1.70 mmol) was added, followed by stirring at room temperature for 1 hour. The reaction mixture was filtered through Celite and concentrated under reduced pressure. The residue was purified by flash column chromatography (amine silica gel, n-Hex:EtOAc=4:1) to obtain 3-(difluoro(phenyl)methyl)aniline (200.0 mg, 81%) as a white solid.
LC/MS ESI (+): 220 (M+1)

(c) Synthesis of N-(3-(difluoro(phenyl)methyl)phenyl)-6-(methylsulfonamido)-1H-indole-2-carboxamide 6-(Methylsulfonamido)-1H-indole-2-carboxylic acid hydrochloride (35.0 mg, 0.14 mmol), 3-(difluoro(phenyl)methyl)aniline (30.0 mg, 0.14 mmol), and HATU (57.0 mg, 0.15 mmol) were dissolved in anhydrous DMF (1.4 mL), and DIPEA (37.0 µL, 0.21 mmol) was added. After stirring at room temperature for 15 hours, the reaction mixture was extracted with CH₂Cl₂. The organic extract was washed with brine, dried over anhydrous Na₂SO₄, concentrated under reduced pressure. The residue was purified by flash column chromatography (amine silica gel, CH₂Cl₂:MeOH=95:5) to obtain N-(3-(difluoro(phenyl)methyl)phenyl)-6-(methylsulfonamido)-1H-indole-2-carboxamide (23.0 mg, 36%) as a white solid.
LC/MS ESI (+): 456 (M+1)
¹H-NMR (300MHz, DMSO-d₆): δ 11.74 (s, 1H), 10.34 (s, 1H), 9.64 (s, 1H), 7.96-8.00 (m, 2H), 7.63 (d, 1H, J=8.8Hz), 7.47-7.56 (m, 6H), 7.39 (s, 2H), 7.26 (d, 1H, J=7.6Hz), 6.98 (dd, 1H, J=8.4, 1.9Hz), 2.94 (s, 3H)

Through the synthetic method according to Example 387, compounds from Example 388 to Example 390 were synthesized, and the data of each example are as follows.

TABLE 27

| Ex. | Compound | Analysis data |
|---|---|---|
| 388 | N-(3-(difluoro(pyridin-4-yl)methyl)phenyl)-6-(methylsulfonamido)-1H-indole-2-carboxamide | LC/MS ESI (+): 457 (M + 1)<br>¹H-NMR (300 MHz, DMSO-d₆): δ 11.75 (s, 1H), 10.36 (s, 1H), 9.64 (s, 1H), 8.77 (d, 2H, J = 6.1 Hz), 7.97~8.01 (m, 2H), 7.63 (d, 1H, J = 8.4 Hz), 7.58 (d, 2H, J = 6.1 Hz), 7.52 (t, 1H, J = 8.0 Hz), 7.39 (s, 2H), 7.29 (d, 1H, J = 8.4 Hz), 6.98 (dd, 1H, J = 8.5, 1.7 Hz), 2.94 (s, 3H) |
| 389 | N-(3-(difluoro(pyridin-2-yl)methyl)phenyl)-6-(methylsulfonamido)-1H-indole-2-carboxamide | LC/MS ESI (+): 457 (M + 1)<br>¹H-NMR (300 MHz, DMSO-d₆): δ 11.73 (s, 1H), 10.34 (s, 1H), 9.64 (s, 1H), 8.66 (d, 1H, J = 5.0 Hz), 7.96~8.02 (m, 3H), 7.84 (d, 1H, J = 7.6 Hz), 7.63 (d, 1H, J = 8.8 Hz), 7.55 (dd, 1H, J = 7.6, 4.6 Hz), 7.48 (t, 1H, J = 7.6 Hz), 7.39 (dd, 2H, J = 5.3, 1.9 Hz), 7.28 (d, 1H, J = 8.8 Hz), 6.98 (dd, 1H, J = 8.8, 1.9 Hz), 2.94 (s, 3H) |

TABLE 27-continued

| Ex. | Compound | Analysis data |
|---|---|---|
| 390 | N-(3-((3-cyanophenyl)difluoromethyl)phenyl)-6-(methylsulfonamido)-1H-indole-2-carboxamide | LC/MS ESI (+): 481 (M + 1)<br>$^1$H-NMR (300 MHz, DMSO-d$_6$): δ 11.76 (s, 1H), 10.36 (s, 1H), 9.65 (s, 1H), 8.11 (s, 1H), 7.98~8.07 (m, 3H), 7.90 (d, 1H, J = 8.4 Hz), 7.76 (t, 1H, J = 8.0 Hz), 7.64 (d, 1H, J = 8.0 Hz), 7.53 (t, 1H, J = 8.8 Hz), 7.40 (s, 2H), 7.31 (d, 1H, J = 8.0 Hz), 6.99 (dd, 1H, J = 8.4, 1.9 Hz), 2.95 (s, 3H) |

Example 391

Synthesis of N-(3-((3-cyanophenyl)difluoromethyl)-5-(2,2-difluoroethoxy)phenyl)-6-(methylsulfonamido)-1H-indole-2-carboxamide (a) Synthesis of 4-methoxybenzyl 3-((4-methoxybenzyl)oxy)-5-nitrobenzoate 3-Hydroxy-5-nitrobenzoic acid (5.0 g, 27.17 mmol) was dissolved in anhydrous DMF (60.0 mL), and K$_2$CO$_3$ (15.0 g, 108.68 mmol) and 4-methoxybenzyl chloride (11.1 mL, 81.51 mmol) were added. The reaction mixture was stirred at room temperature for 2 hours, and heated at 65° C. for 3 hours, water was added to quench the reaction. The reaction mixture was extracted with EtOAc. The organic extract was washed with brine, dried over anhydrous Na$_2$SO$_4$, concentrated under reduced pressure. The residue was recrystallized with a mixture of EtOAc/n-Hex, and the precipitate was filtered to obtain 4-methoxybenzyl 3-((4-methoxybenzyl)oxy)-5-nitrobenzoate (10.6 g, 92%) as a yellow solid.

$^1$H-NMR (300MHz, DMSO-d$_6$): δ 8.18 (m, 1H), 8.03 (m, 1H), 7.87 (m, 1H), 7.39-7.44 (m, 4H), 6.93-6.97 (m, 4H), 5.31 (s, 2H), 5.22 (s, 2H), 3.76 (s, 3H), 3.75 (s, 3H)

(b) Synthesis of 3-((4-methoxybenzyl)oxy)-5-nitrobenzoic acid

4-Methoxybenzyl 3-((4-methoxybenzyl)oxy)-5-nitrobenzoate (1.5 g, 3.54 mmol) was dissolved in a mixture of MeOH/THF/H$_2$O (32.0 mL, 2/1/0.5 v/v), and NaOH (283.0 mg, 7.08 mmol) was added, followed by stirring at room temperature for 20 hours. The reaction mixture was concentrated under reduced pressure, and the residue was dissolved in water. 1 N HCl was added for the acidification to pH 1-2, and the precipitate was filtered and dried under reduced pressure to obtain 3-((4-methoxybenzyl)oxy)-5-nitrobenzoic acid (1.1 g, 98%) as an off-white solid.

$^1$H-NMR (300MHz, DMSO-d$_6$): δ 13.78 (brs, 1H), 8.21 (m, 1H), 8.02 (m, 1H), 7.88 (m, 1H), 7.42 (d, 2H, J=8.4Hz), 6.97 (d, 2H, J=8.8Hz), 5.23 (s, 2H), 3.76 (s, 3H)

(c) Synthesis of 3-((4-methoxybenzyl)oxy)-5-nitrobenzoyl chloride 3-((4-Methoxybenzyl)oxy)-5-nitrobenzoic acid (472.0 mg, 1.56 mmol) was dissolved in anhydrous CH$_2$Cl$_2$ (20.0 mL), and (COCl)$_2$ (149.0 μL, 1.71 mmol) and a catalytic amount of anhydrous DMF were added. After stirring at 0° C. for 2 hours, the reaction mixture was dried under reduced pressure to obtain 3-(4-methoxybenzyl)oxy)-5-nitrobenzoyl chloride (501.9 mg) as a yellow solid.

(d) Synthesis of 3-(3-((4-methoxybenzyl)oxy)-5-nitrobenzoyl)benzonitrile

To a solution of crude 3-((4-methoxybenzyl)oxy)-5-nitrobenzoyl chloride (501.9 mg) and Pd$_2$(dba)$_3$·CHCl$_3$ (80.5 mg, 0.08 mmol) in anhydrous THF (15.0 mL), 0.5 M solution of 3-cyanophenylzinc iodide in THF (3.42 mL, 1.71 mmol) was added at 0° C., followed by stirring for 41 hours. Water was added to quench the reaction, and the reaction mixture was extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=3:1) to obtain 3-(3-((4-methoxybenzyl)oxy)-5-nitrobenzoyl)benzonitrile (181.8 mg, 2 step yield: 30%) as an off-white solid.

$^1$H-NMR (300MHz, DMSO-d$_6$): δ 8.17-8.21 (m, 2H), 8.06-8.10 (m, 2H), 8.02 (m, 1H), 7.79 (t, 1H, J=8.0Hz), 7.74 (m, 1H), 7.42 (d, 2H, J=8.4Hz), 6.97 (d, 2H, J=8.4Hz) 5.25 (s, 2H), 3.76 (s, 3H)

(e) Synthesis of 3-(difluoro(3-((4-methoxybenzyl)oxy)-5-nitrophenyl)methyl)benzonitrile In 3-(3-((4-methoxybenzyl)oxy)-5-nitrobenzoyl)benzonitrile (180.0 mg, 0.46 mmol) in a sealed tube, 50% solution of Deoxo-Fluor in THF (985.0 μL, 2.32 mmol) was added, and THF was distilled under reduced pressure, followed by stirring at 90° C. for 5 hours. The reaction mixture was cooled to room temperature and concentrated under reduced pressure. The residue was purified by flash column chromatography (silica gel, n-Hex:EtOAc=4:1) to obtain 3-(difluoro(3-((4-methoxybenzyl)oxy)-5-nitrophenyl)methyl)benzonitrile (100.6 mg, 53%) as a yellow oil.

$^1$H-NMR (300MHz, DMSO-d$_6$): δ 8.25 (s, 1H), 7.98-8.03 (m, 3H), 7.92 (m, 1H), 7.69-7.75 (m, 2H), 7.40 (d, 2H, J=8.4Hz), 6.94 (d, 2H, J=8.8Hz), 5.21 (s, 2H), 3.75 (s, 3H)

(f) Synthesis of 3-(difluoro(3-hydroxy-5-nitrophenyl)methyl)benzonitrile 3-(Difluoro(3-((4-methoxybenzyl)oxy)-5-nitrophenyl)methyl)benzonitrile (455.0 mg, 1.11 mmol) was dissolved in CH$_2$Cl$_2$ (5.0 mL), and TFA (2.5 mL) was added at room temperature. After stirring at room temperature for 1 hour, the reaction mixture was concentrated under reduced pressure. The residue was extracted with CH$_2$Cl$_2$, and the organic extract was washed with brine, dried over anhydrous Na$_2$SO$_4$ and concentrated under reduced pressure. The residue was purified by flash column chromatography (silica gel, n-Hex:EtOAc=2:1) to obtain 3-(difluoro(3-hydroxy-5-nitrophenyl)methyl)benzonitrile (300.0 mg, 100%) as a colorless oil.

$^1$H-NMR (300MHz, DMSO-d$_6$): δ 11.07 (brs, 1H), 8.20 (s, 1H), 8.02 (d, 1H, J=8.0Hz), 7.97 (d, 1H, J=8.0Hz), 7.79 (s, 1H), 7.73 (t, 1H, J=8.0Hz), 7.66 (t, 1H, J=2.3Hz), 7.36 (t, 1H, J=1.9Hz)

(g) Synthesis of 3-((3-(2,2-difluoroethoxy)-5-nitrophenyl)difluoromethyl)benzonitrile 3-(Difluoro(3-hydroxy-5-nitrophenyl)methyl)benzonitrile (120.0 mg, 0.41 mmol) was dissolved in toluene (5.0 mL), and 2,2-difluoroethanol (52.0 μL, 0.83 mmol) and (cyanomethylene)tributylphosphorane (216.0 μL, 0.83 mmol) were added, followed by stirring at 120° C. for 40 hours. The reaction mixture was cooled to room temperature and concentrated under reduced pressure. The residue was purified by flash column chromatography (silica gel, n-Hex:EtOAc=5:1) to obtain 3-((3-(2,2-difluoroethoxy)-5-nitrophenyl)difluoromethyl)benzonitrile (115.4 mg, 79%) as a yellow solid.

LC/MS ESI (+): 377 (M+Na)

$^1$H-NMR (300MHz, DMSO-$d_6$): δ 8.27 (s, 1H), 8.00-8.06 (m, 3H), 7.96 (t, 1H, J=2.3Hz), 7.70-7.75 (m, 2H), 6.43 (tt, 1H, J=54.2, 3.1Hz), 4.58 (td, 2H, J=14.5, 3.1Hz)

(h) Synthesis of 3-(difluoro(3-isobutoxy-5-nitrophenyl)methyl)benzonitrile 3-(Difluoro(3-hydroxy-5-nitrophenyl)methyl)benzonitrile (87.0 mg, 0.30 mmol) was dissolved in anhydrous DMF (5.0 mL), and 1-bromo-2-methylpropane (39.0 μL, 0.36 mmol) and $K_2CO_3$ (83.0 mg, 0.60 mmol) were added, followed by stirring at room temperature for 40 hours. The reaction mixture was extracted with EtOAc, and the organic extract was washed with brine, dried over anhydrous $Na_2SO_4$, concentrated under reduced pressure. The residue was purified by flash column chromatography (silica gel, n-Hex:EtOAc=5:1) to obtain 3-(difluoro(3-isobutoxy-5-nitrophenyl)methyl)benzonitrile (69.6 mg, 67%) as a white solid.

LC/MS ESI (+): 369 (M+Na)

$^1$H-NMR (300MHz, DMSO-$d_6$): δ 8.26 (s, 1H), 8.03 (t, 2H, J=8.0Hz), 7.95 (s, 1H), 7.83 (t, 1H, J=2.3Hz), 7.73 (t, 1H, J=8.0Hz), 7.63 (s, 1H), 3.93 (d, 2H, J=6.9Hz), 1.97-2.10 (m, 1H), 0.99 (d, 6H, J=6.5Hz)

(i) Synthesis of 3-((3-amino-5-(2,2-difluoroethoxy)phenyl)difluoromethyl)benzonitrile 3-((3-(2,2-Difluoroethoxy)-5-nitrophenyl)difluoromethyl)benzonitrile (114.0 mg, 0.33 mmol) was dissolved in a mixture of THF/MeOH/$H_2O$ (6.6 mL, 1/1/0.1 v/v), and Zn (322.0 mg, 4.92 mmol) and $NH_4Cl$ (88.0 mg, 1.64 mmol) were added at room temperature. The reaction mixture was ultrasonificated at 40° C. for 1.5 hours, cooled to room temperature, filtered through Celite and concentrated under reduced pressure. The residue was purified by flash column chromatography (amine silica gel, n-Hex:EtOAc=5:1) to obtain 3-((3-amino-5-(2,2-difluoroethoxy)phenyl)difluoromethyl)benzonitrile (78.0 mg, 73%) as a white solid.

LC/MS ESI (+): 325 (M+1)

(j) Synthesis of N-(3-((3-cyanophenyl)difluoromethyl)-5-(2,2-difluoroethoxy)phenyl)-6-(methylsulfonamido)-1H-indole-2-carboxamide 6-(Methylsulfonamido)-1H-indole-2-carboxylic acid hydrochloride (34.9 mg, 0.12 mmol), 3-((3-amino-5-(2,2-difluoroethoxy)phenyl)difluoromethyl)benzonitrile (39.0 mg, 0.12 mmol), HATU (54.8 mg, 0.14 mmol), and DIPEA (63.0 μL, 0.36 mmol) were dissolved in anhydrous DMF (1.0 mL), followed by stirring at 40° C. for 19 hours. The reaction mixture was extracted with EtOAc, and the organic extract was washed with brine, dried over anhydrous $Na_2SO_4$, concentrated under reduced pressure. The residue was purified by flash column chromatography (amine silica gel, $CH_2Cl_2$:MeOH=20:1) to obtain N-(3-((3-cyanophenyl)difluoromethyl)-5-(2,2-difluoroethoxy)phenyl)-6-(methylsulfonamido)-1H-indole-2-carboxamide (22.6 mg, 34%) as a white solid.

LC/MS ESI (+): 561 (M+1)

$^1$H-NMR (300MHz, DMSO-$d_6$): δ 11.72 (s, 1H), 10.32 (s, 1H), 9.64 (s, 1H), 8.12 (s, 1H), 8.03 (d, 1H, J=8.0Hz), 7.92 (d, 1H, J=8.0Hz), 7.72-7.78 (m, 2H), 7.61-7.64 (m, 2H), 7.38 (s, 1H), 7.37 (s, 1H), 6.69-7.00 (m, 2H), 6.42 (t, 1H, J=54.6Hz), 4.40 (td, 2H, J=14.1, 3.8Hz), 2.93 (s, 3H)

Through the synthetic method according to Example 391, compounds of Example 392 and Example 393 were synthesized, and the data of each example are as follows.

TABLE 28

| Ex. | Compound | Analysis data |
| --- | --- | --- |
| 392 | N-(3-((3-cyanophenyl)difluoromethyl)-5-isobutoxyphenyl)-6-(methylsulfonamido)-1H-indole-2-carboxamide | LC/MS ESI (+): 553 (M + 1)<br>$^1$H-NMR (300 MHz, DMSO-$d_6$): δ 11.71 (s, 1H), 10.27 (s, 1H), 9.64 (s, 1H), 8.11 (s, 1H), 8.03 (d, 1H, J = 7.6 Hz), 7.90 (d, 1H, J = 8.0 Hz), 7.75 (t, 1H, J = 8.0 Hz), 7.61~7.65 (m, 2H), 7.55 (s, 1H), 7.38 (s, 2H), 6.98 (dd, 1H, J = 8.8, 1.9 Hz), 6.86 (s, 1H) 3.79 (d, 2H, J = 6.5 Hz), 2.94 (s, 3H), 2.04 (m, 1H), 1.00 (d, 6H, J = 6.9 Hz) |
| 393 | N-(3-(cyanomethoxy)-5-((3-cyanophenyl)difluoromethyl)phenyl)-6-(methylsulfonamido)-1H-indole-2-carboxamide | LC/MS ESI (+): 536 (M + 1)<br>$^1$H-NMR (300 MHz, DMSO-$d_6$): δ 11.76 (s, 1H), 10.40 (s, 1H), 9.65 (s, 1H), 8.12 (s, 1H), 8.04 (d, 1H, J = 7.6 Hz), 7.92 (d, 1H, J = 8.0 Hz), 7.73~7.80 (m, 2H), 7.62~7.65 (m, 2H), 7.37~7.39 (m, 2H), 7.06 (s, 1H), 6.98 (dd, 1H, J = 8.8, 1.9 Hz), 5.25 (s, 2H), 2.94 (s, 3H) |

Example 394

Synthesis of N-(3-((4-methoxyphenyl)sulfonyl)phenyl)-6-(methylsulfonamido)-1H-indole-2-carboxamide (a) Synthesis of (4-methoxyphenyl)(3-nitrophenyl)sulfane 1-Bromo-3-nitrobenzene (500.0 mg, 2.48 mmol) was dissolved in 1,4-dioxane (10.0 mL), and 4-methoxybenzenethiol (383.0 mg, 2.73 mmol), $Pd_2dba_3 \cdot CHCl_3$ (227.0 mg, 0.22 mmol), Xantphos (287.0 mg, 0.50 mmol), and DIPEA (0.9 mL, 5.46 mmol) were added, followed by refluxing at 100° C. for 15 hours. The reaction mixture was cooled to room temperature and concentrated under reduced pressure. The residue was extracted with EtOAc, and the organic extract was washed with brine, dried over anhydrous $Na_2SO_4$ and concentrated under reduced pressure. The residue was purified by flash column chromatography (amine silica gel, n-Hex) to obtain (4-methoxyphenyl)(3-nitrophenyl)sulfane (501.0 mg, 77%) as a yellow oil.

¹H-NMR (300MHz, CDCl₃): δ 7.89-7.95 (m, 2H), 7.48 (d, 2H J=8.8Hz), 7.36-7.40 (m, 2H), 6.97 (d, 2H, J=8.8Hz), 3.86 (s, 3H).

(b) Synthesis of (1-((4-methoxyphenyl)sulfonyl)-3-nitrobenzene (4-Methoxyphenyl)(3-nitrophenyl)sulfane (501.0 mg, 1.92 mmol) was dissolved in CH₂Cl₂ (10.0 mL), and mCPBA (994.0 mg, 5.76 mmol) was added, followed by stirring at room temperature for 15 hours. The reaction mixture was concentrated under reduced pressure, and the residue was extracted with CH₂Cl₂. The organic extract was washed with sat. NaHCO₃ aqueous solution and brine, dried over anhydrous Na₂SO₄ and concentrated under reduced pressure to obtain (1-(4-methoxyphenyl)sulfonyl)-3-nitrobenzene (548.0 mg, 100%) as a yellow solid.

¹H-NMR (300MHz, CDCl₃): δ 8.74 (s, 1H), 8.40 (d, 1H, J=8.0Hz), 8.25 (d, 1H, J=7.6Hz), 7.92 (d, 2H, J=9.2Hz), 7.72 (t, 1H, J=8.0Hz), 7.01 (d, 2H, J=9.2Hz), 3.87 (s, 3H)

(c) Synthesis of 3-((4-methoxyphenyl)sulfonyl)aniline (1-((4-Methoxyphenyl)sulfonyl)-3-nitrobenzene (548.0 mg, 1.92 mmol) was dissolved in MeOH (5.0 mL). Under an atmosphere of hydrogen gas, an excessive amount of Ra—Ni (0.2 g, 3.41 mmol) was added, followed by stirring at room temperature for 2 hours. The reaction mixture was filtered through Celite and concentrated under reduced pressure. The residue was purified by flash column chromatography (silica gel, n-Hex:EtOAc=4:1) to obtain 3-((4-methoxyphenyl)sulfonyl)aniline (285.0 mg, 56%) as a bright yellow solid.

LC/MS ESI (+): 264 (M+1)

(d) Synthesis of N-(3-((4-methoxyphenyl)sulfonyl)phenyl)-6-(methylsulfonamido)-1H-indole-2-carboxamide 6-(Methylsulfonamido)-1H-indole-2-carboxylic acid hydrochloride (70.0 mg, 0.28 mmol), 3-((4-methoxyphenyl)sulfonyl)aniline (77.0 mg, 0.29 mmol), and HATU (128.0 mg, 0.34 mmol) were dissolved in anhydrous DMF (1.0 mL), and DIPEA (73.0 µL, 0.42 mmol) was added. After stirring at 80° C. for 15 hours, the reaction mixture was extracted with EtOAc. The organic extract was washed with brine, dried over anhydrous Na₂SO₄, concentrated under reduced pressure. The residue was purified by flash column chromatography (amine silica gel, CH₂Cl₂:MeOH=95:5) to obtain N-(3-(4-methoxyphenyl)sulfonyl)phenyl)-6-(methylsulfonamido)-1H-indole-2-carboxamide (1.2 mg, 1%) as a yellow solid.

LC/MS ESI (+): 500 (M+1)

¹H-NMR (300MHz, DMSO-d₆): δ 11.78 (s, 1H), 10.53 (s, 1H), 9.69 (s, 1H), 8.42 (s, 1H), 8.10 (m, 1H), 7.81-7.92 (m, 2H) 7.57-7.69 (m, 3H), 7.36-7.56 (m, 2H), 7.11-7.23 (m, 2H), 6.98 (m, 1H), 3.89 (s, 3H), 2.98 (s, 3H)

Through the synthetic method according to Example 394, compounds from Example 395 to Example 399 were synthesized, and the data of each example are as follows.

TABLE 29

| Ex. | Compound | Analysis data |
| --- | --- | --- |
| 395 | 6-(methylsulfonamido)-N-(3-(phenylsulfonyl)phenyl)-1H-indole-2-carboxamide | LC/MS ESI (+): 470 (M + 1)<br>¹H-NMR (300 MHz, DMSO-d₆): δ 11.77 (s, 1H), 10.52 (s, 1H), 9.66 (s, 1H), 8.45 (s, 1H), 8.11 (m, 1H), 7.95~7.97 (m, 2H) 7.59~7.74 (m, 6H), 7.40 (m, 2H), 6.97 (m, 1H), 2.45 (s, 3H) |
| 396 | 6-(methylsulfonamido)-N-(3-((3-(trifluoromethoxy)phenyl)sulfonyl)phenyl)-1H-indole-2-carboxamide | LC/MS ESI (+): 554 (M + 1)<br>¹H-NMR (300 MHz, DMSO-d₆): δ 11.78 (s, 1H), 10.54 (s, 1H), 9.65 (s, 1H), 8.45 (s, 1H), 8.14 (m, 1H), 8.00 (m, 1H), 7.92 (s, 1H), 7.73~7.82 (m, 3H), 7.62~7.65 (m, 2H), 7.39~7.42 (m, 2H), 6.98 (m, 1H), 2.94 (s, 3H) |
| 397 | N-(3-methoxy-5-((3-(trifluoromethoxy)phenyl)sulfonyl)phenyl)-6-(methylsulfonamido)-1H-indole-2-carboxamide | LC/MS ESI (+): 584 (M + 1)<br>¹H-NMR (300 MHz, DMSO-d₆): δ 11.78 (s, 1H), 10.50 (s, 1H), 9.68 (s, 1H), 7.97~8.06 (m, 3H), 7.79~7.80 (m, 3H) 7.64 (d, 1H, J = 8.1 Hz), 7.39~7.41 (m, 2H), 7.27 (s, 1H), 7.00 (m, 1H), 3.86 (s, 3H), 2.94 (s, 3H) |
| 398 | 6-(methylsulfonamido)-N-(3-((3-(trifluoromethoxy)phenyl)sulfonyl)-5-(trifluoromethyl)phenyl)-1H-indole-2-carboxamide | LC/MS ESI (+): 622 (M + 1)<br>¹H-NMR (300 MHz, DMSO-d₆): δ 11.81 (s, 1H), 10.81 (s, 1H), 9.68 (brs, 1H), 8.75 (s, 1H), 8.55 (s, 1H), 8.07~8.17 (m, 3H) 7.78~7.92 (m, 2H), 7.67 (d, 1H, J = 8.4 Hz), 7.42 (d, 2H, J = 10.7 Hz), 6.99 (dd, 1H, J = 8.4, 1.5 Hz), 2.95 (s, 3H) |
| 399 | N-(3-cyano-5-((3-(trifluoromethoxy)phenyl)sulfonyl)phenyl)-6-(methylsulfonamido)-1H-indole-2-carboxamide | ¹H-NMR (300 MHz, DMSO-d₆): δ 11.81 (s, 1H), 10.78 (s, 1H), 9.89 (brs, 1H), 8.68 (s, 1H), 8.55 (s, 1H), 8.32 (s, 1H), 8.04~8.10 (m, 2H), 7.81~7.84 (m, 2H), 7.66 (d, 1H, J = 8.5 Hz), 7.42 (s, 1H), 7.39 (s, 1H), 6.97~7.00 (m, 1H), 2.94 (s, 3H) |

Example 400

Synthesis of N-(3-isobutoxy-5-((3-(trifluoromethoxy)phenyl)sulfonyl)phenyl)-6-(methylsulfonamido)-1H-indole-2-carboxamide (a) Synthesis of 3-nitro-5-((3-(trifluoromethoxy)phenyl)sulfonyl)phenol 1-Methoxy-3-nitro-5-((3-(trifluoromethoxy)phenyl)sulfonyl)benz ene (0.3 g, 0.80 mmol) was dissolved in CH$_2$Cl$_2$ (5.0 mL), and 1.0 M solution of BBr$_3$ in CH$_2$Cl$_2$ (8.0 mL, 8.00 mmol) was added at 0° C. After stirring at room temperature for 15 hours, the reaction mixture was extracted with CH$_2$Cl$_2$. The organic extract was washed with sat. NaHCO$_3$ aqueous solution and brine, dried over anhydrous Na$_2$SO$_4$ and concentrated under reduced pressure. The residue was purified by flash column chromatography (silica gel, n-Hex:EtOAc=2:1) to obtain 3-nitro-5-((3-(trifluoromethoxy)phenyl)sulfonyl)phenol (213.0 mg, 68%) as a pink amorphous solid.

$^1$H-NMR (300MHz, CDCl$_3$): δ 8.30 (t, 1H, J=1.9Hz), 7.89-7.93 (m, 2H), 7.82 (s, 1H), 7.75 (dd, 1H, J=2.3, 1.9Hz), 7.63 (t, 1H, J=8.4Hz), 7.50 (d, 1H, J=8.4Hz), 6.83 (s, 1H).

(b) Synthesis of 1-isobutoxy-3-nitro-5-((3-(trifluoromethoxy)phenyl)sulfonyl)benzene 3-Nitro-5-((3-(trifluoromethoxy)phenyl)sulfonyl)phenol (100.0 mg, 0.28 mmol) was dissolved in THF (2.0 mL), and 2-methylpropan-1-ol (21.0 mg, 0.28 mmol), DIAD (54.0 μL, 0.28 mmol), and PPh$_3$ (73.0 mg, 0.28 mmol) were added, followed by stirring at room temperature for 15 hours. The reaction mixture was concentrated under reduced pressure, and the residue was purified by flash column chromatography (silica gel, n-Hex:EtOAc=3:1) to obtain 1-isobutoxy-3-nitro-5-((3-(trifluoromethoxy)phenyl)sulfonyl)benzene (54.0 mg, 46%) as a yellow oil.

LC/MS ESI (+): 420 (M+1)

(c) Synthesis of 3-isobutoxy-5-(3-(trifluoromethoxy)phenylsulfonyl)aniline

1-Isobutoxy-3-nitro-5-((3-(trifluoromethoxy)phenyl)sulfonyl)benzene (54.0 mg, 0.13 mmol) was dissolved in a mixture of THF/MeOH/H$_2$O (1.6 mL, 10/5/0.1 v/v), and Zn (85.0 mg, 1.30 mmol) and NH$_4$Cl (20.9 mg, 0.39 mmol) were added. The reaction mixture was ultrasonificated at 40° C. for 1 hour. The reaction mixture was filtered through Celite and extracted with CH$_2$Cl$_2$. The organic extract was washed with brine, dried over anhydrous Na$_2$SO$_4$, concentrated under reduced pressure. The residue was purified by flash column chromatography (amine silica gel, n-Hex:EtOAc=60:40) to obtain 3-isobutoxy-5-(3-(trifluoromethoxy)phenyl sulfonyl)aniline (17.2 mg, 34%) as a yellow oil.

LC/MS ESI (+): 390 (M+1)

(d) Synthesis of N-(3-isobutoxy-5-((3-(trifluoromethoxy)phenyl)sulfonyl)phenyl)-6-(methylsulfonamido)-1H-indole-2-carboxamide 6-(Methylsulfonamido)-1H-indole-2-carboxylic acid hydrochloride (17.2 mg, 0.04 mmol), 3-isobutoxy-5-((3-(trifluoromethoxy)phenyl)sulfonyl)aniline (13.5 mg, 0.05 mmol), and HATU (21.7 mg, 0.06 mmol) were dissolved in anhydrous DMF (3.0 mL), and DIPEA (11.5 μL, 0.07 mmol) was added. After stirring at 50° C. for 15 hours, the reaction mixture was extracted with EtOAc. The organic extract was washed with brine, dried over anhydrous Na$_2$SO$_4$, concentrated under reduced pressure. The residue was purified by flash column chromatography (silica gel, CH$_2$Cl$_2$:MeOH=96:4) to obtain N-(3-isobutoxy-5-((3-(trifluoromethoxy)phenyl)sulfonyl)phenyl)-6-(methylsulfonamido)-1H-indole-2-carboxamide (1.9 mg, 7%) as a white solid.

LC/MS ESI (+): 626 (M+1)

$^1$H-NMR (300MHz, DMSO-d$_6$): δ 11.76 (brs, 1H), 10.46 (brs, 1H), 9.67 (brs, 1H), 7.97-8.05 (m, 3H), 7.75-7.84 (m, 3H), 7.64 (d, 1H, J=8.4Hz), 7.40 (m, 2H), 7.25 (m, 1H), 7.00 (dd, 1H, J=8.4, 1.5Hz), 3.84 (d, 2H, J=6.5Hz), 2.95 (s, 3H), 2.02-2.06 (m, 1H), 0.99 (d, 6H, J=6.9Hz)

Through the synthetic method according to Example 400, a compound of Example 401 was synthesized, and the data of the example are as follows.

TABLE 30

| Ex. | Compound | Analysis data |
|---|---|---|
| 401 | N-(3-(2,2-difluoroethoxy)-5-((3-(trifluoromethoxy)phenyl)sulfonyl)phenyl)-6-(methylsulfonamido)-1H-indole-2-carboxamide | LC/MS ESI (+): 634 (M + 1)<br>$^1$H-NMR (300 MHz, DMSO-d$_6$): δ 11.78 (s, 1H), 10.51 (s, 1H), 9.67 (m, 1H), 8.03~8.09 (m, 3H), 7.76~7.87 (m, 3H), 7.65 (d, 1H, J = 8.4 Hz), 7.39~7.41 (m, 3H), 7.00 (dd, 1H, J = 9.0, 1.8 Hz), 6.43 (t, 1H, J = 71.7 Hz), 4.47 (td, 2H, J = 14.7, 3.3 Hz), 2.94 (s, 3H) |

Example 402

Synthesis of N-(3-((3-cyanophenyl)sulfonyl)phenyl)-6-(methylsulfonamido)-1H-indole-2-carboxamide (a) Synthesis of tert-butyl(3-mercaptophenyl)carbamate 3-Aminobenzenethiol (456.2 mg, 3.64 mmol) and Boc$_2$O (835.0 mg, 3.83 mmol) were dissolved in acetone (5.0 mL) at 0° C., and 5% NaHCO$_3$ aqueous solution (2.5 mL) was slowly added. The mixture was stirred at 0° C. for 30 minutes and at room temperature for 48 hours. The reaction mixture was extracted with EtOAc, and the organic extract was washed with brine, dried over anhydrous Na$_2$SO$_4$ and concentrated under reduced pressure. The residue was purified by flash column chromatography (silica gel, n-Hex:EtOAc=5:1) to obtain tert-butyl(3-mercaptophenyl)carbamate (297.0 mg, 36%) as a white solid.

$^1$H-NMR (300MHz, DMSO-d$_6$): δ 9.35 (s, 1H), 7.48 (s, 1H), 7.07-7.12 (m, 2H), 6.87 (dt, 1H, J=6.9, 1.9Hz), 5.39 (s, 1H), 1.46 (s, 9H)

(b) Synthesis of tert-butyl (3-((3-cyanophenyl)thio)phenyl)carbamate tert-Butyl(3-mercaptophenyl)carbamate (100.0 mg, 0.37 mmol) was dissolved in 1,4-dioxane (3.0 mL), and 3-bromobenzonitrile (67.0 mg, 0.37 mmol) and Pd$_2$dba$_3$ (38.0 mg, 0.04 mmol), Xantphos (42.6 mg, 0.07 mmol), and DIPEA (128.0 µL, 0.74 mmol) were added, followed by refluxing at 100° C. for 15 hours. The reaction mixture was cooled to room temperature and concentrated under reduced pressure. The residue was extracted with EtOAc, and the organic extract was washed with brine, dried over anhydrous Na$_2$SO$_4$ and concentrated under reduced pressure. The residue was purified by flash column chromatography (silica gel, n-Hex:EtOAc=5:1) to obtain tert-butyl (3-((3-cyanophenyl)thio)phenyl)carbamate (100.8 mg, 84%) as a yellow oil.

$^1$H-NMR (500MHz, DMSO-d$_6$): δ 9.48 (s, 1H), 7.71-7.73 (m, 1H), 7.67 (s, 1H), 7.59 (s, 1H), 7.52-7.55 (m, 2H), 7.47 (d, 1H, J=8.4Hz), 7.33 (t, 1H, J=7.6Hz), 7.03 (d, 1H, J=8.0Hz), 1.45 (s, 9H)

(c) Synthesis of tert-butyl (3-((3-cyanophenyl)sulfonyl)phenyl)carbamate tert-Butyl (3-((3-cyanophenyl)thio)phenyl)carbamate (618.0 mg, 1.89 mmol) was dissolved in CH$_2$Cl$_2$ (10.0 mL), and mCPBA (1.0 g, 5.68 mmol) was added, followed by stirring at room temperature for 3 hours. The reaction mixture was concentrated under reduced pressure, and the residue was extracted with CH$_2$Cl$_2$. The organic extract was washed with brine, dried over anhydrous Na$_2$SO$_4$ and concentrated under reduced pressure. The residue was purified by flash column chromatography (amine silica gel, n-Hex:EtOAc=1:1) to obtain tert-butyl (3-((3-cyanophenyl)sulfonyl)phenyl)carbamate (545.0 mg, 80%) as a white solid.

$^1$H-NMR (300MHz, DMSO-d$_6$): δ 9.78 (s, 1H), 8.42 (s, 1H), 8.16-8.23 (m, 3H), 7.83 (t, 1H, J=7.6Hz), 7.60-7.67 (m, 2H), 7.52 (t, 1H, J=7.6Hz), 1.47 (s, 9H)

(d) Synthesis of 3-((3-aminophenyl)sulfonyl)benzonitrile tert-Butyl (3-((3-cyanophenyl)sulfonyl)phenyl)carbamate (546.0 mg, 1.52 mmol) was dissolved in CH$_2$Cl$_2$ (5.0 mL), and TFA (2.5 mL, 32.65 mmol) was added, followed by stirring at room temperature for 14 hours. The reaction mixture was concentrated under reduced pressure, and the residue was extracted with CH$_2$Cl$_2$. The organic extract was washed with brine, dried over anhydrous Na$_2$SO$_4$ and concentrated under reduced pressure. The residue was purified by flash column chromatography (silica gel, n-Hex:EtOAc=1:1) to obtain 3-((3-aminophenyl)sulfonyl)benzonitrile (240.0 mg, 61%) as a yellow solid.

$^1$H-NMR (300MHz, DMSO-d$_6$): δ 8.37 (t, 1H, J=1.5Hz), 8.14-8.19 (m, 2H), 7.82 (t, 1H, J=8.0Hz), 7.23 (t, 1H, J=8.0Hz), 7.05-7.11 (m, 2H), 6.80 (dd, 1H, J=8.0, 2.3Hz), 5.71 (s, 2H)

(e) Synthesis of N-(3-((3-cyanophenyl)sulfonyl)phenyl)-6-(methylsulfonamido)-1H-indole-2-carboxamide 6-(Methylsulfonamido)-1H-indole-2-carboxylic acid hydrochloride (70.0 mg, 0.28 mmol), 3-((3-aminophenyl)sulfonyl)benzonitrile (59.1 mg, 0.23 mmol), and HATU (104.6 mg, 0.28 mmol) were dissolved in anhydrous DMF (1.0 mL), and DIPEA (58.0 µL, 0.33 mmol) was added. After stirring at 60° C. for 13 hours, the reaction mixture was extracted with EtOAc. The organic extract was washed with brine, dried over anhydrous Na$_2$SO$_4$, concentrated under reduced pressure. The residue was purified by flash column chromatography (amine silica gel, CH$_2$Cl$_2$:MeOH=95:5) to obtain N-(3-((3-cyanophenyl)sulfonyl)phenyl)-6-(methylsulfonamido)-1H-indole-2-carboxamide (14.3 mg, 13%) as an off-white solid.

LC/MS ESI (+): 495 (M+1)

$^1$H-NMR (300MHz, DMSO-d$_6$): δ 11.78 (s, 1H), 10.54 (s, 1H), 9.67 (s, 1H), 8.48 (s, 1H), 8.47 (s, 1H), 8.27 (d, 1H, J=8.0Hz), 8.20 (d, 1H, J=7.6Hz), 8.14 (d, 1H, J=7.6Hz), 7.86 (t, 1H, J=8.0Hz), 7.76 (d, 1H, J=7.6Hz), 7.65 (t, 1H, J=7.6Hz), 7.65 (d, 1H, J=8.4Hz), 7.42 (s, 1H), 7.39 (s, 1H), 6.99 (dd, 1H, J=8.4, 1.5Hz), 2.94 (s, 3H)

Through the synthetic method according to Example 402, compounds from Example 403 to Example 417 were synthesized, and the data of each example are as follows.

TABLE 31

| Ex. | Compound | Analysis data |
|---|---|---|
| 403 | 6-(methylsulfonamido)-N-(3-(pyridin-2-ylsulfonyl)phenyl)-1H-indole-2-carboxamide | LC/MS ESI (+): 471 (M + 1)<br>$^1$H-NMR (300 MHz, DMSO-d$_6$): δ 11.74 (s, 1H), 10.54 (s, 1H), 9.66 (s, 1H), 8.73 (d, 1H, J = 4.6 Hz), 8.48 (s, 1H), 8.15~8.26 (m, 3H), 7.61~7.73 (m, 4H), 7.43 (s, 1H), 7.38 (s, 1H), 6.98 (d, 1H, J = 8.4 Hz), 2.93 (s, 3H) |
| 404 | 6-(methylsulfonamido)-N-(3-(pyridin-3-ylsulfonyl)phenyl)-1H-indole-2-carboxamide | LC/MS ESI (+): 471 (M + 1)<br>$^1$H-NMR (300 MHz, DMSO-d$_6$): δ 11.78 (s, 1H), 10.54 (s, 1H), 9.66 (s, 1H), 9.14 (d, 1H, J = 2.3 Hz), 8.89 (d, 1H, J = 4.2 Hz), 8.49 (s, 1H), 8.36 (d, 1H, J = 8.0 Hz), 8.14 (d, 1H, J = 7.3 Hz), 7.63~7.77 (m, 4H), 7.42 (s, 1H), 7.39 (s, 1H), 6.99 (dd, 1H, J = 8.4, 1.5 Hz), 2.94 (s, 3H) |
| 405 | N-(3-((3-chlorophenyl)sulfonyl)phenyl)-6-(methylsulfonamido)-1H-indole-2-carboxamide | LC/MS ESI (+): 504 (M + 1)<br>$^1$H-NMR (300 MHz, DMSO-d$_6$): δ 11.78 (s, 1H), 10.53 (s, 1H), 9.66 (s, 1H), 8.47 (m, 1H), 8.14 (m, 1H), 7.98 (s, 1H), 7.93 (d, 1H, J = 7.8 Hz), 7.62~7.83 (m, 5H), 7.32~7.45 (m, 2H), 6.99 (dd, 1H, J = 8.4, 1.7 Hz), 2.95 (s, 3H) |
| 406 | N-(3-((6-cyanopyridin-2-yl)sulfonyl)phenyl)-6-(methylsulfonamido)-1H-indole-2-carboxamide | LC/MS ESI (+): 496 (M + 1)<br>$^1$H-NMR (300 MHz, DMSO-d$_6$): δ 11.77 (s, 1H), 10.58 (s, 1H), 9.66 (s, 1H), 8.49~8.54 (m, 2H), 8.43 (d, 1H, J = 7.8 Hz), 8.33 (m, 1H), 8.24 (m, 1H), 7.53~7.73 (m, 3H), 7.39~7.44 (m, 2H), 6.99 (dd, 1H, J = 8.6, 1.7 Hz), 2.95 (s, 3H) |

TABLE 31-continued

| Ex. | Compound | Analysis data |
|---|---|---|
| 407 | N-(3-((5-methoxypyridin-3-yl)sulfonyl)phenyl)-6-(methylsulfonamido)-1H-indole-2-carboxamide | LC/MS ESI (+): 501 (M + 1)<br>$^1$H-NMR (300 MHz, DMSO-$d_6$): δ 11.78 (s, 1H), 10.54 (s, 1H), 9.66 (s, 1H), 8.70 (d, 1H, J = 1.9 Hz), 8.60 (d, 1H, J = 2.9 Hz), 8.49 (m, 1H), 8.14 (m, 1H), 7.79~7.82 (m, 2H), 7.62~7.68 (m, 2H), 7.37~7.44 (m, 2H), 6.99 (dd, 1H, J = 8.8, 1.9 Hz), 3.93 (s, 3H), 2.95 (s, 3H) |
| 408 | N-(3-((6-methoxypyridin-2-yl)sulfonyl)phenyl)-6-(methylsulfonamido)-1H-indole-2-carboxamide | LC/MS ESI (+): 501 (M + 1)<br>$^1$H-NMR (300 MHz, DMSO-$d_6$): δ 11.75 (s, 1H), 10.53 (s, 1H), 9.65 (s, 1H), 8.56 (m, 1H), 8.16 (m, 1H), 8.02 (m, 1H), 7.79 (d, 1H, J = 7.4 Hz), 7.61~7.73 (m, 3H), 7.39~7.43 (m, 2H), 7.13 (d, 1H, J = 8.4 Hz), 6.99 (dd, 1H, J = 8.4, 1.1 Hz), 3.83 (s, 3H), 2.95 (s, 3H) |
| 409 | N-(3-(benzo[b]thiophen-5-ylsulfonyl)phenyl)-6-(methylsulfonamido)-1H-indole-2-carboxamide | LC/MS ESI (+): 526 (M + 1)<br>$^1$H-NMR (300 MHz, DMSO-$d_6$): δ 11.76 (s, 1H), 10.50 (s, 1H), 9.64 (brs, 1H), 8.56 (s, 1H), 8.48 (s, 1H), 8.29 (d, 1H, J = 8.4 Hz), 8.08 (d, 1H, J = 7.6 Hz), 8.01 (d, 1H, J = 5.3 Hz), 7.83 (dd, 1H, J = 8.4, 1.5 Hz), 7.69 (d, 2H, J = 5.7 Hz), 7.63 (dd, 2H, J = 8.0, 3.8 Hz), 7.39 (d, 2H, J = 7.3 Hz), 6.99 (dd, 1H, J = 8.4, 1.9 Hz), 2.94 (s, 3H) |
| 410 | N-(3-((2-methylbenzo[d]thiazol-6-yl)sulfonyl)phenyl)-6-(methylsulfonamido)-1H-indole-2-carboxamide | LC/MS ESI (+): 541 (M + 1)<br>$^1$H-NMR (300 MHz, DMSO-$d_6$): δ 11.78 (s, 1H), 10.53 (s, 1H), 9.67 (brs, 1H), 8.82 (s, 1H), 8.49 (s, 1H), 8.09~8.14 (m, 1H), 7.98 (dd, 1H, J = 8.8, 1.9 Hz), 7.61~7.74 (m, 5H), 7.41 (d, 1H, J = 8.4 Hz), 7.01 (dd, 1H, J = 8.4, 1.5 Hz), 2.95 (s, 3H), 2.86 (s, 3H) |
| 411 | N-(3-((3-cyano-5-methoxyphenyl)sulfonyl)phenyl)-6-(methylsulfonamido)-1H-indole-2-carboxamide | LC/MS ESI (+): 525 (M + 1)<br>$^1$H-NMR (300 MHz, DMSO-$d_6$): δ 11.78 (s, 1H), 10.53 (s, 1H), 9.66 (brs, 1H), 8.46 (s, 1H), 8.15 (d, 1H, J = 8.0 Hz), 7.99 (s, 1H), 7.83 (s, 1H) 7.78 (d, 1H, J = 7.6 Hz), 7.70~7.73 (m, 1H), 7.62~7.67 (m, 2H), 7.41 (d, 2H, J = 8.8 Hz), 7.00 (dd, 1H, J = 8.4, 1.9 Hz), 3.91 (s, 3H), 2.95 (s, 3H) |
| 412 | N-(3-((3-(cyanomethyl)phenyl)sulfonyl)phenyl)-6-(methylsulfonamido)-1H-indole-2-carboxamide | LC/MS ESI (+): 509 (M + 1)<br>$^1$H-NMR (300 MHz, DMSO-$d_6$): δ 11.77 (s, 1H), 10.54 (s, 1H), 9.67 (s, 1H), 8.46 (s, 1H), 8.13 (d, 1H, J = 7.8 Hz), 7.91~7.96 (m, 2H), 7.61~7.70 (m, 5H), 7.38~7.42 (m, 2H), 6.98 (d, 1H, J = 8.4 Hz), 4.21 (s, 2H), 2.94 (s, 3H) |
| 413 | 6-(methylsulfonamido)-N-(3-((4-oxo-4H-chromen-7-yl)sulfonyl)phenyl)-1H-indole-2-carboxamide | LC/MS ESI (+): 538 (M + 1)<br>$^1$H-NMR (300 MHz, DMSO-$d_6$): δ 11.78 (s, 1H), 10.53 (s, 1H), 9.65 (brs, 1H), 8.52 (d, 1H, J = 2.3 Hz), 8.48 (t, 1H, J = 1.9 Hz), 8.38 (d, 1H, J = 6.1 Hz), 8.29 (dd, 1H, J = 8.8, 2.3 Hz), 8.14~8.17 (m, 1H), 7.91 (d, 1H, J = 8.8 Hz), 7.73~7.76 (m, 1H), 7.61~7.67 (m, 2H), 7.40 (dd, 2H, J = 8.8, 1.5 Hz), 7.00 (dd, 1H, J = 8.4, 1.9 Hz), 6.48 (d, 1H, J = 6.1 Hz), 2.94 (s, 3H) |
| 414 | N-(3-((3-bromophenyl)sulfonyl)phenyl)-6-(methylsulfonamido)-1H-indole-2-carboxamide | LC/MS ESI (+): 548 (M + 1)<br>$^1$H-NMR (300 MHz, DMSO-$d_6$): δ 11.78 (s, 1H), 10.53 (s, 1H), 9.66 (s, 1H), 8.46 (s, 1H), 8.14 (d, 1H, J = 8.0 Hz), 8.09 (s, 1H), 7.93~7.98 (m, 2H), 7.74 (d, 1H, J = 8.4 Hz), 7.59~7.67 (m, 3H), 7.42 (s, 1H), 7.40 (s, 1H), 6.99 (d, 1H, J = 9.2 Hz), 2.95 (s, 3H) |
| 415 | N-(3-((3-aminophenyl)sulfonyl)phenyl)-6-(methylsulfonamido)-1H-indole-2-carboxamide | LC/MS ESI (+): 485 (M + 1)<br>$^1$H-NMR (300 MHz, DMSO-$d_6$): δ 11.76 (s, 1H), 10.52 (s, 1H), 9.65 (brs, 1H), 8.42 (s, 1H), 8.07~8.11 (m, 1H), 7.56~7.66 (m, 3H), 7.41 (d, 2H, J = 10.3 Hz), 7.23 (t, 1H, J = 8.0 Hz), 6.97~7.09 (m, 1H), 6.97~7.02 (m, 2H), 6.78 (dd, 1H, J = 8.0, 2.3 Hz), 5.70 (brs, 2H), 2.95 (s, 3H) |
| 416 | N-(3-((3-ethynylphenyl)sulfonyl)phenyl)-6-(methylsulfonamido)-1H-indole-2-carboxamide | LC/MS ESI (+): 494 (M + 1)<br>$^1$H-NMR (300 MHz, DMSO-$d_6$): δ 11.78 (s, 1H), 10.52 (s, 1H), 9.66 (s, 1H), 8.46 (s, 1H), 8.14 (d, 1H, J = 8.4 Hz), 7.97~7.99 (m, 2H), 7.81 (d, 1H, J = 7.6 Hz), 7.61~7.73 (m, 4H), 7.42 (s, 1H), 7.39 (s, 1H), 6.99 (dd, 1H, J = 8.4, 1.9 Hz), 4.48 (s, 1H), 2.95 (s, 3H) |
| 417 | N-(3-((3-cyano-5-hydroxyphenyl)sulfonyl)phenyl)-6-(methylsulfonamido)-1H-indole-2-carboxamide | LC/MS ESI (+): 511 (M + 1)<br>$^1$H-NMR (300 MHz, DMSO-$d_6$): δ 11.79 (s, 1H), 11.30 (brs, 1H), 10.54 (s, 1H), 9.66 (brs, 1H), 8.45 (s, 1H), 8.15 (d, 1H, J = 8.9 Hz), 7.61~7.77 (m, 4H), 7.52 (s, 1H), 7.39~7.43 (m, 3H), 6.99 (dd, 1H, J = 8.4, 2.1 Hz), 2.95 (s, 3H) |

Example 418

Synthesis of N-(3-bromo-5-((7-fluoro-3,4-dihydroisoquinolin-2(1H)-yl)sulfonyl)phenyl)-5-(methylsulfonamido)benzo[b]thiophene-2-carboxamide (a) Synthesis of 2-((3-bromo-5-nitrophenyl)sulfonyl)-7-fluoro-1,2,3,4-tetrahydroisoquinoline 7-Fluoro-1,2,3,4-tetrahydroisoquinoline (100.0 mg, 0.66 mmol) was dissolved in $CH_2Cl_2$ (5.0 mL), and DIPEA (172.0 µL, 0.99 mmol) and 3-bromo-5-nitrobenzenesulfonyl chloride (198.0 mg, 0.66 mmol) were added, followed by stirring for 2 hours. The reaction mixture was concentrated under reduced pressure, and the residue was purified by flash column chromatography (silica gel, n-Hex:$CH_2Cl_2$=1:3) to obtain 2-((3-bromo-5-nitrophenyl)sulfonyl)-7-fluoro-1,2,3,4-tetrahydroisoquinoline (270.0 mg, 98%) as a white solid.

LC/MS ESI (+): 415 (M+1)

$^1$H-NMR (400MHz, $CDCl_3$): δ 8.55-8.57 (m, 2H), 8.26 (d, 1H, J=1.6Hz), 7.06 (dd, 1H, J=8.4, 5.2Hz), 6.89 (td, 1H, J=8.4, 2.8Hz), 6.80 (dd, 1H, J=8.8, 2.8Hz), 4.37 (s, 2H), 3.51 (t, 2H, J=6.0Hz), 2.91 (t, 2H, J=6.0Hz)

(b) Synthesis of 3-bromo-5-((7-fluoro-3,4-dihydroisoquinolin-2(1H)-yl)sulfonyl)aniline The synthesis procedure of Intermediate 40 was repeated except for using 2-((3-bromo-5-nitrophenyl)sulfonyl)-7-fluoro-1,2,3,4-tetrahydroisoquinoline (130.0 mg, 0.31 mmol) to obtain 3-bromo-5-((7-fluoro-3,4-dihydroisoquinolin-2(1H)-yl)sulfonyl)aniline (105.0 mg, 87%).

LC/MS ESI (+): 385 (M+1)

$^1$H-NMR (400MHz, $CDCl_3$): δ 7.28 (s, 1H), 7.06 (dd, 1H, J=8.4, 6.0Hz), 7.00 (s, 1H), 6.98 (s, 1H), 6.87 (td, 1H, J=8.4, 2.4Hz), 6.76 (dd, 1H, J=9.6, 6.4Hz), 4.26 (s, 2H), 3.99 (brs, 2H), 3.39 (t, 2H, J=6.0Hz), 2.90 (t, 2H, J=6.0Hz)

(c) Synthesis of N-(3-bromo-5-((7-fluoro-3,4-dihydroisoquinolin-2(1H)-yl)sulfonyl)phenyl)-5-(methylsulfonamido)benzo[b]thiophene-2-carboxamide The synthesis procedure of Example 1 was repeated except for using 3-bromo-5-((7-fluoro-3,4-dihydroisoquinolin-2(1H)-yl)sulfonyl)aniline (70.9 mg, 0.31 mmol) to obtain N-(3-bromo-5-((7-fluoro-3,4-dihydroisoquinolin-2(1H)-yl)sulfonyl)phenyl)-5-(methylsulfonamido)benzo[b]thiophene-2-carboxamide (32.8 mg, 28%).

LC/MS ESI (+): 638 (M+1)

$^1$H-NMR (400MHz, DMSO-$d_6$): δ 10.88 (s, 1H), 9.89 (s, 1H), 8.34 (s, 2H), 8.27 (t, 1H, J=1.6Hz), 8.05 (d, 1H, J=8.8Hz), 7.83 (d, 1H, J=2.0Hz), 7.67 (t, 1H, J=1.6Hz), 7.39 (dd, 1H, J=8.8, 2.0Hz), 7.15 (dd, 1H, J=8.4, 6.0Hz), 7.08 (dd, 1H, J=10.0, 2.8Hz), 6.99 (dd, 1H, J=8.4, 2.8Hz), 4.33 (s, 2H), 3.42 (t, 2H, J=6.0Hz), 3.03 (s, 3H), 2.84 (t, 2H, J=6.0Hz)

Example 419

Synthesis of N-(3-bromo-5-((5,7-difluoro-3,4-dihydroisoquinolin-2(1H)-yl)sulfonyl)phenyl)-5-(methylsulfonamido)benzo[b]thiophene-2-carboxamide The synthesis procedure of Example 418 was repeated except for using 5,7-difluoro-1,2,3,4-tetrahydroisoquinoline (100.0 mg, 0.58 mmol) to obtain N-(3-bromo-5-((5,7-difluoro-3,4-dihydroisoquinolin-2(1H)-yl)sulfonyl)phenyl)-5-(methylsulfonamido)benzo[b]thiophene-2-carboxamide (12.7 mg).

LC/MS ESI (+): 656 (M+1)

$^1$H-NMR (400MHz, DMSO-$d_6$): δ 10.90 (s, 1H), 9.91 (s, 1H), 8.34-8.35 (m, 2H), 8.29 (s, 1H), 8.07 (d, 1H, J=8.4Hz), 7.85 (d, 1H, J=2.0Hz), 7.68 (t, 1H, J=1.6Hz), 7.40 (dd, 1H, J=8.8, 2.0Hz), 7.06 (m, 2H), 4.37 (s, 2H), 3.48 (t, 2H, J=6.0Hz), 3.04 (s, 3H), 2.76 (t, 2H, J=6.0Hz)

Example 420

Synthesis of N-(3-bromo-5-((4,4-difluoropiperidin-1-yl)sulfonyl)phenyl)-5-(methylsulfonamido)benzo[b]thiophene-2-carboxamide The synthesis procedure of Example 418 was repeated except for using 4,4-difluoropiperidine (58.0 mg, 0.33 mmol) to obtain N-(3-bromo-5-((4,4-difluoropiperidin-1-yl)sulfonyl)phenyl)-5-(methylsulfonamido)benzo[b]thiophene-2-carboxamide (30.0 mg).

LC/MS ESI (+): 608 (M+1)

$^1$H-NMR (400MHz, DMSO-$d_6$): δ 10.91 (s, 1H), 9.90 (brs, 1H), 8.39 (s, 1H), 8.34 (s, 1H), 8.22 (s, 1H), 8.04 (d, 1H, J=8.7Hz), 7.82 (s, 1H), 7.66 (s, 1H), 7.38 (dd, 1H, J=8.7, 2.1Hz), 3.15-3.18 (m, 4H), 3.02 (s, 3H), 2.05-2.15 (m, 4H)

Example 421

Synthesis of 5-(methylsulfonamido)-N-(3-(1-phenylcyclopropyl)phenyl)benzo[b]thiophene-2-carboxamide (a) Synthesis of 1-nitro-3-(1-phenylvinyl)benzene Bromo(methyl)triphenylphosphorane (1.2 g, 4.40 mmol) was dissolved in THF (7.6 mL), and n-BuLi (2.8 mL, 4.40 mmol) was slowly added at 0° C., followed by stirring for 30 minutes. The reaction mixture was slowly added to a mixture of (3-nitrophenyl)(phenyl)methanone (500.0 mg, 2.20 mmol) dissolved in THF (1.8 mL) at 0° C. After stirring at room temperature for 12 hours, the reaction mixture was extracted with EtOAc. The organic extract was washed with brine, dried over anhydrous $Na_2SO_4$, concentrated under reduced pressure. The residue was purified by flash column chromatography (silica gel, n-Hex:$CH_2Cl_2$=2:1) to obtain 1-nitro-3-(1-phenylvinyl)benzene (321.0 mg, 65%) as a yellow solid.

$^1$H-NMR (300MHz, $CDCl_3$): δ 8.22 (s, 1H), 8.18 (d, 1H, J=7.3Hz), 7.66 (d, 1H, J=7.7Hz), 7.51-7.53 (m, 1H), 7.36-7.39 (m, 3H), 7.28-7.36 (m, 2H), 5.61 (s, 1H), 5.57 (s, 1H)

(b) Synthesis of 1-nitro-3-(1-phenylcyclopropyl)benzene

1-Nitro-3-(1-phenylvinyl)benzene (319.0 mg, 1.42 mmol) and $CH_2I_2$ (1.1 mL, 14.20 mmol) were dissolved in 1,2-dichloroethane, and 1.0 M solution of $Et_2Zn$ in hexane (7.1 mL, 7.08 mmol) was slowly added, followed by stirring at room temperature for 12 hours. The reaction mixture was filtered through Celite and concentrated under reduced pressure. The residue was purified by flash column chromatography (silica gel, n-Hex:EtOAc=4:1) to obtain a mixture of yellow solid compounds 1-nitro-3-(1-phenylvinyl)benzene and 1-nitro-3-(1-phenylcyclopropyl)benzene (129.0 mg).

(c) Synthesis of 1-(2,2-dibromo-1-phenylcyclopropyl)-3-nitrobenzene

1-Nitro-3-(1-phenylvinyl)benzene (135.0 mg, 0.60 mmol), CHBr$_3$ (71.2 μL, 0.82 mmol), and benzyltriethylammonium chloride (24.6 mg, 0.11 mmol) were dissolved in 1,2-dichloroethane (0.6 mL), and NaOH (910.0 mg, 22.8 mmol) dissolved in H$_2$O (0.9 mL) was added. After stirring at 40° C. for 24 hours, the reaction mixture was extracted with CH$_2$Cl$_2$. The organic extract was washed with brine, dried over anhydrous Na$_2$SO$_4$ and concentrated under reduced pressure. The residue was purified by flash column chromatography (silica gel, n-Hex:EtOAc=9:1) to obtain 1-(2,2-dibromo-1-phenylcyclopropyl)-3-nitrobenzene (151.6 mg, 63%) as a colorless oil.

$^1$H-NMR (300MHz, CDCl$_3$): δ 8.34-8.35 (m, 1H), 8.09-8.13 (m, 1H), 7.88-7.92 (m, 1H), 7.49-7.54 (m, 3H), 7.33-7.39 (m, 2H), 7.25-7.31 (m, 1H), 2.58 (d, 1H, J=8.0Hz), 2.52 (d, 1H, J=8.0Hz)

(d) Synthesis of 3-(1-phenylcyclopropyl)aniline

The mixture of 1-nitro-3-(1-phenylvinyl)benzene and 1-nitro-3-(1-phenylcyclopropyl)benzene (129.0 mg), Zn (562.0 mg), and NH$_4$Cl (153.0 mg) were dissolved in a mixture of THF/MeOH/H$_2$O (12.0 mL, 1/1/0.5 v/v), and ultrasonificated at 40° C. for 3 hours. The reaction mixture was filtered through Celite and concentrated under reduced pressure. The residue was purified by flash column chromatography (silica gel, n-Hex:CH$_2$Cl$_2$=1:1) to obtain a mixture of white solid compounds of 3-(1-phenylvinyl)aniline and 3-(1-phenylcyclopropyl)aniline (59.0 mg).

LC/MS ESI (+): 210 (M+1)

(e) Synthesis of 5-(methylsulfonamido)-N-(3-(1-phenylcyclopropyl)phenyl)benzo[b]thiophene-2-carboxamide 5-(Methylsulfonamido)benzo[b]thiophene-2-carboxylic acid (81.0 mg, 0.30 mmol), the mixture of 3-(1-phenylvinyl)aniline and 3-(1-phenylcyclopropyl)aniline (58.0 mg), and HATU (125.0 mg, 0.33 mmol) were dissolved in anhydrous DMF (3.0 mL), and DIPEA (78.0 μL, 0.45 mmol) was added. After stirring at 40° C. for 24 hours, the reaction mixture was extracted with EtOAc. The organic extract was washed with brine, dried over anhydrous Na$_2$SO$_4$, concentrated under reduced pressure. The residue was first purified by flash column chromatography (silica gel, n-Hex: EtOAc=1:2). The residue was secondly purified by reversed-phase column chromatography (C18-silica gel, CH$_3$CN: H$_2$O=52:48) to obtain 5-(methylsulfonamido)-N-(3-(1-phenylcyclopropyl)phenyl)benzo[b]thiophene-2-carboxamide (8.5 mg, 7%) as a white solid.

LC/MS ESI (+): 463 (M+1)

$^1$H-NMR (300MHz, DMSO-d$_6$): δ 10.41 (s, 1H), 9.87 (s, 1H), 8.29 (s, 1H), 8.01 (d, 1H, J=8.8Hz), 7.78 (d, 1H, J=2.2Hz), 7.63-7.66 (m, 2H), 7.35 (dd, 1H, J=8.8, 2.2Hz), 7.16-7.33 (m, 6H), 7.01 (d, 1H, J=7.7Hz), 3.01 (s, 3H), 1.27 (s, 4H)

Through the synthetic method according to Example 421, compounds from Example 422 to Example 433 were synthesized, and the data of each example are as follows.

TABLE 32

| Ex. | Compound | Analysis data |
|---|---|---|
| 422 | 6-(methylsulfonamido)-N-(3-(1-phenylcyclopropyl)phenyl)-1H-indole-2-carboxamide | LC/MS ESI (+): 446 (M + 1)<br>$^1$H-NMR (300 MHz, DMSO-d$_6$): δ 11.66 (s, 1H), 10.08 (s, 1H), 9.59 (s, 1H), 7.70 (d, 1H, J = 8.4 Hz), 7.67 (s, 1H), 7.61 (d, 1H, J = 8.4 Hz), 7.37 (dd, 2H, J = 4.6, 2.3 Hz), 7.19~7.32 (m, 6H), 6.96~7.00 (m, 2H), 2.94 (s, 3H), 1.27 (s, 4H) |
| 423 | 5-(methylsulfonamido)-N-(3-(1-phenylvinyl)phenyl)benzo[b]thiophene-2-carboxamide | LC/MS ESI (+): 449 (M + 1)<br>$^1$H-NMR (300 MHz, DMSO-d$_6$): δ 10.48 (s, 1H), 9.85 (s, 1H), 8.29 (s, 1H), 8.01 (d, 1H, J = 8.8 Hz), 7.84 (d, 1H, J = 8.1 Hz), 7.77 (s, 1H), 7.67 (s, 1H), 7.33~7.43 (m, 7H), 7.10 (d, 1H, J = 7.7 Hz), 5.53 (s, 1H), 5.50 (s, 1H), 3.01 (s, 3H) |
| 424 | N-(3-(1-(4-fluorophenyl)cyclopropyl)phenyl)-5-(methylsulfonamido)benzo[b]thiophene-2-carboxamide | LC/MS ESI (+): 481 (M + 1)<br>$^1$H-NMR (300 MHz, DMSO-d$_6$): δ 10.39 (s, 1H), 9.85 (s, 1H), 8.28 (s, 1H), 8.01 (d, 1H, J = 8.8 Hz), 7.79 (d, 1H, J = 1.9 Hz), 7.63~7.65 (m, 2H), 7.35 (dd, 1H, J = 8.8, 1.9 Hz), 7.26~7.31 (m, 3H), 7.09~7.15 (m, 2H), 6.99 (d, 1H, J = 7.3 Hz), 3.01 (s, 3H), 1.26 (s, 4H) |
| 425 | N-(3-(1-(4-fluorophenyl)cyclopropyl)phenyl)-6-(methylsulfonamido)-1H-indole-2-carboxamide | LC/MS ESI (+): 464 (M + 1)<br>$^1$H-NMR (300 MHz, DMSO-d$_6$): δ 11.66 (s, 1H), 10.07 (s, 1H), 9.58 (s, 1H), 7.69 (d, 1H, J = 8.0 Hz), 7.64 (s, 1H), 7.60 (d, 1H, J = 8.8 Hz), 7.38 (s, 1H), 7.36 (s, 1H), 7.24~7.32 (m, 3H), 7.08~7.14 (m, 2H), 6.93~7.00 (m, 2H), 2.94 (s, 3H), 1.26 (s, 4H) |
| 426 | N-(3-bromo-5-(1-(2,4-difluorophenyl)cyclopropyl)phenyl)-5-(methylsulfonamido)benzo[b]thiophene-2-carboxamide | LC/MS ESI (+): 577 (M + 1)<br>$^1$H-NMR (300 MHz, DMSO-d$_6$): δ 10.49 (s, 1H), 9.85 (s, 1H), 8.27 (s, 1H), 8.02 (d, 1H, J = 8.8 Hz), 7.94 (s, 1H), 7.80 (s, 1H), 7.56~7.64 (m, 1H), 7.49 (s, 1H), 7.36 (dd, 1H, J = 8.8, 1.9 Hz), 7.19~7.26 (m, 1H), 7.11 (d, 1H, J = 7.3 Hz), 7.03 (s, 1H), 3.01 (s, 3H), 1.23~1.38 (m, 4H) |
| 427 | N-(3-methoxy-5-(1-(3-methoxy-5-(trifluoromethoxy)phenyl)cyclopropyl)phenyl)-5-(methylsulfonamido)benzo[b]thiophene-2-carboxamide | LC/MS ESI (+): 607 (M + 1)<br>$^1$H-NMR (300 MHz, DMSO-d$_6$): δ 10.37 (s, 1H), 9.87 (brs, 1H), 8.28 (s, 1H), 8.01 (d, 1H, J = 8.4 Hz), 7.78 (d, 1H, J = 1.9 Hz), 7.34~7.38 (m, 2H), 7.27 (s, 1H), 6.77~6.80 (m, 2H), 6.72 (s, 1H), 6.60 (s, 1H), 3.77 (s, 3H), 3.74 (s, 3H), 3.01 (s, 3H), 1.29~1.30 (m, 4H) |

TABLE 32-continued

| Ex. | Compound | Analysis data |
|---|---|---|
| 428 | N-(3-(difluoromethoxy)-5-(1-(4-fluorophenyl)cyclopropyl)phenyl)-6-(methylsulfonamido)-1H-indole-2-carboxamide | LC/MS ESI (+): 530 (M + 1)<br>$^1$H-NMR (300 MHz, DMSO-d$_6$): δ 11.72 (s, 1H), 10.23 (s, 1H), 9.62 (s, 1H), 7.65 (s, 1H), 7.62 (d, 1H, J = 9.2 Hz) 7.48 (s, 1H), 7.38 (s, 2H), 7.30~7.34 (m, 2H + 0.3H), 7.11~7.21 (m, 2H + 0.4H), 6.98 (d, 1H + 0.3H, J = 8.0 Hz), 6.71 (s, 1H), 2.93 (s, 3H), 1.29 (s, 4H) |
| 429 | N-(3-(difluoromethoxy)-5-(1-(4-fluorophenyl)cyclopropyl)phenyl)-5-(methylsulfonamido)benzo[b]thiophene-2-carboxamide | LC/MS ESI (+): 547 (M + 1)<br>$^1$H-NMR (300 MHz, DMSO-d$_6$): δ 10.51 (s, 1H), 9.83 (brs, 1H), 8.28 (s, 1H), 8.01 (d, 1H, J = 8.4 Hz), 7.79 (s, 1H), 7.59 (s, 1H), 7.46 (s, 1H), 7.30~7.38 (m, 3H), 7.21 (t, 1H, J = 73.6 Hz), 7.11~7.21 (m, 2H), 6.76 (s, 1H), 3.01 (s, 3H), 1.29 (s, 4H) |
| 430 | N-(3-chloro-5-(1-(3-isopropoxy-5-(trifluoromethoxy)phenyl)cyclopropyl)phenyl)-6-fluoro-5-(N-methylmethylsulfonamido)benzo[b]thiophene-2-carboxamide | LC/MS ESI (+): 671 (M + 1)<br>$^1$H-NMR (400 MHz, DMSO-d$_6$): δ 10.71 (s, 1H), 8.31 (brs, 1H), 8.21 (d, 1H, J = 7.4 Hz), 8.15 (d, 1H, J = 10.5 Hz), 7.85 (m, 1H), 7.60 (s, 1H), 7.11 (s, 1H), 6.78 (m, 2H), 6.73 (s, 1H), 4.63~4.66 (m, 1H), 3.30 (s, 3H), 3.14 (s, 3H), 1.32~1.34 (m, 4H), 1.25 (d, 6H, J = 6.0 Hz) |
| 431 | N-(3-chloro-5-(1-(3-isopropoxy-5-(trifluoromethoxy)phenyl)cyclopropyl)phenyl)-5-(methylsulfonamido)benzo[b]thiophene-2-carboxamide | LC/MS ESI (+): 639 (M + 1)<br>$^1$H-NMR (400 MHz, DMSO-d$_6$): δ 10.56 (s, 1H), 9.87 (brs, 1H), 8.29 (s, 1H), 8.02 (d, 1H, J = 8.7 Hz), 7.85 (s, 1H), 7.80 (d, 1H, J = 2.0 Hz), 7.59 (s, 1H), 7.36 (dd, 1H, J = 8.7, 2.1 Hz), 7.09 (s, 1H), 6.76 (s, 1H), 6.75 (s, 1H), 6.72 (s, 1H), 4.62~4.68 (m, 1H), 3.02 (s, 3H), 1.32 (d, 4H, J = 9.5 Hz), 1.23 (d, 6H, J = 6.0 Hz) |
| 432 | N-(3-chloro-5-(1-(4-chlorophenyl)cyclopropyl)phenyl)-5-(methylsulfonamido)benzo[b]thiophene-2-carboxamide | LC/MS ESI (+): 531 (M + 1)<br>$^1$H-NMR (400 MHz, DMSO-d$_6$): δ 10.53 (s, 1H), 9.89 (brs, 1H), 8.26 (s, 1H), 7.99 (d, 1H, J = 8.7 Hz), 7.84 (s, 1H), 7.76 (s, 1H), 7.54 (s, 1H), 7.38 (d, 2H, J = 8.4 Hz), 7.33 (d, 1H, J = 8.7 Hz), 7.28 (d, 2H, J = 8.4 Hz), 7.02 (s, 1H), 2.98 (s, 3H), 1.31 (d, 4H, J = 6.2 Hz) |
| 433 | 6-chloro-N-(3-chloro-5-(1-(4-chlorophenyl)cyclopropyl)phenyl)-5-(methylsulfonamido)benzo[b]thiophene-2-carboxamide | LC/MS ESI (+): 565 (M + 1)<br>$^1$H-NMR (400 MHz, DMSO-d$_6$): δ 10.66 (s, 1H), 9.65 (s, 1H), 8.36 (s, 1H), 8.30 (s, 1H), 8.05 (s, 1H), 7.84 (t, 1H, J = 1.9 Hz), 7.53 (s, 1H), 7.39 (d, 2H, J = 8.5 Hz), 7.29 (d, 2H, J = 8.5 Hz), 7.04 (t, 1H, J = 1.6 Hz), 3.07 (s, 3H), 1.32 (d, 4H, J = 5.9 Hz) |

Example 434

Synthesis of N-(3-benzoylphenyl)-6-(methylsulfonamido)-1H-indole-2-carboxamide 6-(methylsulfonamido)-1H-indole-2-carboxylic acid hydrochloride (30.0 mg, 0.12 mmol), 3-aminobenzophenone (26.0 mg, 0.13 mmol), and HATU (49.0 mg, 0.13 mmol) were dissolved in anhydrous DMF (2.0 mL), and DIPEA (42.0 μL, 0.24 mmol) was added. After stirring at 30° C. for 2 hours, the reaction mixture was extracted with EtOAc. The organic extract was washed with brine, dried over anhydrous Na$_2$SO$_4$, concentrated under reduced pressure. The residue was purified by flash column chromatography (silica gel, n-Hex:EtOAc=2:3) to obtain N-(3-benzoylphenyl)-6-(methylsulfonamido)-1H-indole-2-carboxamide (20.0 mg, 38%) as a white solid.

LC/MS ESI (+): 434 (M+1)

$^1$H-NMR (300MHz, DMSO-d$_6$): δ 11.76 (s, 1H), 10.42 (s, 1H), 9.64 (brs, 1H), 8.24 (s, 1H), 8.16 (d, 1H, J=8.0Hz), 7.78 (d, 2H, J=6.9Hz), 7.71 (t, 1H, J=7.3Hz), 7.62 (m, 4H), 7.47 (d, 1H, J=7.6Hz), 7.41 (dd, 2H, J=8.8, 1.9Hz), 6.99 (dd, 1H, J=8.4, 1.9Hz), 2.94 (s, 3H)

Example 435

Synthesis of N-(3-(1-hydroxy-1-phenylethyl)phenyl)-6-(methylsulfonamido)-1H-indole-2-carboxamide (a) Synthesis of 1-(3-nitrophenyl)-1-phenylethanol (3-Nitrophenyl)(phenyl)methanone (100.0 mg, 0.44 mmol) was dissolved in toluene (4.0 mL), and 1 M solution of Al(CH$_3$)$_3$ in n-heptane (1.8 mL, 1.76 mmol) and a catalytic amount of AcOH were added, followed by refluxing at 110° C. for 15 hours. The reaction mixture was cooled to room temperature and extracted with CH$_2$Cl$_2$. The organic extract was washed with brine, dried over anhydrous Na$_2$SO$_4$, concentrated under reduced pressure. The residue was purified by flash column chromatography (silica gel, n-Hex:EtOAc=4:1) to obtain 1-(3-nitrophenyl)-1-phenylethanol (50.0 mg, 47%) as a colorless oil.

$^1$H-NMR (300MHz, CDCl$_3$): δ 8.35 (s, 1H), 8.09 (d, 1H, J=8.1Hz), 7.73 (d, 1H, J=7.8Hz), 7.28-7.49 (m, 6H), 2.29 (s, 1H), 2.00 (s, 3H)

(b) Synthesis of 1-(3-aminophenyl)-1-phenylethanol 1-(3-Nitrophenyl)-1-phenylethanol (50.0 mg, 0.21 mmol) was dissolved in a mixture of MeOH/$H_2O$ (2.2 mL, 10/1 v/v), and Zn (54.0 mg, 0.82 mmol) and $NH_4Cl$ (44.0 mg, 0.82 mmol) were added, and then ultrasonificated at 40° C. for 1 hour. The reaction mixture was filtered through Celite and extracted with $CH_2Cl_2$. The organic extract was washed with brine, dried over anhydrous $Na_2SO_4$, concentrated under reduced pressure. The residue was purified by flash column chromatography (silica gel, n-Hex:EtOAc=5:1) to obtain 1-(3-aminophenyl)-1-phenylethanol (17.0 mg, 38%) as a colorless oil.

LC/MS ESI (+): 214 (M+1)

(c) Synthesis of N-(3-(1-hydroxy-1-phenylethyl)phenyl)-6-(methylsulfonamido)-1H-indole-2-carboxamide 6-(Methylsulfonamido)-1H-indole-2-carboxylic acid hydrochloride (22.0 mg, 0.09 mmol), 1-(3-aminophenyl)-1-phenylethanol (17.0 mg, 0.08 mmol), HATU (34.0 mg, 0.09 mmol), and DIPEA (21.0 μL, 0.17 mmol) were dissolved in anhydrous DMF (0.8 mL), followed by stirring at room temperature for 15 hours. The reaction mixture was extracted with $CH_2Cl_2$, and the organic extract was washed with brine, dried over anhydrous $Na_2SO_4$, concentrated under reduced pressure. The residue was purified by flash column chromatography (amine silica gel, $CH_2Cl_2$:MeOH=9:1) to obtain N-(3-(1-hydroxy-1-phenylethyl)phenyl)-6-(methylsulfonamido)-1H-indole-2-carboxamide (15.0 mg, 39%) as a white solid.

LC/MS ESI (+): 450 (M+1)
$^1$H-NMR (300MHz, DMSO-$d_6$): δ 11.68 (s, 1H), 10.13 (s, 1H), 9.61 (s, 1H), 7.81 (s, 1H), 7.75 (d, 1H, J=8.0Hz), 7.60 (d, 1H, J=8.8Hz), 7.44 (d, 2H, J=8.0Hz), 7.38 (s, 2H), 7.13-7.31 (m, 5H), 6.98 (dd, 1H J=8.4, 1.9Hz), 5.75 (s, 1H), 2.93 (s, 3H), 1.84 (s, 3H)

Example 436 and Example 437

Synthesis of 6-(N-(2-amino-2-oxoethyl)methylsulfonamido)-N-(3-(2-(3-hydroxy-5-(trifluoromethoxy)phenyl)propan-2-yl)phenyl)-1H-indole-2-carboxamide and N-(3-(2-(3-(2-amino-2-oxoethoxy)-5-(trifluoromethoxy)phenyl)propan-2-yl)phenyl)-6-(N-(2-amino-2-oxoethyl)methylsulfonamido)-1H-indole-2-carboxamide

(a) Synthesis of N-3-(2-(3-hydroxy-5-(trifluoromethoxy)phenyl)propan-2-yl)phenyl)-6-(methylsulfonamido)-1H-indole-2-carboxamide To a solution of N-(3-(2-(3-methoxy-5-(trifluoromethoxy)phenyl)propan-2-yl)phenyl)-6-(methylsulfonamido)-1H-indole-2-carboxamide (30.0 mg, 0.05 mmol) in anhydrous $CH_2Cl_2$ (1.0 mL), 1.0 M solution of $BBr_3$ in $CH_2Cl_2$ (160.0 μL, 0.16 mmol) was added at 0° C., followed by stirring at room temperature for 1 hour and 20 minutes. Water was added at 0° C. to quench the reaction, and the reaction mixture was extracted with $CH_2Cl_2$. The organic extract was washed with brine, dried over anhydrous $Na_2SO_4$, concentrated under reduced pressure. The residue was purified by flash column chromatography (amine silica gel, $CH_2Cl_2$:MeOH=9:1) to obtain N-(3-(2-(3-hydroxy-5-(trifluoromethoxy)phenyl)propan-2-yl)phenyl)-6-(methylsulfonamido)-1H-indole-2-carboxamide (28.7 mg, 98%) as an off-white oil.

LC/MS ESI (+): 548 (M+1)

(b) Synthesis of 6-(N-(2-amino-2-oxoethyl)methylsulfonamido)-N-(3-(2-(3-hydroxy-5-(trifluoromethoxy)phenyl)propan-2-yl)phenyl)-1H-indole-2-carboxamide N-(3-(2-(3-hydroxy-5-(trifluoromethoxy)phenyl)propan-2-yl)phenyl)-6-(methylsulfonamido)-1H-indole-2-carboxamide (48.0 mg, 0.09 mmol) was dissolved in anhydrous DMF (1.5 mL), and $K_2CO_3$ (18.2 mg, 0.13 mmol) and 2-iodoacetamide (19.5 mg, 0.11 mmol) were added. The reaction mixture was heated at 40° C. for 12 hours, water was added to quench the reaction, and the reaction mixture was extracted with EtOAc. The organic extract was washed with brine, dried over anhydrous $Na_2SO_4$, concentrated under reduced pressure. The residue was purified by flash column chromatography (amine silica gel, $CH_2Cl_2$:MeOH=9:1) to obtain 6-(N-(2-amino-2-oxoethyl)methylsulfonamido)-N-(3-(2-(3-hydroxy-5-(trifluoromethoxy)phenyl)propan-2-yl)phenyl)-1H-indole-2-carboxamide (6.8 mg, 13%) as a white solid and N-(3-(2-(3-(2-amino-2-oxoethoxy)-5-(trifluoromethoxy)phenyl)propan-2-yl)phenyl)-6-(N-(2-amino-2-oxoethyl)methylsulfonamido)-1H-indole-2-carboxamide (2.1 mg, 4%) as a white solid.

Example 436

LC/MS ESI (+): 605 (M+1)
$^1$H-NMR (300MHz, DMSO-$d_6$): δ 11.92 (s, 1H), 10.22 (s, 1H), 9.94 (s, 1H), 7.78 (d, 1H, J=8.0Hz), 7.68 (d, 1H, J=8.8Hz), 7.65 (s, 1H), 7.60 (s, 1H), 7.46 (s, 1H), 7.42 (s, 1H), 7.30 (t, 1H, J=8.0Hz), 7.18-7.21 (m, 2H), 6.98 (d, 1H, J=7.6Hz), 6.61 (s, 2H), 6.53 (s, 1H), 4.25 (s, 2H), 3.12 (s, 3H), 1.62 (s, 6H)

Example 437

LC/MS ESI (+): 662 (M+1)
$^1$H-NMR (300MHz, DMSO-$d_6$): δ 11.93 (s, 1H), 10.22 (s, 1H), 7.78 (m, 1H), 7.66-7.69 (m, 2H), 7.63 (s, 1H), 7.59 (m, 1H), 7.42-7.46 (m, 3H), 7.30 (t, 1H, J=8.0Hz), 7.17-7.21 (m, 2H), 6.97 (m, 1H), 6.91 (m, 1H), 6.78 (m, 1H), 6.73 (m, 1H), 4.44 (s, 2H), 4.24 (s, 2H), 3.12 (s, 3H), 1.65 (s, 6H)

Example 438

Synthesis of N-(3-chloro-5-((2,4-difluorophenyl)amino)phenyl)-5-(methylsulfonamido)benzo[b]thiophene-2-carboxamide

(a) Synthesis of N-(3-chloro-5-nitrophenyl)-2,4-difluoroaniline

1-Bromo-3-chloro-5-nitrobenzene (100.0 mg, 0.42 mmol), 2,4-difluoroaniline (35.6 μL, 0.35 mmol), $Pd_2(dba)_3$·$CHCl_3$ (18.3 mg, 0.02 mmol), BINAP (21.9 mg, 0.04 mmol) and NaOt-Bu (47.5 mg, 0.49 mmol) were added to anhydrous toluene (3.5 mL). The reaction was performed in a microwave with 150 W, at 110° C. for 30 minutes, and the reaction mixture was cooled to room temperature. Water was added, and the reaction mixture was extracted with EtOAc. The organic extract was washed with brine, dried over anhydrous $Na_2SO_4$, concentrated under reduced pressure.

The residue was purified by flash column chromatography (silica gel, n-Hex:EtOAc=9:1) to obtain N-(3-chloro-5-nitrophenyl)-2,4-difluoroaniline (76.6 mg, 76%) as a yellow solid.

LC/MS ESI (+): 285 (M+1)

$^1$H-NMR (400MHz, CDCl$_3$): δ 7.68 (m, 1H), 7.58 (m, 1H), 7.31 (m, 1H), 7.11 (m, 1H), 6.91-7.00 (m, 2H), 5.79 (s, 1H)

(b) Synthesis of 5-chloro-N$^1$-(2,4-difluorophenyl) benzene-1,3-diamine

The synthesis procedure of Example 400-c was repeated except for using N-(3-chloro-5-nitrophenyl)-2,4-difluoroaniline (76.6 mg, 0.27 mmol) to obtain 5-chloro-N$^1$-(2,4-difluorophenyl)benzene-1,3-diamine (64.5 mg, 95%) as a red oil.

LC/MS ESI (+): 255 (M+1)

$^1$H-NMR (400MHz, CDCl$_3$): δ 7.27 (m, 1H), 6.80-6.91 (m, 2H), 6.36 (m, 1H), 6.26 (m, 1H), 6.13 (m, 1H), 5.46 (s, 1H), 3.68 (s, 2H)

(c) Synthesis of N-(3-chloro-5-((2,4-difluorophenyl) amino)phenyl)-5-(methylsulfonamido)benzo[b]thiophene-2-carboxamide The synthesis procedure of Example 1 was repeated except for using 5-chloro-N$^1$-(2,4-difluorophenyl)benzene-1,3-diamine (64.5 mg, 0.25 mmol) to obtain N-(3-chloro-5-((2,4-difluorophenyl)amino)phenyl)-5-(methylsulfonamido)benzo[b]thiophene-2-carboxamide (67.6 mg, 53%) as an off-white solid.

LC/MS ESI (+): 508 (M+1)

$^1$H-NMR (400MHz, DMSO-d$_6$): δ 10.41 (s, 1H), 9.87 (brs, 1H), 8.27 (s, 1H), 8.19 (s, 1H), 8.00 (d, 1H, J=8.8Hz), 7.78 (d, 1H, J=2.0Hz), 7.33-7.41 (m, 4H), 7.22 (s, 1H), 7.10 (m, 1H), 6.59 (m, 1H), 3.00 (s, 3H)

Example 439

Synthesis of N-(3-chloro-5-((2,4-difluorophenyl) (methyl)amino)phenyl)-5-(methylsulfonamido)benzo[b]thiophene-2-carboxamide To a solution of N-(3-chloro-5-((2,4-difluorophenyl) amino)phenyl)-5-(methylsulfonamido)benzo[b]thiophene-2-carboxamide (Example 438) (22.3 mg, 0.04 mmol) in anhydrous CH$_3$CN (0.4 mL), 37 wt % formaldehyde aqueous solution (49.0 μL, 0.66 mmol), AcOH (3.8 μL, 0.07 mmol), and NaBH$_3$CN (5.5 mg, 0.09 mmol) were added. The reaction mixture was stirred at room temperature for 21 hours, water was added, and extracted with EtOAc. The organic extract was washed with brine, dried over anhydrous Na$_2$SO$_4$, concentrated under reduced pressure. The residue was purified by flash column chromatography (silica gel, n-Hex:EtOAc=1:1) to obtain N-(3-chloro-5-((2,4-difluorophenyl)(methyl)amino)phenyl)-5-(methylsulfonamido)benzo[b]thiophene-2-carboxamide (3.9 mg, 17%) as a white solid.

LC/MS ESI (+): 522 (M+1)

$^1$H-NMR (400MHz, DMSO-d$_6$): δ 10.36 (s, 1H), 9.87 (brs, 1H), 8.23 (s, 1H), 7.98 (d, 1H, J=8.6Hz), 7.76 (s, 1H), 7.41-7.52 (m, 3H), 7.33 (d, 1H, J=7.3Hz), 7.22 (m, 1H), 6.93 (s, 1H), 6.46 (s, 1H), 3.22 (s, 3H), 2.98 (s, 3H)

Example 440

Synthesis of N-(3-chloro-5-((4-chlorophenyl) (methyl)amino)phenyl)-5-(methylsulfonamido)benzo[L]thiophene-2-carboxamide (a) Synthesis of 3-chloro-N-(4-chlorophenyl)-5-nitroaniline 1-Bromo-3-chloro-5-nitrobenzene (200.0 mg, 0.85 mmol) and 4-chloroaniline (89.9 mg, 0.71 mmol) were dissolved in toluene (3.5 mL), and Pd$_2$(dba)$_3$·CHCl$_3$ (36.5 mg, 0.04 mmol), BINAP (43.9 mg, 0.07 mmol) and NaOt-Bu (94.9 mg, 0.99 mmol) were added, followed by stirring in a microwave at 110° C. for 30 minutes. After cooling to room temperature, the reaction mixture was extracted with EtOAc, washed with brine, dried over anhydrous Na$_2$SO$_4$, concentrated under reduced pressure. The residue was purified by flash column chromatography (silica gel, n-Hex:EtOAc=4:1) to obtain 3-chloro-N-(4-chlorophenyl)-5-nitroaniline (107.1 mg, 54%) as an orange solid.

LC/MS ESI (+): 283 (M+1)

$^1$H-NMR (400MHz, CDCl$_3$): δ 7.67 (s, 1H), 7.65 (s, 1H), 7.35 (d, 2H, J=8.6Hz), 7.20 (s, 1H), 7.09 (d, 2H, J=8.6Hz), 5.94 (s, 1H)

(b) Synthesis of 3-chloro-N-(4-chlorophenyl)-N-methyl-5-nitroaniline

3-Chloro-N-(4-chlorophenyl)-5-nitroaniline (70.7 mg, 0.25 mmol) was dissolved in anhydrous DMF (2.5 mL), and 60% NaH in mineral oil (15.0 mg, 0.38 mmol) was added at 0° C. The reaction mixture was stirred at 0° C. for 30 minutes, and CH$_3$I (31.1 μL, 0.50 mmol) was added. After stirring at room temperature for 5 hours, the residue was extracted with EtOAc. The organic extract was washed with brine, dried over anhydrous Na$_2$SO$_4$ and concentrated under reduced pressure. The residue was purified by flash column chromatography (silica gel, n-Hex:EtOAc=4:1) to obtain 3-chloro-N-(4-chlorophenyl)-N-methyl-5-nitroaniline (68.1 mg, 92%) as a yellow solid.

LC/MS ESI (+): 297 (M+1)

$^1$H-NMR (400MHz, CDCl$_3$): δ 7.59 (m, 1H), 7.47 (m, 1H), 7.40 (d, 2H, J=8.7Hz), 7.13 (d, 2H, J=8.7Hz), 6.97 (m, 1H), 3.34 (s, 3H)

(c) Synthesis of 5-chloro-N$^1$-(4-chlorophenyl)-N$^1$-methylbenzene-1,3-diamine The synthesis procedure of Intermediate 40 was repeated except for using 3-chloro-N-(4-chlorophenyl)-N-methyl-5-nitroaniline (73.3 mg, 0.25 mmol) to obtain 5-chloro-N$^1$-(4-chlorophenyl)-N$^1$-methylbenzene-1,3-diamine (59.1 mg, 90%) as a brown liquid.

LC/MS ESI (+): 267 (M+1)

$^1$H-NMR (400MHz, CDCl$_3$): δ 7.26 (d, 2H, J=8.9Hz), 7.00 (d, 2H, J=8.9Hz), 6.31 (m, 1H), 6.25 (m, 1H), 6.08 (m, 1H), 3.64 (s, 2H), 3.23 (s, 3H)

(d) Synthesis of N-(3-chloro-5-((4-chlorophenyl) (methyl)amino)phenyl)-5-(methylsulfonamido)benzo[b]thiophene-2-carboxamide The synthesis procedure of Example 1 was repeated except for using 5-chloro-N$^1$-(4-chlorophenyl)-N$^1$-methylbenzene-1,3-diamine (29.5 mg, 0.11 mmol) to obtain N-(3-chloro-5-((4-chlorophenyl)(methyl)amino)phenyl)-5-(methylsulfonamido)benzo[b]thiophene-2-carboxamide (19.7 mg, 35%).

LC/MS ESI (+): 520 (M+1)

$^1$H-NMR (400MHz, DMSO-d$_6$): δ 10.44 (s, 1H), 9.87 (brs, 1H), 8.26 (s, 1H), 8.01 (d, 1H, J=8.7Hz), 7.79 (d, 1H, J=1.9Hz), 7.52 (m, 1H), 7.42 (d, 2H, J=8.8Hz), 7.35 (dd, 1H, J=8.7, 2.1Hz), 7.24 (m, 1H), 7.19 (d, 2H, J=8.8Hz), 6.72 (m, 1H), 3.27 (s, 3H), 3.01 (s, 3H)

Through the synthetic method according to Example 440, compounds of Example 441 and Example 442 were synthesized, and the data of each example are as follows.

TABLE 33

| Ex. | Compound | Analysis data |
| --- | --- | --- |
| 441 | 6-chloro-N-(3-chloro-5-((4-chlorophenyl)(methyl)amino)phenyl)-5-(methylsulfonamido)benzo[b]thiophene-2-carboxamide | LC/MS ESI (+): 554 (M + 1)<br>$^1$H-NMR (400 MHz, DMSO-d$_6$): δ 10.53 (s, 1H),<br>9.62 (s, 1H), 8.34 (s, 1H), 8.27 (s, 1H), 8.03 (s, 1H),<br>7.51 (s, 1H), 7.42 (d, 2H, J = 8.7 Hz), 7.18~7.22 (m, 3H),<br>6.73 (s, 1H), 3.27 (s, 3H), 3.06 (s, 3H) |
| 442 | 6-chloro-N-(3-chloro-5-((2,4-difluorophenyl)(methyl)amino)phenyl)-5-(methylsulfonamido)benzo[b]thiophene-2-carboxamide | LC/MS ESI (+): 556 (M + 1)<br>$^1$H-NMR (400 MHz, DMSO-d$_6$): δ 10.46 (s, 1H),<br>9.61 (s, 1H), 8.33 (s, 1H), 8.25 (s, 1H), 8.02 (s, 1H),<br>7.41~7.52 (m, 3H), 7.21 (m, 1H), 6.90 (s, 1H),<br>6.48 (s, 1H), 3.22 (s, 3H), 3.05 (s, 3H) |

Example 443

Synthesis of N-(3-chloro-5-((3-isopropoxy-5-(trifluoromethoxy)phenyl)(methyl)amino)phenyl)-5-(methylsulfonamido)benzo[b]thiophene-2-carboxamide (a) Synthesis of 3-isopropoxy-N-methyl-5-(trifluoromethoxy)aniline 1-Bromo-3-isopropoxy-5-(trifluoromethoxy)benzene (300.0 mg, 1.00 mmol) and 2.0 M solution of methylamine in THF (7.5 mL, 15.0 mmol) were added to toluene (5.0 mL), and Pd$_2$(dba)$_3$·CHCl$_3$ (51.9 mg, 0.05 mmol), BINAP (93.7 mg, 0.15 mmol) and Cs$_2$CO$_3$ (490.2 mg, 1.51 mmol) were added, followed by stirring at 100° C. for 16 hours. After cooling to room temperature, the reaction mixture was extracted with EtOAc, washed with brine, dried over anhydrous Na$_2$SO$_4$, concentrated under reduced pressure. The residue was purified by flash column chromatography (silica gel, n-Hex:EtOAc=9:1) to obtain 3-isopropoxy-N-methyl-5-(trifluoromethoxy)aniline (120.9 mg, 48%) as a yellow solid.

LC/MS ESI (+): 250 (M+1)

$^1$H-NMR (400MHz, CDCl$_3$): δ 6.11 (s, 1H), 6.03-6.04 (m, 2H), 4.48 (m, 1H), 3.82 (s, 1H), 2.81 (d, 3H, J=4.3Hz), 1.32 (d, 6H, J=6.0Hz)

(b) Synthesis of 3-chloro-N-(3-isopropoxy-5-(trifluoromethoxy)phenyl)-N-methyl-5-nitroaniline 3-Isopropoxy-N-methyl-5-(trifluoromethoxy)aniline (120.9 mg, 0.49 mmol) and 1-bromo-3-chloro-5-nitrobenzene (137.6 mg, 0.58 mmol) were added to toluene (2.4 mL), and Pd$_2$(dba)$_3$·CHCl$_3$ (25.1 mg, 0.02 mmol), BINAP (30.2 mg, 0.05 mmol) and NaOt-Bu (65.3 mg, 0.68 mmol) were added, followed by stirring at 110° C. for 40 minutes by using a microwave. The reaction mixture was cooled to room temperature, extracted with EtOAc, washed with brine, dried over anhydrous Na$_2$SO$_4$, concentrated under reduced pressure. The residue was purified by flash column chromatography (silica gel, n-Hex:EtOAc=9:1) to obtain 3-chloro-N-(3-isopropoxy-5-(trifluoromethoxy)phenyl)-N-methyl-5-nitroaniline (151.3 mg, 77%) as a yellow liquid.

LC/MS ESI (+): 405 (M+1)

$^1$H-NMR (400MHz, CDCl$_3$): δ 7.66 (s, 1H), 7.59 (s, 1H), 7.11 (s, 1H), 6.55-6.60 (m, 3H), 4.50 (m, 1H), 3.35 (s, 3H), 1.35 (d, 6H, J=6.0Hz)

(c) Synthesis of 5-chloro-N$^1$-(3-isopropoxy-5-(trifluoromethoxy)phenyl)-N$^1$-methylbenzene-1,3-diamine The synthesis procedure of Intermediate 40 was repeated except for using 3-chloro-N-(3-isopropoxy-5-(trifluoromethoxy)phenyl)-N-methyl-5-nitroaniline (151.3 mg, 0.37 mmol) to obtain 5-chloro-N$^1$-(3-isopropoxy-5-(trifluoromethoxy)phenyl)-N$^1$-methylbenzene-1,3-diamine (123.7 mg, 88%) as a brown liquid.

LC/MS ESI (+): 375 (M+1)

$^1$H-NMR (400MHz, CDCl$_3$): δ 6.45 (s, 1H), 6.37-6.40 (m, 2H), 6.36 (s, 1H), 6.33 (s, 1H), 6.24 (s, 1H), 4.46 (m, 1H), 3.69 (s, 2H), 3.29 (s, 3H), 1.31 (d, 6H, J=6.0Hz)

(d) Synthesis of N-(3-chloro-5-((3-isopropoxy-5-(trifluoromethoxy)phenyl)(methyl)amino)phenyl)-5-(methylsulfonamido)benzo[b]thiophene-2-carboxamide The synthesis procedure of Example 1 was repeated except for using 5-chloro-N$^1$-(3-isopropoxy-5-(trifluoromethoxy)phenyl)-N$^1$-methylbenz ene-1,3-diamine (40.0 mg, 0.11 mmol) to obtain N-(3-chloro-5-((3-isopropoxy-5-(trifluoromethoxy)phenyl)(methyl)amino)phenyl)-5-(methylsulfonamido)benzo[b]thiophene-2-carboxamide (25.4 mg, 38%).

LC/MS ESI (+): 628 (M+1)

$^1$H-NMR (400MHz, DMSO-d$_6$): δ 10.51 (s, 1H), 9.87 (brs, 1H), 8.27 (s, 1H), 8.01 (d, 1H, J=8.7Hz), 7.79 (m, 1H), 7.64 (s, 1H), 7.44 (s, 1H), 7.36 (dd, 1H, J=8.8, 1.7Hz), 6.90 (s, 1H), 6.52-6.55 (m, 3H), 4.61 (m, 1H), 3.29 (s, 3H), 3.01 (s, 3H), 1.25 (d, 6H, J=6.0Hz)

Example 444

Synthesis of N-(3-chloro-5-(2,4-difluorophenoxy)phenyl)-5-(methylsulfonamido)benzo[b]thiophene-2-carboxamide

(a) Synthesis of 1-(3-chloro-5-nitrophenoxy)-2,4-difluorobenzene

1-Bromo-3-chloro-5-nitrobenzene (100.0 mg, 0.42 mmol), 2,4-difluorophenol (40.4 μL, 0.42 mmol), CuI (40.3 mg, 0.21 mmol), N,N-dimethylglycine (43.6 mg, 0.42 mmol) and $Cs_2CO_3$ (413.5 mg, 1.27 mmol) were added to anhydrous 1,4-dioxane (2.1 mL). The reaction was performed in a microwave with 100 W, at 90° C. for 1 hour, and the reaction mixture was cooled to room temperature. Water was added, followed by extracting with EtOAc. The organic extract was washed with brine, dried over anhydrous $Na_2SO_4$, concentrated under reduced pressure. The residue was purified by flash column chromatography (silica gel, n-Hex:EtOAc=9:1) to obtain 1-(3-chloro-5-nitrophenoxy)-2,4-difluorobenzene (31.1 mg, 26%) as a yellow oil.

$^1$H-NMR (400MHz, $CDCl_3$): δ 7.93 (m, 1H), 7.61 (m, 1H), 7.24 (m, 1H), 7.18 (m, 1H), 6.94-7.05 (m, 2H)

(b) Synthesis of 3-chloro-5-(2,4-difluorophenoxy)aniline

The synthesis procedure of Intermediate 40 was repeated except for using 1-(3-chloro-5-nitrophenoxy)-2,4-difluorobenzene (31.1 mg, 0.11 mmol) to obtain 3-chloro-5-(2,4-difluorophenoxy)aniline (22.3 mg, 80%) as a yellowish brown oil.

LC/MS ESI (+): 256 (M+1)

$^1$H-NMR (400MHz, $CDCl_3$): δ 7.09 (m, 1H), 6.95 (m, 1H), 6.87 (m, 1H), 6.39 (m, 1H), 6.27 (m, 1H), 6.13 (m, 1H), 3.76 (s, 2H)

(c) Synthesis of N-(3-chloro-5-(2,4-difluorophenoxy)phenyl)-5-(methylsulfonamido)benzo[b]thiophene-2-carboxamide The synthesis procedure of Example 1 was repeated except for using 3-chloro-5-(2,4-difluorophenoxy)aniline (22.3 mg, 0.08 mmol) to obtain N-(3-chloro-5-(2,4-difluorophenoxy)phenyl)-5-(methylsulfonamido)benzo[b]thiophene-2-carboxamide (11.5 mg, 27%) as a white solid.

LC/MS ESI (+): 509 (M+1)

$^1$H-NMR (400MHz, DMSO-$d_6$): δ 10.57 (s, 1H), 9.87 (brs, 1H), 8.24 (s, 1H), 7.99 (d, 1H, J=8.7Hz), 7.77 (s, 1H), 7.73 (s, 1H), 7.56 (m, 1H), 7.45 (m, 1H), 7.34 (d, 1H, J=8.7Hz), 7.30 (s, 1H), 7.21 (m, 1H), 6.89 (s, 1H), 2.98 (s, 3H)

Through the synthetic method according to Example 444, compounds from Example 445 to Example 485 were synthesized, and the data of each example are as follows.

TABLE 34

| Ex. | Compound | Analysis data |
|---|---|---|
| 445 | N-(3-chloro-5-(4-chlorophenoxy)phenyl)-5-(methylsulfonamido)benzo[b]thiophene-2-carboxamide | LC/MS ESI (+): 507 (M + 1)<br>$^1$H-NMR (400 MHz, DMSO-$d_6$): δ 10.54 (s, 1H), 9.80 (s, 1H), 8.20 (s, 1H), 7.95 (d, 1H, J = 8.7 Hz), 7.73 (s, 1H), 7.69 (s, 1H), 7.44 (d, 2H, J = 8.9 Hz), 7.28~7.31 (m, 2H), 7.11 (d, 2H, J = 8.9 Hz), 6.85 (s, 1H), 2.95 (s, 3H) |
| 446 | N-(3-chloro-5-(4-fluorophenoxy)phenyl)-5-(methylsulfonamido)benzo[b]thiophene-2-carboxamide | LC/MS ESI (+): 491 (M + 1)<br>$^1$H-NMR (400 MHz, DMSO-$d_6$):<br>δ 10.58 (s, 1H), 9.87 (brs, 1H), 8.26 (s, 1H), 8.01 (d, 1H, J = 8.8 Hz), 7.79 (m, 1H), 7.72 (s, 1H), 7.36 (dd, 1H, J = 8.7, 2.0 Hz), 7.28~7.33 (m, 3H), 7.19~7.22 (m, 2H), 6.86 (m, 1H), 3.01 (s, 3H) |
| 447 | N-(3-chloro-5-(4-methoxyphenoxy)phenyl)-5-(methylsulfonamido)benzo[b]thiophene-2-carboxamide | LC/MS ESI (+): 503 (M + 1)<br>$^1$H-NMR (400 MHz, DMSO-$d_6$): δ 10.56 (s, 1H), 9.86 (brs, 1H), 8.26 (s, 1H), 8.01 (d, 1H, J = 8.7 Hz), 7.78 (d, 1H, J = 1.9 Hz), 7.69 (m, 1H), 7.35 (dd, 1H, J = 8.7, 2.1 Hz), 7.27 (m, 1H), 7.11 (d, 2H, J = 9.1 Hz), 7.02 (d, 2H, J = 9.1 Hz), 6.78 (m, 1H), 3.78 (s, 3H), 3.00 (s, 3H) |
| 448 | N-(3-chloro-5-(2,5-difluorophenoxy)phenyl)-5-(methylsulfonamido)benzo[b]thiophene-2-carboxamide | LC/MS ESI (+): 509 (M + 1)<br>$^1$H-NMR (400 MHz, DMSO-$d_6$): δ 10.61 (s, 1H), 9.86 (brs, 1H), 8.26 (s, 1H), 8.01 (d, 1H, J = 8.7 Hz), 7.79 (d, 1H, J = 1.9 Hz), 7.76 (m, 1H), 7.53 (m, 1H), 7.32~7.37 (m, 3H), 7.20 (m, 1H), 6.96 (m, 1H), 3.00 (s, 3H) |
| 449 | 6-chloro-N-(3-chloro-5-(4-chlorophenoxy)phenyl)-5-(methylsulfonamido)benzo[b]thiophene-2-carboxamide | LC/MS ESI (+): 541 (M + 1)<br>$^1$H-NMR (400 MHz, DMSO-$d_6$): δ 10.69 (s, 1H), 9.63 (s, 1H), 8.31 (s, 1H), 8.26 (s, 1H), 8.01 (s, 1H), 7.75 (s, 1H), 7.51 (d, 2H, J = 8.8 Hz), 7.34 (s, 1H), 7.17 (d, 2H, J = 8.8 Hz), 6.92 (s, 1H), 3.03 (s, 3H) |
| 450 | N-(3-chloro-5-(3-(trifluoromethoxy)phenoxy)phenyl)-5-(methylsulfonamido)benzo[b]thiophene-2-carboxamide | LC/MS ESI (+): 557 (M + 1)<br>$^1$H-NMR (400 MHz, DMSO-$d_6$): δ 10.65 (s, 1H), 9.88 (brs, 1H), 8.28 (s, 1H), 8.02 (d, 1H, J = 8.8 Hz), 7.80 (s, 2H), 7.60 (t, 1H, J = 8.0 Hz), 7.45 (s, 1H), 7.37 (d, 1H, J = 8.8 Hz), 7.25 (d, 1H, J = 8.8 Hz), 7.20 (s, 1H), 7.17 (d, 1H, J = 8.4 Hz), 6.99 (s, 1H), 3.01 (s, 3H) |
| 451 | N-(3-chloro-5-(4-cyanophenoxy)phenyl)-5-(methylsulfonamido)benzo[b]thiophene-2-carboxamide | LC/MS ESI (+): 498 (M + 1)<br>$^1$H-NMR (400 MHz, DMSO-$d_6$): δ 10.60 (s, 1H), 9.80 (brs, 1H), 8.21 (s, 1H), 7.95 (d, 1H, J = 8.8 Hz), 7.85 (d, 2H, J = 8.8 Hz), 7.74 (d, 2H, J = 5.6 Hz), 7.43 (s, 1H), 7.29 (d, 1H, J = 8.8 Hz), 7.19 (d, 2H, J = 8.4 Hz), 7.00 (s, 1H), 2.94 (s, 3H) |

TABLE 34-continued

| Ex. | Compound | Analysis data |
|---|---|---|
| 452 | N-(3-chloro-5-(3-isopropoxy-5-(trifluoromethoxy)phenoxy)phenyl)-5-(methylsulfonamido)benzo[b]thiophene-2-carboxamide | LC/MS ESI (+): 615 (M + 1)<br>$^1$H-NMR (400 MHz, DMSO-d$_6$): δ 10.64 (s, 1H), 9.87 (brs, 1H), 8.27 (s, 1H), 8.02 (d, 1H, J = 8.7 Hz), 7.79~7.80 (m, 2H), 7.43 (s, 1H), 7.36 (dd, 1H, J = 8.7, 1.9 Hz), 6.97 (s, 1H), 6.76 (s, 1H), 6.69 (m, 1H), 6.66 (s, 1H), 4.68 (m, 1H). 3.01 (s, 3H), 1.26 (d, 6H, J = 6.0 Hz) |
| 453 | 6-bromo-N-(3-chloro-5-(4-chlorophenoxy)phenyl)-5-(methylsulfonamido)benzo[b]thiophene-2-carboxamide | LC/MS ESI (+): 585 (M + 1)<br>$^1$H-NMR (400 MHz, DMSO-d$_6$): δ 10.64 (s, 1H), 9.49 (s, 1H), 8.42 (s, 1H), 8.19 (s, 1H), 7.96 (s, 1H), 7.68 (s, 1H), 7.44 (d, 2H, J = 8.8 Hz), 7.28 (s, 1H), 7.11 (d, 2H, J = 8.8 Hz), 6.86 (s, 1H), 2.99 (s, 3H) |
| 454 | N-(3-chloro-5-(4-(trifluoromethoxy)phenoxy)phenyl)-5-(methylsulfonamido)benzo[b]thiophene-2-carboxamide | LC/MS ESI (+): 557 (M + 1)<br>$^1$H-NMR (400 MHz, DMSO-d$_6$): δ 10.62 (s, 1H), 9.93 (brs, 1H), 8.26 (s, 1H), 7.99 (d, 1H, J = 8.8 Hz), 7.77~7.80 (m, 2H), 7.47 (d, 2H, J = 8.8 Hz), 7.41 (s, 1H), 7.35 (d, 1H, J = 8.4 Hz), 7.26 (d, 2H, J = 8.8 Hz), 6.96 (s, 1H), 2.99 (s, 3H) |
| 455 | N-(3-chloro-5-(3-(trifluoromethyl)phenoxy)phenyl)-5-(methylsulfonamido)benzo[b]thiophene-2-carboxamide | LC/MS ESI (+): 541 (M + 1)<br>$^1$H-NMR (400 MHz, DMSO-d$_6$): δ 10.64 (s, 1H), 9.86 (brs, 1H), 8.27 (s, 1H), 8.02 (d, 1H, J = 8.7 Hz), 7.79 (m, 1H), 7.78 (m, 1H), 7.69 (t, 1H, J = 7.9 Hz), 7.59 (d, 1H, J = 7.8 Hz), 7.49 (s, 1H), 7.40~7.44 (m, 2H), 7.36 (dd, 1H, J = 8.7, 2.0 Hz), 6.98 (s, 1H), 3.01 (s, 3H) |
| 456 | N-(3-chloro-5-(3-chlorophenoxy)phenyl)-5-(methylsulfonamido)benzo[b]thiophene-2-carboxamide | LC/MS ESI (+): 507 (M + 1)<br>$^1$H-NMR (400 MHz, DMSO-d$_6$): δ 10.63 (s, 1H), 9.93 (brs, 1H), 8.27 (s, 1H), 8.01 (d, 1H, J = 8.0 Hz), 7.79 (s, 2H), 7.49 (t, 1H, J = 8.0 Hz), 7.40 (s, 1H), 7.31~7.37 (m, 2H), 7.26 (s, 1H), 7.13 (dd, 1H, J = 8.0, 4.0 Hz), 6.97 (s, 1H), 3.00 (s, 3H) |
| 457 | N-(3-chloro-5-(3-methoxyphenoxy)phenyl)-5-(methylsulfonamido)benzo[b]thiophene-2-carboxamide | LC/MS ESI (+): 503 (M + 1)<br>$^1$H-NMR (400 MHz, DMSO-d$_6$): δ 10.61 (s, 1H), 9.88 (brs, 1H), 8.29 (s, 1H), 8.03 (d, 1H, J = 8.4 Hz), 7.80 (s, 1H), 7.75 (s, 1H), 7.35~7.39 (m, 3H), 6.89 (s, 1H), 6.83 (dd, 1H, J = 8.0, 2.0 Hz), 6.73 (s, 1H), 6.69 (dd, 1H, J = 8.0, 2.0 Hz), 3.78 (s, 3H), 3.02 (s, 3H) |
| 458 | N-(3-chloro-5-(3-chloro-5-cyanophenoxy)phenyl)-5-(methylsulfonamido)benzo[b]thiophene-2-carboxamide | LC/MS ESI (+): 532 (M + 1)<br>$^1$H-NMR (400 MHz, DMSO-d$_6$): δ 10.67 (s, 1H), 9.89 (brs, 1H), 8.29 (s, 1H), 8.04 (d, 1H, J = 8.8 Hz), 7.92 (s, 1H), 7.82~7.83 (m, 2H), 7.71 (s, 1H), 7.66 (t, 1H, J = 2.0 Hz), 7.44 (s, 1H), 7.37 (dd, 1H, J = 8.8, 2.0 Hz), 7.06 (s, 1H), 3.03 (s, 3H) |
| 459 | N-(3-chloro-5-(3-cyanophenoxy)phenyl)-5-(methylsulfonamido)benzo[b]thiophene-2-carboxamide | LC/MS ESI (+): 498 (M + 1)<br>$^1$H-NMR (400 MHz, DMSO-d$_6$): δ 10.65 (s, 1H), 9.88 (brs, 1H), 8.29 (s, 1H), 8.04 (d, 1H, J = 8.8 Hz), 7.80~7.81 (m, 2H), 7.65~7.73 (m, 3H), 7.49~7.52 (m, 1H), 7.41 (t, 1H, J = 2.0 Hz), 7.38 (dd, 1H, J = 8.8, 2.0 Hz), 7.00 (s, 1H), 3.03 (s, 3H) |
| 460 | N-(3-chloro-5-(3,4-difluorophenoxy)phenyl)-5-(methylsulfonamido)benzo[b]thiophene-2-carboxamide | LC/MS ESI (+): 509 (M + 1)<br>$^1$H-NMR (400 MHz, DMSO-d$_6$): δ 10.60 (s, 1H), 9.89 (brs, 1H), 8.27 (s, 1H), 8.01 (d, 1H, J = 8.7 Hz), 7.79 (d, 1H, J = 2.0 Hz), 7.76 (m, 1H), 7.54 (m, 1H), 7.34~7.42 (m, 3H), 7.02 (m, 1H), 6.92 (m, 1H), 3.00 (s, 3H) |
| 461 | N-(3-chloro-5-(3-chloro-4-fluorophenoxy)phenyl)-5-(methylsulfonamido)benzo[b]thiophene-2-carboxamide | LC/MS ESI (+): 525 (M + 1)<br>$^1$H-NMR (400 MHz, DMSO-d$_6$): δ 10.60 (s, 1H), 9.89 (brs, 1H), 8.26 (s, 1H), 8.01 (d, 1H, J = 8.7 Hz), 7.79 (d, 1H, J = 2.0 Hz), 7.76 (m, 1H), 7.48~7.54 (m, 2H), 7.33~7.37 (m, 2H), 7.20 (m, 1H), 6.93 (m, 1H), 3.00 (s, 3H) |
| 462 | N-(3-chloro-5-(2,4-dichlorophenoxy)phenyl)-5-(methylsulfonamido)benzo[b]thiophene-2-carboxamide | LC/MS ESI (+): 541 (M + 1)<br>$^1$H-NMR (400 MHz, DMSO-d$_6$): δ 10.58 (s, 1 H), 9.90 (brs, 1H), 8.25 (s, 1H), 8.00 (d, 1H, J = 8.7 Hz), 7.86 (d, 1H, J = 2.5 Hz), 7.76~7.78 (m, 2H), 7.53 (dd, 1H, J = 8.7, 2.5 Hz), 7.33~7.36 (m, 2H), 7.25 (m, 1H), 6.92 (m, 1H), 2.99 (s, 3H) |
| 463 | N-(3-chloro-5-(3,5-difluorophenoxy)phenyl)-5-(methylsulfonamido)benzo[b]thiophene-2-carboxamide | LC/MS ESI (+): 509 (M + 1)<br>$^1$H-NMR (400 MHz, DMSO-d$_6$): δ 10.64 (s, 1H), 9.89 (brs, 1H), 8.28 (s, 1H), 8.01 (d, 1H, J = 8.8 Hz), 7.79~7.81 (m, 2H), 7.45 (m, 1H), 7.35 (dd, 1H, J = 8.7, 2.1 Hz), 7.11 (tt, 1H, J = 9.4, 2.3 Hz), 7.02 (m, 1H), 6.90~6.97 (m, 2H), 3.00 (s, 3H) |
| 464 | N-(3-chloro-5-(3,5-dichlorophenoxy)phenyl)-5-(methylsulfonamido)benzo[b]thiophene-2-carboxamide | LC/MS ESI (+): 541 (M + 1)<br>$^1$H-NMR (400 MHz, DMSO-d$_6$): δ 10.65 (s, 1H), 9.89 (brs, 1H), 8.28 (s, 1H), 8.02 (d, 1H, J = 8.8 Hz), 7.80~7.82 (m, 2H), 7.48 (m, 1H), 7.41 (m, 1H), 7.36 (dd, 1H, J = 8.7, 2.1 Hz), 7.26 (d, 2H, J = 1.8 Hz), 7.03 (m, 1H), 3.01 (s, 3H) |

TABLE 34-continued

| Ex. | Compound | Analysis data |
|---|---|---|
| 465 | N-(3-chloro-5-(4-(trifluoromethyl)phenoxy)phenyl)-5-(methylsulfonamido)benzo[b]thiophene-2-carboxamide | LC/MS ESI (+): 541 (M + 1)<br>$^1$H-NMR (400 MHz, DMSO-$d_6$): δ 10.64 (s, 1H), 9.89 (brs, 1H), 8.27 (s, 1H), 8.01 (d, 1H, J = 8.8 Hz), 7.79~7.82 (m, 4H), 7.46 (s, 1H), 7.35 (dd, 1H, J = 8.7, 2.0 Hz), 7.29 (d, 2H, J = 8.6 Hz), 7.05 (s, 1H), 3.00 (s, 3H) |
| 466 | N-(3-chloro-5-(4-chloro-3-fluorophenoxy)phenyl)-5-(methylsulfonamido)benzo[b]thiophene-2-carboxamide | LC/MS ESI (+): 525 (M + 1)<br>$^1$H-NMR (400 MHz, DMSO-$d_6$): δ 10.63 (s, 1H), 9.89 (brs, 1H), 8.27 (s, 1H), 8.02 (d, 1H, J = 8.8 Hz), 7.78~7.80 (m, 2H), 7.66 (t, 1H, J = 8.7 Hz), 7.40 (m, 1H), 7.33~7.37 (m, 2H), 7.02 (m, 1H), 6.99 (m, 1H), 3.01 (s, 3H) |
| 467 | N-(3-chloro-5-(3-chloro-5-(trifluoromethoxy)phenoxy)phenyl)-5-(methylsulfonamido)benzo[b]thiophene-2-carboxamide | LC/MS ESI (+): 591 (M + 1)<br>$^1$H-NMR (400 MHz, DMSO-$d_6$): δ 10.66 (s, 1H), 9.89 (brs, 1H), 8.28 (s, 1H), 8.02 (d, 1H, J = 8.7 Hz), 7.80~7.82 (m, 2H), 7.46 (m, 1H), 7.42 (m, 1H), 7.36 (dd, 1H, J = 8.7, 2.1 Hz), 7.30 (m, 1H), 7.21 (m, 1H), 7.05 (m, 1H), 3.01 (s, 3H) |
| 468 | N-(3-chloro-5-(4-chloro-3-(trifluoromethoxy)phenoxy)phenyl)-5-(methylsulfonamido)benzo[b]thiophene-2-carboxamide | LC/MS ESI (+): 591 (M + 1)<br>$^1$H-NMR (400 MHz, DMSO-$d_6$): δ 10.57 (s, 1H), 9.88 (brs, 1H), 8.20 (s, 1H), 7.94 (d, 1H, J = 8.7 Hz), 7.72~7.73 (m, 2H), 7.69 (d, 1H, J = 8.9 Hz), 7.36~7.37 (m, 2H), 7.28 (dd, 1H, J = 8.7, 2.1 Hz), 7.14 (dd, 1H, J = 8.9, 2.8 Hz), 6.95 (s, 1H), 2.93 (s, 3H) |
| 469 | N-(3-chloro-5-(3-chloro-5-fluorophenoxy)phenyl)-5-(methylsulfonamido)benzo[b]thiophene-2-carboxamide | LC/MS ESI (+): 525 (M + 1)<br>$^1$H-NMR (400 MHz, DMSO-$d_6$): δ 10.66 (s, 1H), 9.90 (brs, 1H), 8.29 (s, 1H), 8.02 (m, 1H), 7.82 (s, 1H), 7.80 (m, 1H), 7.44 (s, 1H), 7.31~7.38 (m, 2H), 7.09~7.12 (m, 2H), 7.04 (s, 1H), 3.01 (s, 3H) |
| 470 | N-(3-chloro-5-(4-fluoro-3-(trifluoromethoxy)phenoxy)phenyl)-5-(methylsulfonamido)benzo[b]thiophene-2-carboxamide | LC/MS ESI (+): 575 (M + 1)<br>$^1$H-NMR (400 MHz, DMSO-$d_6$): δ 10.63 (s, 1H), 9.89 (brs, 1H), 8.28 (s, 1H), 8.03 (d, 1H, J = 9.2 Hz), 7.81 (s, 1H), 7.78 (s, 1H), 7.63 (t, 1H, J = 9.2 Hz), 7.51 (m, 1H), 7.40 (s, 1H), 7.37 (dd, 1H, J = 8.8, 2.0 Hz), 7.27 (m, 1H), 6.96 (s, 1H), 3.02 (s, 3H) |
| 471 | 6-chloro-N-(3-chloro-5-(thiazol-2-yloxy)phenyl)-5-(methylsulfonamido)benzo[b]thiophene-2-carboxamide | LC/MS ESI (+): 514 (M + 1)<br>$^1$H-NMR (400 MHz, DMSO-$d_6$): δ 10.76 (s, 1H), 9.67 (s, 1H), 8.27 (s, 1H), 8.24 (s, 1H), 7.98 (s, 1H), 7.78 (s, 1H), 7.67 (s, 1H), 7.28~7.31 (m, 2H), 7.21 (s, 1H), 2.98 (s, 3H) |
| 472 | 6-chloro-N-(3-chloro-5-(thiazol-5-yloxy)phenyl)-5-(methylsulfonamido)benzo[b]thiophene-2-carboxamide | LC/MS ESI (+): 514 (M + 1)<br>$^1$H-NMR (400 MHz, DMSO-$d_6$): δ 10.70 (s, 1H), 9.58 (s, 1H), 8.81 (s, 1H), 8.28 (s, 1H), 8.22 (s, 1H), 7.97 (s, 1H), 7.72 (s, 1H), 7.69 (s, 1H), 7.45 (s, 1H), 6.99 (s, 1H), 2.98 (s, 3H) |
| 473 | 6-chloro-N-(3-chloro-5-((5-chlorothiophen-2-yl)oxy)phenyl)-5-(methylsulfonamido)benzo[b]thiophene-2-carboxamide | LC/MS ESI (+): 547 (M + 1)<br>$^1$H-NMR (400 MHz, DMSO-$d_6$): δ 10.77 (s, 1H), 9.67 (brs, 1H), 8.32 (s, 1H), 8.28 (s, 1H), 8.02 (s, 1H), 7.79 (s, 1H), 7.54 (s, 1H), 7.04 (d, 1H, J = 4.1 Hz), 7.03 (s, 1H), 6.77 (d, 1H, J = 4.1 Hz), 3.03 (s, 3H) |
| 474 | 6-chloro-N-(3-chloro-5-(3-chloro-5-methoxyphenoxy)phenyl)-5-(methylsulfonamido)benzo[b]thiophene-2-carboxamide | LC/MS ESI (+): 571 (M + 1)<br>$^1$H-NMR (400 MHz, DMSO-$d_6$): δ 10.73 (s, 1H), 9.63 (brs, 1H), 8.36 (s, 1H), 8.29 (s, 1H), 8.05 (s, 1H), 7.78 (m, 1H), 7.37 (m, 1H), 6.96 (m, 1H), 6.92 (m, 1H), 6.77 (m, 1H), 6.71 (m, 1H), 3.79 (s, 3H), 3.06 (s, 3H) |
| 475 | 6-chloro-N-(3-chloro-5-(3-chloro-5-hydroxyphenoxy)phenyl)-5-(methylsulfonamido)benzo[b]thiophene-2-carboxamide | LC/MS ESI (+): 557 (M + 1)<br>$^1$H-NMR (400 MHz, DMSO-$d_6$): δ 10.66 (s, 1H), 10.24 (s, 1H), 8.20~8.24 (m, 2H), 7.95 (s, 1H), 7.78 (m, 1H), 7.37 (m, 1H), 6.96 (m, 1H), 6.66 (m, 1H), 6.43 (m, 1H), 2.94 (s, 3H) |
| 476 | 6-chloro-N-(3-chloro-5-(3-chloro-4-fluorophenoxy)phenyl)-5-(methylsulfonamido)benzo[b]thiophene-2-carboxamide | LC/MS ESI (+): 559 (M + 1)<br>$^1$H-NMR (400 MHz, DMSO-$d_6$): δ 10.70 (s, 1H), 9.64 (s, 1H), 8.34 (s, 1H), 8.28 (s, 1H), 8.04 (s, 1H), 7.76 (m, 1H), 7.49~7.54 (m, 2H), 7.32 (m, 1H), 7.20 (m, 1H), 6.94 (m, 1H), 3.05 (s, 3H) |
| 477 | 6-chloro-N-(3-chloro-5-(4-chloro-3-fluorophenoxy)phenyl)-5-(methylsulfonamido)benzo[b]thiophene-2-carboxamide | LC/MS ESI (+): 559 (M + 1)<br>$^1$H-NMR (400 MHz, DMSO-$d_6$): δ 10.73 (s, 1H), 9.65 (s, 1H), 8.35 (s, 1H), 8.28 (s, 1H), 8.04 (s, 1H), 7.78 (m, 1H), 7.66 (t, 1H, J = 8.7 Hz), 7.39 (m, 1H), 7.35 (dd, 1H, J = 10.4, 2.7 Hz), 7.00~7.04 (m, 2H), 3.05 (s, 3H) |
| 478 | 6-chloro-N-(3-chloro-5-(4-fluorophenoxy)phenyl)-5-(methylsulfonamido)benzo[b]thiophene-2-carboxamide | LC/MS ESI (+): 525 (M + 1)<br>$^1$H-NMR (400 MHz, DMSO-$d_6$): δ 10.62 (s, 1H), 9.57 (brs, 1H), 8.28 (s, 1H), 8.21 (s, 1H), 7.97 (s, 1H), 7.66 (s, 1H), 7.22~7.26 (m, 3H), 7.12~7.16 (m, 2H), 6.80 (s, 1H), 2.98 (s, 3H) |

TABLE 34-continued

| Ex. | Compound | Analysis data |
|---|---|---|
| 479 | 6-chloro-N-(3-chloro-5-(3-(trifluoromethoxy)phenoxy)phenyl)-5-(methylsulfonamido)benzo[b]thiophene-2-carboxamide | LC/MS ESI (+): 591 (M + 1)<br>$^1$H-NMR (400 MHz, DMSO-$d_6$): δ 10.68 (s, 1H), 9.58 (brs, 1H), 8.28 (s, 1H), 8.21 (s, 1H), 7.97 (s, 1H), 7.72 (s, 1H), 7.50 (t, 1H, J = 8.0 Hz), 7.35 (s, 1H), 7.08~7.18 (m, 3H), 6.92 (s, 1H), 2.98 (s, 3H) |
| 480 | 6-chloro-N-(3-chloro-5-(4-(trifluoromethoxy)phenoxy)phenyl)-5-(methylsulfonamido)benzo[b]thiophene-2-carboxamide | LC/MS ESI (+): 591 (M + 1)<br>$^1$H-NMR (400 MHz, DMSO-$d_6$): δ 10.73 (s, 1H), 9.69 (brs, 1H), 8.32 (s, 1H), 8.27 (s, 1H), 8.02 (s, 1H), 7.78 (s, 1H), 7.46 (d, 2H, J = 8.7 Hz), 7.37 (s, 1H), 7.25 (d, 2H, J = 9.0 Hz), 6.96 (s, 1H), 3.03 (s, 3H) |
| 481 | 6-chloro-N-(3-chloro-5-(3,4-difluorophenoxy)phenyl)-5-(methylsulfonamido)benzo[b]thiophene-2-carboxamide | LC/MS ESI (+): 543 (M + 1)<br>$^1$H-NMR (400 MHz, DMSO-$d_6$): δ 10.63 (s, 1H), 9.60 (brs, 1H), 8.25 (s, 1H), 8.20 (s, 1H), 7.95 (s, 1H), 7.69 (s, 1H), 7.48 (m, 1H), 7.35 (m, 1H), 7.28 (m, 1H), 6.96 (m, 1H), 6.87 (t, 1H, J = 1.9 Hz), 2.96 (s, 3H) |
| 482 | 6-chloro-N-(3-chloro-5-(4-(trifluoromethyl)phenoxy)phenyl)-5-(methylsulfonamido)benzo[b]thiophene-2-carboxamide | LC/MS ESI (+): 575 (M + 1)<br>$^1$H-NMR (400 MHz, DMSO-$d_6$): δ 10.77 (s, 1H), 9.67 (s, 1H), 8.35 (s, 1H), 8.28 (s, 1H), 8.04 (s, 1H), 7.80~7.82 (m, 3H), 7.44 (s, 1H), 7.30 (d, 2H, J = 8.3 Hz), 7.07 (s, 1H), 3.05 (s, 3H) |
| 483 | 6-chloro-N-(3-chloro-5-(3-chloro-5-fluorophenoxy)phenyl)-5-(methylsulfonamido)benzo[b]thiophene-2-carboxamide | LC/MS ESI (+): 559 (M + 1)<br>$^1$H-NMR (400 MHz, DMSO-$d_6$): δ 10.74 (s, 1H), 9.63 (brs, 1H), 8.33 (s, 1H), 8.28 (s, 1H), 8.03 (s, 1H), 7.80 (m, 1H), 7.42 (m, 1H), 7.31 (dt, 1H, J = 8.6, 2.0 Hz), 7.07~7.11 (m, 2H), 7.03 (m, 1H), 3.04 (s, 3H) |
| 484 | 6-chloro-N-(3-chloro-5-(3-fluoro-5-methoxyphenoxy)phenyl)-5-(methylsulfonamido)benzo[b]thiophene-2-carboxamide | LC/MS ESI (+): 555 (M + 1)<br>$^1$H-NMR (400 MHz, DMSO-$d_6$): δ 10.67 (s, 1H), 9.66 (brs, 1H), 8.24~8.26 (m, 2H), 7.98 (m, 1H), 7.77 (m, 1H), 7.39 (m, 1H), 6.95 (m, 1H), 6.72 (dt, 1H, J = 10.9, 2.2 Hz), 6.56~6.60 (m, 2H), 3.78 (s, 3H), 2.98 (s, 3H) |
| 485 | 5-chloro-N-(3-chloro-5-(4-chlorophenoxy)phenyl)-6-(methylsulfonamido)benzo[b]thiophene-2-carboxamide | LC/MS ESI (+): 541 (M + 1)<br>$^1$H-NMR (400 MHz, DMSO-$d_6$): δ 10.73 (s, 1H), 9.68 (s, 1H), 8.22~8.23 (m, 2H), 8.14 (s, 1H), 7.75 (m, 1H), 7.51 (d, 2H, J = 8.9 Hz), 7.35 (m, 1H), 7.18 (d, 2H, J = 8.9 Hz), 6.93 (m, 1H), 3.11 (s, 3H) |

Example 486

Synthesis of 6-chloro-N-(3-chloro-5-(cyclohexyloxy)phenyl)-5-(methylsulfonamido)benzo[b]thiophene-2-carboxamide (a) Synthesis of 1-chloro-3-(cyclohexyloxy)-5-nitrobenzene 3-Chloro-5-nitrophenol (50.0 mg, 0.29 mmol) was dissolved in anhydrous THF (2.9 mL), and cyclohexanol (58.0 mg, 0.58 mmol), 2.2 M solution of DEAD in toluene (0.3 mL, 0.58 mmol) and PPh$_3$ (152.0 mg, 0.58 mmol) were added at 0° C. The reaction mixture was stirred at room temperature for 15 hours, and the residue was extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain 1-chloro-3-(cyclohexyloxy)-5-nitrobenzene (45.0 mg, 61%) as a colorless liquid.

$^1$H-NMR (400MHz, CDCl$_3$): δ 7.76 (s, 1H), 7.62 (s, 1H), 7.19 (s, 1H), 4.33 (m, 1H), 1.95-1.99 (m, 2H), 1.79-1.82 (m, 2H), 1.55-1.61 (m, 2H), 1.37-1.47 (m, 4H)

(b) Synthesis of 3-chloro-5-(cyclohexyloxy)aniline

The synthesis procedure of Intermediate 40 was repeated except for using 1-chloro-3-(cyclohexyloxy)-5-nitrobenzene (45.0 mg, 0.18 mmol) to obtain 3-chloro-5-(cyclohexyloxy)aniline (22.0 mg, 55%) as a colorless liquid.

LC/MS ESI (+): 226 (M+1)

$^1$H-NMR (400MHz, CDCl$_3$): δ 6.31 (s, 1H), 6.26 (s, 1H), 6.10 (s, 1H), 4.15 (m, 1H), 3.67 (brs, 2H), 1.93-1.97 (m, 2H), 1.76-1.79 (m, 2H), 1.44-1.53 (m, 2H), 1.25-1.39 (m, 4H)

(c) Synthesis of 6-chloro-N-(3-chloro-5-(cyclohexyloxy)phenyl)-5-(methylsulfonamido)benzo[b]thiophene-2-carboxamide The synthesis procedure of Example 1 was repeated except for using 3-chloro-5-(cyclohexyloxy)aniline (33.0 mg, 0.11 mmol) to obtain 6-chloro-N-(3-chloro-5-(cyclohexyloxy)phenyl)-5-(methylsulfonamido)benzo[b]thiophene-2-carboxamide (8.0 mg, 18%).

LC/MS ESI (+): 513 (M+1)

$^1$H-NMR (400MHz, DMSO-$d_6$): δ 10.52 (s, 1H), 9.59 (brs, 1H), 8.25 (s, 1H), 8.22 (s, 1H), 7.96 (s, 1H), 7.41 (s, 1H), 7.28 (s, 1H), 6.73 (s, 1H), 4.28 (m, 1H), 2.96 (s, 3H), 1.84-1.89 (m, 2H), 1.63-1.68 (m, 2H), 1.21-1.49 (m, 6H)

Example 487

Synthesis of 6-chloro-N-(3-chloro-5-((5-methylthiophen-2-yl)oxy)phenyl)-5-(methylsulfonamido)benzo[b]thiophene-2-carboxamide (a) Synthesis of 5-(3-chloro-5-nitrophenoxy)thiophene-2-carbaldehyde 3-Chloro-5-nitrophenol (200.0 mg, 1.15 mmol) and 5-bromothiophene-2-carbaldehyde (136.0 μL, 0.32 mmol) were dissolved in DMSO (4.0 mL), and K$_2$CO$_3$ (318.4 mg, 2.30 mmol) was added, followed by stirring in a microwave at 90° C. for 3 hours. After cooling to room temperature, the reaction mixture was extracted with EtOAc, washed with brine, dried over anhydrous Na₂SO₄, concentrated under reduced pressure. The residue was purified by flash column chromatography (silica gel, n-Hex:EtOAc=5:1) to obtain 5-(3-chloro-5-nitrophenoxy)thiophene-2-carbaldehyde (130.0 mg, 40%) as a colorless liquid.

LC/MS ESI (+): 284 (M+1)

$^1$H-NMR (400MHz, CDCl$_3$): δ, 9.81 (s, 1H), 8.07 (s, 1H), 7.90 (s, 1H), 7.62 (d, 1H, J=4.0Hz), 7.49 (s, 1H), 6.71 (d, 1H, J=4.0Hz)

(b) Synthesis of 3-chloro-5-((5-methylthiophen-2-yl)oxy)aniline 5-(3-Chloro-5-nitrophenoxy)thiophene-2-carbaldehyde (88.0 mg, 0.31 mmol) and hydrazine monohydrate (35.7 μL, 0.93 mmol) were dissolved in diethylene glycol (0.1 mL), followed by stirring at 180° C. for 1 hour. After cooling to 100° C., KOH (52.1 mg, 0.93 mmol) was added to the reaction mixture, followed by stirring at 120° C. for another 2 hours. After cooling to room temperature, the reaction mixture was extracted with Et₂O, washed with brine, dried over anhydrous Na₂SO₄, concentrated under reduced pressure. The residue was purified by flash column chromatography (silica gel, n-Hex:EtOAc=4:1) to obtain 3-chloro-5-((5-methylthiophen-2-yl)oxy)aniline (40.0 mg, 54%) as a yellow liquid.

LC/MS ESI (+): 240 (M+1)

$^1$H-NMR (400MHz, CDCl$_3$): δ, 6.44-6.46 (m, 2H), 6.38 (s, 1H), 6.36 (d, 1H, J=3.6Hz), 6.25 (s, 1H), 3.76 (brs, 2H), 2.41 (s, 3H)

(c) Synthesis of 6-chloro-N-(3-chloro-5-((5-methyl-thiophen-2-yl)oxy)phenyl)-5-(methylsulfonamido)benzo[b]thiophene-2-carboxamide The synthesis procedure of Example 1 was repeated except for using 3-chloro-5-((5-methylthiophen-2-yl)oxy)aniline (35.0 mg, 0.15 mmol) to obtain 6-chloro-N-(3-chloro-5-((5-methylthiophen-2-yl)oxy)phenyl)-5-(methylsulfonamido)benzo[b]thiophene-2-carboxamide (4.0 mg, 5%).

LC/MS ESI (+): 527 (M+1)

$^1$H-NMR (400MHz, DMSO-d$_6$): δ 10.68 (s, 1H), 9.69 (brs, 1H), 8.24 (s, 1H), 8.21 (s, 1H), 7.95 (s, 1H), 7.68 (s, 1H), 7.42 (s, 1H), 6.87 (s, 1H), 6.54-6.58 (m, 2H), 2.95 (s, 3H), 2.34 (s, 3H)

Example 488

Synthesis of 4-bromo-N-(3-chloro-5-(2-(3-isopropoxy-5-methylphenyl)propan-2-yl)phenyl)-5-(methylsulfonamido)benzo[b]thiophene-2-carboxamide (a) Synthesis of 3-chloro-5-(2-(3-isopropoxy-5-methylphenyl)propan-2-yl)aniline The synthesis procedure of Intermediate 33 was repeated except for using 1-chloro-3-(2-(3-isopropoxy-5-methylphenyl)propan-2-yl)-5-nitrobenzene (125.4 mg, 0.36 mmol) to obtain 3-chloro-5-(2-(3-isopropoxy-5-methylphenyl)propan-2-yl)aniline (102.4 mg, 89%) as a yellow solid.

LC/MS ESI (+): 318 (M+1)

$^1$H-NMR (400MHz, CDCl$_3$): δ 6.65 (m, 1H), 6.58 (s, 1H), 6.56 (m, 1H), 6.53 (s, 1H), 6.49 (m, 1H), 6.36 (m, 1H), 4.48 (m, 1H), 3.62 (s, 2H), 2.27 (s, 3H), 1.58 (s, 6H), 1.30 (d, 6H, J=6.1Hz)

(b) Synthesis of N-(3-chloro-5-(2-(3-isopropoxy-5-methylphenyl)propan-2-yl)phenyl)-5-(methylsulfonamido)benzo[b]thiophene-2-carboxamide The synthesis procedure of Example 1 was repeated except for using 3-chloro-5-(2-(3-isopropoxy-5-methylphenyl)propan-2-yl)aniline (102.4 mg, 0.32 mmol) to obtain N-(3-chloro-5-(2-(3-isopropoxy-5-methylphenyl)propan-2-yl)phenyl)-5-(methylsulfonamido)benzo[b]thiophene-2-carboxamide (140.3 mg, 76%) as an off-white solid.

LC/MS ESI (+): 571 (M+1)

$^1$H-NMR (400MHz, DMSO-d$_6$): δ 10.53 (s, 1H), 9.94 (s, 1H), 8.28 (s, 1H), 8.00 (d, 1H, J=8.7Hz), 7.88 (s, 1H), 7.77 (m, 1H), 7.52 (s, 1H), 7.34 (dd, 1H, J=8.7, 1.9Hz), 7.00 (s, 1H), 6.60 (s, 1H), 6.58 (s, 1H), 6.48 (s, 1H), 4.53 (m, 1H), 2.99 (s, 3H), 2.24 (s, 3H), 1.61 (s, 6H), 1.22 (d, 6H, J=6.0Hz)

(c) Synthesis of 4-bromo-N-(3-chloro-5-(2-(3-isopropoxy-5-methylphenyl)propan-2-yl)phenyl)-5-(methylsulfonamido)benzo[b]thiophene-2-carboxamide To a solution of N-(3-chloro-5-(2-(3-isopropoxy-5-methylphenyl)propan-2-yl)phenyl)-5-(methylsulfonamido)benzo[b]thiophene-2-carboxamide (50.0 mg, 0.09 mmol) in anhydrous 1,4-dioxane (2.0 mL), NBS (15.6 mg, 0.09 mmol) and AIBN (2.8 mg, 0.02 mmol) were added at room temperature. The reaction mixture was heated at 80° C. for 4 hours, water was added at room temperature, followed by extracting with EtOAc. The organic extract was washed with brine, dried over anhydrous Na₂SO₄, concentrated under reduced pressure. The residue was purified by flash column chromatography (silica gel, CH₂Cl₂:MeOH=95:5) to obtain 4-bromo-N-(3-chloro-5-(2-(3-isopropoxy-5-methylphenyl)propan-2-yl)phenyl)-5-(methylsulfonamido)benzo[b]thiophene-2-carboxamide (23.0 mg, 40%) as a white solid.

LC/MS ESI (+): 649 (M+1)

$^1$H-NMR (400MHz, DMSO-d$_6$): δ 10.78 (s, 1H), 9.61 (s, 1H), 8.48 (s, 1H), 8.08 (d, 1H, J=8.7Hz), 7.89 (s, 1H), 7.54-7.56 (m, 2H), 7.02 (s, 1H), 6.61 (s, 1H), 6.58 (s, 1H), 6.49 (s, 1H), 4.53 (m, 1H), 3.08 (s, 3H), 2.24 (s, 3H), 1.62 (s, 6H), 1.22 (d, 6H, J=6.0Hz).

Example 489

Synthesis of N-(2-chloro-6-(4-chlorophenoxy)pyridin-4-yl)-5-(methylsulfonamido)benzo[b]thiophene-2-carboxamide (a) Synthesis of 2-chloro-6-(4-chlorophenoxy)pyridin-4-amine 2,6-Dichloropyridin-4-amine (2.0 g, 12.27 mmol) and 4-chlorophenol (3.2 g, 24.54 mmol) were dissolved in anhydrous DMSO (123.0 mL), and K₂CO₃ (3.4 g, 24.54 mmol) was added, followed by stirring at 150° C. for 2 days. After cooling to room temperature, a saturated NH₄Cl aqueous solution (15.0 mL) was added to the reaction mixture. Then, the reaction mixture was extracted with EtOAc, washed with brine, dried over anhydrous Na₂SO₄, and concentrated under reduced pressure. The residue was purified by reversed-phase column chromatography (C18- silica gel, 0.1% formic acid in CH₃CN:0.1% formic acid in H₂O=65:35), purified by flash column chromatography (silica gel, n-Hex:EtOAc=2:1) to obtain 2-chloro-6-(4-chlorophenoxy)pyridin-4-amine (690.0 mg, 22%) as a white solid.

LC/MS ESI (+): 255 (M+1)
¹H-NMR (400MHz, DMSO-d₆): δ 7.32 (d, 2H, J=8.8Hz), 7.05 (d, 2H, J=8.8Hz), 6.33 (d, 1H, J=1.6Hz), 5.91 (d, 1H, J=1.6Hz), 4.29 (brs, 2H)

(b) Synthesis of 5-(methylsulfonamido)benzo[b]thiophene-2-carbonyl chloride 5-(Methylsulfonamido)benzo[b]thiophene-2-carboxylic acid (300.0 mg, 1.11 mmol) was dissolved in anhydrous CH₂Cl₂ (10.0 mL), and oxalyl chloride (0.15 mL, 1.66 mmol) and a catalytic amount of anhydrous DMF were added. After stirring at 110° C. for 30 minutes, the reaction mixture was cooled to room temperature and dried for 1 hour under reduced pressure. 320.0 mg of 5-(methylsulfonamido)benzo[b]thiophene-2-carbonyl chloride was obtained as a yellow liquid.

(c) Synthesis of N-(2-chloro-6-(4-chlorophenoxy)pyridin-4-yl)-5-(methylsulfonamido)benzo[b]thiophene-2-carboxamide 5-(Methylsulfonamido)benzo[b]thiophene-2-carbonyl chloride (39.0 mg, 0.14 mmol) and 2-chloro-6-(4-chlorophenoxy)pyridin-4-amine (23.0 mg, 0.09 mmol) were dissolved in anhydrous 1,4-dioxane (0.3 mL), followed by stirring at 75° C. for 15 hours. The residue was extracted with EtOAc, and the organic extract was washed with brine, dried over anhydrous Na₂SO₄, and concentrated under reduced pressure. The residue was purified by flash column chromatography (silica gel, n-Hex:EtOAc=2:1) to obtain N-(2-chloro-6-(4-chlorophenoxy)pyridin-4-yl)-5-(methylsulfonamido)benzo[b]thiophene-2-carboxamide (15.0 mg, 33%) as a white solid.

LC/MS ESI (+): 508 (M+1)
¹H-NMR (400MHz, DMSO-d₆): δ 10.90 (brs, 1H), 9.98 (brs, 1H), 8.33 (s, 1H), 8.05 (d, 1H, J=8.8Hz), 7.83 (d, 1H, J=1.6Hz), 7.67 (s, 1H), 7.53 (d, 2H, J=8.8Hz), 7.83 (dd, 1H, J=4.4, 1.0Hz), 7.32 (s, 1H), 7.26 (d, 2H, J=8.8Hz), 3.02 (s, 3H)

Through the synthetic method according to Example 489, compounds from Example 490 to Example 492 were synthesized, and the data of each example are as follows.

Example 493

Synthesis of N-(2-chloro-6-((6-(trifluoromethyl)pyridin-3-yl)oxy)pyridin-4-yl)-5-(methylsulfonamido)benzo[b]thiophene-2-carboxamide (a) Synthesis of 2-chloro-4-iodo-6-((6-(trifluoromethyl)pyridin-3-yl)oxy)pyridine 2,6-Dichloro-4-iodopyridine (500.0 mg, 1.83 mmol) and 6-(trifluoromethyl)pyridin-3-ol (298.0 mg, 1.83 mmol) were dissolved in anhydrous DMF (9.1 mL), and K₂CO₃ (378.0 mg, 2.74 mmol) was added, followed by stirring at 100° C. for 3 hours. After cooling to room temperature, the reaction mixture was extracted with EtOAc, washed with brine, dried over anhydrous Na₂SO₄, concentrated under reduced pressure. The residue was purified by flash column chromatography (silica gel, n-Hex:EtOAc=9:1) to obtain 2-chloro-4-iodo-6-((6-(trifluoromethyl)pyridin-3-yl)oxy)pyridine (170.0 mg, 23%) as a white solid.

¹H-NMR (400MHz, CDCl₃): δ 8.60 (s, 1H), 7.69-7.77 (m, 2H), 7.51 (s, 1H), 7.38 (s, 1H)

(b) Synthesis of 2-chloro-6-((6-(trifluoromethyl)pyridin-3-yl)oxy)pyridin-4-amine The synthesis procedure of Example 337-b was repeated except for using 2-chloro-4-iodo-6-((6-(trifluoromethyl)pyridin-3-yl)oxy)pyridine (230.0 mg, 0.57 mmol) to obtain 2-chloro-6-((6-(trifluoromethyl)pyridin-3-yl)oxy)pyridin-4-amine (90.0 mg, 54%) as a white solid.

¹H-NMR (400MHz, CDCl₃): δ 8.56 (s, 1H), 7.64-7.75 (m, 2H), 6.40 (s, 1H), 6.12 (s, 1H), 4.41 (brs, 2H)

(c) Synthesis of N-(2-chloro-6-((6-(trifluoromethyl)pyridin-3-yl)oxy)pyridin-4-yl)-5-(methylsulfonamido)benzo[b]thiophene-2-carboxamide The synthesis procedure of Example 489-c was repeated except for using 2-chloro-6-((6-(trifluoromethyl)pyridin-3-yl)oxy)pyridin-4-amine (26.0 mg, 0.09 mmol) to obtain N-(2-chloro-6-((6-(trifluoromethyl)pyridin-3-yl)oxy)pyri-

TABLE 35

| Ex. | Compound | Analysis data |
|---|---|---|
| 490 | 6-chloro-N-(2-chloro-6-(4-chlorophenoxy)pyridin-4-yl)-5-(methylsulfonamido)benzo[b]thiophene-2-carboxamide | LC/MS ESI (+): 542 (M + 1)<br>¹H-NMR (400 MHz, DMSO-d₆): δ 11.08 (s, 1H), 9.69 (brs, 1H), 8.33 (d, 2H, J = 6.4 Hz), 8.06 (s, 1H), 7.67 (s, 1H), 7.53 (d, 2H, J = 8.8 Hz), 7.31 (s, 1H), 7.27 (d, 2H, J = 8.8 Hz), 3.03 (s, 3H) |
| 491 | N-(2-chloro-6-((6-chloropyridin-3-yl)oxy)pyridin-4-yl)-5-(methylsulfonamido)benzo[b]thiophene-2-carboxamide | LC/MS ESI (+): 509 (M + 1)<br>¹H-NMR (400 MHz, DMSO-d₆): δ 11.03 (brs, 1H), 9.86 (brs, 1H), 8.41 (d, 1H, J = 2.9 Hz), 8.35 (s, 1H), 8.05 (d, 1H, J = 8.7 Hz), 7.82~7.85 (m, 2H), 7.68 (d, 1H, J = 1.4 Hz), 7.64 (d, 1H, J = 8.7 Hz), 7.45 (d, 1H, J = 1.4 Hz), 7.38 (dd, 1H, J = 8.7, 2.1 Hz), 3.05 (s, 3H) |
| 492 | 6-chloro-N-(2-chloro-6-((6-chloropyridin-3-yl)oxy)pyridin-4-yl)-5-(methylsulfonamido)benzo[b]thiophene-2-carboxamide | LC/MS ESI (+): 543 (M + 1)<br>¹H-NMR (400 MHz, DMSO-d₆): δ 11.19 (brs, 1H), 9.66 (brs, 1H), 8.40 (d, 1H, J = 2.9 Hz), 8.33 (s, 1H), 8.32 (s, 1H), 8.05 (s, 1H), 7.83 (dd, 1H J = 8.7, 3.0 Hz), 7.67 (d, 1H, J = 1.2 Hz), 7.64 (d, 1H, J = 8.7 Hz), 7.43 (d, 1H, J = 1.2 Hz), 3.01 (s, 3H) | din-4-yl)-5-(methylsulfonamido)benzo[b]thiophene-2-carboxamide (17.8 mg, 37%) as a white solid.

LC/MS ESI (+): 543 (M+1)

$^1$H-NMR (400MHz, DMSO-d$_6$): δ 11.03 (brs, 1H), 9.86 (brs, 1H), 8.69 (d, 1H, J=2.4Hz), 8.30 (s, 1H), 7.95-8.01 (m, 3H), 7.79 (d, 1H, J=2.0Hz), 7.65 (d, 1H, J=1.4Hz), 7.46 (d, 1H, J=1.4Hz), 7.33 (dd, 1H, J=8.7, 2.1Hz), 2.97 (s, 3H).

Through the synthetic method according to Example 493, compounds from Example 494 to Example 496 were synthesized, and the data of each example are as follows.

TABLE 36

| Ex. | Compound | Analysis data |
| --- | --- | --- |
| 494 | 6-chloro-N-(2-chloro-6-((6-(trifluoromethyl)pyridin-3-yl)oxy)pyridin-4-yl)-5-(methylsulfonamido)benzo[b]thiophene-2-carboxamide | LC/MS ESI (+): 577 (M + 1)<br>$^1$H-NMR (400 MHz, DMSO-d$_6$): δ 11.19 (brs, 1H), 9.66 (brs, 1H), 8.74 (d, 1H, J = 2.4 Hz), 8.38 (s, 1H), 8.36 (s, 1H), 8.10 (s, 1H), 8.00~8.06 (m, 2H), 7.70 (d, 1H, J = 1.4 Hz), 7.51 (d, 1H, J = 1.4 Hz), 3.07 (s, 3H) |
| 495 | N-(2-chloro-6-(4-(trifluoromethyl)phenoxy)pyridin-4-yl)-5-(methylsulfonamido)benzo[b]thiophene-2-carboxamide | LC/MS ESI (+): 542 (M + 1)<br>$^1$H-NMR(400 MHz, DMSO-d$_6$): δ 11.07 (brs, 1H), 9.93 (brs, 1H), 8.35 (s, 1H), 8.06 (d, 1H, J = 8.8 Hz), 7.85~7.87 (m, 3H), 7.72 (s, 1H), 7.39~7.46 (m, 4H), 3.03 (s, 3H) |
| 496 | 6-chloro-N-(2-chloro-6-(4-(trifluoromethyl)phenoxy)pyridin-4-yl)-5-(methylsulfonamido)benzo[b]thiophene-2-carboxamide | LC/MS ESI (+): 576 (M + 1)<br>$^1$H-NMR(400 MHz, DMSO-d$_6$): δ 11.14 (brs, 1H), 9.68 (brs, 1H), 8.35~8.37 (m, 2H), 8.09 (s, 1H), 7.86 (d, 2H, J = 8.4 Hz), 7.72 (d, 1H, J = 1.6 Hz), 7.45 (d, 2H, J = 8.4 Hz), 7.42 (d, 1H, J = 1.6 Hz), 3.07 (s, 3H) |

Example 497

Synthesis of N-(3-chloro-5-(2-(4-chlorophenyl)propan-2-yl)phenyl)-6-methoxy-5-(methylsulfonamido)benzo[b]thiophene-2-carboxamide (a) Synthesis of 2-fluoro-4-methoxy-5-nitrobenzaldehyde 2-Fluoro-4-methoxybenzaldehyde (1.0 g, 6.49 mmol) was dissolved in concentrated H$_2$SO$_4$ (6.0 mL), and a 70% HNO$_3$ aqueous solution (0.8 mL, 6.49 mmol) and concentrated H$_2$SO$_4$ (0.8 mL, 14.92 mmol) were slowly added at −15° C., followed by stirring for 2 hours. The reaction mixture was poured in ice water, and the precipitate was filtered, dissolved in CH$_2$Cl$_2$, and neutralized with a saturated NaHCO$_3$ aqueous solution. An organic layer was dried over anhydrous Na$_2$SO$_4$, concentrated under reduced pressure. The residue was purified by flash column chromatography (silica gel, n-Hex:CH$_2$Cl$_2$=3:1) to obtain 2-fluoro-4-methoxy-5-nitrobenzaldehyde (1.2 g, 91%) as a white solid.

$^1$H-NMR (400MHz, CDCl$_3$): δ 10.21 (s, 1H), 8.46 (d, 1H, J=7.2Hz), 6.88 (d, 1H, J=11.6Hz), 4.06 (s, 3H)

(b) Synthesis of methyl 6-methoxy-5-nitrobenzo[b]thiophene-2-carboxylate

The synthesis procedure of Intermediate 26-a was repeated except for using 2-fluoro-4-methoxy-5-nitrobenzaldehyde (1.2 g, 5.93 mmol) to obtain methyl 6-methoxy-5-nitrobenzo[b]thiophene-2-carboxylate (1.3 g, 81%) as a yellow solid.

$^1$H-NMR (400MHz, CDCl$_3$): δ 8.34 (s, 1H), 8.03 (s, 1H), 7.47 (s, 1H), 4.04 (s, 3H), 3.96 (s, 3H)

(c) Synthesis of methyl 5-amino-6-methoxybenzo[b]thiophene-2-carboxylate

The synthesis procedure of Intermediate 13-b was repeated except for using methyl 6-methoxy-5-nitrobenzo[b]thiophene-2-carboxylate (1.3 g, 4.83 mmol) to obtain methyl 5-amino-6-methoxybenzo[b]thiophene-2-carboxylate (1.1 g, 93%) as a yellow solid.

$^1$H-NMR (400MHz, CDCl$_3$): δ 7.84 (s, 1H), 7.17 (s, 1H), 7.12 (s, 1H), 3.95 (brs, 5H), 3.91 (s, 3H)

(d) Synthesis of methyl 6-methoxy-5-(methylsulfonamido)benzo[b]thiophene-2-carboxylate The synthesis procedure of Intermediate 6-a was repeated except for using methyl 5-amino-6-methoxybenzo[b]thiophene-2-carboxylate (200.0 mg, 0.84 mmol) to obtain methyl 6-methoxy-5-(methylsulfonamido)benzo[b]thiophene-2-carboxylate (266.0 mg, 100%) as a yellow solid.

$^1$H-NMR (400MHz, CDCl$_3$): δ 8.00 (s, 1H), 7.96 (s, 1H), 7.32 (s, 1H), 6.89 (s, 1H), 3.99 (s, 3H), 3.94 (s, 3H), 2.98 (s, 3H)

(e) Synthesis of 6-methoxy-5-(methylsulfonamido)benzo[b]thiophene-2-carboxylic acid The synthesis procedure of Intermediate 6-b was repeated except for using methyl 6-methoxy-5-(methylsulfonamido)benzo[b]thiophene-2-carboxylate (266.0 mg, 0.84 mmol) to obtain 6-methoxy-5-(methylsulfonamido)benzo[b]thiophene-2-carboxylic acid (246.0 mg, 97%) as a white solid.

$^1$H-NMR (300MHz, DMSO-d$_6$): δ 13.33 (brs, 1H), 9.08 (brs, 1H), 8.02 (s, 1H), 7.86 (s, 1H), 7.72 (s, 1H), 3.91 (s, 3H), 2.98 (s, 3H)

(f) Synthesis of N-(3-chloro-5-(2-(4-chlorophenyl)propan-2-yl)phenyl)-6-methoxy-5-(methylsulfonamido)benzo[b]thiophene-2-carboxamide The synthesis procedure of Example 1 was repeated except for using 6-methoxy-5-(methylsulfonamido)benzo[b]thiophene-2-carboxylic acid (50.0 mg, 0.17 mmol) to obtain N-(3-chloro-5-(2-(4-chlorophenyl)propan-2-yl)phenyl)-6-methoxy-5-(methylsulfonamido)benzo[b]thiophene-2-carboxamide (22.1 mg, 24%) as a white solid.

LC/MS ESI (+): 563 (M+1)

$^1$H-NMR (400MHz, DMSO-d$_6$); δ 10.48 (brs, 1H), 9.11 (brs, 1H), 8.22 (s, 1H), 7.88 (m, 1H), 7.81 (s, 1H), 7.74 (s, 1H), 7.50 (m, 1H), 7.38 (d, 2H, J=8.7Hz), 7.28 (d, 2H, J=8.7Hz), 7.02 (m, 1H), 3.92 (s, 3H), 2.97 (s, 3H), 1.65 (s, 6H)

Through the synthetic method according to Example 497, a compound of Example 498 was synthesized, and the data of the example are as follows.

TABLE 37

| Ex. | Compound | Analysis data |
|---|---|---|
| 498 | N-(3-chloro-5-(4-chlorophenoxy)phenyl)-6-methoxy-5-(methylsulfonamido)benzo[b]thiophene-2-carboxamide | LC/MS ESI (+): 537 (M + 1)<br>$^1$H-NMR(400 MHz, DMSO-$d_6$): δ 10.53 (brs, 1H), 9.12 (brs, 1H), 8.19 (s, 1H), 7.81 (s, 1H), 7.75 (m, 1H), 7.72 (m, 1H), 7.52 (d, 2H, J = 8.9 Hz), 7.36 (m, 1H), 7.19 (d, 2H, J = 8.9 Hz), 6.91 (m, 1H), 3.91 (s, 3H), 2.95 (s, 3H) |

EXPERIMENTAL EXAMPLES

Experiments were performed as shown below for the compounds prepared in Examples above.

Experimental Example 1

Experiment on the Inhibition of STAT3 and STAT1 activities via reporter gene assay 1-1) Experiment on the Inhibition of STAT3 Activity A human prostate cancer cell line (LNCaP stable cell line; plasmid pSTAT3-TA-luc), which contains a stably operating STAT3 promoter, was cultured in RPMI1640 medium (Cat No. 11875, Life Technologies) containing 10% fetal bovine serum (FBS) (Cat No. SH30396, Thermo Scientific) and 150 µg/mL G-418 solution (Cat No. 04 727 894 001, Roche). The reporter gene assay using LNCaP stable cell line was performed in RPMI1640 medium containing 3% DCC-FBS without G-418 solution. LNCaP stable cells were plated in two (2) white 96-well plates with 30,000 cells/50 µL in each well. The cells were cultured at 37° C., under 5% $CO_2$ for 24 hours, and then treated with the compounds listed in Examples which were diluted in various concentrations. Subsequently, IL-6 was added to each well with a final concentration of 10 ng/mL. Upon completion of the treatment with the compounds and IL-6, the cells were cultured at 37° C., under 5% $CO_2$ for from 24 to 48 hours. The plates were observed under microscope and drug precipitation and particular findings were investigated and recorded.

The luciferase assay and the cell viability assay were performed respectively with one of the two plates. For the luciferase assay, the liquid media in the 96-well plate was removed, and then, 20 µL of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 µL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

1-2) Experiment on the Inhibition of STAT1 Activity

A human osteosarcoma cell line (U2OS stable cell line; pGL4-STAT1-TA-luc), which contains a stably operating STAT1 promoter, was cultured in McCoy 5'A medium (Cat No. 16600, Life Technologies) containing 10% FBS (Cat No. SH30396, Thermo Scientific) and 1000 µg/mL G418 solution (Cat No. 04 727 894 001, Roche). The reporter gene assay using U2OS stable cell line was performed in McCoy 5'A medium containing 10% FBS without G-418 solution. U2OS stable cells were plated in two (2) white 96-well plates with 25,000 cells/50 µL in each well. The cells were cultured at 37° C., under 5% $CO_2$ for from 8 to 24 hours, and then treated with the compounds listed in Examples which were diluted in various concentrations. Subsequently, IFN-γ was added to each well with a final concentration of 50 ng/mL. Upon completion of the treatment with the compounds and IFN-γ, the cells were cultured at 37° C., under 5% $CO_2$ for 24 hours. The plates were observed under microscope and drug precipitation and particular findings were investigated and recorded.

The luciferase assay and the cell viability assay were performed respectively with one of two plates. For the luciferase assay, the liquid media in the 96-well plate was removed, and then, 20 µL of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 µL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

The results of evaluation on the inhibitory effect of the compounds listed in the Examples on the dimerization of STAT3 and STAT1 obtained via the STAT3 and STAT1 reporter gene assays are shown in Table 38 below.

TABLE 38

| Example | $IC_{50}$ (µM) pSTAT3 | $IC_{50}$ (µM) pSTAT1 | Example | $IC_{50}$ (µM) pSTAT3 | $IC_{50}$ (µM) pSTAT1 |
|---|---|---|---|---|---|
| 1 | 0.190 | >10 | 2 | 0.200 | >10 |
| 3 | 0.220 | >10 | 4 | 0.340 | >10 |
| 5 | 1.200 | >10 | 6 | >10 | >10 |
| 7 | 0.310 | >10 | 8 | 0.120 | >10 |
| 9 | 0.056 | >10 | 10 | 0.430 | >10 |
| 11 | 0.200 | >10 | 12 | 0.260 | >10 |
| 13 | 0.220 | >10 | 14 | 0.130 | >10 |
| 15 | 0.120 | >10 | 16 | 0.112 | >10 |
| 17 | 0.140 | >10 | 18 | 5.400 | >10 |
| 19 | 0.120 | >10 | 20 | 0.290 | >10 |
| 21 | 0.220 | >10 | 22 | 0.110 | >10 |
| 23 | 0.045 | >10 | 24 | 0.051 | >10 |
| 25 | 3.300 | >10 | 26 | 0.059 | >10 |
| 27 | 0.080 | >10 | 28 | 0.610 | >10 |
| 29 | 0.530 | >10 | 30 | 0.430 | >10 |
| 31 | 0.190 | >10 | 32 | 0.034 | >10 |
| 33 | 0.035 | >10 | 34 | 0.051 | >10 |
| 35 | 0.076 | >10 | 36 | 0.027 | >10 |
| 37 | 0.046 | >10 | 38 | 0.100 | >10 |
| 39 | 0.048 | >10 | 40 | 0.076 | >10 |
| 41 | 0.028 | >10 | 42 | 0.007 | >10 |
| 43 | 2.700 | >10 | 44 | 1.400 | >10 |

TABLE 38-continued

| Example | IC$_{50}$ (μM) pSTAT3 | IC$_{50}$ (μM) pSTAT1 | Example | IC$_{50}$ (μM) pSTAT3 | IC$_{50}$ (μM) pSTAT1 | Example | IC$_{50}$ (μM) pSTAT3 | IC$_{50}$ (μM) pSTAT1 | Example | IC$_{50}$ (μM) pSTAT3 | IC$_{50}$ (μM) pSTAT1 |
|---|---|---|---|---|---|---|---|---|---|---|---|
| 45 | 1.300 | >10 | 46 | 0.082 | >10 | 199 | 0.650 | >10 | 200 | 0.069 | >10 |
| 47 | 0.008 | >10 | 48 | 0.007 | >10 | 201 | 0.029 | >10 | 202 | 0.007 | >10 |
| 49 | 0.007 | >10 | 50 | 0.150 | >10 | 203 | 0.006 | >10 | 204 | 0.051 | >10 |
| 51 | 0.550 | >10 | 52 | 1.500 | >10 | 205 | 0.300 | >10 | 206 | 0.190 | >10 |
| 53 | 0.026 | >10 | 54 | 0.048 | >10 | 207 | 3.000 | >10 | 208 | 0.170 | >10 |
| 55 | 0.160 | >10 | 56 | 0.072 | >10 | 209 | 0.043 | >10 | 210 | 0.140 | >10 |
| 57 | 0.067 | >10 | 58 | 0.007 | >10 | 211 | 0.007 | >10 | 212 | 0.010 | >10 |
| 59 | 0.021 | >10 | 60 | 0.063 | >10 | 213 | 0.018 | >10 | 214 | 0.170 | >10 |
| 61 | 0.066 | >10 | 62 | 0.011 | >10 | 215 | 0.002 | >10 | 216 | 0.380 | >10 |
| 63 | 0.034 | >10 | 64 | 0.065 | >10 | 217 | 2.060 | >10 | 218 | >10 | >10 |
| 65 | 0.064 | >10 | 66 | >10 | >10 | 219 | 1.190 | >10 | 220 | 0.012 | >10 |
| 67 | 0.067 | >10 | 68 | 0.011 | >10 | 221 | 0.011 | >10 | 222 | 6.100 | 5.0 |
| 69 | 0.052 | >10 | 70 | 0.068 | >10 | 223 | 0.240 | 2.3 | 224 | 0.260 | >10 |
| 71 | 0.009 | >10 | 72 | 0.021 | >10 | 225 | >10 | >10 | 226 | 6.300 | >10 |
| 73 | 0.010 | >10 | 74 | 2.700 | >10 | 227 | >10 | >10 | 228 | >10 | >10 |
| 75 | 0.008 | >10 | 76 | 3.000 | >10 | 229 | 1.400 | >10 | 230 | 1.100 | >10 |
| 77 | 0.120 | >10 | 78 | 0.017 | >10 | 231 | 2.900 | >10 | 232 | >10 | >10 |
| 79 | 0.014 | >10 | 80 | 0.016 | >10 | 233 | >10 | >10 | 234 | >10 | >10 |
| 81 | 0.055 | >10 | 82 | 0.024 | >10 | 235 | >10 | >10 | 236 | 0.310 | >10 |
| 83 | 0.023 | >10 | 84 | 0.004 | >10 | 237 | 0.110 | >10 | 238 | 0.270 | >10 |
| 85 | 0.016 | >10 | 86 | 0.072 | >10 | 239 | >10 | >10 | 240 | >10 | >10 |
| 87 | 0.016 | >10 | 88 | 0.015 | >10 | 241 | 1.800 | >10 | 242 | 0.960 | >10 |
| 89 | 0.047 | >10 | 90 | 0.043 | >10 | 243 | 7.200 | >10 | 244 | >10 | >10 |
| 91 | 0.032 | >10 | 92 | 0.067 | >10 | 245 | 1.400 | >10 | 246 | 8.400 | >10 |
| 93 | 0.091 | >10 | 94 | 1.120 | >10 | 247 | >10 | 6.2 | 248 | 6.100 | >10 |
| 95 | 0.110 | >10 | 96 | 3.400 | 8.7 | 249 | >10 | >10 | 250 | >10 | >10 |
| 97 | 2.100 | >10 | 98 | 0.098 | >10 | 251 | >10 | >10 | 252 | >10 | >10 |
| 99 | 0.220 | >10 | 100 | 0.042 | >10 | 253 | 4.700 | >10 | 254 | >10 | >10 |
| 101 | 0.280 | >10 | 102 | 4.600 | >10 | 255 | >10 | >10 | 256 | >10 | >10 |
| 103 | 0.110 | >10 | 104 | 0.224 | >10 | 257 | 3.500 | >10 | 258 | 2.700 | >10 |
| 105 | 0.005 | >10 | 106 | 0.520 | >10 | 259 | 1.100 | >10 | 260 | 0.710 | >10 |
| 107 | 0.420 | >10 | 108 | 0.078 | >10 | 261 | 2.400 | >10 | 262 | 5.300 | >10 |
| 109 | 0.078 | >10 | 110 | 4.300 | >10 | 263 | >10 | >10 | 264 | 1.900 | >10 |
| 111 | >10 | >10 | 112 | 6.800 | >10 | 265 | 4.200 | >10 | 266 | 6.800 | >10 |
| 113 | 8.900 | >10 | 114 | 0.020 | >10 | 267 | 2.000 | >10 | 268 | >10 | >10 |
| 115 | 2.500 | >10 | 116 | 0.053 | >10 | 269 | 2.300 | >10 | 270 | 0.380 | >10 |
| 117 | 0.230 | >10 | 118 | >10 | >10 | 271 | 5.900 | >10 | 272 | 0.500 | >10 |
| 119 | >10 | >10 | 120 | 0.660 | >10 | 273 | 2.200 | >10 | 274 | >10 | >10 |
| 121 | 1.800 | >10 | 122 | 0.120 | >10 | 275 | 3.300 | >10 | 276 | 3.100 | >10 |
| 123 | 0.046 | >10 | 124 | 4.000 | >10 | 277 | 0.380 | >10 | 278 | 4.500 | >10 |
| 125 | 0.890 | >10 | 126 | 0.100 | >10 | 279 | 6.200 | >10 | 280 | 1.700 | >10 |
| 127 | 0.150 | >10 | 128 | 0.270 | >10 | 281 | 7.100 | >10 | 282 | >10 | >10 |
| 129 | 0.070 | >10 | 130 | 0.308 | >10 | 283 | 7.400 | >10 | 284 | 1.900 | >10 |
| 131 | 0.085 | >10 | 132 | 0.350 | >10 | 285 | 2.500 | >10 | 286 | >10 | >10 |
| 133 | 0.150 | >10 | 134 | 0.270 | >10 | 287 | >10 | >10 | 288 | >10 | >10 |
| 135 | 0.140 | >10 | 136 | 0.059 | >10 | 289 | >10 | >10 | 290 | 7.000 | >10 |
| 137 | 0.220 | >10 | 138 | 0.020 | >10 | 291 | 3.200 | >10 | 292 | >10 | >10 |
| 139 | 0.110 | >10 | 140 | 0.090 | >10 | 293 | 2.700 | >10 | 294 | 2.600 | >10 |
| 141 | 0.380 | >10 | 142 | 0.130 | >10 | 295 | >10 | >10 | 296 | >10 | >10 |
| 143 | 0.290 | >10 | 144 | 5.200 | >10 | 297 | >10 | >10 | 298 | >10 | >10 |
| 145 | 0.067 | >10 | 146 | 0.073 | >10 | 299 | 3.100 | >10 | 300 | 5.300 | >10 |
| 147 | 0.670 | >10 | 148 | >10 | >10 | 301 | 3.300 | >10 | 302 | 0.400 | >10 |
| 149 | 0.070 | >10 | 150 | 0.014 | >10 | 303 | 0.230 | 9.0 | 304 | 4.000 | >10 |
| 151 | 2.200 | >10 | 152 | 0.120 | >10 | 305 | 0.067 | >10 | 306 | 0.280 | >10 |
| 153 | 0.150 | >10 | 154 | 0.140 | >10 | 307 | 1.100 | >10 | 308 | 5.600 | >10 |
| 155 | 0.078 | >10 | 156 | 0.230 | >10 | 309 | 1.500 | >10 | 310 | 0.800 | >10 |
| 157 | 0.063 | >10 | 158 | 0.120 | >10 | 311 | 5.700 | >10 | 312 | 0.240 | >10 |
| 159 | 0.310 | >10 | 160 | 3.300 | >10 | 313 | 3.600 | >10 | 314 | 4.500 | >10 |
| 161 | >10 | >10 | 162 | 0.069 | >10 | 315 | 2.600 | >10 | 316 | 3.600 | >10 |
| 163 | 0.011 | >10 | 164 | 0.720 | >10 | 317 | 0.280 | >10 | 318 | 8.100 | >10 |
| 165 | 0.130 | >10 | 166 | 0.310 | >10 | 319 | >10 | >10 | 320 | 6.200 | >10 |
| 167 | 2.600 | >10 | 168 | 0.130 | >10 | 321 | 8.200 | >10 | 322 | 0.028 | >10 |
| 169 | 0.039 | >10 | 170 | 0.068 | >10 | 323 | 0.110 | >10 | 324 | 0.530 | >10 |
| 171 | 0.074 | >10 | 172 | 0.016 | >10 | 325 | 0.240 | >10 | 326 | 0.100 | >10 |
| 173 | 0.011 | >10 | 174 | 0.100 | >10 | 327 | 0.041 | >10 | 328 | 0.340 | >10 |
| 175 | 0.007 | >10 | 176 | 0.036 | >10 | 329 | 0.010 | >10 | 330 | 0.029 | >10 |
| 177 | 0.047 | >10 | 178 | 0.025 | >10 | 331 | 0.051 | >10 | 332 | 0.061 | >10 |
| 179 | 0.004 | >10 | 180 | 0.010 | >10 | 333 | 0.016 | 9.9 | 334 | 0.096 | >10 |
| 181 | 0.005 | >10 | 182 | 0.012 | >10 | 335 | 5.700 | >10 | 336 | 0.130 | >10 |
| 183 | 0.010 | >10 | 184 | 0.042 | >10 | 337 | 0.270 | >10 | 338 | 0.920 | >10 |
| 185 | 0.007 | >10 | 186 | 0.100 | >10 | 339 | 0.760 | 1.9 | 340 | >10 | >10 |
| 187 | 0.110 | >10 | 188 | 0.054 | >10 | 341 | 3.300 | >10 | 342 | 0.390 | >10 |
| 189 | >10 | >10 | 190 | 2.370 | >10 | 343 | 1.800 | >10 | 344 | 0.150 | >10 |
| 191 | 0.540 | >10 | 192 | 0.750 | — | 345 | 1.600 | >10 | 346 | 0.200 | >10 |
| 193 | 0.380 | >10 | 194 | >10 | >10 | 347 | 1.500 | >10 | 348 | >10 | >10 |
| 195 | 0.011 | >10 | 196 | 0.020 | >10 | 349 | 0.480 | >10 | 350 | 1.500 | >10 |
| 197 | 0.012 | >10 | 198 | 0.030 | >10 | 351 | 0.300 | >10 | 352 | 0.820 | 8.8 |

TABLE 38-continued

| Example | IC$_{50}$ (μM) pSTAT3 | IC$_{50}$ (μM) pSTAT1 | Example | IC$_{50}$ (μM) pSTAT3 | IC$_{50}$ (μM) pSTAT1 |
|---|---|---|---|---|---|
| 353 | 0.760 | >10 | 354 | 0.330 | 7.4 |
| 355 | 0.210 | >10 | 356 | 3.600 | >10 |
| 357 | 1.700 | >10 | 358 | 1.700 | >10 |
| 359 | >10 | >10 | 360 | >10 | >10 |
| 361 | >10 | >10 | 362 | 0.720 | >10 |
| 363 | 1.300 | >10 | 364 | >10 | >10 |
| 365 | 0.400 | >10 | 366 | 1.200 | >10 |
| 367 | 0.380 | >10 | 368 | 2.700 | >10 |
| 369 | 0.700 | >10 | 370 | 0.210 | >10 |
| 371 | 0.900 | >10 | 372 | 0.340 | >10 |
| 373 | 1.500 | >10 | 374 | 6.400 | >10 |
| 375 | 0.140 | >10 | 376 | 5.200 | >10 |
| 377 | >10 | >10 | 378 | >10 | >10 |
| 379 | >10 | >10 | 380 | >10 | >10 |
| 381 | >10 | >10 | 382 | 0.330 | >10 |
| 383 | 0.090 | 2.3 | 384 | >10 | >10 |
| 385 | 4.300 | >10 | 386 | 3.400 | >10 |
| 387 | 2.400 | >10 | 388 | 3.800 | >10 |
| 389 | 5.800 | >10 | 390 | 3.700 | >10 |
| 391 | 2.400 | >10 | 392 | 1.800 | >10 |
| 393 | >10 | >10 | 394 | 3.300 | >10 |
| 395 | 2.100 | >10 | 396 | 2.500 | >10 |
| 397 | 3.000 | >10 | 398 | 1.600 | >10 |
| 399 | 2.800 | >10 | 400 | 3.200 | >10 |
| 401 | 4.000 | >10 | 402 | 6.300 | >10 |
| 403 | 8.200 | >10 | 404 | >10 | >10 |
| 405 | 2.400 | >10 | 406 | >10 | >10 |
| 407 | 5.700 | >10 | 408 | 2.400 | >10 |
| 409 | 2.900 | >10 | 410 | 3.100 | >10 |
| 411 | 3.600 | >10 | 412 | 3.400 | >10 |
| 413 | >10 | >10 | 414 | 1.700 | >10 |
| 415 | 6.800 | >10 | 416 | 6.000 | >10 |
| 417 | >10 | >10 | 418 | 0.840 | >10 |
| 419 | 0.670 | >10 | 420 | 0.820 | >10 |
| 421 | 0.200 | >10 | 422 | 0.760 | >10 |
| 423 | 0.260 | >10 | 424 | 0.150 | >10 |
| 425 | 0.460 | >10 | 426 | 0.082 | >10 |
| 427 | 0.130 | >10 | 428 | 1.000 | >10 |
| 429 | 0.190 | >10 | 430 | 0.012 | >10 |
| 431 | 0.053 | >10 | 432 | 0.049 | >10 |
| 433 | 0.013 | >10 | 434 | 6.500 | >10 |
| 435 | 5.800 | >10 | 436 | 5.200 | >10 |
| 437 | 6.300 | >10 | 438 | 0.200 | >10 |
| 439 | 0.053 | >10 | 440 | 0.036 | >10 |
| 441 | 0.009 | >10 | 442 | 0.021 | >10 |
| 443 | 0.065 | >10 | 444 | 0.083 | >10 |
| 445 | 0.066 | >10 | 446 | 0.096 | >10 |
| 447 | 0.270 | >10 | 448 | 0.230 | >10 |
| 449 | 0.024 | >10 | 450 | 0.100 | >10 |
| 451 | 0.140 | >10 | 452 | 0.079 | >10 |
| 453 | 0.022 | >10 | 454 | 0.120 | >10 |
| 455 | 0.190 | >10 | 456 | 0.190 | >10 |
| 457 | 0.280 | >10 | 458 | 0.250 | >10 |
| 459 | 0.360 | >10 | 460 | 0.150 | >10 |
| 461 | 0.140 | >10 | 462 | 0.130 | >10 |
| 463 | 0.190 | >10 | 464 | 0.170 | >10 |
| 465 | 0.120 | >10 | 466 | 0.120 | >10 |
| 467 | 0.220 | >10 | 468 | 0.170 | >10 |
| 469 | 0.360 | >10 | 470 | 0.320 | >10 |
| 471 | 0.075 | >10 | 472 | 0.100 | >10 |
| 473 | 0.100 | >10 | 474 | 0.048 | >10 |
| 475 | >10 | >10 | 476 | 0.021 | >10 |
| 477 | 0.025 | >10 | 478 | 0.022 | >10 |
| 479 | 0.014 | >10 | 480 | 0.019 | >10 |
| 481 | 0.015 | >10 | 482 | 0.016 | >10 |
| 483 | 0.014 | >10 | 484 | 0.021 | >10 |
| 485 | 0.129 | >10 | 486 | 0.110 | >10 |
| 487 | 0.059 | >10 | 488 | 0.350 | >10 |
| 489 | 0.110 | >10 | 490 | 0.016 | >10 |
| 491 | 0.130 | >10 | 492 | 0.008 | >10 |
| 493 | 0.140 | >10 | 494 | 0.018 | >10 |
| 495 | 0.080 | >10 | 496 | 0.009 | >10 |
| 497 | 0.005 | >10 | 498 | 0.060 | >10 |

As shown in Table 38, the compounds according to the present invention exhibited excellent inhibitory effects against the activity of STAT3 protein but showed almost no inhibitory effect against the activity of STAT1 protein.

Experimental Example 2

Cell Growth Inhibition Assay

The inhibitory effects of the compounds of the present invention against the growth of cancer cells were evaluated as shown below. The cancer cell lines including stomach cancer cell line (AGS), breast cancer cell lines (MDA-MB-231, MDA-MB-468, and BT-549), prostate cancer cell lines (LNCaP and DU-145), colon cancer cell line (HCT116), ovarian cancer cell line (SW626), liver cancer cell line (Hep3B), kidney cancer cell line (ACHN), lung cancer cell line (NCI-H23) and blood cancer cell lines (HEL92.1.7 and U266) were cultured under the protocol provided by each supplier. A medium supplemented with 10 ng/mL of IL-6 was used for LNCaP, a prostate cancer cell line, when treated with a drug. Each type of cells to be used in experiments were sub-cultured in a 96-well plate by counting the exact number of cells using Tali™ Image-based Cytometer (Life Technologies). In a 96-well plate, AGS, HCT116, and DU-145 were employed with 3,000 cells/well; NCI-H23, SW626, Hep3B, ACHN, BT-549, MDA-MB-231, HEL92.1.7, and U266 were employed with 5,000 cells/well; and LNCaP and MDA-MB-468 were employed with 10,000 cells/well. The cells were treated with the compounds listed in Examples which were diluted in various concentrations. Upon completion of the compounds treatment, AGS, HCT116, SW626, DU145, NCI-H23, Hep3B, ACHN, BT-549, LNCaP, HEL92.1.7, and U266 cells were cultured at 37° C. under 5% $CO_2$ for from 72 to 96 hours, and MDA-MB-231 and MDA-MB-468 cells were cultured at 37° C. in air for from 72 to 96 hours. Subsequently, the cells were observed under microscope and drug precipitation and particular findings were investigated and recorded. And then, the 96-well plate was placed at room temperature for 30 minutes, added with 20 μL/well of CellTiter-Glo solution (Cat No. G7573, Promega) and shaken for 10 minutes, followed by being subjected to the measurement using PHERAstar™ microplate reader (BMG LABTECH) according to the supplier's general luminometer protocol. Wells where only culture liquid added without cell plating were used as a negative control, whereas wells where culture liquid containing 0.1% DMSO instead of the compounds listed in Examples were used as a positive control.

The results of the inhibitory effects of the compounds prepared in Examples against the growth of cancer cells are shown in Tables 39 to 46 below.

TABLE 39

| Ex. | IC$_{50}$ (μM) LNCap | Ex. | IC$_{50}$ (μM) LNCap | Ex. | IC$_{50}$ (μM) LNCap | Ex. | IC$_{50}$ (μM) LNCap |
|---|---|---|---|---|---|---|---|
| 1 | 2.500 | 2 | 5.300 | 3 | 1.100 | 4 | 0.820 |
| 5 | 4.700 | 6 | >10 | 7 | 2.400 | 8 | 0.870 |
| 9 | 0.780 | 10 | 1.700 | 11 | 1.800 | 12 | 1.400 |
| 13 | 0.480 | 14 | 0.550 | 15 | 0.290 | 16 | 0.480 |
| 17 | 0.920 | 18 | 9.600 | 19 | 0.520 | 20 | 1.100 |
| 21 | 0.900 | 22 | 0.290 | 23 | 0.170 | 24 | 0.083 |
| 25 | 4.200 | 26 | 0.360 | 27 | 0.670 | 28 | 4.700 |
| 29 | 3.800 | 30 | 2.900 | 31 | 0.490 | 32 | 0.150 |
| 33 | 0.150 | 34 | 0.240 | 35 | 0.067 | 36 | 0.210 |
| 37 | 0.390 | 38 | 0.800 | 39 | 0.220 | 40 | 0.370 |
| 41 | 0.110 | 42 | 0.032 | 43 | 5.800 | 44 | 5.200 |
| 45 | 4.400 | 46 | 0.130 | 47 | 0.031 | 48 | 0.077 |

TABLE 39-continued

| Ex. | IC$_{50}$ (μM) LNCap | Ex. | IC$_{50}$ (μM) LNCap | Ex. | IC$_{50}$ (μM) LNCap | Ex. | IC$_{50}$ (μM) LNCap |
|---|---|---|---|---|---|---|---|
| 49 | 0.049 | 50 | 0.760 | 51 | 3.500 | 52 | 4.700 |
| 53 | 0.070 | 54 | 0.170 | 55 | 0.540 | 56 | 0.250 |
| 57 | 0.160 | 58 | 0.032 | 59 | 0.120 | 60 | 0.370 |
| 61 | 0.130 | 62 | 0.075 | 63 | 0.037 | 64 | 0.100 |
| 66 | >1.1 | 67 | 0.037 | 68 | 0.019 | 69 | 0.058 |
| 70 | 0.290 | 71 | 0.091 | 72 | 0.034 | 73 | 0.033 |
| 74 | 6.600 | 75 | 0.029 | 76 | 0.230 | 77 | 0.300 |
| 78 | 0.038 | 79 | 0.039 | 80 | 0.068 | 81 | 0.150 |
| 82 | 0.030 | 83 | 0.025 | 84 | 0.008 | 85 | 0.025 |
| 86 | 0.075 | 87 | 0.028 | 88 | 0.024 | 89 | 0.070 |
| 90 | 0.220 | 91 | 0.056 | 92 | 0.071 | 93 | 0.055 |
| 94 | 0.270 | 95 | 0.015 | 96 | >1.1 | 98 | 0.760 |
| 99 | 1.500 | 100 | >10 | 101 | 1.100 | 103 | 0.035 |
| 104 | 0.420 | 105 | 0.002 | 106 | 0.110 | 107 | 1.200 |
| 108 | 0.310 | 109 | 0.420 | 110 | >10 | 111 | >10 |
| 112 | 8.600 | 113 | >10 | 114 | 0.061 | 115 | 5.600 |
| 116 | 0.220 | 117 | 2.600 | 118 | >10 | 119 | >10 |
| 120 | 3.600 | 121 | 3.700 | 122 | 0.240 | 123 | 0.150 |
| 124 | 6.500 | 125 | 2.100 | 126 | 0.110 | 127 | 0.140 |
| 128 | 0.410 | 129 | 0.120 | 130 | 0.760 | 131 | 0.260 |
| 132 | 0.970 | 133 | 0.700 | 134 | 0.840 | 135 | 0.850 |
| 136 | 0.380 | 137 | 0.400 | 138 | 0.054 | 139 | 0.170 |
| 140 | 0.130 | 141 | 0.360 | 142 | 0.330 | 143 | 0.470 |
| 144 | 2.600 | 145 | 0.040 | 146 | 0.022 | 147 | 0.800 |
| 148 | 0.580 | 149 | 0.050 | 150 | 0.016 | 151 | 0.360 |
| 152 | 0.059 | 153 | 0.100 | 154 | 0.110 | 155 | 0.034 |
| 156 | 0.140 | 157 | 0.079 | 158 | 0.056 | 159 | 0.160 |
| 160 | >1.1 | 161 | >1.1 | 162 | 0.064 | 163 | 0.013 |
| 164 | 0.900 | 165 | 0.110 | 166 | 1.000 | 167 | 2.300 |
| 168 | 0.096 | 169 | 0.073 | 170 | 0.059 | 171 | 0.071 |
| 172 | 0.009 | 173 | 0.110 | 174 | 0.091 | 175 | 0.016 |
| 176 | 0.071 | 177 | 0.089 | 178 | 0.042 | 179 | 0.007 |
| 180 | <0.005 | 181 | 0.006 | 182 | 0.018 | 183 | 0.013 |
| 184 | 0.350 | 185 | 0.072 | 186 | 0.039 | 187 | 0.100 |
| 188 | 0.056 | 189 | >10 | 190 | >1.1 | 191 | 2.200 |
| 193 | 0.990 | 194 | >1.1 | 195 | 0.035 | 196 | 0.084 |
| 197 | 0.065 | 198 | 0.046 | 199 | 0.340 | 200 | 0.280 |
| 201 | 0.064 | 202 | 0.014 | 203 | 0.023 | 204 | 0.095 |
| 205 | 0.310 | 206 | 0.190 | 207 | >1.1 | 208 | 0.220 |
| 209 | 0.053 | 210 | 0.280 | 211 | 0.050 | 212 | 0.075 |
| 213 | 0.025 | 214 | 0.990 | 215 | 0.006 | 216 | 1.100 |
| 217 | >1.1 | 218 | 7.700 | 219 | 0.190 | 220 | 0.013 |
| 221 | 0.011 | 222 | >1.1 | 223 | 0.170 | 224 | 0.270 |
| 225 | >10 | 226 | >10 | 227 | >10 | 228 | >10 |
| 229 | 5.400 | 230 | 2.700 | 231 | >10 | 232 | >10 |
| 233 | >10 | 234 | 1.560 | 235 | >10 | 236 | 2.700 |
| 237 | 0.610 | 238 | 2.400 | 239 | 8.300 | 240 | >10 |
| 241 | 5.400 | 242 | 4.000 | 243 | 6.400 | 244 | >10 |
| 245 | 4.900 | 246 | 9.200 | 247 | 3.700 | 248 | 9.600 |
| 249 | >10 | 250 | >10 | 251 | >10 | 252 | >10 |
| 253 | 8.500 | 254 | >10 | 255 | >10 | 256 | >10 |
| 257 | 2.800 | 258 | 5.200 | 259 | 2.000 | 260 | 4.100 |
| 261 | 2.900 | 262 | 9.800 | 263 | 8.000 | 264 | 6.200 |
| 265 | >10 | 266 | >10 | 267 | 3.200 | 268 | >10 |
| 269 | 4.100 | 270 | 1.010 | 271 | 8.600 | 272 | 2.600 |
| 273 | 4.100 | 274 | >10 | 275 | 9.000 | 276 | 1.300 |
| 277 | 1.800 | 278 | 5.900 | 279 | >10 | 280 | 2.700 |
| 281 | >10 | 282 | >10 | 283 | >10 | 284 | 3.100 |
| 285 | 3.300 | 286 | >10 | 287 | >10 | 288 | >10 |
| 289 | >10 | 290 | >10 | 291 | 8.100 | 292 | >10 |
| 293 | 4.600 | 294 | 3.500 | 295 | >10 | 296 | >10 |
| 297 | 8.600 | 298 | >10 | 299 | >10 | 300 | >10 |
| 301 | 3.900 | 302 | 2.500 | 303 | 0.720 | 304 | >10 |
| 305 | 0.072 | 306 | 1.700 | 307 | 4.800 | 308 | >10 |
| 309 | 5.900 | 310 | 3.200 | 311 | 6.700 | 312 | 1.300 |
| 313 | 3.700 | 314 | 3.700 | 315 | 3.000 | 316 | 7.000 |
| 317 | 0.370 | 318 | >10 | 319 | >10 | 320 | >10 |
| 321 | >10 | 322 | 0.021 | 323 | 0.063 | 324 | 0.480 |
| 325 | 0.160 | 326 | 0.140 | 327 | 0.088 | 328 | 0.340 |
| 329 | 0.008 | 330 | 0.011 | 331 | 0.150 | 332 | 0.170 |
| 333 | 0.015 | 334 | 0.140 | 335 | >1.1 | 336 | 0.210 |
| 337 | 0.940 | 338 | >1.1 | 339 | 0.560 | 340 | >1.1 |
| 341 | 6.200 | 342 | 5.000 | 343 | 2.800 | 344 | 0.014 |
| 345 | 3.500 | 346 | 0.463 | 347 | 7.900 | 348 | 7.200 |
| 349 | 2.300 | 350 | 6.500 | 351 | >10 | 352 | 7.600 |
| 353 | 2.400 | 354 | 5.700 | 355 | 1.800 | 356 | 9.900 |
| 357 | 6.600 | 358 | 8.000 | 359 | >10 | 360 | >10 |
| 361 | >10 | 362 | 2.600 | 363 | 2.400 | 364 | >10 |
| 365 | 2.800 | 366 | 6.200 | 367 | 7.400 | 368 | 9.800 |
| 369 | 3.800 | 370 | 0.600 | 371 | 7.800 | 372 | 3.500 |
| 373 | 4.400 | 374 | 9.900 | 375 | 1.100 | 376 | 7.700 |
| 377 | >10 | 378 | >10 | 379 | >10 | 380 | >10 |
| 381 | >10 | 382 | 3.800 | 383 | 4.300 | 384 | >10 |
| 385 | >10 | 386 | 8.000 | 387 | 3.500 | 388 | 8.200 |
| 389 | 9.100 | 390 | 2.500 | 391 | >10 | 392 | 8.300 |
| 393 | >10 | 394 | >10 | 395 | >10 | 396 | 8.900 |
| 397 | 5.800 | 398 | 2.600 | 399 | >10 | 400 | >10 |
| 401 | 8.000 | 402 | >10 | 403 | >10 | 404 | >10 |
| 405 | 8.600 | 406 | >10 | 407 | >10 | 408 | >10 |
| 409 | >10 | 410 | >10 | 411 | >10 | 412 | >10 |
| 413 | >10 | 414 | 9.600 | 415 | >10 | 416 | 9.000 |
| 417 | >10 | 418 | 1.600 | 419 | 1.000 | 420 | 1.700 |
| 421 | 1.100 | 422 | 2.100 | 423 | 1.100 | 424 | 0.500 |
| 425 | 1.300 | 426 | 0.300 | 427 | 0.410 | 428 | 1.400 |
| 429 | 0.350 | 430 | 0.006 | 431 | 0.034 | 432 | 0.073 |
| 433 | 0.010 | 434 | >10 | 435 | >10 | 436 | >10 |
| 437 | >10 | 438 | 0.420 | 439 | 0.150 | 440 | 0.021 |
| 441 | 0.012 | 442 | 0.036 | 443 | 0.039 | 444 | 0.240 |
| 445 | 0.074 | 446 | 0.130 | 447 | 0.490 | 448 | 0.350 |
| 449 | 0.022 | 450 | 0.099 | 451 | 0.510 | 452 | 0.330 |
| 453 | 0.350 | 454 | 0.830 | 455 | 0.220 | 456 | 0.300 |
| 457 | 0.370 | 458 | 0.330 | 459 | 0.790 | 460 | 0.230 |
| 461 | 0.240 | 462 | 0.330 | 463 | 0.270 | 464 | 0.310 |
| 465 | 0.063 | 466 | 0.079 | 467 | 0.039 | 468 | 0.040 |
| 469 | 0.120 | 470 | 0.067 | 471 | 0.110 | 472 | 0.370 |
| 473 | 0.015 | 474 | 0.059 | 475 | >1.1 | 476 | 0.022 |
| 477 | 0.013 | 478 | 0.018 | 479 | 0.008 | 480 | 0.010 |
| 481 | 0.036 | 482 | 0.013 | 483 | 0.020 | 484 | 0.037 |
| 485 | >1.1 | 486 | 0.083 | 487 | 0.036 | 488 | 2.500 |
| 489 | 0.110 | | | | | | |

TABLE 40

| Ex. | IC$_{50}$ (μM) MDA-MB-231 | Ex. | IC$_{50}$ (μM) MDA-MB-231 | Ex. | IC$_{50}$ (μM) MDA-MB-231 | Ex. | IC$_{50}$ (μM) MDA-MB-231 |
|---|---|---|---|---|---|---|---|
| 1 | 0.230 | 2 | 0.140 | 3 | 0.090 | 4 | 0.052 |
| 5 | 1.200 | 6 | >10 | 7 | 0.350 | 8 | 0.018 |
| 9 | 0.012 | 10 | 0.180 | 11 | 0.060 | 12 | 0.034 |
| 13 | 0.030 | 14 | 0.062 | 15 | 0.068 | 16 | 0.025 |
| 17 | 0.190 | 18 | 8.700 | 19 | 0.088 | 20 | 0.150 |
| 21 | 0.054 | 22 | 0.007 | 23 | 0.028 | 24 | 0.027 |
| 25 | 3.200 | 26 | 0.008 | 27 | 0.033 | 28 | 1.000 |
| 29 | 0.470 | 30 | 0.370 | 31 | 0.026 | 32 | 0.021 |
| 33 | 0.003 | 34 | 0.007 | 35 | 0.027 | 36 | 0.005 |
| 37 | 0.016 | 38 | 0.049 | 39 | 0.050 | 40 | 0.006 |
| 41 | 0.024 | 42 | 0.005 | 43 | 3.600 | 44 | 4.000 |
| 45 | 0.380 | 46 | 0.029 | 47 | 0.006 | 48 | 0.002 |
| 49 | 0.001 | 50 | 0.240 | 51 | 0.620 | 52 | 0.700 |
| 53 | 0.022 | 54 | 0.036 | 55 | 0.081 | 68 | 0.041 |
| 98 | 0.590 | 107 | 0.290 | 108 | 0.073 | 109 | 0.090 |
| 110 | 3.300 | 111 | 6.300 | 112 | >10 | 113 | 6.400 |
| 115 | 1.500 | 116 | 0.055 | 117 | 2.200 | 118 | 8.600 |
| 119 | 6.100 | 224 | 0.033 | 236 | 0.410 | 237 | 0.010 |
| 238 | 0.550 | 239 | >10 | 240 | >10 | 241 | 2.700 |
| 242 | 0.540 | 243 | 1.600 | 245 | 2.600 | 246 | 3.500 |
| 260 | 0.920 | 269 | 2.100 | 270 | 0.700 | 275 | >10 |
| 293 | 1.000 | 301 | 0.720 | 302 | 0.110 | 303 | 0.020 |
| 304 | 5.300 | 305 | 0.001 | 306 | 0.370 | 307 | 0.840 |
| 308 | 8.100 | 309 | 1.200 | 310 | 0.390 | 311 | 1.000 |
| 312 | 0.220 | 313 | 0.140 | 314 | 0.370 | 316 | 4.600 |
| 317 | 0.019 | 318 | >10 | 319 | >10 | 320 | >10 |
| 321 | >10 | 341 | 7.500 | 342 | 0.520 | 344 | 0.100 |
| 346 | 0.180 | 347 | 0.610 | 348 | >10 | 349 | 0.320 |
| 350 | 2.300 | 351 | 9.900 | 352 | 2.400 | 353 | 0.440 |
| 354 | 0.710 | 355 | 0.280 | 356 | 3.300 | 357 | 1.200 |
| 358 | 1.200 | 359 | 2.600 | 360 | 1.800 | 361 | >10 |

TABLE 40-continued

| Ex. | IC$_{50}$ (μM) MDA-MB-231 | Ex. | IC$_{50}$ (μM) MDA-MB-231 | Ex. | IC$_{50}$ (μM) MDA-MB-231 | Ex. | IC$_{50}$ (μM) MDA-MB-231 |
|---|---|---|---|---|---|---|---|
| 362 | 0.690 | 363 | 0.880 | 364 | >10 | 365 | 0.320 |
| 366 | 0.580 | 367 | 1.100 | 368 | 1.700 | 369 | 0.280 |
| 370 | 0.032 | 371 | 1.400 | 372 | 0.460 | 373 | 1.000 |
| 374 | 2.700 | 375 | 0.028 | 376 | 1.300 | 382 | 0.910 |
| 383 | 2.330 | 384 | >10 | 387 | 1.170 | 390 | 1.100 |
| 391 | 3.300 | 393 | 5.000 | 395 | 4.200 | 396 | 1.200 |
| 397 | 2.800 | 398 | 1.200 | 399 | 3.400 | 400 | 3.500 |
| 401 | 2.500 | 415 | 8.400 | 416 | 2.600 | 417 | >10 |
| 421 | 0.089 | 422 | 0.540 | 423 | 0.094 | 424 | 0.100 |
| 425 | 0.380 | 426 | 0.074 | 427 | 0.085 | 428 | 0.390 |
| 429 | 0.086 | 434 | 2.900 | 435 | 4.300 | 436 | 4.700 |
| 437 | >10 | | | | | | |

TABLE 41

| Ex. | IC$_{50}$ (μM) AGS | Ex. | IC$_{50}$ (μM) AGS | Ex. | IC$_{50}$ (μM) AGS | Ex. | IC$_{50}$ (μM) AGS |
|---|---|---|---|---|---|---|---|
| 16 | 0.044 | 36 | 0.009 | 225 | >50 | 226 | 6.9 |
| 227 | 30.0 | 228 | 41.4 | 229 | 16.1 | 230 | 17.6 |
| 231 | 19.3 | 232 | 20.5 | 233 | >50 | 234 | 1.6 |
| 235 | 37.0 | 244 | 30.6 | 247 | >50 | 248 | 15.7 |
| 249 | 8.4 | 250 | 22.0 | 251 | 26.7 | 252 | 11.4 |
| 253 | 7.6 | 254 | >50 | 255 | 18.1 | 256 | >50 |
| 257 | 11.0 | 258 | 16.3 | 260 | 2.7 | 261 | 28.4 |
| 262 | >50 | 263 | >50 | 264 | 13.0 | 265 | 11.4 |
| 266 | 8.5 | 267 | 9.2 | 268 | 27.1 | 271 | 26.1 |
| 272 | 18.8 | 273 | 10.0 | 274 | 17.9 | 275 | 5.7 |
| 276 | 11.9 | 277 | 2.1 | 278 | 20.0 | 279 | 40.7 |
| 280 | 2.7 | 281 | 16.6 | 282 | 23.8 | 283 | 18.2 |
| 284 | 11.3 | 285 | 13.6 | 286 | 10.2 | 287 | 23.6 |
| 288 | >50 | 289 | 32.0 | 290 | 20.9 | 291 | 13.9 |
| 292 | 43.7 | 293 | 24.6 | 294 | 16.1 | 295 | >50 |
| 296 | >50 | 297 | 21.6 | 298 | 31.7 | 299 | 43.1 |
| 300 | >50 | 301 | 5.7 | 315 | 25.9 | 341 | 5.3 |
| 342 | 9.6 | 343 | 5.8 | 345 | 6.9 | 347 | 19.7 |
| 348 | 4.8 | 366 | 8.9 | 367 | 9.5 | 368 | 11.5 |
| 377 | 15.2 | 378 | 39.9 | 379 | 30.1 | 380 | 42.6 |
| 381 | >50 | 385 | 26.3 | 386 | 7.6 | 388 | 9.8 |
| 389 | 20.3 | 390 | 9.6 | 391 | 18.1 | 392 | 9.0 |
| 393 | 10.3 | 394 | 20.0 | 395 | 20.6 | 396 | 11.8 |
| 397 | 8.7 | 398 | 5.2 | 399 | 13.2 | 400 | 14.9 |
| 401 | 7.3 | 402 | 22.1 | 403 | 34.4 | 404 | 30.3 |
| 405 | 14.6 | 406 | 17.6 | 407 | 45.5 | 408 | 24.2 |
| 409 | 17.3 | 410 | 31.3 | 411 | 35.2 | 412 | 22.0 |
| 413 | >50 | 414 | 14.4 | | | | |

TABLE 42

| Ex. | IC$_{50}$ (μM) DU-145 | Ex. | IC$_{50}$ (μM) DU-145 | Ex. | IC$_{50}$ (μM) DU-145 | Ex. | IC$_{50}$ (μM) DU-145 |
|---|---|---|---|---|---|---|---|
| 9 | 0.035 | 15 | 0.250 | 16 | 0.024 | 19 | 0.150 |
| 21 | 0.190 | 22 | 0.048 | 24 | 0.044 | 32 | 0.044 |
| 33 | 0.037 | 34 | 0.023 | 35 | 0.060 | 36 | 0.006 |
| 42 | 0.009 | 43 | 4.900 | 48 | 0.008 | 49 | 0.007 |
| 50 | 0.360 | 54 | 0.046 | 56 | 0.069 | 57 | 0.047 |
| 58 | 0.006 | 59 | 0.039 | 60 | 0.170 | 61 | 0.060 |
| 62 | 0.016 | 63 | 0.010 | 64 | 0.043 | 65 | 0.005 |
| 66 | >1.1 | 67 | 0.042 | 68 | 0.006 | 69 | 0.052 |
| 70 | 0.120 | 71 | 0.048 | 72 | 0.006 | 73 | 0.006 |
| 74 | 2.600 | 75 | 0.003 | 76 | 0.340 | 77 | 0.050 |
| 78 | 0.009 | 79 | 0.008 | 80 | 0.010 | 81 | 0.110 |
| 82 | 0.008 | 83 | 0.012 | 84 | 0.002 | 85 | 0.007 |
| 86 | 0.047 | 87 | 0.009 | 88 | 0.008 | 89 | 0.048 |
| 90 | 0.048 | 91 | 0.012 | 92 | 0.017 | 93 | 0.021 |
| 94 | 0.200 | 95 | 0.011 | 96 | >1.1 | 97 | 0.170 |
| 98 | 0.310 | 99 | 0.800 | 100 | 0.330 | 101 | 0.440 |

TABLE 42-continued

| Ex. | IC$_{50}$ (μM) DU-145 | Ex. | IC$_{50}$ (μM) DU-145 | Ex. | IC$_{50}$ (μM) DU-145 | Ex. | IC$_{50}$ (μM) DU-145 |
|---|---|---|---|---|---|---|---|
| 102 | >1.1 | 103 | 0.045 | 104 | 0.580 | 105 | 0.001 |
| 106 | 0.031 | 114 | 0.014 | 115 | 1.700 | 116 | 0.058 |
| 117 | 1.200 | 120 | 2.200 | 121 | 0.710 | 122 | 0.049 |
| 123 | 0.042 | 124 | 2.100 | 125 | 0.460 | 126 | 0.110 |
| 127 | 0.066 | 128 | 0.150 | 129 | 0.060 | 130 | 0.170 |
| 131 | 0.100 | 132 | 0.410 | 133 | 0.220 | 134 | 0.160 |
| 135 | 0.300 | 136 | 0.051 | 137 | 0.100 | 138 | 0.018 |
| 139 | 0.073 | 140 | 0.053 | 141 | 0.140 | 142 | 0.090 |
| 143 | 0.180 | 144 | 1.000 | 145 | 0.060 | 146 | 0.019 |
| 147 | 0.470 | 148 | 0.380 | 149 | 0.030 | 150 | 0.008 |
| 151 | >1.1 | 152 | 0.047 | 153 | 0.150 | 154 | 0.170 |
| 155 | 0.061 | 156 | 0.250 | 157 | 0.060 | 158 | 0.048 |
| 159 | 0.140 | 160 | >1.1 | 161 | 0.720 | 162 | 0.052 |
| 163 | 0.016 | 164 | >1.1 | 165 | 0.070 | 166 | 0.410 |
| 167 | >1.1 | 168 | 0.130 | 169 | 0.021 | 170 | 0.005 |
| 171 | 0.038 | 172 | 0.005 | 173 | 0.009 | 174 | 0.033 |
| 175 | 0.005 | 176 | 0.038 | 177 | 0.058 | 178 | 0.024 |
| 179 | 0.004 | 180 | <0.005 | 181 | 0.005 | 182 | 0.005 |
| 183 | 0.005 | 184 | 0.040 | 185 | 0.007 | 186 | 0.023 |
| 187 | 0.042 | 188 | 0.026 | 189 | >1.1 | 190 | >1.1 |
| 191 | 0.740 | 193 | 0.390 | 194 | >1.1 | 195 | 0.007 |
| 196 | 0.022 | 197 | 0.016 | 198 | 0.017 | 199 | 0.150 |
| 200 | 0.190 | 201 | 0.018 | 202 | 0.007 | 203 | 0.008 |
| 204 | 0.017 | 205 | 0.063 | 206 | 0.051 | 207 | >1.1 |
| 208 | 0.080 | 209 | 0.027 | 210 | 0.073 | 211 | 0.014 |
| 212 | 0.022 | 213 | 0.011 | 214 | 0.300 | 215 | 0.002 |
| 216 | 0.300 | 217 | 0.580 | 218 | >1.1 | 219 | 0.180 |
| 220 | 0.007 | 221 | 0.008 | 222 | >1.1 | 223 | 0.005 |
| 302 | 0.570 | 305 | 0.030 | 322 | 0.011 | 323 | 0.035 |
| 324 | 0.400 | 325 | 0.150 | 326 | 0.064 | 327 | 0.034 |
| 328 | 0.390 | 329 | 0.004 | 330 | 0.005 | 331 | 0.034 |
| 332 | 0.042 | 333 | 0.004 | 334 | 0.059 | 335 | >1.1 |
| 336 | 0.065 | 337 | 0.430 | 338 | 0.430 | 339 | 0.310 |
| 340 | >1.1 | 346 | 0.370 | 418 | 0.980 | 419 | 0.650 |
| 420 | 0.950 | 426 | 0.130 | 430 | 0.006 | 431 | 0.038 |
| 432 | 0.060 | 433 | 0.006 | 438 | 0.160 | 439 | 0.089 |
| 440 | 0.012 | 441 | 0.026 | 442 | 0.013 | 443 | 0.020 |
| 444 | 0.130 | 445 | 0.055 | 446 | 0.065 | 447 | 0.140 |
| 448 | 0.160 | 449 | 0.010 | 450 | 0.060 | 451 | 0.190 |
| 452 | 0.027 | 453 | 0.018 | 454 | 0.059 | 455 | 0.190 |
| 456 | 0.250 | 457 | 0.440 | 458 | 0.170 | 459 | 0.590 |
| 460 | 0.130 | 461 | 0.110 | 462 | 0.130 | 463 | 0.150 |
| 464 | 0.160 | 465 | 0.048 | 466 | 0.063 | 467 | 0.048 |
| 468 | 0.028 | 469 | 0.086 | 470 | 0.043 | 471 | 0.049 |
| 472 | 0.130 | 473 | 0.015 | 474 | 0.022 | 475 | >1.1 |
| 476 | 0.005 | 477 | 0.010 | 478 | 0.012 | 479 | 0.006 |
| 480 | 0.007 | 481 | 0.008 | 482 | 0.005 | 483 | 0.010 |
| 484 | 0.021 | 485 | 0.380 | 486 | 0.048 | 487 | 0.025 |
| 488 | 1.100 | 489 | 0.031 | | | | |

TABLE 43

| Ex. | IC$_{50}$ (μM) U-266 | Ex. | IC$_{50}$ (μM) U-266 | Ex. | IC$_{50}$ (μM) U-266 | Ex. | IC$_{50}$ (μM) U-266 |
|---|---|---|---|---|---|---|---|
| 9 | 0.740 | 16 | 0.250 | 22 | 0.130 | 24 | 0.130 |
| 34 | 0.290 | 36 | 0.220 | 42 | 0.023 | 48 | 0.044 |
| 49 | 0.014 | 50 | 0.840 | 56 | 0.430 | 57 | 0.330 |
| 58 | 0.005 | 59 | 0.160 | 61 | 0.220 | 68 | 0.019 |
| 69 | 0.140 | 70 | 0.460 | 71 | 0.170 | 72 | 0.100 |
| 73 | 0.058 | 75 | 0.021 | 77 | 0.220 | 80 | 0.063 |
| 82 | 0.045 | 98 | 0.560 | 116 | 0.160 | 122 | 0.180 |
| 123 | 0.130 | 127 | 0.430 | 129 | 0.280 | 130 | 0.740 |

TABLE 44

| Ex. | IC$_{50}$ (μM) HEL92.1.7 | Ex. | IC$_{50}$ (μM) HEL92.1.7 | Ex. | IC$_{50}$ (μM) HEL92.1.7 | Ex. | IC$_{50}$ (μM) HEL92.1.7 |
|---|---|---|---|---|---|---|---|
| 9 | 0.950 | 15 | 1.800 | 16 | 0.140 | 22 | 0.130 |
| 24 | 0.120 | 34 | 0.200 | 35 | 0.280 | 36 | 0.270 |
| 42 | 0.044 | 48 | 0.026 | 49 | 0.023 | 50 | 0.830 |
| 56 | 0.300 | 57 | 0.180 | 58 | 0.074 | 59 | 0.420 |
| 61 | 0.140 | 64 | 0.110 | 66 | >1.1 | 67 | 0.110 |
| 68 | 0.024 | 69 | 0.090 | 70 | 0.360 | 71 | 0.130 |
| 72 | 0.087 | 73 | 0.056 | 75 | 0.020 | 77 | 0.068 |
| 80 | 0.057 | 81 | 0.340 | 82 | 0.048 | 83 | 0.100 |
| 84 | 0.014 | 85 | 0.076 | 86 | 0.230 | 87 | 0.091 |
| 88 | 0.087 | 89 | 0.220 | 90 | 0.230 | 91 | 0.078 |
| 92 | 0.100 | 93 | 0.120 | 94 | 0.350 | 95 | 0.690 |
| 96 | >1.1 | 98 | 0.860 | 103 | 0.160 | 116 | 0.130 |
| 122 | 0.190 | 123 | 0.110 | 127 | 0.340 | 129 | 0.240 |
| 130 | >1.1 | 138 | 0.260 | 139 | 0.690 | 140 | 0.300 |
| 141 | 1.050 | 142 | 0.330 | 143 | 0.480 | 144 | >1.1 |
| 145 | 0.160 | 146 | 0.320 | 147 | 1.040 | 148 | 1.000 |
| 149 | 0.140 | 150 | 0.031 | 151 | 4.700 | 152 | 0.210 |
| 153 | 0.390 | 154 | 0.340 | 155 | 0.130 | 156 | 0.740 |
| 157 | 0.230 | 158 | 0.220 | 162 | 0.200 | 163 | 0.019 |
| 164 | >1.1 | 166 | >1.1 | 167 | >1.1 | 168 | 0.390 |
| 169 | 0.090 | 189 | >1.1 | 190 | >1.1 | 194 | >1.1 |
| 195 | 0.029 | 196 | 0.120 | 199 | 0.680 | 200 | 0.300 |
| 201 | 0.053 | 202 | 0.013 | 203 | 0.017 | 204 | 0.050 |
| 205 | 0.580 | 206 | 0.350 | 207 | >1.1 | 208 | 0.330 |
| 209 | 0.099 | 210 | 0.570 | 211 | 0.066 | 212 | 0.081 |
| 214 | >1.1 | 215 | 0.007 | 216 | 0.950 | 217 | >1.1 |
| 218 | >1.1 | 219 | 0.900 | 270 | 1.700 | 302 | 2.700 |
| 305 | 0.240 | 322 | 0.049 | 323 | 0.097 | 324 | 0.830 |
| 325 | 0.390 | 326 | 0.260 | 327 | 0.082 | 328 | 0.500 |
| 329 | 0.009 | 330 | 0.057 | 344 | 0.490 | 346 | 1.300 |
| 418 | 2.200 | 419 | 1.800 | 420 | 2.400 | 430 | 0.014 |
| 431 | 0.007 | 438 | 0.480 | 439 | 0.640 | 440 | 0.085 |
| 444 | 0.650 | 445 | 0.150 | | | | |

TABLE 45

| Ex. | IC$_{50}$ (μM) MDA-MB-468 | IC$_{50}$ (μM) ACHN | IC$_{50}$ (μM) HCT-116 | IC$_{50}$ (μM) Hep3B | IC$_{50}$ (μM) SW626 | IC$_{50}$ (μM) NCI-H23 | IC$_{50}$ (μM) BT-549 |
|---|---|---|---|---|---|---|---|
| 16 | 0.020 | 0.004 | 0.310 | 2.100 | 0.066 | 0.300 | 0.260 |
| 34 | <0.00064 | — | — | 0.028 | — | — | 3.400 |
| 36 | <0.0076 | <0.00085 | <0.072 | 2.200 | 0.013 | <0.210 | 0.043 |
| 346 | 0.140 | 0.370 | 1.500 | 2.200 | 0.290 | 1.700 | 1.000 |

TABLE 46

| Ex. | IC$_{50}$ (μM) NCI-H508 | IC$_{50}$ (μM) SW1417 | IC$_{50}$ (μM) HCC1500 | IC$_{50}$ (μM) MDA-MB-361 | IC$_{50}$ (μM) NCI-H661 | IC$_{50}$ (μM) NCI-H1650 | IC$_{50}$ (μM) Raji | IC$_{50}$ (μM) IM-9 | IC$_{50}$ (μM) C-33A |
|---|---|---|---|---|---|---|---|---|---|
| 346 | 0.22 | 0.35 | 1.03 | 0.28 | 0.09 | 0.62 | 0.57 | 0.51 | 0.30 |

As shown in Tables 39 to 46, the compounds according to the present invention exhibited excellent inhibitory effects against the growth of various kinds of cancer cells.

While the invention has been described with respect to the above specific embodiments, it should be recognized that various modifications and changes may be made to the invention by those skilled in the art which also fall within the scope of the invention as defined by the appended claims.

What is claimed is:

1. A compound selected from the group consisting of a heterocyclic derivative represented by formula (I), and a pharmaceutically acceptable salt and a stereoisomer thereof:

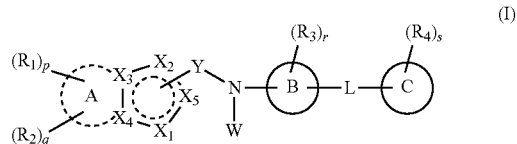

wherein

A is a saturated or unsaturated $C_{3-10}$ carbocycle or a 5- to 10-membered heterocycle;

B is a benzene or a 5- to 12-membered heterocycle;

C is a benzene, a 5- to 6-membered heterocycle, or $C_{3-6}$ carbocycle;

Y is —C(═O)— connected to $X_2$ or $X_5$;
$X_1$ is —O—, —S—, —S(═O)—, —S(═O)$_2$—, or —N(W$_1$)—;
$X_2$ is a carbon atom connected to Y, or —N═, —NH—, —C(W$_2$)═ or —CH(W$_2$)— not connected to Y;
$X_3$ and $X_4$ are each independently a carbon or nitrogen atom;
$X_5$ is a carbon atom connected to Y, or —CH═ not connected to Y;
wherein the 5-membered ring comprising $X_1$ to $X_5$ is aromatic or non-aromatic;
W is hydrogen, halogen, $C_{1-6}$ alkyl, or 5- or 6-membered heterocyclyl-$C_{1-3}$ alkyl;
$W_1$ is hydrogen, $C_{1-6}$ alkyl, $C_{1-6}$ alkoxycarbonyl, or 5- to 8-membered heterocyclyl-$C_{1-4}$ alkyl;
$W_2$ is hydrogen, halogen, $C_{1-6}$ alkyl, or 5- to 8-membered heterocyclyl-$C_{1-4}$ alkyl;
L is —(CR$_9$R$_{10}$)$_m$—, —O—, —NH—, —N(C$_{1-6}$ alkyl)-, —S(═O)$_2$—, —C(CH$_2$)—, or $C_{3-7}$ cycloalkylene, wherein m is an integer of 0 to 3, and $R_9$ and $R_{10}$ are each independently hydrogen, hydroxy, halogen, or $C_{1-6}$ alkyl, wherein when $R_9$ and $R_{10}$ are both hydrogen, —(CR$_9$R$_{10}$)$_m$— is —(CH$_2$)$_2$— or —(CH$_2$)$_3$—;
$R_1$ is nitro, amino, $C_{1-6}$ alkylsulfonyl, haloC$_{1-6}$ alkoxy, or any one of the following structural formulae i) to iv):

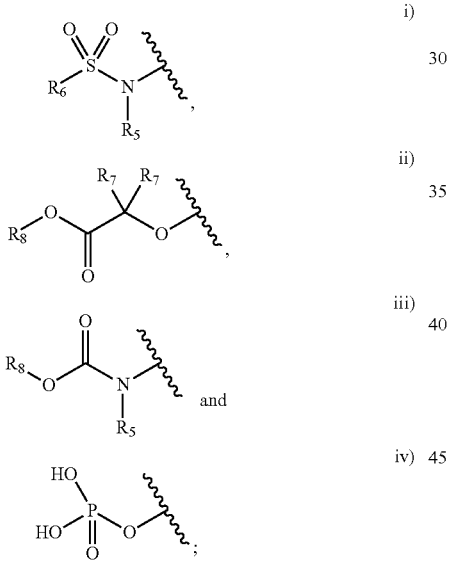

$R_2$ is hydrogen, halogen, nitro, amino, $C_{1-6}$alkoxy, haloC$_{1-6}$alkoxy, $C_{1-6}$ alkylsulfonyl, or 5- or 6-membered heterocycloalkyl;
$R_3$ is hydrogen, halogen, cyano, $C_{1-6}$ alkyl, haloC$_{1-6}$ alkyl, cyanoC$_{1-6}$ alkyl, $C_{1-6}$ alkylcarbonyl, $C_{1-6}$ alkoxy, haloC$_{1-6}$ alkoxy, cyanoC$_{1-6}$ alkoxy, $C_{1-6}$ alkylamino, diC$_{1-6}$ alkylamino, $C_{1-6}$ alkylthio, $C_{1-6}$ alkylaminocarbonyl, diC$_{1-6}$ alkylaminocarbonyl, $C_{2-8}$ alkynyl, $C_{6-10}$ aryl, haloC$_{6-10}$ aryl, 5- to 10-membered heterocyclyl, or 5- to 10-membered heterocyclylcarbonyl, wherein the heterocyclyl moiety is optionally substituted with one to three substituents selected from the group consisting of halogen, hydroxy, cyano, amino, $C_{1-6}$ alkyl, haloC$_{1-6}$ alkyl, $C_{1-6}$ alkoxy and $C_{1-6}$ alkoxycarbonyl;
$R_4$ is hydrogen, halogen, hydroxy, cyano, nitro, amino, oxo, aminosulfonyl, sulfonylamido, $C_{1-6}$ alkylamino, $C_{1-6}$ alkyl, haloC$_{1-6}$ alkyl, cyanoC$_{1-6}$ alkyl, $C_{1-6}$ alkoxy, haloC$_{1-6}$ alkoxy, cyanoC$_{1-6}$ alkoxy, $C_{3-8}$cycloalkyl-oxy, $C_{2-8}$ alkynyl, $C_{1-6}$ alkylamino-$C_{1-6}$ alkoxy, diC$_{1-6}$ alkylamino-$C_{1-6}$ alkoxy, $C_{1-6}$ alkoxy-carbonyl, carbamoyl, carbamoyl-$C_{1-6}$ alkoxy, $C_{1-6}$ alkylthio, $C_{1-6}$ alkylsulfinyl, $C_{1-6}$ alkylsulfonyl, 5- to 10-membered heterocyclyl, 5- to 10-membered heterocyclyl-$C_{1-6}$ alkyl, 5- to 10-membered heterocyclyl-$C_{1-6}$ alkoxy, or 5- to 10-membered heterocyclyl-oxy, wherein the heterocyclyl moiety is optionally substituted with one or two substituents selected from the group consisting of hydroxy, oxo, $C_{1-6}$ alkyl, $C_{1-6}$ alkylcarbonyl, $C_{1-6}$ alkoxycarbonyl, $C_{1-6}$ alkylsulfonyl, diC$_{1-3}$ alkylsulfonyl, $C_{1-6}$ alkylcarbonyl, $C_{1-6}$ alkylaminocarbonyl, diC$_{1-3}$ alkylaminocarbonyl, $C_{1-6}$ alkylaminosulfonyl, and non-substituted or $C_{1-6}$ alkyl-substituted 5- to 10-membered heterocyclyl;
$R_5$ is hydrogen, $C_{1-6}$ alkyl, carbamoylC$_{1-6}$ alkyl, $C_{1-6}$ alkylaminoC$_{1-6}$ alkyl, diC$_{1-6}$ alkylaminoC$_{1-6}$ alkyl, or 5- to 10-membered heterocyclylC$_{1-6}$ alkyl, or is fused with $R_6$ to form $C_{3-4}$ alkylene;
$R_6$ is $C_{1-6}$ alkyl, haloC$_{1-6}$ alkyl, $C_{1-6}$ alkoxyC$_{1-6}$ alkyl, $C_{1-6}$ alkylcarbonylC$_{1-6}$ alkyl, $C_{2-7}$ alkenyl, amino, aminoC$_{1-6}$ alkyl, $C_{3-7}$ cycloalkyl, 5- to 10-membered heterocyclyl, or 5- to 10-membered heterocyclyl-$C_{1-6}$ alkyl, or is fused with $R_5$ to form $C_{3-4}$ alkylene, wherein the amino moiety is optionally substituted with one or two substituents selected from hydroxy or $C_{1-6}$ alkyl, and the heterocyclyl moiety is optionally substituted with one to four substituents selected from the group consisting of oxo, $C_{1-6}$ alkyl and $C_{1-6}$ alkylcarbonyl;
$R_7$ and $R_8$ are each independently hydrogen or $C_{1-6}$ alkyl;
p is 1 and q is independently 0 or 1;
r is an integer of 0 to 3, and, when r is 2 or higher, $R_3$ moieties are the same or different; and
s is an integer of 0 to 3, and, when s is 2 or higher, $R_4$ moieties are the same or different;
all of said heterocycle or heterocyclyl moieties each independently have a saturated or unsaturated single or multiple ring and contain one to three heteroatoms selected from N, O or S; and
all of said aryl moieties each independently have an aromatic single or multiple ring,
wherein when L is —O—, r is an integer of 1 to 3 and $R_3$ is not hydrogen, and wherein when L is —NH—, $R_4$ is halogen.

2. The compound according to claim 1, wherein
A is a saturated or unsaturated $C_{3-10}$ carbocycle, or a 5- to 10-membered heterocycle containing one to three heteroatoms selected from N, O or S;
B is benzene or a 5- to 12-membered heterocycle containing one to three N atoms;
C is benzene, or a 5- to 6-membered heterocycle containing one to three heteroatoms selected from N, O or S;
Y is —C(═O)— connected to $X_5$;
$X_1$ is —O—, —S—, —S(═O)—, —S(═O)$_2$—, or —N(W$_1$)—;
$X_2$ is —N═, —C(W$_2$)═ or —CH(W$_2$)— not connected to Y;
$X_3$ and $X_4$ are a carbon atom;
$X_5$ is a carbon atom connected to Y;
wherein the 5-membered ring comprising $X_1$ to $X_5$ is aromatic or non-aromatic;
W is hydrogen, halogen, or $C_{1-6}$ alkyl;
$W_1$ is hydrogen, $C_{1-6}$ alkyl, $C_{1-6}$ alkoxycarbonyl, or 5- to 8-membered heterocycloalkyl-$C_{1-4}$ alkyl containing one or two heteroatoms selected from N or O;

$W_2$ is hydrogen, $C_{1-6}$ alkyl, or 5- to 8-membered heterocycloalkyl-$C_{1-4}$ alkyl containing one or two heteroatoms selected from N or O;

L is —(CR$_9$R$_{10}$)$_m$—, —NH—, —N(C$_{1-6}$ alkyl)-, —S(=O)$_2$—, —C(=CH$_2$)—, —O—, or $C_{3-7}$ cycloalkylene, wherein m is an integer of 0 to 3, and $R_9$ and $R_{10}$ are each independently hydrogen, hydroxy, halogen, or $C_{1-6}$ alkyl;

$R_1$ is amino, $C_{1-6}$ alkylsulfonyl, halo$C_{1-6}$ alkoxy, or any one of the following structural formulae i) to iv):

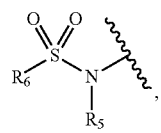

i)

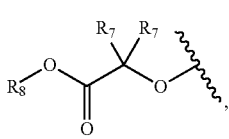

ii)

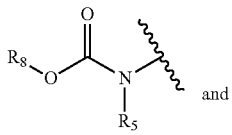

iii)

and

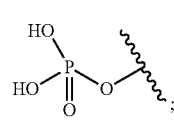

iv)

;

$R_2$ is hydrogen, halogen, $C_{1-6}$ alkoxy, halo$C_{1-6}$ alkoxy, or $C_{1-6}$ alkylsulfonyl;

$R_3$ is hydrogen, halogen, cyano, $C_{1-6}$ alkyl, halo$C_{1-6}$ alkyl, cyano$C_{1-6}$ alkyl, $C_{1-6}$ alkylcarbonyl, $C_{1-6}$ alkoxy, halo$C_{1-6}$ alkoxy, cyano$C_{1-6}$ alkoxy, $C_{1-6}$ alkylamino, di$C_{1-6}$ alkylamino, $C_{1-6}$ alkylthio, $C_{1-6}$ alkylaminocarbonyl, di$C_{1-6}$ alkylaminocarbonyl, $C_{2-8}$ alkynyl, $C_{6-10}$ aryl, 5- to 10-membered heteroaryl containing one or two heteroatoms selected from N or S, 5- to 10-membered heterocycloalkyl containing one or two heteroatoms selected from N or O, or 5- to 10-membered heterocycloalkyl-carbonyl containing one or two heteroatoms selected from N or O;

$R_4$ is hydrogen, halogen, hydroxy, cyano, nitro, amino, oxo, aminosulfonyl, sulfonylamido, $C_{1-6}$ alkylamino, $C_{1-6}$ alkyl, halo$C_{1-6}$ alkyl, cyano$C_{1-6}$ alkyl, $C_{1-6}$ alkoxy, halo$C_{1-6}$ alkoxy, cyano$C_{1-6}$ alkoxy, $C_{3-8}$ cycloalkyloxy, $C_{2-8}$ alkynyl, $C_{1-6}$ alkylamino-$C_{1-6}$ alkoxy, $C_{1-6}$ alkoxycarbonyl, carbamoyl, carbamoyl-$C_{1-6}$ alkoxy, $C_{1-6}$ alkylthio, $C_{1-6}$ alkylsulfonyl, 5- to 10-membered heterocyclyl-$C_{1-6}$ alkyl containing one or two heteroatoms selected from N or O, 5- to 10-membered heterocyclyl-$C_{1-6}$ alkoxy containing one or two heteroatoms selected from N or O, or 5- to 10-membered heterocyclyl-oxy containing one or two heteroatoms selected from N or O, wherein the heterocyclyl moiety is optionally substituted with one or two substituents selected from the group consisting of hydroxy, $C_{1-6}$ alkoxycarbonyl, $C_{1-6}$ alkylsulfonyl, $C_{1-6}$ alkylcarbonyl, $C_{1-6}$ alkylaminocarbonyl, $C_{1-6}$ alkylaminosulfonyl, and non-substituted or $C_{1-6}$ alkyl-substituted 5- to 10-membered heterocyclyl containing one or two heteroatoms selected from N, O or S;

$R_5$ is hydrogen, $C_{1-6}$ alkyl, carbamoyl$C_{1-6}$ alkyl, $C_{1-6}$ alkylamino-$C_{1-6}$ alkyl, or 5- to 10-membered heterocycloalkyl-$C_{1-6}$ alkyl containing one to three heteroatoms selected from N, O or S;

$R_6$ is $C_{1-6}$ alkyl, halo$C_{1-6}$ alkyl, $C_{1-6}$ alkoxy$C_{1-6}$ alkyl, $C_{1-6}$ alkylcarbonyl$C_{1-6}$ alkyl, $C_{2-7}$ alkenyl, amino, amino$C_{1-6}$ alkyl, $C_{3-7}$cycloalkyl, 5- to 10-membered heterocyclyl containing one to three heteroatoms selected from N, O or S, or 5- to 10-membered heterocyclyl$C_{1-6}$ alkyl containing one to three heteroatoms selected from N, O or S, wherein the amino moiety is optionally substituted with one or two substituents selected from hydroxy or $C_{1-6}$ alkyl, and the heterocyclyl moiety is optionally substituted with one to four substituents selected from the group consisting of $C_{1-6}$ alkyl and $C_{1-6}$ alkylcarbonyl;

$R_7$ and $R_8$ are each independently hydrogen or $C_{1-6}$ alkyl;

p is 1, and q is 0 or 1;

r is an integer of 0 to 3, and, when r is 2 or higher, $R_3$ moieties are the same or different; and s is an integer of 0 to 3, and, when s is 2 or higher, $R_4$ moieties are the same or different;

all of said heterocycle or heterocyclyl moieties each independently have a saturated or unsaturated single or multiple ring;

all of said heterocycloalkyl moieties each independently have a saturated single or multiple ring; and all of said aryl or heteroaryl moieties each independently have an aromatic single or multiple ring.

3. The compound according to claim 2, wherein,

A is a saturated or unsaturated $C_6$ carbocycle, or 6-membered heterocycle containing one to three N atoms, B is benzene, or a 5- to 10-membered heterocycle containing one to three N atoms, C is benzene, or a 5- to 6-membered heteroaryl containing one to three heteroatoms selected from N, O or S, L is —(CR$_9$R$_{10}$)$_m$—, —O—, —NH—, —N(C$_{1-6}$ alkyl)-, —S(=O)$_2$—, —C(=CH$_2$)—, or $C_{3-7}$ cycloalkylene, wherein m is an integer of 0 to 3, and $R_9$ and $R_{10}$ are each independently hydrogen, hydroxy, halogen or $C_{1-6}$ alkyl; and $R_1$ is nitro, amino, or any one of the following structural formulae i) to iv):

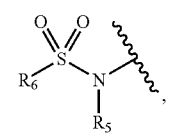

i)

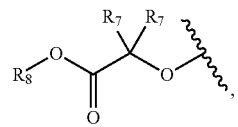

ii)

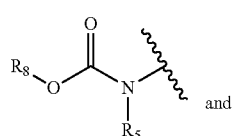

iii)

and

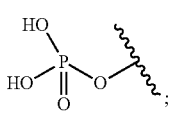

iv)

;

wherein $R_5$ to $R_8$ are the same as defined in claim 2;

all of said heterocycle moieties each independently have a saturated or unsaturated single or multiple ring; and said heteroaryl moiety has an aromatic single or multiple ring.

4. The compound according to claim 2, wherein
A is saturated or unsaturated $C_{3-10}$ carbocycle, or 5- to 10-membered heterocycle containing one to three heteroatoms selected from N, O or S;
B is benzene or a 9- to 12-membered heterocycle containing one to three N atoms;
C is benzene, or a 5- to 6-membered heterocycle containing one to three heteroatoms selected from N, O or S;
$R_3$ is hydrogen, halogen, cyano, $C_{1-6}$ alkyl, halo$C_{1-6}$ alkyl, cyano$C_{1-6}$ alkyl, $C_{1-6}$ alkoxy, halo$C_{1-6}$ alkoxy, cyano$C_{1-6}$ alkoxy, $C_{1-6}$ alkylamino, di$C_{1-6}$ alkylamino, $C_{1-6}$ alkylaminocarbonyl, di$C_{1-6}$ alkylaminocarbonyl, $C_{2-8}$ alkynyl, 5- to 10-membered heterocyclyl containing one to three heteroatoms selected from N, O or S, or 5- to 10-membered heterocycloalkyl-carbonyl containing one or two heteroatoms selected from N or O, wherein the heterocyclyl moiety is optionally substituted with one to three substituents selected from the group consisting of halogen, hydroxy, cyano, amino, $C_{1-6}$ alkyl, halo$C_{1-6}$ alkyl, $C_{1-6}$ alkoxy, and $C_{1-6}$ alkoxycarbonyl; and
r is 0 or 1;
all of said heterocycle moieties and heterocyclyl moieties each independently have a saturated or unsaturated single or multiple ring; and
said heterocycloalkyl moiety has a saturated single or multiple ring.

5. The compound according to claim 4, wherein A is a saturated or unsaturated $C_6$ carbocycle, or a 6-membered heterocycle containing one to three N atoms.

6. The compound according to claim 4, wherein B is

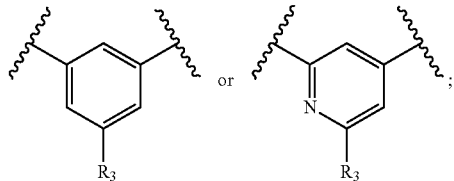

and
$R_3$ is the same as defined in claim 4.

7. The compound according to claim 1, wherein
A is benzene or 6-membered heterocycle containing one to three N atoms;
B is benzene, or a 6- to 10-membered heterocycle containing one to three N atoms;
C is benzene, a 6-membered heterocycle containing one to three heteroatoms selected from N, O or S, or $C_{5-6}$ carbocycle;
Y is —C(=O)— connected to $X_2$ or $X_5$; e34
$X_1$ is —O—, —S—, —S(=O)—, —S(=O)$_2$—, or —N($W_1$)—;
$X_2$ is a carbon atom connected to Y, or —NH—, —C($W_2$)= or —CH($W_2$)— not connected to Y;
$X_3$ and $X_4$ are each independently a carbon or nitrogen atom;
$X_5$ is a carbon atom connected to Y, or —CH= not connected to Y;
wherein the 5-membered ring comprising of $X_1$ to $X_5$ is aromatic or non-aromatic;
W is hydrogen, $C_{1-3}$ alkyl, or 5- or 6-membered heterocycloalkyl-$C_{1-3}$ alkyl containing one or two heteroatoms selected from N or O;
$W_1$ is hydrogen, $C_{1-3}$ alkyl, t-butoxycarbonyl, or 5- or 6-membered heterocycloalkyl-$C_{1-3}$ alkyl containing one or two heteroatoms selected from N or O;
$W_2$ is hydrogen, halogen, or $C_{1-3}$ alkyl;
L is —(CR$_9$R$_{10}$)$_m$—, —O—, —S(=O)$_2$—, $C_{3-6}$ cycloalkylene, —NH—, —N($C_{1-3}$ alkyl)-, —C(=CH$_2$)—, or wherein m is 1, and $R_9$ and $R_{10}$ are each independently hydrogen, halogen, hydroxy or $C_{1-3}$ alkyl;
$R_1$ is any one of the following structural formulae i) to iv):

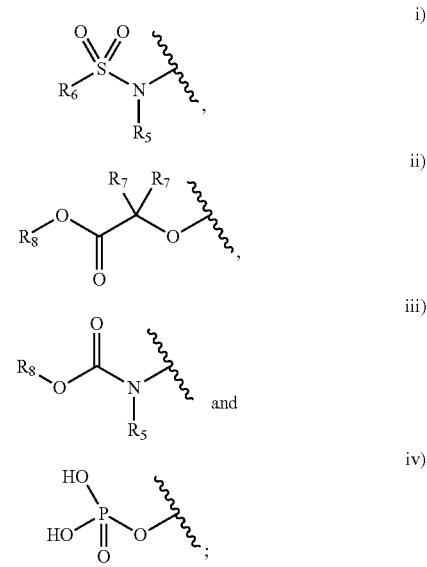

$R_2$ is hydrogen, halogen, nitro, amino, $C_{1-3}$ alkoxy, halo$C_{1-3}$ alkoxy, $C_{1-3}$ alkylsulfonyl, or 5- or 6-membered heterocycloalkyl containing one or two heteroatoms selected from N or O;
$R_3$ is hydrogen, halogen, $C_{1-3}$ alkylcarbonyl, cyano, cyano$C_{1-3}$ alkyl, $C_{1-3}$ alkyl, halo$C_{1-3}$ alkyl, $C_{2-3}$ alkynyl, halo$C_{1-3}$ alkoxy, cyano$C_{1-3}$ alkoxy, $C_{1-6}$ alkoxy, $C_{1-3}$ alkylamino, di$C_{1-3}$ alkylamino, $C_{1-3}$ alkylaminocarbonyl, di$C_{1-3}$ alkylaminocarbonyl, phenyl, halophenyl, 5- or 6-membered heterocyclyl, or 5- or 6-membered heterocyclyl-carbonyl, wherein the heterocyclyl moiety contains one to three heteroatoms selected from N, O or S, and is optionally substituted with one to three substituents selected from the group consisting of halogen, hydroxy, cyano, amino, $C_{1-3}$ alkyl, halo$C_{1-3}$ alkyl, $C_{1-3}$ alkoxy, and t-butoxycarbonyl;
$R_4$ is hydrogen, oxo, hydroxy, nitro, cyano, halogen, aminosulfonyl, amino, $C_{1-3}$ alkylamino, di$C_{1-3}$ alkylamino-$C_{1-3}$ alkoxy, $C_{1-3}$ alkylthio, $C_{1-3}$ alkylsulfinyl, $C_{1-3}$ alkylsulfonyl, $C_{1-3}$ alkyl, cyano$C_{1-3}$ alkyl, $C_{2-4}$ alkynyl, $C_{1-3}$ alkoxy, cyano$C_{1-3}$ alkoxy, halo$C_{1-3}$ alkoxy, carbamoyl-$C_{1-3}$ alkoxy, $C_{3-6}$ cycloalkyl-oxy, 4- to 10-membered heterocyclyl, 4- to 10-membered heterocyclyl-oxy, or 4- to 10-membered heterocyclyl-$C_{1-3}$ alkyl, wherein the heterocyclyl moiety contains one to three heteroatoms selected from N, O or S, and is optionally substituted with one or two substituents selected from the group consisting of hydroxy, oxo, $C_{1-3}$ alkyl, t-butylcarbonyl, t-butoxycarbonyl, $C_{1-3}$ alkylsulfonyl, di$C_{1-3}$ alkylsulfonyl, di$C_{1-3}$ alkylaminocarbonyl, 4- to 6-membered heterocyclyl and $C_{1-6}$ alkyl-substituted 4- to 6-membered heterocyclyl;

R₅ is hydrogen, $C_{1-3}$ alkyl, carbamoyl$C_{1-3}$ alkyl, di$C_{1-3}$ alkylamino-$C_{1-3}$ alkyl, or morpholino-$C_{1-3}$ alkyl, or is fused with R₆ to form $C_{3-4}$ alkylene;

R₆ is $C_{1-3}$ alkyl, halo$C_{1-3}$ alkyl, $C_{1-3}$ alkoxy$C_{1-3}$ alkyl, $C_{2-3}$ alkenyl, amino, amino$C_{1-3}$ alkyl, $C_{3-6}$ cycloalkyl, 5- or 6-membered heterocyclyl, or 5- or 6-membered heterocyclyl-$C_{1-3}$ alkyl, or is fused with R₅ to form $C_{3-4}$ alkylene, wherein the heterocyclyl moiety contains one to three heteroatoms selected from N, O or S, and is optionally substituted with one to four substituents selected from the group consisting of hydrogen, oxo, $C_{1-3}$ alkyl and acetyl, and the amino moiety is unsubstituted or substituted with one or two substituents selected from hydroxy or $C_{1-3}$ alkyl;

R₇ is hydrogen or $C_{1-3}$ alkyl;

R₈ is hydrogen or $C_{1-6}$ alkyl;

P is 1 and q is independently 0 or 1;

r is 0 or 1; and s is an integer of 0 to 3, and, when s is 2 or higher, R₄ moieties are the same or different;

all of said heterocycle and heterocyclyl moieties each independently have a saturated or unsaturated single or double ring.

8. The compound according to claim 7, wherein B is

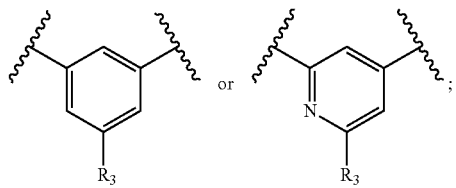

and

R₃ is the same as defined in claim 7.

9. The compound according to claim 7, wherein
R₉ and R₁₀ are each independently halogen, hydroxy, or $C_{1-3}$ alkyl.

10. The compound according to claim 7, wherein
R₃ is hydrogen, phenyl, halophenyl, saturated or unsaturated 5- or 6-membered heterocyclyl or 5- to 6-membered heterocyclyl-carbonyl wherein the heterocyclyl moiety contains one to three heteroatoms selected from N, O or S, and is optionally substituted with one to three substituents selected from the group consisting of halogen, hydroxy, cyano, amino, $C_{1-3}$ alkyl, halo$C_{1-3}$ alkyl, $C_{1-3}$ alkoxy, and t-butoxycarbonyl.

11. The compound according to claim 7, wherein
X₁ is —S— or —NH—;
X₂ is —CH═ not connected to Y;
X₃ and X₄ are a carbon atom; and
R₁ is the structural formula i).

12. A compound selected from the group consisting of:
1) N-(3-(2-(4-fluorophenyl)propan-2-yl)phenyl)-6-(methylsulfonamido)-1H-indole-2-carboxamide;
2) 6-(methylsulfonamido)-N-(3-(2-phenylpropan-2-yl)phenyl)-1H-indole-2-carboxamide;
3) N-(3-(2-(4-fluorophenyl)propan-2-yl)phenyl)-5-methoxy-6-(methylsulfonamido)-1H-indole-2-carboxamide;
4) N-(3-methoxy-5-(2-(3-(trifluoromethoxy)phenyl)propan-2-yl)phenyl)-6-(methylsulfonamido)-1H-indole-2-carboxamide;
5) N-(3-(2-(4-fluorophenyl)propan-2-yl)phenyl)-6-((N-methylsulfamoyl)amino)-1H-indole-2-carboxamide;
6) N-(3-(2-(4-fluorophenyl)propan-2-yl)phenyl)-6-(methylsulfonyl)-1H-indole-2-carboxamide;
7) N-(3-(2-(2-fluorophenyl)propan-2-yl)phenyl)-6-(methylsulfonamido)-1H-indole-2-carboxamide;
8) 6-(methylsulfonamido)-N-(3-(2-(3-(trifluoromethoxy)phenyl)propan-2-yl)phenyl)-1H-indole-2-carboxamide;
9) N-(3-(2-(3-methoxy-5-(trifluoromethoxy)phenyl)propan-2-yl)phenyl)-6-(methylsulfonamido)-1H-indole-2-carboxamide;
10) N-(3-(1-(3-methoxy-5-(trifluoromethoxy)phenyl)ethyl)phenyl)-6-(methylsulfonamido)-1H-indole-2-carboxamide;
11) N-(3-(2-(2,4-difluorophenyl)propan-2-yl)phenyl)-6-(methylsulfonamido)-1H-indole-2-carboxamide;
12) N-(3-(2-(3-methoxyphenyl)propan-2-yl)phenyl)-6-(methylsulfonamido)-1H-indole-2-carboxamide;
13) N-(3-methoxy-5-(2-(3-methoxy-5-(trifluoromethoxy)phenyl)propan-2-yl)phenyl)-6-(methylsulfonamido)-1H-indole-2-carboxamide;
14) N-(3-bromo-5-(2-(4-fluorophenyl)propan-2-yl)phenyl)-6-(methylsulfonamido)-1H-indole-2-carboxamide;
15) N-(3-bromo-5-(2-(2,4-difluorophenyl)propan-2-yl)phenyl)-6-(methylsulfonamido)-1H-indole-2-carboxamide;
16) N-(3-bromo-5-(2-(3-methoxy-5-(trifluoromethoxy)phenyl)propan-2-yl)phenyl)-6-(methylsulfonamido)-1H-indole-2-carboxamide;
17) N-(3-(difluoromethoxy)-5-(2-(4-fluorophenyl)propan-2-yl)phenyl)-6-(methylsulfonamido)-1H-indole-2-carboxamide;
18) N-(3-(2-(3-(2-amino-2-oxoethoxy)phenyl)propan-2-yl)-5-bromophenyl)-6-(methylsulfonamido)-1H-indole-2-carboxamide;
19) N-(3-bromo-5-(2-(4-fluorophenyl)propan-2-yl)phenyl)-5-methoxy-6-(methylsulfonamido)-1H-indole-2-carboxamide;
20) N-(3-bromo-5-(2-(3-(difluoromethoxy)phenyl)propan-2-yl)phenyl)-6-(methylsulfonamido)-1H-indole-2-carboxamide;
21) N-(3-chloro-5-(2-(4-fluorophenyl)propan-2-yl)phenyl)-6-(methylsulfonamido)-1H-indole-2-carboxamide;
22) N-(3-bromo-5-(2-(3-ethoxy-5-(trifluoromethoxy)phenyl)propan-2-yl)phenyl)-6-(methylsulfonamido)-1H-indole-2-carboxamide;
23) N-(3-bromo-5-(2-(2-fluoro-5-(trifluoromethoxy)phenyl)propan-2-yl)phenyl)-6-(methylsulfonamido)-1H-indole-2-carboxamide;
24) N-(3-chloro-5-(2-(3-methoxy-5-(trifluoromethoxy)phenyl)propan-2-yl)phenyl)-6-(methylsulfonamido)-1H-indole-2-carboxamide;
25) N-(3-(2-(4-fluorophenyl)propan-2-yl)phenyl)-5-(trifluoromethoxy)-1H-indole-2-carboxamide;
26) N-(3-(2-(4-fluorophenyl)propan-2-yl)phenyl)-5-(methylsulfonamido)benzo[b]thiophene-2-carboxamide;
27) N-(3-(2-(2,4-difluorophenyl)propan-2-yl)phenyl)-5-(methylsulfonamido)benzo[b]thiophene-2-carboxamide;
28) N-(3-(2-(4-fluorophenyl)propan-2-yl)phenyl)-5-(methylsulfonamido)benzofuran-2-carboxamide;
29) N-(3-(2-(2,4-difluorophenyl)propan-2-yl)phenyl)-5-(methylsulfonamido)benzofuran-2-carboxamide;

30) N-(3-(2-(4-fluorophenyl)propan-2-yl)phenyl)-6-(methylsulfonamido)benzo[b]thiophene-2-carboxamide;
31) N-(3-(2-(2-fluorophenyl)propan-2-yl)phenyl)-5-(methylsulfonamido)benzo[b]thiophene-2-carboxamide;
32) N-(3-bromo-5-(2-(4-fluorophenyl)propan-2-yl)phenyl)-5-(methylsulfonamido)benzo[b]thiophene-2-carboxamide;
33) N-(3-(2-(3-methoxy-5-(trifluoromethoxy)phenyl)propan-2-yl)phenyl)-5-(methylsulfonamido)benzo[b]thiophene-2-carboxamide;
34) N-(3-methoxy-5-(2-(3-methoxy-5-(trifluoromethoxy)phenyl)propan-2-yl)phenyl)-5-(methylsulfonamido)benzo[b]thiophene-2-carboxamide;
35) N-(3-bromo-5-(2-(2,4-difluorophenyl)propan-2-yl)phenyl)-5-(methylsulfonamido)benzo[b]thiophene-2-carboxamide;
36) N-(3-bromo-5-(2-(3-methoxy-5-(trifluoromethoxy)phenyl)propan-2-yl)phenyl)-5-(methylsulfonamido)benzo[b]thiophene-2-carboxamide;
37) 5-(methylsulfonamido)-N-(3-(2-(3-(trifluoromethoxy)phenyl)propan-2-yl)phenyl)benzo[b]thiophene-2-carboxamide;
38) N-(3-(2-(3-methoxyphenyl)propan-2-yl)phenyl)-5-(methylsulfonamido)benzo[b]thiophene-2-carboxamide;
39) N-(3-(difluoromethoxy)-5-(2-(4-fluorophenyl)propan-2-yl)phenyl)-5-(methylsulfonamido)benzo[b]thiophene-2-carboxamide;
40) N-(3-chloro-5-(2-(4-fluorophenyl)propan-2-yl)phenyl)-5-(methylsulfonamido)benzo[b]thiophene-2-carboxamide;
41) N-(3-(difluoromethoxy)-5-(2-(3-methoxy-5-(trifluoromethoxy)phenyl)propan-2-yl)phenyl)-5-(methylsulfonamido)benzo[b]thiophene-2-carboxamide;
42) N-(3-chloro-5-(2-(3-methoxy-5-(trifluoromethoxy)phenyl)propan-2-yl)phenyl)-5-(methylsulfonamido)benzo[b]thiophene-2-carboxamide;
43) N-(3-(2-(3-(2-amino-2-oxoethoxy)phenyl)propan-2-yl)-5-bromophenyl)-5-(methylsulfonamido)benzo[b]thiophene-2-carboxamide;
44) N-(3-(2-(5-(2-amino-2-oxoethoxy)-2-fluorophenyl)propan-2-yl)-5-bromophenyl)-5-(methylsulfonamido)benzo[b]thiophene-2-carboxamide;
45) N-(3-(2-(3-((1-amino-2-methyl-1-oxopropan-2-yl)oxy)phenyl)propan-2-yl)-5-bromophenyl)-5-(methylsulfonamido)benzo[b]thiophene-2-carboxamide;
46) N-(3-bromo-5-(2-(3-(difluoromethoxy)phenyl)propan-2-yl)phenyl)-5-(methylsulfonamido)benzo[b]thiophene-2-carboxamide;
47) N-(3-bromo-5-(2-(2-fluoro-5-(trifluoromethoxy)phenyl)propan-2-yl)phenyl)-5-(methylsulfonamido)benzo[b]thiophene-2-carboxamide;
48) N-(3-bromo-5-(2-(3-ethoxy-5-(trifluoromethoxy)phenyl)propan-2-yl)phenyl)-5-(methylsulfonamido)benzo[b]thiophene-2-carboxamide;
49) N-(3-bromo-5-(2-(3-isopropoxy-5-(trifluoromethoxy)phenyl)propan-2-yl)phenyl)-5-(methylsulfonamido)benzo[b]thiophene-2-carboxamide;
50) N-(3-bromo-5-(2-(3-(morpholinomethyl)phenyl)propan-2-yl)phenyl)-5-(methylsulfonamido)benzo[b]thiophene-2-carboxamide;
51) N-(3-(2-(4-fluorophenyl)propan-2-yl)phenyl)-3-methyl-6-(methylsulfonamido)benzo[b]thiophene-2-carboxamide;
52) N-(3-(2-(4-fluorophenyl)propan-2-yl)phenyl)-3-methyl-5-(methylsulfonamido)benzo[b]thiophene-2-carboxamide;
53) N-(3-bromo-5-(3-(4-fluorophenyl)pentan-3-yl)phenyl)-5-(methylsulfonamido)benzo[b]thiophene-2-carboxamide;
54) N-(3-methoxy-5-(3-(3-methoxy-5-(trifluoromethoxy)phenyl)pentan-3-yl)phenyl)-5-(methylsulfonamido)benzo[b]thiophene-2-carboxamide;
55) N-(3-methoxy-5-(3-(3-methoxy-5-(trifluoromethoxy)phenyl)pentan-3-yl)phenyl)-6-(methylsulfonamido)-1H-indole-2-carboxamide;
56) N-(3-bromo-5-(2-(3-methoxy-5-(trifluoromethoxy)phenyl)propan-2-yl)phenyl)-5-(methylsulfonamido)thieno[2,3-b]pyridine-2-carboxamide;
57) N-(3-chloro-5-(2-(3-methoxy-5-(trifluoromethoxy)phenyl)propan-2-yl)phenyl)-5-(methylsulfonamido)thieno[2,3-b]pyridine-2-carboxamide;
58) N-(3-chloro-5-(2-(3-ethoxy-5-(trifluoromethoxy)phenyl)propan-2-yl)phenyl)-5-(methylsulfonamido)benzo[b]thiophene-2-carboxamide;
59) N-(3-chloro-5-(2-(3-ethoxy-5-(trifluoromethoxy)phenyl)propan-2-yl)phenyl)-6-(methylsulfonamido)-1H-indole-2-carboxamide;
60) N-(3-bromo-5-(2-(3-ethoxy-5-(trifluoromethoxy)phenyl)propan-2-yl)phenyl)-5-(methylsulfonamido)thieno[3,2-b]pyridine-2-carboxamide;
61) N-(3-bromo-5-(2-(3-ethoxy-5-(trifluoromethoxy)phenyl)propan-2-yl)phenyl)-5-(methylsulfonamido)thieno[2,3-c]pyridine-2-carboxamide;
62) N-(3-chloro-5-(2-(2-fluoro-5-(trifluoromethoxy)phenyl)propan-2-yl)phenyl)-5-(methylsulfonamido)benzo[b]thiophene-2-carboxamide;
63) N-(3-fluoro-5-(2-(3-methoxy-5-(trifluoromethoxy)phenyl)propan-2-yl)phenyl)-5-(methylsulfonamido)benzo[b]thiophene-2-carboxamide;
64) N-(3-chloro-5-(2-phenylpropan-2-yl)phenyl)-5-(methylsulfonamido)benzo[b]thiophene-2-carboxamide;
65) N-(3-chloro-5-(2-(3-fluorophenyl)propan-2-yl)phenyl)-5-(methylsulfonamido)benzo[b]thiophene-2-carboxamide;
66) N-(3-chloro-5-(2-(3-isopropoxy-5-(trifluoromethoxy)phenyl)propan-2-yl)phenyl)-5-(methylsulfonamido)-4-morpholinobenzo[b]thiophene-2-carboxamide;
67) N-(3-chloro-5-(2-(3-fluoro-5-methoxyphenyl)propan-2-yl)phenyl)-5-(methylsulfonamido)benzo[b]thiophene-2-carboxamide;
68) N-(3-chloro-5-(2-(3-isopropoxy-5-(trifluoromethoxy)phenyl)propan-2-yl)phenyl)-5-(methylsulfonamido)benzo[b]thiophene-2-carboxamide;
69) N-(3-chloro-5-(2-(3-isopropoxy-5-(trifluoromethoxy)phenyl)propan-2-yl)phenyl)-5-(methylsulfonamido)thieno[2,3-b]pyridine-2-carboxamide;
70) N-(3-chloro-5-(2-(3-isopropoxy-5-(trifluoromethoxy)phenyl)propan-2-yl)phenyl)-5-(methylsulfonamido)thieno[3,2-b]pyridine-2-carboxamide;
71) N-(3-chloro-5-(2-(3-isopropoxy-5-(trifluoromethoxy)phenyl)propan-2-yl)phenyl)-5-(methylsulfonamido)thieno[2,3-c]pyridine-2-carboxamide;
72) N-(3-chloro-5-(2-(3-isobutoxy-5-(trifluoromethoxy)phenyl)propan-2-yl)phenyl)-5-(methylsulfonamido)benzo[b]thiophene-2-carboxamide;
73) N-(3-chloro-5-(2-(3-propoxy-5-(trifluoromethoxy)phenyl)propan-2-yl)phenyl)-5-(methylsulfonamido)benzo[b]thiophene-2-carboxamide;

74) N-(3-chloro-5-(2-(3-isopropoxy-5-(trifluoromethoxy)phenyl)propan-2-yl)phenyl)-6-(methylsulfonamido)imidazo[1,2-a]pyridine-2-carboxamide;
75) N-(3-(2-(3-(but-2-yn-1-yloxy)-5-(trifluoromethoxy)phenyl)propan-2-yl)-5-chlorophenyl)-5-(methylsulfonamido)benzo[b]thiophene-2-carboxamide;
76) N-(3-chloro-5-(2-(3-(oxetan-3-yloxy)-5-(trifluoromethoxy)phenyl)propan-2-yl)phenyl)-5-(methylsulfonamido)benzo[b]thiophene-2-carboxamide;
77) N-(3-chloro-5-(2-(3-(cyanomethoxy)-5-(trifluoromethoxy)phenyl)propan-2-yl)phenyl)-5-(methylsulfonamido)benzo[b]thiophene-2-carboxamide;
78) N-(3-(2-(3-(allyloxy)-5-(trifluoromethoxy)phenyl)propan-2-yl)-5-chlorophenyl)-5-(methylsulfonamido)benzo[b]thiophene-2-carboxamide;
79) N-(3-chloro-5-(2-(3-cyclopropoxy-5-(trifluoromethoxy)phenyl)propan-2-yl)phenyl)-5-(methylsulfonamido)benzo[b]thiophene-2-carboxamide;
80) N-(3-chloro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;
81) N-(3-chloro-5-(2-(3-isopropoxy-5-(trifluoromethoxy)phenyl)propan-2-yl)phenyl)-5-(methylsulfonamido)benzo[d]thiazole-2-carboxamide;
82) N-(3-fluoro-5-(2-(3-isopropoxy-5-(trifluoromethoxy)phenyl)propan-2-yl)phenyl)-5-(methylsulfonamido)benzo[b]thiophene-2-carboxamide;
83) N-(3-chloro-5-(2-(3-(2,2-difluoroethoxy)-5-(trifluoromethoxy)phenyl)propan-2-yl)phenyl)-5-(methylsulfonamido)benzo[b]thiophene-2-carboxamide;
84) N-(3-chloro-5-(2-(3-isopropoxy-5-(trifluoromethoxy)phenyl)propan-2-yl)phenyl)-6-fluoro-5-(methylsulfonamido)benzo[b]thiophene-2-carboxamide;
85) N-(3-fluoro-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;
86) N-(3-fluoro-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide;
87) N-(3-bromo-5-(2-(3-(1,1,2,2-tetrafluoroethoxy)-5-(trifluoromethoxy)phenyl)propan-2-yl)phenyl)-5-(methylsulfonamido)benzo[b]thiophene-2-carboxamide;
88) N-(3-chloro-5-(2-(3-(2,2,2-trifluoroethoxy)-5-(trifluoromethoxy)phenyl)propan-2-yl)phenyl)-5-(methylsulfonamido)benzo[b]thiophene-2-carboxamide;
89) N-(3-bromo-5-(2-(3-(1,1,2,2-tetrafluoroethoxy)-5-(trifluoromethoxy)phenyl)propan-2-yl)phenyl)-5-(methylsulfonamido)thieno[2,3-c]pyridine-2-carboxamide;
90) N-(3-chloro-5-(2-(3-(2-morpholinoethoxy)-5-(trifluoromethoxy)phenyl)propan-2-yl)phenyl)-5-(methylsulfonamido)benzo[b]thiophene-2-carboxamide;
91) N-(3-(2-(3-bromo-5-isopropoxyphenyl)propan-2-yl)-5-chlorophenyl)-5-(methylsulfonamido)benzo[b]thiophene-2-carboxamide;
92) N-(3-chloro-5-(2-(3-chloro-5-isopropoxyphenyl)propan-2-yl)phenyl)-5-(methylsulfonamido)benzo[b]thiophene-2-carboxamide;
93) N-(3-chloro-5-(2-(3-isopropoxy-5-(trifluoromethoxy)phenyl)propan-2-yl)phenyl)-4-fluoro-5-(methylsulfonamido)benzo[b]thiophene-2-carboxamide;
94) N-(3-chloro-5-(2-(3-(2-(dimethylamino)ethoxy)-5-(trifluoromethoxy)phenyl)propan-2-yl)phenyl)-5-(methylsulfonamido)benzo[b]thiophene-2-carboxamide;
95) tert-butyl 4-(3-(2-(3-chloro-5-(5-(methylsulfonamido)benzo[b]thiophene-2-carboxamido)phenyl)propan-2-yl)-5-(trifluoromethoxy)phenoxy)piperidine-1-carboxylate;
96) N-(3-chloro-5-(2-(3-(piperidin-4-yloxy)-5-(trifluoromethoxy)phenyl)propan-2-yl)phenyl)-5-(methylsulfonamido)benzo[b]thiophene-2-carboxamide;
97) N-(3-chloro-5-(2-(3-isopropoxy-5-(trifluoromethoxy)phenyl)propan-2-yl)phenyl)-5-(methylsulfonyl)-4,5,6,7-tetrahydrothieno[3,2-c]pyridine-2-carboxamide;
98) N-(3-bromo-5-(2-(3-methoxy-5-(trifluoromethoxy)phenyl)propan-2-yl)phenyl)-6-(methylsulfonamido)-1H-pyrrolo[3,2-c]pyridine-2-carboxamide;
99) N-(3-bromo-5-(2-(3-methoxy-5-(trifluoromethoxy)phenyl)propan-2-yl)phenyl)-5-(methylsulfonamido)-1H-pyrrolo[2,3-c]pyridine-2-carboxamide 2,2,2-trifluoroacetate;
100) N-(3-chloro-5-(2-(3-isopropoxy-5-(trifluoromethoxy)phenyl)propan-2-yl)phenyl)-6-(methylsulfonamido)-1H-pyrrolo[2,3-b]pyridine-2-carboxamide;
101) N-(3-chloro-5-(2-(3-isopropoxy-5-(trifluoromethoxy)phenyl)propan-2-yl)phenyl)-6-(methylsulfonamido)-1H-pyrrolo[3,2-c]pyridine-2-carboxamide;
102) N-(3-chloro-5-(2-(3-isopropoxy-5-(trifluoromethoxy)phenyl)propan-2-yl)phenyl)-4-(methylsulfonamido)thiophene-2-carboxamide;
103) N-(3-chloro-5-(2-(3-isopropoxy-5-(trifluoromethoxy)phenyl)propan-2-yl)phenyl)-5-(morpholine-4-sulfonamido)benzo[b]thiophene-2-carboxamide;
104) N-(3-chloro-5-(2-(3-isopropoxy-5-(trifluoromethoxy)phenyl)propan-2-yl)phenyl)-5-(methylsulfonamido)-4,5,6,7-tetrahydrothieno[3,2-c]pyridine-2-carboxamide;
105) 6-chloro-N-(3-chloro-5-(2-(3-isopropoxy-5-(trifluoromethoxy)phenyl)propan-2-yl)phenyl)-5-(methylsulfonamido)benzo[b]thiophene-2-carboxamide;
106) N-(3-chloro-5-(2-(3-methoxyphenyl)propan-2-yl)phenyl)-5-(methylsulfonamido)benzo[b]thiophene-2-carboxamide;
107) N-(3-ethynyl-5-(2-(4-fluorophenyl)propan-2-yl)phenyl)-6-(methylsulfonamido)-1H-indole-2-carboxamide;
108) N-(3-ethynyl-5-(2-(4-fluorophenyl)propan-2-yl)phenyl)-5-(methylsulfonamido)benzo[b]thiophene-2-carboxamide;
109) N-(3-(2-(2,4-difluorophenyl)propan-2-yl)-5-ethynylphenyl)-5-(methylsulfonamido)benzo[b]thiophene-2-carboxamide;
110) 3-chloro-N-(3-(2-(4-fluorophenyl)propan-2-yl)phenyl)-6-(methylsulfonamido)benzo[b]thiophene-2-carboxamide;
111) 3-chloro-N-(2',4'-difluoro-[1,1'-biphenyl]-3-yl)-6-(methylsulfonamido)benzo[b]thiophene-2-carboxamide;
112) N-(2',4'-difluoro-[1,1'-biphenyl]-3-yl)-7-methoxy-5-(methylsulfonamido)benzofuran-2-carboxamide;
113) N-(3-(2-(4-fluorophenyl)propan-2-yl)phenyl)-7-methoxy-5-(methylsulfonamido)benzofuran-2-carboxamide;
114) N-(3-chloro-5-(2-(3-(prop-1-yn-1-yl)-5-(trifluoromethoxy)phenyl)propan-2-yl)phenyl)-5-(methylsulfonamido)benzo[b]thiophene-2-carboxamide;

115) N-(3-bromo-5-(2-(3-((4-methylpiperazin-1-yl) methyl)phenyl)propan-2-yl)phenyl)-5-(methylsulfonamido)benzo[b]thiophene-2-carboxamide;

116) tert-butyl 4-(3-(2-(3-bromo-5-(5-(methylsulfonamido)benzo[b]thiophene-2-carboxamido)phenyl)propan-2-yl)benzyl)piperazine-1-carboxylate;

117) tert-butyl 4-(3-(2-(3-bromo-5-(6-(methylsulfonamido)-1H-indole-2-carboxamido)phenyl)propan-2-yl)benzyl)piperazine-1-carboxylate;

118) N-(3-bromo-5-(2-(3-(piperazin-1-ylmethyl)phenyl)propan-2-yl)phenyl)-5-(methylsulfonamido)benzo[b]thiophene-2-carboxamide;

119) N-(3-bromo-5-(2-(3-(piperazin-1-ylmethyl)phenyl)propan-2-yl)phenyl)-6-(methylsulfonamido)-1H-indole-2-carboxamide;

120) N-(3-(2-(3-((1H-imidazol-1-yl)methyl)phenyl)propan-2-yl)-5-bromophenyl)-5-(methylsulfonamido)benzo[b]thiophene-2-carboxamide;

121) N-(3-chloro-5-(2-(3-((2-hydroxyazetidin-1-yl)methyl)-5-isopropoxyphenyl)propan-2-yl)phenyl)-5-(methylsulfonamido)benzo[b]thiophene-2-carboxamide;

122) N-(3-bromo-5-(2-(3-isopropoxy-5-(morpholinomethyl)phenyl)propan-2-yl)phenyl)-5-(methylsulfonamido)benzo[b]thiophene-2-carboxamide;

123) tert-butyl 4-(3-(2-(3-bromo-5-(5-(methylsulfonamido)benzo[b]thiophene-2-carboxamido)phenyl)propan-2-yl)-5-isopropoxybenzyl)piperazine-1-carboxylate;

124) N-(3-bromo-5-(2-(3-isopropoxy-5-(piperazin-1-ylmethyl)phenyl)propan-2-yl)phenyl)-5-(methylsulfonamido)benzo[b]thiophene-2-carboxamide;

125) N-(3-chloro-5-(2-(3-isopropoxy-5-(pyrrolidin-1-ylmethyl)phenyl)propan-2-yl)phenyl)-5-(methylsulfonamido)benzo[b]thiophene-2-carboxamide;

126) N-(3-chloro-5-(2-(3-isopropoxy-5-(morpholinomethyl)phenyl)propan-2-yl)phenyl)-5-(methylsulfonamido)benzo[b]thiophene-2-carboxamide;

127) N-(3-chloro-5-(2-(3-isopropoxy-5-((4-pivaloylpiperazin-1-yl)methyl)phenyl)propan-2-yl)phenyl)-5-(methylsulfonamido)benzo[b]thiophene-2-carboxamide;

128) N-(3-chloro-5-(2-(3-isopropoxy-5-((4-(methylsulfonyl)piperazin-1-yl)methyl)phenyl)propan-2-yl)phenyl)-5-(methylsulfonamido)benzo[b]thiophene-2-carboxamide;

129) N-(3-chloro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide;

130) N-(3-chloro-5-(2-(3-isopropoxy-5-((4-(oxetan-3-yl)piperazin-1-yl)methyl)phenyl)propan-2-yl)phenyl)-5-(methylsulfonamido)benzo[b]thiophene-2-carboxamide;

131) N-(3-chloro-5-(2-(3-((4-(N,N-dimethylsulfamoyl)piperazin-1-yl)methyl)-5-isopropoxyphenyl)propan-2-yl)phenyl)-5-(methylsulfonamido)benzo[b]thiophene-2-carboxamide;

132) N-(3-chloro-5-(2-(3-((1,1-dioxidothiomorpholino)methyl)-5-isopropoxyphenyl)propan-2-yl)phenyl)-5-(methylsulfonamido)benzo[b]thiophene-2-carboxamide;

133) 4-(3-(2-(3-chloro-5-(5-(methylsulfonamido)benzo[b]thiophene-2-carboxamido)phenyl)propan-2-yl)-5-isopropoxybenzyl)-N,N-dimethylpiperazine-1-carboxamide;

134) N-(3-(2-(3-((2-oxa-7-azaspiro[3.5]nonan-7-yl)methyl)-5-isopropoxyphenyl)propan-2-yl)-5-chlorophenyl)-5-(methylsulfonamido)benzo[b]thiophene-2-carboxamide;

135) N-(3-chloro-5-(2-(3-isopropoxy-5-((4-(5-isopropyl-1,3,4-oxadiazol-2-yl)piperazin-1-yl)methyl)phenyl)propan-2-yl)phenyl)-5-(methylsulfonamido)benzo[b]thiophene-2-carboxamide;

136) N-(3-fluoro-5-(2-(3-isopropoxy-5-((4-(5-isopropyl-1,2,4-oxadiazol-3-yl)piperazin-1-yl)methyl)phenyl)propan-2-yl)phenyl)-5-(methylsulfonamido)benzo[b]thiophene-2-carboxamide;

137) N-(3-fluoro-5-(2-(3-isopropoxy-5-(morpholinomethyl)phenyl)propan-2-yl)phenyl)-5-(methylsulfonamido)benzo[b]thiophene-2-carboxamide;

138) N-(3-chloro-5-(2-(3-((1-methyl-1H-pyrazol-4-yl)methyl)-5-(1,1,2,2-tetrafluoroethoxy)phenyl)propan-2-yl)phenyl)-5-(methylsulfonamido)benzo[b]thiophene-2-carboxamide;

139) N-(3-bromo-5-(2-(3-((4-(N,N-dimethylsulfamoyl)piperazin-1-yl)methyl)-5-(1,1,2,2-tetrafluoroethoxy)phenyl)propan-2-yl)phenyl)-5-(methylsulfonamido)benzo[b]thiophene-2-carboxamide;

140) N-(3-fluoro-5-(2-(3-(morpholinomethyl)-5-(1,1,2,2-tetrafluoroethoxy)phenyl)propan-2-yl)phenyl)-5-(methylsulfonamido)benzo[b]thiophene-2-carboxamide;

141) N-(3-bromo-5-(2-(3-((4-(oxetan-3-yl)piperazin-1-yl)methyl)-5-(1,1,2,2-tetrafluoroethoxy)phenyl)propan-2-yl)phenyl)-5-(methylsulfonamido)benzo[b]thiophene-2-carboxamide;

142) N-(3-chloro-5-(2-(3-isopropoxy-5-(1-methyl-1H-pyrazol-5-yl)phenyl)propan-2-yl)phenyl)-5-(methylsulfonamido)benzo[b]thiophene-2-carboxamide;

143) N-(3-chloro-5-(2-(3-isopropoxy-5-(1-methyl-1H-pyrazol-4-yl)phenyl)propan-2-yl)phenyl)-5-(methylsulfonamido)benzo[b]thiophene-2-carboxamide;

144) N-(3-chloro-5-(2-(3-(3-hydroxy-4-methylpiperazin-1-yl)-5-isopropoxyphenyl)propan-2-yl)phenyl)-5-(methylsulfonamido)benzo[b]thiophene-2-carboxamide;

145) N-(3-chloro-5-(2-(3-isopropoxy-5-morpholinophenyl)propan-2-yl)phenyl)-5-(methylsulfonamido)benzo[b]thiophene-2-carboxamide;

146) N-(3-chloro-5-(2-(3-isopropoxy-5-(pyrrolidin-1-yl)phenyl)propan-2-yl)phenyl)-5-(methylsulfonamido)benzo[b]thiophene-2-carboxamide;

147) N-(3-chloro-5-(2-(3-isopropoxy-5-(4-methylpiperazin-1-yl)phenyl)propan-2-yl)phenyl)-5-(methylsulfonamido)benzo[b]thiophene-2-carboxamide;

148) N-(6-chloro-4-(2-(3-methoxy-5-(trifluoromethoxy)phenyl)propan-2-yl)pyridin-2-yl)-5-(methylsulfonamido)benzo[b]thiophene-2-carboxamide;

149) N-(2-chloro-6-(2-(3-methoxy-5-(trifluoromethoxy)phenyl)propan-2-yl)pyridin-4-yl)-5-(methylsulfonamido)benzo[b]thiophene-2-carboxamide;

150) N-(4-chloro-6-(2-(3-methoxy-5-(trifluoromethoxy)phenyl)propan-2-yl)pyridin-2-yl)-5-(methylsulfonamido)benzo[b]thiophene-2-carboxamide;

151) N-(3-chloro-5-(2-(3-isopropoxy-5-(trifluoromethoxy)phenyl)propan-2-yl)phenyl)-2-(methylsulfonamido)thieno[2,3-b]pyrazine-6-carboxamide;

152) N-(3-(2-(4-bromophenyl)propan-2-yl)-5-chlorophenyl)-5-(methylsulfonamido)benzo[b]thiophene-2-carboxamide;

153) N-(3-chloro-5-(2-(3,4-dimethoxyphenyl)propan-2-yl)phenyl)-5-(methylsulfonamido)benzo[b]thiophene-2-carboxamide;
154) N-(3-chloro-5-(2-(2,4-dimethoxyphenyl)propan-2-yl)phenyl)-5-(methylsulfonamido)benzo[b]thiophene-2-carboxamide;
155) N-(3-chloro-5-(2-(4-methoxyphenyl)propan-2-yl)phenyl)-5-(methylsulfonamido)benzo[b]thiophene-2-carboxamide;
156) N-(3-chloro-5-(2-(2,5-dimethoxyphenyl)propan-2-yl)phenyl)-5-(methylsulfonamido)benzo[b]thiophene-2-carboxamide;
157) N-(3-chloro-5-(2-(4-(methylthio)phenyl)propan-2-yl)phenyl)-5-(methylsulfonamido)benzo[b]thiophene-2-carboxamide;
158) N-(3-chloro-5-(2-(4-chlorophenyl)propan-2-yl)phenyl)-5-(methylsulfonamido)benzo[b]thiophene-2-carboxamide;
159) N-(3-chloro-5-(2-(4-(1-methyl-1H-pyrazol-5-yl)phenyl)propan-2-yl)phenyl)-5-(methylsulfonamido)benzo[b]thiophene-2-carboxamide;
160) N-(3-chloro-5-(2-(4-(methylsulfinyl)phenyl)propan-2-yl)phenyl)-5-(methylsulfonamido)benzo[b]thiophene-2-carboxamide;
161) N-(3-chloro-5-(2-(4-(methylsulfonyl)phenyl)propan-2-yl)phenyl)-5-(methylsulfonamido)benzo[b]thiophene-2-carboxamide;
162) N-(3-chloro-5-(2-(3,4-difluorophenyl)propan-2-yl)phenyl)-5-(methylsulfonamido)benzo[b]thiophene-2-carboxamide;
163) N-(3-chloro-5-(2-(4-chlorophenyl)propan-2-yl)phenyl)-6-fluoro-5-(N-methylmethylsulfonamido)benzo[b]thiophene-2-carboxamide;
164) N-(3-chloro-5-(2-(piperidin-1-yl)propan-2-yl)phenyl)-5-(methylsulfonamido)benzo[b]thiophene-2-carboxamide;
165) 6-chloro-N-(3-chloro-5-(2-(piperidin-1-yl)propan-2-yl)phenyl)-5-(methylsulfonamido)benzo[b]thiophene-2-carboxamide;
166) N-(3-(2-(1H-pyrrol-2-yl)propan-2-yl)-5-chlorophenyl)-5-(methylsulfonamido)benzo[b]thiophene-2-carboxamide;
167) N-(3-(2-(1H-pyrrol-3-yl)propan-2-yl)-5-chlorophenyl)-5-(methylsulfonamido)benzo[b]thiophene-2-carboxamide;
168) N-(3-chloro-5-(2-(1-methyl-1H-pyrrol-3-yl)propan-2-yl)phenyl)-5-(methylsulfonamido)benzo[b]thiophene-2-carboxamide;
169) N-(3-chloro-5-(2-(1-methyl-1H-pyrrol-2-yl)propan-2-yl)phenyl)-5-(methylsulfonamido)benzo[b]thiophene-2-carboxamide;
170) N-(3-chloro-5-(2-(thiophen-2-yl)propan-2-yl)phenyl)-5-(methylsulfonamido)benzo[b]thiophene-2-carboxamide;
171) N-(3-chloro-5-(2-(thiophen-3-yl)propan-2-yl)phenyl)-5-(methylsulfonamido)benzo[b]thiophene-2-carboxamide;
172) 6-chloro-N-(3-chloro-5-(2-(4-chlorophenyl)propan-2-yl)phenyl)-5-(methylsulfonamido)benzo[b]thiophene-2-carboxamide;
173) 6-bromo-N-(3-chloro-5-(2-(4-chlorophenyl)propan-2-yl)phenyl)-5-(methylsulfonamido)benzo[b]thiophene-2-carboxamide;
174) N-(3-chloro-5-(2-(5-chlorothiophen-2-yl)propan-2-yl)phenyl)-5-(methylsulfonamido)benzo[b]thiophene-2-carboxamide;
175) 6-chloro-N-(3-chloro-5-(2-(5-chlorothiophen-2-yl)propan-2-yl)phenyl)-5-(methylsulfonamido)benzo[b]thiophene-2-carboxamide;
176) N-(3-chloro-5-(2-(2-methoxythiophen-3-yl)propan-2-yl)phenyl)-5-(methylsulfonamido)benzo[b]thiophene-2-carboxamide;
177) N-(3-chloro-5-(2-(5-methoxythiophen-2-yl)propan-2-yl)phenyl)-5-(methylsulfonamido)benzo[b]thiophene-2-carboxamide;
178) N-(3-chloro-5-(2-(5-methylthiophen-2-yl)propan-2-yl)phenyl)-5-(methylsulfonamido)benzo[b]thiophene-2-carboxamide;
179) 6-chloro-N-(3-chloro-5-(2-(5-methylthiophen-2-yl)propan-2-yl)phenyl)-5-(methylsulfonamido)benzo[b]thiophene-2-carboxamide;
180) 6-chloro-N-(3-chloro-5-(2-(5-isopropylthiophen-2-yl)propan-2-yl)phenyl)-5-(methylsulfonamido)benzo[b]thiophene-2-carboxamide;
181) 6-chloro-N-(3-chloro-5-(2-(4-methylthiophen-2-yl)propan-2-yl)phenyl)-5-(methylsulfonamido)benzo[b]thiophene-2-carboxamide;
182) 6-chloro-N-(3-chloro-5-(2-(4-fluorophenyl)propan-2-yl)phenyl)-5-(methylsulfonamido)benzo[b]thiophene-2-carboxamide;
183) 6-chloro-N-(3-chloro-5-(2-(4-methoxyphenyl)propan-2-yl)phenyl)-5-(methylsulfonamido)benzo[b]thiophene-2-carboxamide;
184) 5-chloro-N-(3-chloro-5-(2-(4-chlorophenyl)propan-2-yl)phenyl)-6-(methylsulfonamido)benzo[b]thiophene-2-carboxamide;
185) 6-chloro-N-(3-chloro-5-(2-(4-chlorophenyl)propan-2-yl)phenyl)-5-((2-methoxyethyl)sulfonamido)benzo[b]thiophene-2-carboxamide;
186) 6-chloro-N-(3-chloro-5-(2-(5-cyanothiophen-2-yl)propan-2-yl)phenyl)-5-(methylsulfonamido)benzo[b]thiophene-2-carboxamide;
187) N-(3-chloro-5-(2-(1-ethyl-1H-pyrrol-2-yl)propan-2-yl)phenyl)-5-(methylsulfonamido)benzo[b]thiophene-2-carboxamide;
188) 6-chloro-N-(3-chloro-5-(2-(4-chlorophenyl)propan-2-yl)phenyl)-5-((2-hydroxyethyl)sulfonamido)benzo[b]thiophene-2-carboxamide;
189) N-(3-chloro-5-(2-(pyrimidin-2-yloxy)propan-2-yl)phenyl)-5-(methylsulfonamido)benzo[b]thiophene-2-carboxamide;
190) N-(3-chloro-5-(2-(6-oxopyridazin-1(6H)-yl)propan-2-yl)phenyl)-5-(methylsulfonamido)benzo[b]thiophene-2-carboxamide;
191) N-(3-chloro-5-(2-(pyridin-4-yl)propan-2-yl)phenyl)-5-(methylsulfonamido)benzo[b]thiophene-2-carboxamide;
192) 2-((3-bromo-5-(2-(3-isopropoxy-5-(trifluoromethoxy)phenyl)propan-2-yl)phenyl)carbamoyl)benzo[b]thiophen-5-yl dihydrogen phosphate;
193) 2-((3-chloro-5-(2-(3-isopropoxy-5-(trifluoromethoxy)phenyl)propan-2-yl)phenyl)carbamoyl)benzo[b]thiophen-5-yl dihydrogen phosphate;
194) tert-butyl (2-((3-chloro-5-(2-(3-isopropoxy-5-(trifluoromethoxy)phenyl)propan-2-yl)phenyl)carbamoyl)benzo[b]thiophen-5-yl)carbamate;
195) N-(3-chloro-5-(2-(3-isopropoxy-5-(trifluoromethoxy)phenyl)propan-2-yl)phenyl)-5-((2-methoxyethyl)sulfonamido)benzo[b]thiophene-2-carboxamide;

196) N-(3-chloro-5-(2-(3-isopropoxy-5-(trifluoromethoxy)phenyl)propan-2-yl)phenyl)-5-(((tetrahydrofuran-3-yl)methyl)sulfonamido)benzo[b]thiophene-2-carboxamide;
197) N-(3-chloro-5-(2-(3-isopropoxy-5-(trifluoromethoxy)phenyl)propan-2-yl)phenyl)-5-(((tetrahydrofuran-2-yl)methyl)sulfonamido)benzo[b]thiophene-2-carboxamide;
198) N-(3-chloro-5-(2-(3-isopropoxy-5-(trifluoromethoxy)phenyl)propan-2-yl)phenyl)-5-(((tetrahydro-2H-pyran-4-yl)methyl)sulfonamido)benzo[b]thiophene-2-carboxamide;
199) N-(3-chloro-5-(2-(3-isopropoxy-5-(trifluoromethoxy)phenyl)propan-2-yl)phenyl)-5-((3,5-dimethylisoxazole)-4-sulfonamido)benzo[b]thiophene-2-carboxamide;
200) N-(3-chloro-5-(2-(3-isopropoxy-5-(trifluoromethoxy)phenyl)propan-2-yl)phenyl)-5-((1-methyl-1H-pyrazole)-3-sulfonamido)benzo[b]thiophene-2-carboxamide;
201) N-(3-chloro-5-(2-(3-isopropoxy-5-(trifluoromethoxy)phenyl)propan-2-yl)phenyl)-5-((1-methyl-1H-pyrazole)-4-sulfonamido)benzo[b]thiophene-2-carboxamide;
202) N-(3-chloro-5-(2-(3-isopropoxy-5-(trifluoromethoxy)phenyl)propan-2-yl)phenyl)-5-(ethylsulfonamido)benzo[b]thiophene-2-carboxamide;
203) N-(3-chloro-5-(2-(3-isopropoxy-5-(trifluoromethoxy)phenyl)propan-2-yl)phenyl)-5-((1-methylethyl)sulfonamido)benzo[b]thiophene-2-carboxamide;
204) N-(3-chloro-5-(2-(3-isopropoxy-5-(trifluoromethoxy)phenyl)propan-2-yl)phenyl)-5-((tetrahydrofuran)-3-sulfonamido)benzo[b]thiophene-2-carboxamide;
205) N-(3-chloro-5-(2-(3-isopropoxy-5-(trifluoromethoxy)phenyl)propan-2-yl)phenyl)-5-((1,1-dioxidotetrahydro-2H-thiopyran)-4-sulfonamido)benzo[b]thiophene-2-carboxamide;
206) 5-((1-acetylpiperidine)-4-sulfonamido)-N-(3-chloro-5-(2-(3-isopropoxy-5-(trifluoromethoxy)phenyl)propan-2-yl)phenyl)benzo[b]thiophene-2-carboxamide;
207) N-(3-chloro-5-(2-(3-isopropoxy-5-(trifluoromethoxy)phenyl)propan-2-yl)phenyl)-5-(vinylsulfonamido)benzo[b]thiophene-2-carboxamide;
208) N-(3-chloro-5-(2-(3-isopropoxy-5-(trifluoromethoxy)phenyl)propan-2-yl)phenyl)-5-((2-(dimethylamino)ethyl)sulfonamido)benzo[b]thiophene-2-carboxamide;
209) N-(3-chloro-5-(2-(3-isopropoxy-5-(trifluoromethoxy)phenyl)propan-2-yl)phenyl)-5-(2-morpholinoethyl)sulfonamido)benzo[b]thiophene-2-carboxamide;
210) N-(3-chloro-5-(2-(3-isopropoxy-5-(trifluoromethoxy)phenyl)propan-2-yl)phenyl)-5-((2-(hydroxy(methyl)amino)ethyl)sulfonamido)benzo[b]thiophene-2-carboxamide;
211) N-(3-chloro-5-(2-(3-isopropoxy-5-(trifluoromethoxy)phenyl)propan-2-yl)phenyl)-5-(1,1-dioxido-1,2-thiazinan-2-yl)benzo[b]thiophene-2-carboxamide;
212) N-(3-chloro-5-(2-(3-isopropoxy-5-(trifluoromethoxy)phenyl)propan-2-yl)phenyl)-5-(1,1-dioxidoisothiazolidin-2-yl)benzo[b]thiophene-2-carboxamide;
213) N-(3-iodo-5-(2-(3-isopropoxy-5-(trifluoromethoxy)phenyl)propan-2-yl)phenyl)-5-(methylsulfonamido)benzo[b]thiophene-2-carboxamide;
214) 3-iodo-N-(3-iodo-5-(2-(3-isopropoxy-5-(trifluoromethoxy)phenyl)propan-2-yl)phenyl)-5-(methylsulfonamido)benzo[b]thiophene-2-carboxamide;
215) N-(3-chloro-5-(2-(3-isopropoxy-5-(trifluoromethoxy)phenyl)propan-2-yl)phenyl)-6-fluoro-5-(N-methylmethylsulfonamido)benzo[b]thiophene-2-carboxamide;
216) N-(3-chloro-5-(2-(3-isopropoxy-5-(trifluoromethoxy)phenyl)propan-2-yl)phenyl)-6-fluoro-N-methyl-5-(N-methylmethylsulfonamido)benzo[b]thiophene-2-carboxamide;
217) N-(3-chloro-5-(2-(3-isopropoxy-5-(trifluoromethoxy)phenyl)propan-2-yl)phenyl)-6-fluoro-5-(N-(2-morpholinoethyl)methylsulfonamido)benzo[b]thiophene-2-carboxamide;
218) N-(3-chloro-5-(2-(3-isopropoxy-5-(trifluoromethoxy)phenyl)propan-2-yl)phenyl)-6-fluoro-N-(2-morpholinoethyl)-5-(N-(2-morpholinoethyl)methylsulfonamido)benzo[b]thiophene-2-carboxamide;
219) N-(3-chloro-5-(2-(3-isopropoxy-5-(trifluoromethoxy)phenyl)propan-2-yl)phenyl)-5-(N-(2-(dimethylamino)ethyl)methylsulfonamido)-6-fluorobenzo[b]thiophene-2-carboxamide;
220) N-(3-chloro-5-(4-chlorophenoxy)phenyl)-5-(N-methylmethylsulfonamido)benzo[b]thiophene-2-carboxamide;
221) N-(3-chloro-5-(2-(4-chlorophenyl)propan-2-yl)phenyl)-5-(N-methylmethylsulfonamido)benzo[b]thiophene-2-carboxamide;
222) N-(3-chloro-5-(2-(3-isopropoxy-5-(trifluoromethoxy)phenyl)propan-2-yl)phenyl)-5-(methylsulfonamido)benzo[b]thiophene-2-carboxamide 1,1-dioxide;
223) N-(3-chloro-5-(2-(3-isopropoxy-5-(trifluoromethoxy)phenyl)propan-2-yl)phenyl)-5-(methylsulfonamido)benzo[b]thiophene-2-carboxamide 1-oxide;
224) N-(3-(2-(3-cyanophenyl)propan-2-yl)phenyl)-5-(methylsulfonamido)benzo[b]thiophene-2-carboxamide;
236) N-(2',4'-difluoro-[1,1'-biphenyl]-3-yl)-5-methoxy-6-(methylsulfonamido)-1H-indole-2-carboxamide;
237) N-(2',4'-difluoro-[1,1'-biphenyl]-3-yl)-5-(methylsulfonamido)benzo[b]thiophene-2-carboxamide;
238) N-(2',4'-difluoro-[1,1'-biphenyl]-3-yl)-5-(methylsulfonamido)benzofuran-2-carboxamide;
239) N-(2',4'-difluoro-[1,1'-biphenyl]-3-yl)-5-(trifluoromethoxy)-1H-indole-2-carboxamide;
240) N-(2',4'-difluoro-[1,1'-biphenyl]-3-yl)-6-(methylsulfonyl)-1H-indole-2-carboxamide;
241) N-(2',4'-difluoro-[1,1'-biphenyl]-3-yl)-3-methyl-6-(methylsulfonamido)benzo[b]thiophene-2-carboxamide;
242) N-(2',4'-difluoro-[1,1'-biphenyl]-3-yl)-6-(methylsulfonamido)benzo[b]thiophene-2-carboxamide;
243) N-(2',4'-difluoro-[1,1'-biphenyl]-3-yl)-3-methyl-5-(methylsulfonamido)benzo[b]thiophene-2-carboxamide;
245) N-(5-acetyl-2',4'-difluoro-[1,1'-biphenyl]-3-yl)-6-(methylsulfonamido)-1H-indole-2-carboxamide;
246) N-(4-(2,4-difluorophenyl)-1H-indazol-6-yl)-6-(methylsulfonamido)-1H-indole-2-carboxamide;
248) N-(2',4'-difluoro-[1,1'-biphenyl]-3-yl)-1-methyl-6-(methylsulfonamido)-1H-indole-2-carboxamide;

253) 1-methyl-6-(methylsulfonamido)-N-(2'-(trifluoromethyl)-[1,1'-biphenyl]-3-yl)-1H-indole-2-carboxamide;
254) 2-((2-((2',4'-difluoro-[1,1'-biphenyl]-3-yl)carbamoyl)-1H-indol-6-yl)oxy)-2-methylpropanoic acid;
255) ethyl 2-((2-((2',4'-difluoro-[1,1'-biphenyl]-3-yl)carbamoyl)-1H-indol-6-yl)oxy)acetate;
256) 2-((2-((2',4'-difluoro-[1,1'-biphenyl]-3-yl)carbamoyl)-1H-indol-6-yl)oxy)acetic acid;
257) N-(2',4'-difluoro-[1,1'-biphenyl]-3-yl)-6-((N-methylsulfamoyl)amino)-1H-indole-2-carboxamide;
258) 5-amino-N-(2'-(trifluoromethyl)-[1,1'-biphenyl]-3-yl)-1H-indole-2-carboxamide;
259) 5-(methylsulfonamido)-N-(2'-(trifluoromethyl)-[1,1'-biphenyl]-3-yl)-1H-indole-2-carboxamide;
260) 6-(methylsulfonamido)-N-(2'-(trifluoromethyl)-[1,1'-biphenyl]-3-yl)-1H-indole-2-carboxamide;
261) N-(2',4'-difluoro-[1,1'-biphenyl]-3-yl)-6-(methylsulfonamido)indoline-2-carboxamide;
262) N-(4'-fluoro-2'-(trifluoromethyl)-[1,1'-biphenyl]-3-yl)-6-(methylsulfonamido)indoline-2-carboxamide;
264) 6-(2,2,2-trifluoroethylsulfonamido)-N-(2'-(trifluoromethyl)-[1,1'-biphenyl]-3-yl)-1H-indole-2-carboxamide;
265) 6-(sulfamoylamino)-N-(2'-(trifluoromethyl)-[1,1'-biphenyl]-3-yl)-1H-indole-2-carboxamide;
266) 6-(methylsulfonamido)-N-(2'-(trifluoromethyl)-[1,1'-biphenyl]-3-yl)-1H-indole-3-carboxamide;
267) 6-((N,N-dimethylsulfamoyl)amino)-N-(2'-(trifluoromethyl)-[1,1'-biphenyl]-3-yl)-1H-indole-2-carboxamide;
268) N-(2'-(trifluoromethyl)-[1,1'-biphenyl]-3-yl)-6-(trifluoromethylsulfonamido)-1H-indole-2-carboxamide;
269) 6-((N-methylsulfamoyl)amino)-N-(2'-(trifluoromethyl)-[1,1'-biphenyl]-3-yl)-1H-indole-2-carboxamide;
270) N-(2',4'-difluoro-[1,1'-biphenyl]-3-yl)-6-(methylsulfonamido)-1H-indole-2-carboxamide;
271) 6-amino-N-(2',4'-difluoro-[1,1'-biphenyl]-3-yl)-1H-indole-2-carboxamide;
272) N-(2',4'-difluoro-[1,1'-biphenyl]-3-yl)-5-(methylsulfonamido)-1H-indole-2-carboxamide;
273) N-(2',4'-difluoro-[1,1'-biphenyl]-3-yl)-6-(2,2,2-trifluoroethylsulfonamido)-1H-indole-2-carboxamide;
274) N-(2',4'-difluoro-[1,1'-biphenyl]-3-yl)-6-(sulfamoylamino)-1H-indole-2-carboxamide;
275) N-(2',4'-difluoro-[1,1'-biphenyl]-3-yl)-6-(methylsulfonamido)-1H-indole-3-carboxamide;
276) N-(2',4'-difluoro-[1,1'-biphenyl]-3-yl)-6-((N,N-dimethylsulfamoyl)amino)-1H-indole-2-carboxamide;
277) N-(4'-fluoro-2'-(trifluoromethyl)-[1,1'-biphenyl]-3-yl)-6-(methylsulfonamido)-1H-indole-2-carboxamide;
278) 6-(cyclopropanesulfonamido)-N-(4-(2,4-difluorophenyl)pyridin-2-yl)-1H-indole-2-carboxamide;
279) N-(4-(2,4-difluorophenyl)pyridin-2-yl)-6-(methylsulfonamido)-1H-indole-2-carboxamide;
280) N-(2',4'-difluoro-[1,1'-biphenyl]-3-yl)-N-methyl-6-(methylsulfonamido)-1H-indole-2-carboxamide;
281) N-(5'-methoxy-2'-(trifluoromethyl)-[1,1'-biphenyl]-3-yl)-6-(methylsulfonamido)-1H-indole-2-carboxamide;
283) 6-(methylsulfonamido)-N-(4'-sulfamoyl-2'-(trifluoromethyl)-[1,1'-biphenyl]-3-yl)-1H-indole-2-carboxamide;
284) N-(4'-cyano-2'-(trifluoromethyl)-[1,1'-biphenyl]-3-yl)-6-(methylsulfonamido)-1H-indole-2-carboxamide;
285) 6-(methylsulfonamido)-N-(4'-nitro-2'-(trifluoromethyl)-[1,1'-biphenyl]-3-yl)-1H-indole-2-carboxamide;
287) methyl 3'-(6-(methylsulfonamido)-1H-indole-2-carboxamido)-6-(trifluoromethyl)-[1,1'-biphenyl]-3-carboxylate;
289) methyl 4-methoxy-3'-(6-(methylsulfonamido)-1H-indole-2-carboxamido)-6-(trifluoromethyl)-[1,1'-biphenyl]-3-carboxylate;
290) 6-(methylsulfonamido)-N-(3-(3-(trifluoromethyl)pyridin-2-yl)phenyl)-1H-indole-2-carboxamide;
291) 6-(methylsulfonamido)-N-(3-(4-(trifluoromethyl)pyridin-3-yl)phenyl)-1H-indole-2-carboxamide;
293) 6-(methylsulfonamido)-N-(3-(2-(trifluoromethyl)pyridin-3-yl)phenyl)-1H-indole-2-carboxamide;
294) N-(3-(6-chloro-4-(trifluoromethyl)pyridin-3-yl)phenyl)-6-(methylsulfonamido)-1H-indole-2-carboxamide;
296) tert-butyl 2-((2'-fluoro-4'-methoxy-[1,1'-biphenyl]-3-yl)carbamoyl)-6-(methylsulfonamido)-1H-indole-1-carboxylate;
299) methyl 6-chloro-3'-(6-(methylsulfonamido)-1H-indole-2-carboxamido)-[1,1'-biphenyl]-3-carboxylate;
300) methyl 4-chloro-3-(2-(6-(methylsulfonamido)-1H-indole-2-carboxamido)pyridin-4-yl)benzoate;
301) N-(5-cyano-2',4'-difluoro-[1,1'-biphenyl]-3-yl)-6-(methylsulfonamido)-1H-indole-2-carboxamide;
302) N-(5-bromo-2',4'-difluoro-[1,1'-biphenyl]-3-yl)-6-(methylsulfonamido)-1H-indole-2-carboxamide;
303) N-(5-bromo-2',4'-difluoro-[1,1'-biphenyl]-3-yl)-5-methoxy-6-(methylsulfonamido)-1H-indole-2-carboxamide;
304) N-(5-bromo-2',4'-difluoro-[1,1'-biphenyl]-3-yl)-6-(methylsulfonyl)-1H-indole-2-carboxamide;
305) N-(5-bromo-2',4'-difluoro-[1,1'-biphenyl]-3-yl)-5-(methylsulfonamido)benzo[b]thiophene-2-carboxamide;
306) N-(5-bromo-2',4'-difluoro-[1,1'-biphenyl]-3-yl)-5-(methylsulfonamido)benzofuran-2-carboxamide;
307) N-(5-bromo-2',4'-difluoro-[1,1'-biphenyl]-3-yl)-6-((N-methylsulfamoyl)amino)-1H-indole-2-carboxamide;
308) N-(5-bromo-2',4'-difluoro-[1,1'-biphenyl]-3-yl)-5-(trifluoromethoxy)-1H-indole-2-carboxamide;
309) N-(5-bromo-2',4'-difluoro-[1,1'-biphenyl]-3-yl)-3-methyl-6-(methylsulfonamido)benzo[b]thiophene-2-carboxamide;
310) N-(5-bromo-2',4'-difluoro-[1,1'-biphenyl]-3-yl)-6-(methylsulfonamido)benzo[b]thiophene-2-carboxamide;
311) N-(5-bromo-2',4'-difluoro-[1,1'-biphenyl]-3-yl)-3-methyl-5-(methylsulfonamido)benzo[b]thiophene-2-carboxamide;
312) 6-(methylsulfonamido)-N-(2',4',5-trifluoro-[1,1'-biphenyl]-3-yl)-1H-indole-2-carboxamide;
313) N-(2',4'-difluoro-5-(trifluoromethyl)-[1,1'-biphenyl]-3-yl)-6-(methylsulfonamido)-1H-indole-2-carboxamide;
314) N-(2',4'-difluoro-5-methoxy-[1,1'-biphenyl]-3-yl)-6-(methylsulfonamido)-1H-indole-2-carboxamide;
315) N-(5-cyano-4'-fluoro-2'-(trifluoromethyl)-[1,1'-biphenyl]-3-yl)-6-(methylsulfonamido)-1H-indole-2-carboxamide;
316) N-(2',4'-difluoro-5-methoxy-[1,1'-biphenyl]-3-yl)-3-methyl-6-(methylsulfonamido)benzo[b]thiophene-2-carboxamide;
317) N-(2',4'-difluoro-5-methoxy-[1,1'-biphenyl]-3-yl)-5-(methylsulfonamido)benzo[b]thiophene-2-carboxamide;

318) N-(2',4'-difluoro-5-(methylcarbamoyl)-[1,1'-biphenyl]-3-yl)-6-(methylsulfonamido)-1H-indole-2-carboxamide;
319) N-(5-(dimethylcarbamoyl)-2',4'-difluoro-[1,1'-biphenyl]-3-yl)-6-(methylsulfonamido)-1H-indole-2-carboxamide;
320) N-(2',4'-difluoro-5-(piperidine-1-carbonyl)-[1,1'-biphenyl]-3-yl)-6-(methylsulfonamido)-1H-indole-2-carboxamide;
321) N-(2',4'-difluoro-5-(morpholine-4-carbonyl)-[1,1'-biphenyl]-3-yl)-6-(methylsulfonamido)-1H-indole-2-carboxamide;
322) N-(5-chloro-2',4'-difluoro-[1,1'-biphenyl]-3-yl)-6-fluoro-5-(methylsulfonamido)benzo[b]thiophene-2-carboxamide;
323) N-(5-chloro-2',4'-difluoro-[1,1'-biphenyl]-3-yl)-5-(methylsulfonamido)benzo[b]thiophene-2-carboxamide;
324) N-(5-chloro-3'-methoxy-5'-(trifluoromethoxy)-[1,1'-biphenyl]-3-yl)-5-(methylsulfonamido)benzo[b]thiophene-2-carboxamide;
325) N-(5-chloro-3'-methoxy-5'-(trifluoromethoxy)-[1,1'-biphenyl]-3-yl)-6-fluoro-5-(methylsulfonamido)benzo[b]thiophene-2-carboxamide;
326) N-(5-chloro-3'-methoxy-5'-(trifluoromethoxy)-[1,1'-biphenyl]-3-yl)-6-fluoro-5-(N-methylmethylsulfonamido)benzo[b]thiophene-2-carboxamide;
327) N-(5-chloro-2',4'-difluoro-[1,1'-biphenyl]-3-yl)-5-((tetrahydrofuran)-3-sulfonamido)benzo[b]thiophene-2-carboxamide;
328) N-(5-chloro-3'-methoxy-5'-(trifluoromethoxy)-[1,1'-biphenyl]-3-yl)-5-((tetrahydrofuran)-3-sulfonamido)benzo[b]thiophene-2-carboxamide;
329) N-(5-chloro-2',4'-difluoro-[1,1'-biphenyl]-3-yl)-6-fluoro-5-(N-methylmethylsulfonamido)benzo[b]thiophene-2-carboxamide;
330) N-(5-chloro-2',4'-difluoro-[1,1'-biphenyl]-3-yl)-6-fluoro-5-((tetrahydrofuran)-3-sulfonamido)benzo[b]thiophene-2-carboxamide;
331) N-(4-chloro-6-(2,4-difluorophenyl)pyridin-2-yl)-5-(methylsulfonamido)benzo[b]thiophene-2-carboxamide;
332) N-(3-chloro-5-(thiophen-3-yl)phenyl)-5-(methylsulfonamido)benzo[b]thiophene-2-carboxamide;
333) 6-chloro-N-(5-chloro-2',4'-difluoro-[1,1'-biphenyl]-3-yl)-5-(methylsulfonamido)benzo[b]thiophene-2-carboxamide;
334) N-(3-chloro-5-(1-methyl-1H-pyrrol-2-yl)phenyl)-5-(methylsulfonamido)benzo[b]thiophene-2-carboxamide;
335) N-(5-chloro-2',4'-difluoro-[1,1'-biphenyl]-3-yl)-3-hydroxy-5-(methylsulfonamido)benzo[b]thiophene-2-carboxamide;
336) N-(3-chloro-5-(thiophen-2-yl)phenyl)-5-(methylsulfonamido)benzo[b]thiophene-2-carboxamide;
337) N-(6-chloro-4-(2,4-difluorophenyl)pyridin-2-yl)-5-(methylsulfonamido)benzo[b]thiophene-2-carboxamide;
338) N-(3-chloro-5-(pyrazin-2-yl)phenyl)-5-(methylsulfonamido)benzo[b]thiophene-2-carboxamide;
339) N-(3-chloro-5-(6-chloropyrazin-2-yl)phenyl)-5-(methylsulfonamido)benzo[b]thiophene-2-carboxamide;
340) N-(3-chloro-5-(1-methyl-1H-imidazol-5-yl)phenyl)-5-(methylsulfonamido)benzo[b]thiophene-2-carboxamide;
341) N-(5-bromo-2',4'-difluoro-[1,1'-biphenyl]-3-yl)-1-methyl-6-(N-methylmethylsulfonamido)-1H-indole-2-carboxamide;
342) N-(5-bromo-2',4'-difluoro-[1,1'-biphenyl]-3-yl)-6-(N-methylmethylsulfonamido)-1H-indole-2-carboxamide;
343) 1-methyl-6-(N-methylmethylsulfonamido)-N-(2'-(trifluoromethyl)-[1,1'-biphenyl]-3-yl)-1H-indole-2-carboxamide;
344) N-(2',4'-difluoro-[1,1'-biphenyl]-3-yl)-6-(N-methylmethylsulfonamido)-1H-indole-2-carboxamide;
345) N-(2',4'-difluoro-[1,1'-biphenyl]-3-yl)-1-methyl-6-(N-methylmethylsulfonamido)-1H-indole-2-carboxamide;
346) 6-(N-methylmethylsulfonamido)-N-(2'-(trifluoromethyl)-[1,1'-biphenyl]-3-yl)-1H-indole-2-carboxamide;
347) N-(2',4'-difluoro-5-methoxy-[1,1'-biphenyl]-3-yl)-6-(N-methylmethylsulfonamido)-1H-indole-2-carboxamide;
348) N-(2',4'-difluoro-5-methoxy-[1,1'-biphenyl]-3-yl)-1-methyl-6-(N-methylmethylsulfonamido)-1H-indole-2-carboxamide;
349) N-(2',4'-difluoro-5-(6-fluoropyridin-3-yl)-[1,1'-biphenyl]-3-yl)-6-(methylsulfonamido)-1H-indole-2-carboxamide;
350) tert-butyl 2-(2',4'-difluoro-5-(6-(methylsulfonamido)-1H-indole-2-carboxamido)-[1,1'-biphenyl]-3-yl)-1H-pyrrole-1-carboxylate;
351) N-(2',4'-difluoro-5-(1H-pyrazol-3-yl)-[1,1'-biphenyl]-3-yl)-6-(methylsulfonamido)-1H-indole-2-carboxamide;
352) N-(2',4'-difluoro-5-(1H-pyrrol-2-yl)-[1,1'-biphenyl]-3-yl)-6-(methylsulfonamido)-1H-indole-2-carboxamide;
353) N-(2',4'-difluoro-5-(1-methyl-1H-pyrrol-2-yl)-[1,1'-biphenyl]-3-yl)-6-(methylsulfonamido)-1H-indole-2-carboxamide;
354) N-(2',4'-difluoro-5-(thiophen-2-yl)-[1,1'-biphenyl]-3-yl)-6-(methylsulfonamido)-1H-indole-2-carboxamide;
355) N-(2',4'-difluoro-5-(thiophen-3-yl)-[1,1'-biphenyl]-3-yl)-6-(methylsulfonamido)-1H-indole-2-carboxamide;
356) N-(2',4'-difluoro-5-(pyridin-4-yl)-[1,1'-biphenyl]-3-yl)-6-(methylsulfonamido)-1H-indole-2-carboxamide;
357) N-(2',4'-difluoro-5-(pyridin-3-yl)-[1,1'-biphenyl]-3-yl)-6-(methylsulfonamido)-1H-indole-2-carboxamide;
358) N-(2',4'-difluoro-5-(6-(trifluoromethyl)pyridin-3-yl)-[1,1'-biphenyl]-3-yl)-6-(methylsulfonamido)-1H-indole-2-carboxamide;
359) N-(5-(6-cyanopyridin-3-yl)-2',4'-difluoro-[1,1'-biphenyl]-3-yl)-6-(methylsulfonamido)-1H-indole-2-carboxamide;
360) N-(2',4'-difluoro-5-(pyrimidin-5-yl)-[1,1'-biphenyl]-3-yl)-6-(methylsulfonamido)-1H-indole-2-carboxamide;
361) N-(5-(2-aminopyrimidin-5-yl)-2',4'-difluoro-[1,1'-biphenyl]-3-yl)-6-(methylsulfonamido)-1H-indole-2-carboxamide;
362) 6-(methylsulfonamido)-N-(2,2'',4,4''-tetrafluoro-[1,1':3',1''-terphenyl]-5'-yl)-1H-indole-2-carboxamide;
363) N-(5-(cyanomethyl)-2',4'-difluoro-[1,1'-biphenyl]-3-yl)-6-(methylsulfonamido)-1H-indole-2-carboxamide;
364) N-(2',4'-difluoro-5-(6-hydroxypyridin-3-yl)-[1,1'-biphenyl]-3-yl)-6-(methylsulfonamido)-1H-indole-2-carboxamide;

365) N-(5-ethynyl-2',4'-difluoro-[1,1'-biphenyl]-3-yl)-6-(methylsulfonamido)-1H-indole-2-carboxamide;
366) N-(5-(2,2-difluoroethoxy)-2',4'-difluoro-[1,1'-biphenyl]-3-yl)-6-(methylsulfonamido)-1H-indole-2-carboxamide;
367) N-(2',4'-difluoro-5-isobutoxy-[1,1'-biphenyl]-3-yl)-6-(methylsulfonamido)-1H-indole-2-carboxamide;
368) N-(5-(cyanomethoxy)-2',4'-difluoro-[1,1'-biphenyl]-3-yl)-6-(methylsulfonamido)-1H-indole-2-carboxamide;
369) N-(5-(difluoromethoxy)-2',4'-difluoro-[1,1'-biphenyl]-3-yl)-6-(methylsulfonamido)-1H-indole-2-carboxamide;
370) N-(5-(difluoromethoxy)-2',4'-difluoro-[1,1'-biphenyl]-3-yl)-5-(methylsulfonamido)benzo[b]thiophene-2-carboxamide;
371) N-(2',4'-difluoro-5-(piperidin-1-yl)-[1,1'-biphenyl]-3-yl)-6-(methylsulfonamido)-1H-indole-2-carboxamide;
372) N-(5-(dimethylamino)-2',4'-difluoro-[1,1'-biphenyl]-3-yl)-6-(methylsulfonamido)-1H-indole-2-carboxamide;
373) N-(2',4'-difluoro-5-(methylamino)-[1,1'-biphenyl]-3-yl)-6-(methylsulfonamido)-1H-indole-2-carboxamide;
374) N-(2',4'-difluoro-5-morpholino-[1,1'-biphenyl]-3-yl)-6-(methylsulfonamido)-1H-indole-2-carboxamide;
375) N-(5-(dimethylamino)-2',4'-difluoro-[1,1'-biphenyl]-3-yl)-5-(methylsulfonamido)benzo[b]thiophene-2-carboxamide;
376) N-(5-(dimethylamino)-2',4'-difluoro-[1,1'-biphenyl]-3-yl)-5-(methylsulfonamido)benzofuran-2-carboxamide;
377) N-(5'-carbamoyl-4'-methoxy-2'-(trifluoromethyl)-[1,1'-biphenyl]-3-yl)-6-(methylsulfonamido)-1H-indole-2-carboxamide;
378) N-(5'-carbamoyl-4'-hydroxy-2'-(trifluoromethyl)-[1,1'-biphenyl]-3-yl)-6-(methylsulfonamido)-1H-indole-2-carboxamide;
379) N-(5'-carbamoyl-2'-(trifluoromethyl)-[1,1'-biphenyl]-3-yl)-6-(methylsulfonamido)-1H-indole-2-carboxamide;
380) N-(5'-carbamoyl-2'-chloro-[1,1'-biphenyl]-3-yl)-6-(methylsulfonamido)-1H-indole-2-carboxamide;
381) N-(4-(5-carbamoyl-2-chlorophenyl)pyridin-2-yl)-6-(methylsulfonamido)-1H-indole-2-carboxamide;
382) N-(2',4'-difluoro-5-(6-methoxypyridin-3-yl)-[1,1'-biphenyl]-3-yl)-6-(methylsulfonamido)-1H-indole-2-carboxamide;
383) N-(2',4'-difluoro-5-(6-methoxypyridin-2-yl)-[1,1'-biphenyl]-3-yl)-6-(methylsulfonamido)-1H-indole-2-carboxamide;
384) N-(2',4'-difluoro-5-(6-hydroxypyridin-2-yl)-[1,1'-biphenyl]-3-yl)-6-(methylsulfonamido)-1H-indole-2-carboxamide;
385) N-(4'-amino-2'-(trifluoromethyl)-[1,1'-biphenyl]-3-yl)-6-(methylsulfonamido)-1H-indole-2-carboxamide;
386) N-(4'-(methylamino)-2'-(trifluoromethyl)-[1,1'-biphenyl]-3-yl)-6-(methylsulfonamido)-1H-indole-2-carboxamide;
387) N-(3-(difluoro(phenyl)methyl)phenyl)-6-(methylsulfonamido)-1H-indole-2-carboxamide;
388) N-(3-(difluoro(pyridin-4-yl)methyl)phenyl)-6-(methylsulfonamido)-1H-indole-2-carboxamide;
389) N-(3-(difluoro(pyridin-2-yl)methyl)phenyl)-6-(methylsulfonamido)-1H-indole-2-carboxamide;
390) N-(3-((3-cyanophenyl)difluoromethyl)phenyl)-6-(methylsulfonamido)-1H-indole-2-carboxamide;
391) N-(3-((3-cyanophenyl)difluoromethyl)-5-(2,2-difluoroethoxy)phenyl)-6-(methylsulfonamido)-1H-indole-2-carboxamide;
392) N-(3-((3-cyanophenyl)difluoromethyl)-5-isobutoxyphenyl)-6-(methylsulfonamido)-1H-indole-2-carboxamide;
393) N-(3-(cyanomethoxy)-5-((3-cyanophenyl)difluoromethyl)phenyl)-6-(methylsulfonamido)-1H-indole-2-carboxamide;
394) N-(3-((4-methoxyphenyl)sulfonyl)phenyl)-6-(methylsulfonamido)-1H-indole-2-carboxamide;
395) 6-(methylsulfonamido)-N-(3-(phenylsulfonyl)phenyl)-1H-indole-2-carboxamide;
396) 6-(methylsulfonamido)-N-(3-((3-(trifluoromethoxy)phenyl)sulfonyl)phenyl)-1H-indole-2-carboxamide;
397) N-(3-methoxy-5-((3-(trifluoromethoxy)phenyl)sulfonyl)phenyl)-6-(methylsulfonamido)-1H-indole-2-carboxamide;
398) 6-(methylsulfonamido)-N-(3-((3-(trifluoromethoxy)phenyl)sulfonyl)-5-(trifluoromethyl)phenyl)-1H-indole-2-carboxamide;
399) N-(3-cyano-5-((3-(trifluoromethoxy)phenyl)sulfonyl)phenyl)-6-(methylsulfonamido)-1H-indole-2-carboxamide;
400) N-(3-isobutoxy-5-((3-(trifluoromethoxy)phenyl)sulfonyl)phenyl)-6-(methylsulfonamido)-1H-indole-2-carboxamide;
401) N-(3-(2,2-difluoroethoxy)-5-((3-(trifluoromethoxy)phenyl)sulfonyl)phenyl)-6-(methylsulfonamido)-1H-indole-2-carboxamide;
402) N-(3-((3-cyanophenyl)sulfonyl)phenyl)-6-(methylsulfonamido)-1H-indole-2-carboxamide;
403) 6-(methylsulfonamido)-N-(3-(pyridin-2-ylsulfonyl)phenyl)-1H-indole-2-carboxamide;
404) 6-(methylsulfonamido)-N-(3-(pyridin-3-ylsulfonyl)phenyl)-1H-indole-2-carboxamide;
405) N-(3-((3-chlorophenyl)sulfonyl)phenyl)-6-(methylsulfonamido)-1H-indole-2-carboxamide;
406) N-(3-((6-cyanopyridin-2-yl)sulfonyl)phenyl)-6-(methylsulfonamido)-1H-indole-2-carboxamide;
407) N-(3-((5-methoxypyridin-3-yl)sulfonyl)phenyl)-6-(methylsulfonamido)-1H-indole-2-carboxamide;
408) N-(3-((6-methoxypyridin-2-yl)sulfonyl)phenyl)-6-(methylsulfonamido)-1H-indole-2-carboxamide;
409) N-(3-(benzo[b]thiophen-5-ylsulfonyl)phenyl)-6-(methylsulfonamido)-1H-indole-2-carboxamide;
410) N-(3-((2-methylbenzo[d]thiazol-6-yl)sulfonyl)phenyl)-6-(methylsulfonamido)-1H-indole-2-carboxamide;
411) N-(3-((3-cyano-5-methoxyphenyl)sulfonyl)phenyl)-6-(methylsulfonamido)-1H-indole-2-carboxamide;
412) N-(3-((3-(cyanomethyl)phenyl)sulfonyl)phenyl)-6-(methylsulfonamido)-1H-indole-2-carboxamide;
413) 6-(methylsulfonamido)-N-(3-((4-oxo-4H-chromen-7-yl)sulfonyl)phenyl)-1H-indole-2-carboxamide;
414) N-(3-((3-bromophenyl)sulfonyl)phenyl)-6-(methylsulfonamido)-1H-indole-2-carboxamide;
415) N-(3-((3-aminophenyl)sulfonyl)phenyl)-6-(methylsulfonamido)-1H-indole-2-carboxamide;
416) N-(3-((3-ethynylphenyl)sulfonyl)phenyl)-6-(methylsulfonamido)-1H-indole-2-carboxamide;
417) N-(3-((3-cyano-5-hydroxyphenyl)sulfonyl)phenyl)-6-(methylsulfonamido)-1H-indole-2-carboxamide;

418) N-(3-bromo-5-((7-fluoro-3,4-dihydroisoquinolin-2(1H)-yl)sulfonyl)phenyl)-5-(methylsulfonamido)benzo[b]thiophene-2-carboxamide;
419) N-(3-bromo-5-((5,7-difluoro-3,4-dihydroisoquinolin-2(1H)-yl)sulfonyl)phenyl)-5-(methylsulfonamido)benzo[b]thiophene-2-carboxamide;
420) N-(3-bromo-5-((4,4-difluoropiperidin-1-yl)sulfonyl)phenyl)-5-(methylsulfonamido)benzo[b]thiophene-2-carboxamide;
421) 5-(methylsulfonamido)-N-(3-(1-phenylcyclopropyl)phenyl)benzo[b]thiophene-2-carboxamide;
422) 6-(methylsulfonamido)-N-(3-(1-phenylcyclopropyl)phenyl)-1H-indole-2-carboxamide;
423) 5-(methylsulfonamido)-N-(3-(1-phenylvinyl)phenyl)benzo[b]thiophene-2-carboxamide;
424) N-(3-(1-(4-fluorophenyl)cyclopropyl)phenyl)-5-(methylsulfonamido)benzo[b]thiophene-2-carboxamide;
425) N-(3-(1-(4-fluorophenyl)cyclopropyl)phenyl)-6-(methylsulfonamido)-1H-indole-2-carboxamide;
426) N-(3-bromo-5-(1-(2,4-difluorophenyl)cyclopropyl)phenyl)-5-(methylsulfonamido)benzo[b]thiophene-2-carboxamide;
427) N-(3-methoxy-5-(1-(3-methoxy-5-(trifluoromethoxy)phenyl)cyclopropyl)phenyl)-5-(methylsulfonamido)benzo[b]thiophene-2-carboxamide;
428) N-(3-(difluoromethoxy)-5-(1-(4-fluorophenyl)cyclopropyl)phenyl)-6-(methylsulfonamido)-1H-indole-2-carboxamide;
429) N-(3-(difluoromethoxy)-5-(1-(4-fluorophenyl)cyclopropyl)phenyl)-5-(methylsulfonamido)benzo[b]thiophene-2-carboxamide;
430) N-(3-chloro-5-(1-(3-isopropoxy-5-(trifluoromethoxy)phenyl)cyclopropyl)phenyl)-6-fluoro-5-(N-methylmethylsulfonamido)benzo[b]thiophene-2-carboxamide;
431) N-(3-chloro-5-(1-(3-isopropoxy-5-(trifluoromethoxy)phenyl)cyclopropyl)phenyl)-5-(methylsulfonamido)benzo[b]thiophene-2-carboxamide;
432) N-(3-chloro-5-(1-(4-chlorophenyl)cyclopropyl)phenyl)-5-(methylsulfonamido)benzo[b]thiophene-2-carboxamide;
433) 6-chloro-N-(3-chloro-5-(1-(4-chlorophenyl)cyclopropyl)phenyl)-5-(methylsulfonamido)benzo[b]thiophene-2-carboxamide;
434) N-(3-benzoylphenyl)-6-(methylsulfonamido)-1H-indole-2-carboxamide;
435) N-(3-(1-hydroxy-1-phenylethyl)phenyl)-6-(methylsulfonamido)-1H-indole-2-carboxamide;
436) 6-(N-(2-amino-2-oxoethyl)methylsulfonamido)-N-(3-(2-(3-hydroxy-5-(trifluoromethoxy)phenyl)propan-2-yl)phenyl)-1H-indole-2-carboxamide;
437) N-(3-(2-(3-(2-amino-2-oxoethoxy)-5-(trifluoromethoxy)phenyl)propan-2-yl)phenyl)-6-(N-(2-amino-2-oxoethyl)methylsulfonamido)-1H-indole-2-carboxamide;
438) N-(3-chloro-5-((2,4-difluorophenyl)amino)phenyl)-5-(methylsulfonamido)benzo[b]thiophene-2-carboxamide;
439) N-(3-chloro-5-((2,4-difluorophenyl)(methyl)amino)phenyl)-5-(methylsulfonamido)benzo[b]thiophene-2-carboxamide;
440) N-(3-chloro-5-((4-chlorophenyl)(methyl)amino)phenyl)-5-(methylsulfonamido)benzo[b]thiophene-2-carboxamide;
441) 6-chloro-N-(3-chloro-5-((4-chlorophenyl)(methyl)amino)phenyl)-5-(methylsulfonamido)benzo[b]thiophene-2-carboxamide;
442) 6-chloro-N-(3-chloro-5-((2,4-difluorophenyl)(methyl)amino)phenyl)-5-(methylsulfonamido)benzo[b]thiophene-2-carboxamide;
443) N-(3-chloro-5-((3-isopropoxy-5-(trifluoromethoxy)phenyl)(methyl)amino)phenyl)-5-(methylsulfonamido)benzo[b]thiophene-2-carboxamide;
444) N-(3-chloro-5-(2,4-difluorophenoxy)phenyl)-5-(methylsulfonamido)benzo[b]thiophene-2-carboxamide;
445) N-(3-chloro-5-(4-chlorophenoxy)phenyl)-5-(methylsulfonamido)benzo[b]thiophene-2-carboxamide;
446) N-(3-chloro-5-(4-fluorophenoxy)phenyl)-5-(methylsulfonamido)benzo[b]thiophene-2-carboxamide;
447) N-(3-chloro-5-(4-methoxyphenoxy)phenyl)-5-(methylsulfonamido)benzo[b]thiophene-2-carboxamide;
448) N-(3-chloro-5-(2,5-difluorophenoxy)phenyl)-5-(methylsulfonamido)benzo[b]thiophene-2-carboxamide;
449) 6-chloro-N-(3-chloro-5-(4-chlorophenoxy)phenyl)-5-(methylsulfonamido)benzo[b]thiophene-2-carboxamide;
450) N-(3-chloro-5-(3-(trifluoromethoxy)phenoxy)phenyl)-5-(methylsulfonamido)benzo[b]thiophene-2-carboxamide;
451) N-(3-chloro-5-(4-cyanophenoxy)phenyl)-5-(methylsulfonamido)benzo[b]thiophene-2-carboxamide;
452) N-(3-chloro-5-(3-isopropoxy-5-(trifluoromethoxy)phenoxy)phenyl)-5-(methylsulfonamido)benzo[b]thiophene-2-carboxamide;
453) 6-bromo-N-(3-chloro-5-(4-chlorophenoxy)phenyl)-5-(methylsulfonamido)benzo[b]thiophene-2-carboxamide;
454) N-(3-chloro-5-(4-(trifluoromethoxy)phenoxy)phenyl)-5-(methylsulfonamido)benzo[b]thiophene-2-carboxamide;
455) N-(3-chloro-5-(3-(trifluoromethyl)phenoxy)phenyl)-5-(methylsulfonamido)benzo[b]thiophene-2-carboxamide;
456) N-(3-chloro-5-(3-chlorophenoxy)phenyl)-5-(methylsulfonamido)benzo[b]thiophene-2-carboxamide;
457) N-(3-chloro-5-(3-methoxyphenoxy)phenyl)-5-(methylsulfonamido)benzo[b]thiophene-2-carboxamide;
458) N-(3-chloro-5-(3-chloro-5-cyanophenoxy)phenyl)-5-(methylsulfonamido)benzo[b]thiophene-2-carboxamide;
459) N-(3-chloro-5-(3-cyanophenoxy)phenyl)-5-(methylsulfonamido)benzo[b]thiophene-2-carboxamide;
460) N-(3-chloro-5-(3,4-difluorophenoxy)phenyl)-5-(methylsulfonamido)benzo[b]thiophene-2-carboxamide;
461) N-(3-chloro-5-(3-chloro-4-fluorophenoxy)phenyl)-5-(methylsulfonamido)benzo[b]thiophene-2-carboxamide;
462) N-(3-chloro-5-(2,4-dichlorophenoxy)phenyl)-5-(methylsulfonamido)benzo[b]thiophene-2-carboxamide;
463) N-(3-chloro-5-(3,5-difluorophenoxy)phenyl)-5-(methylsulfonamido)benzo[b]thiophene-2-carboxamide;
464) N-(3-chloro-5-(3,5-dichlorophenoxy)phenyl)-5-(methylsulfonamido)benzo[b]thiophene-2-carboxamide;

465) N-(3-chloro-5-(4-(trifluoromethyl)phenoxy)phenyl)-5-(methylsulfonamido)benzo[b]thiophene-2-carboxamide;
466) N-(3-chloro-5-(4-chloro-3-fluorophenoxy)phenyl)-5-(methylsulfonamido)benzo[b]thiophene-2-carboxamide;
467) N-(3-chloro-5-(3-chloro-5-(trifluoromethoxy)phenoxy)phenyl)-5-(methylsulfonamido)benzo[b]thiophene-2-carboxamide;
468) N-(3-chloro-5-(4-chloro-3-(trifluoromethoxy)phenoxy)phenyl)-5-(methylsulfonamido)benzo[b]thiophene-2-carboxamide;
469) N-(3-chloro-5-(3-chloro-5-fluorophenoxy)phenyl)-5-(methylsulfonamido)benzo[b]thiophene-2-carboxamide;
470) N-(3-chloro-5-(4-fluoro-3-(trifluoromethoxy)phenoxy)phenyl)-5-(methylsulfonamido)benzo[b]thiophene-2-carboxamide;
471) 6-chloro-N-(3-chloro-5-(thiazol-2-yloxy)phenyl)-5-(methylsulfonamido)benzo[b]thiophene-2-carboxamide;
472) 6-chloro-N-(3-chloro-5-(thiazol-5-yloxy)phenyl)-5-(methylsulfonamido)benzo[b]thiophene-2-carboxamide;
473) 6-chloro-N-(3-chloro-5-((5-chlorothiophen-2-yl)oxy)phenyl)-5-(methylsulfonamido)benzo[b]thiophene-2-carboxamide;
474) 6-chloro-N-(3-chloro-5-(3-chloro-5-methoxyphenoxy)phenyl)-5-(methylsulfonamido)benzo[b]thiophene-2-carboxamide;
475) 6-chloro-N-(3-chloro-5-(3-chloro-5-hydroxyphenoxy)phenyl)-5-(methylsulfonamido)benzo[b]thiophene-2-carboxamide;
476) 6-chloro-N-(3-chloro-5-(3-chloro-4-fluorophenoxy)phenyl)-5-(methylsulfonamido)benzo[b]thiophene-2-carboxamide;
477) 6-chloro-N-(3-chloro-5-(4-chloro-3-fluorophenoxy)phenyl)-5-(methylsulfonamido)benzo[b]thiophene-2-carboxamide;
478) 6-chloro-N-(3-chloro-5-(4-fluorophenoxy)phenyl)-5-(methylsulfonamido)benzo[b]thiophene-2-carboxamide;
479) 6-chloro-N-(3-chloro-5-(3-(trifluoromethoxy)phenoxy)phenyl)-5-(methylsulfonamido)benzo[b]thiophene-2-carboxamide;
480) 6-chloro-N-(3-chloro-5-(4-(trifluoromethoxy)phenoxy)phenyl)-5-(methylsulfonamido)benzo[b]thiophene-2-carboxamide;
481) 6-chloro-N-(3-chloro-5-(3,4-difluorophenoxy)phenyl)-5-(methylsulfonamido)benzo[b]thiophene-2-carboxamide;
482) 6-chloro-N-(3-chloro-5-(4-(trifluoromethyl)phenoxy)phenyl)-5-(methylsulfonamido)benzo[b]thiophene-2-carboxamide;
483) 6-chloro-N-(3-chloro-5-(3-chloro-5-fluorophenoxy)phenyl)-5-(methylsulfonamido)benzo[b]thiophene-2-carboxamide;
484) 6-chloro-N-(3-chloro-5-(3-fluoro-5-methoxyphenoxy)phenyl)-5-(methylsulfonamido)benzo[b]thiophene-2-carboxamide;
485) 5-chloro-N-(3-chloro-5-(4-chlorophenoxy)phenyl)-6-(methylsulfonamido)benzo[b]thiophene-2-carboxamide;
486) 6-chloro-N-(3-chloro-5-(cyclohexyloxy)phenyl)-5-(methylsulfonamido)benzo[b]thiophene-2-carboxamide;
487) 6-chloro-N-(3-chloro-5-((5-methylthiophen-2-yl)oxy)phenyl)-5-(methylsulfonamido)benzo[b]thiophene-2-carboxamide;
488) 4-bromo-N-(3-chloro-5-(2-(3-isopropoxy-5-methylphenyl)propan-2-yl)phenyl)-5-(methylsulfonamido)benzo[b]thiophene-2-carboxamide;
489) ro-6-(4-chlorophenoxy)pyridin-4-yl)-5-(methylsulfonamido)benzo[b]thiophene-2-carboxamide;
490) 6-chloro-N-(2-chloro-6-(4-chlorophenoxy)pyridin-4-yl)-5-(methylsulfonamido)benzo[b]thiophene-2-carboxamide;
491) N-(2-chloro-6-((6-chloropyridin-3-yl)oxy)pyridin-4-yl)-5-(methylsulfonamido)benzo[b]thiophene-2-carboxamide;
492) 6-chloro-N-(2-chloro-6-((6-chloropyridin-3-yl)oxy)pyridin-4-yl)-5-(methylsulfonamido)benzo[b]thiophene-2-carboxamide;
493) N-(2-chloro-6-((6-(trifluoromethyl)pyridin-3-yl)oxy)pyridin-4-yl)-5-(methylsulfonamido)benzo[b]thiophene-2-carboxamide;
494) 6-chloro-N-(2-chloro-6-((6-(trifluoromethyl)pyridin-3-yl)oxy)pyridin-4-yl)-5-(methylsulfonamido)benzo[b]thiophene-2-carboxamide;
495) N-(2-chloro-6-(4-(trifluoromethyl)phenoxy)pyridin-4-yl)-5-(methylsulfonamido)benzo[b]thiophene-2-carboxamide;
496) 6-chloro-N-(2-chloro-6-(4-(trifluoromethyl)phenoxy)pyridin-4-yl)-5-(methylsulfonamido)benzo[b]thiophene-2-carboxamide;
497) N-(3-chloro-5-(2-(4-chlorophenyl)propan-2-yl)phenyl)-6-methoxy-5-(methylsulfonamido)benzo[b]thiophene-2-carboxamide; and
498) N-(3-chloro-5-(4-chlorophenoxy)phenyl)-6-methoxy-5-(methylsulfonamido)benzo[b]thiophene-2-carboxamide.

13. A pharmaceutical composition for treating diseases associated with the activation of STAT3 protein, comprising the compound as defined in claim 1 as an active ingredient.

14. The pharmaceutical composition according to claim 13, wherein the diseases associated with the activation of STAT3 protein is selected from the group consisting of solid cancers, hematological or blood cancers, radio- or chemo-resistant cancers, metastatic cancers, inflammatory diseases, immunological diseases, diabetes, macular degeneration, human papillomavirus infection and tuberculosis.

15. The pharmaceutical composition according to claim 13, wherein the diseases associated with the activation of STAT3 protein are selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, auto-immune diseases, diabetes, macular degeneration, human papillomavirus infection, and tuberculosis.

16. A method for treating diseases associated with the activation of STAT3 protein in a mammal, which comprises administering the compound as defined in claim 1 to the mammal.

17. A method for the manufacture of a medicament for treating diseases associated with the activation of STAT3 protein comprising a step of preparing a medicament comprising the compound as defined in claim 1.

18. The pharmaceutical composition according to claim 15, wherein the auto-immune diseases are selected from the group consisting of rheumatoid arthritis, psoriasis, hepatitis, inflammatory bowel disease, and Crohn's disease.

* * * * *

UNITED STATES PATENT AND TRADEMARK OFFICE
CERTIFICATE OF CORRECTION

PATENT NO. : 10,562,912 B2
APPLICATION NO. : 14/892378
DATED : February 18, 2020
INVENTOR(S) : Park et al.

Page 1 of 1

It is certified that error appears in the above-identified patent and that said Letters Patent is hereby corrected as shown below:

In the Claims

<u>Column 225,</u>
Line 24, "$R_1$ is nitro, amino" should read --$R_1$ is amino--.

<u>Column 241,</u>
Line 53, "(2-mor-" should read --((2-mor- --.

Signed and Sealed this
Twenty-fifth Day of August, 2020

Andrei Iancu
*Director of the United States Patent and Trademark Office*